US012692212B2

(12) United States Patent
Nakano et al.

(10) Patent No.: US 12,692,212 B2
(45) Date of Patent: Jul. 28, 2026

(54) COMPOUND, ORGANIC ELECTROLUMINESCENT ELEMENT AND ELECTRONIC DEVICE

(71) Applicant: IDEMITSU KOSAN CO., LTD., Tokyo (JP)

(72) Inventors: Yuki Nakano, Tokyo (JP); Satomi Tasaki, Tokyo (JP); Kazuki Nishimura, Tokyo (JP); Hiroaki Itoi, Tokyo (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 946 days.

(21) Appl. No.: 17/918,737

(22) PCT Filed: Mar. 11, 2021

(86) PCT No.: PCT/JP2021/009830
§ 371 (c)(1),
(2) Date: Oct. 13, 2022

(87) PCT Pub. No.: WO2021/210304
PCT Pub. Date: Oct. 21, 2021

(65) Prior Publication Data

US 2023/0242465 A1 Aug. 3, 2023

(30) Foreign Application Priority Data

Apr. 15, 2020 (JP) ................................ 2020-073002

(51) Int. Cl.
*H01L 51/50* (2006.01)
*C07C 13/66* (2006.01)
(Continued)

(52) U.S. Cl.
CPC .............. *C07C 15/38* (2013.01); *C07C 13/66* (2013.01); *C07D 211/54* (2013.01);
(Continued)

(58) Field of Classification Search
None
See application file for complete search history.

(56) References Cited

U.S. PATENT DOCUMENTS

2005/0064233 A1 3/2005 Matsuura et al.
2006/0033421 A1 2/2006 Matsuura et al.
(Continued)

FOREIGN PATENT DOCUMENTS

CN 106565705 A * 4/2017 ........... C07D 409/04
JP 2006-140235 A 6/2006
(Continued)

OTHER PUBLICATIONS

Office Action issued in corresponding Korean Patent Application No. 10-2022-7039849 dated Jul. 8, 2025.
(Continued)

*Primary Examiner* — Gregory D Clark
(74) *Attorney, Agent, or Firm* — Foley & Lardner LLP

(57) ABSTRACT

A compound represented by a formula (1) and having at least one deuterium atom is provided. In the formula (1), n is 1 to 4, $L_1$ is a divalent group or a group represented by a formula (11) and $R_{111}$ to $R_{119}$ and $R_{211}$ to $R_{219}$ are each independently a hydrogen atom or a substituent, where the compound represented by the formula (1) does not include a group represented by —$N(R_{906})$ $(R_{907})$ and $R_{906}$ and $R_{907}$ are each independently a hydrogen atom, an alkyl group having 1 to 50 carbon atoms, or the like. In the formula (11), $X_{13}$ is an oxygen atom or a sulfur atom, $Y_1$ to $Y_8$ are each independently $CR_{300}$ or a nitrogen atom, and two of $R_{300}$ are a single bond bonded with *a or other $L_1$ and a single bond bonded with *b or other $L_1$.
(Continued)

(1)

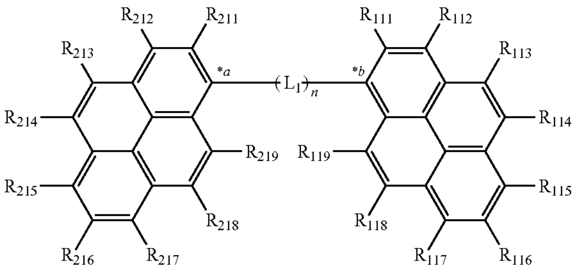

(11)

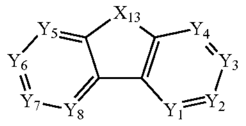

23 Claims, 2 Drawing Sheets

Figure 1:
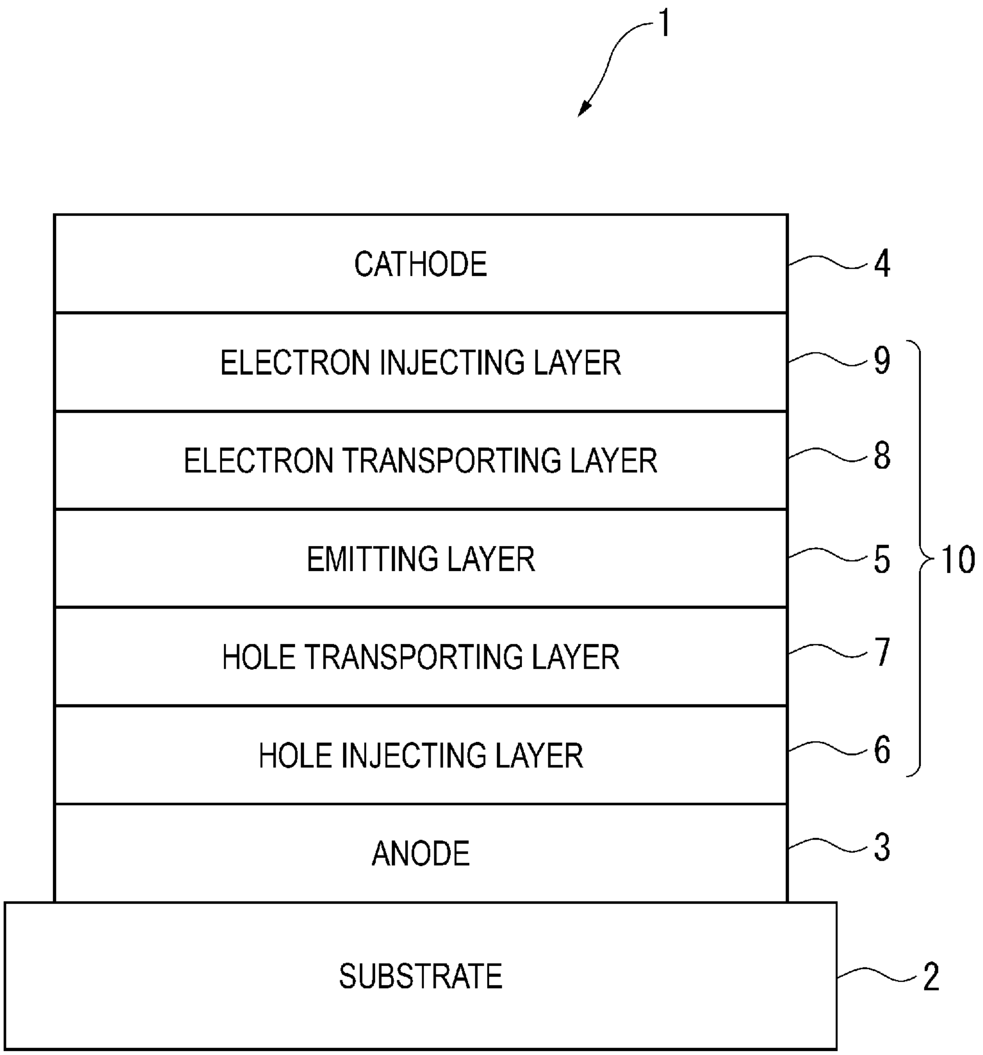

(51) Int. Cl.
*C07C 15/38* (2006.01)
*C07D 211/54* (2006.01)
*C07D 307/91* (2006.01)
*C07D 333/76* (2006.01)
*H10K 50/11* (2023.01)
*H10K 85/60* (2023.01)

(52) U.S. Cl.
CPC ......... *C07D 307/91* (2013.01); *C07D 333/76* (2013.01); *H10K 50/11* (2023.02); *H10K 85/622* (2023.02); *H10K 85/626* (2023.02); *H10K 85/6572* (2023.02); *H10K 85/6574* (2023.02); *H10K 85/6576* (2023.02); *C07B 2200/05* (2013.01)

(56) References Cited

U.S. PATENT DOCUMENTS

2006/0110623 A1 5/2006 Funahashi et al.
2006/0154107 A1 7/2006 Kubota et al.
2007/0237984 A1 10/2007 Matsuura et al.
2007/0243411 A1 10/2007 Takashima et al.
2009/0096356 A1 4/2009 Murase et al.
2010/0308718 A1 12/2010 Kubota et al.
2012/0187826 A1 7/2012 Kawamura et al.
2013/0221333 A1 8/2013 Takashima et al.
2014/0061629 A1 3/2014 Murase et al.
2014/0183500 A1 7/2014 Ikeda et al.
2015/0162540 A1 6/2015 Lim et al.
2017/0110667 A1 4/2017 Nishimura et al.
2017/0324043 A1 11/2017 Ikeda et al.
2019/0036055 A1* 1/2019 Lin ........................ H10K 50/11
2019/0280209 A1 9/2019 Fujita
2022/0255009 A1* 8/2022 Ryu ................... H10K 85/6576

FOREIGN PATENT DOCUMENTS

JP 2013-157552 A 8/2013
JP 2017-123352 A 7/2017
JP 2018-125504 A 8/2018
JP 2019-161218 A 9/2019
WO WO-2004/018588 A1 3/2004
WO WO-2005/115950 A1 12/2005
WO WO-2007/029798 A1 3/2007
WO WO-2007/100010 A1 9/2007
WO WO-2011/077691 A1 6/2011
WO WO-2014/003405 A1 1/2014
WO WO-2014/104144 A1 7/2014
WO WO-2015/005440 A1 1/2015

OTHER PUBLICATIONS

Tsuji et al., "The hydrogen/deuterium isotope effect of the host material on the lifetime of organic light-emitting diodes", Chem. Commun., 2014, vol. 50, No. 94, pp. 14870-14872.
International Searching Authority, "Written Opinion," issued in connection with International Patent Application No. PCT/JP2021/009830, dated May 11, 2021 (English Translation dated Oct. 13, 2022).
International Searching Authority, "International Search Report," issued in connection with International Patent Application No. PCT/JP2021/009830, dated May 11, 2021.
International Searching Authority, "Written Opinion," issued in connection with International Patent Application No. PCT/JP2021/009830, dated May 11, 2021.
European Extended Search Report issued in corresponding European Patent Application No. 21789325.4 dated Mar. 28, 2024 (5 pages).

* cited by examiner

COMPOUND, ORGANIC ELECTROLUMINESCENT ELEMENT AND ELECTRONIC DEVICE

CROSS-REFERENCE TO RELATED APPLICATIONS

The present application claims priority under 37 U.S.C. § 371 to International Patent Application No. PCT/JP2021/009830, filed Mar. 11, 2021, which claims priority to and the benefit of Japanese Patent Application No. 2020-073002, filed on Apr. 15, 2020. The contents of these applications are hereby incorporated by reference in their entireties.

TECHNICAL FIELD

The present invention relates to a compound, an organic electroluminescence device, and an electronic device.

BACKGROUND ART

An organic electroluminescence device (hereinafter, occasionally referred to as "organic EL device") has found its application in a full-color display for mobile phones, televisions and the like. When a voltage is applied to an organic EL device, holes and electrons are injected from an anode and a cathode, respectively, into an emitting layer. The injected holes and electrons are recombined in the emitting layer to form excitons. Specifically, according to the electron spin statistics theory, singlet excitons and triplet excitons are generated at a ratio of 25%:75%.

Various studies have been made on a compound to be used for an organic EL device in order to enhance the performance of the organic EL device (see, for instance, Patent Literatures 1 to 5). The performance of the organic EL device is evaluable in terms of, for instance, luminance, emission wavelength, chromaticity, emission efficiency, drive voltage, and lifetime.

CITATION LIST

Patent Literature(s)

Patent Literature 1: JP 2013-157552 A
Patent Literature 2: WO 2005/115950 A
Patent Literature 3: WO 2011/077691 A
Patent Literature 4: JP 2018-125504 A
Patent Literature 5: US 2019/280209 A

SUMMARY OF THE INVENTION

Problems to be Solved by the Invention

An object of the invention is to provide a compound capable of increasing a device lifetime, an organic electroluminescence device containing the compound, and an electronic device including the organic electroluminescence device.

Means for Solving the Problem(s)

According to an aspect of the invention, a compound represented by a formula (1) below and having at least one deuterium atom is provided.

[Formula 1]

(1)

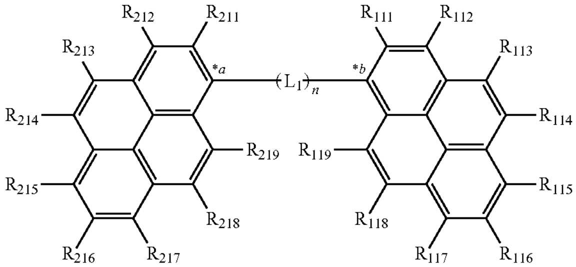

In the formula (1): n is 1, 2, 3, or 4, a plurality of $L_1$ being mutually the same or different when n is 2, 3, or 4;

$L_1$ is a divalent group derived by removing one hydrogen atom from a group selected from the group consisting of a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted chrysenyl group, a substituted or unsubstituted triphenylenyl group, a substituted or unsubstituted fluorenyl group, a substituted or unsubstituted 9,9'-spirobifluorenyl group, a substituted or unsubstituted 9,9-dimethylfluorenyl group, and a substituted or unsubstituted 9,9-diphenylfluorenyl group, or a group represented by a formula (11) below;

$R_{111}$ to $R_{119}$ and $R_{211}$ to $R_{219}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms; and the compound represented by the (1) does not include a group represented by $-N(R_{906})(R_{907})$, and $R_{906}$ and $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

[Formula 2]

(11)

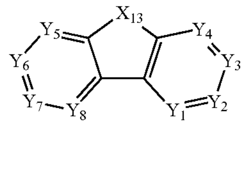

In the formula (11): $X_{13}$ is an oxygen atom or a sulfur atom, and $Y_1$ to $Y_8$ are each independently $CR_{300}$ or a nitrogen atom;

a plurality of $R_{300}$ are mutually the same or different;

at least one combination of adjacent two or more of the plurality of $R_{300}$ are mutually bonded to form a substituted or unsubstituted monocyclic ring, mutually bonded to form a substituted or unsubstituted fused ring, or not mutually bonded;

two of $R_{300}$ forming neither the substituted or unsubstituted monocyclic ring nor the substituted or unsubstituted fused ring are respectively a single bond bonded with *a or other $L_1$ in the formula (1) and a single bond bonded with *b or other $L_1$ in the formula (1);

$R_{300}$ forming neither the substituted or unsubstituted monocyclic ring nor the substituted or unsubstituted fused ring and not being the single bond bonded with *a, *b, or other $L_1$ in the formula (1) are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms.

In the compound represented by the formula (1), $R_{901}$, $R_{902}$, $R_{903}$, $R_{904}$, $R_{905}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

According to another aspect of the invention, there is provided an organic electroluminescence device including: an anode; a cathode; an emitting layer provided between the anode and the cathode, in which the emitting layer contains a compound M2 in a form of the compound according to the above aspect of the invention.

According to still another aspect of the invention, an electronic device including the organic electroluminescence device according to the above aspect of the invention is provided.

According to the above aspects of the invention, a compound capable of increasing a device lifetime, an organic electroluminescence device containing the compound, and an electronic device including the organic electroluminescence device can be provided.

BRIEF DESCRIPTION OF DRAWING(S)

FIG. 1 schematically shows an arrangement of an organic electroluminescence device according to a third exemplary embodiment of the invention.

Figure 2:
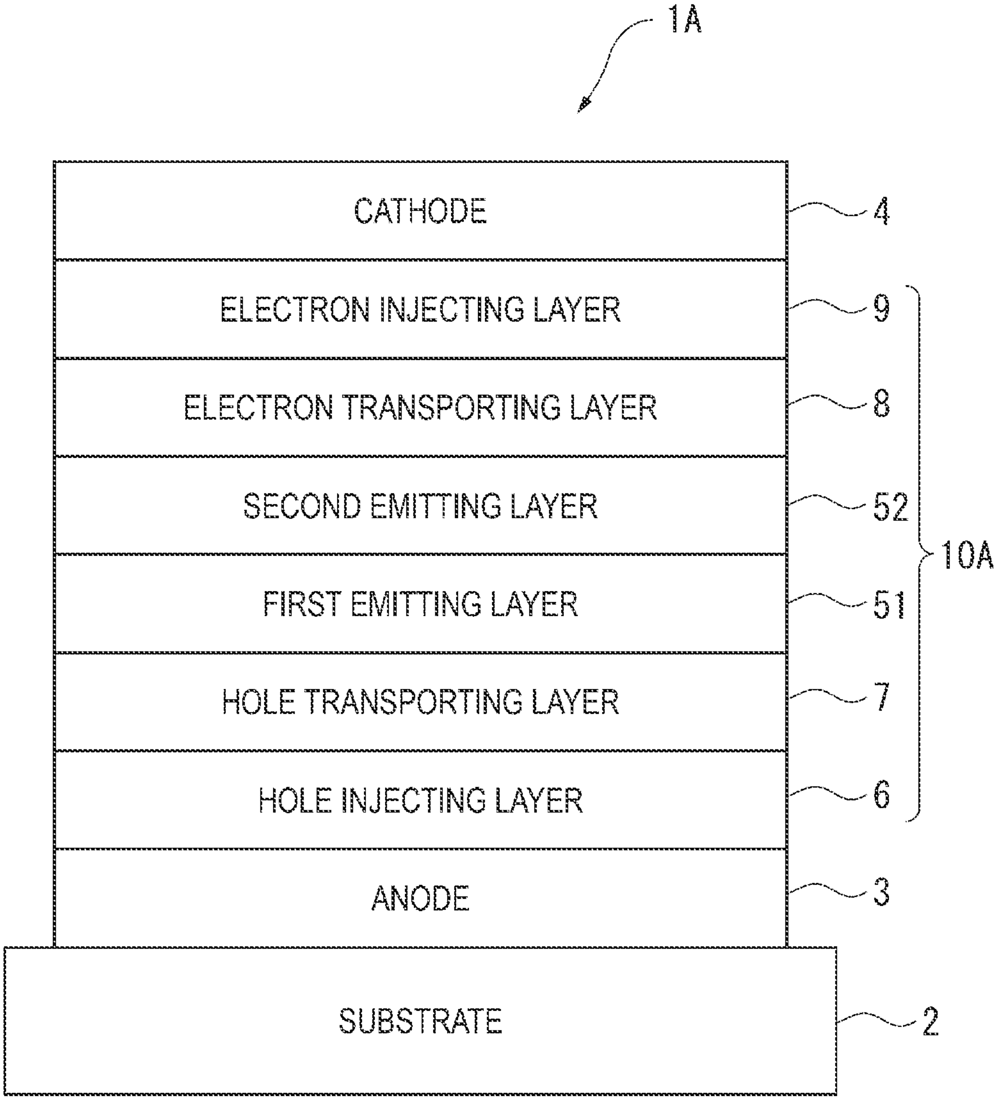

FIG. 2 schematically shows an arrangement of an organic electroluminescence device according to a fourth exemplary embodiment of the invention.

DESCRIPTION OF EMBODIMENT(S)

Definitions

Herein, a hydrogen atom includes isotopes having different numbers of neutrons, specifically, protium, deuterium and tritium.

In chemical formulae herein, it is assumed that a hydrogen atom (i.e. protium, deuterium and tritium) is bonded to each of bondable positions that are not annexed with signs "R" or the like or "D" representing a deuterium.

Herein, the ring carbon atoms refer to the number of carbon atoms among atoms forming a ring of a compound (e.g., a monocyclic compound, fused-ring compound, cross-linking compound, carbon ring compound, and heterocyclic compound) in which the atoms are bonded to each other to form the ring. When the ring is substituted by a substituent(s), carbon atom(s) contained in the substituent(s) is not counted in the ring carbon atoms. Unless otherwise specified, the same applies to the "ring carbon atoms" described later. For instance, a benzene ring has 6 ring carbon atoms, a naphthalene ring has 10 ring carbon atoms, a pyridine ring has 5 ring carbon atoms, and a furan ring has 4 ring carbon atoms. Further, for instance, 9,9-diphenylfluorenyl group has 13 ring carbon atoms and 9,9'-spirobifluorenyl group has 25 ring carbon atoms.

When a benzene ring is substituted by a substituent in a form of, for instance, an alkyl group, the number of carbon atoms of the alkyl group is not counted in the number of the ring carbon atoms of the benzene ring. Accordingly, the benzene ring substituted by an alkyl group has 6 ring carbon atoms. When a naphthalene ring is substituted by a substituent in a form of, for instance, an alkyl group, the number of carbon atoms of the alkyl group is not counted in the number of the ring carbon atoms of the naphthalene ring. Accordingly, the naphthalene ring substituted by an alkyl group has 10 ring carbon atoms.

Herein, the ring atoms refer to the number of atoms forming a ring of a compound (e.g., a monocyclic compound, fused-ring compound, cross-linking compound, carbon ring compound, and heterocyclic compound) in which the atoms are bonded to each other to form the ring (e.g., monocyclic ring, fused ring, and ring assembly). Atom(s) not forming the ring (e.g., hydrogen atom(s) for saturating the valence of the atom which forms the ring) and atom(s) in a substituent by which the ring is substituted are not counted as the ring atoms. Unless otherwise specified, the same applies to the "ring atoms" described later. For instance, a pyridine ring has 6 ring atoms, a quinazoline ring has 10 ring atoms, and a furan ring has 5 ring atoms. For instance, the number of hydrogen atom(s) bonded to a pyridine ring or the number of atoms forming a substituent are not counted as the pyridine ring atoms. Accordingly, a pyridine ring bonded to a hydrogen atom(s) or a substituent(s) has 6 ring atoms. For instance, the hydrogen atom(s) bonded to carbon atom(s) of a quinazoline ring or the atoms forming a substituent are not counted as the quinazoline ring atoms. Accordingly, a quinazoline ring bonded to hydrogen atom(s) or a substituent(s) has 10 ring atoms.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. Herein, "YY" is larger than "XX," "XX" representing an integer of 1 or more and "YY" representing an integer of 2 or more.

Herein, "XX to YY atoms" in the description of "substituted or unsubstituted ZZ group having XX to YY atoms" represent atoms of an unsubstituted ZZ group and do not include atoms of a substituent(s) of the substituted ZZ group. Herein, "YY" is larger than "XX," "XX" representing an integer of 1 or more and "YY" representing an integer of 2 or more.

Herein, an unsubstituted ZZ group refers to an "unsubstituted ZZ group" in a "substituted or unsubstituted ZZ group," and a substituted ZZ group refers to a "substituted ZZ group" in a "substituted or unsubstituted ZZ group."

Herein, the term "unsubstituted" used in a "substituted or unsubstituted ZZ group" means that a hydrogen atom(s) in the ZZ group is not substituted with a substituent(s). The hydrogen atom(s) in the "unsubstituted ZZ group" is protium, deuterium, or tritium.

Herein, the term "substituted" used in a "substituted or unsubstituted ZZ group" means that at least one hydrogen atom in the ZZ group is substituted with a substituent. Similarly, the term "substituted" used in a "BB group substituted by AA group" means that at least one hydrogen atom in the BB group is substituted with the AA group.

Substituents Mentioned Herein

Substituents mentioned herein will be described below.

An "unsubstituted aryl group" mentioned herein has, unless otherwise specified herein, 6 to 50, preferably 6 to 30, more preferably 6 to 18 ring carbon atoms.

An "unsubstituted heterocyclic group" mentioned herein has, unless otherwise specified herein, 5 to 50, preferably 5 to 30, more preferably 5 to 18 ring atoms.

An "unsubstituted alkyl group" mentioned herein has, unless otherwise specified herein, 1 to 50, preferably 1 to 20, more preferably 1 to 6 carbon atoms.

An "unsubstituted alkenyl group" mentioned herein has, unless otherwise specified herein, 2 to 50, preferably 2 to 20, more preferably 2 to 6 carbon atoms.

An "unsubstituted alkynyl group" mentioned herein has, unless otherwise specified herein, 2 to 50, preferably 2 to 20, more preferably 2 to 6 carbon atoms.

An "unsubstituted cycloalkyl group" mentioned herein has, unless otherwise specified herein, 3 to 50, preferably 3 to 20, more preferably 3 to 6 ring carbon atoms.

An "unsubstituted arylene group" mentioned herein has, unless otherwise specified herein, 6 to 50, preferably 6 to 30, more preferably 6 to 18 ring carbon atoms.

An "unsubstituted divalent heterocyclic group" mentioned herein has, unless otherwise specified herein, 5 to 50, preferably 5 to 30, more preferably 5 to 18 ring atoms.

An "unsubstituted alkylene group" mentioned herein has, unless otherwise specified herein, 1 to 50, preferably 1 to 20, more preferably 1 to 6 carbon atoms.

Substituted or Unsubstituted Aryl Group

Specific examples (specific example group G1) of the "substituted or unsubstituted aryl group" mentioned herein include unsubstituted aryl groups (specific example group G1A) below and substituted aryl groups (specific example group G1B) below. (Herein, an unsubstituted aryl group refers to an "unsubstituted aryl group" in a "substituted or unsubstituted aryl group," and a substituted aryl group refers to a "substituted aryl group" in a "substituted or unsubstituted aryl group.") A simply termed "aryl group" herein includes both of an "unsubstituted aryl group" and a "substituted aryl group."

The "substituted aryl group" refers to a group derived by substituting at least one hydrogen atom in an "unsubstituted aryl group" with a substituent. Examples of the "substituted aryl group" include a group derived by substituting at least one hydrogen atom in the "unsubstituted aryl group" in the specific example group G1A below with a substituent, and examples of the substituted aryl group in the specific example group G1B below. It should be noted that the examples of the "unsubstituted aryl group" and the "substituted aryl group" mentioned herein are merely exemplary, and the "substituted aryl group" mentioned herein includes a group derived by further substituting a hydrogen atom bonded to a carbon atom of a skeleton of a "substituted aryl group" in the specific example group G1B below, and a group derived by further substituting a hydrogen atom of a substituent of the "substituted aryl group" in the specific example group G1B below.

Unsubstituted Aryl Group (Specific Example Group G1A):

a phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, benzanthryl group, phenanthryl group, benzophenanthryl group, phenalenyl group, pyrenyl group, chrysenyl group, benzochrysenyl group, triphenylenyl group, benzotriphenylenyl group, tetracenyl group, pentacenyl group, fluorenyl group, 9,9'-spirobifluorenyl group, benzofluorenyl group, dibenzofluorenyl group, fluoranthenyl group, benzofluoranthenyl group, perylenyl group, and a monovalent aryl group derived by removing one hydrogen atom from cyclic structures represented by formulae (TEMP-1) to (TEMP-15) below.

[Formula 3]

(TEMP-1)

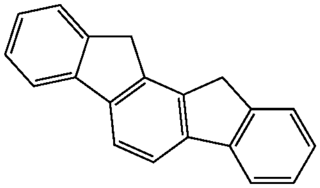

(TEMP-2)

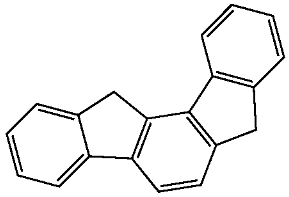

-continued (TEMP-3)

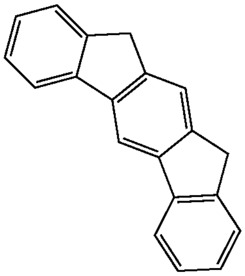

(TEMP-4)

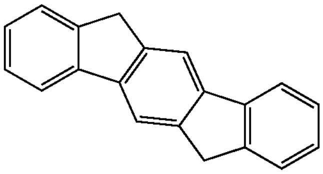

(TEMP-5)

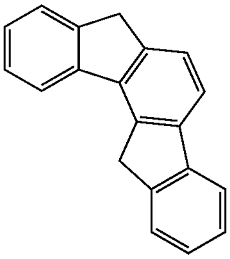

(TEMP-6)

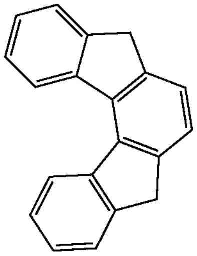

(TEMP-7)

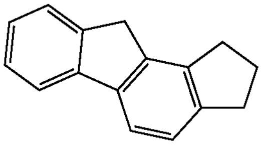

(TEMP-8)

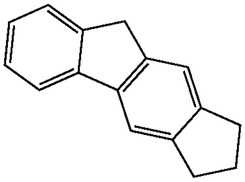

(TEMP-9)

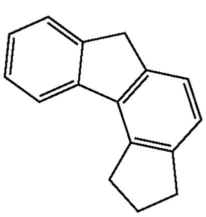

-continued

[Formula 4]

(TEMP-10)

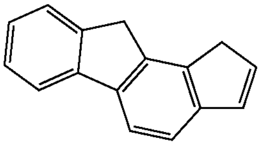

(TEMP-11)

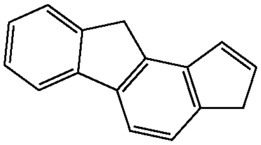

(TEMP-12)

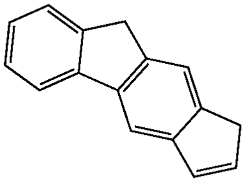

(TEMP-13)

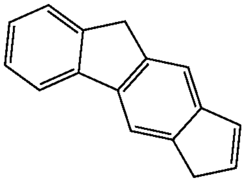

(TEMP-14)

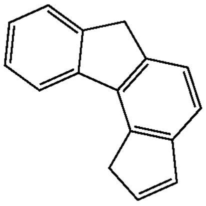

(TEMP-15)

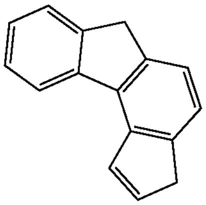

Substituted Aryl Group (Specific Example Group G1B):

o-tolyl group, m-tolyl group, p-tolyl group, para-xylyl group, meta-xylyl group, ortho-xylyl group, para-isopropylphenyl group, meta-isopropylphenyl group, ortho-isopropylphenyl group, para-t-butylphenyl group, meta-t-butylphenyl group, ortho-t-butylphenyl group, 3,4,5-trimethylphenyl group, 9,9-dimethylfluorenyl group, 9,9-diphenylfluorenyl group, 9,9-bis(4-methylphenyl)fluorenyl group, 9,9-bis(4-isopropylphenyl)fluorenyl group, 9,9-bis(4-t-butylphenyl)fluorenyl group, cyanophenyl group, triphenylsilylphenyl group, trimethylsilylphenyl group, phenylnaphthyl group, naphthylphenyl group, and a group derived by substituting at least one hydrogen atom of a monovalent group derived from one of the cyclic structures represented by the formulae (TEMP-1) to (TEMP-15) with a substituent.

Substituted or Unsubstituted Heterocyclic Group

The "heterocyclic group" mentioned herein refers to a cyclic group having at least one hetero atom in the ring atoms. Specific examples of the hetero atom include a nitrogen atom, oxygen atom, sulfur atom, silicon atom, phosphorus atom, and boron atom.

The "heterocyclic group" mentioned herein is a monocyclic group or a fused-ring group.

The "heterocyclic group" mentioned herein is an aromatic heterocyclic group or a non-aromatic heterocyclic group.

Specific examples (specific example group G2) of the "substituted or unsubstituted heterocyclic group" mentioned herein include unsubstituted heterocyclic groups (specific example group G2A) and substituted heterocyclic groups (specific example group G2B). (Herein, an unsubstituted heterocyclic group refers to an "unsubstituted heterocyclic group" in a "substituted or unsubstituted heterocyclic group," and a substituted heterocyclic group refers to a "substituted heterocyclic group" in a "substituted or unsubstituted heterocyclic group.") A simply termed "heterocyclic group" herein includes both of "unsubstituted heterocyclic group" and "substituted heterocyclic group."

The "substituted heterocyclic group" refers to a group derived by substituting at least one hydrogen atom in an "unsubstituted heterocyclic group" with a substituent. Specific examples of the "substituted heterocyclic group" include a group derived by substituting at least one hydrogen atom in the "unsubstituted heterocyclic group" in the specific example group G2A below with a substituent, and examples of the substituted heterocyclic group in the specific example group G2B below. It should be noted that the examples of the "unsubstituted heterocyclic group" and the "substituted heterocyclic group" mentioned herein are merely exemplary, and the "substituted heterocyclic group" mentioned herein includes a group derived by further substituting a hydrogen atom bonded to a ring atom of a skeleton of a "substituted heterocyclic group" in the specific example group G2B below, and a group derived by further substituting a hydrogen atom of a substituent of the "substituted heterocyclic group" in the specific example group G2B below.

The specific example group G2A includes, for instance, unsubstituted heterocyclic groups including a nitrogen atom (specific example group G2A1) below, unsubstituted heterocyclic groups including an oxygen atom (specific example group G2A2) below, unsubstituted heterocyclic groups including a sulfur atom (specific example group G2A3) below, and monovalent heterocyclic groups (specific example group G2A4) derived by removing a hydrogen atom from cyclic structures represented by formulae (TEMP-16) to (TEMP-33) below.

The specific example group G2B includes, for instance, substituted heterocyclic groups including a nitrogen atom (specific example group G2B1) below, substituted heterocyclic groups including an oxygen atom (specific example group G2B2) below, substituted heterocyclic groups including a sulfur atom (specific example group G2B3) below, and groups derived by substituting at least one hydrogen atom of the monovalent heterocyclic groups (specific example group G2B4) derived from the cyclic structures represented by formulae (TEMP-16) to (TEMP-33) below.

Unsubstituted Heterocyclic Groups Including Nitrogen Atom (Specific Example Group G2A1):

pyrrolyl group, imidazolyl group, pyrazolyl group, triazolyl group, tetrazolyl group, oxazolyl group, isoxazolyl group, oxadiazolyl group, thiazolyl group, isothiazolyl group, thiadiazolyl group, pyridyl group, pyridazynyl group, pyrimidinyl group, pyrazinyl group, triazinyl group, indolyl group, isoindolyl group, indolizinyl group, quinolizinyl group, quinolyl group, isoquinolyl group, cinnolyl group, phthalazinyl group, quinazolinyl group, quinoxalinyl group, benzimidazolyl group, indazolyl group, phenanthrolinyl group, phenanthridinyl group, acridinyl group, phenazinyl group, carbazolyl group, benzocarbazolyl group, morpholino group, phenoxazinyl group, phenothiazinyl group, azacarbazolyl group, and diazacarbazolyl group.

Unsubstituted Heterocyclic Groups Including Oxygen Atom (Specific Example Group G2A2):

furyl group, oxazolyl group, isoxazolyl group, oxadiazolyl group, xanthenyl group, benzofuranyl group, isobenzofuranyl group, a dibenzofuranyl group, naphthobenzofuranyl group, benzoxazolyl group, benzisoxazolyl group, phenoxazinyl group, morpholino group, dinaphthofuranyl group, azadibenzofuranyl group, diazadibenzofuranyl group, azanaphthobenzofuranyl group, and diazanaphthobenzofuranyl group.

Unsubstituted Heterocyclic Groups Including Sulfur Atom (Specific Example Group G2A3):

thienyl group, thiazolyl group, isothiazolyl group, thiadiazolyl group, benzothiophenyl group (benzothienyl group), isobenzothiophenyl group (isobenzothienyl group), dibenzothiophenyl group (dibenzothienyl group), naphthobenzothiophenyl group (nahthobenzothienyl group), benzothiazolyl group, benzisothiazolyl group, phenothiazinyl group, dinaphthothiophenyl group (dinaphthothienyl group), azadibenzothiophenyl group (azadibenzothienyl group), diazadibenzothiophenyl group (diazadibenzothienyl group), azanaphthobenzothiophenyl group (azanaphthobenzothienyl group), and diazanaphthobenzothiophenyl group (diazanaphthobenzothienyl group).

Monovalent Heterocyclic Groups Derived by Removing One Hydrogen Atom from Cyclic Structures Represented by Formulae (TEMP-16) to (TEMP-33) (Specific Example Group G2A4):

[Formula 5]

(TEMP-16)

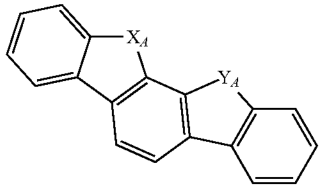

(TEMP-17)

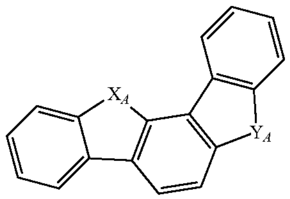

(TEMP-18)

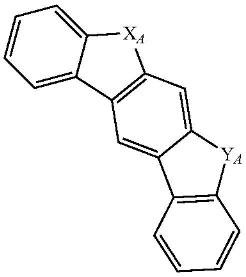

-continued
(TEMP-19)
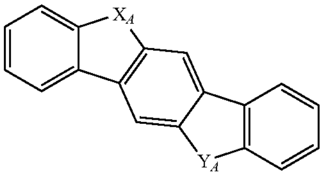
(TEMP-20)
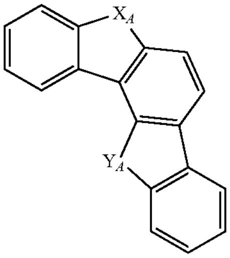
(TEMP-21)
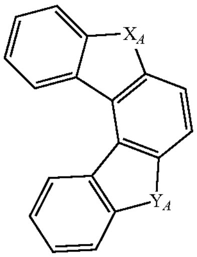
(TEMP-22)
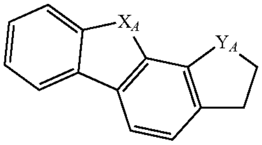
(TEMP-23)
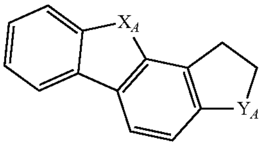
(TEMP-24)
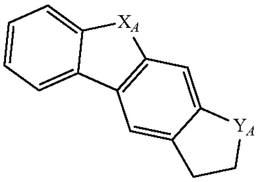
[Formula 6]
(TEMP-25)
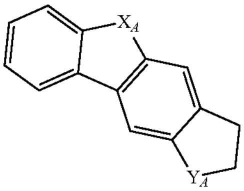
-continued
(TEMP-26)
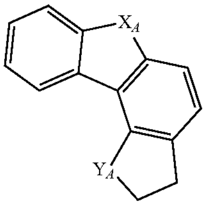
(TEMP-27)
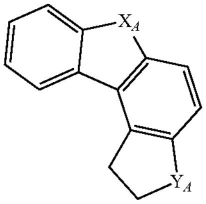
(TEMP-28)
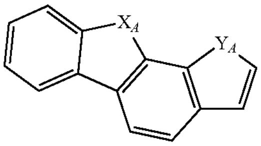
(TEMP-29)
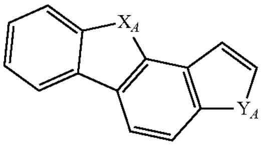
(TEMP-30)
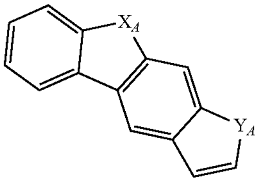
(TEMP-31)
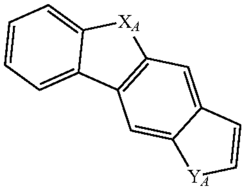
(TEMP-32)
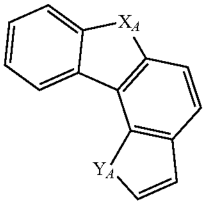
(TEMP-33)
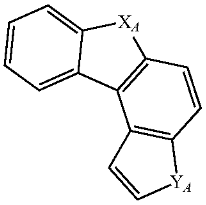
In the formulae (TEMP-16) to (TEMP-33), $X_A$ and $Y_A$ are each independently an oxygen atom, a sulfur atom, NH, or $CH_2$, with a proviso that at least one of $X_A$ or $Y_A$ is an oxygen atom, a sulfur atom, or NH.

When at least one of $X_A$ or $Y_A$ in the formulae (TEMP-16) to (TEMP-33) is NH or $CH_2$, the monovalent heterocyclic groups derived from the cyclic structures represented by the formulae (TEMP-16) to (TEMP-33) include a monovalent group derived by removing one hydrogen atom from NH or $CH_2$.

Substituted Heterocyclic Groups Including Nitrogen Atom (Specific Example Group G2B1):

(9-phenyl)carbazolyl group, (9-biphenylyl)carbazolyl group, (9-phenyl)phenylcarbazolyl group, (9-naphthyl)carbazolyl group, diphenylcarbazole-9-yl group, phenylcarbazole-9-yl group, methylbenzimidazolyl group, ethylbenzimidazolyl group, phenyltriazinyl group, biphenylyltriazinyl group, diphenyltriazinyl group, phenylquinazolinyl group, and biphenylquinazolinyl group.

Substituted Heterocyclic Groups Including Oxygen Atom (Specific Example Group G2B2):

phenyldibenzofuranyl group, methyldibenzofuranyl group, t-butyldibenzofuranyl group, and monovalent residue of spiro[9H-xanthene-9,9'-[9H]fluorene].

Substituted Heterocyclic Groups Including Sulfur Atom (Specific Example Group G2B3):

phenyldibenzothiophenyl group, methyldibenzothiophenyl group, t-butyldibenzothiophenyl group, and monovalent residue of spiro[9H-thioxanthene-9,9'-[9H]fluorene].

Groups Obtained by Substituting at Least One Hydrogen Atom of Monovalent Heterocyclic Group Derived from Cyclic Structures Represented by Formulae (TEMP-16) to (TEMP-33) with Substituent (Specific Example Group G2B4):

The "at least one hydrogen atom of a monovalent heterocyclic group" means at least one hydrogen atom selected from a hydrogen atom bonded to a ring carbon atom of the monovalent heterocyclic group, a hydrogen atom bonded to a nitrogen atom of at least one of $X_A$ or $Y_A$ in a form of NH, and a hydrogen atom of one of $X_A$ and $Y_A$ in a form of a methylene group ($CH_2$).

Substituted or Unsubstituted Alkyl Group

Specific examples (specific example group G3) of the "substituted or unsubstituted alkyl group" mentioned herein include unsubstituted alkyl groups (specific example group G3A) and substituted alkyl groups (specific example group G3B) below. (Herein, an unsubstituted alkyl group refers to an "unsubstituted alkyl group" in a "substituted or unsubstituted alkyl group," and a substituted alkyl group refers to a "substituted alkyl group" in a "substituted or unsubstituted alkyl group.") A simply termed "alkyl group" herein includes both of "unsubstituted alkyl group" and "substituted alkyl group."

The "substituted alkyl group" refers to a group derived by substituting at least one hydrogen atom in an "unsubstituted alkyl group" with a substituent. Specific examples of the "substituted alkyl group" include a group derived by substituting at least one hydrogen atom of an "unsubstituted alkyl group" (specific example group G3A) below with a substituent, and examples of the substituted alkyl group (specific example group G3B) below. Herein, the alkyl group for the "unsubstituted alkyl group" refers to a chain alkyl group. Accordingly, the "unsubstituted alkyl group" include linear "unsubstituted alkyl group" and branched "unsubstituted alkyl group." It should be noted that the examples of the "unsubstituted alkyl group" and the "substituted alkyl group" mentioned herein are merely exemplary, and the "substituted alkyl group" mentioned herein includes a group derived by further substituting a hydrogen atom of a skeleton of the "substituted alkyl group" in the specific example group G3B, and a group derived by further substituting a hydrogen atom of a substituent of the "substituted alkyl group" in the specific example group G3B.

Unsubstituted Alkyl Group (Specific Example Group G3A):

methyl group, ethyl group, n-propyl group, isopropyl group, n-butyl group, isobutyl group, s-butyl group, and t-butyl group.

Substituted Alkyl Group (Specific Example Group G3B):

heptafluoropropyl group (including isomer thereof), pentafluoroethyl group, 2,2,2-trifluoroethyl group, and trifluoromethyl group.

Substituted or Unsubstituted Alkenyl Group

Specific examples (specific example group G4) of the "substituted or unsubstituted alkenyl group" mentioned herein include unsubstituted alkenyl groups (specific example group G4A) and substituted alkenyl groups (specific example group G4B). (Herein, an unsubstituted alkenyl group refers to an "unsubstituted alkenyl group" in a "substituted or unsubstituted alkenyl group," and a substituted alkenyl group refers to a "substituted alkenyl group" in a "substituted or unsubstituted alkenyl group.") A simply termed "alkenyl group" herein includes both of "unsubstituted alkenyl group" and "substituted alkenyl group."

The "substituted alkenyl group" refers to a group derived by substituting at least one hydrogen atom in an "unsubstituted alkenyl group" with a substituent. Specific examples of the "substituted alkenyl group" include an "unsubstituted alkenyl group" (specific example group G4A) substituted by a substituent, and examples of the substituted alkenyl group (specific example group G4B) below. It should be noted that the examples of the "unsubstituted alkenyl group" and the "substituted alkenyl group" mentioned herein are merely exemplary, and the "substituted alkenyl group" mentioned herein includes a group derived by further substituting a hydrogen atom of a skeleton of the "substituted alkenyl group" in the specific example group G4B with a substituent, and a group derived by further substituting a hydrogen atom of a substituent of the "substituted alkenyl group" in the specific example group G4B with a substituent.

Unsubstituted Alkenyl Group (Specific Example Group G4A):

vinyl group, allyl group, 1-butenyl group, 2-butenyl group, and 3-butenyl group.

Substituted Alkenyl Group (Specific Example Group G4B):

1,3-butanedienyl group, 1-methylvinyl group, 1-methylallyl group, 1,1-dimethylallyl group, 2-methylallyl group, and 1,2-dimethylallyl group.

Substituted or Unsubstituted Alkynyl Group

Specific examples (specific example group G5) of the "substituted or unsubstituted alkynyl group" mentioned herein include unsubstituted alkynyl groups (specific example group G5A) below. (Herein, an unsubstituted alkynyl group refers to an "unsubstituted alkynyl group" in a "substituted or unsubstituted alkynyl group.") A simply termed "alkynyl group" herein includes both of "unsubstituted alkynyl group" and "substituted alkynyl group."

The "substituted alkynyl group" refers to a group derived by substituting at least one hydrogen atom in an "unsubstituted alkynyl group" with a substituent. Specific examples of the "substituted alkynyl group" include a group derived by substituting at least one hydrogen atom of the "unsubstituted alkynyl group" (specific example group G5A) below with a substituent.

Unsubstituted Alkynyl Group (Specific Example Group G5A):

Ethynyl group.

Substituted or Unsubstituted Cycloalkyl Group

Specific examples (specific example group G6) of the "substituted or unsubstituted cycloalkyl group" mentioned herein include unsubstituted cycloalkyl groups (specific example group G6A) and substituted cycloalkyl groups (specific example group G6B). (Herein, an unsubstituted cycloalkyl group refers to an "unsubstituted cycloalkyl group" in a "substituted or unsubstituted cycloalkyl group," and a substituted cycloalkyl group refers to a "substituted cycloalkyl group" in a "substituted or unsubstituted cycloalkyl group.") A simply termed "cycloalkyl group" herein includes both of "unsubstituted cycloalkyl group" and "substituted cycloalkyl group."

The "substituted cycloalkyl group" refers to a group derived by substituting at least one hydrogen atom of an "unsubstituted cycloalkyl group" with a substituent. Specific examples of the "substituted cycloalkyl group" include a group derived by substituting at least one hydrogen atom of the "unsubstituted cycloalkyl group" (specific example group G6A) below with a substituent, and examples of the substituted cycloalkyl group (specific example group G6B) below. It should be noted that the examples of the "unsubstituted cycloalkyl group" and the "substituted cycloalkyl group" mentioned herein are merely exemplary, and the "substituted cycloalkyl group" mentioned herein includes a group derived by substituting at least one hydrogen atom bonded to a carbon atom of a skeleton of the "substituted cycloalkyl group" in the specific example group G6B with a substituent, and a group derived by further substituting a hydrogen atom of a substituent of the "substituted cycloalkyl group" in the specific example group G6B with a substituent.

Unsubstituted Cycloalkyl Group (Specific Example Group G6A):

cyclopropyl group, cyclobutyl group, cyclopentyl group, cyclohexyl group, 1-adamantyl group, 2-adamantyl group, 1-norbornyl group, and 2-norbornyl group.

Substituted Cycloalkyl Group (Specific Example Group G6B):

4-methylcyclohexyl group.

Group Represented by —Si($R_{901}$)($R_{902}$)($R_{903}$)

Specific examples (specific example group G7) of the group represented herein by —Si($R_{901}$)($R_{902}$)($R_{903}$) include: —Si(G1)(G1)(G1); —Si(G1)(G2)(G2); —Si(G1)(G1)(G2); —Si(G2)(G2)(G2); —Si(G3)(G3)(G3); and —Si(G6)(G6)(G6), where:

G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3;

G6 represents a "substituted or unsubstituted cycloalkyl group" in the specific example group G6;

a plurality of G1 in —Si(G1)(G1)(G1) are mutually the same or different;

a plurality of G2 in —Si(G1)(G2)(G2) are mutually the same or different;

a plurality of G1 in —Si(G1)(G1)(G2) are mutually the same or different;

a plurality of G2 in —Si(G2)(G2)(G2) are mutually the same or different;

a plurality of G3 in —Si(G3)(G3)(G3) are mutually the same or different; and a plurality of G6 in —Si(G6)(G6)(G6) are mutually the same or different.

Group Represented by —O—($R_{904}$)

Specific examples (specific example group G8) of a group represented by —O—($R_{904}$) herein include: —O(G1); —O(G2); —O(G3); and —O(G6), where:

G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3; and G6 represents a "substituted or unsubstituted cycloalkyl group" in the specific example group G6.

Group Represented by —S—($R_{905}$)

Specific examples (specific example group G9) of a group represented herein by —S—($R_{905}$) include: —S(G1); —S(G2); —S(G3); and —S(G6), where:

G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3; and G6 represents a "substituted or unsubstituted cycloalkyl group" in the specific example group G6.

Group Represented by —N($R_{906}$)($R_{907}$)

Specific examples (specific example group G10) of a group represented herein by —N($R_{906}$)($R_{907}$) include: —N(G1)(G1); —N(G2)(G2); —N(G1)(G2); —N(G3)(G3); and —N(G6)(G6), where:

G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3;

G6 represents a "substituted or unsubstituted cycloalkyl group" in the specific example group G6;

a plurality of G1 in —N(G1)(G1) are mutually the same or different;

a plurality of G2 in —N(G2)(G2) are mutually the same or different;

a plurality of G3 in —N(G3)(G3) are mutually the same or different; and a plurality of G6 in —N(G6)(G6) are mutually the same or different.

Halogen Atom

Specific examples (specific example group G11) of "halogen atom" mentioned herein include a fluorine atom, chlorine atom, bromine atom, and iodine atom.

Substituted or Unsubstituted Fluoroalkyl Group

The "substituted or unsubstituted fluoroalkyl group" mentioned herein refers to a group derived by substituting at least one hydrogen atom bonded to at least one of carbon atoms forming an alkyl group in the "substituted or unsubstituted alkyl group" with a fluorine atom, and also includes a group (perfluoro group) derived by substituting all of hydrogen atoms bonded to carbon atoms forming the alkyl group in the "substituted or unsubstituted alkyl group" with fluorine atoms. An "unsubstituted fluoroalkyl group" has, unless otherwise specified herein, 1 to 50, preferably 1 to 30, more preferably 1 to 18 carbon atoms. The "substituted fluoroalkyl group" refers to a group derived by substituting at least one hydrogen atom in a "fluoroalkyl group" with a substituent. It should be noted that the examples of the "substituted fluoroalkyl group" mentioned herein include a group derived by further substituting at least one hydrogen atom bonded to a carbon atom of an alkyl chain of a "substituted fluoroalkyl group" with a substituent, and a group derived by further substituting at least one hydrogen atom of a substituent of the "substituted fluoroalkyl group" with a substituent. Specific examples of the "substituted fluoroalkyl group" include a group derived by substituting at least one hydrogen atom of the "alkyl group" (specific example group G3) with a fluorine atom.

Substituted or Unsubstituted Haloalkyl Group

The "substituted or unsubstituted haloalkyl group" mentioned herein refers to a group derived by substituting at least one hydrogen atom bonded to carbon atoms forming the alkyl group in the "substituted or unsubstituted alkyl group" with a halogen atom, and also includes a group derived by substituting all hydrogen atoms bonded to carbon atoms forming the alkyl group in the "substituted or unsubstituted alkyl group" with halogen atoms. An "unsubstituted haloalkyl group" has, unless otherwise specified herein, 1 to 50, preferably 1 to 30, more preferably 1 to 18 carbon atoms. The "substituted haloalkyl group" refers to a group derived by substituting at least one hydrogen atom in a "haloalkyl group" with a substituent. It should be noted that the examples of the "substituted haloalkyl group" mentioned herein include a group derived by further substituting at least one hydrogen atom bonded to a carbon atom of an alkyl chain of a "substituted haloalkyl group" with a substituent, and a group derived by further substituting at least one hydrogen atom of a substituent of the "substituted haloalkyl group" with a substituent. Specific examples of the "unsubstituted haloalkyl group" include a group derived by substituting at least one hydrogen atom of the "alkyl group" (specific example group G3) with a halogen atom. The haloalkyl group is sometimes referred to as a halogenated alkyl group.

Substituted or Unsubstituted Alkoxy Group

Specific examples of a "substituted or unsubstituted alkoxy group" mentioned herein include a group represented by —O(G3), G3 being the "substituted or unsubstituted alkyl group" in the specific example group G3. An "unsubstituted alkoxy group" has, unless otherwise specified herein, 1 to 50, preferably 1 to 30, more preferably 1 to 18 carbon atoms.

Substituted or Unsubstituted Alkylthio Group

Specific examples of a "substituted or unsubstituted alkylthio group" mentioned herein include a group represented by —S(G3), G3 being the "substituted or unsubstituted alkyl group" in the specific example group G3. An "unsubstituted alkylthio group" has, unless otherwise specified herein, 1 to 50, preferably 1 to 30, more preferably 1 to 18 carbon atoms.

Substituted or Unsubstituted Aryloxy Group

Specific examples of a "substituted or unsubstituted aryloxy group" mentioned herein include a group represented by —O(G1), G1 being the "substituted or unsubstituted aryl group" in the specific example group G1. An "unsubstituted aryloxy group" has, unless otherwise specified herein, 6 to 50, preferably 6 to 30, more preferably 6 to 18 ring carbon atoms.

Substituted or Unsubstituted Arylthio Group

Specific examples of a "substituted or unsubstituted arylthio group" mentioned herein include a group represented by —S(G1), G1 being the "substituted or unsubstituted aryl group" in the specific example group G1. An "unsubstituted arylthio group" has, unless otherwise specified herein, 6 to 50, preferably 6 to 30, more preferably 6 to 18 ring carbon atoms.

Substituted or Unsubstituted Trialkylsilyl Group

Specific examples of a "trialkylsilyl group" mentioned herein include a group represented by —Si(G3)(G3)(G3), G3 being the "substituted or unsubstituted alkyl group" in the specific example group G3. The plurality of G3 in —Si(G3)(G3)(G3) are mutually the same or different. Each of the alkyl groups in the "trialkylsilyl group" has, unless otherwise specified herein, 1 to 50, preferably 1 to 20, more preferably 1 to 6 carbon atoms.

Substituted or Unsubstituted Aralkyl Group

Specific examples of a "substituted or unsubstituted aralkyl group" mentioned herein include a group represented by (G3)-(G1), G3 being the "substituted or unsubstituted alkyl group" in the specific example group G3, G1 being the "substituted or unsubstituted aryl group" in the specific example group G1. Accordingly, the "aralkyl group" is a group derived by substituting a hydrogen atom of the "alkyl group" with a substituent in a form of the "aryl group," which is an example of the "substituted alkyl group." An "unsubstituted aralkyl group," which is an "unsubstituted alkyl group" substituted by an "unsubstituted aryl group," has, unless otherwise specified herein, 7 to 50 carbon atoms, preferably 7 to 30 carbon atoms, more preferably 7 to 18 carbon atoms.

Specific examples of the "substituted or unsubstituted aralkyl group" include a benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

Preferable examples of the substituted or unsubstituted aryl group mentioned herein include, unless otherwise specified herein, a phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, phenanthryl group, pyrenyl group, chrysenyl group, triphenylenyl group, fluorenyl group, 9,9'-spirobifluorenyl group, 9,9-dimethylfluorenyl group, and 9,9-diphenylfluorenyl group.

Preferable examples of the substituted or unsubstituted heterocyclic group mentioned herein include, unless otherwise specified herein, a pyridyl group, pyrimidinyl group, triazinyl group, quinolyl group, isoquinolyl group, quinazolinyl group, benzimidazolyl group, phenanthrolinyl group, carbazolyl group (1-carbazolyl group, 2-carbazolyl group, 3-carbazolyl group, 4-carbazolyl group, or 9-carbazolyl group), benzocarbazolyl group, azacarbazolyl group, diazacarbazolyl group, dibenzofuranyl group, naphthobenzofuranyl group, azadibenzofuranyl group, diazadibenzofuranyl group, dibenzothiophenyl group, naphthobenzothiophenyl group, azadibenzothiophenyl group, diazadibenzothiophenyl group, (9-phenyl)carbazolyl group ((9-phenyl)carbazole-1-yl group, (9-phenyl)carbazole-2-yl group, (9-phenyl)carbazole-3-yl group, or (9-phenyl)carbazole-4-yl group), (9-biphenylyl)carbazolyl group, (9-phenyl)phenylcarbazolyl group, diphenylcarbazole-9-yl group, phenylcarbazole-9-yl group, phenyltriazinyl group, biphenylyltriazinyl group, diphenyltriazinyl group, phenyldibenzofuranyl group, and phenyldibenzothiophenyl group.

The carbazolyl group mentioned herein is, unless otherwise specified herein, specifically a group represented by one of formulae below.

[Formula 7]

(TEMP-Cz1)

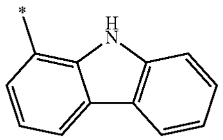

(TEMP-Cz2)

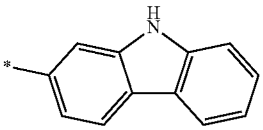

(TEMP-Cz3)

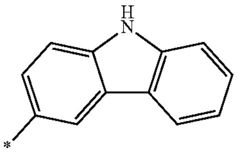

(TEMP-Cz4

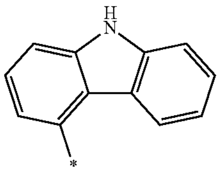

(TEMP-Cz5)

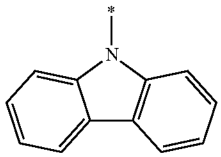

The (9-phenyl)carbazolyl group mentioned herein is, unless otherwise specified herein, specifically a group represented by one of formulae below.

[Formula 8]

(TEMP-Cz6)

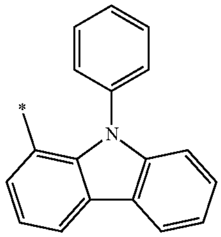

(TEMP-Cz7)

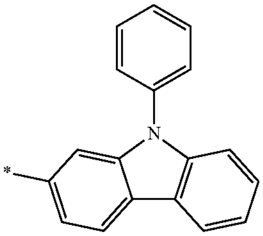

-continued (TEMP-Cz8)

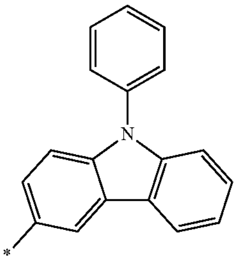

(TEMP-Cz9)

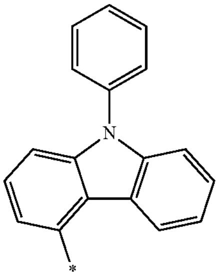

In the formulae (TEMP-Cz1) to (TEMP-Cz9), * represents a bonding position.

The dibenzofuranyl group and dibenzothiophenyl group mentioned herein are, unless otherwise specified herein, each specifically represented by one of formulae below.

[Formula 9]

(TEMP-34)

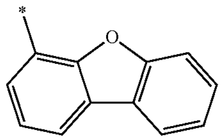

(TEMP-35)

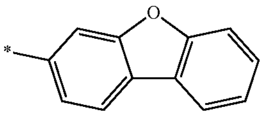

(TEMP-36)

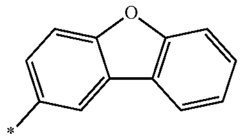

(TEMP-37)

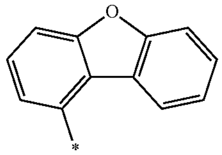

(TEMP-38)

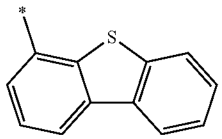

-continued (TEMP-39)

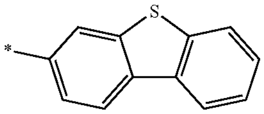

(TEMP-40)

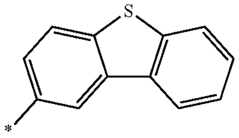

(TEMP-41)

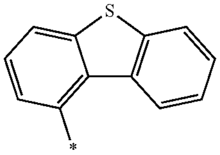

In the formulae (TEMP-34) to (TEMP-41), * represents a bonding position.

Preferable examples of the substituted or unsubstituted alkyl group mentioned herein include, unless otherwise specified herein, a methyl group, ethyl group, propyl group, isopropyl group, n-butyl group, isobutyl group, and t-butyl group.

Substituted or Unsubstituted Arylene Group

The "substituted or unsubstituted arylene group" mentioned herein is, unless otherwise specified herein, a divalent group derived by removing one hydrogen atom on an aryl ring of the "substituted or unsubstituted aryl group." Specific examples of the "substituted or unsubstituted arylene group" (specific example group G12) include a divalent group derived by removing one hydrogen atom on an aryl ring of the "substituted or unsubstituted aryl group" in the specific example group G1.

Substituted or Unsubstituted Divalent Heterocyclic Group

The "substituted or unsubstituted divalent heterocyclic group" mentioned herein is, unless otherwise specified herein, a divalent group derived by removing one hydrogen atom on a heterocycle of the "substituted or unsubstituted heterocyclic group." Specific examples of the "substituted or unsubstituted divalent heterocyclic group" (specific example group G13) include a divalent group derived by removing one hydrogen atom on a heterocyclic ring of the "substituted or unsubstituted heterocyclic group" in the specific example group G2.

Substituted or Unsubstituted Alkylene Group

The "substituted or unsubstituted alkylene group" mentioned herein is, unless otherwise specified herein, a divalent group derived by removing one hydrogen atom on an alkyl chain of the "substituted or unsubstituted alkyl group." Specific examples of the "substituted or unsubstituted alkylene group" (specific example group G14) include a divalent group derived by removing one hydrogen atom on an alkyl chain of the "substituted or unsubstituted alkyl group" in the specific example group G3.

The substituted or unsubstituted arylene group mentioned herein is, unless otherwise specified herein, preferably any one of groups represented by formulae (TEMP-42) to (TEMP-68) below.

[Formula 10]

(TEMP-42)

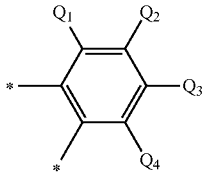

(TEMP-43)

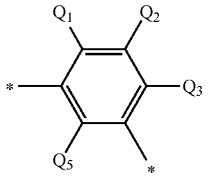

(TEMP-44)

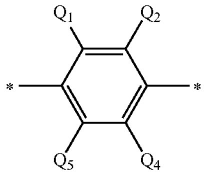

(TEMP-45)

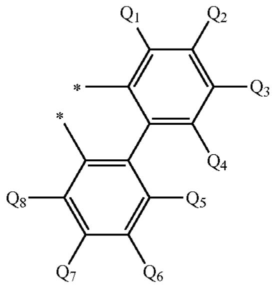

(TEMP-46)

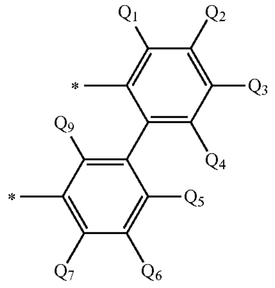

(TEMP-47)

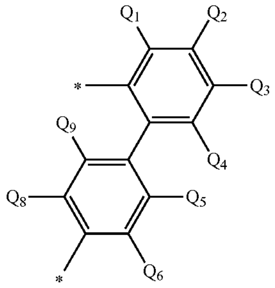

-continued
[Formula 11]
(TEMP-48)
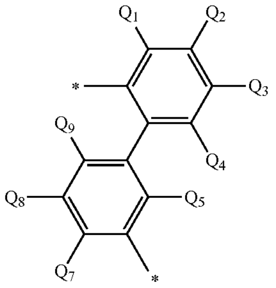
(TEMP-49)
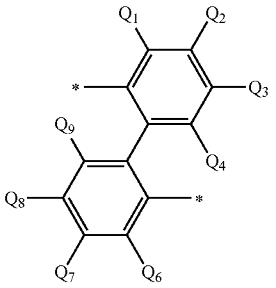
(TEMP-50)
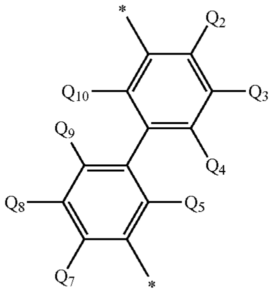
(TEMP-51)
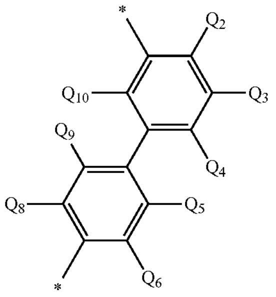
(TEMP-52)
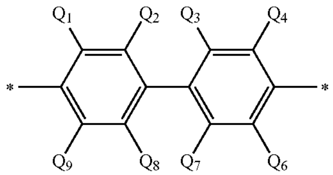
In the formulae (TEMP-42) to (TEMP-52), $Q_1$ to $Q_{10}$ are each independently a hydrogen atom or a substituent.
In the formulae (TEMP-42) to (TEMP-52), * represents a bonding position.
[Formula 12]
(TEMP 53)
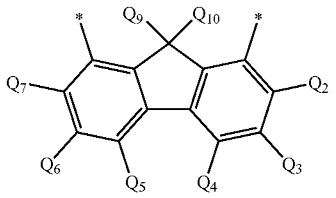
(TEMP 54)
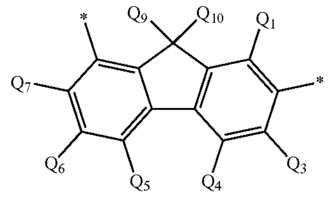
(TEMP 55)
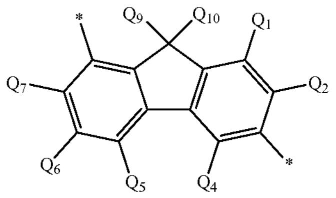
(TEMP 56)
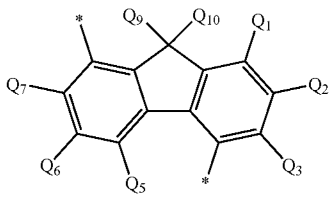
(TEMP 57)
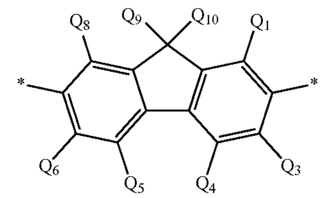
(TEMP 58)
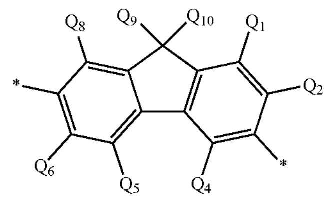
(TEMP 59)
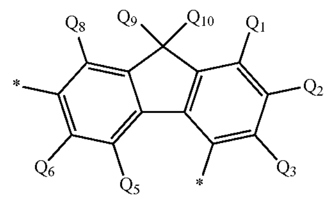

-continued (TEMP 60)

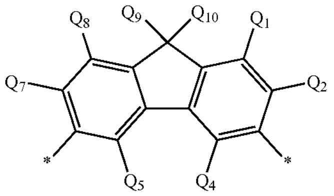

(TEMP 61)

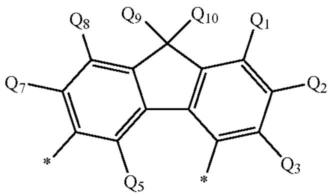

(TEMP 62)

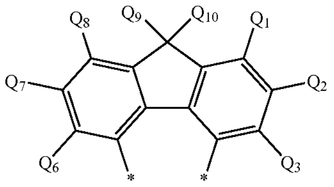

In the formulae (TEMP-53) to (TEMP-62), $Q_1$ to $Q_{10}$ are each independently a hydrogen atom or a substituent.

In the formulae, $Q_9$ and $Q_{10}$ may be mutually bonded through a single bond to form a ring.

In the formulae (TEMP-53) to (TEMP-62), * represents a bonding position.

[Formula 13]

(TEMP-63)

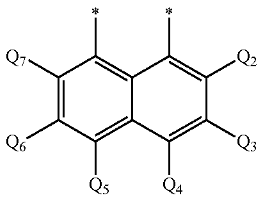

(TEMP-64)

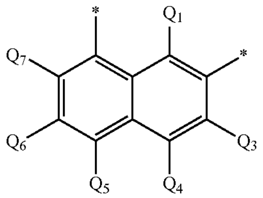

(TEMP-65)

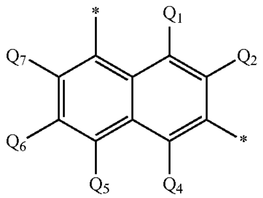

-continued (TEMP-66)

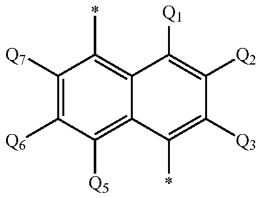

(TEMP-67)

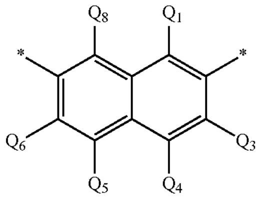

(TEMP-68)

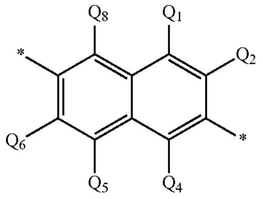

In the formulae (TEMP-63) to (TEMP-68), $Q_1$ to $Q_8$ are each independently a hydrogen atom or a substituent.

In the formulae (TEMP-63) to (TEMP-68), * represents a bonding position.

The substituted or unsubstituted divalent heterocyclic group mentioned herein is, unless otherwise specified herein, preferably a group represented by any one of formulae (TEMP-69) to (TEMP-102) below.

[Formula 14]

(TEMP-69)

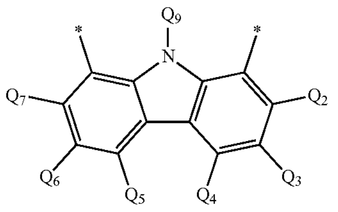

(TEMP-70)

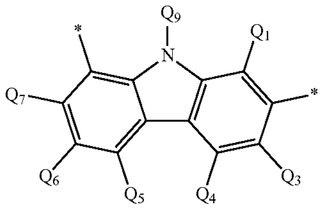

(TEMP-71)

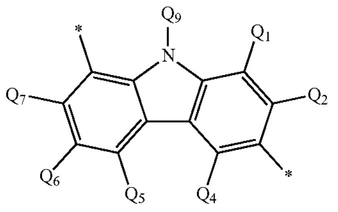

-continued
(TEMP-72)
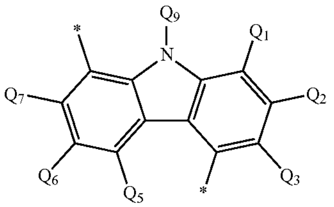
(TEMP-73)
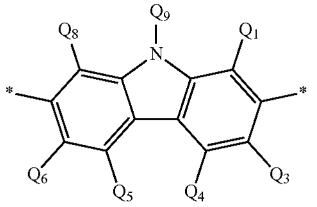
(TEMP-74)
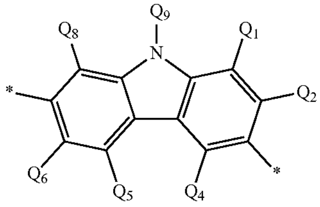
[Formula 15]
(TEMP-75)
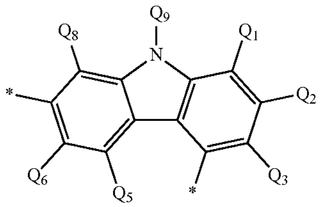
(TEMP-76)
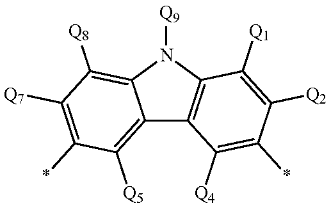
(TEMP-77)
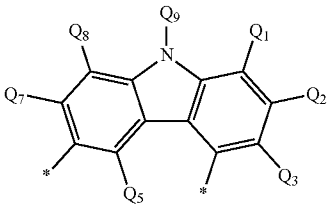
(TEMP-78)
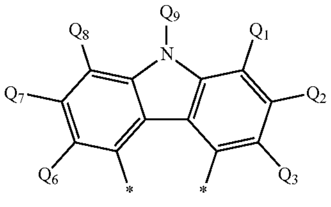
-continued
(TEMP-79)
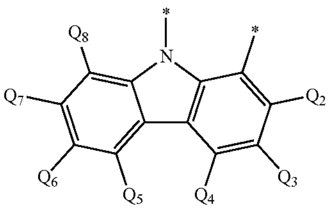
(TEMP-80)
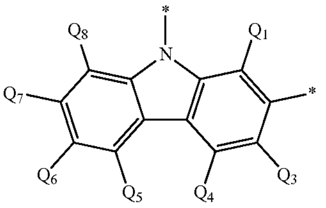
[Formula 16]
(TEMP-81)
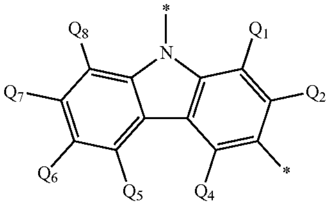
(TEMP-82)
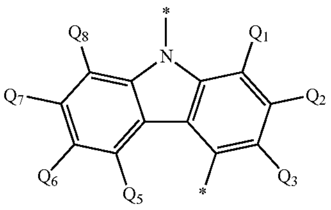
In the formulae (TEMP-69) to (TEMP-82), $Q_1$ to $Q_9$ are each independently a hydrogen atom or a substituent.
[Formula 17]
(TEMP-83)
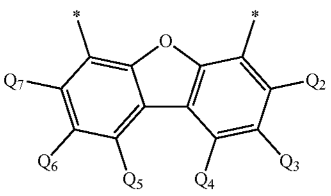
(TEMP-84)
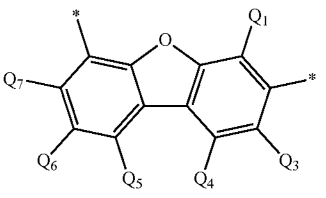

-continued
(TEMP-85)
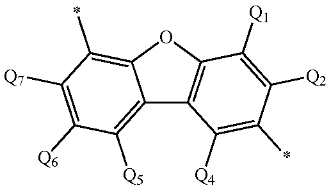
(TEMP-86)
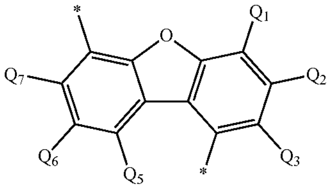
(TEMP-87)
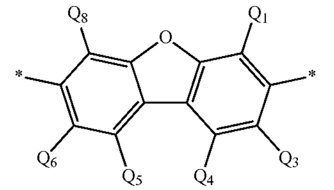
(TEMP-88)
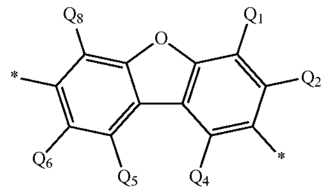
[Formula 18]
(TEMP-89)
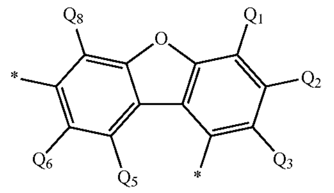
(TEMP-90)
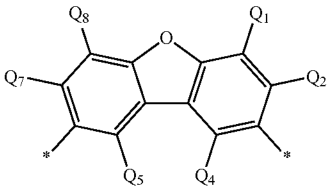
(TEMP-91)
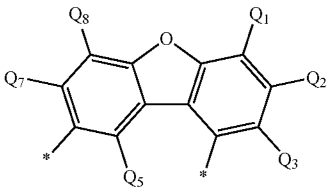
(TEMP-92)
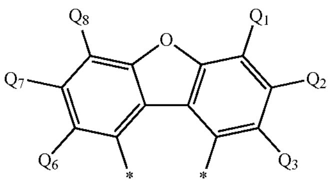
-continued
[Formula 19]
(TEMP-93)
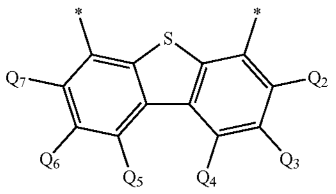
(TEMP-94)
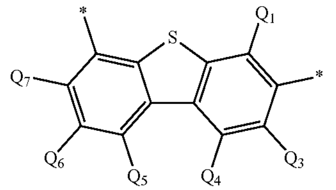
(TEMP-95)
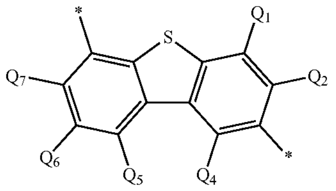
(TEMP-96)
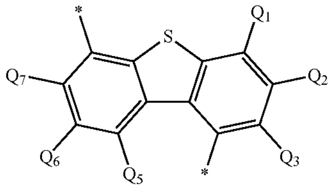
(TEMP-97)
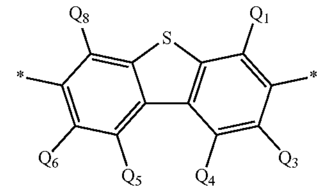
(TEMP-98)
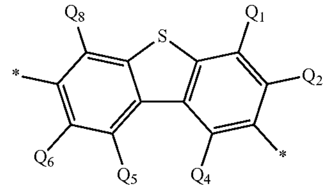
[Formula 20]
(TEMP-99)
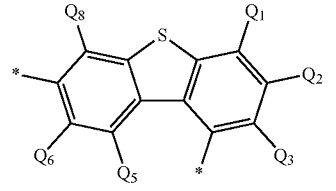

-continued (TEMP-100)

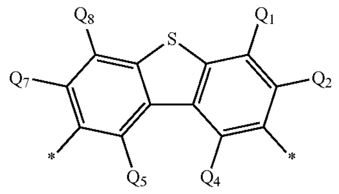

(TEMP-101)

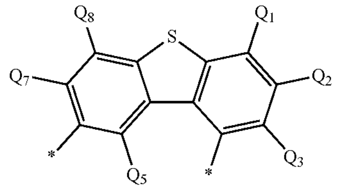

(TEMP-102)

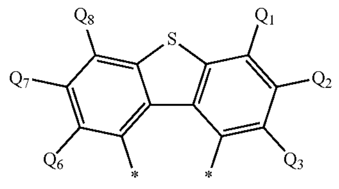

In the formulae (TEMP-83) to (TEMP-102), $Q_1$ to $Q_8$ are each independently a hydrogen atom or a substituent.

The substituent mentioned herein has been described above.

Instance of "Bonded to Form Ring"

Instances where "at least one combination of adjacent two or more (of . . . ) are mutually bonded to form a substituted or unsubstituted monocyclic ring, mutually bonded to form a substituted or unsubstituted fused ring, or not mutually bonded" mentioned herein refer to instances where "at least one combination of adjacent two or more (of . . . ) are mutually bonded to form a substituted or unsubstituted monocyclic ring, "at least one combination of adjacent two or more (of . . . ) are mutually bonded to form a substituted or unsubstituted fused ring," and "at least one combination of adjacent two or more (of . . . ) are not mutually bonded."

Instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (these instances will be sometimes collectively referred to as an instance of "bonded to form a ring" hereinafter) will be described below. An anthracene compound having a basic skeleton in a form of an anthracene ring and represented by a formula (TEMP-103) below will be used as an example for the description.

[Formula 21]

(TEMP-103)

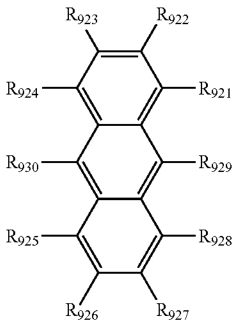

For instance, when "at least one combination of adjacent two or more of $R_{921}$ to $R_{930}$ are mutually bonded to form a ring," the combination of adjacent ones of $R_{921}$ to $R_{930}$ (i.e. the combination at issue) is a combination of $R_{921}$ and $R_{922}$, a combination of $R_{922}$ and $R_{923}$, a combination of $R_{923}$ and $R_{924}$, a combination of $R_{924}$ and $R_{930}$, a combination of $R_{930}$ and $R_{925}$, a combination of $R_{925}$ and $R_{926}$, a combination of $R_{926}$ and $R_{927}$, a combination of $R_{927}$ and $R_{928}$, a combination of $R_{928}$ and $R_{929}$, or a combination of $R_{929}$ and $R_{921}$.

The term "at least one combination" means that two or more of the above combinations of adjacent two or more of $R_{921}$ to $R_{930}$ may simultaneously form rings. For instance, when $R_{921}$ and $R_{922}$ are mutually bonded to form a ring $Q_A$ and $R_{925}$ and $R_{926}$ are simultaneously mutually bonded to form a ring $Q_B$, the anthracene compound represented by the formula (TEMP-103) is represented by a formula (TEMP-104) below.

[Formula 22]

(TEMP-104)

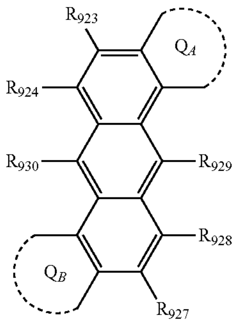

The instance where the "combination of adjacent two or more" form a ring means not only an instance where the "two" adjacent components are bonded but also an instance where adjacent "three or more" are bonded. For instance, $R_{921}$ and $R_{922}$ are mutually bonded to form a ring $Q_A$ and $R_{922}$ and $R_{923}$ are mutually bonded to form a ring $Q_C$, and mutually adjacent three components ($R_{921}$, $R_{922}$ and $R_{923}$) are mutually bonded to form a ring fused to the anthracene basic skeleton. In this case, the anthracene compound represented by the formula (TEMP-103) is represented by a formula (TEMP-105) below. In the formula (TEMP-105) below, the ring $Q_A$ and the ring $Q_C$ share $R_{922}$.

[Formula 23]

(TEMP-105)

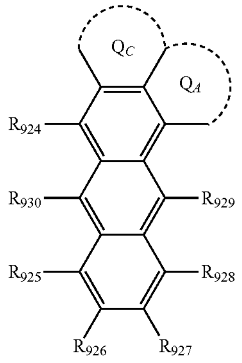

The formed "monocyclic ring" or "fused ring" may be, in terms of the formed ring in itself, a saturated ring or an unsaturated ring. When the "combination of adjacent two" form a "monocyclic ring" or a "fused ring," the "monocyclic ring" or "fused ring" may be a saturated ring or an unsaturated ring. For instance, the ring $Q_A$ and the ring $Q_B$ formed in the formula (TEMP-104) are each independently a "monocyclic ring" or a "fused ring." Further, the ring $Q_A$ and the ring $Q_C$ formed in the formula (TEMP-105) are each a "fused ring." The ring $Q_A$ and the ring $Q_C$ in the formula (TEMP-105) are fused to form a fused ring. When the ring $Q_A$ in the formula (TMEP-104) is a benzene ring, the ring $Q_A$ is a monocyclic ring. When the ring $Q_A$ in the formula (TMEP-104) is a naphthalene ring, the ring $Q_A$ is a fused ring.

The "unsaturated ring" represents an aromatic hydrocarbon ring or an aromatic heterocycle. The "saturated ring" represents an aliphatic hydrocarbon ring or a non-aromatic heterocycle.

Specific examples of the aromatic hydrocarbon ring include a ring formed by terminating a bond of a group in the specific example of the specific example group G1 with a hydrogen atom.

Specific examples of the aromatic heterocycle include a ring formed by terminating a bond of an aromatic heterocyclic group in the specific example of the specific example group G2 with a hydrogen atom.

Specific examples of the aliphatic hydrocarbon ring include a ring formed by terminating a bond of a group in the specific example of the specific example group G6 with a hydrogen atom.

The phrase "to form a ring" herein means that a ring is formed only by a plurality of atoms of a basic skeleton, or by a combination of a plurality of atoms of the basic skeleton and one or more optional atoms. For instance, the ring $Q_A$ formed by mutually bonding $R_{921}$ and $R_{922}$ shown in the formula (TEMP-104) is a ring formed by a carbon atom of the anthracene skeleton bonded to $R_{921}$, a carbon atom of the anthracene skeleton bonded to $R_{922}$, and one or more optional atoms. Specifically, when the ring $Q_A$ is a monocyclic unsaturated ring formed by $R_{921}$ and $R_{922}$, the ring formed by a carbon atom of the anthracene skeleton bonded to $R_{921}$, a carbon atom of the anthracene skeleton bonded to $R_{922}$, and four carbon atoms is a benzene ring.

The "optional atom" is, unless otherwise specified herein, preferably at least one atom selected from the group consisting of a carbon atom, nitrogen atom, oxygen atom, and sulfur atom. A bond of the optional atom (e.g. a carbon atom and a nitrogen atom) not forming a ring may be terminated by a hydrogen atom or the like or may be substituted by an "optional substituent" described later. When the ring includes an optional element other than carbon atom, the resultant ring is a heterocycle.

The number of "one or more optional atoms" forming the monocyclic ring or fused ring is, unless otherwise specified herein, preferably in a range from 2 to 15, more preferably in a range from 3 to 12, further preferably in a range from 3 to 5.

Unless otherwise specified herein, the ring, which may be a "monocyclic ring" or "fused ring," is preferably a "monocyclic ring."

Unless otherwise specified herein, the ring, which may be a "saturated ring" or "unsaturated ring," is preferably an "unsaturated ring."

Unless otherwise specified herein, the "monocyclic ring" is preferably a benzene ring.

Unless otherwise specified herein, the "unsaturated ring" is preferably a benzene ring.

When "at least one combination of adjacent two or more" (of . . . ) are "mutually bonded to form a substituted or unsubstituted monocyclic ring" or "mutually bonded to form a substituted or unsubstituted fused ring," unless otherwise specified herein, at least one combination of adjacent two or more of components are preferably mutually bonded to form a substituted or unsubstituted "unsaturated ring" formed of a plurality of atoms of the basic skeleton, and 1 to 15 atoms of at least one element selected from the group consisting of carbon, nitrogen, oxygen and sulfur.

When the "monocyclic ring" or the "fused ring" has a substituent, the substituent is the substituent described in later-described "optional substituent." When the "monocyclic ring" or the "fused ring" has a substituent, specific examples of the substituent are the substituents described in the above under the subtitle "Substituent Mentioned Herein."

When the "saturated ring" or the "unsaturated ring" has a substituent, the substituent is the substituent described in later-described "optional substituent." When the "monocyclic ring" or the "fused ring" has a substituent, specific examples of the substituent are the substituents described in the above under the subtitle "Substituent Mentioned Herein."

The above is the description for the instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (sometimes referred to as an instance of "bonded to form a ring").

Substituent for Substituted or Unsubstituted Group

In an exemplary embodiment herein, a substituent for the substituted or unsubstituted group (sometimes referred to as an "optional substituent" hereinafter) is, for instance, a group selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, an unsubstituted aryl group having 6 to 50 ring carbon atoms and an unsubstituted heterocyclic group having 5 to 50 ring atoms;

$R_{901}$ to $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when two or more $R_{901}$ are present, the two or more $R_{901}$ are mutually the same or different;

when two or more $R_{902}$ are present, the two or more $R_{902}$ are mutually the same or different;

when two or more $R_{903}$ are present, the two or more $R_{903}$ are mutually the same or different;

when two or more $R_{904}$ are present, the two or more $R_{904}$ are mutually the same or different;

when two or more $R_{905}$ are present, the two or more $R_{905}$ are mutually the same or different;

when two or more $R_{906}$ are present, the two or more $R_{906}$ are mutually the same or different; and when two or more $R_{907}$ are present, the two or more $R_{907}$ are mutually the same or different.

In an exemplary embodiment, a substituent for the substituted or unsubstituted group is selected from the group consisting of an alkyl group having 1 to 50 carbon atoms, an aryl group having 6 to 50 ring carbon atoms, and a heterocyclic group having 5 to 50 ring atoms.

In an exemplary embodiment, a substituent for the substituted or unsubstituted group is selected from the group consisting of an alkyl group having 1 to 18 carbon atoms, an aryl group having 6 to 18 ring carbon atoms, and a heterocyclic group having 5 to 18 ring atoms.

Specific examples of the above optional substituent are the same as the specific examples of the substituent described in the above under the subtitle "Substituent Mentioned Herein."

Unless otherwise specified herein, adjacent ones of the optional substituents may form a "saturated ring" or an "unsaturated ring," preferably a substituted or unsubstituted saturated five-membered ring, a substituted or unsubstituted saturated six-membered ring, a substituted or unsubstituted unsaturated five-membered ring, or a substituted or unsubstituted unsaturated six-membered ring, more preferably a benzene ring.

Unless otherwise specified herein, the optional substituent may further include a substituent. Examples of the substituent for the optional substituent are the same as the examples of the optional substituent.

Herein, numerical ranges represented by "AA to BB" represent a range whose lower limit is the value (AA) recited before "to" and whose upper limit is the value (BB) recited after "to."

First Exemplary Embodiment

Compound

A compound according to a first exemplary embodiment is a compound represented by a formula (1) below and having at least one deuterium atom.

[Formula 24]

(1)

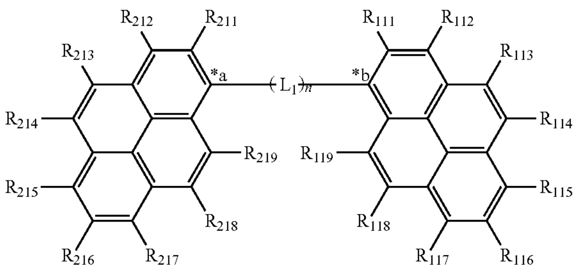

In the formula (1): n is 1, 2, 3, or 4, a plurality of $L_1$ being mutually the same or different when n is 2, 3, or 4;

$L_1$ is a divalent group derived by removing one hydrogen atom from a group selected from the group consisting of a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted chrysenyl group, a substituted or unsubstituted triphenylenyl group, a substituted or unsubstituted fluorenyl group, a substituted or unsubstituted 9,9'-spirobifluorenyl group, a substituted or unsubstituted 9,9-dimethylfluorenyl group, and a substituted or unsubstituted 9,9-diphenylfluorenyl group, or a group represented by a formula (11) below;

$R_{111}$ to $R_{119}$ and $R_{211}$ to $R_{219}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms; and the compound represented by the formula (1) does not include a group represented by $-N(R_{906})(R_{907})$, and $R_{906}$ and $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

[Formula 25]

(11)

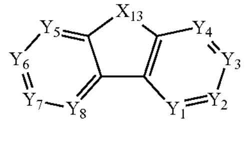

In the formula (11): $X_{13}$ is an oxygen atom or a sulfur atom, and $Y_1$ to $Y_8$ are each independently $CR_{300}$ or a nitrogen atom;

a plurality of $R_{300}$ are mutually the same or different;

at least one combination of adjacent two or more of the plurality of $R_{300}$ are mutually bonded to form a substituted or unsubstituted monocyclic ring, mutually bonded to form a substituted or unsubstituted fused ring, or not mutually bonded;

two of $R_{300}$ forming neither the substituted or unsubstituted monocyclic ring nor the substituted or unsubstituted fused ring are respectively a single bond bonded with *a or other $L_1$ in the formula (1) and a single bond bonded with *b or other $L_1$ in the formula (1); and $R_{300}$ forming neither the substituted or unsubstituted monocyclic ring nor the substituted or unsubstituted fused ring and not being the single bond bonded with *a, *b, or other $L_1$ in the formula (1) are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms.

In the compound represented by the formula (1), $R_{901}$, $R_{902}$, $R_{903}$, $R_{904}$, $R_{905}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

The "compound represented by the formula (1) and having at least one deuterium atom" herein means that the hydrogen atoms in the compound (i.e. the compound represented by the formula (1)) are not composed only of protium atoms.

The ratio of the number of the deuterium atoms to the total number of the hydrogen atoms of the compound (the compound represented by the formula (1)) herein is also preferably 10% or more, also preferably 20% or more, also preferably 30% or more, also preferably 40% or more, also preferably 50% or more, also preferably 60% or more, also preferably 70% or more, and also preferably 80% or more.

Confirmation Method for the Presence of Deuterium Atom in Compound and Specifying Method of Bonding Position of Deuterium Atom in Compound The presence of the deuterium atom in the compound is confirmed by mass spectrometry or $^1$H-NMR spectrometry. A bonding position of the deuterium atom in the compound is specified by the $^1$H-NMR spectrometry.

Specifically, mass spectrometry is performed on a target compound. When a molecular weight of the target compound is increased by, for example, one as compared with a related compound in which all the hydrogen atoms in the target compound are replaced by protium atoms, it is determined that the target compound has one deuterium atom. Further, since a signal of a deuterium atom does not appear in $^1$H-NMR spectrometry, the number of deuterium atoms in a molecule is determined by an integral value obtained by performing $^1$H-NMR spectrometry on the target compound. Furthermore, a bonding position of a deuterium atom is determined by conducting $^1$H-NMR spectrometry on the target compound to perform signal assignment.

In the compound according to the present exemplary embodiment, n is preferably 1, 2, or 3.

In the compound according to the present exemplary embodiment, n is preferably 1 or 2.

In the compound of the present exemplary embodiment, $L_1$ is preferably a divalent group derived by removing one hydrogen atom from a group selected from the group consisting of a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted fluorenyl group, a substituted or unsubstituted 9,9-dimethylfluorenyl group, and a substituted or unsubstituted 9,9-diphenylfluorenyl group, or a group represented by the formula (11).

In the compound of the present exemplary embodiment, the group represented by the formula (11) is preferably a group represented by a formula (12) below.

[Formula 26]

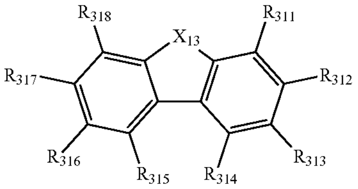

(12)

In the formula (12): $X_{13}$ represents the same as $X_{13}$ in the formula (11);

at least one combination of adjacent two or more of $R_{311}$ to $R_{318}$ are mutually bonded to form a substituted or unsubstituted monocyclic ring, mutually bonded to form a substituted or unsubstituted fused ring, or not mutually bonded;

two of $R_{311}$ to $R_{318}$ forming neither the substituted or unsubstituted monocyclic ring nor the substituted or unsubstituted fused ring are respectively a single bond bonded with *a or other $L_1$ in the formula (1) and a single bond bonded with *b or other $L_1$ in the formula (1); and $R_{311}$ to $R_{318}$ forming neither the substituted or unsubstituted monocyclic ring nor the substituted or unsubstituted fused ring and not being the single bond bonded with *a, *b, or other $L_1$ in the formula (1) each independently represent the same as $R_{300}$ in the formula (11).

It is generally known that a lifetime of a device is increased when a compound is deuterated.

The compound according to the present exemplary embodiment, which is the deuterated compound, has a group linking two pyrene rings in a form of the specific linking group $L_1$ to increase the lifetime of the device. For instance, since a compound represented by the formula (1) and having the linking group $L_1$ in a form of an electron-rich substituent (e.g. carbazolylene group) is likely to be reactive during a film formation for producing the device and thus may provide only limited effect for increasing the lifetime even after deuteration, such a group is excluded from the list of the linking group $L_1$ in the formula (1).

Meanwhile, in order to enhance productivity when the organic EL device is manufactured in quantity, an organic layer (e.g. emitting layer) is sometimes formed at a high speed (e.g. vapor-deposition rate of 20 Å/s). For instance, it is more expectable that the effect for increasing the lifetime by deuteration can be achieved during the high-speed film formation of the emitting layer with the use of the linking group $L_1$ in the formula (1) in a form of a non-electron-rich substituent (e.g. aryl group), which can prevent the reaction during the film formation.

With the use of the linking group $L_1$ in a form of the group represented by the formula (11) or a group other than a heteroarylene group such as a carbazolylene group, the compound represented by the formula (1) is prevented from being electron-rich and is less reactive during the high-speed film formation, as a result of which it is believed that the device lifetime is more easily improvable.

Accordingly, the linking group $L_1$ is preferably an arylene group. It should be noted that when a compound having a linking group that has, among arylene groups, a small number of ring carbon atoms (i.e. small molecular weight) (e.g. 9,9-dimethylfluorene ring) is used for the high-speed film formation of the emitting layer, the effect for increasing the lifetime by deuteration is more effectively achieved as compared with an instance of using a compound having a linking group with a large number of ring carbon atoms (i.e. large molecular weight) (e.g. benzospirofluorene ring) for the high-speed film formation of the emitting layer.

It is believed that when the linking group is an arylene group having a large number of ring carbon atoms (i.e. with a large molecular weight), the compound represented by the formula (1), which is subjected to an environment more likely to cause thermal decomposition during a high-speed film formation, is easily thermally decomposed to cause decrease in the device lifetime.

In contrast, when the linking group is an arylene group having a small number of ring carbon atoms (i.e. with a small molecular weight), the compound represented by the formula (1) is not easily thermally decomposed even under an environment more likely to cause thermal decomposition during a high-speed film formation, thereby enhancing the device lifetime.

Accordingly, the compound according to the present exemplary embodiment, in which the linking group $L_1$ whose number of ring carbon atoms is small (e.g. a linking group with total number of carbon atoms included in $-(L_1)n-$ of 21 or less) is selected, more effectively achieves the effect for increasing the lifetime by deuteration even in a high-speed film formation.

In the compound of the present exemplary embodiment, in order to more effectively achieve the effect for increasing the lifetime by deuteration even during a high-speed film formation: $L_1$ is preferably a divalent group derived by removing one hydrogen atom from a group selected from the group consisting of a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted chrysenyl group, a substituted or unsubstituted triphenylenyl group, a substituted or unsubstituted fluorenyl group, a substituted or unsubstituted 9,9'-spirobifluorenyl group, a substituted or unsubstituted 9,9-dimethylfluorenyl group, and a substituted or unsubstituted 9,9-diphenylfluorenyl group.

In the compound of the present exemplary embodiment, in order to more effectively achieve the effect for increasing the lifetime by deuteration even during a high-speed film formation: $L_1$ is more preferably a divalent group derived by removing one hydrogen atom from a group selected from the group consisting of a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted chrysenyl group, a substituted or unsubstituted triphenylenyl group, and a substituted or unsubstituted 9,9-dialkylfluorenyl group.

In the compound of the present exemplary embodiment, in order to more effectively achieve the effect for increasing the lifetime by deuteration even during a high-speed film formation, $L_1$ is further preferably a divalent group derived by removing one hydrogen atom from a group selected from the group consisting of a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted chrysenyl group, a substituted or unsubstituted triphenylenyl group, and a substituted or unsubstituted 9,9-dimethylfluorenyl group.

In the compound of the present exemplary embodiment, in order to more effectively achieve the effect for increasing the lifetime by deuteration even during a high-speed film formation, $L_1$ is further preferably a divalent group derived by removing one hydrogen atom from a group selected from the group consisting of a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted chrysenyl group, and a substituted or unsubstituted 9,9-dimethylfluorenyl group.

In the compound of the present exemplary embodiment, in order to more effectively achieve the effect for increasing the lifetime by deuteration even in a high-speed film formation, a total number of the carbon atoms included in $-(L_1)n-$ is more preferably 21 or less, further preferably 13 or less.

With the total number of the carbon atoms included in $-(L_1)n-$ being 21 or less, the effect for increasing the lifetime by deuteration can be more effectively achieved in mass production of organic EL device, for instance, even when vapor-deposition rate is increased in forming the emitting layer with the use of the compound represented by the formula (1) as compared with the use of a compound having a linking group with a large number of ring carbon atoms (i.e. with a large molecular weight) (e.g. benzospirofluorene ring) between two pyrene rings. The compound to be used for forming an organic layer (e.g. emitting layer) at a high speed is subjected to an environment more likely to cause thermal decomposition. Accordingly, it is assumed that the compound having, between two pyrene rings, a linking group having a large number of ring carbon atoms (i.e. with a large molecular weight) is likely to be thermally decomposed during a high-speed film formation, which results in decrease in the device lifetime.

In the compound of the present exemplary embodiment, the total number of the carbon atoms included in $R_{111}$ to $R_{119}$ and $R_{211}$ to $R_{219}$ is also preferably 21 or less.

In the compound of the present exemplary embodiment, the total number of the carbon atoms included in $R_{111}$ to $R_{119}$, $R_{211}$ to $R_{219}$, and $-(L_1)n-$ is also preferably 21 or less, and also preferably 13 or less.

In the compound of the present exemplary embodiment, $L_1$ is preferably a group represented by any one of formulae (L-1) to (L-18) below.

[Formula 27]

(L-1)

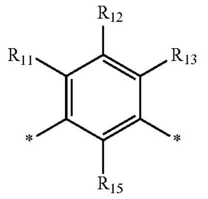

(L-2)

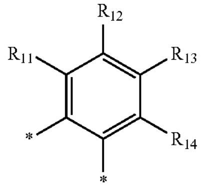

(L-3)

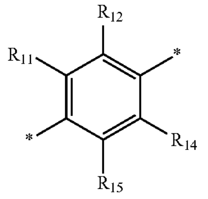

(L-4)

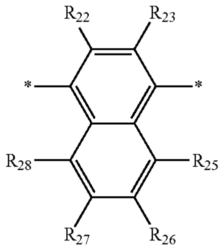

-continued (L-5)

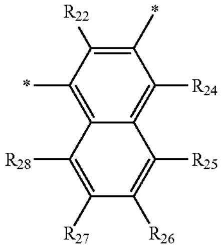

(L-6)

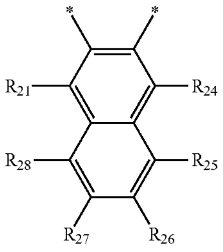

(L-7)

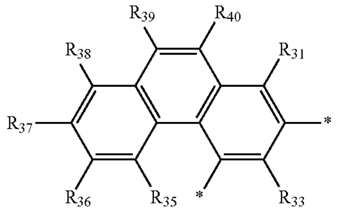

(L-8)

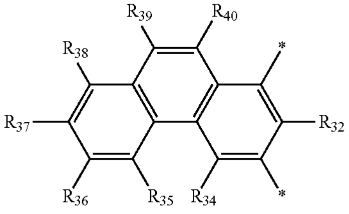

[Formula 28]

(L-9)

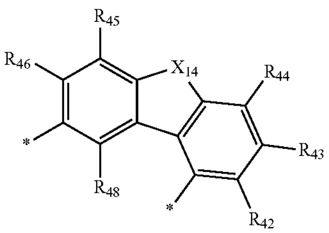

(L-10)

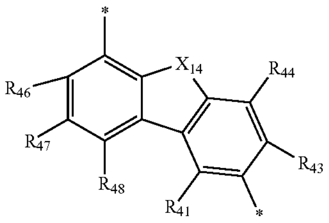

-continued (L-11)

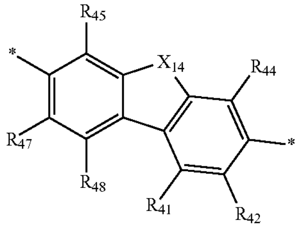

(L-12)

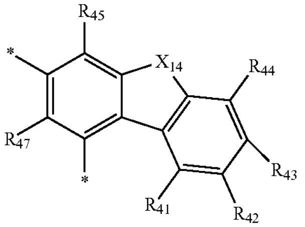

(L-13)

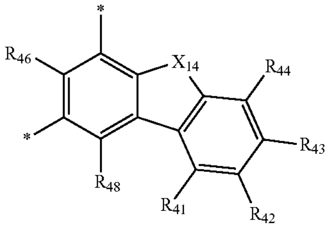

(L-14)

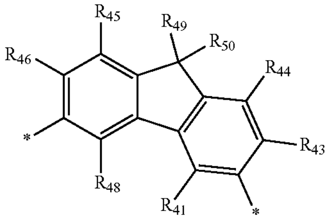

(L-15)

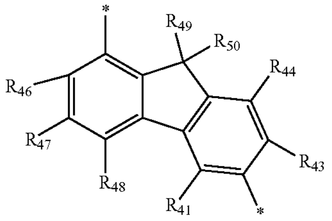

(L-16)

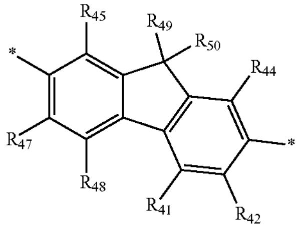

(L-17)

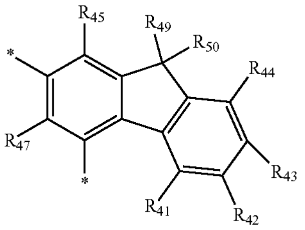

-continued (L-18)

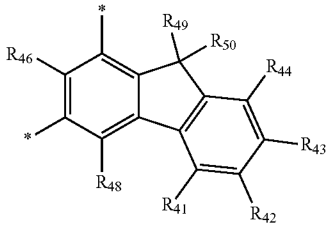

In the formulae (L-1) to (L-18): $X_{14}$ is an oxygen atom or a sulfur atom;

at least one combination of adjacent two or more of $R_{11}$ to $R_{15}$ are mutually bonded to form a substituted or unsubstituted monocyclic ring, mutually bonded to form a substituted or unsubstituted fused ring, or not mutually bonded;

at least one combination of adjacent two or more of $R_{21}$ to $R_{28}$ are mutually bonded to form a substituted or unsubstituted monocyclic ring, mutually bonded to form a substituted or unsubstituted fused ring, or not mutually bonded;

at least one combination of adjacent two or more of $R_{31}$ to $R_{40}$ are mutually bonded to form a substituted or unsubstituted monocyclic ring, mutually bonded to form a substituted or unsubstituted fused ring, or not mutually bonded;

at least one combination of adjacent two or more of $R_{41}$ to $R_{48}$ are mutually bonded to form a substituted or unsubstituted monocyclic ring, mutually bonded to form a substituted or unsubstituted fused ring, or not mutually bonded;

two of $R_{11}$ to $R_{15}$ forming neither the substituted or unsubstituted monocyclic ring nor the substituted or unsubstituted fused ring are respectively a single bond bonded with *a or other $L_1$ in the formula (1) and a single bond bonded with *b or other $L_1$ in the formula (1);

two of $R_{21}$ to $R_{28}$ forming neither the substituted or unsubstituted monocyclic ring nor the substituted or unsubstituted fused ring are respectively a single bond bonded with *a or other $L_1$ in the formula (1) and a single bond bonded with *b or other $L_1$ in the formula (1);

two of $R_{31}$ to $R_{40}$ forming neither the substituted or unsubstituted monocyclic ring nor the substituted or unsubstituted fused ring are respectively a single bond bonded with *a or other $L_1$ in the formula (1) and a single bond bonded with *b or other $L_1$ in the formula (1);

two of $R_{41}$ to $R_{50}$ forming neither the substituted or unsubstituted monocyclic ring nor the substituted or unsubstituted fused ring are respectively a single bond bonded with *a or other $L_1$ in the formula (1) and a single bond bonded with *b or other $L_1$ in the formula (1); and $R_{11}$ to $R_{15}$, $R_{21}$ to $R_{28}$, $R_{31}$ to $R_{40}$, and $R_{41}$ to $R_{50}$ forming neither the substituted or unsubstituted monocyclic ring nor the substituted or unsubstituted fused ring and not being the single bond bonded with *a, *b, or other $L_1$ in the formula (1) each independently represent the same as $R_{300}$ in the formula (11).

In the compound of the present exemplary embodiment, it is preferable that: when n is 1, $-(L_1)n-$ is a group selected from the group consisting of groups represented by the formulae (L-1) to (L-18); when n is 2, -($L_1$)n- is a group formed of mutually bonded two groups selected from the group consisting of groups represented by the formulae (L-1) to (L-18); and when n is 3, -($L_1$)n- is a group formed of mutually bonded three groups selected from the group consisting of groups represented by the formulae (L-1) to (L-18).

In the formulae (L-14) to (L-18), it is preferable that at least one combination of adjacent two or more of $R_{41}$ to $R_{48}$ forms neither a substituted or unsubstituted monocyclic ring nor a substituted or unsubstituted fused ring.

In the compound of the present exemplary embodiment, in order to more effectively achieve the effect for increasing the lifetime by deuteration even in a high-speed film formation: when n is 1, -($L_1$)n- is preferably a group selected from the group consisting of groups represented by the formulae (L-1) to (L-8) and (L-14) to (L-18); when n is 2, -($L_1$)n- is preferably a group formed of mutually bonded two groups selected from the group consisting of groups represented by the formulae (L-1) to (L-8) and (L-14) to (L-18); and when n is 3, -($L_1$)n- is preferably a group formed of mutually bonded three groups selected from the group consisting of groups represented by the formulae (L-1) to (L-8) and (L-14) to (L-18).

In the compound of the present exemplary embodiment, in order to more effectively achieve the effect for increasing the lifetime by deuteration even during a high-speed film formation: it is more preferable that $L_1$ is a divalent group derived by removing one hydrogen atom from a group selected from the group consisting of a substituted or unsubstituted phenyl group, substituted or unsubstituted biphenyl group, substituted or unsubstituted terphenyl group, substituted or unsubstituted naphthyl group, substituted or unsubstituted phenanthryl group, substituted or unsubstituted chrysenyl group, substituted or unsubstituted triphenylenyl group, group represented by the formula (L-14), group represented by the formula (L-15), group represented by the formula (L-16), group represented by the formula (L-17), and group represented by the formula (L-18); and a total number of the carbon atoms included in -($L_1$)n- is 21 or less.

It is further preferable that $L_1$ is a divalent group derived by removing one hydrogen atom from a group selected from the group consisting of a substituted or unsubstituted phenyl group, substituted or unsubstituted biphenyl group, substituted or unsubstituted terphenyl group, substituted or unsubstituted naphthyl group, substituted or unsubstituted phenanthryl group, substituted or unsubstituted chrysenyl group, group represented by the formula (L-14), group represented by the formula (L-15), group represented by the formula (L-16), group represented by the formula (L-17), and group represented by the formula (L-18); and a total number of the carbon atoms included in -($L_1$)n- is 21 or less.

In this arrangement, when $L_1$ is a divalent group derived by removing one hydrogen atom from a group selected from the group consisting of a group represented by the formula (L-14), group represented by the formula (L-15), group represented by the formula (L-16), group represented by the formula (L-17), and group represented by the formula (L-18): it is preferable that in the formulae (L-14) to (L-18), $R_{49}$ and $R_{50}$ are each independently a hydrogen atom or a substituted or unsubstituted alkyl group having 1 to 6 carbon atoms; $R_{41}$ to $R_{48}$ are each independently a hydrogen atom, or a substituted or unsubstituted alkyl group; $R_{41}$ to $R_{48}$ are each independently a hydrogen atom, a substituted or unsubstituted alkyl group, a substituted or unsubstituted haloalkyl group, a substituted or unsubstituted alkenyl group, a substituted or unsubstituted alkynyl group, a substituted or unsubstituted cycloalkyl group, a group represented by —Si($R_{901}$)($R_{902}$)($R_{903}$), a group represented by —O—($R_{904}$), a group represented by —S—($R_{905}$), a substituted or unsubstituted aralkyl group, a group represented by —C(═O)$R_{801}$, a group represented by —COO$R_{802}$, a halogen atom, a cyano group, a nitro group, a substituted or unsubstituted aryl group, or a substituted or unsubstituted heterocyclic group; and $R_{901}$, $R_{902}$, $R_{903}$, $R_{904}$, $R_{905}$, $R_{801}$ and $R_{802}$ are each independently a hydrogen atom, a substituted or unsubstituted alkyl group, a substituted or unsubstituted cycloalkyl group, a substituted or unsubstituted aryl group, or a substituted or unsubstituted heterocyclic group.

In the compound of the present exemplary embodiment, it is preferable that $L_1$ includes at least one deuterium atom.

In the compound of the present exemplary embodiment, at least one of $R_{11}$ to $R_{15}$, $R_{21}$ to $R_{28}$, $R_{31}$ to $R_{40}$, or $R_{41}$ to $R_{50}$ is preferably a deuterium atom.

In the compound of the present exemplary embodiment, it is preferable that at least one of $R_{11}$ to $R_{15}$, $R_{21}$ to $R_{28}$, $R_{31}$ to $R_{40}$, or $R_{41}$ to $R_{50}$ is a substituent, and at least one of $R_{11}$ to $R_{15}$, $R_{21}$ to $R_{28}$, $R_{31}$ to $R_{40}$, or $R_{41}$ to $R_{50}$ as the substituent each independently includes one or more deuterium atom(s).

In the compound of the present exemplary embodiment, it is preferable that -($L_1$)n- is a group represented by any one of formulae ($L_n$-1) to ($L_n$-18) below.

[Formula 29]

($L_n$-1)

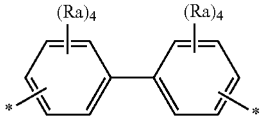

($L_n$-2)

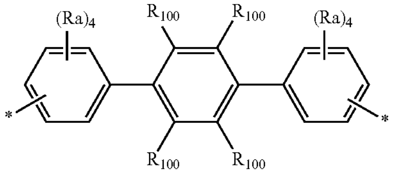

($L_n$-3)

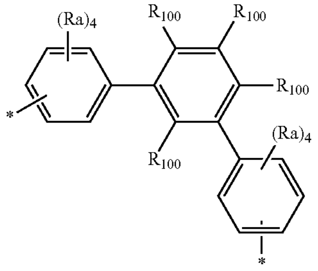

($L_n$-4)

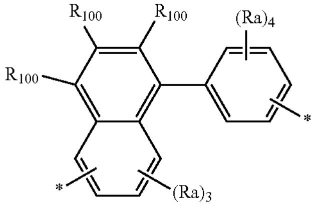

-continued
(L$_n$-5)
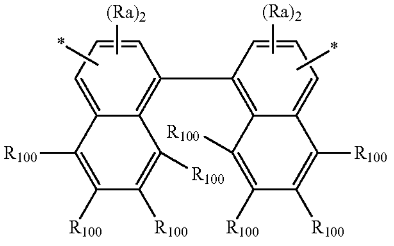
(L$_n$-6)
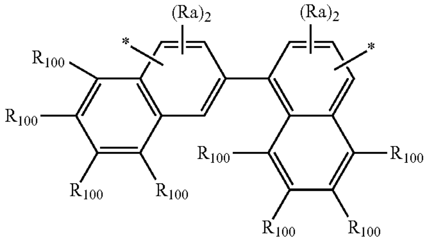
(L$_n$-7)
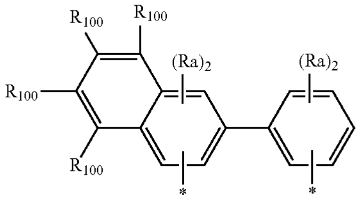
(L$_n$-8)
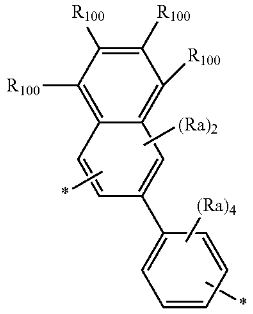
[Formula 30]
(L$_n$-9)
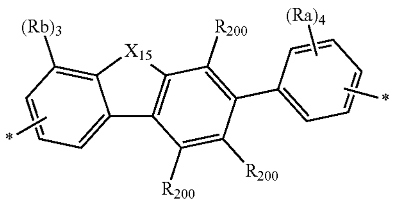
(L$_n$-10)
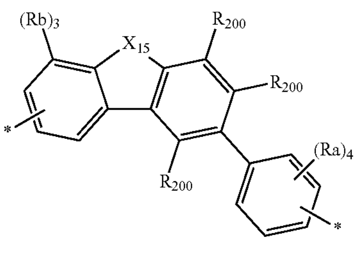
-continued
(L$_n$-11)
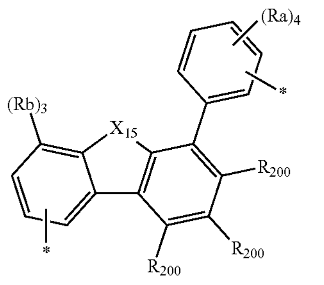
(L$_n$-12)
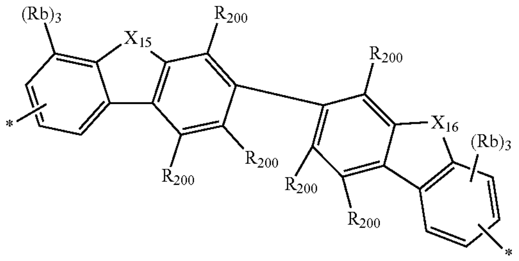
(L$_n$-13)
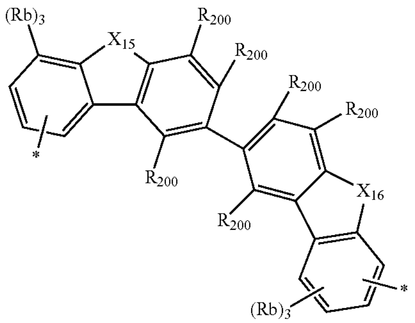
(L$_n$-14)
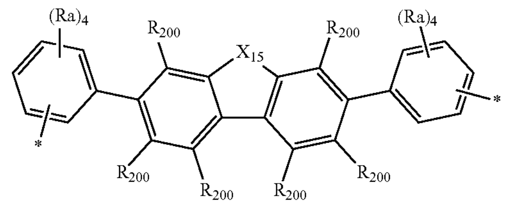
(L$_n$-15)
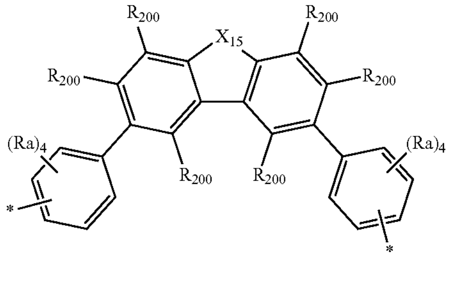

-continued

[Formula 31]

($L_n$-16)

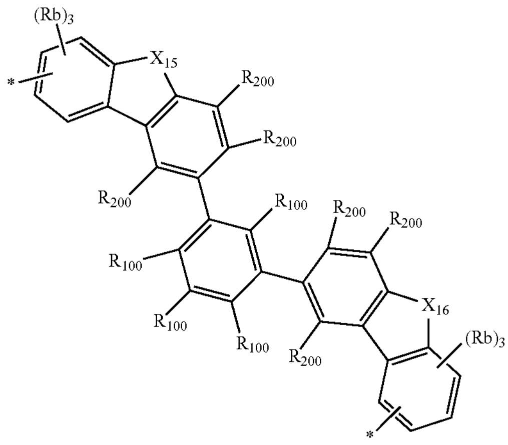

($L_n$-17)

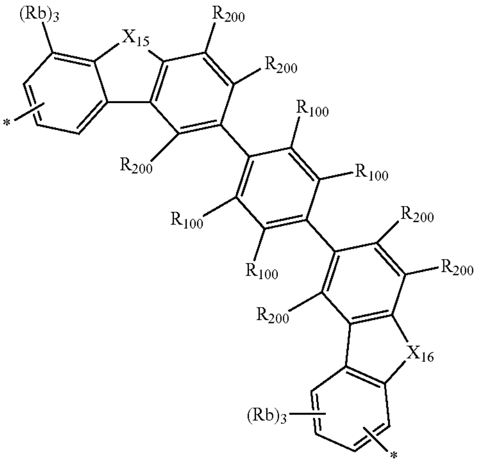

($L_n$-18)

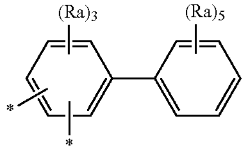

In the formulae ($L_n$-1) to ($L_n$-18): $X_{15}$ and $X_{16}$ are each independently an oxygen atom, a sulfur atom or $CR_{15A}R_{16A}$;

at least one combination of adjacent two or more of a plurality of Ra are mutually bonded to form a substituted or unsubstituted monocyclic ring, mutually bonded to form a substituted or unsubstituted fused ring, or not mutually bonded;

at least one combination of adjacent two or more of a plurality of Rb are mutually bonded to form a substituted or unsubstituted monocyclic ring, mutually bonded to form a substituted or unsubstituted fused ring, or not mutually bonded;

at least one combination of adjacent two or more of a plurality of $R_{100}$ are mutually bonded to form a substituted or unsubstituted monocyclic ring, mutually bonded to form a substituted or unsubstituted fused ring, or not mutually bonded;

at least one combination of adjacent two or more of a plurality of $R_{200}$ are mutually bonded to form a substituted or unsubstituted monocyclic ring, mutually bonded to form a substituted or unsubstituted fused ring, or not mutually bonded;

the plurality of Ra are mutually the same or different;

the plurality of Rb are mutually the same or different;

the plurality of $R_{100}$ are mutually the same or different;

the plurality of $R_{200}$ are mutually the same or different;

Ra, Rb, $R_{100}$ and $R_{200}$ forming neither the substituted or unsubstituted monocyclic ring nor the substituted or unsubstituted fused ring, $R_{15A}$ and $R_{16A}$ each independently represent the same as $R_{300}$ in the formula (11); and one of two * in the formulae ($L_n$-1) to ($L_n$-18) represents a bonding position with *a in the formula (1) and the other * represents a bonding position with *b in the formula (1).

In the compound of the present exemplary embodiment, in order to more effectively achieve the effect for increasing the lifetime by deuteration even in a high-speed film formation, -($L_1$)n- is preferably a group selected from the group consisting of groups represented by the formulae ($L_n$-1) to ($L_n$-8) and ($L_n$-18).

In the compound of the present exemplary embodiment, in order to more effectively achieve the effect for increasing the lifetime by deuteration even in a high-speed film formation, when -($L_1$)n- is a group selected from the group consisting of groups represented by the formulae ($L_n$-9) to ($L_n$-17), the groups represented by the formulae ($L_n$-9) to ($L_n$-17) more preferably each include neither a divalent group derived by removing one hydrogen atom from a substituted or unsubstituted 9,9'-spirobifluorenyl group nor a divalent group derived by removing one hydrogen atom from a substituted or unsubstituted 9,9-diphenylfluorenyl group.

In the compound of the present exemplary embodiment, at least one of the plurality of Ra, the plurality of Rb, the plurality of $R_{100}$, the plurality of $R_{200}$, $R_{15A}$, or $R_{16A}$ is preferably a deuterium atom.

In the compound of the present exemplary embodiment, it is preferable that at least one of the plurality of Ra, the plurality of Rb, the plurality of $R_{100}$, the plurality of $R_{200}$, $R_{15A}$, or $R_{16A}$ is a substituent and at least one of Ra, Rb, $R_{100}$, $R_{200}$, $R_{15A}$, or $R_{16A}$ as a substituent each independently includes at least one deuterium atom.

In the compound of the present exemplary embodiment, $R_{111}$ to $R_{119}$, $R_{211}$ to $R_{219}$, $R_{300}$, $R_{901}$, $R_{902}$, $R_{903}$, $R_{904}$, $R_{905}$, $R_{801}$, and $R_{802}$ are preferably each independently a hydrogen atom, a substituted or unsubstituted alkyl group having 1 to 30 carbon atoms, a substituted or unsubstituted aryl group having 6 to 30 ring carbon atoms, or a substituted or unsubstituted heterocyclic group having 5 to 30 ring atoms.

In the compound of the present exemplary embodiment, $R_{111}$ to $R_{119}$, $R_{211}$ to $R_{219}$, $R_{300}$, $R_{901}$, $R_{902}$, $R_{903}$, $R_{904}$, $R_{905}$, $R_{801}$, and $R_{802}$ are preferably each independently a hydrogen atom, a substituted or unsubstituted alkyl group having 1 to 18 carbon atoms, a substituted or unsubstituted phenyl group, a substituted or unsubstituted biphenyl group, a substituted or unsubstituted terphenyl group, a substituted or unsubstituted naphthyl group, a substituted or unsubstituted anthryl group, a substituted or unsubstituted phenanthryl group, a substituted or unsubstituted fluorenyl group, a substituted or unsubstituted 9,9-dimethylfluorenyl group, a substituted or unsubstituted 9,9-diphenylfluorenyl group, a substituted or unsubstituted dibenzofuranyl group, a substituted or unsubstituted naphthobenzofuranyl group, a substituted or unsubstituted dibenzothiophenyl group, or a substituted or unsubstituted naphthobenzothiophenyl group.

In the compound of the present exemplary embodiment, $R_{111}$ to $R_{119}$, $R_{211}$ to $R_{219}$, $R_{300}$, $R_{901}$, $R_{902}$, $R_{903}$, $R_{904}$, $R_{905}$, $R_{801}$, and $R_{802}$ are more preferably each independently a hydrogen atom, an unsubstituted alkyl group having 1 to 18 carbon atoms, an unsubstituted phenyl group, an unsubstituted biphenyl group, an unsubstituted terphenyl group, an unsubstituted naphthyl group, an unsubstituted anthryl group, an unsubstituted phenanthryl group, a substituted or unsubstituted fluorenyl group, an unsubstituted 9,9-dimethylfluorenyl group, an unsubstituted 9,9-diphenylfluorenyl group, an unsubstituted dibenzofuranyl group, an unsubstituted naphthobenzofuranyl group, an unsubstituted dibenzothiophenyl group, or an unsubstituted naphthobenzothiophenyl group.

In the compound according to the present exemplary embodiment, it is preferable that $R_{111}$ to $R_{119}$ and $R_{211}$ to $R_{219}$ are each independently a hydrogen atom, a substituted or unsubstituted alkyl group having 1 to 30 carbon atoms, a substituted or unsubstituted cycloalkyl group having 1 to 30 carbon atoms, a group represented by —Si($R_{901}$)($R_{902}$)($R_{903}$), a substituted or unsubstituted aryl group having 6 to 30 ring carbon atoms, or a substituted or unsubstituted heterocyclic group having 5 to 30 ring atoms; and $R_{901}$, $R_{902}$, and $R_{903}$ in the group represented by —Si($R_{901}$)($R_{902}$)($R_{903}$) are each independently a substituted or unsubstituted alkyl group having 1 to 30 carbon atoms or a substituted or unsubstituted aryl group having 6 to 30 ring carbon atoms.

In the compound according to the present exemplary embodiment, it is more preferable that $R_{111}$ to $R_{119}$ and $R_{211}$ to $R_{219}$ are each independently a hydrogen atom, a substituted or unsubstituted alkyl group having 1 to 18 carbon atoms, a substituted or unsubstituted cycloalkyl group having 1 to 18 carbon atoms, a group represented by —Si($R_{901}$)($R_{902}$)($R_{903}$), a substituted or unsubstituted aryl group having 6 to 18 ring carbon atoms, or a substituted or unsubstituted heterocyclic group having 5 to 18 ring atoms; and $R_{901}$, $R_{902}$, and $R_{903}$ in the group represented by —Si($R_{901}$)($R_{902}$)($R_{903}$) are each independently an unsubstituted alkyl group having 1 to 18 carbon atoms or an unsubstituted aryl group having 6 to 18 ring carbon atoms.

In the compound of the present exemplary embodiment, at least one of $R_{111}$ to $R_{119}$, $R_{211}$ to $R_{219}$, $R_{300}$, $R_{901}$, $R_{902}$, $R_{903}$, $R_{904}$, $R_{905}$, $R_{801}$, or $R_{802}$ is preferably a deuterium atom.

In the compound of the present exemplary embodiment, it is preferable that $R_{111}$ to $R_{119}$ are deuterium atoms or $R_{211}$ to $R_{219}$ are deuterium atoms.

In the compound of the present exemplary embodiment, $R_{111}$ to $R_{119}$ and $R_{211}$ to $R_{219}$ are preferably deuterium atoms.

In the compound of the present exemplary embodiment, it is preferable that at least one of $R_{111}$ to $R_{119}$, $R_{211}$ to $R_{219}$, $R_{300}$, $R_{901}$, $R_{902}$, $R_{903}$, $R_{904}$, $R_{905}$, $R_{801}$, or $R_{802}$ is a substituent and at least one of $R_{111}$ to $R_{119}$, $R_{211}$ to $R_{219}$, $R_{300}$, $R_{901}$, $R_{902}$, $R_{903}$, $R_{904}$, $R_{905}$, $R_{801}$, or $R_{802}$ as the substituent each independently includes one or more deuterium atom(s).

In the compound of the present exemplary embodiment, a substituent for "substituted or unsubstituted" group in $L_1$, $R_{111}$ to $R_{119}$, $R_{211}$ to $R_{219}$, $R_{300}$, $R_{311}$ to $R_{318}$, $R_{901}$, $R_{902}$, $R_{903}$, $R_{904}$, $R_{905}$, $R_{801}$ and $R_{802}$ is preferably each independently a substituted or unsubstituted alkyl group having 1 to 50 carbon atoms, a substituted or unsubstituted phenyl group, a substituted or unsubstituted biphenyl group, a substituted or unsubstituted terphenyl group, a substituted or unsubstituted naphthyl group, a substituted or unsubstituted anthryl group, a substituted or unsubstituted phenanthryl group, a substituted or unsubstituted chrysenyl group, a substituted or unsubstituted triphenylenyl group, a substituted or unsubstituted fluorenyl group, a substituted or unsubstituted 9,9'-spirobifluorenyl group, a substituted or unsubstituted 9,9-dimethylfluorenyl group, a substituted or unsubstituted 9,9-diphenylfluorenyl group, a substituted or unsubstituted pyridyl group, a substituted or unsubstituted pyrimidinyl group, a substituted or unsubstituted triazinyl group, a substituted or unsubstituted quinolyl group, a substituted or unsubstituted isoquinolyl group, a substituted or unsubstituted quinazolinyl group, a substituted or unsubstituted benzimidazolyl group, a substituted or unsubstituted phenanthrolinyl group, a substituted or unsubstituted 1-carbazolyl group, a substituted or unsubstituted 2-carbazolyl group, a substituted or unsubstituted 3-carbazolyl group, a substituted or unsubstituted 4-carbazolyl group, a substituted or unsubstituted 9-carbazolyl group, a substituted or unsubstituted benzocarbazolyl group, a substituted or unsubstituted azacarbazolyl group, a substituted or unsubstituted diazacarbazolyl group, a substituted or unsubstituted dibenzofuranyl group, a substituted or unsubstituted naphthobenzofuranyl group, a substituted or unsubstituted azadibenzofuranyl group, a substituted or unsubstituted diazadibenzofuranyl group, a substituted or unsubstituted dibenzothiophenyl group, a substituted or unsubstituted naphthobenzothiophenyl group, a substituted or unsubstituted azadibenzothiophenyl group, or a substituted or unsubstituted diazadibenzothiophenyl group.

In the compound of the present exemplary embodiment, a substituent for "substituted or unsubstituted" group in $L_1$, $R_{111}$ to $R_{119}$, $R_{211}$ to $R_{219}$, $R_{300}$, $R_{311}$ to $R_{318}$, $R_{901}$, $R_{902}$, $R_{903}$, $R_{904}$, $R_{905}$, $R_{801}$, and $R_{802}$ is more preferably each independently a substituted or unsubstituted alkyl group having 1 to 18 carbon atoms, a substituted or unsubstituted phenyl group, a substituted or unsubstituted naphthyl group, a substituted or unsubstituted phenanthrolinyl group, a substituted or unsubstituted fluorenyl group, a substituted or unsubstituted dibenzofuranyl group, a substituted or unsubstituted dibenzothiophenyl group, a substituted or unsubstituted 9,9-dimethylfluorenyl group, or a substituted or unsubstituted 9,9-diphenylfluorenyl group.

In the compound of the present exemplary embodiment, all substituents for "substituted or unsubstituted" groups in $L_1$, $R_{111}$ to $R_{119}$, $R_{211}$ to $R_{219}$, $R_{300}$, $R_{311}$ to $R_{318}$, $R_{901}$, $R_{902}$, $R_{903}$, $R_{904}$, $R_{905}$, $R_{801}$, and $R_{802}$ are preferably "unsubstituted" groups.

In the compound of the present exemplary embodiment, a substituent for "substituted or unsubstituted" group in $L_1$, $R_{111}$ to $R_{119}$, $R_{211}$ to $R_{219}$, $R_{300}$, $R_{311}$ to $R_{318}$, $R_{901}$, $R_{902}$, $R_{903}$, $R_{904}$, $R_{905}$, $R_{801}$, and $R_{802}$ is more preferably each independently an unsubstituted alkyl group having 1 to 18 carbon atoms, an unsubstituted phenyl group, an unsubstituted naphthyl group, an unsubstituted phenanthrolinyl group, a substituted or unsubstituted fluorenyl group, an unsubstituted dibenzofuranyl group, an unsubstituted dibenzothiophenyl group, an unsubstituted 9,9-dimethylfluorenyl group, or an unsubstituted 9,9-diphenylfluorenyl group.

In an exemplary embodiment, the compound represented by the formula (1) and having at least one deuterium atom is also preferably one of compounds of arrangements A to D below.

Compound of Arrangement A

The compound according to the arrangement A is represented by a formula (120-1) below. A compound represented by the formula (120-1) includes at least one deuterium atom.

[Formula 32]

(120-1)

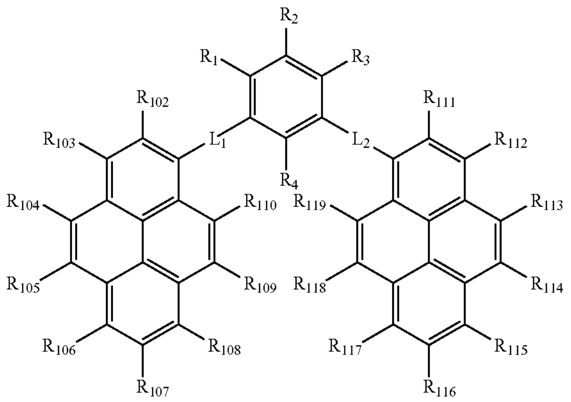

In the formula (120-1):

$R_1$ to $R_4$ are each independently a hydrogen atom, a group represented by a formula (120A) below, a group represented by a formula (120B) below, a group represented by a formula (120C) below, or a group represented by a formula (120D) below;

$R_1$ to $R_4$ are not simultaneously each a hydrogen atom;

$L_1$ and $L_2$ are each independently a single bond, a substituted or unsubstituted arylene group having 6 to 50 ring carbon atoms, or a substituted or unsubstituted divalent heterocyclic group having 5 to 50 ring atoms;

$R_{102}$ to $R_{119}$ are each independently a hydrogen atom, a substituted or unsubstituted alkyl group having 1 to 50 carbon atoms, a substituted or unsubstituted aryl group having 6 to 50 ring carbon atoms, or substituted or unsubstituted heterocyclic group having 5 to 50 ring atoms; and a substituent for "substituted or unsubstituted" group in $L_1$ and $L_2$ is each independently a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

[Formula 33]

(120A)

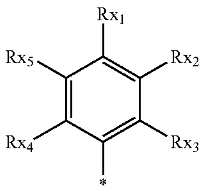

(120B)

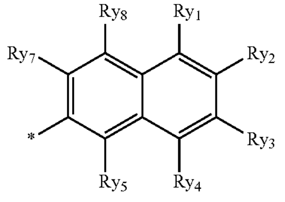

-continued (120C)

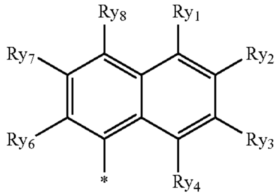

(120D)

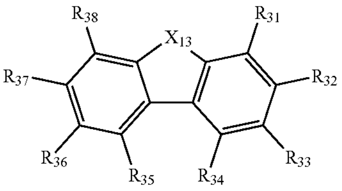

In the formulae (120A) to (120C):

$Rx_1$ to $Rx_5$ and $Ry_1$ to $Ry_8$ are each independently a hydrogen atom, substituted or unsubstituted phenyl group, substituted or unsubstituted biphenyl group, substituted or unsubstituted terphenyl group, substituted or unsubstituted naphthyl group, substituted or unsubstituted phenanthryl group, substituted or unsubstituted chrysenyl group, substituted or unsubstituted triphenylenyl group, substituted or unsubstituted fluorenyl group, substituted or unsubstituted 9,9'-spirobifluorenyl group, substituted or unsubstituted 9,9-dimethylfluorenyl group, substituted or unsubstituted 9,9-diphenylfluorenyl group, substituted or unsubstituted pyridyl group, substituted or unsubstituted pyrimidinyl group, substituted or unsubstituted triazinyl group, substituted or unsubstituted quinolyl group, substituted or unsubstituted isoquinolyl group, substituted or unsubstituted quinazolinyl group, substituted or unsubstituted benzimidazolyl group, substituted or unsubstituted phenanthrolinyl group, substituted or unsubstituted 1-carbazolyl group, substituted or unsubstituted 2-carbazolyl group, substituted or unsubstituted 3-carbazolyl group, substituted or unsubstituted 4-carbazolyl group, substituted or unsubstituted benzocarbazolyl group, substituted or unsubstituted azacarbazolyl group, substituted or unsubstituted diazacarbazolyl group, substituted or unsubstituted dibenzofuranyl group, substituted or unsubstituted naphthobenzofuranyl group, substituted or unsubstituted azadibenzofuranyl group, substituted or unsubstituted diazadibenzofuranyl group, substituted or unsubstituted dibenzothiophenyl group, substituted or unsubstituted naphthobenzothiophenyl group, substituted or unsubstituted azadibenzothiophenyl group, or substituted or unsubstituted diazadibenzothiophenyl group; and at least one of $Rx_1$ to $Rx_5$ is not a hydrogen atom and * in the formulae (120A), (120B), and (120C) represents a bonding position.

In the formula (120D):

$X_{13}$ is an oxygen atom, a sulfur atom, $NR_{39}$, or $CR_{39A}R_{39B}$;

at least one combination of adjacent two or more of $R_{31}$ to $R_{38}$ are mutually bonded to form a substituted or unsubstituted monocyclic ring, mutually bonded to form a substituted or unsubstituted fused ring, or not mutually bonded;

one of $R_{31}$ to $R_{38}$ forming neither the substituted or unsubstituted monocyclic ring nor the substituted or unsubstituted fused ring is a single bond bonded with at least one of $R_1$, $R_2$, $R_3$, or $R_4$;

$R_{31}$ to $R_{39}$ forming neither the substituted or unsubstituted monocyclic ring nor the substituted or unsubstituted fused ring each independently represent the same as $Rx_1$ to $Rx_5$ and $Ry_1$ to $Ry_8$;

a combination of $R_{39A}$ and $R_{39B}$ are mutually bonded to form a substituted or unsubstituted monocyclic ring, mutually bonded to form a substituted or unsubstituted fused ring, or not mutually bonded; and $R_{39A}$ and $R_{39B}$ forming neither the substituted or unsubstituted monocyclic ring nor the substituted or unsubstituted fused ring are each independently a hydrogen atom, substituted or unsubstituted alkyl group having 1 to 50 carbon atoms, substituted or unsubstituted aryl group having 6 to 50 ring carbon atoms, or substituted or unsubstituted heterocyclic group having 5 to 50 ring atoms.

In the compound of the arrangement A, in order to more effectively achieve the effect for increasing the lifetime by deuteration even in a high-speed film formation, a total number of carbon atoms included in the group linking two pyrene rings (i.e. a pyrene ring having $R_{111}$ to $R_{119}$ and a pyrene ring having $R_{102}$ to $R_{110}$) is more preferably 21 or less.

The group linking the two pyrene rings is a group formed of $L_1$, phenylene group having $R_1$ to $R_4$, and $L_2$ in the formula (120-1).

In the compound of the arrangement A, $Rx_1$ to $Rx_5$, $Ry_1$ to $Ry_8$, and $R_{31}$ to $R_{39}$ are preferably each independently a hydrogen atom, substituted or unsubstituted phenyl group, substituted or unsubstituted naphthyl group, substituted or unsubstituted phenanthrolinyl group, substituted or unsubstituted fluorenyl group, substituted or unsubstituted dibenzofuranyl group, substituted or unsubstituted dibenzothiophenyl group, substituted or unsubstituted 9,9-dimethylfluorenyl group, or substituted or unsubstituted 9,9-diphenylfluorenyl group.

In the compound of the arrangement A, at least one of $Rx_1$ to $Rx_5$, $Ry_1$ to $Ry_8$, or $R_{31}$ to $R_{39}$ is preferably a deuterium atom.

In the compound of the arrangement A, it is preferable that at least one combination of adjacent two or more of $R_{31}$ to $R_{38}$ are mutually bonded to form a substituted or unsubstituted monocyclic ring or a substituted or unsubstituted fused ring, and $R_{31}$ to $R_{38}$ forming neither the substituted or unsubstituted monocyclic ring nor the substituted or unsubstituted fused ring are each independently a hydrogen atom, substituted or unsubstituted phenyl group, substituted or unsubstituted naphthyl group, substituted or unsubstituted phenanthrolinyl group, substituted or unsubstituted fluorenyl group, substituted or unsubstituted dibenzofuranyl group, substituted or unsubstituted dibenzothiophenyl group, substituted or unsubstituted 9,9-dimethylfluorenyl group, or substituted or unsubstituted 9,9-diphenylfluorenyl group.

In the compound of the arrangement A, the compound represented by the formula (120-1) is preferably represented by a formula (121), (122), (123), (124), or (125) below.

[Formula 34]

(121)

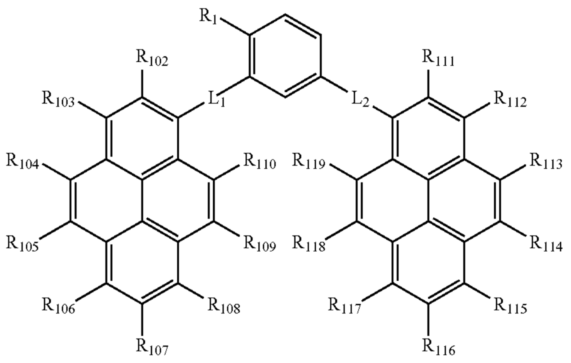

(122)

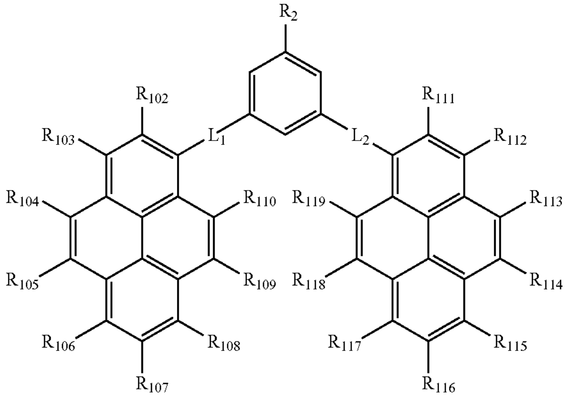

(123)

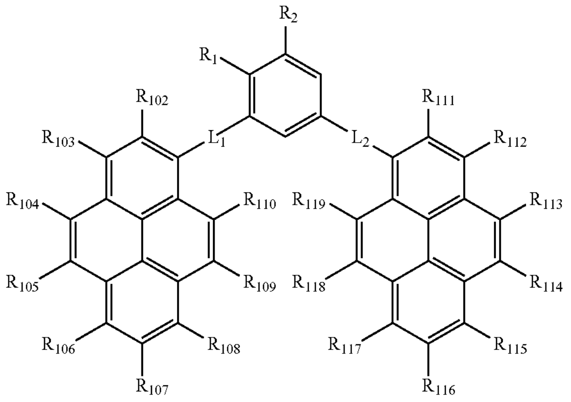

-continued

[Formula 35]

(124)

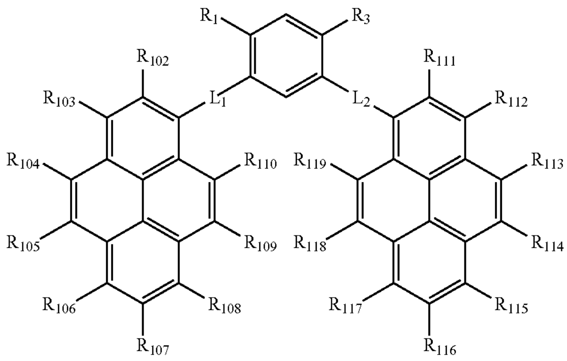

(125)

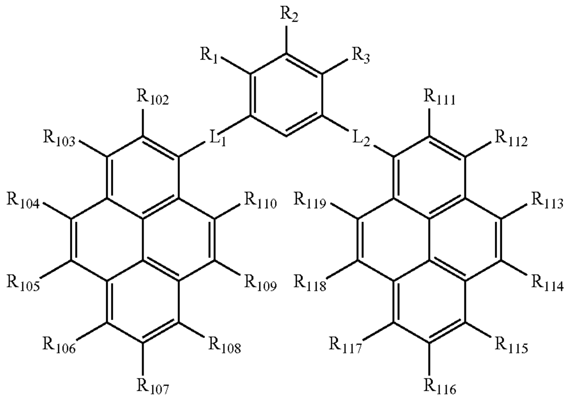

In the formulae (121) to (125): $R_1$ to $R_3$ each independently represent the same as $R_1$ to $R_3$ in the formula (120-1); $R_1$ to $R_3$ are not hydrogen atoms; $L_1$ and $L_2$ each independently represent the same as $L_1$ and $L_2$ in the formula (120-1); and $R_{102}$ to $R_{119}$ each independently represent the same as $R_{102}$ to $R_{119}$ in the formula (120-1).

In the compound of the arrangement A, $L_1$ and $L_2$ are preferably each independently a single bond, substituted or unsubstituted arylene group having 6 to 30 ring carbon atoms, or substituted or unsubstituted divalent heterocyclic group having 5 to 30 ring atoms.

In the compound of the present exemplary embodiment, $L_1$ and $L_2$ are more preferably each independently a single bond, substituted or unsubstituted arylene group having 6 to 18 ring carbon atoms, or substituted or unsubstituted divalent heterocyclic group having 5 to 18 ring atoms.

In the compound of the arrangement A, $L_1$ and $L_2$ are preferably each independently a single bond or a group represented by any one of formulae (141) to (150) below.

[Formula 36]

(141)

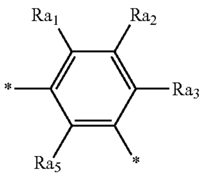

-continued (142)

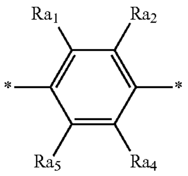

(143)

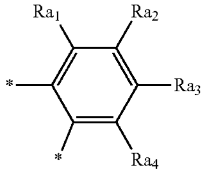

(144)

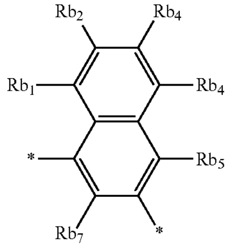

(145)

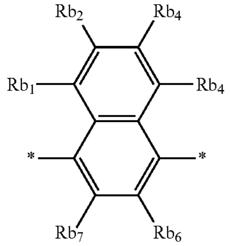

(146)

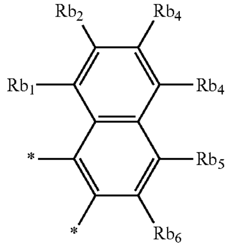

(147)

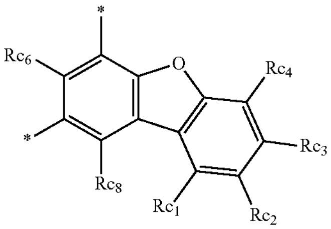

(149)

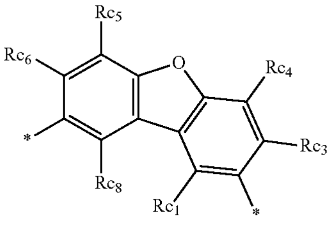

-continued (149)

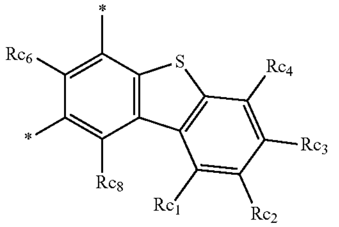

(150)

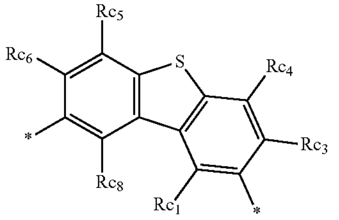

In the formulae (141) to (150), $Ra_1$ to $Ra_5$, $Rb_1$ to $Rb_7$, and $Rc_1$ to $Rc_8$ are each independently a hydrogen atom, substituted or unsubstituted alkyl group having 1 to 50 carbon atoms, substituted or unsubstituted aryl group having 6 to 50 ring carbon atoms, or substituted or unsubstituted heterocyclic group having 5 to 50 ring atoms and * represents a bonding position.

In the compound of the arrangement A, $L_1$ preferably has at least one deuterium atom. $L_2$ preferably has at least one deuterium atom.

In the compound of the arrangement A, it is preferable that at least one of $R_1$ to $R_4$ is a deuterium atom. It is preferable that at least one of $R_1$ to $R_4$ is a substituent and at least one of $R_1$ to $R_4$ as the substituent is each independently one or more deuterium atom(s).

In the formulae (141) to (150), it is preferable that at least one of $Ra_1$ to $Ra_5$, $Rb_1$ to $Rb_7$, or $Rc_1$ to $Rc_8$ is a deuterium atom.

In the formulae (141) to (150), it is preferable that at least one of $Ra_1$ to $Ra_5$, $Rb_1$ to $Rb_7$, or $Rc_1$ to $Rc_8$ is a substituent and at least one of Ra, Rb, $R_{100}$, $R_{200}$, $R_{15A}$, or $R_{16A}$ as the substituent is each independently one or more deuterium atom(s).

In the compound of the arrangement A, $R_{102}$ to $R_{119}$ are preferably each independently a hydrogen atom, a substituted or unsubstituted alkyl group having 1 to 20 carbon atoms, a substituted or unsubstituted aryl group having 6 to 18 ring carbon atoms, or a substituted or unsubstituted heterocyclic group having 5 to 18 ring atoms.

In the compound of the arrangement A, it is preferable that $R_{102}$ to $R_{110}$ are deuterium atoms or $R_{111}$ to $R_{119}$ are deuterium atoms. $R_{102}$ to $R_{119}$ are preferably deuterium atoms. It is preferable that at least one of $R_{102}$ to $R_{119}$ is a substituent and at least one of $R_{102}$ to $R_{119}$ as the substituent is each independently one or more deuterium atom(s).

Compound of Arrangement B

The compound of the arrangement B is a compound represented by a formula (120-2) below. The compound represented by the formula (120-2) below includes at least one deuterium atom.

[Formula 37]

(120-2)

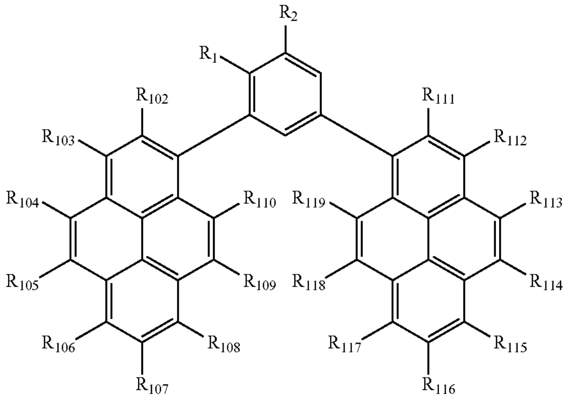

In the formula (120-2):

a combination of $R_1$ and $R_2$ are mutually bonded to form a substituted or unsubstituted monocyclic ring, mutually bonded to form a substituted or unsubstituted fused ring, or not mutually bonded;

the substituted or unsubstituted monocyclic ring formed of mutually bonded combination of $R_1$ and $R_2$ is not a heterocycle and the substituted or unsubstituted fused ring formed of mutually bonded combination of $R_1$ and $R_2$ is not a heterocycle;

$R_1$ forming neither the substituted or unsubstituted monocyclic ring nor the substituted or unsubstituted fused ring is a substituted or unsubstituted alkyl group having 1 to 50 carbon atoms, substituted or unsubstituted heterocyclic group having 5 to 50 ring atoms, substituted or unsubstituted phenyl group, substituted or unsubstituted biphenyl group, substituted or unsubstituted terphenyl group, substituted or unsubstituted naphthyl group, substituted or unsubstituted anthryl group, substituted or unsubstituted phenanthryl group, substituted or unsubstituted chrysenyl group, substituted or unsubstituted triphenylenyl group, substituted or unsubstituted fluorenyl group, substituted or unsubstituted 9,9'-spirobifluorenyl group, substituted or unsubstituted 9,9-dimethylfluorenyl group, or substituted or unsubstituted 9,9-diphenylfluorenyl group;

$R_2$ forming neither the substituted or unsubstituted monocyclic ring nor the substituted or unsubstituted fused ring is a hydrogen atom, substituted or unsubstituted alkyl group having 1 to 50 carbon atoms, substituted or unsubstituted heterocyclic group having 5 to 50 ring atoms, substituted or unsubstituted phenyl group, substituted or unsubstituted biphenyl group, substituted or unsubstituted terphenyl group, substituted or unsubstituted naphthyl group, substituted or unsubstituted anthryl group, substituted or unsubstituted phenanthryl group, substituted or unsubstituted chrysenyl group, substituted or unsubstituted triphenylenyl group, substituted or unsubstituted fluorenyl group, substituted or unsubstituted 9,9'-spirobifluorenyl group, substituted or unsubstituted 9,9-dimethylfluorenyl group, or substituted or unsubstituted 9,9-diphenylfluorenyl group; and $R_{102}$ to $R_{119}$ are each independently a hydrogen atom, substituted or unsubstituted alkyl group having 1 to 50 carbon atoms, substituted or unsubstituted cycloalkyl group having 1 to 50 carbon atoms, group represented by Si(Rx)(Ry)(Rz), substituted or unsubstituted aryl group having 6 to 50 ring carbon atoms, or substituted or unsubstituted heterocyclic group having 5 to 50 ring atoms, Rx, Ry, and Rz in Si(Rx)(Ry)(Rz) being each independently a substituted or unsubstituted alkyl group having 1 to 50 carbon atoms or substituted or unsubstituted aryl group having 6 to 50 ring carbon atoms.

In the compound of the arrangement B, in order to more effectively achieve the effect for increasing the lifetime by deuteration even in a high-speed film formation, a total number of carbon atoms included in the group linking two pyrene rings (i.e. a pyrene ring having $R_{111}$ to $R_{119}$ and a pyrene ring having $R_{102}$ to $R_{110}$) is more preferably 21 or less.

The group linking the two pyrene rings is a phenylene group having $R_1$ to $R_2$ in the formula (120-2).

In the compound of the arrangement B, the combination of $R_1$ and $R_2$ are preferably not mutually bonded.

In the compound of the arrangement B, when the combination of $R_1$ and $R_2$ are not mutually bonded, the compound represented by the formula (120-2) is preferably represented by a formula (121) or (122) below.

[Formula 38]

(121)

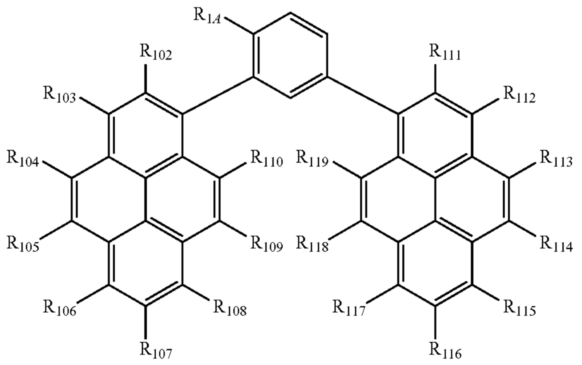

(122)

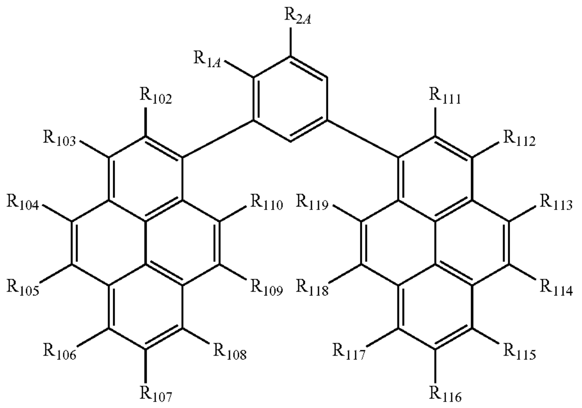

In the formulae (121) and (122), $R_{1A}$ and $R_{2A}$ each independently represent the same as $R_1$ and $R_2$ in the formula (120-2), and $R_{1A}$ and $R_{2A}$ are substituents and $R_{102}$ and $R_{119}$ each independently represent the same as $R_{102}$ to $R_{119}$ in the formula (120-2).

In the compound of the arrangement B, $R_1$ is preferably a substituted or unsubstituted alkyl group having 1 to 18 carbon atoms, substituted or unsubstituted phenyl group, substituted or unsubstituted biphenyl group, substituted or unsubstituted terphenyl group, substituted or unsubstituted naphthyl group, substituted or unsubstituted anthryl group, substituted or unsubstituted phenanthryl group, substituted or unsubstituted chrysenyl group, substituted or unsubstituted triphenylenyl group, substituted or unsubstituted fluorenyl group, substituted or unsubstituted 9,9'-spirobifluorenyl group, substituted or unsubstituted 9,9-dimethylfluorenyl group, substituted or unsubstituted 9,9-diphenylfluorenyl group, substituted or unsubstituted pyridyl group, substituted or unsubstituted pyrimidinyl group, substituted or unsubstituted triazinyl group, substituted or unsubstituted quinolyl group, substituted or unsubstituted isoquinolyl group, substituted or unsubstituted quinazolinyl group, substituted or unsubstituted benzimidazolyl group, substituted or unsubstituted phenanthrolinyl group, substituted or unsubstituted 1-carbazolyl group, substituted or unsubstituted 2-carbazolyl group, substituted or unsubstituted 3-carbazolyl group, substituted or unsubstituted 4-carbazolyl group, substituted or unsubstituted 9-carbazolyl group, substituted or unsubstituted benzocarbazolyl group, substituted or unsubstituted azacarbazolyl group, substituted or unsubstituted diazacarbazolyl group, substituted or unsubstituted dibenzofuranyl group, substituted or unsubstituted naphthobenzofuranyl group, substituted or unsubstituted azadibenzofuranyl group, substituted or unsubstituted diazadibenzofuranyl group, substituted or unsubstituted dibenzothiophenyl group, substituted or unsubstituted naphthobenzothiophenyl group, substituted or unsubstituted azadibenzothiophenyl group, or substituted or unsubstituted diazadibenzothiophenyl group.

In the compound of the arrangement B, $R_2$ is a hydrogen atom, substituted or unsubstituted alkyl group having 1 to 18 carbon atoms, substituted or unsubstituted phenyl group, substituted or unsubstituted biphenyl group, substituted or unsubstituted terphenyl group, substituted or unsubstituted naphthyl group, substituted or unsubstituted anthryl group, substituted or unsubstituted phenanthryl group, substituted or unsubstituted chrysenyl group, substituted or unsubstituted triphenylenyl group, substituted or unsubstituted fluorenyl group, substituted or unsubstituted 9,9'-spirobifluorenyl group, substituted or unsubstituted 9,9-dimethylfluorenyl group, substituted or unsubstituted 9,9-diphenylfluorenyl group, substituted or unsubstituted pyridyl group, substituted or unsubstituted pyrimidinyl group, substituted or unsubstituted triazinyl group, substituted or unsubstituted quinolyl group, substituted or unsubstituted isoquinolyl group, substituted or unsubstituted quinazolinyl group, substituted or unsubstituted benzimidazolyl group, substituted or unsubstituted phenanthrolinyl group, substituted or unsubstituted 1-carbazolyl group, substituted or unsubstituted 2-carbazolyl group, substituted or unsubstituted 3-carbazolyl group, substituted or unsubstituted 4-carbazolyl group, substituted or unsubstituted 9-carbazolyl group, substituted or unsubstituted benzocarbazolyl group, substituted or unsubstituted azacarbazolyl group, substituted or unsubstituted diazacarbazolyl group, substituted or unsubstituted dibenzofuranyl group, substituted or unsubstituted naphthobenzofuranyl group, substituted or unsubstituted azadibenzofuranyl group, substituted or unsubstituted diazadibenzofuranyl group, substituted or unsubstituted dibenzothiophenyl group, substituted or unsubstituted naphthobenzothi.

In the compound of the arrangement B, the combination of $R_1$ and $R_2$ are also preferably mutually bonded to form a substituted or unsubstituted monocyclic ring or a substituted or unsubstituted fused ring.

In the compound of the arrangement B, it is preferable that at least one of $R_1$ or $R_2$ is a deuterium atom. It is preferable that at least one of $R_1$ or $R_2$ is a substituent and at least one of $R_1$ or $R_2$ as the substituent is each independently one or more deuterium atom(s).

In the compound of the arrangement B, it is preferable that, when the combination of $R_1$ and $R_2$ are mutually bonded to form a substituted or unsubstituted monocyclic ring or a substituted or unsubstituted fused ring, the monocyclic ring or the fused ring is a substituted or unsubstituted benzene ring, substituted or unsubstituted naphthalene ring, substituted or unsubstituted anthracene ring, substituted or unsubstituted phenanthrene ring, substituted or unsubstituted chrysene ring, substituted or unsubstituted fluorene ring, substituted or unsubstituted 9,9'-spirobifluorene ring, substituted or unsubstituted 9,9-diphenylfluorene ring, or substituted or unsubstituted 9,9-dimethylfluorene ring.

In the compound of the arrangement B, it is preferable that, when the combination of $R_1$ and $R_2$ are mutually bonded to form a substituted or unsubstituted monocyclic ring or substituted or unsubstituted fused ring, the compound represented by the formula (120-2) is represented by a formula (123) or (124) below.

[Formula 39]

(123)

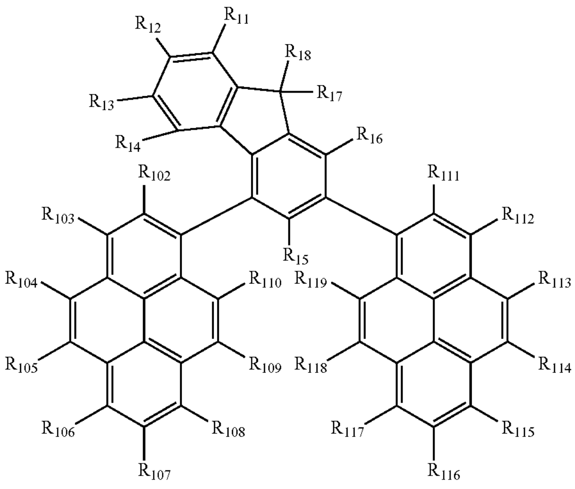

(124)

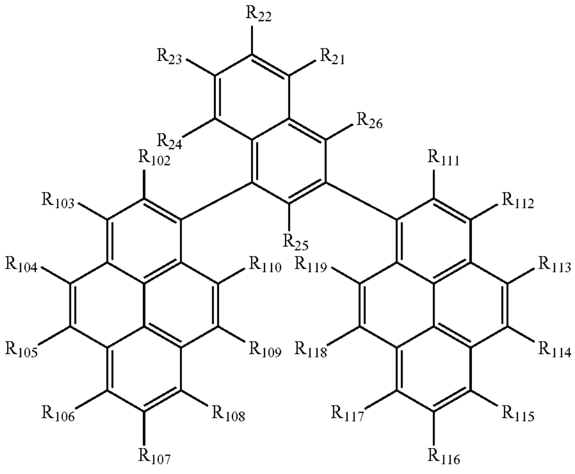

In the formulae (123) and (124):

$R_{102}$ to $R_{119}$ each independently represent the same as $R_{102}$ to $R_{119}$ in the formula (120-2);

at least one combination of a combination of adjacent two or more of $R_{11}$ to $R_{14}$ or a combination of $R_{17}$ and $R_{18}$ are mutually bonded to form a substituted or unsubstituted monocyclic ring, mutually bonded to form a substituted or unsubstituted fused ring, or not mutually bonded;

at least one combination of adjacent two or more of $R_{21}$ to $R_{24}$ and $R_{26}$ are mutually bonded to form a substituted or unsubstituted monocyclic ring, mutually bonded to form a substituted or unsubstituted fused ring, or not mutually bonded; and $R_{11}$ to $R_{18}$ and $R_{21}$ to $R_{26}$ forming neither the substituted or unsubstituted monocyclic ring nor the substituted or unsubstituted fused ring are each independently a hydrogen atom, substituted or unsubstituted alkyl group having 1 to 50 carbon atoms, substituted or unsubstituted heterocyclic group having 5 to 50 ring atoms, substituted or unsubstituted phenyl group, substituted or unsubstituted biphenyl group, substituted or unsubstituted terphenyl group, substituted or unsubstituted naphthyl group, substituted or unsubstituted anthryl group, substituted or unsubstituted phenanthryl group, substituted or unsubstituted chrysenyl group, substituted or unsubstituted triphenylenyl group, substituted or unsubstituted fluorenyl group, substituted or unsubstituted 9,9'-spirobifluorenyl group, substituted or unsubstituted 9,9-dimethylfluorenyl group, or substituted or unsubstituted 9,9-diphenylfluorenyl group.

In the formulae (121) to (124), it is preferable that at least one of $R_{1A}$ to $R_{2A}$, $R_{11}$ to $R_{16}$, or $R_{21}$ to $R_{26}$ is a deuterium atom.

In the formulae (121) to (124), it is preferable that at least one of $R_{1A}$ to $R_{2A}$, $R_{11}$ to $R_{16}$, or $R_{21}$ to $R_{26}$ is a substituent and at least one of $R_{1A}$ to $R_{2A}$, $R_{11}$ to $R_{16}$, or $R_{21}$ to $R_{26}$ as the substituent is each independently one or more deuterium atom(s).

In the compound of the arrangement B, it is preferable that $R_{102}$ to $R_{119}$ are each independently a hydrogen atom, a substituted or unsubstituted alkyl group having 1 to 18 carbon atoms, a substituted or unsubstituted cycloalkyl group having 1 to 18 ring carbon atoms, a group represented by Si(Rx)(Ry)(Rz), a substituted or unsubstituted aryl group having 6 to 18 ring carbon atoms, or a substituted or unsubstituted heterocyclic group having 5 to 18 ring atoms. Rx, Ry, and Rz in Si(Rx)(Ry)(Rz) are preferably each independently an unsubstituted alkyl group having 1 to 18 carbon atoms or an unsubstituted aryl group having 6 to 50 ring carbon atoms.

In the compound of the arrangement B, $R_{102}$ to $R_{119}$ are preferably hydrogen atoms.

In the compound of the arrangement B, it is preferable that $R_{102}$ to $R_{110}$ are deuterium atoms or $R_{111}$ to $R_{119}$ are deuterium atoms. $R_{102}$ to $R_{119}$ are preferably deuterium atoms. It is preferable that at least one of $R_{102}$ to $R_{119}$ is a substituent and at least one of $R_{102}$ to $R_{119}$ as the substituent is each independently one or more deuterium atom(s).

Compound of Arrangement C

The compound of the arrangement C is a compound represented by a formula (120-3) below. The compound represented by the formula (120-3) below includes at least one deuterium atom.

[Formula 40]

(120-3)

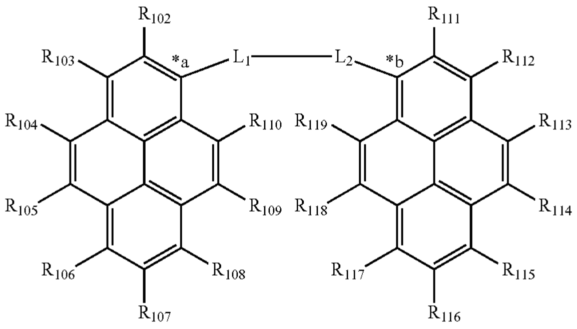

In the formula (120-3): $L_1$ is a group represented by any one of formulae (11) to (13) below and $L_2$ is a group represented by any one of formulae (11A) to (13A);

$R_{102}$ to $R_{119}$ are each independently a hydrogen atom, a substituted or unsubstituted alkyl group having 1 to 50 carbon atoms, a substituted or unsubstituted cycloalkyl group having 1 to 50 carbon atoms, a group represented by Si(Rx)(Ry)(Rz), a substituted or unsubstituted aryl group having 6 to 50 ring carbon atoms, or a substituted or unsubstituted heterocyclic group having 5 to 50 ring atoms;

Rx, Ry, and Rz in Si(Rx)(Ry)(Rz) are each independently a substituted or unsubstituted alkyl group having 1 to 50 carbon atoms, or a substituted or unsubstituted aryl group having 6 to 50 ring carbon atoms; and a substituent for “substituted or unsubstituted” group in $R_{102}$ to $R_{119}$ is each independently a substituted or unsubstituted alkyl group having 1 to 50 carbon atoms, substituted or unsubstituted heterocyclic group having 5 to 50 ring atoms, substituted or unsubstituted phenyl group, substituted or unsubstituted biphenyl group, substituted or unsubstituted terphenyl group, substituted or unsubstituted naphthyl group, substituted or unsubstituted anthryl group, substituted or unsubstituted phenanthryl group, substituted or unsubstituted chrysenyl group, substituted or unsubstituted triphenylenyl group, substituted or unsubstituted fluorenyl group, substituted or unsubstituted 9,9'-spirobifluorenyl group, substituted or unsubstituted 9,9-dimethylfluorenyl group, or substituted or unsubstituted 9,9-diphenylfluorenyl group.

[Formula 41]

(11)

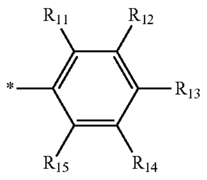

-continued (12)

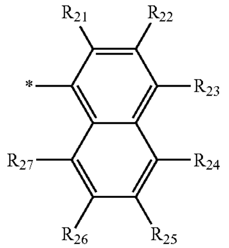

(13)

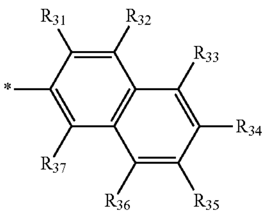

(11A)

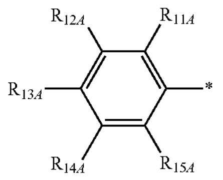

(12A)

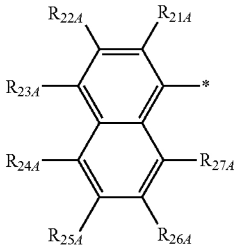

(13A)

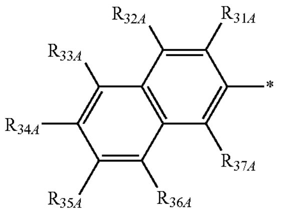

In the formulae (11) to (13) and (11A) to (13A): $R_{11}$ to $R_{15}$, $R_{21}$ to $R_{27}$, $R_{31}$ to $R_{37}$, $R_{11A}$ to $R_{15A}$, $R_{21A}$ to $R_{27A}$, and $R_{31A}$ to $R_{37A}$ are each independently a hydrogen atom, substituted or unsubstituted alkyl group having 1 to 50 carbon atoms, substituted or unsubstituted cycloalkyl group 1 to 50 carbon atoms, group represented by Si(Rx)(Ry)(Rz), substituted or unsubstituted aryl group having 6 to 50 ring carbon atoms, or substituted or unsubstituted heterocyclic group having 5 to 50 ring atoms, Rx, Ry, and Rz in Si(Rx)(Ry)(Rz) being each independently a substituted or unsubstituted alkyl group having 1 to 50 carbon atoms or substituted or unsubstituted aryl group having 6 to 50 ring carbon atoms;

a substituent for “substituted or unsubstituted” group in $R_{11}$ to $R_{15}$, $R_{21}$ to $R_{27}$, and $R_{31}$ to $R_{37}$ is each independently a substituted or unsubstituted alkyl group having 1 to 50 carbon atoms, substituted or unsubstituted heterocyclic group having 5 to 50 ring atoms, substituted or unsubstituted phenyl group, substituted or unsubstituted biphenyl group, substituted or unsubstituted terphenyl group, substituted or unsubstituted naphthyl group, substituted or unsubstituted anthryl group, substituted or unsubstituted phenanthryl group, substituted or unsubstituted chrysenyl group, substituted or unsubstituted triphenylenyl group, substituted or unsubstituted fluorenyl group, substituted or unsubstituted 9,9'-spirobifluorenyl group, substituted or unsubstituted 9,9-dimethylfluorenyl group, or substituted or unsubstituted 9,9-diphenylfluorenyl group;

at least one combination of adjacent two or more of $R_{11}$ to $R_{15}$ are not mutually bonded to form neither a substituted or unsubstituted monocyclic ring nor a substituted or unsubstituted fused ring;

at least one combination of adjacent two or more of $R_{11A}$ to $R_{15A}$ are not mutually bonded to form neither a substituted or unsubstituted monocyclic ring nor a substituted or unsubstituted fused ring;

at least one combination of adjacent two or more of $R_{21}$ to $R_{27}$ are not mutually bonded to form neither a substituted or unsubstituted monocyclic ring nor a substituted or unsubstituted fused ring;

at least one combination of adjacent two or more of $R_{21A}$ to $R_{27A}$ are not mutually bonded to form neither a substituted or unsubstituted monocyclic ring nor a substituted or unsubstituted fused ring;

at least one combination of adjacent two or more of $R_{31}$ to $R_{37}$ are not mutually bonded to form neither a substituted or unsubstituted monocyclic ring nor a substituted or unsubstituted fused ring;

at least one combination of adjacent two or more of $R_{31A}$ to $R_{37A}$ are not mutually bonded to form neither a substituted or unsubstituted monocyclic ring nor a substituted or unsubstituted fused ring;

in the formulae (11) to (13) as $L_1$, * represents a bonding position with *a in the formula (120-3) and one of $R_{11}$ to $R_{15}$, $R_{21}$ to $R_{27}$, and $R_{31}$ to $R_{37}$ is a single bond bonded with $L_2$;

in the formulae (11A) to (13A) as $L_2$, * represents a bonding position with *b in the formula (120-3) and one of $R_{11A}$ to $R_{15A}$, $R_{21A}$ to $R_{27A}$, and $R_{31A}$ to $R_{37A}$ is a single bond bonded with $L_1$;

when $R_{12}$ or $R_{14}$ in $L_1$ is a single bond bonded with $L_2$, one of $R_{11A}$, $R_{13A}$, $R_{15A}$, $R_{21A}$ to $R_{27A}$, and $R_{31A}$ to $R_{37A}$ in $L_2$ is a single bond bonded with $L_1$;

when $R_{11}$ or $R_{15}$ in $L_1$ is a single bond bonded with $L_2$, one of $R_{12A}$, $R_{13A}$, $R_{14A}$, $R_{21A}$ to $R_{27A}$, and $R_{31A}$ to $R_{37A}$ in $L_2$ is a single bond bonded with $L_1$;

when $R_{13}$ in $L_1$ is a single bond bonded with $L_2$, one of $R_{11A}$, $R_{12A}$, $R_{14A}$, $R_{15A}$, $R_{21A}$ to $R_{27A}$, and $R_{31A}$ to $R_{37A}$ in $L_2$ is a single bond bonded with $L_1$;

when $R_{21}$ in $L_1$ is a single bond bonded with $L_2$, one of $R_{11A}$ to $R_{15A}$, $R_{22A}$ to $R_{27A}$, and $R_{31A}$ to $R_{37A}$ in $L_2$ is a single bond bonded with $L_1$;

when $R_{22}$ in $L_1$ is a single bond bonded with $L_2$, one of $R_{11A}$ to $R_{15A}$, $R_{21A}$, $R_{23A}$ to $R_{27A}$, and $R_{31A}$ to $R_{37A}$ in $L_2$ is a single bond bonded with $L_1$;

when $R_{23}$ in $L_1$ is a single bond bonded with $L_2$, one of $R_{11A}$ to $R_{15A}$, $R_{21A}$ to $R_{22A}$, $R_{24A}$ to $R_{27A}$, and $R_{31A}$ to $R_{37A}$ in $L_2$ is a single bond bonded with $L_1$;

when $R_{24}$ in $L_1$ is a single bond bonded with $L_2$, one of $R_{11A}$ to $R_{15A}$, $R_{21A}$ to $R_{23A}$, $R_{25A}$ to $R_{27A}$, and $R_{31A}$ to $R_{37A}$ in $L_2$ is a single bond bonded with $L_1$;

when $R_{25}$ in $L_1$ is a single bond bonded with $L_2$, one of $R_{11A}$ to $R_{15A}$, $R_{21A}$ to $R_{24A}$, $R_{26A}$ to $R_{27A}$, and $R_{31A}$ to $R_{37A}$ in $L_2$ is a single bond bonded with $L_1$;

when $R_{26}$ in $L_1$ is a single bond bonded with $L_2$, one of $R_{11A}$ to $R_{15A}$, $R_{21A}$ to $R_{25A}$, $R_{27A}$, and $R_{31A}$ to $R_{37A}$ in $L_2$ is a single bond bonded with $L_1$;

when $R_{27}$ in $L_1$ is a single bond bonded with $L_2$, one of $R_{11A}$ to $R_{15A}$, $R_{21A}$ to $R_{26A}$, and $R_{31A}$ to $R_{37A}$ in $L_2$ is a single bond bonded with $L_1$;

when $R_{31}$ in $L_1$ is a single bond bonded with $L_2$, one of $R_{11A}$ to $R_{15A}$, $R_{21A}$ to $R_{27A}$, and $R_{32A}$ to $R_{37A}$ in $L_2$ is a single bond bonded with $L_1$;

when $R_{32}$ in $L_1$ is a single bond bonded with $L_2$, one of $R_{11A}$ to $R_{15A}$, $R_{21A}$ to $R_{27A}$, $R_{31A}$, and $R_{33A}$ to $R_{37A}$ in $L_2$ is a single bond bonded with $L_1$;

when $R_{33}$ in $L_1$ is a single bond bonded with $L_2$, one of $R_{11A}$ to $R_{15A}$, $R_{21A}$ to $R_{27A}$, $R_{31A}$ to $R_{32A}$, and $R_{34A}$ to $R_{37A}$ in $L_2$ is a single bond bonded with $L_1$;

when $R_{34}$ in $L_1$ is a single bond bonded with $L_2$, one of $R_{11A}$ to $R_{15A}$, $R_{21A}$ to $R_{27A}$, $R_{31A}$ to $R_{33A}$, and $R_{35A}$ to $R_{37A}$ in $L_2$ is a single bond bonded with $L_1$;

when $R_{35}$ in $L_1$ is a single bond bonded with $L_2$, one of $R_{11A}$ to $R_{15A}$, $R_{21A}$ to $R_{27A}$, $R_{31A}$ to $R_{34A}$, and $R_{36A}$ to $R_{37A}$ in $L_2$ is a single bond bonded with $L_1$;

when $R_{36}$ in $L_1$ is a single bond bonded with $L_2$, one of $R_{11A}$ to $R_{15A}$, $R_{21A}$ to $R_{27A}$, $R_{31A}$ to $R_{35A}$, and $R_{37A}$ in $L_2$ is a single bond bonded with $L_1$; and when $R_{37}$ in $L_1$ is a single bond bonded with $L_2$, one of $R_{11A}$ to $R_{15A}$, $R_{21A}$ to $R_{27A}$, and $R_{31A}$ to $R_{36A}$ in $L_2$ is a single bond bonded with $L_1$.

In the compound of the arrangement C, in order to more effectively achieve the effect for increasing the lifetime by deuteration even in a high-speed film formation, a total number of carbon atoms included in the group linking two pyrene rings (i.e. a pyrene ring having $R_{111}$ to $R_{119}$ and a pyrene ring having $R_{102}$ to $R_{110}$) is more preferably 21 or less.

The group linking the two pyrene rings is a group represented by $-L_1-L_2-$ in the formula (120-3).

In the compound of the arrangement C, $-L_1-L_2-$ is preferably a group represented by one of formulae (13-1) to (13-69) below.

[Formula 42]

(13-1)

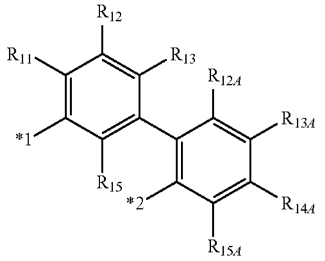

(13-2)

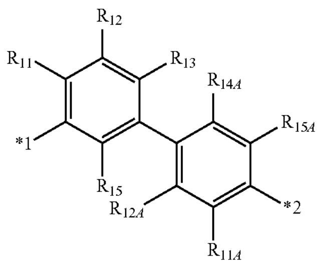

-continued
(13-3)
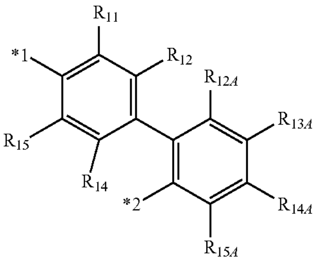
(13-4)
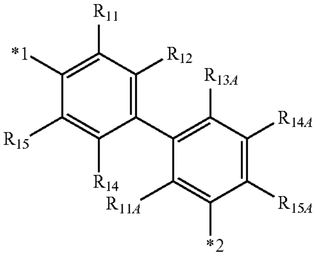
(13-5)
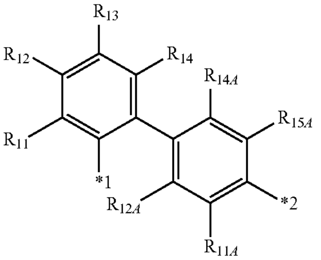
(13-6)
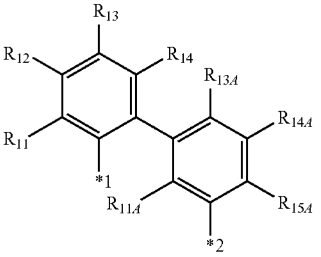
[Formula 43]
(13-7)
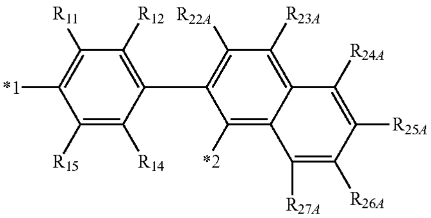
(13-8)
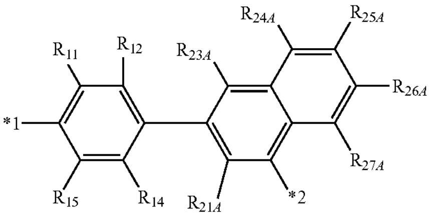
-continued
(13-9)
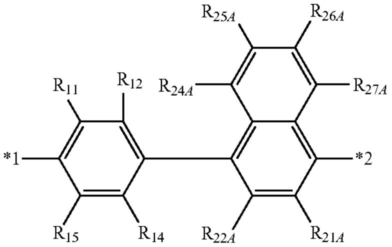
(13-10)
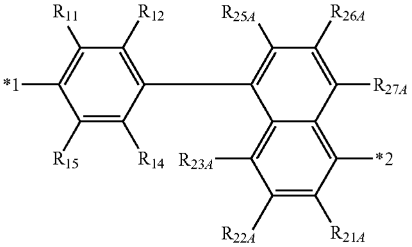
(13-11)
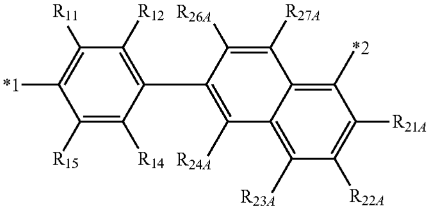
(13-12)
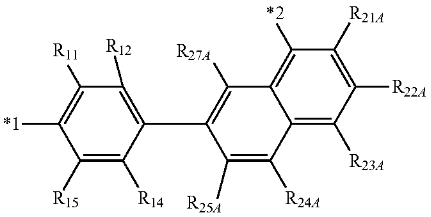
(13-13)
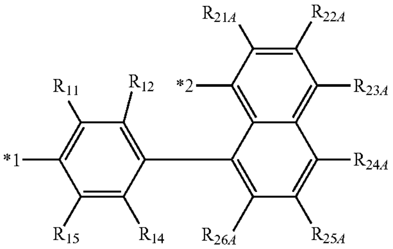
[Formula 44]
(13-14)
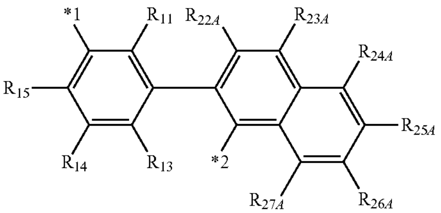

-continued
(13-15)
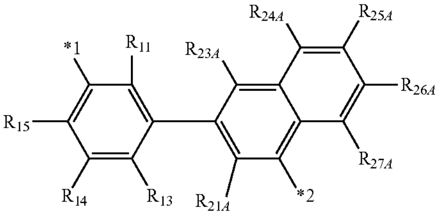
(13-16)
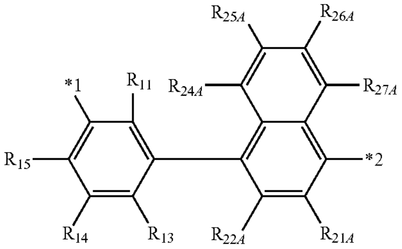
(13-17)
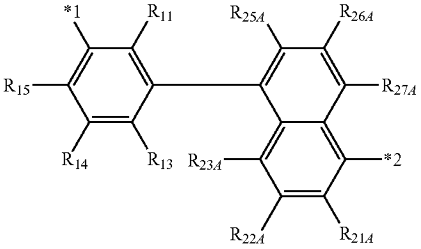
(13-18)
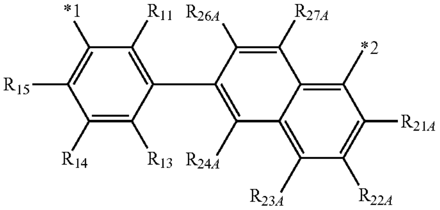
(13-19)
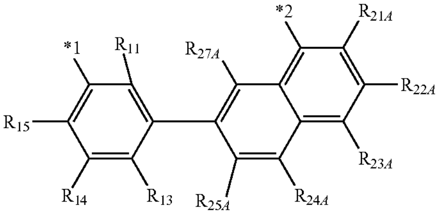
(13-20)
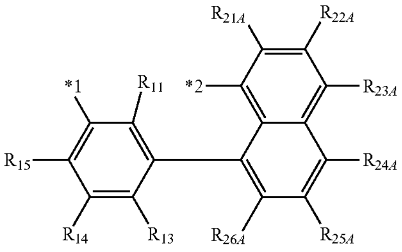
-continued
[Formula 45]
(13-21)
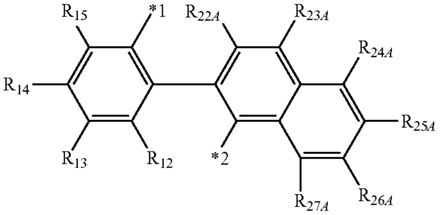
(13-22)
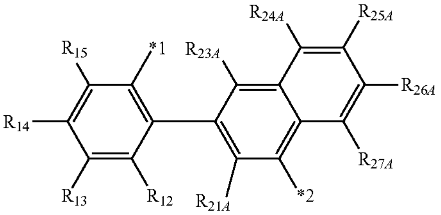
(13-23)
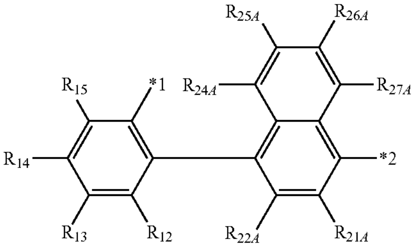
(13-24)
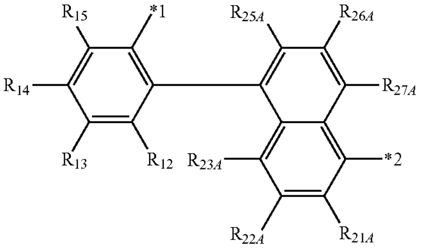
(13-25)
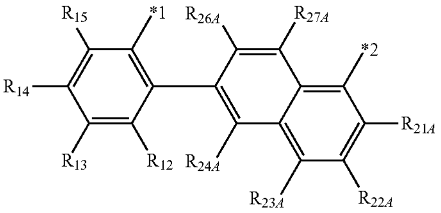
(13-26)
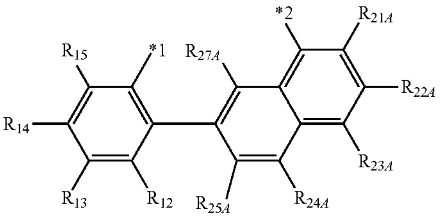

-continued
(13-27)
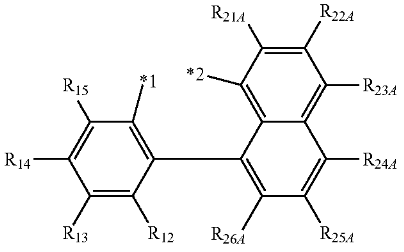
[Formula 46]
(13-28)
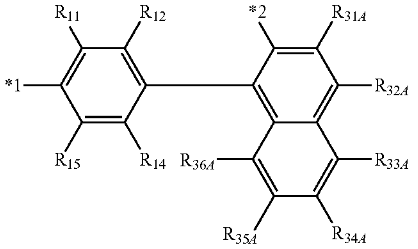
(13-29)
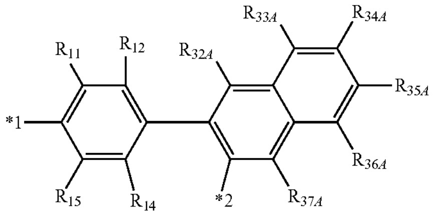
(13-30)
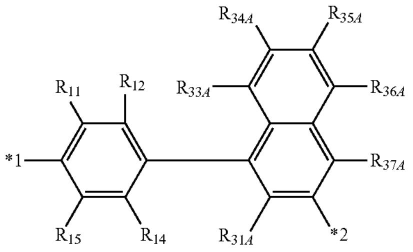
(13-31)
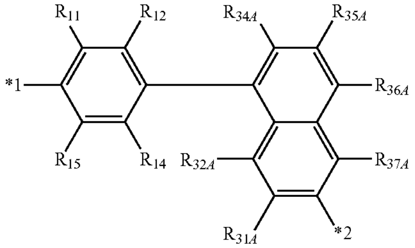
(13-32)
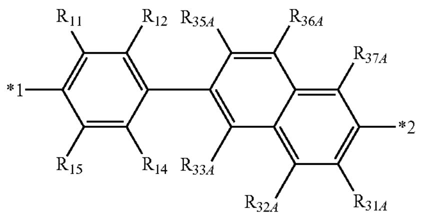
-continued
(13-33)
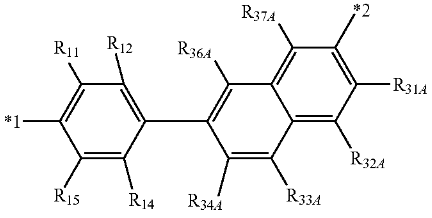
(13-34)
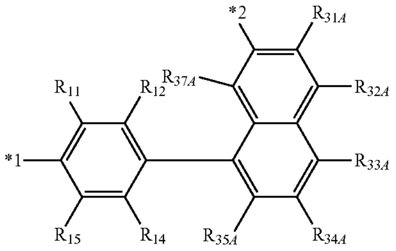
[Formula 47]
(13-35)
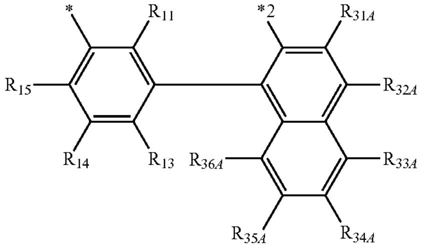
(13-36)
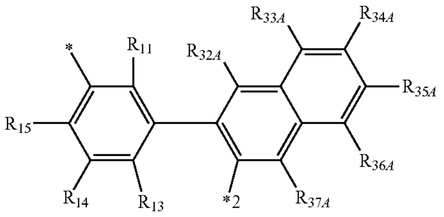
(13-37)
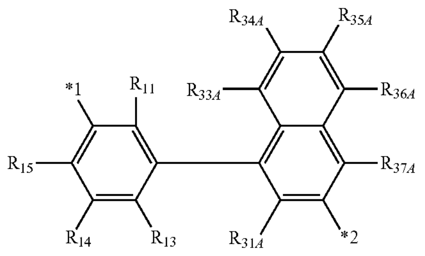
(13-38)
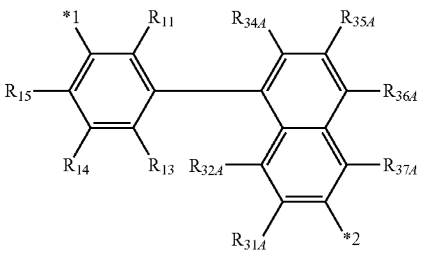

-continued
(13-39)
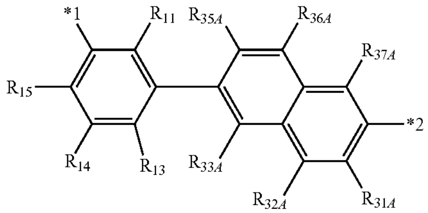
(13-40)
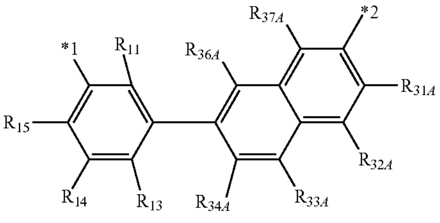
(13-41)
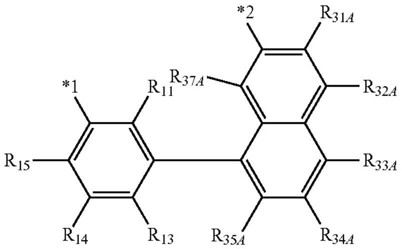
[Formula 48]
(13-42)
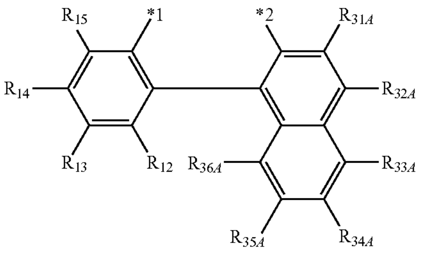
(13-43)
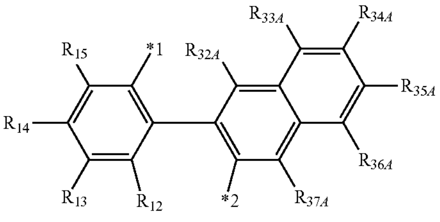
(13-44)
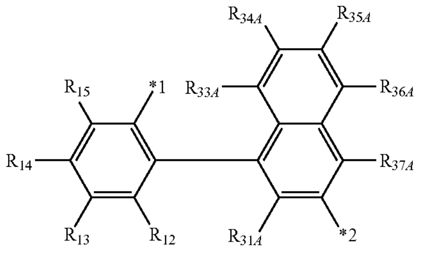
-continued
(13-45)
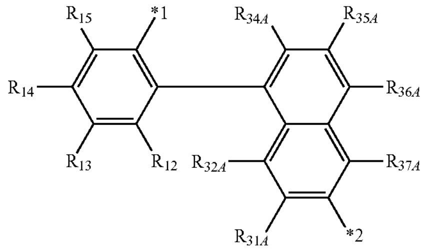
(13-46)
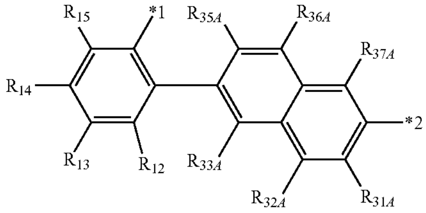
(13-47)
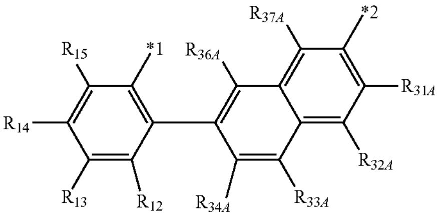
(13-48)
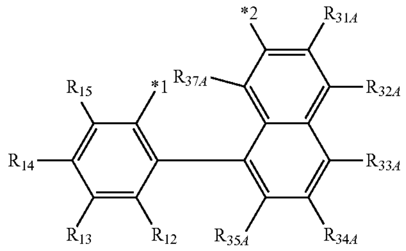
[Formula 49]
(13-49)
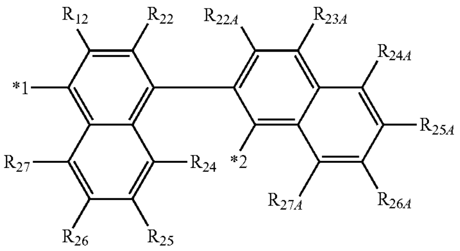
(13-50)
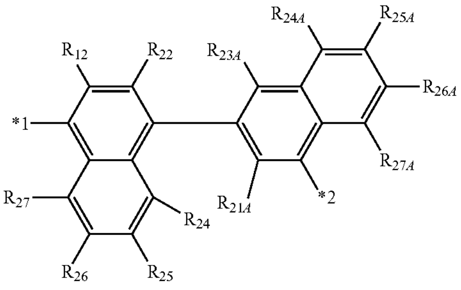

-continued
(13-51)
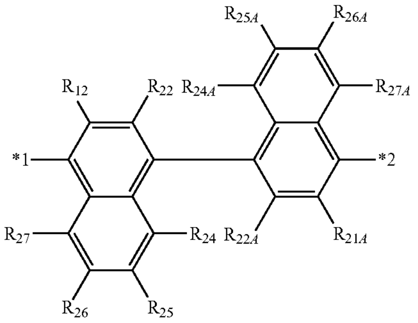
(13-52)
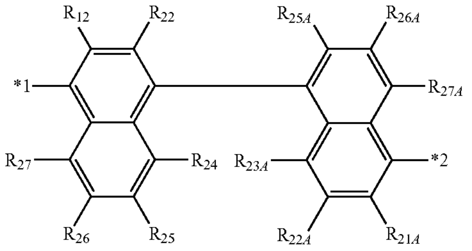
(13-53)
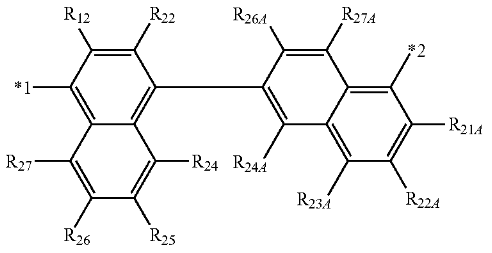
(13-54)
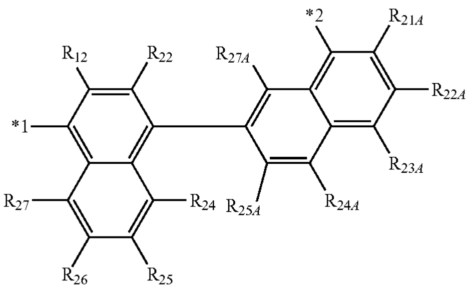
(13-55)
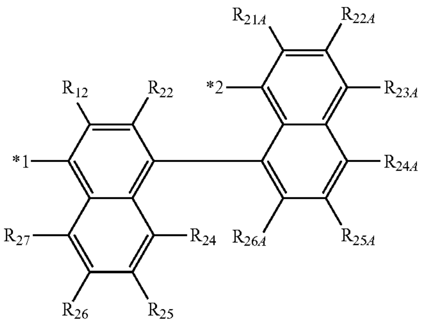
-continued
[Formula 50]
(13-56)
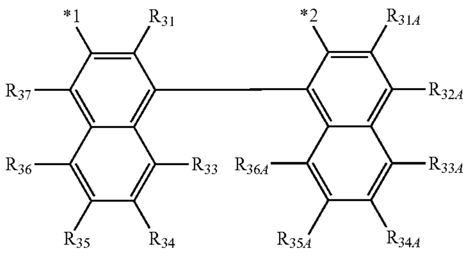
(13-57)
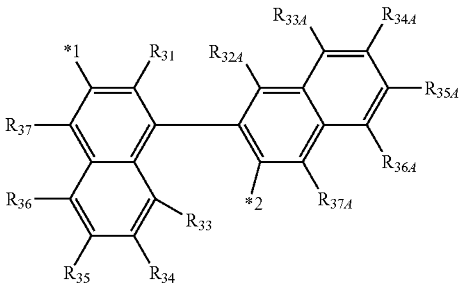
(13-58)
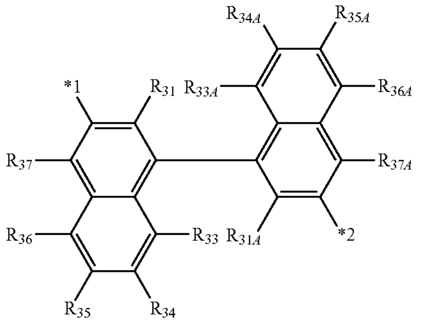
(13-59)
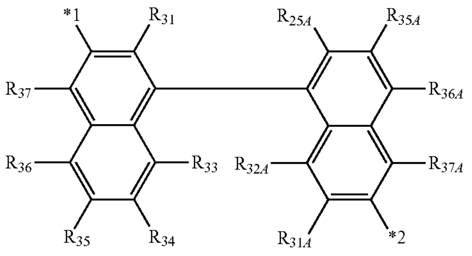
(13-60)
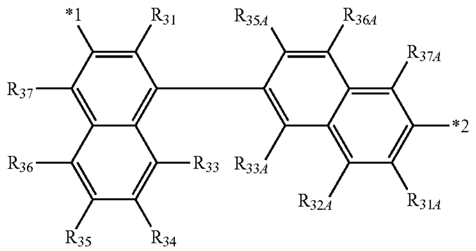

-continued (13-61)

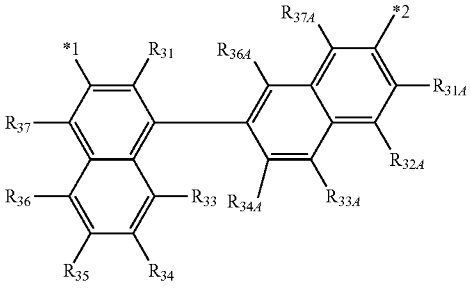

(13-62)

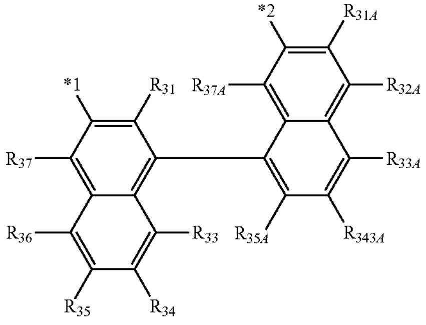

[Formula 51]

(13-63)

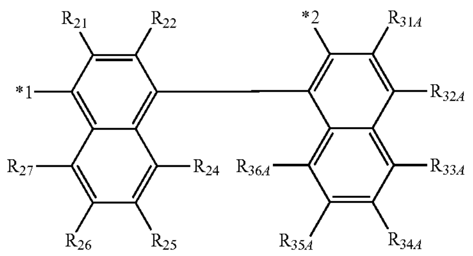

(13-64)

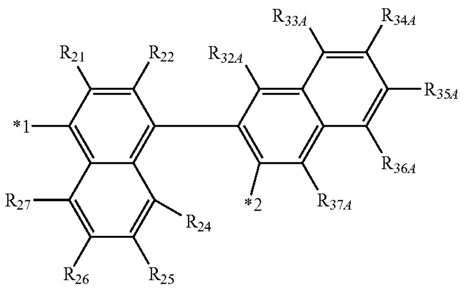

(13-65)

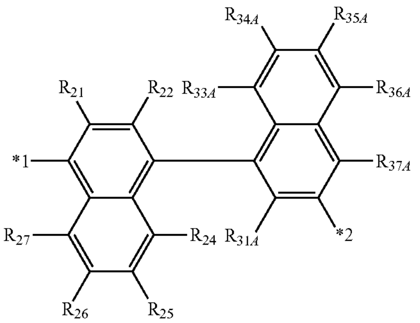

-continued (13-66)

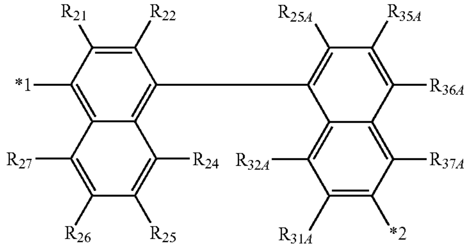

(13-67)

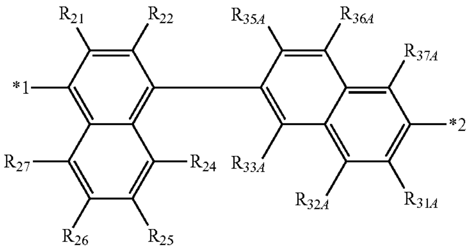

(13-68)

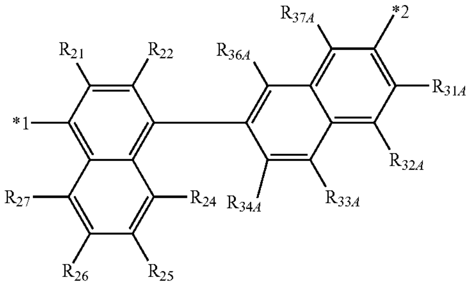

(13-69)

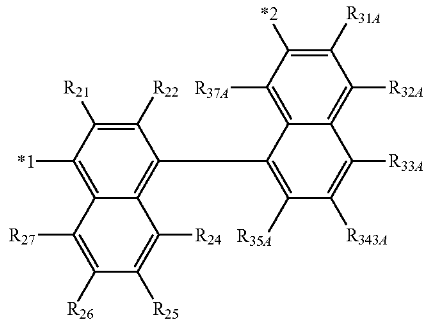

$R_{11}$ to $R_{15}$, $R_{21}$ to $R_{27}$, $R_{31}$ to $R_{37}$, $R_{11A}$ to $R_{15A}$, $R_{21A}$ to $R_{27A}$, and $R_{31A}$ to $R_{37A}$ in the formulae (13-1) to (13-69) each independently represent the same as $R_{11}$ to $R_{15}$, $R_{21}$ to $R_{27}$, $R_{31}$ to $R_{37}$, $R_{11A}$ to $R_{15A}$, $R_{21A}$ to $R_{27A}$, and $R_{31A}$ to $R_{37A}$ in the formulae (11) to (13) and (11A) to (13A), *1 in the formulae (13-1) to (13-69) represents a bonding position with *a in the formula (120-3), and *2 represents a bonding position with *b in the formula (120-3).

In the compound of the arrangement C, the compound represented by the formula (120-3) is preferably represented by any one of formulae (121) to (131) below.
[Formula 52]
(121)
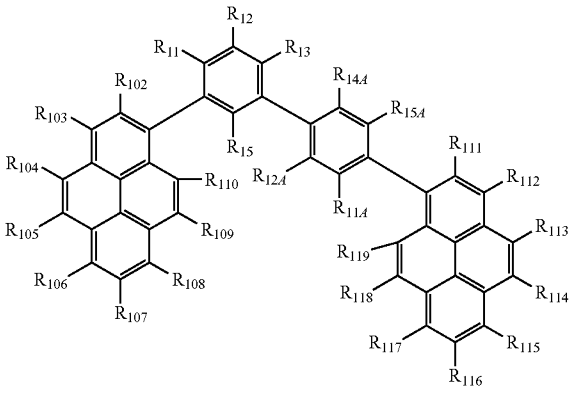
(122)
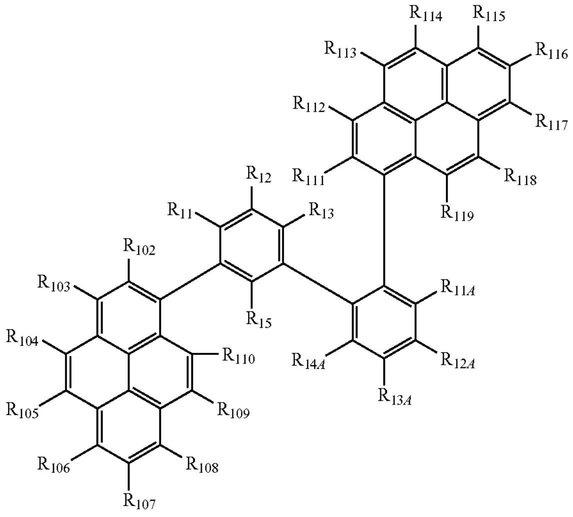
[Formula 53]
(123)
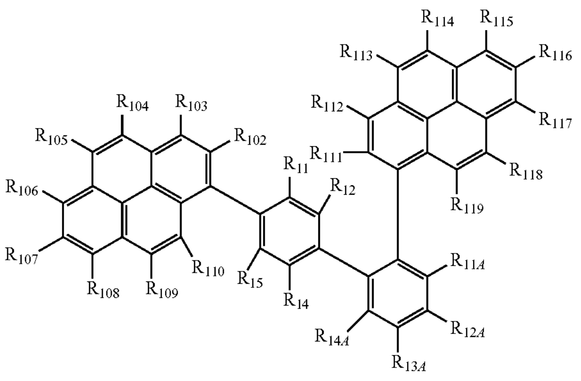
-continued
(124)
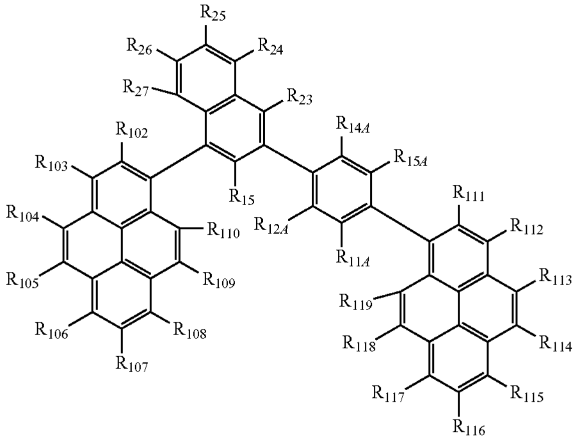
[Formula 54]
(125)
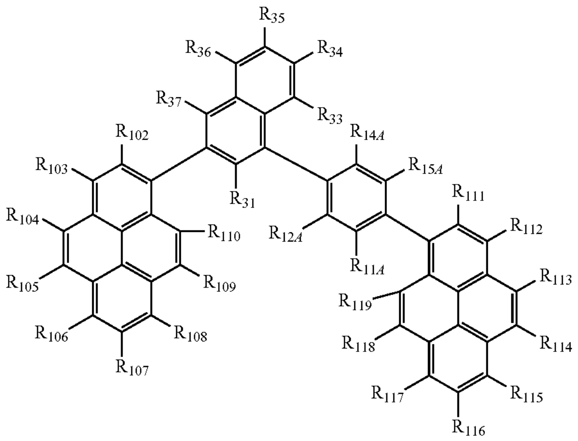
(126)
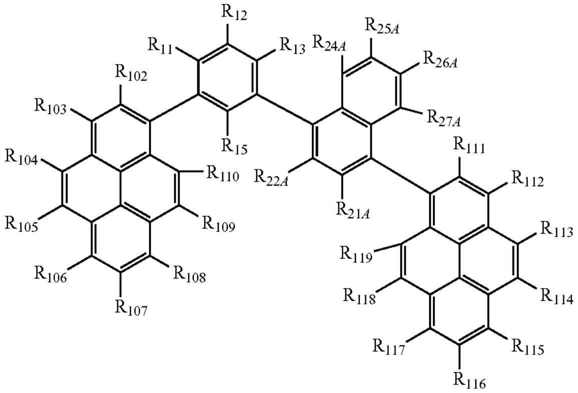

-continued

[Formula 55]

(127)

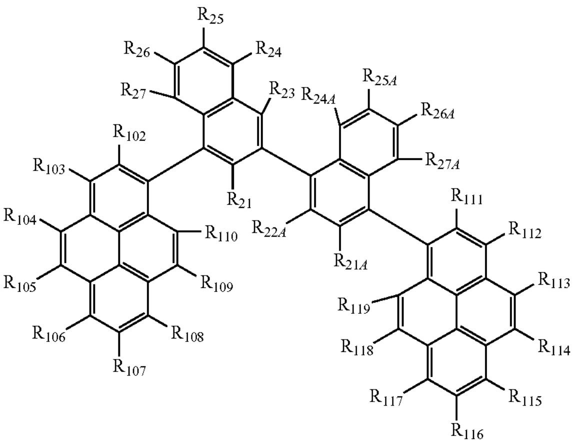

(128)

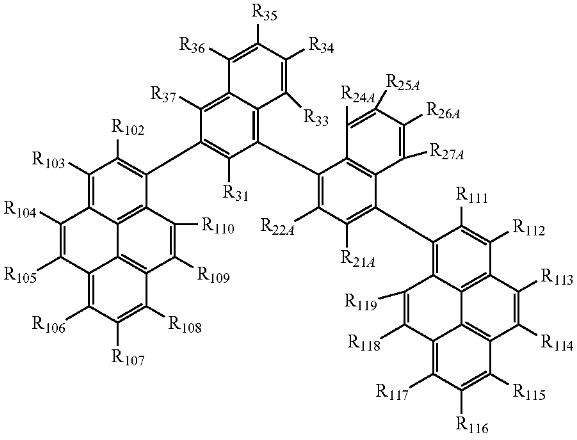

[Formula 56]

(129)

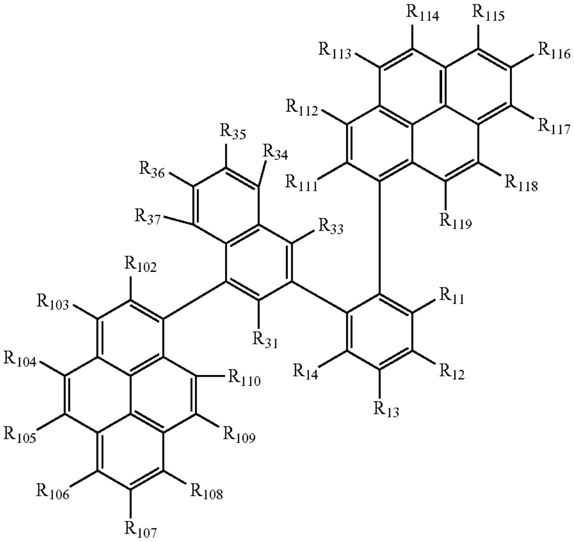

-continued (130)

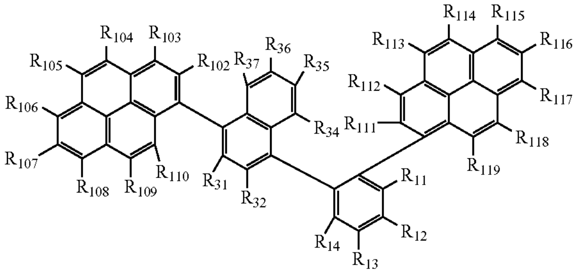

[Formula 57]

(131)

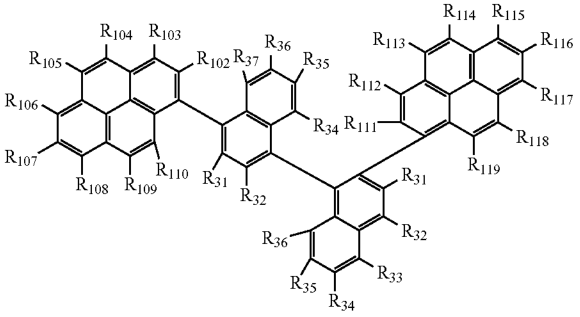

In the formulae (121) to (131):

$R_{11}$ to $R_{15}$, $R_{21}$ to $R_{27}$, $R_{31}$ to $R_{37}$, $R_{11A}$ to $R_{15A}$, $R_{21A}$ to $R_{27A}$, and $R_{31A}$ to $R_{37A}$ each independently represent the same as $R_{11}$ to $R_{15}$, $R_{21}$ to $R_{27}$, $R_{31}$ to $R_{37}$, $R_{11A}$ to $R_{15A}$, $R_{21A}$ to $R_{27A}$, and $R_{31A}$ to $R_{37A}$ in the formulae (11) to (13) and (11A) to (13A) and $R_{102}$ to $R_{119}$ each independently represent the same as $R_{102}$ to $R_{119}$ in the formula (120-3).

In the compound of the arrangement C, it is preferable that $R_{11}$ to $R_{15}$, $R_{21}$ to $R_{27}$, $R_{31}$ to $R_{37}$, $R_{11A}$ to $R_{15A}$, $R_{21A}$ to $R_{27A}$, $R_{31A}$ to $R_{37A}$, and $R_{102}$ to $R_{119}$ are each independently a hydrogen atom, a substituted or unsubstituted alkyl group having 1 to 30 carbon atoms, a substituted or unsubstituted cycloalkyl group having 1 to 30 ring carbon atoms, a group represented by Si(Rx)(Ry)(Rz), a substituted or unsubstituted aryl group having 6 to 30 ring carbon atoms, or a substituted or unsubstituted heterocyclic group having 5 to 30 ring atoms. Rx, Ry, and Rz in Si(Rx)(Ry)(Rz) are preferably each independently an unsubstituted alkyl group having 1 to 30 carbon atoms or an unsubstituted aryl group having 6 to 30 ring carbon atoms.

In the compound of the arrangement C, $R_{11}$ to $R_{15}$, $R_{21}$ to $R_{27}$, $R_{31}$ to $R_{37}$, $R_{11A}$ to $R_{15A}$, $R_{21A}$ to $R_{27A}$, $R_{31A}$ to $R_{37A}$, and $R_{102}$ to $R_{119}$ are preferably each independently a hydrogen atom, substituted or unsubstituted alkyl group having 1 to 18 carbon atoms, substituted or unsubstituted phenyl group, substituted or unsubstituted biphenyl group, substituted or unsubstituted terphenyl group, substituted or unsubstituted naphthyl group, substituted or unsubstituted anthryl group, substituted or unsubstituted phenanthryl group, substituted or unsubstituted chrysenyl group, substituted or unsubstituted triphenylenyl group, substituted or unsubstituted fluorenyl group, substituted or unsubstituted 9,9'-spirobifluorenyl group, substituted or unsubstituted 9,9-dimethylfluorenyl group, substituted or unsubstituted 9,9-diphenylfluorenyl group, substituted or unsubstituted pyridyl group, substituted or unsubstituted pyrimidinyl group, substituted or unsubstituted triazinyl group, substituted or unsubstituted quinolyl group, substituted or unsubstituted isoquinolyl group, substituted or unsubstituted quinazolinyl group, substituted or unsubstituted benzimidazolyl group, substituted or unsubstituted phenanthrolinyl group, substituted or unsubstituted 1-carbazolyl group, substituted or unsubstituted 2-carbazolyl group, substituted or unsubstituted 3-carbazolyl group, substituted or unsubstituted 4-carbazolyl group, substituted or unsubstituted 9-carbazolyl group, substituted or unsubstituted benzocarbazolyl group, substituted or unsubstituted azacarbazolyl group, substituted or unsubstituted diazacarbazolyl group, substituted or unsubstituted dibenzofuranyl group, substituted or unsubstituted naphthobenzofuranyl group, substituted or unsubstituted azadibenzofuranyl group, substituted or unsubstituted diazadibenzofuranyl group, substituted or unsubstituted dibenzothiophenyl group, substituted or unsubstituted naphthobenzothiophenyl group, substituted or unsubstituted azadibenzothiophenyl group, or substituted or unsubstituted diazadibenzothiophenyl group.

In the compound of the arrangement C, $R_{11}$ to $R_{15}$, $R_{21}$ to $R_{27}$, $R_{31}$ to $R_{37}$, $R_{11A}$ to $R_{15A}$, $R_{21A}$ to $R_{27A}$, $R_{31A}$ to $R_{37A}$, and $R_{102}$ to $R_{119}$ are preferably each independently a hydrogen atom, substituted or unsubstituted alkyl group having 1 to 6 carbon atoms, substituted or unsubstituted phenyl group, substituted or unsubstituted naphthyl group, substituted or unsubstituted phenanthryl group, substituted or unsubstituted fluorenyl group, substituted or unsubstituted dibenzofuranyl group, substituted or unsubstituted dibenzothiophenyl group, substituted or unsubstituted 9,9-dimethylfluorenyl group, or substituted or unsubstituted 9,9-diphenylfluorenyl group.

In the compound of the arrangement C, $R_{11}$ to $R_{15}$, $R_{21}$ to $R_{27}$, $R_{31}$ to $R_{37}$, $R_{11A}$ to $R_{15A}$, $R_{21A}$ to $R_{27A}$, and $R_{31A}$ to $R_{37A}$ are preferably hydrogen atoms.

In the compound of the arrangement C, at least one of $R_{11}$ to $R_{15}$, $R_{21}$ to $R_{27}$, $R_{31}$ to $R_{37}$, $R_{11A}$ to $R_{15A}$, $R_{21A}$ to $R_{27A}$, or $R_{31A}$ to $R_{37A}$ is preferably a deuterium atom. It is preferable that at least one of $R_{11}$ to $R_{15}$, $R_{21}$ to $R_{27}$, $R_{31}$ to $R_{37}$, $R_{11A}$ to $R_{15A}$, $R_{21A}$ to $R_{27A}$, or $R_{31A}$ to $R_{37A}$ is a substituent and at least one of $R_{11}$ to $R_{15}$, $R_{21}$ to $R_{27}$, $R_{31}$ to $R_{37}$, $R_{11A}$ to $R_{15A}$, $R_{21A}$ to $R_{27A}$, or $R_{31A}$ to $R_{37A}$ as the substituent is each independently one or more deuterium atom(s).

In the compound of the arrangement C, $R_{102}$ to $R_{119}$ are preferably hydrogen atoms.

In the compound of the arrangement C, it is preferable that $R_{102}$ to $R_{110}$ are deuterium atoms or $R_{111}$ to $R_{119}$ are deuterium atoms. $R_{102}$ to $R_{119}$ are preferably deuterium atoms. It is preferable that at least one of $R_{102}$ to $R_{119}$ is a substituent and at least one of $R_{102}$ to $R_{119}$ as the substituent is each independently one or more deuterium atom(s).

Compound of Arrangement D

The compound of the arrangement D is a compound represented by a formula (120X), (120Y), or (120Z) below. The compound represented by the formula (120X), (120Y), or (120Z) includes at least one deuterium atom.

[Formula 58]

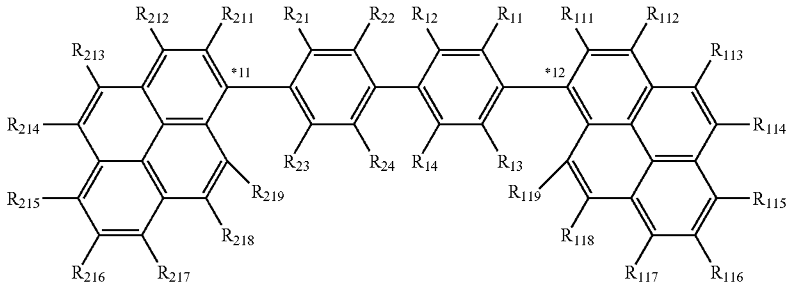

(120X)

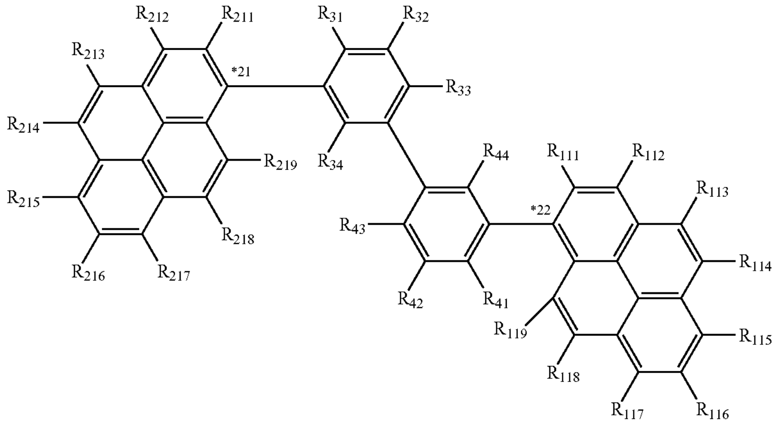

(120Y)

-continued (120Z)

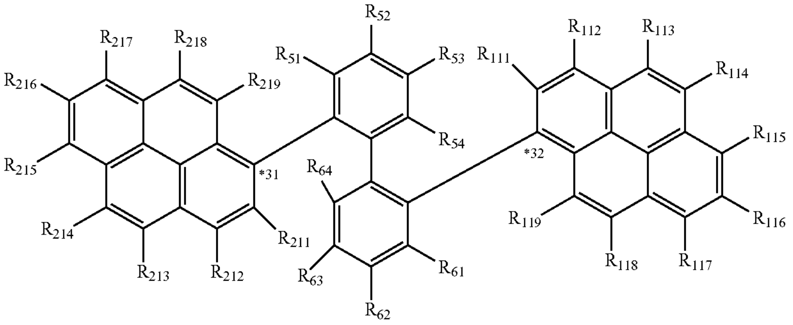

In the formulae (120X), (120Y), and (120Z):

$R_{111}$ to $R_{119}$ and $R_{211}$ to $R_{219}$ are each independently a hydrogen atom, a substituted or unsubstituted alkyl group having 1 to 50 carbon atoms, a substituted or unsubstituted cycloalkyl group having 1 to 50 carbon atoms, a group represented by Si(Rx)(Ry)(Rz), a substituted or unsubstituted aryl group having 6 to 50 ring carbon atoms, or a substituted or unsubstituted heterocyclic group having 5 to 50 ring atoms;

Rx, Ry, and Rz in Si(Rx)(Ry)(Rz) are each independently a substituted or unsubstituted alkyl group having 1 to 50 carbon atoms, or a substituted or unsubstituted aryl group having 6 to 50 ring carbon atoms;

in the formula (120X): at least one combination of a combination of $R_{11}$ and $R_{12}$, a combination of $R_{13}$ and $R_{14}$, a combination of $R_{21}$ and $R_{22}$, or a combination of $R_{23}$ and $R_{24}$ are mutually bonded to form a substituted or unsubstituted monocyclic ring, mutually bonded to form a substituted or unsubstituted fused ring, or not mutually bonded;

$R_{11}$, $R_{13}$, $R_{21}$, and $R_{23}$ forming neither the substituted or unsubstituted monocyclic ring nor the substituted or unsubstituted fused ring are each independently a hydrogen atom, substituted or unsubstituted alkyl group having 1 to 50 carbon atoms, substituted or unsubstituted phenyl group, substituted or unsubstituted biphenyl group, substituted or unsubstituted naphthyl group, substituted or unsubstituted phenanthryl group, substituted or unsubstituted fluorenyl group, substituted or unsubstituted 9,9'-spirobifluorenyl group, or group represented by a formula (4) below;

$R_{12}$, $R_{14}$, $R_{22}$, and $R_{24}$ forming neither the substituted or unsubstituted monocyclic ring nor the substituted or unsubstituted fused ring are each independently a hydrogen atom, substituted or unsubstituted alkyl group having 1 to 50 carbon atoms, substituted or unsubstituted biphenyl group, substituted or unsubstituted naphthyl group, substituted or unsubstituted phenanthryl group, substituted or unsubstituted fluorenyl group, substituted or unsubstituted 9,9'-spirobifluorenyl group, or group represented by the formula (4);

at least one of $R_{11}$ to $R_{14}$ or $R_{21}$ to $R_{24}$ is not a hydrogen atom;

in the formulae (120Y), and (120Z):

at least one combination of adjacent two or more of $R_{31}$ to $R_{33}$, $R_{41}$ to $R_{43}$, $R_{51}$ to $R_{54}$, and $R_{61}$ to $R_{64}$ are mutually bonded to form a substituted or unsubstituted monocyclic ring, mutually bonded to form a substituted or unsubstituted fused ring, or not mutually bonded;

$R_{31}$ to $R_{34}$, $R_{41}$ to $R_{44}$, $R_{51}$ to $R_{54}$, and $R_{61}$ to $R_{64}$ forming neither the substituted or unsubstituted monocyclic ring nor the substituted or unsubstituted fused ring are each independently a hydrogen atom, substituted or unsubstituted alkyl group having 1 to 50 carbon atoms, substituted or unsubstituted phenyl group, substituted or unsubstituted biphenyl group, substituted or unsubstituted naphthyl group, substituted or unsubstituted phenanthryl group, substituted or unsubstituted fluorenyl group, substituted or unsubstituted spirobifluorenyl group, or group represented by the formula (4);

at least one of $R_{31}$ to $R_{34}$ or $R_{41}$ to $R_{44}$ is not a hydrogen atom;

at least one of $R_{51}$ to $R_{54}$ or $R_{61}$ to $R_{64}$ is not a hydrogen atom;

in the compound represented by the formula (120X), a combination of $R_{11}$ and $R_{13}$ and a combination of $R_{21}$ and $R_{23}$ are mutually different or a combination of $R_{12}$ and $R_{14}$ and a combination of $R_{22}$ and $R_{24}$ are mutually different;

in the compound represented by the formula (120Y), a combination of $R_{31}$ and $R_{41}$ and at least one combination of a combination of $R_{32}$ and $R_{42}$, a combination of $R_{33}$ and $R_{43}$, or a combination of $R_{34}$ and $R_{44}$ are mutually different; and in the compound represented by the formula (120Z), a combination of $R_{51}$ and $R_{61}$ and at least one combination of a combination of $R_{52}$ and $R_{62}$, a combination of $R_{53}$ and $R_{63}$, or a combination of $R_{54}$ and $R_{64}$ are mutually different.

[Formula 59]

(4)

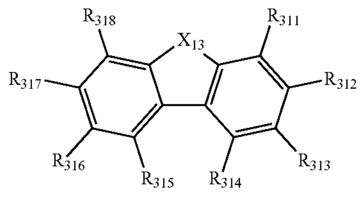

In the formula (4): $X_{13}$ is an oxygen atom, sulfur atom, or $NR_{319}$;

at least one combination of adjacent two or more of $R_{311}$ to $R_{318}$ are mutually bonded to form a substituted or unsubstituted monocyclic ring, mutually bonded to form a substituted or unsubstituted fused ring, or not mutually bonded;

$R_{311}$ to $R_{319}$ forming neither the substituted or unsubstituted monocyclic ring nor the substituted or unsubstituted fused ring are each independently a hydrogen atom, substituted or unsubstituted alkyl group having 1 to 50 carbon atoms, substituted or unsubstituted heterocyclic group having 5 to 50 ring atoms, substituted or unsubstituted phenyl group, substituted or unsubstituted biphenyl group, substituted or unsubstituted terphenyl group, substituted or unsubstituted naphthyl group, substituted or unsubstituted anthryl group, substituted or unsubstituted phenanthryl group, substituted or unsubstituted chrysenyl group, substituted or unsubstituted triphenylenyl group, substituted or unsubstituted fluorenyl group, substituted or unsubstituted 9,9'-spirobifluorenyl group, substituted or unsubstituted 9,9-dimethylfluorenyl group, or substituted or unsubstituted 9,9-diphenylfluorenyl group; and one of $R_{311}$ to $R_{319}$ forming neither the substituted or unsubstituted monocyclic ring nor the substituted or unsubstituted fused ring is a single bond bonded with at least one of $R_{11}$ to $R_{14}$, $R_{21}$ to $R_{24}$, $R_{31}$ to $R_{34}$, $R_{41}$ to $R_{44}$, $R_{51}$ to $R_{54}$, or $R_{61}$ to $R_{64}$.

In the formulae (120X), (120Y), and (120Z), a substituent for "substituted or unsubstituted" group in $R_{11}$ to $R_{14}$, $R_{21}$ to $R_{24}$, $R_{31}$ to $R_{34}$, $R_{41}$ to $R_{44}$, $R_{51}$ to $R_{54}$, $R_{61}$ to $R_{64}$, $R_{111}$ to $R_{119}$, $R_{211}$ to $R_{219}$, and $R_{311}$ to $R_{319}$ is each independently a substituted or unsubstituted alkyl group having 1 to 50 carbon atoms, substituted or unsubstituted heterocyclic group having 5 to 50 ring atoms, substituted or unsubstituted phenyl group, substituted or unsubstituted biphenyl group, substituted or unsubstituted terphenyl group, substituted or unsubstituted naphthyl group, substituted or unsubstituted anthryl group, substituted or unsubstituted phenanthryl group, substituted or unsubstituted chrysenyl group, substituted or unsubstituted triphenylenyl group, substituted or unsubstituted fluorenyl group, substituted or unsubstituted 9,9'-spirobifluorenyl group, substituted or unsubstituted 9,9-dimethylfluorenyl group, or substituted or unsubstituted 9,9-diphenylfluorenyl group.

-continued (1b)

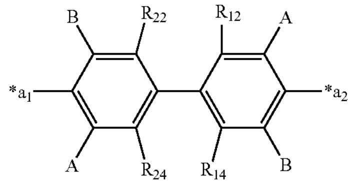

(1c)

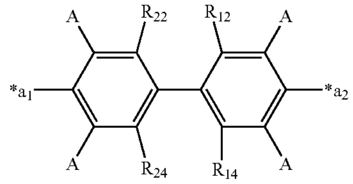

In the formulae (1a), (1b), and (1c):

$R_{12}$, $R_{14}$, $R_{22}$, and $R_{24}$ each independently represent the same as $R_{12}$, $R_{14}$, $R_{22}$, and $R_{24}$ in the formula (120X);

$*a_1$ represents a bonding position with *11 in the formula (120X); and $*a_2$ represents a bonding position with *12 in the formula (120X).

For instance, supposing that $R_{11}$ is "A" and $R_{13}$ is "B," the phrase that the combination of $R_{11}$ and $R_{13}$ is the same as the combination of $R_{21}$ and $R_{23}$ means that $R_{21}$ is "A" and $R_{23}$ is "B" (the formula (1a)), or $R_{21}$ is "B" and $R_{23}$ is "A" (the formula (1b)), where "A" and "B" are mutually different.

[Formula 60]

(120X)

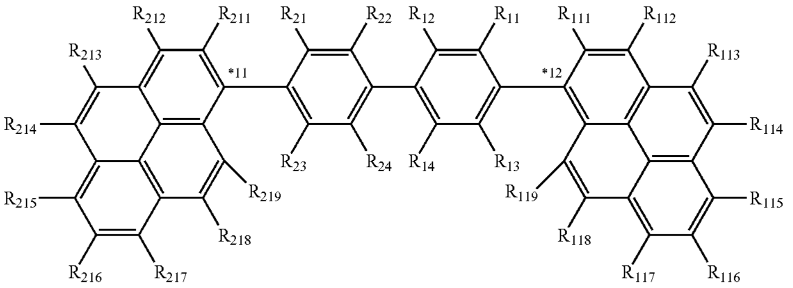

An instance, where "a combination of $R_{11}$ and $R_{13}$ and a combination of $R_{21}$ and $R_{23}$ are mutually different" in the formula (120X), will be exemplarily described below. Formulae (1a), (1 b), and (1c) below each represent a partial structure of the formula (120X).

[Formula 61]

(1a)

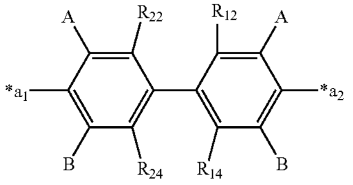

Alternatively, when $R_{11}$ and $R_{13}$ are both "A," the phrase that the combination of $R_{11}$ and $R_{13}$ is the same as the combination of $R_{21}$ and $R_{23}$ means that $R_{21}$ and $R_{23}$ are both "A" (the formula (1c)).

In other words, the phrase that the combination of $R_{11}$ and $R_{13}$ and the combination of $R_{21}$ and $R_{23}$ are mutually different means that when, for instance, $R_{11}$ is "A" and $R_{13}$ is "B," $R_{21}$ and $R_{23}$ are both "A," $R_{21}$ and $R_{23}$ are both "B," or at least one of $R_{21}$ or $R_{23}$ is "C" that is different from "A" and "B."

Alternatively, when $R_{11}$ and $R_{13}$ are both "A" and at least one of $R_{21}$ or $R_{23}$ is "B," at least one of $R_{21}$ or $R_{23}$ is "C" that is different from "A."

The same applies to the phrase "a combination of $R_{12}$ and $R_{14}$ and a combination of $R_{22}$ and $R_{24}$ are mutually different" for the formula (120X).

[Formula 62]

(120Y)

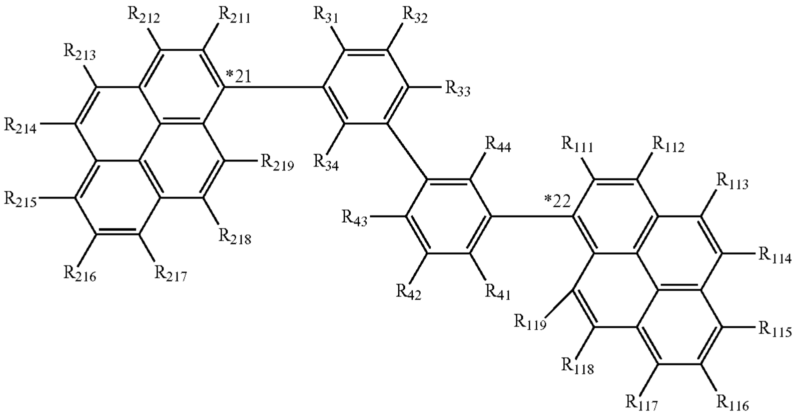

The formula (120Y), where "a combination of $R_{31}$ and $R_{41}$ and at least one combination of a combination of $R_{32}$ and $R_{42}$, a combination of $R_{33}$ and $R_{43}$, or a combination of $R_{34}$ and $R_{44}$ are mutually different," will be described below with reference to an instance where "a combination of $R_{31}$ and $R_{41}$ and a combination of $R_{32}$ and $R_{42}$ are mutually different." It should be noted that formulae (2a), (2b), and (2c) below each represent a partial structure of the formula (120Y).

[Formula 63]

(2a)

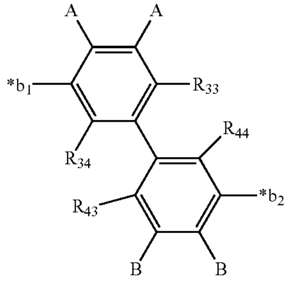

(2b)

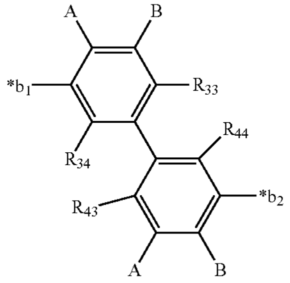

-continued (2c)

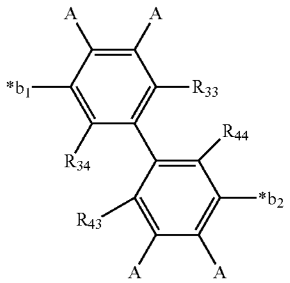

In the formulae (2a), (2b), and (2c):

$R_{33}$, $R_{34}$, $R_{43}$, and $R_{44}$ each independently represent the same as $R_{33}$, $R_{34}$, $R_{43}$, and $R_{44}$ in the formula (120Y);

$*b_1$ represents a bonding position with *21 in the formula (120Y); and $*b_2$ represents a bonding position with *22 in the formula (120Y).

For instance, when $R_{31}$ is "A" and $R_{41}$ is "B" in a combination, the phrase that "a combination of $R_{31}$ and $R_{41}$ and a combination of $R_{32}$ and $R_{42}$ are the same" means that $R_{32}$ is "A" and $R_{42}$ is "B" (the formula (2a)) or $R_{32}$ is "B" and $R_{42}$ is "A" (the formula (2b)), where "A" and "B" are mutually different; and when $R_{31}$ and $R_{41}$ are both "A," the phrase "a combination of $R_{31}$ and $R_{41}$ and a combination of $R_{32}$ and $R_{42}$ are the same" means that $R_{32}$ and $R_{42}$ are both "A" (the formula (2c)).

In other words, the phrase that the combination of $R_{31}$ and $R_{41}$ and the combination of $R_{32}$ and $R_{42}$ are mutually different means that when, for instance, $R_{31}$ is "A" and $R_{41}$ is "B," $R_{32}$ and $R_{42}$ are both "A," $R_{32}$ and $R_{42}$ are both "B" or at least one of $R_{32}$ or $R_{42}$ is "C" that is different from "A" and "B"; and when $R_{31}$ and $R_{41}$ are both "A," and at least one of $R_{32}$ or $R_{42}$ is "B," at least one of $R_{32}$ or $R_{42}$ is "C" that is different from "A."

The same applies to the phrases "a combination of $R_{31}$ and $R_{41}$ and a combination of $R_{33}$ and $R_{43}$ are mutually different" and "a combination of $R_{31}$ and $R_{41}$ and a combination of $R_{34}$ and $R_{44}$ are mutually different" in the formula (120Y).

[Formula 64]

(120Z)

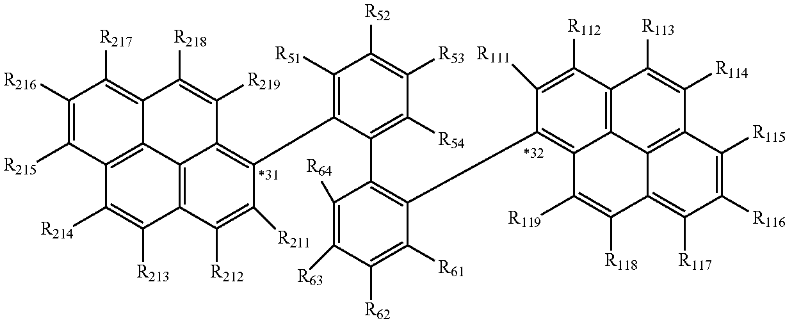

The formula (120Z), where "a combination of $R_{51}$ and $R_{61}$ and at least one combination of a combination of $R_{52}$ and $R_{62}$, a combination of $R_{53}$ and $R_{63}$, and a combination of $R_{54}$ and $R_{64}$ are mutually different," will be described below with reference to an instance where "a combination of $R_{51}$ and $R_{61}$ and a combination of $R_{52}$ and $R_{62}$ are mutually different." Formulae (3a), (3b), and (3c) below each represent a partial structure of the formula (120Z).

[Formula 65]

(3a)

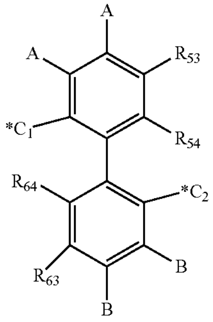

(3b)

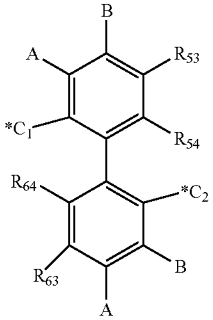

(3c)

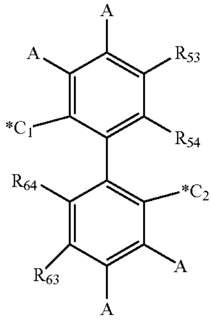

In the formulae (3a), (3b), and (3c):

$R_{53}$, $R_{54}$, $R_{63}$, and $R_{64}$ each independently represent the same as $R_{53}$, $R_{54}$, $R_{63}$, and $R_{64}$ in the formula (120Z);

*c1 represents a bonding position with *31 in the formula (120Z); and

*c2 represents a bonding position with *32 in the formula (120Z).

For instance, when $R_{51}$ is "A" and $R_{61}$ is "B" in a combination, the phrase that the combination of $R_{51}$ and $R_{61}$ is the same as the combination of $R_{52}$ and $R_{62}$ means that $R_{52}$ is "A" and $R_{62}$ is "B" (the formula (3a)) or $R_{52}$ is "B" and $R_{62}$ is "A" (the formula (3b)), where "A" and "B" are mutually different.

Alternatively, when $R_{51}$ and $R_{61}$ are both "A," the phrase that the combination of $R_{51}$ and $R_{61}$ is the same as the combination of $R_{52}$ and $R_{62}$ means that $R_{52}$ and $R_{62}$ are both "A" (the formula (3c)).

In other words, the phrase that the combination of $R_{51}$ and $R_{61}$ and the combination of $R_{52}$ and $R_{62}$ are mutually different means that when, for instance, $R_{51}$ is "A" and $R_{61}$ is "B," $R_{52}$ and $R_{62}$ are both "A," $R_{52}$ and $R_{62}$ are both "B," or at least one of $R_{52}$ or $R_{62}$ is "C" that is different from "A" and "B."

Alternatively, when $R_{51}$ and $R_{61}$ are both "A" and at least one of $R_{52}$ or $R_{62}$ is "B", at least one of $R_{52}$ or $R_{62}$ is "C" that is different from "A."

The same applies to the phrases "a combination of $R_{51}$ and $R_{61}$ and a combination of $R_{53}$ and $R_{63}$ are mutually different" and "a combination of $R_{51}$ and $R_{61}$ and a combination of $R_{54}$ and $R_{64}$ are mutually different" in the formula (120Z).

In the compound of the arrangement D, in order to more effectively achieve the effect for increasing the lifetime by deuteration even in a high-speed film formation, a total number of carbon atoms included in the group linking two pyrene rings (i.e. a pyrene ring having $R_{111}$ to $R_{119}$ and a pyrene ring having $R_{211}$ to $R_{219}$) is more preferably 21 or less.

The group linking the two pyrene rings is a group formed of a phenylene group having $R_{11}$ to $R_{14}$ and phenylene group having $R_{21}$ to $R_{24}$ in the compound represented by the formula (120X), a group formed of a phenylene group having $R_{31}$ to $R_{34}$ and phenylene group having $R_{41}$ to $R_{44}$ in the compound represented by the formula (120Y), and a group formed of a phenylene group having $R_{51}$ to $R_{54}$ and phenylene group having $R_{61}$ to $R_{64}$ in the compound represented by the formula (120Z).

In the compound of the arrangement D, it is preferable that $R_{111}$ to $R_{119}$ and $R_{211}$ to $R_{219}$ are each independently a hydrogen atom, a substituted or unsubstituted alkyl group having 1 to 18 carbon atoms, a substituted or unsubstituted cycloalkyl group having 1 to 18 ring carbon atoms, a group represented by Si(Rx)(Ry)(Rz), a substituted or unsubstituted aryl group having 6 to 18 ring carbon atoms, or a substituted or unsubstituted heterocyclic group having 5 to 18 ring atoms. Rx, Ry, and Rz in Si(Rx)(Ry)(Rz) are preferably each independently an unsubstituted alkyl group having 1 to 18 carbon atoms or an unsubstituted aryl group having 6 to 18 ring carbon atoms.

In the compound of the arrangement D, $R_{111}$ to $R_{119}$ and $R_{211}$ to $R_{219}$ are preferably each independently a hydrogen atom, substituted or unsubstituted alkyl group having 1 to 18 carbon atoms, substituted or unsubstituted phenyl group, substituted or unsubstituted naphthyl group, substituted or unsubstituted phenanthryl group, substituted or unsubstituted fluorenyl group, substituted or unsubstituted dibenzofuranyl group, substituted or unsubstituted dibenzothiophenyl group, substituted or unsubstituted 9,9-dimethylfluorenyl group, or substituted or unsubstituted 9,9-diphenylfluorenyl group.

In the compound of the arrangement D, $R_{111}$ to $R_{119}$ and $R_{211}$ to $R_{219}$ are preferably hydrogen atoms.

In the compound of the arrangement D, it is preferable that at least one combination of a combination of $R_{11}$ and $R_{12}$, a combination of $R_{13}$ and $R_{14}$, a combination of $R_{21}$ and $R_{22}$, or a combination of $R_{23}$ and $R_{24}$ are not mutually bonded and at least one combination of adjacent two or more of $R_{31}$ to $R_{33}$, $R_{41}$ to $R_{43}$, $R_{51}$ to $R_{54}$, and $R_{61}$ and $R_{64}$ are not mutually bonded.

The compound according to the arrangement D is preferably represented by a formula (1-1), (2-1), or (3-1) below.

[Formula 66]

(1-1)

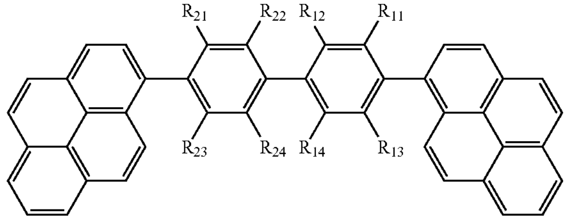

(2-1)

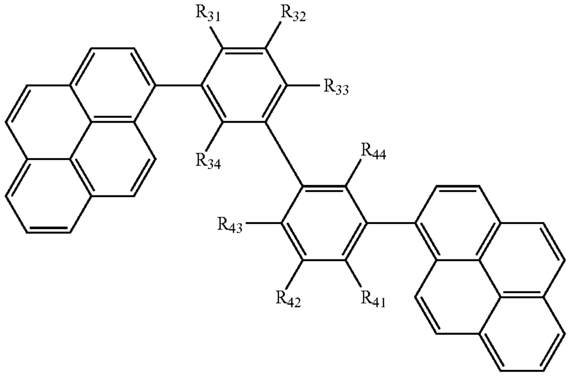

-continued (3-1)

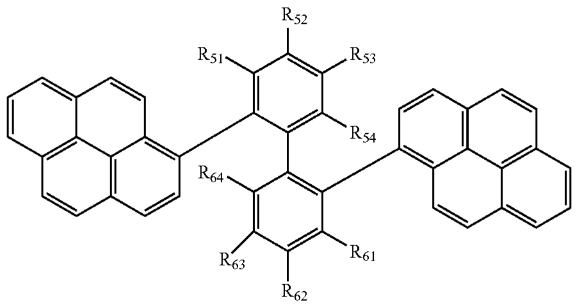

In the formulae (1-1), (2-1), and (3-1): $R_{11}$ to $R_{14}$, $R_{21}$ to $R_{24}$, $R_{31}$ to $R_{34}$, $R_{41}$ to $R_{44}$, $R_{51}$ to $R_{54}$, and $R_{61}$ to $R_{64}$ each independently represent the same as $R_{11}$ to $R_{14}$, $R_{21}$ to $R_{24}$, $R_{31}$ to $R_{34}$, $R_{41}$ to $R_{44}$, $R_{51}$ to $R_{54}$, and $R_{61}$ to $R_{64}$ in the formulae (120X), (120Y), and (120Z).

In the compound of the arrangement D, it is preferable that $R_{11}$ to $R_{14}$, $R_{21}$ to $R_{24}$, $R_{31}$ to $R_{34}$, $R_{41}$ to $R_{44}$, $R_{51}$ to $R_{54}$, and $R_{61}$ to $R_{64}$ are each independently a hydrogen atom, substituted or unsubstituted alkyl group having 1 to 8 carbon atoms, substituted or unsubstituted phenyl group, substituted or unsubstituted biphenyl group, substituted or unsubstituted naphthyl group, substituted or unsubstituted phenanthryl group, substituted or unsubstituted fluorenyl group, substituted or unsubstituted 9,9'-spirobifluorenyl group, substituted or unsubstituted 9,9-dimethylfluorenyl group, substituted or unsubstituted 9,9-diphenylfluorenyl group, substituted or unsubstituted dibenzofuranyl group, or substituted or unsubstituted dibenzothiophenyl group, and $R_{12}$, $R_{14}$, $R_{22}$, and $R_{24}$ are not a substituted or unsubstituted phenyl group.

In the compound of the arrangement D, it is preferable that at least one combination of a combination of $R_{11}$ and $R_{12}$, a combination of $R_{13}$ and $R_{14}$, a combination of $R_{21}$ and $R_{22}$, or a combination of $R_{23}$ and $R_{24}$ are mutually bonded to form a substituted or unsubstituted monocyclic ring or a substituted or unsubstituted fused ring, and at least one combination of adjacent two or more of $R_{31}$ to $R_{33}$, $R_{41}$ to $R_{43}$, $R_{51}$ to $R_{54}$, and $R_{61}$ to $R_{64}$ are mutually bonded to form a substituted or unsubstituted monocyclic ring or a substituted or unsubstituted fused ring.

The compound of the arrangement D is preferably represented by one of formulae (1-2), (2-2) to (2-3), and (3-2) to (3-4) below.

[Formula 67]

(1-2)

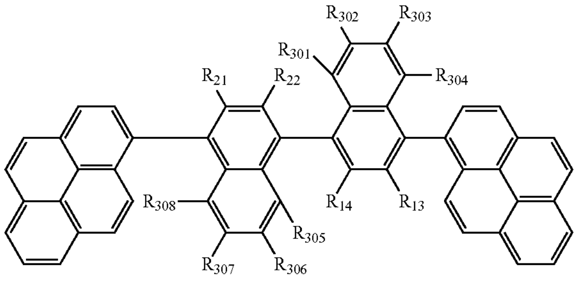

-continued (2-2)

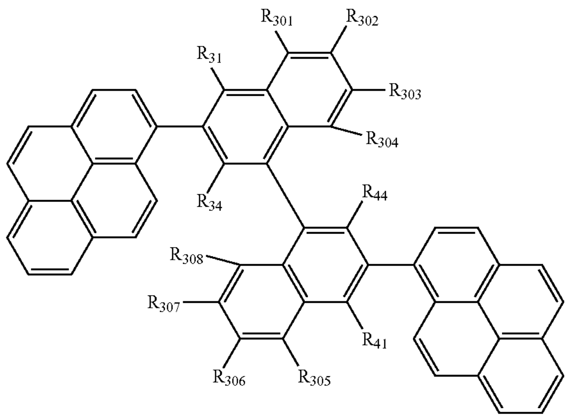

(2-3)

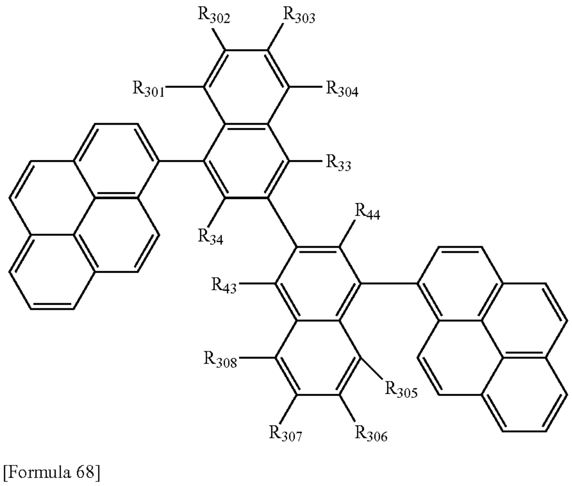

[Formula 68]

(3-2)

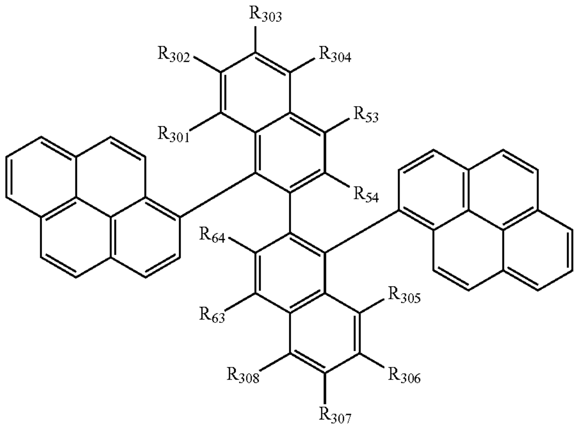

-continued (3-3)

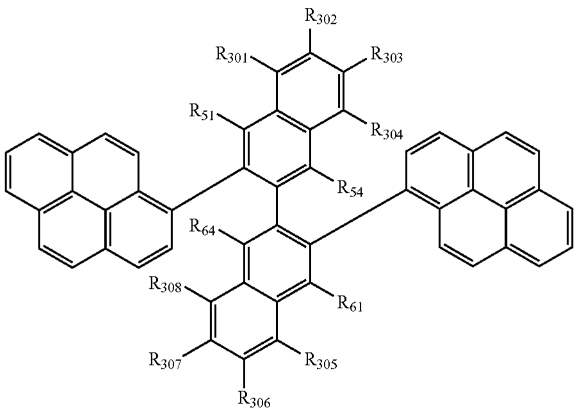

(3-4)

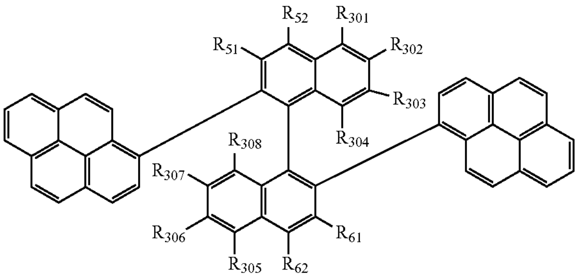

In the formulae (1-2), (2-2) to (2-3), and (3-2) to (3-4): $R_{13}$ to $R_{14}$, $R_{21}$ to $R_{22}$, $R_{31}$, $R_{33}$, $R_{34}$, $R_{41}$, $R_{43}$, $R_{44}$, $R_{51}$ to $R_{54}$, and $R_{61}$ to $R_{64}$ each independently represent the same as $R_{13}$ to $R_{14}$, $R_{21}$ to $R_{22}$, $R_{31}$, $R_{33}$, $R_{34}$, $R_{41}$, $R_{43}$, $R_{44}$, $R_{51}$ to $R_{54}$, and $R_{61}$ to $R_{64}$ in the formulae (120X), (120Y), and (120Z); and $R_{301}$ to $R_{308}$ each independently represent the same as $R_{11}$ to $R_{14}$, $R_{21}$ to $R_{24}$, $R_{31}$ to $R_{34}$, $R_{41}$ to $R_{44}$, $R_{51}$ to $R_{54}$, and $R_{61}$ to $R_{64}$ in the formulae (120X), (120Y), and (120Z).

In the formulae (1-2), (2-2) to (2-3), and (3-2) to (3-4), it is preferable that $R_{13}$ to $R_{14}$, $R_{21}$ to $R_{22}$, $R_{31}$, $R_{33}$, $R_{34}$, $R_{41}$, $R_{43}$, $R_{44}$, $R_{51}$ to $R_{54}$, $R_{61}$ to $R_{64}$, and $R_{304}$ to $R_{308}$ are each independently a hydrogen atom, substituted or unsubstituted alkyl group having 1 to 8 carbon atoms, substituted or unsubstituted phenyl group, substituted or unsubstituted biphenyl group, substituted or unsubstituted naphthyl group, substituted or unsubstituted phenanthryl group, substituted or unsubstituted fluorenyl group, substituted or unsubstituted 9,9'-spirobifluorenyl group, substituted or unsubstituted 9,9-dimethylfluorenyl group, substituted or unsubstituted 9,9-diphenylfluorenyl group, substituted or unsubstituted dibenzofuranyl group, or substituted or unsubstituted dibenzothiophenyl group, and $R_{14}$ and $R_{22}$ are not substituted or unsubstituted phenyl groups.

In the compound of the arrangement D, at least one of $R_{11}$ to $R_{14}$, $R_{21}$ to $R_{24}$, $R_{31}$ to $R_{34}$, $R_{41}$ to $R_{44}$, $R_{51}$ to $R_{54}$, $R_{61}$ to $R_{64}$, or $R_{301}$ to $R_{308}$ is preferably a deuterium atom.

In the compound of the arrangement D, it is preferable that at least one of $R_{11}$ to $R_{14}$, $R_{21}$ to $R_{24}$, $R_{31}$ to $R_{34}$, $R_{41}$ to $R_{44}$, $R_{51}$ to $R_{54}$, $R_{61}$ to $R_{64}$, Or $R_{301}$ to $R_{308}$ is a substituent, and at least one of $R_{11}$ to $R_{14}$, $R_{21}$ to $R_{24}$, $R_{31}$ to $R_{34}$, $R_{41}$ to $R_{44}$, $R_{51}$ to $R_{54}$, $R_{61}$ to $R_{64}$, or $R_{301}$ to $R_{308}$ as the substituent is each independently one or more deuterium atom(s).

In the compound of the arrangement D, it is preferable that $R_{111}$ to $R_{119}$ are deuterium atoms or $R_{211}$ to $R_{219}$ are deuterium atoms. $R_{111}$ to $R_{119}$ and $R_{211}$ to $R_{219}$ are preferably deuterium atoms. It is preferable that at least one of $R_{111}$ to $R_{119}$ or $R_{211}$ to $R_{219}$ is a substituent and at least one of $R_{111}$ to $R_{119}$ or $R_{211}$ to $R_{219}$ as the substituent is each independently one or more deuterium atom(s).

In the compounds of the arrangements A, B, C, and D, a substituent for "substituted or unsubstituted" group is preferably each independently a substituted or unsubstituted alkyl group having 1 to 50 carbon atoms, substituted or unsubstituted phenyl group, substituted or unsubstituted biphenyl group, substituted or unsubstituted terphenyl group, substituted or unsubstituted naphthyl group, substituted or unsubstituted anthryl group, substituted or unsubstituted phenanthryl group, substituted or unsubstituted chrysenyl group, substituted or unsubstituted triphenylenyl group, substituted or unsubstituted fluorenyl group, substituted or unsubstituted 9,9'-spirobifluorenyl group, substituted or unsubstituted 9,9-dimethylfluorenyl group, substituted or unsubstituted 9,9-diphenylfluorenyl group, substituted or unsubstituted pyridyl group, substituted or unsubstituted pyrimidinyl group, substituted or unsubstituted triazinyl group, substituted or unsubstituted quinolyl group, substituted or unsubstituted isoquinolyl group, substituted or unsubstituted quinazolinyl group, substituted or unsubstituted benzimidazolyl group, substituted or unsubstituted phenanthrolinyl group, substituted or unsubstituted 1-carbazolyl group, substituted or unsubstituted 2-carbazolyl group, substituted or unsubstituted 3-carbazolyl group, substituted or unsubstituted 4-carbazolyl group, substituted or unsubstituted 9-carbazolyl group, substituted or unsubstituted benzocarbazolyl group, substituted or unsubstituted azacarbazolyl group, substituted or unsubstituted diazacarbazolyl group, substituted or unsubstituted dibenzofuranyl group, substituted or unsubstituted naphthobenzofuranyl group, substituted or unsubstituted azadibenzofuranyl group, substituted or unsubstituted diazadibenzofuranyl group, substituted or unsubstituted dibenzothiophenyl group, substituted or unsubstituted naphthobenzothiophenyl group, substituted or unsubstituted azadibenzothiophenyl group, or substituted or unsubstituted diazadibenzothiophenyl group.

In the compounds of the arrangements A, B, C, and D, a substituent for "substituted or unsubstituted" group is more preferably each independently a substituted or unsubstituted alkyl group having 1 to 18 carbon atoms, substituted or unsubstituted phenyl group, substituted or unsubstituted naphthyl group, substituted or unsubstituted phenanthrolinyl group, substituted or unsubstituted fluorenyl group, substituted or unsubstituted dibenzofuranyl group, substituted or unsubstituted dibenzothiophenyl group, substituted or unsubstituted 9,9-dimethylfluorenyl group, or substituted or unsubstituted 9,9-diphenylfluorenyl group.

In the compounds of the arrangements A, B, C, and D, a substituent for "substituted or unsubstituted" group is further preferably each independently an unsubstituted alkyl group having 1 to 18 carbon atoms, unsubstituted phenyl group, unsubstituted naphthyl group, unsubstituted phenanthrolinyl group, substituted or unsubstituted fluorenyl group, unsubstituted dibenzofuranyl group, unsubstituted dibenzothiophenyl group, unsubstituted 9,9-dimethylfluorenyl group, or unsubstituted 9,9-diphenylfluorenyl group.

Manufacturing Method of Compound According to Exemplary Embodiment

The compound (the compound represented by the formula (1)) according to the present exemplary embodiment and the compounds of the arrangements A, B, C, and D are producible by any known methods. Further, the compound according to the exemplary embodiment and the compounds of the arrangements A, B, C, and D are also producible by application of known substitution reactions and materials depending on a target compound in accordance with known methods.

Specific examples of the compound (the compound represented by the formula (1)) according to the present exemplary embodiment and the compounds of the arrangements A, B, C, and D include compounds below. However, the invention is not limited to these specific examples. D represents a deuterium atom.

[Formula 69]

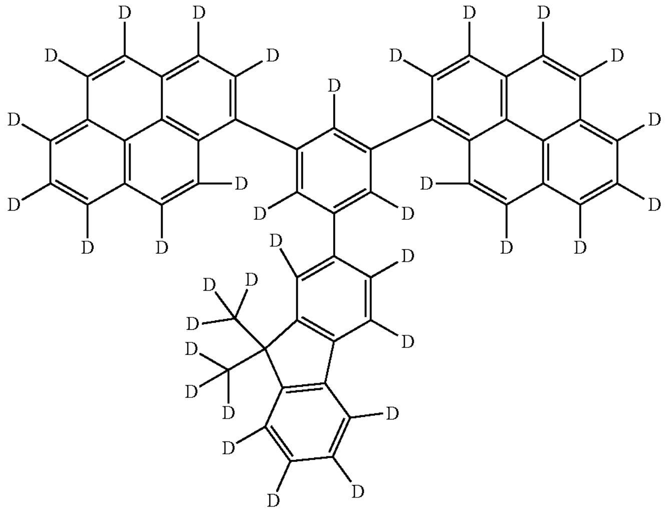

-continued
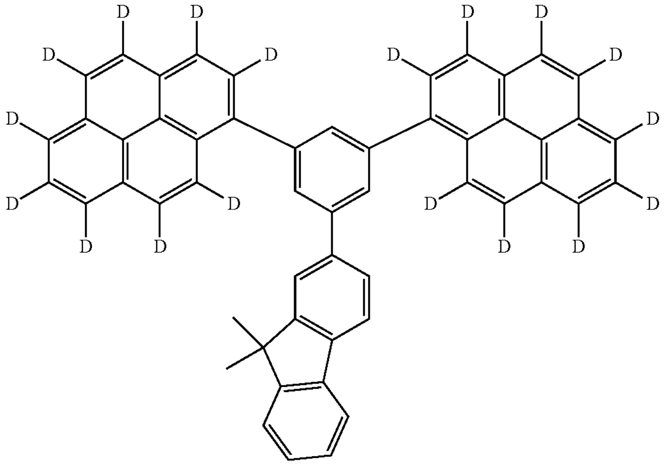
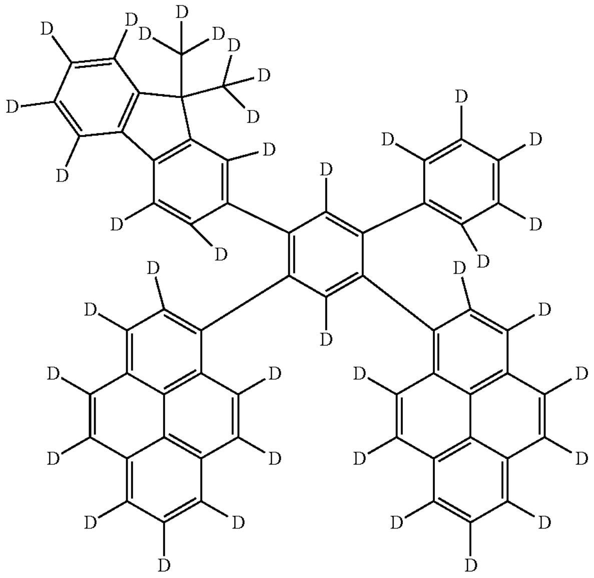
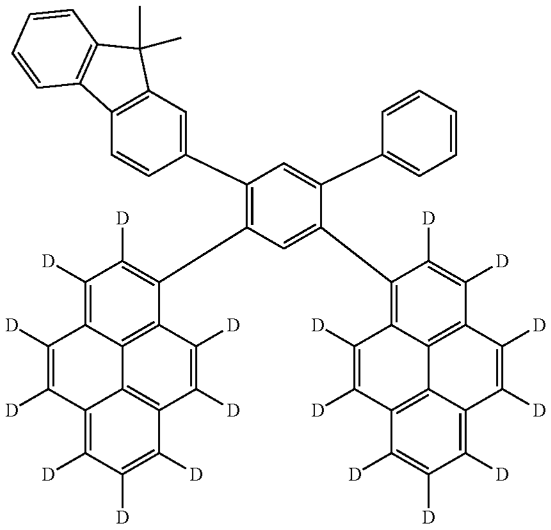
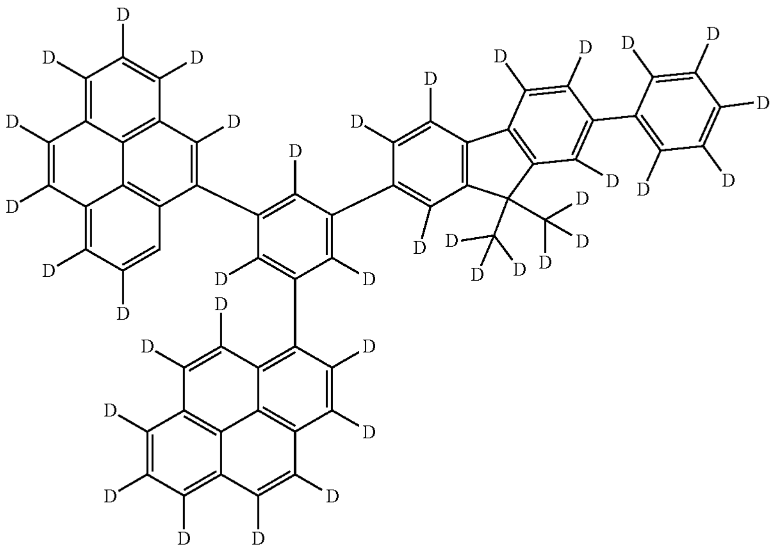

-continued
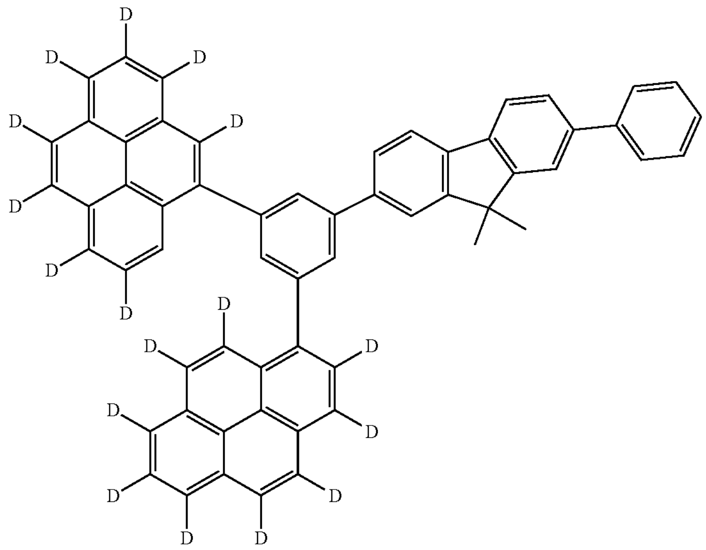
[Formula 70]
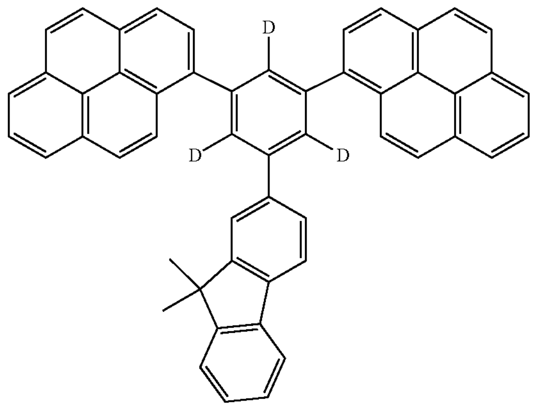
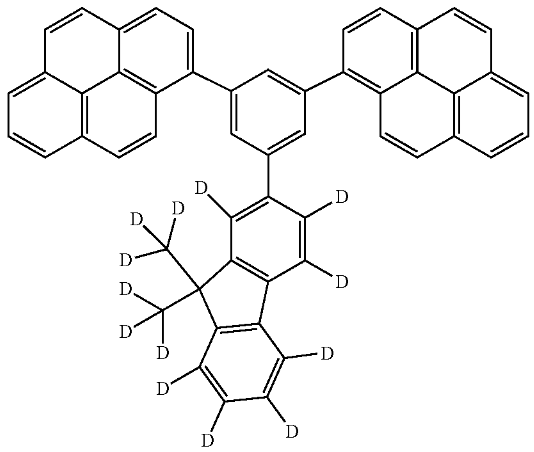
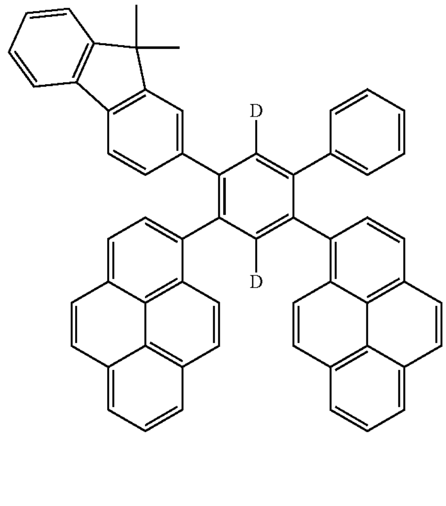
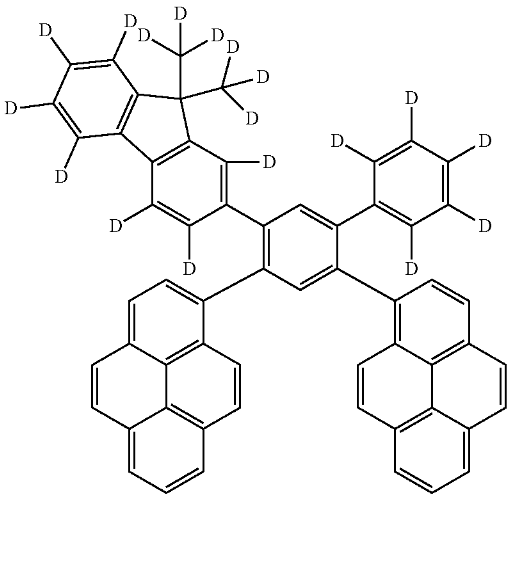

-continued
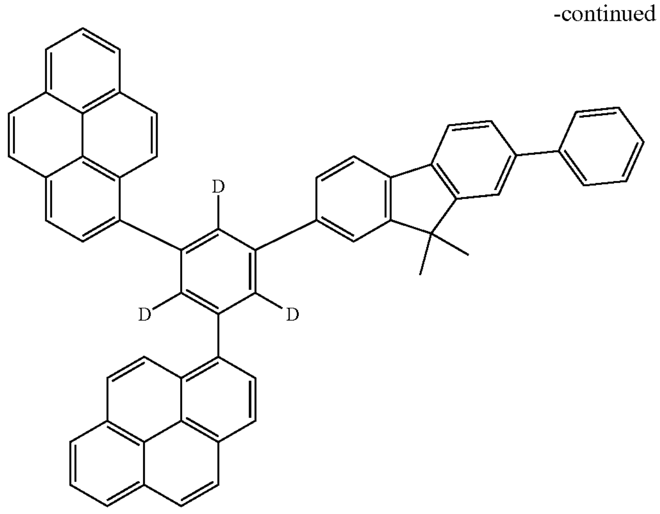
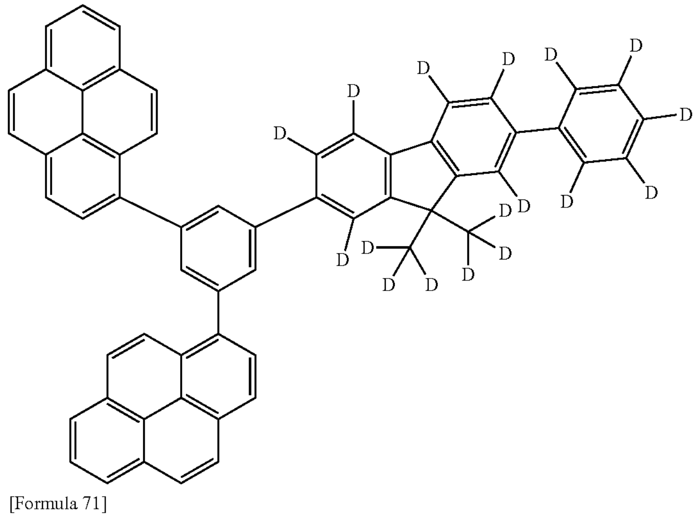
[Formula 71]
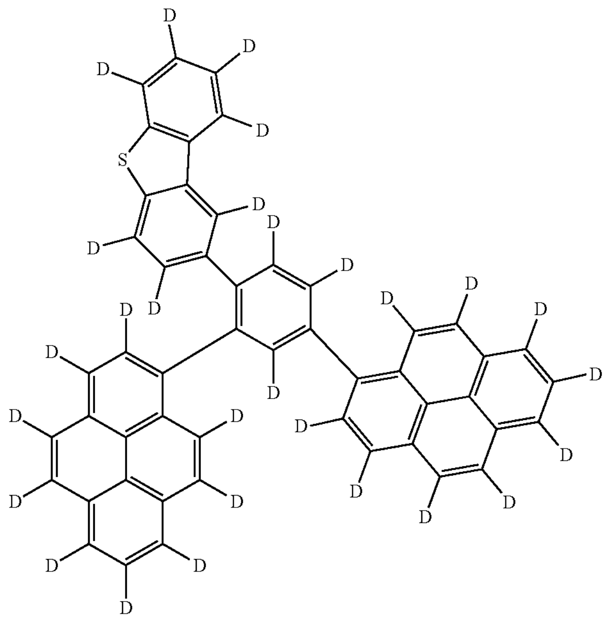
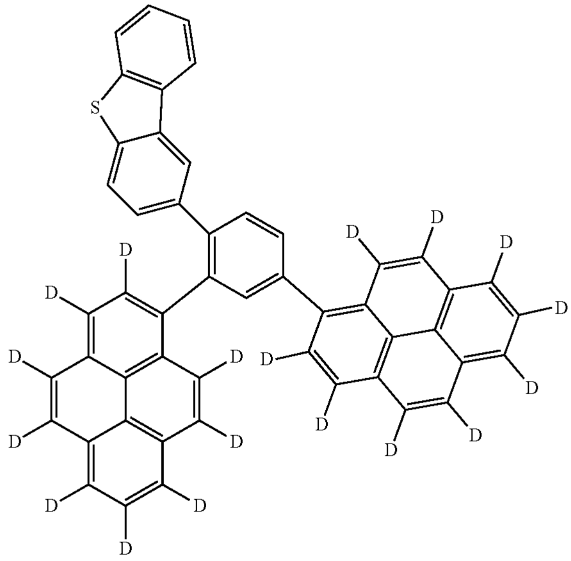

-continued
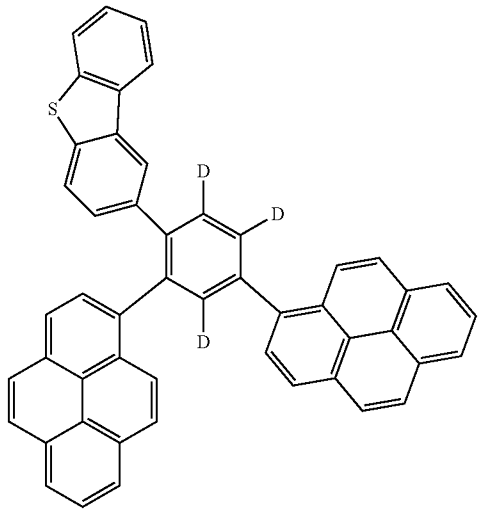
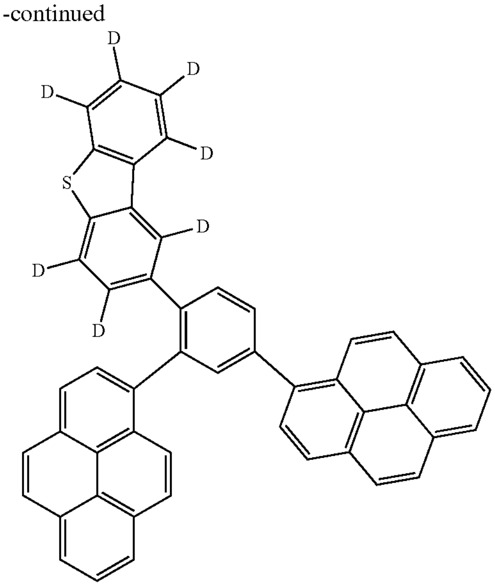
[Formula 72]
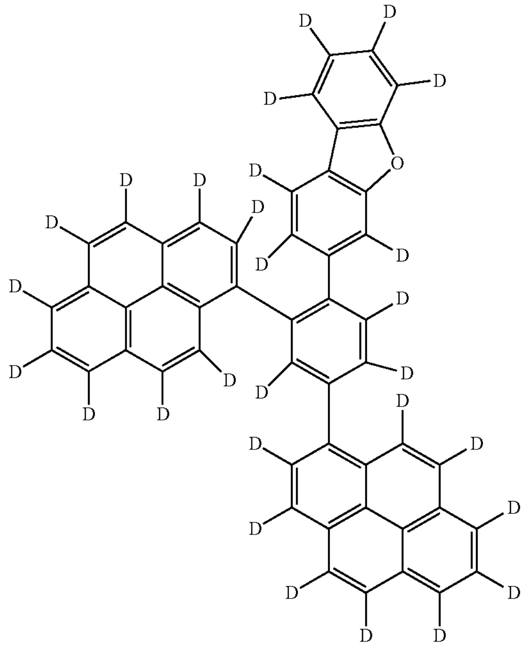
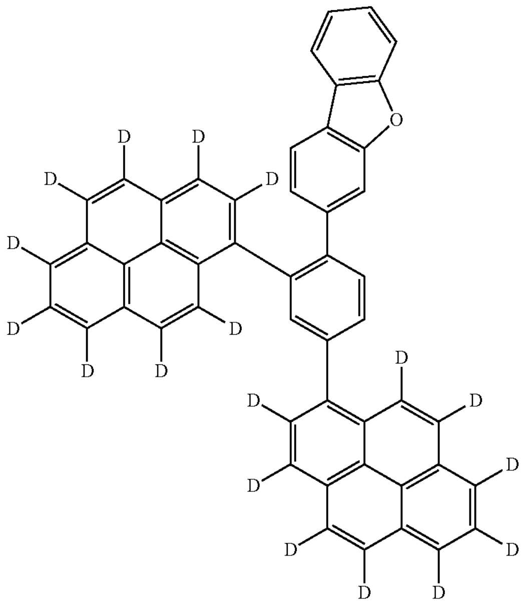

-continued
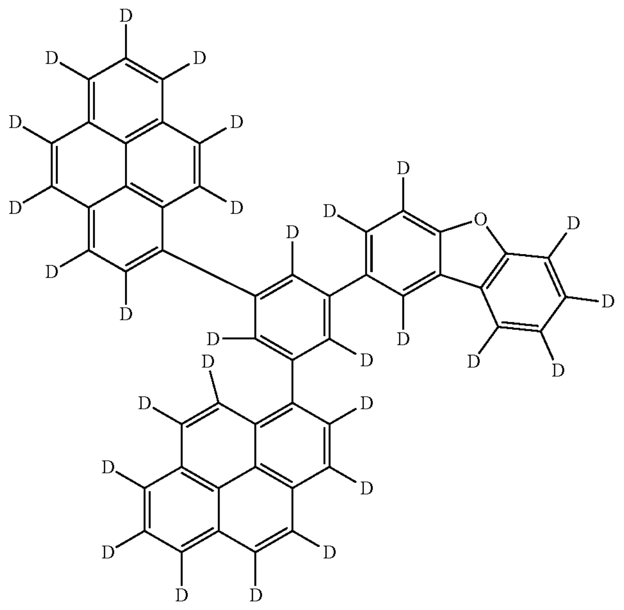
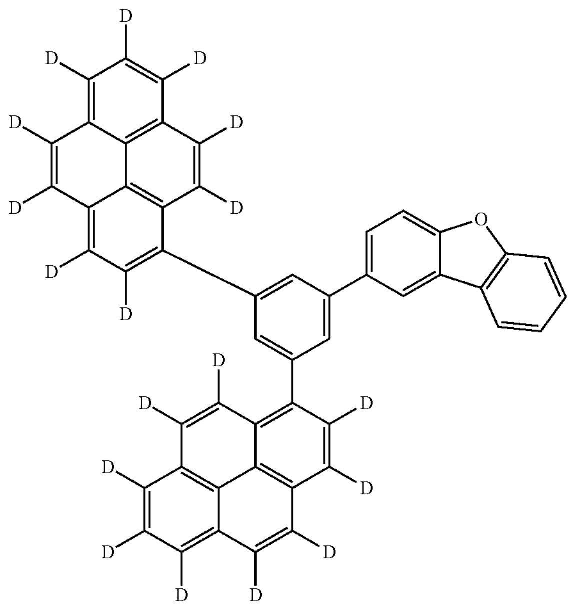
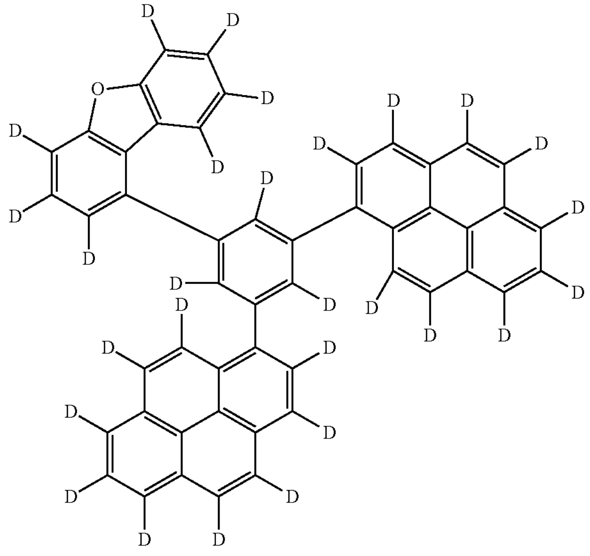
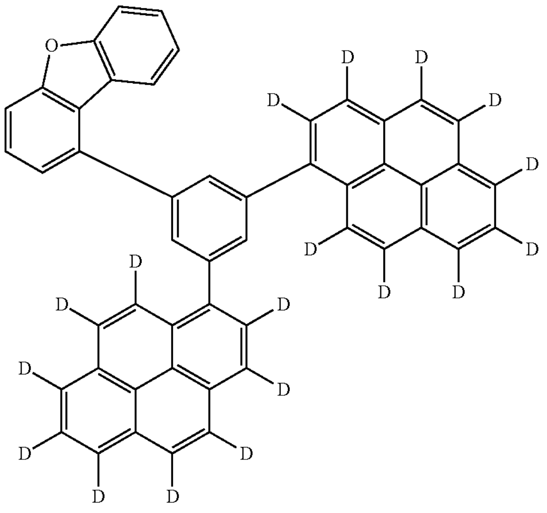

-continued
[Formula 73]
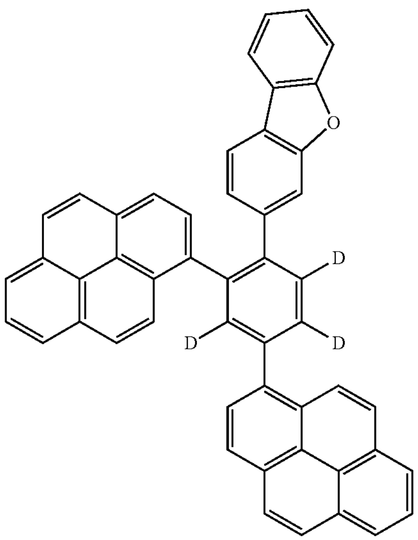
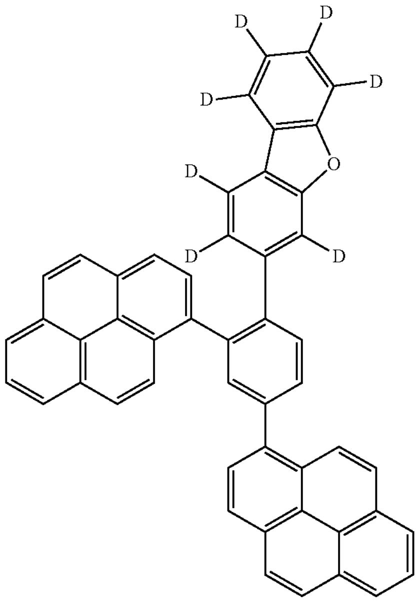
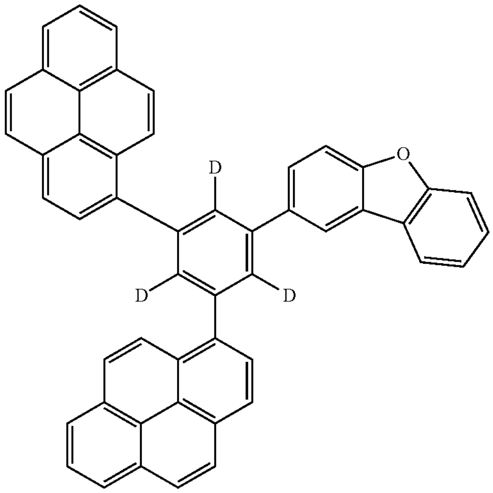
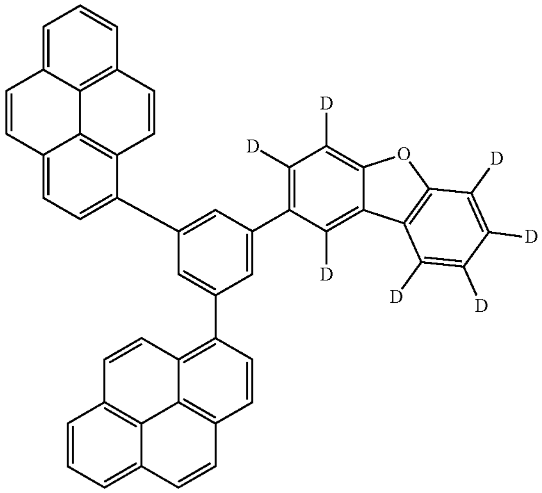
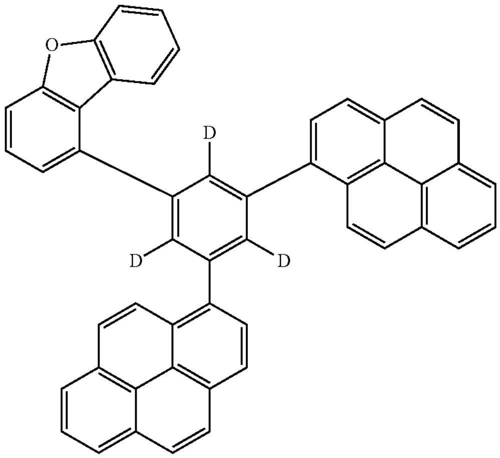
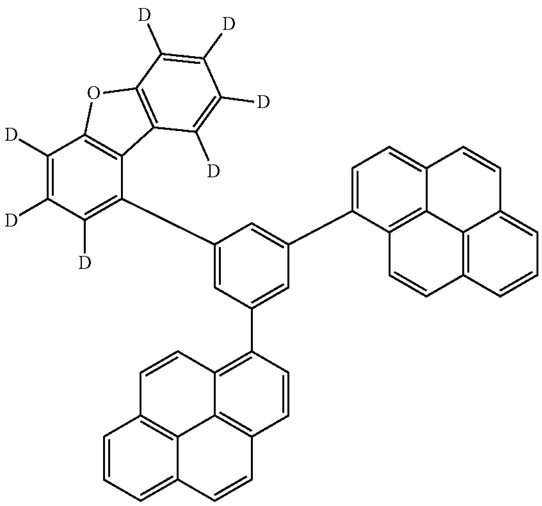

-continued
[Formula 74]
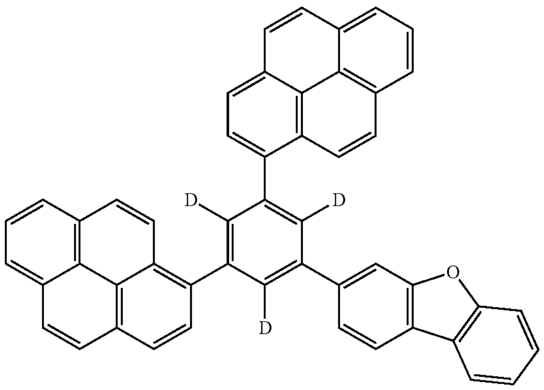
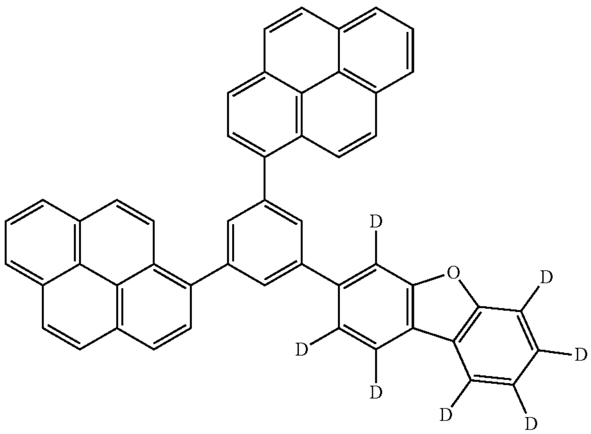
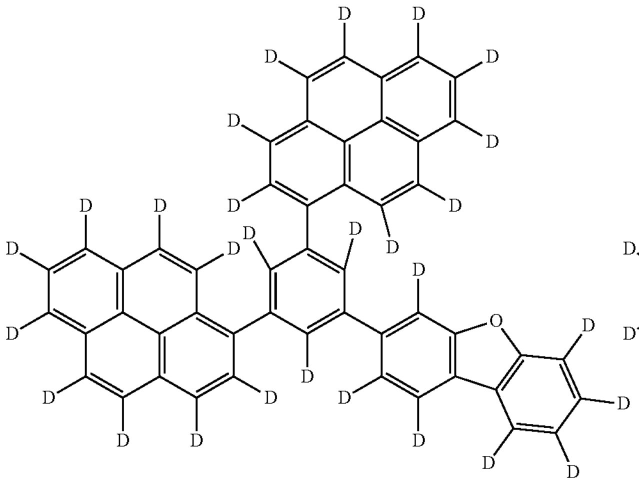
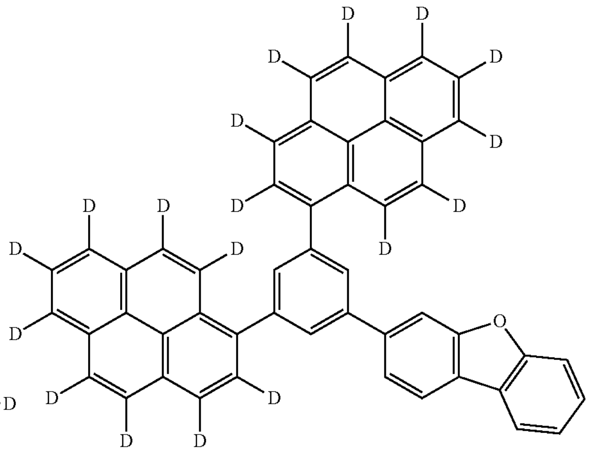
[Formula 75]
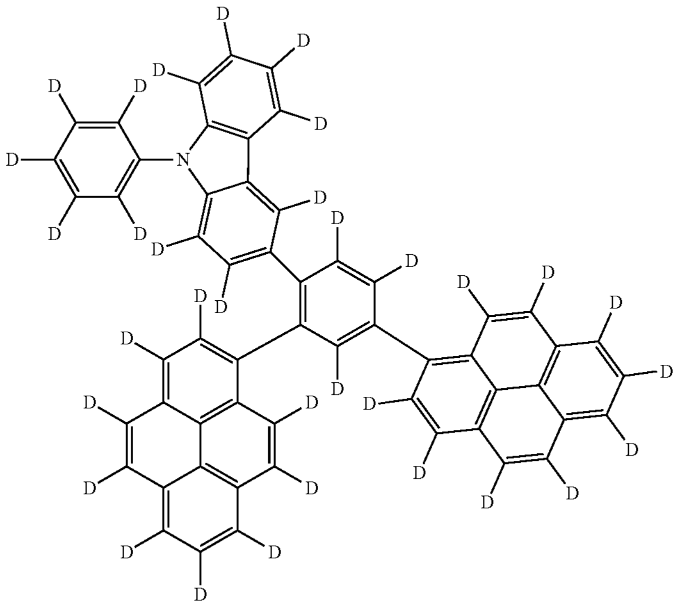

-continued
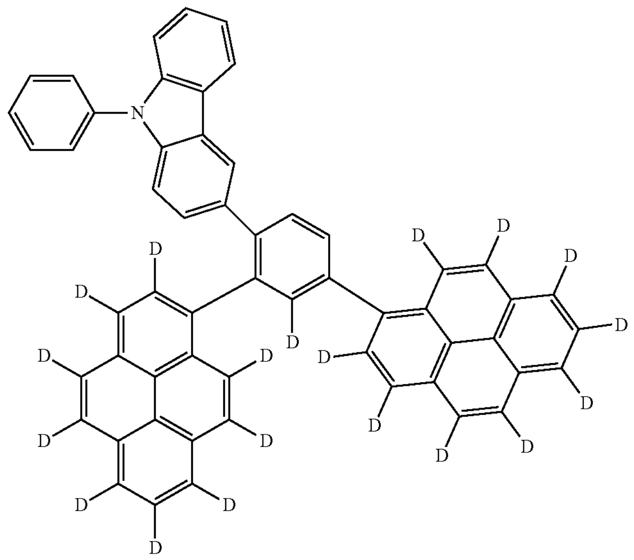
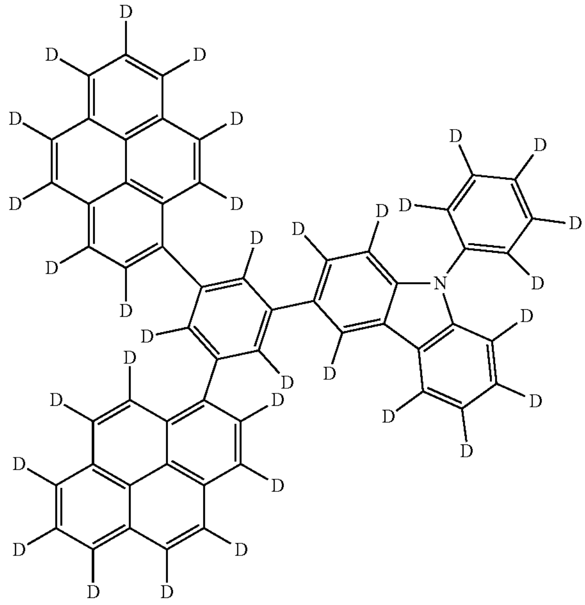
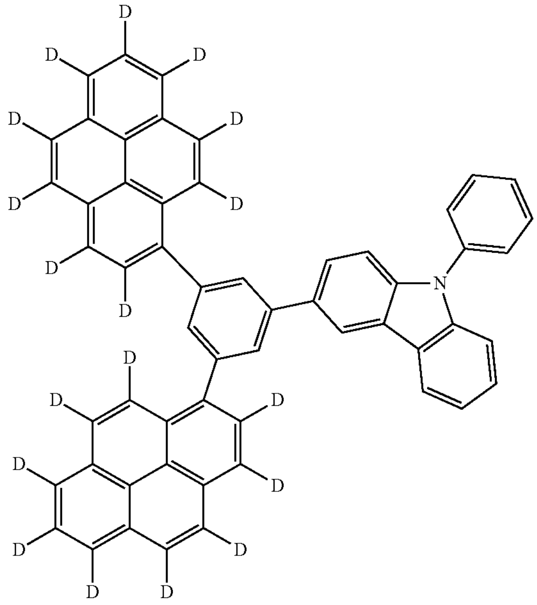

-continued
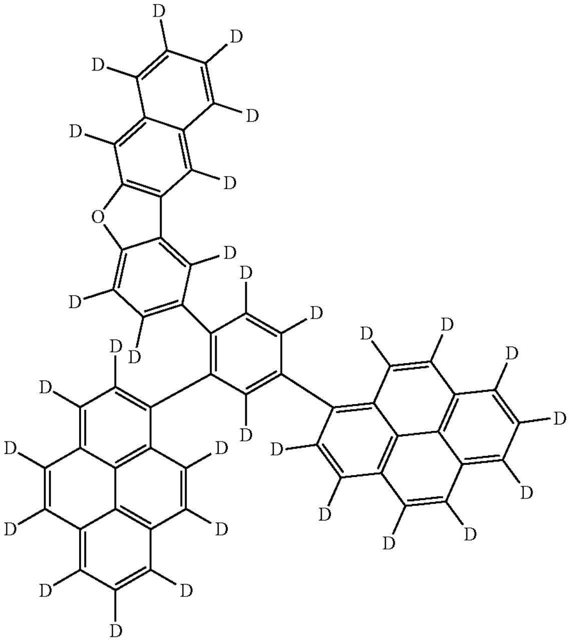
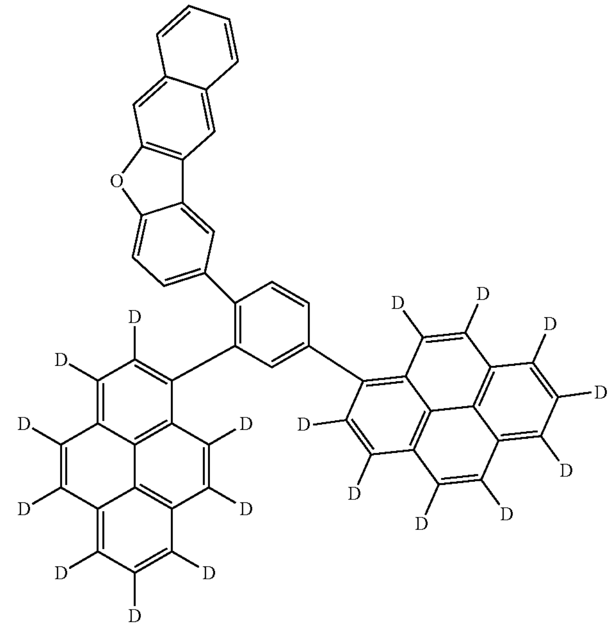
[Formula 76]
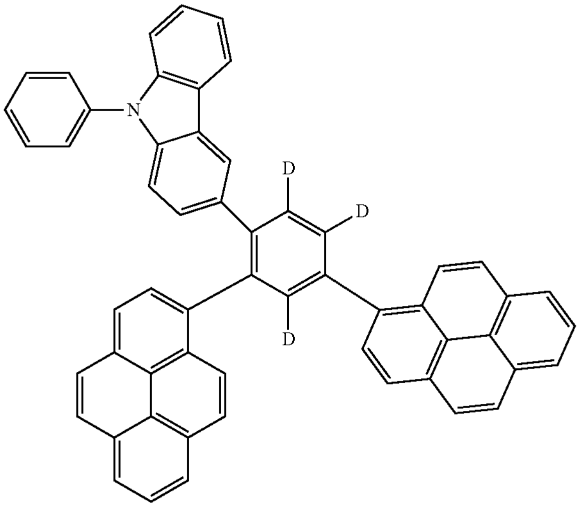
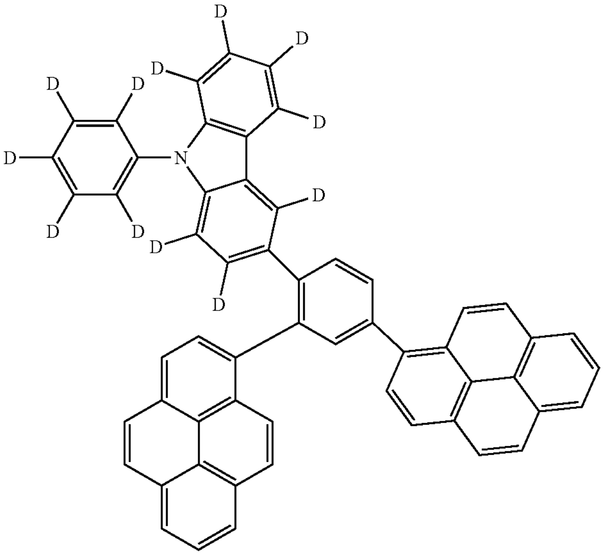
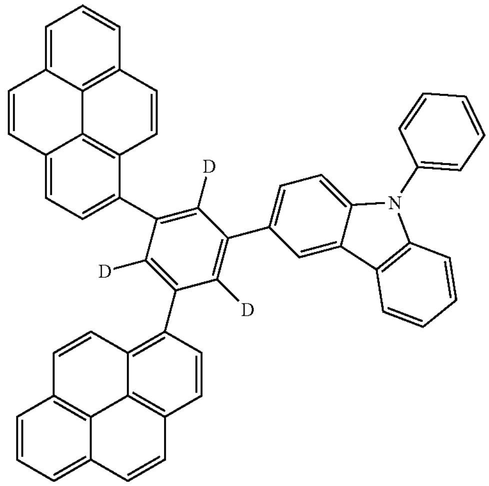
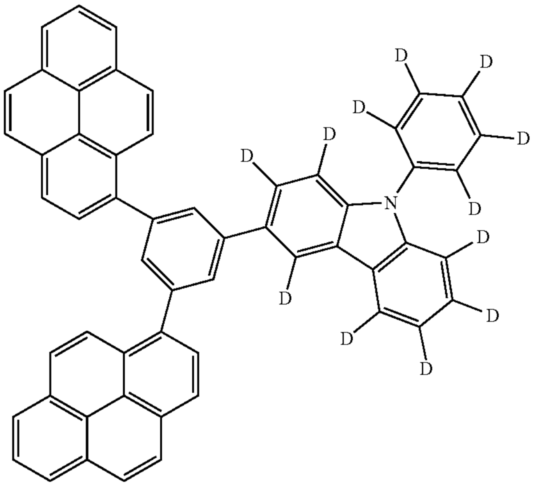

-continued
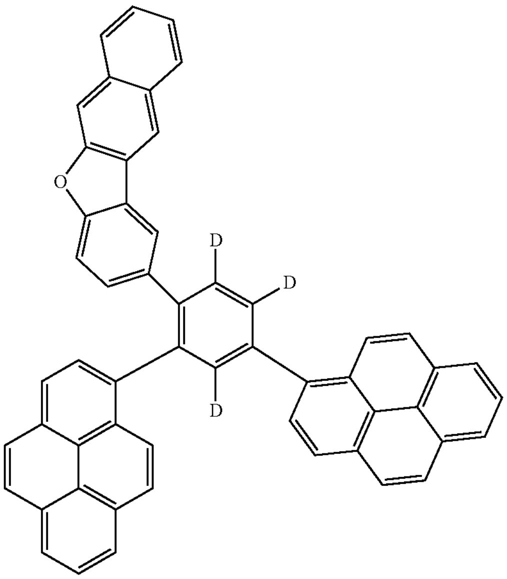
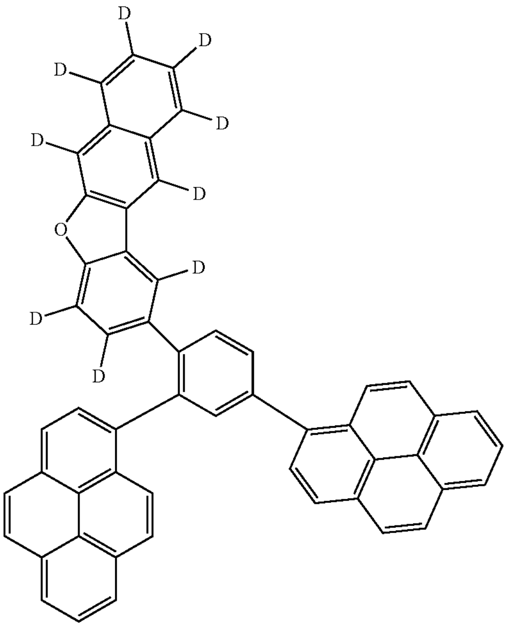
[Formula 77]
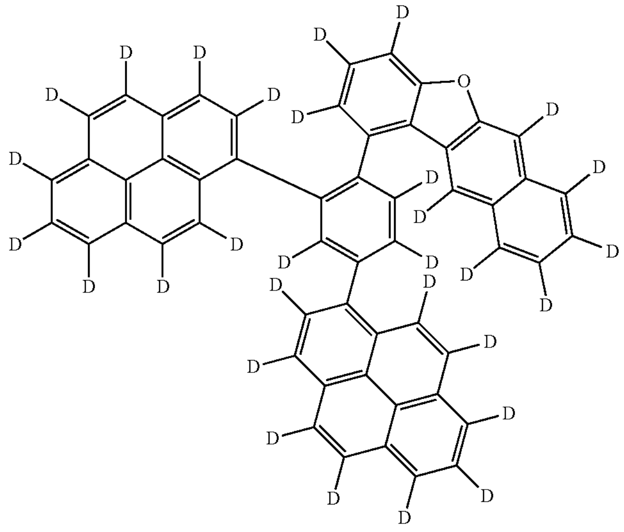
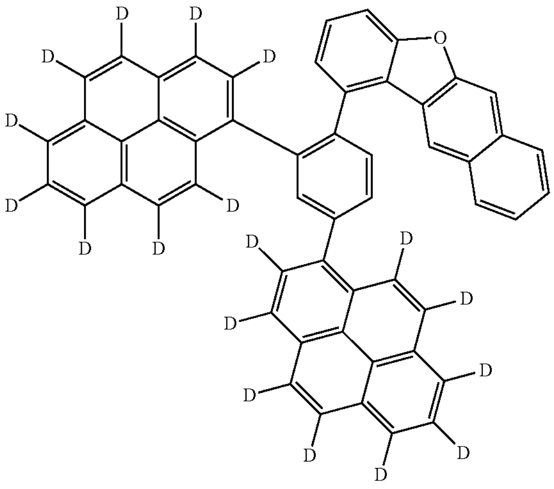
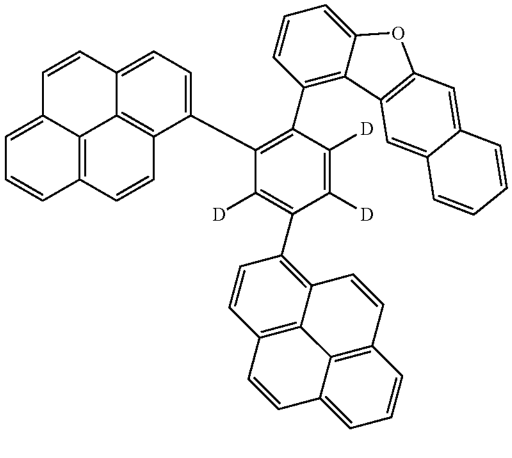
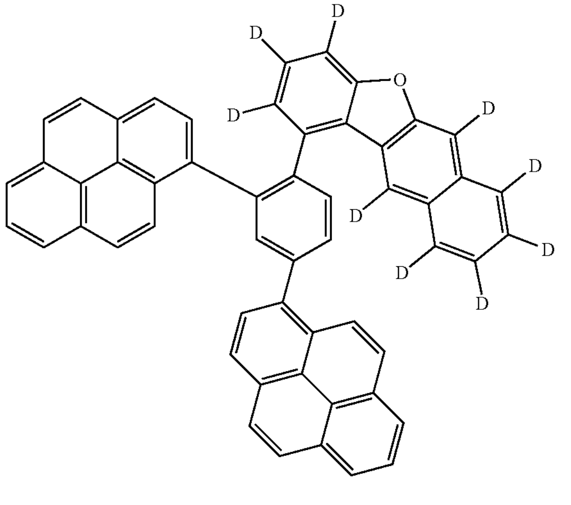

-continued
[Formula 78]
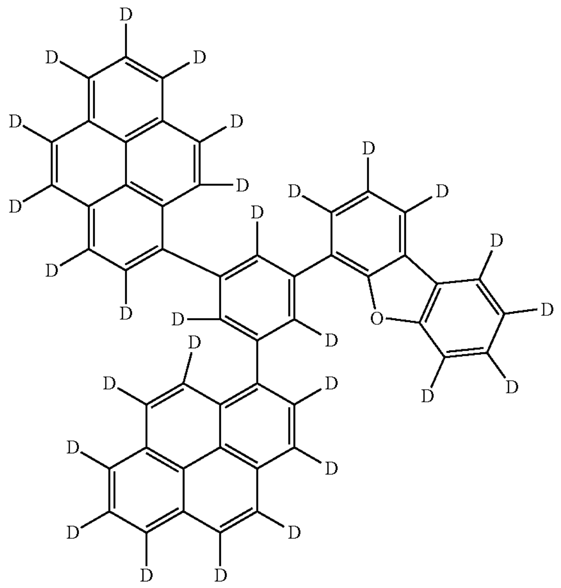
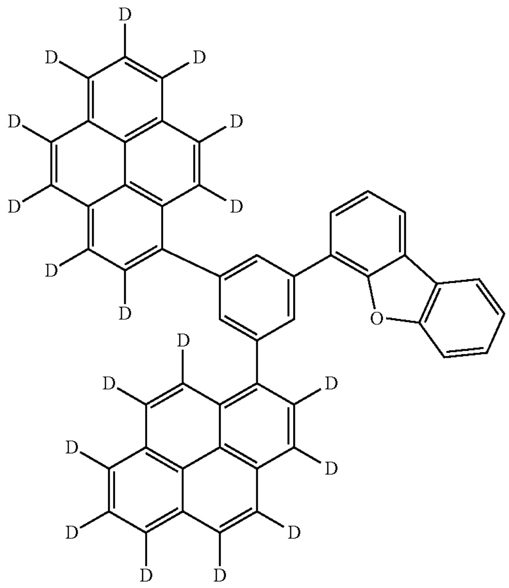
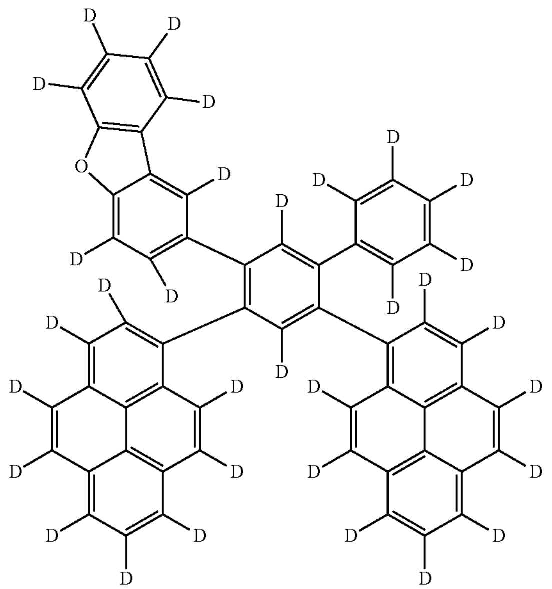
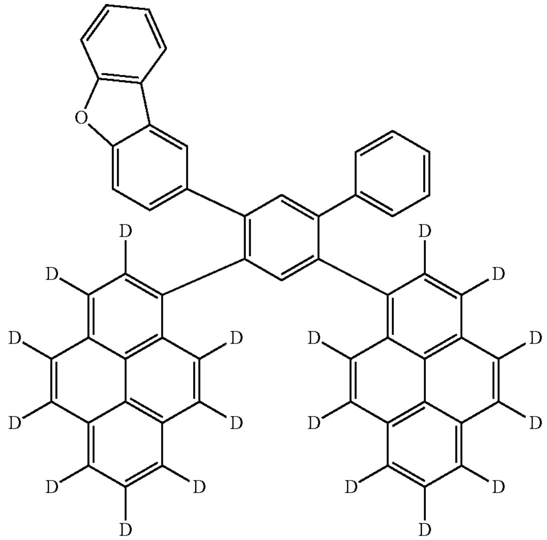

-continued
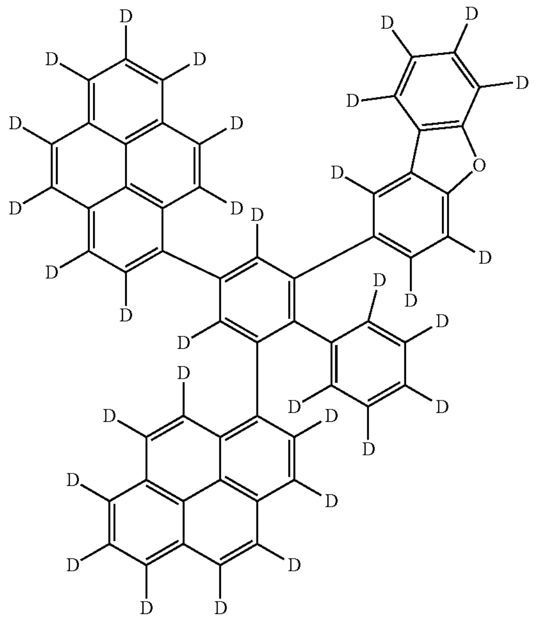
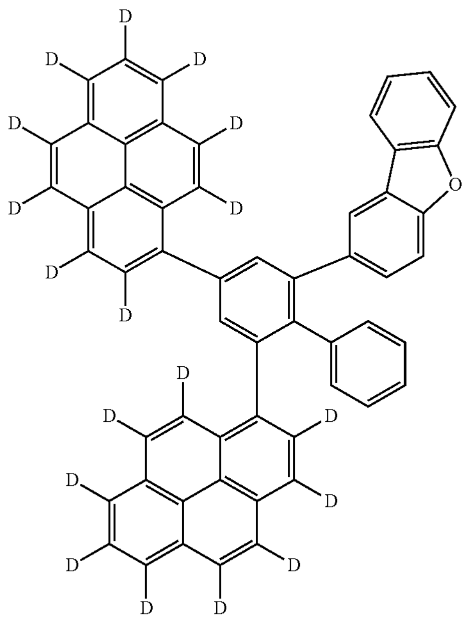
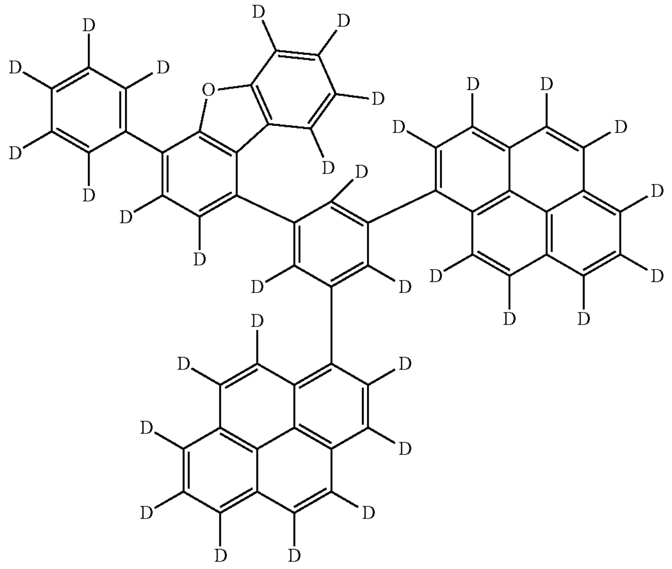
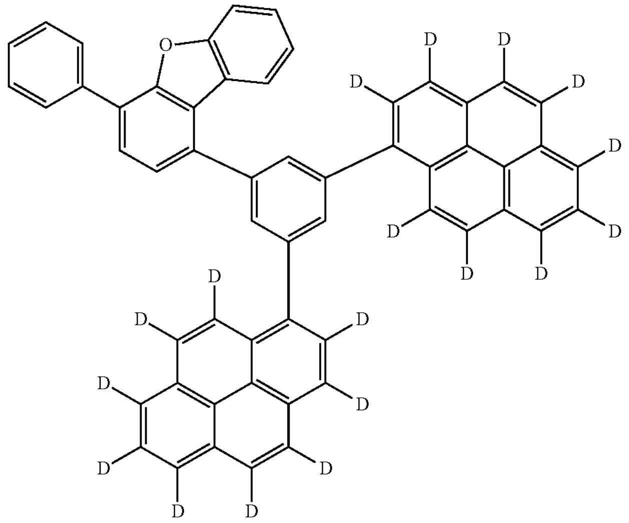

-continued
[Formula 79]
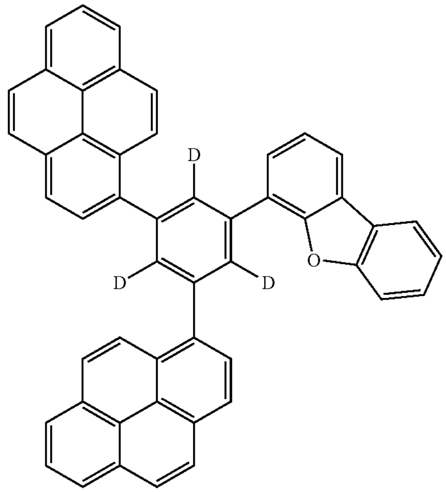
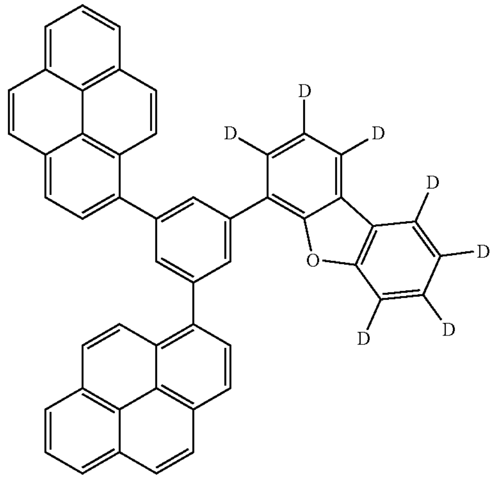
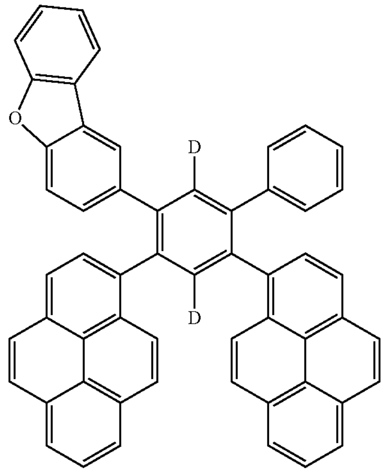
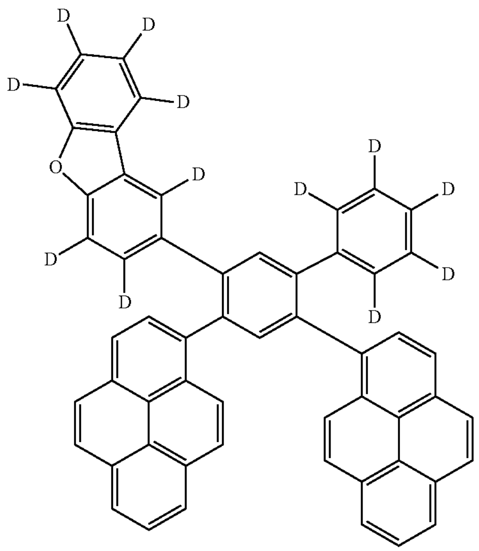
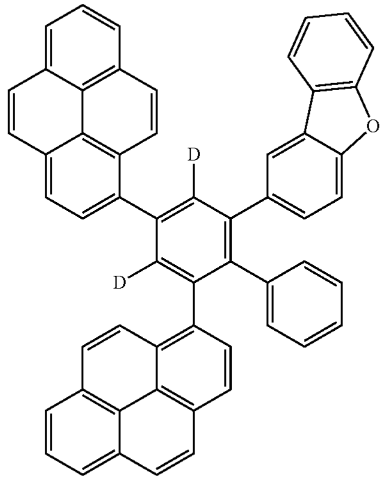
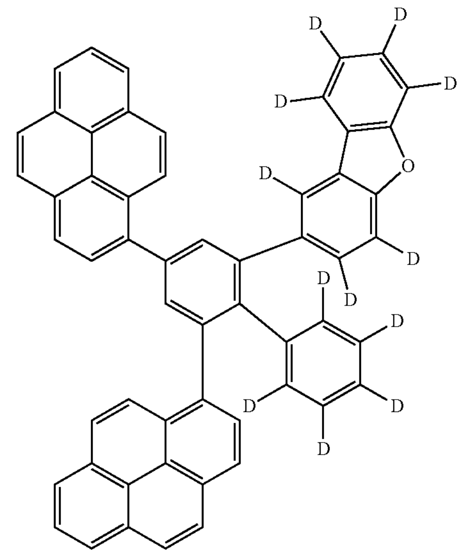

-continued
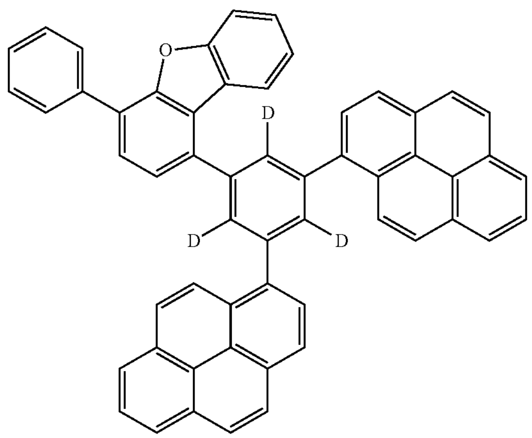
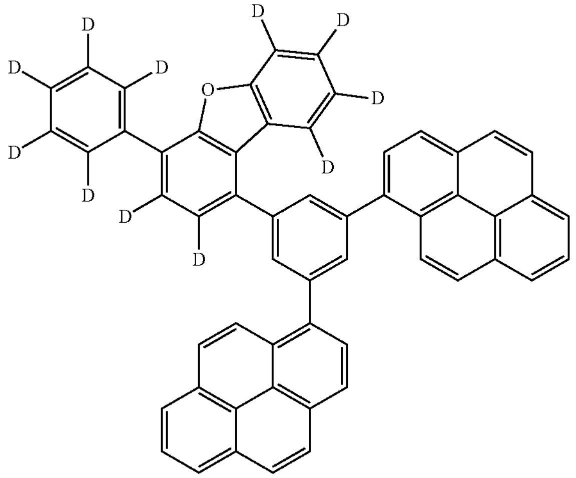
[Formula 80]
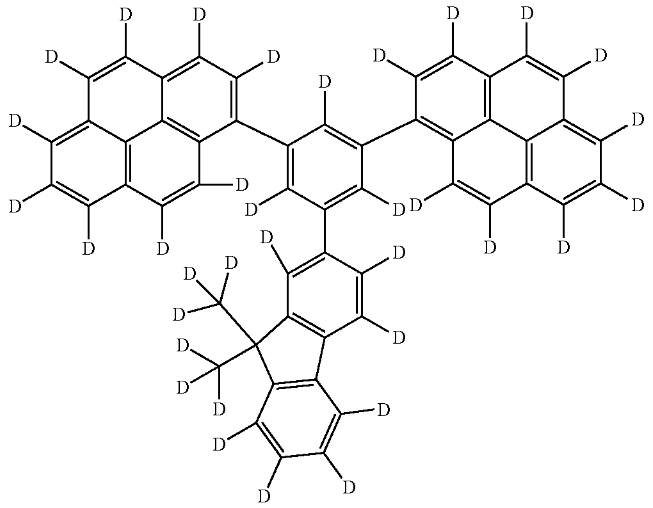
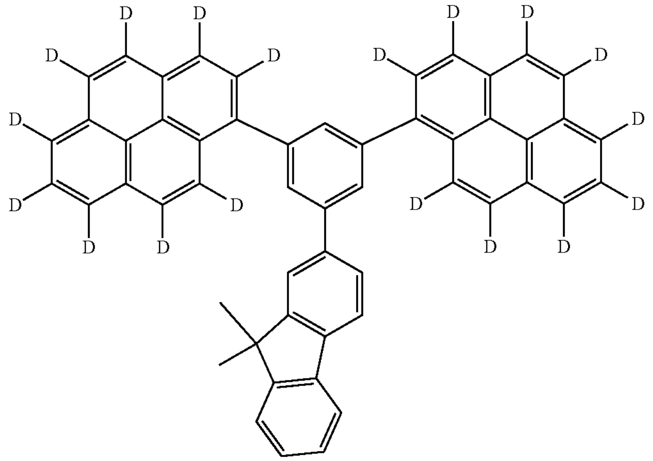

-continued
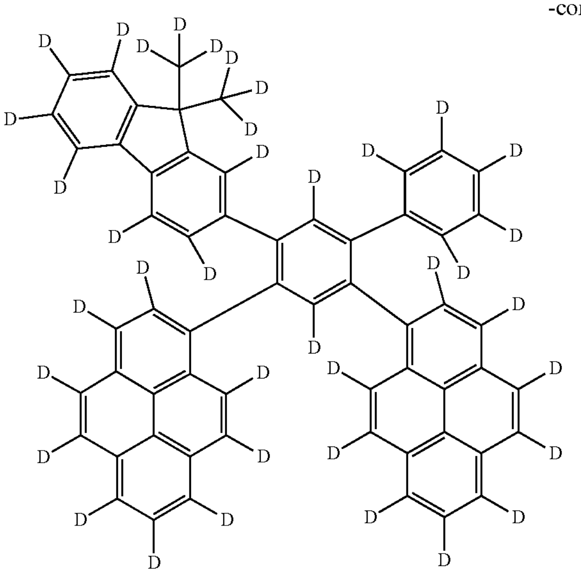
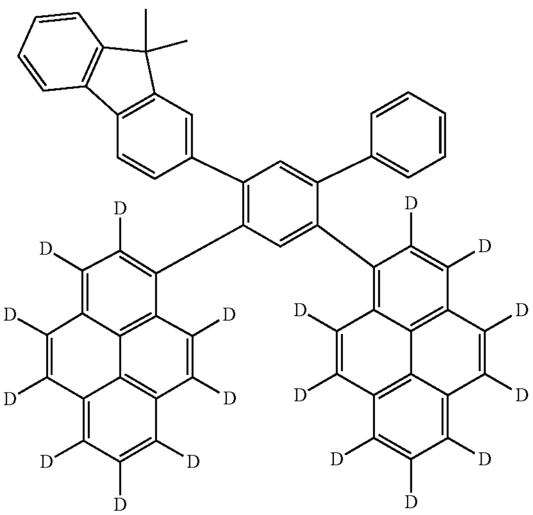
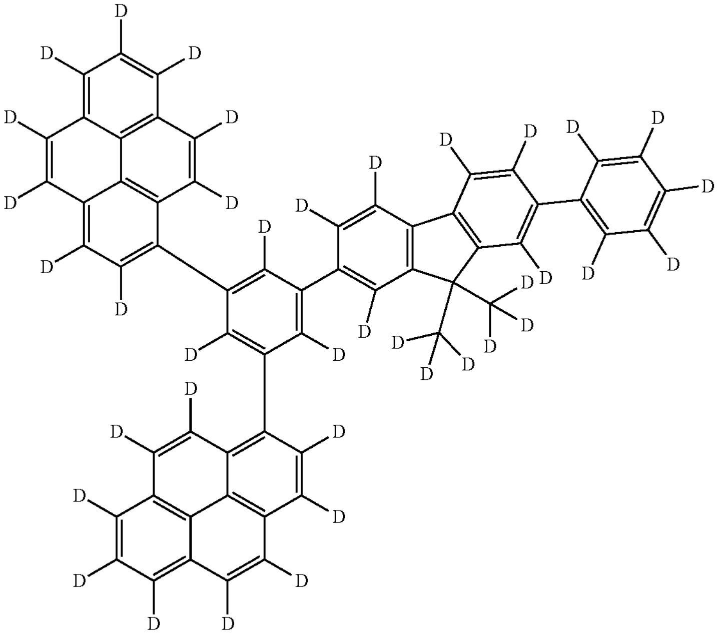

-continued
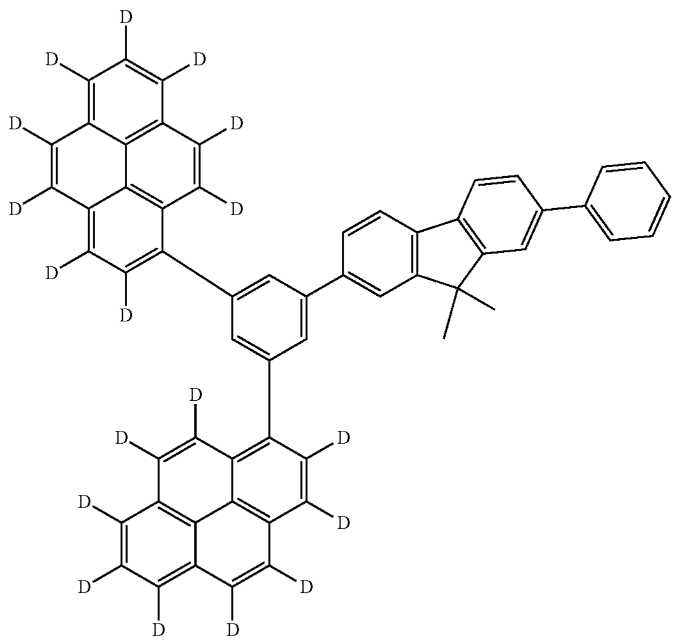
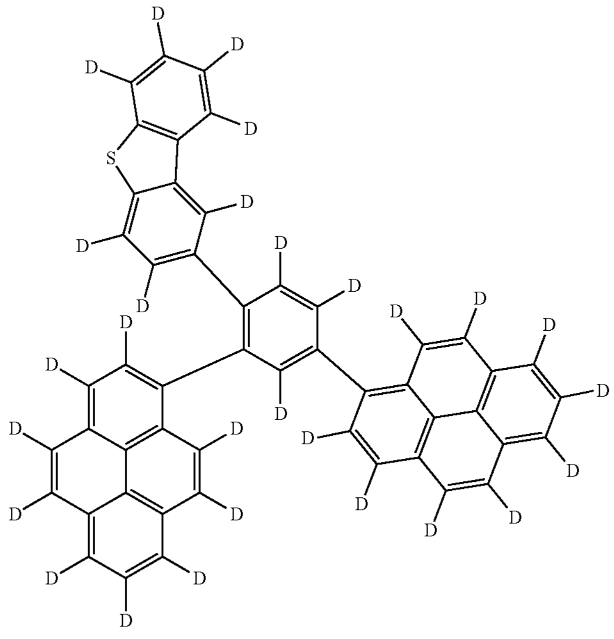
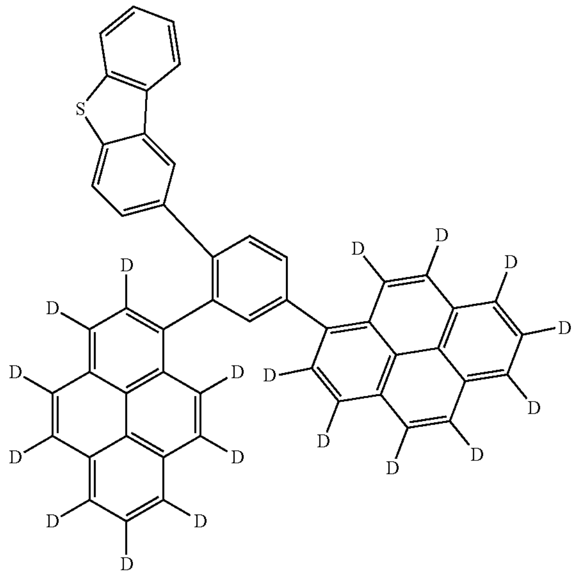

-continued
[Formula 81]
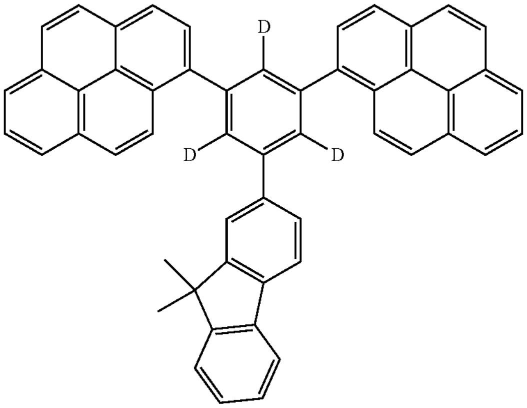
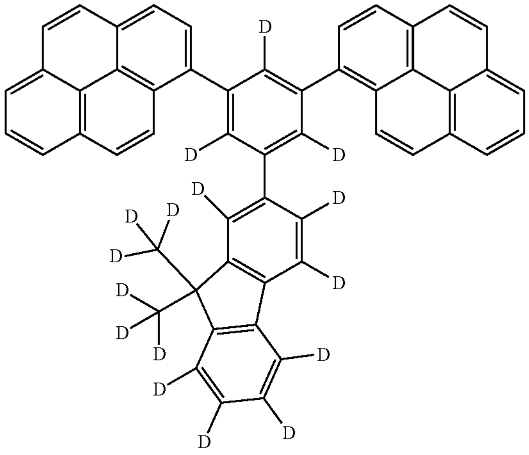
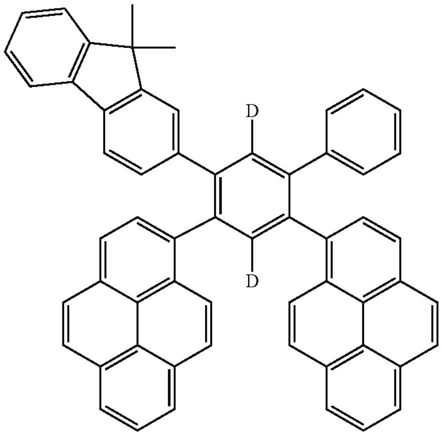
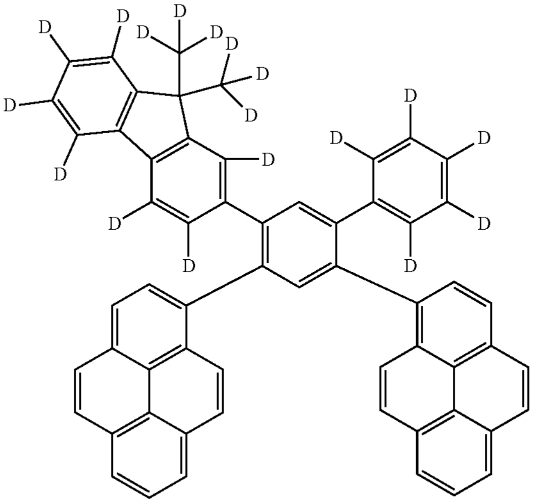
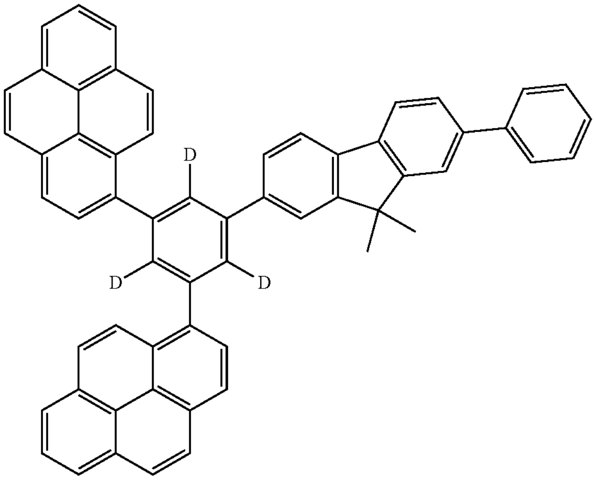

-continued
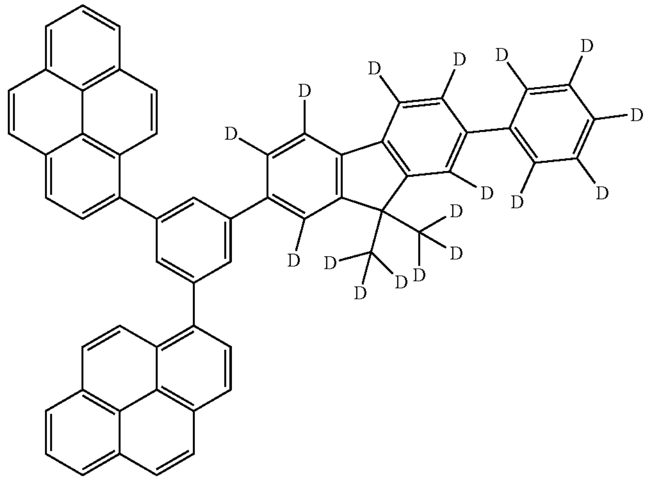
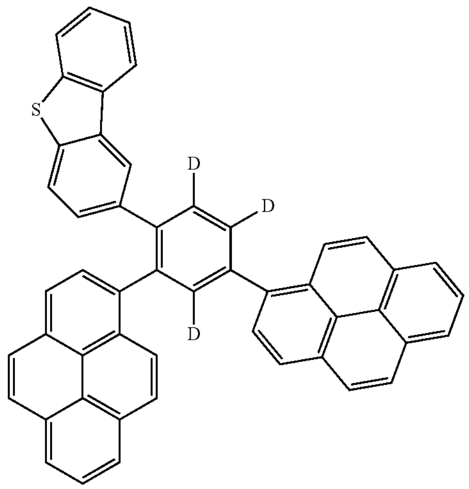
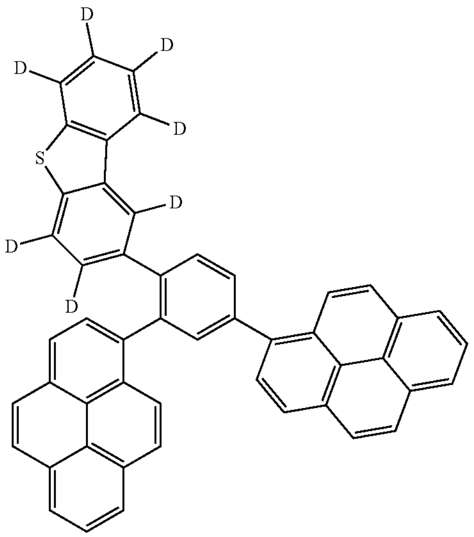
[Formula 82]
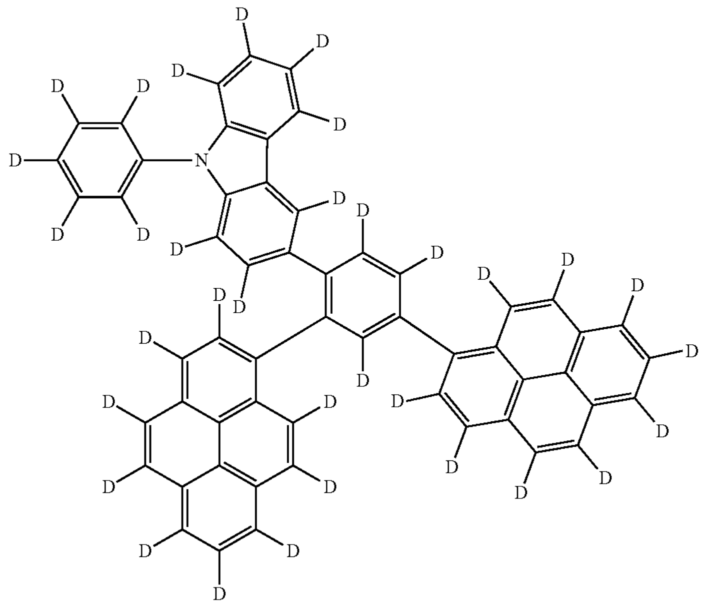

-continued
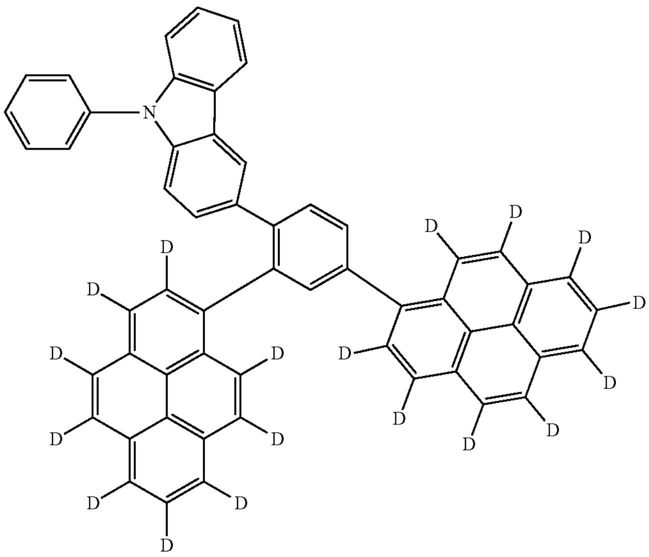
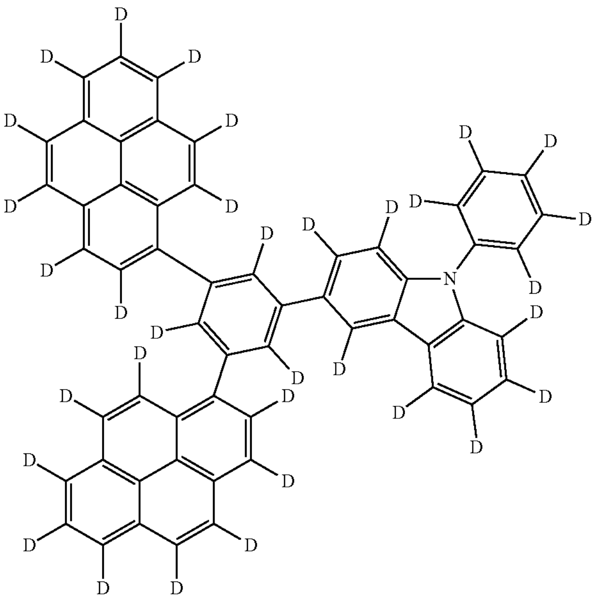
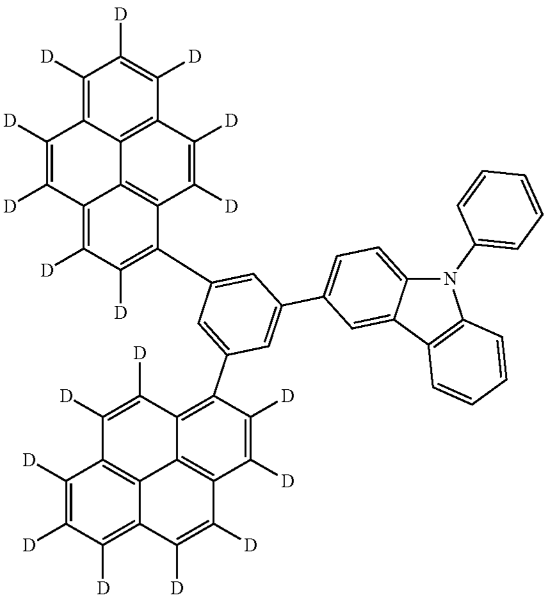

-continued
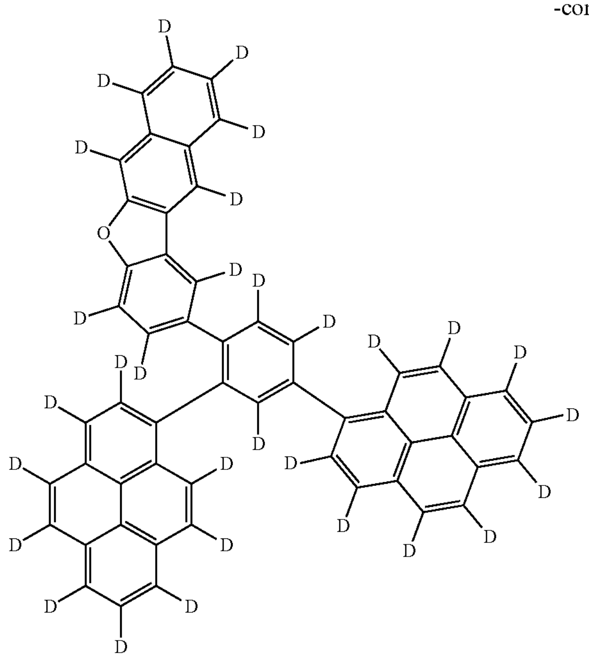
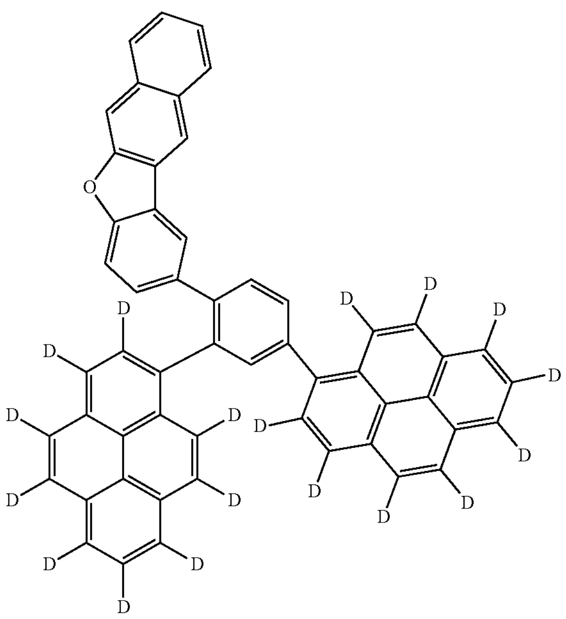
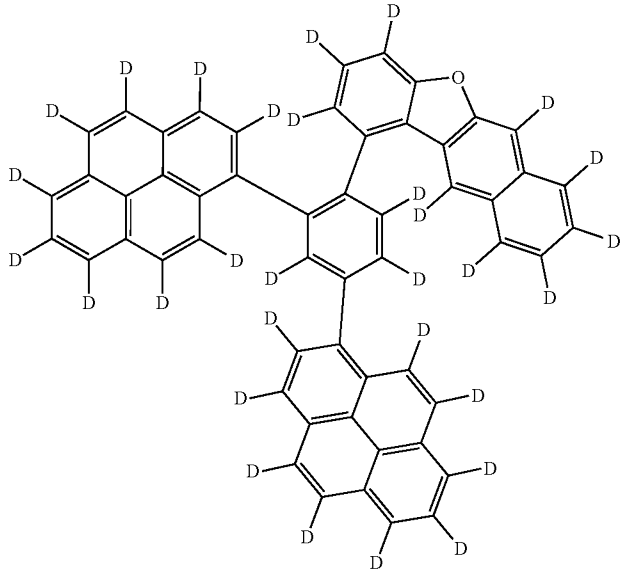
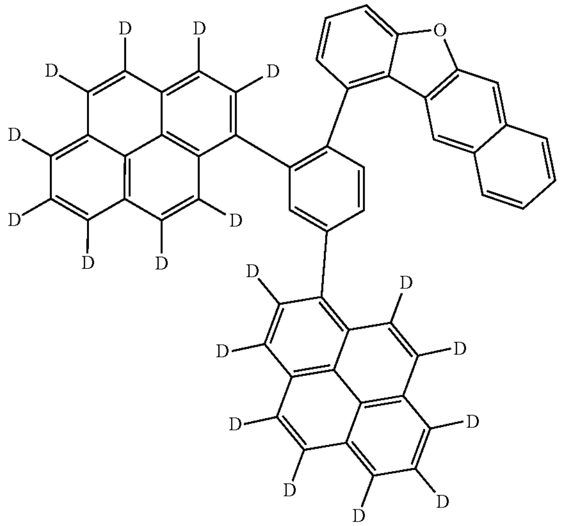

-continued
[Formula 83]
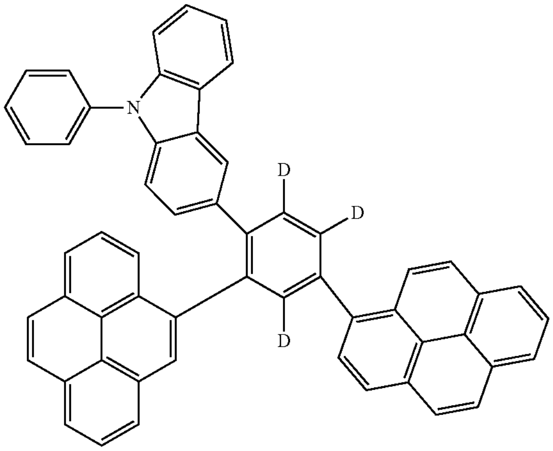
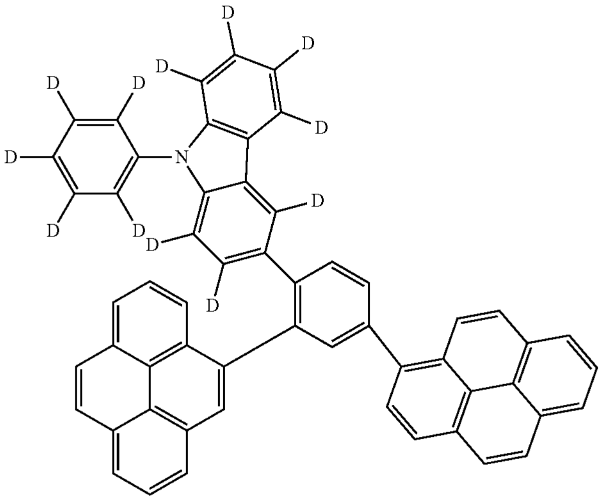
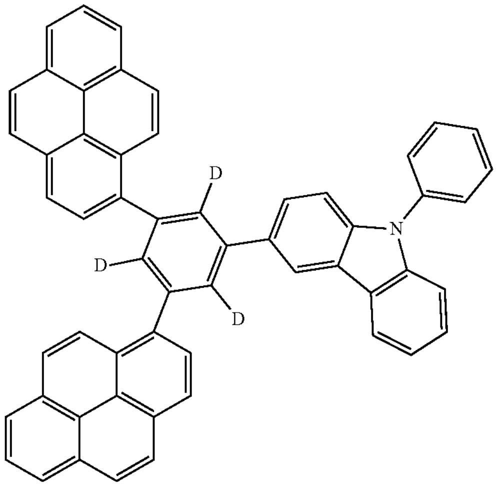
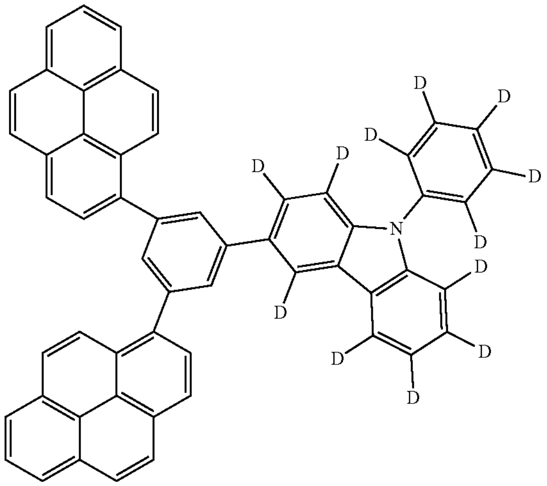
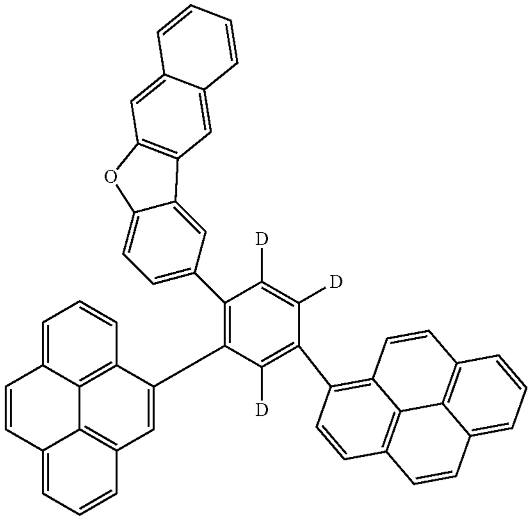
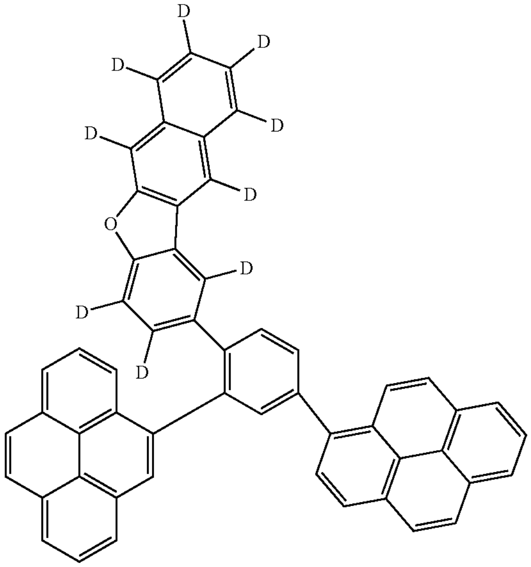

-continued
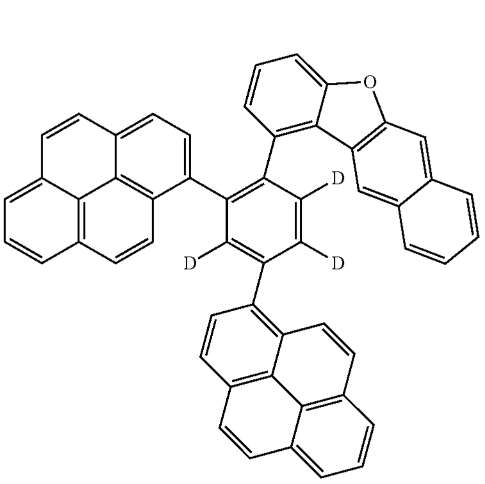
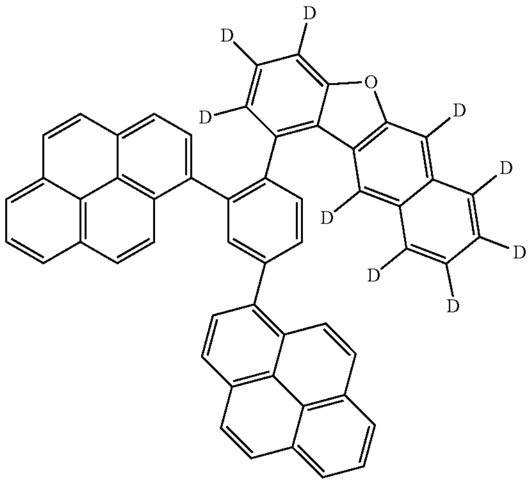
[Formula 84]
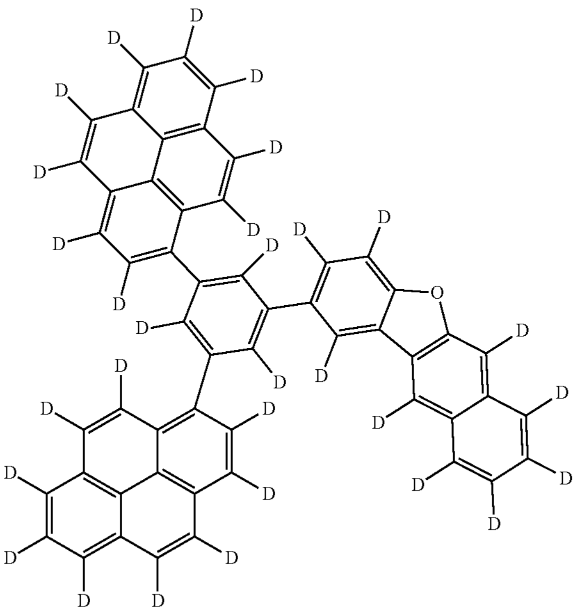
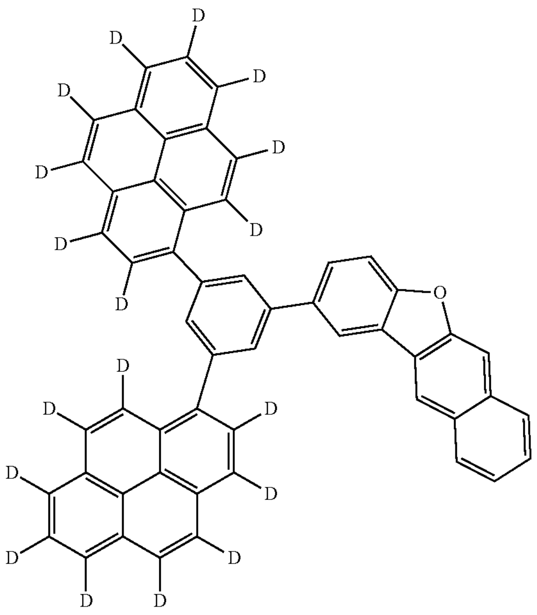
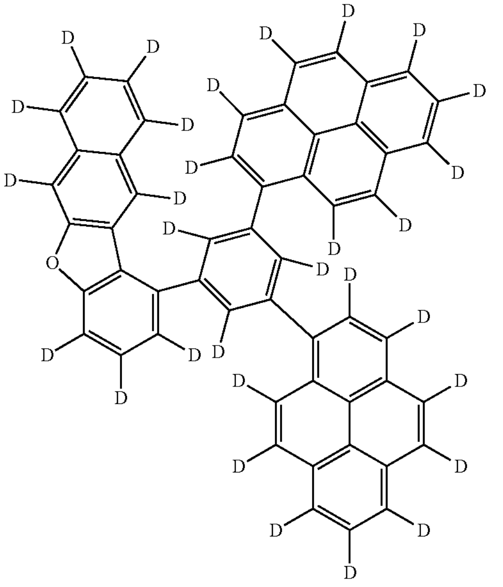
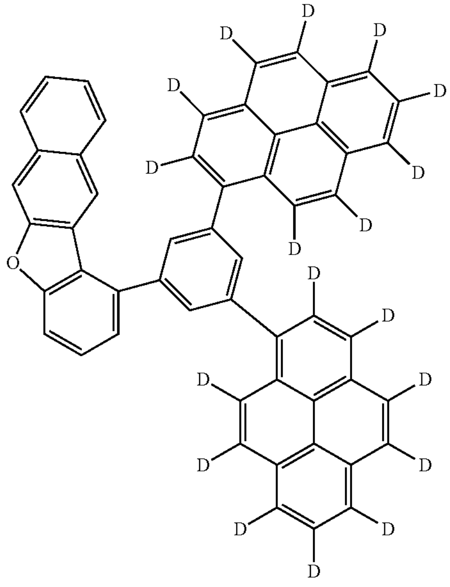

-continued
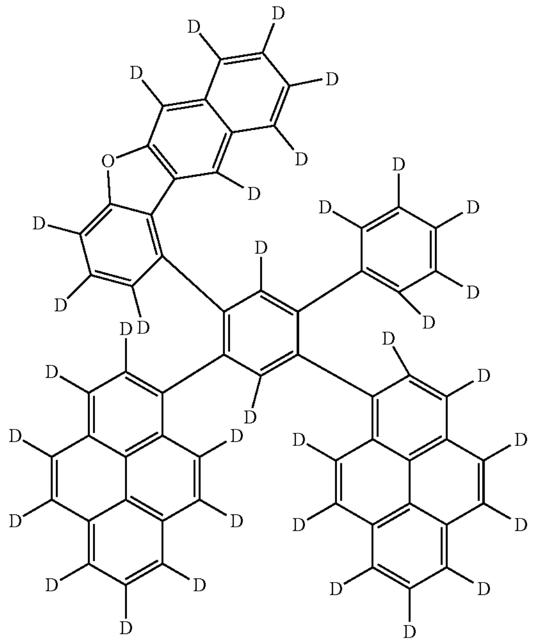
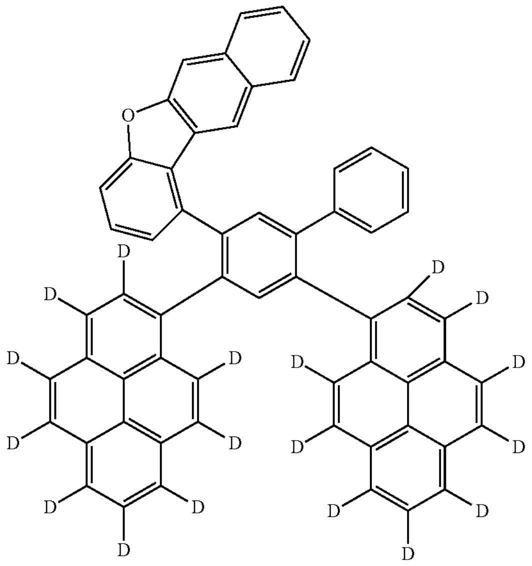
[Formula 85]
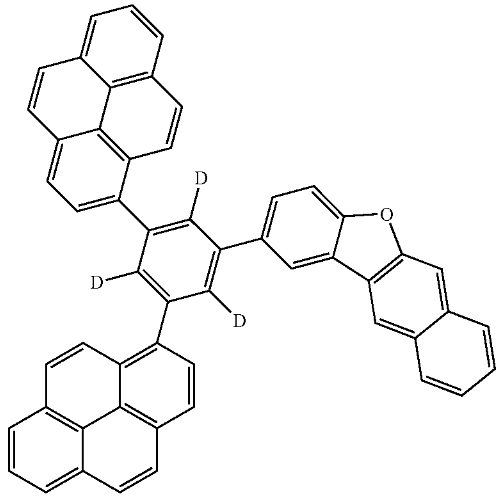
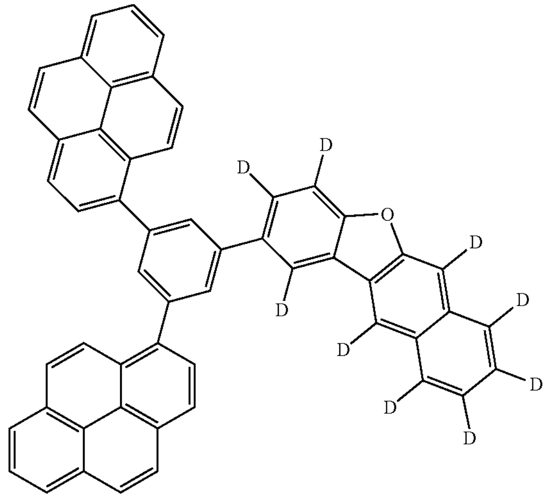
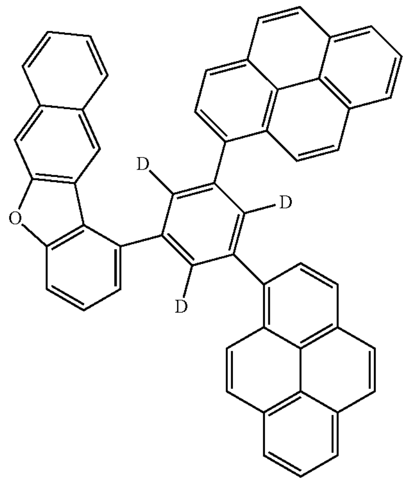
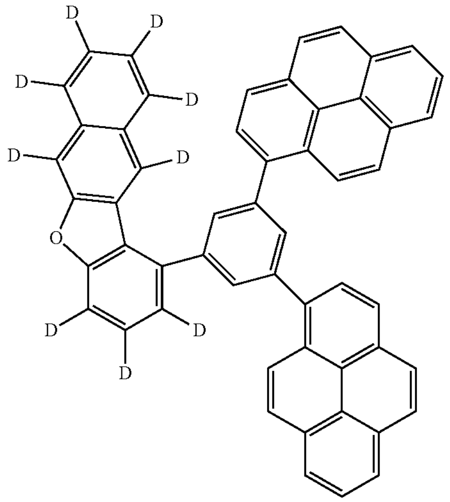

-continued
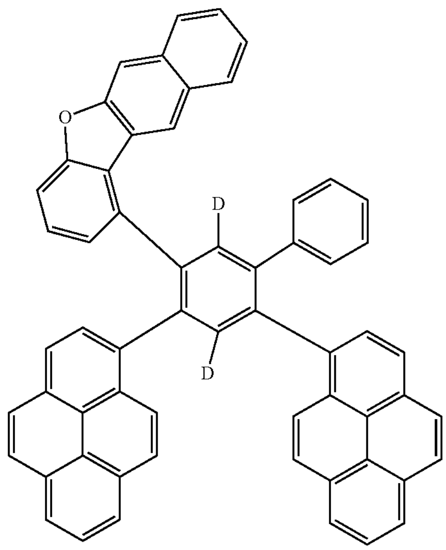
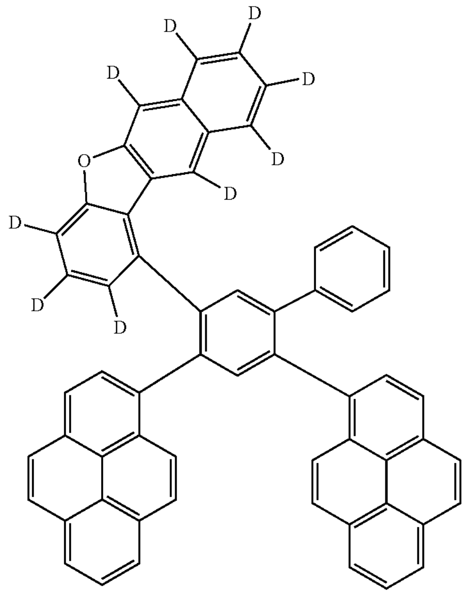
[Formula 86]
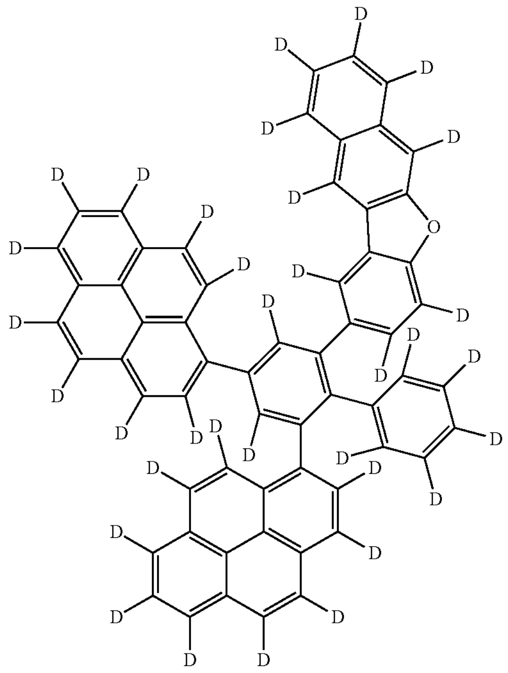
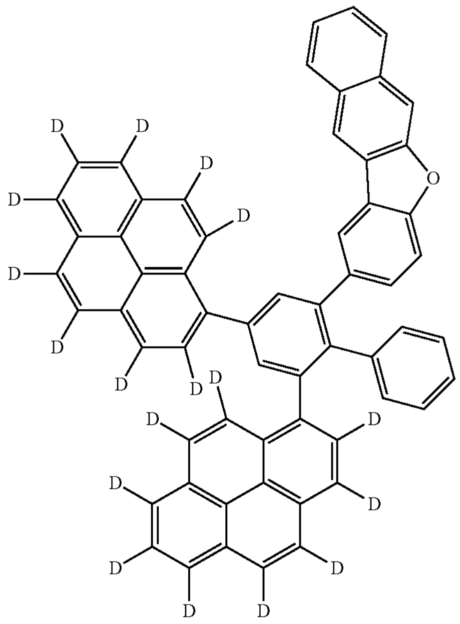

-continued
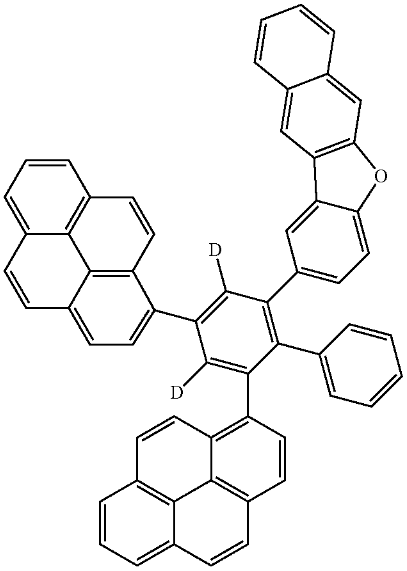
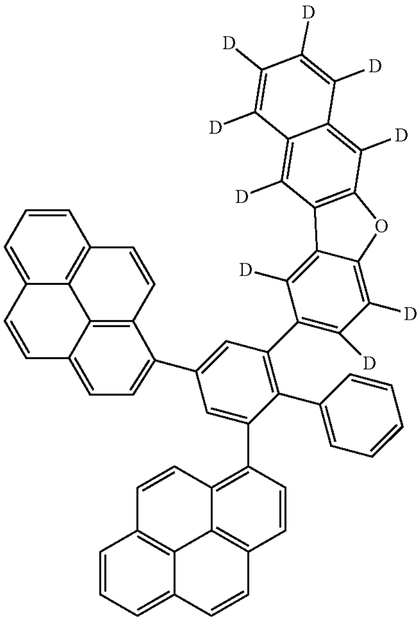
[Formula 87]
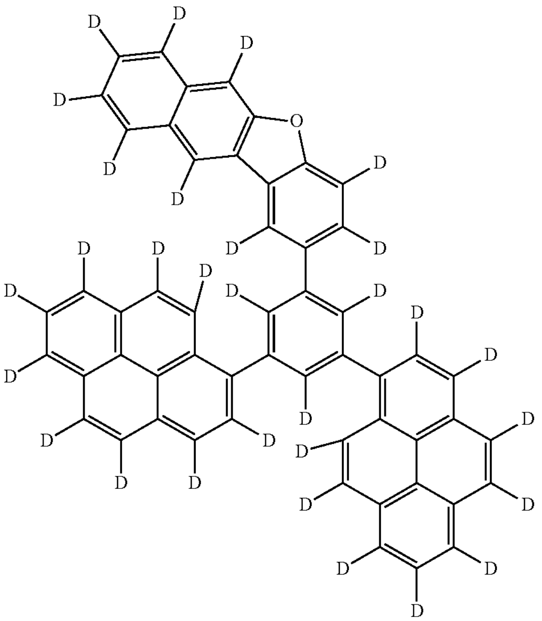
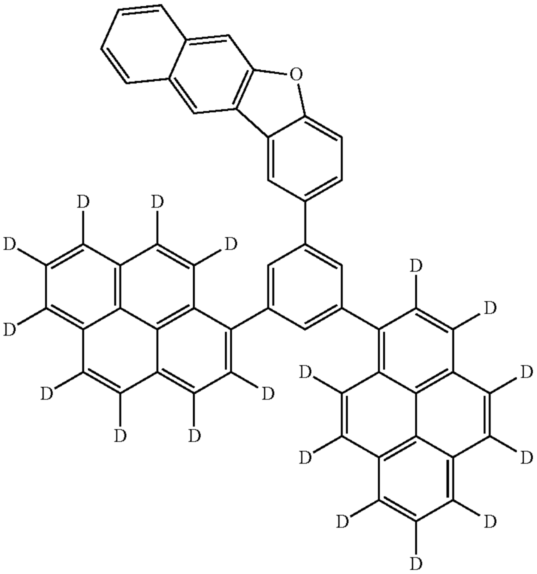

-continued
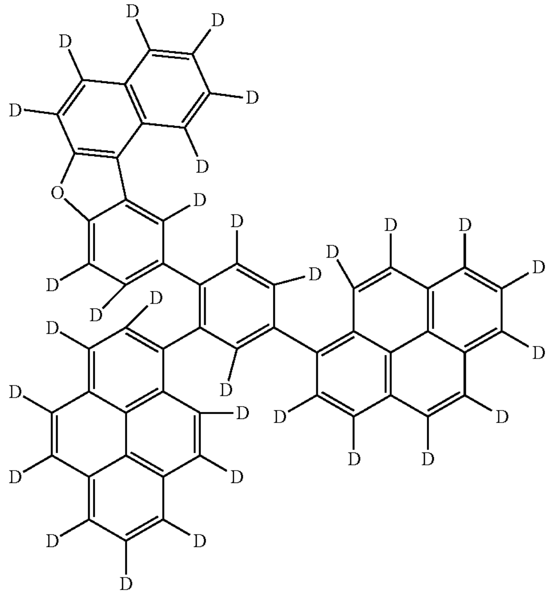
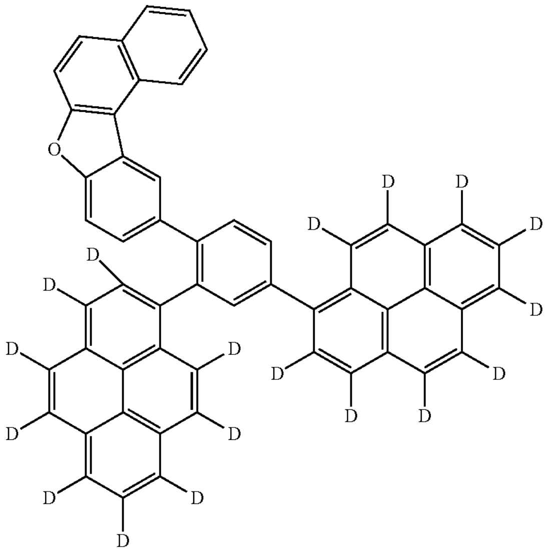
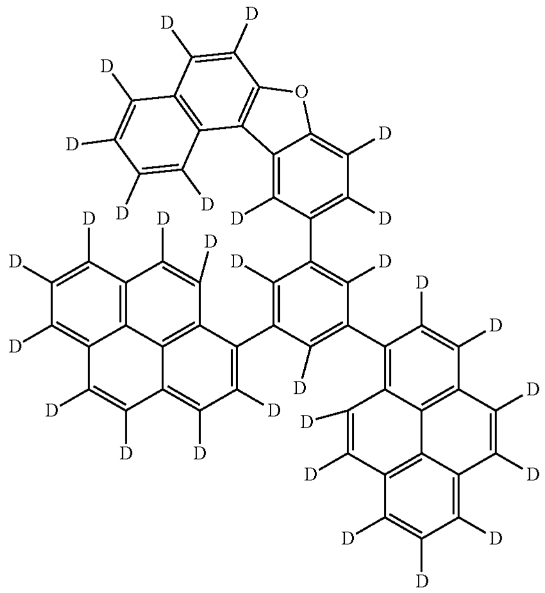
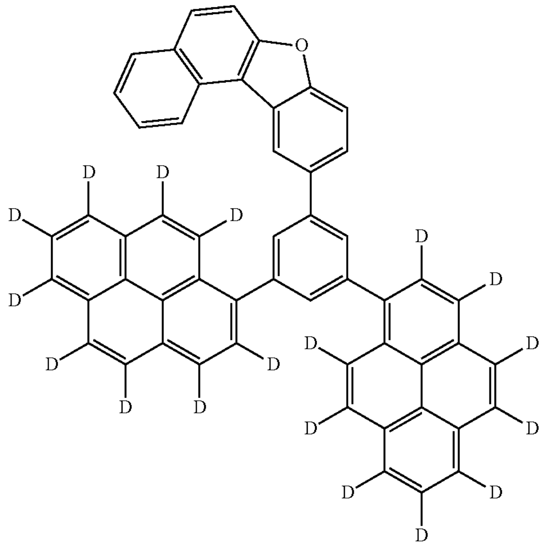

-continued
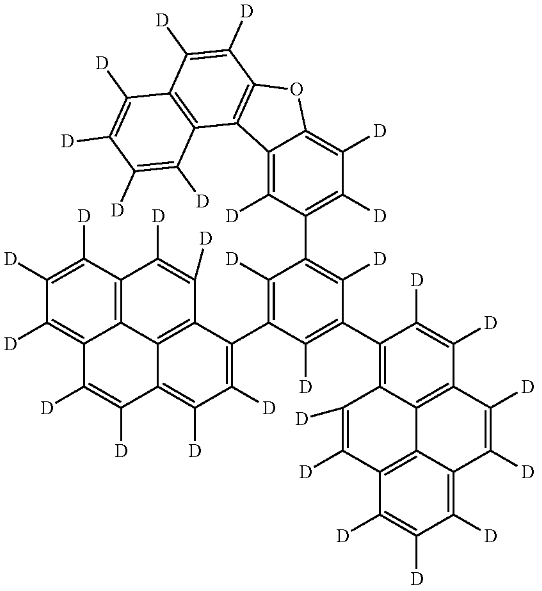
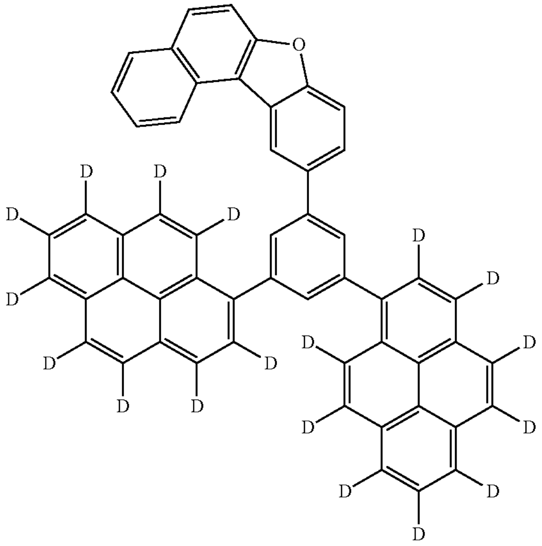
[Formula 88]
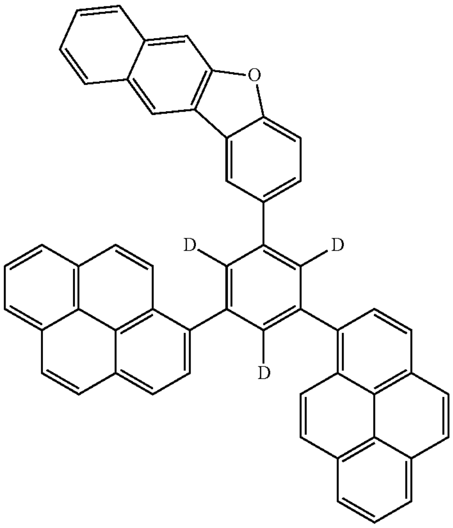
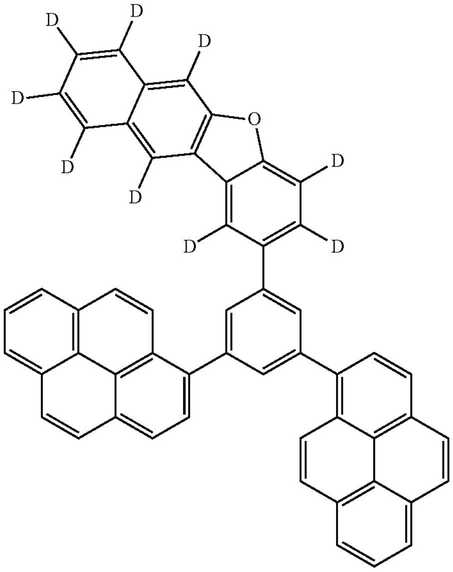

-continued
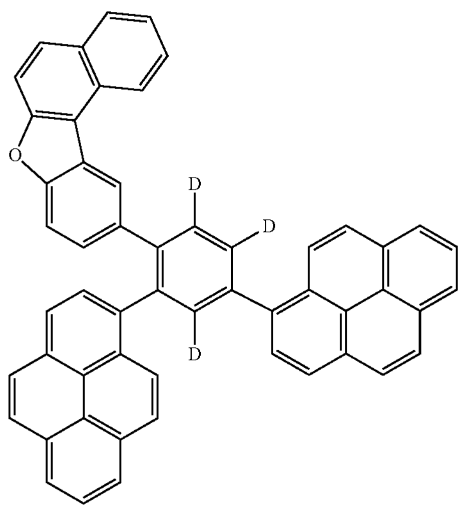
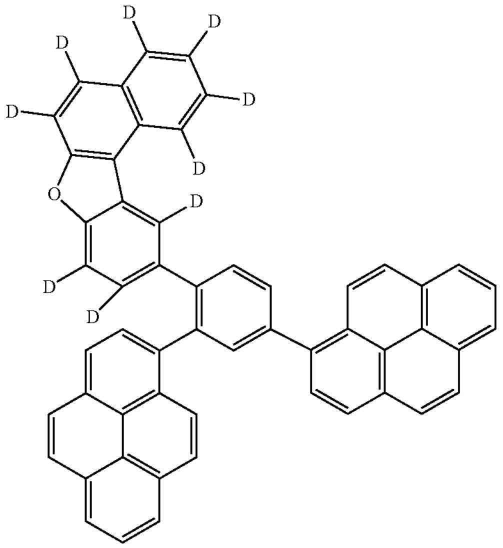
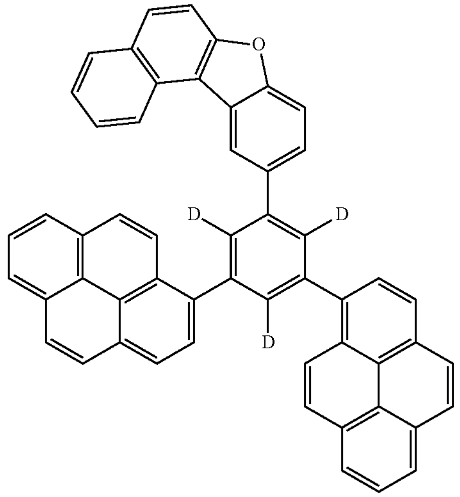
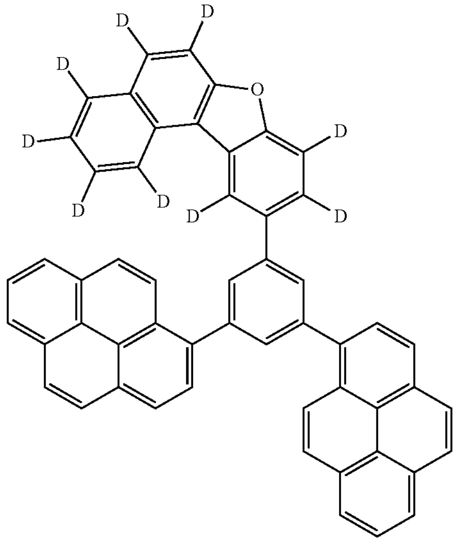
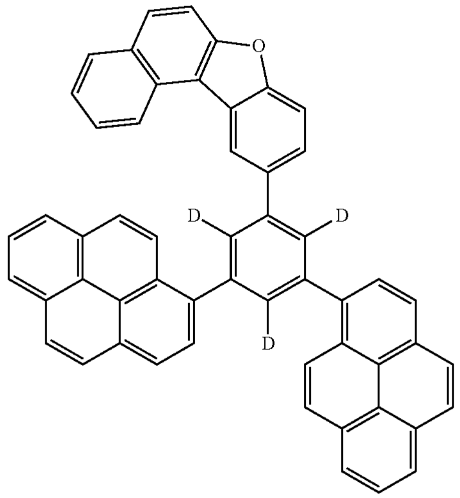
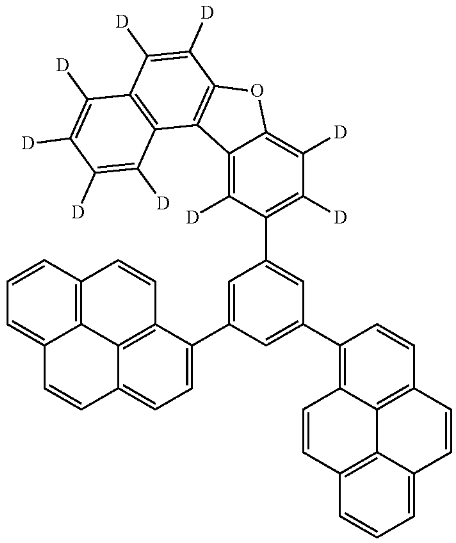

-continued
[Formula 89]
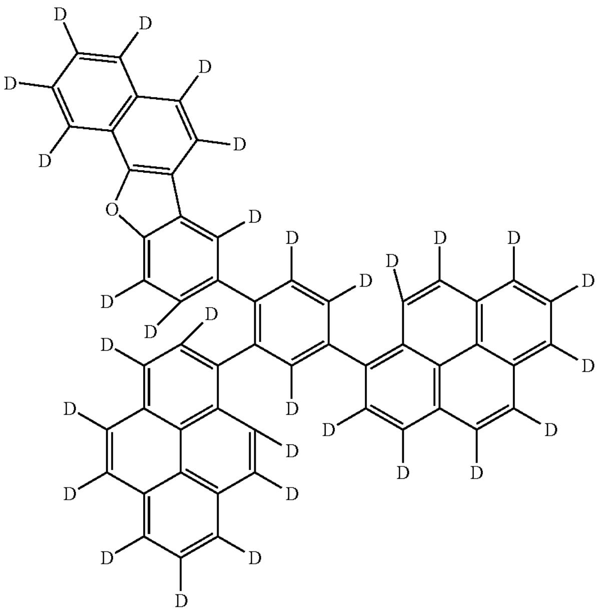
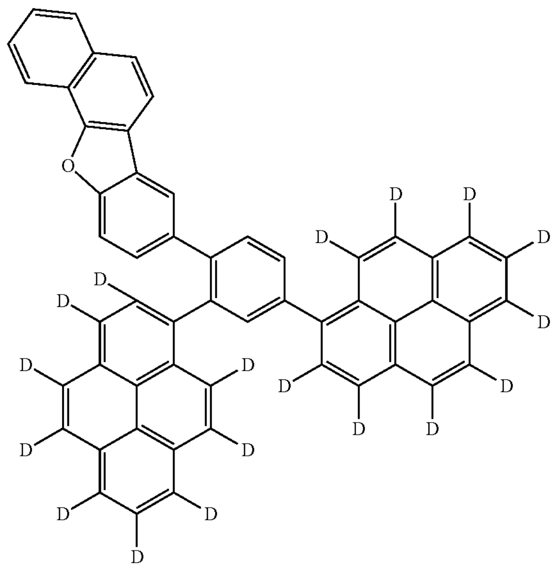
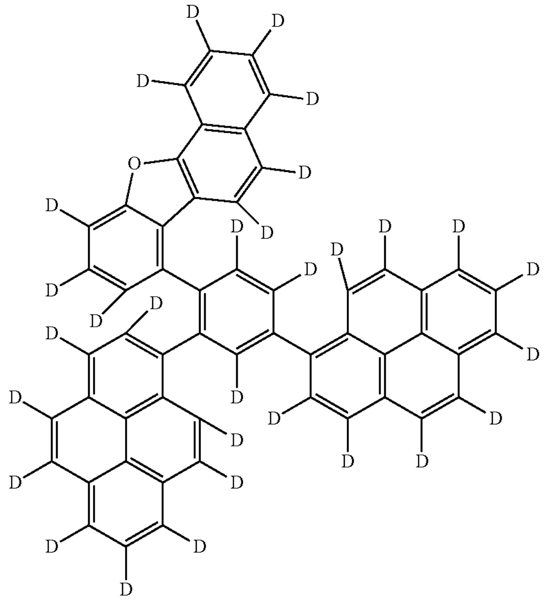
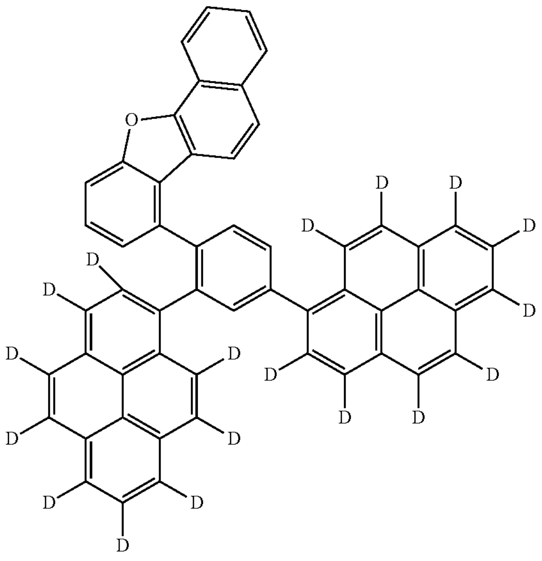

-continued
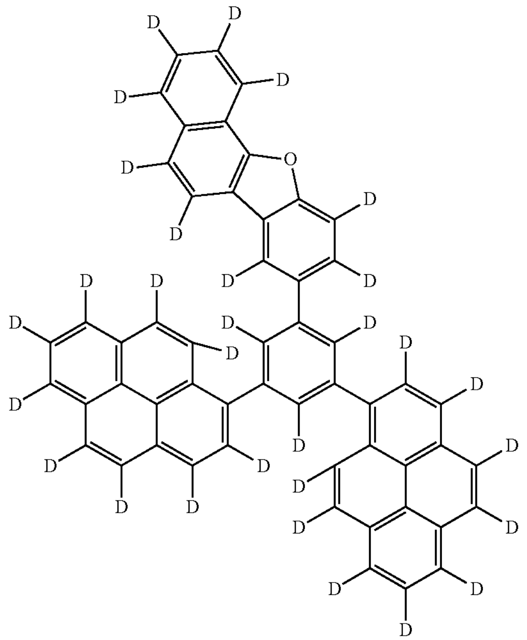
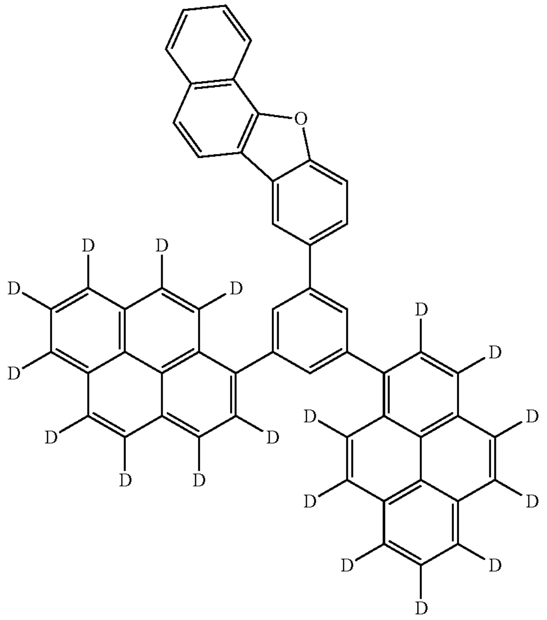
[Formula 90]
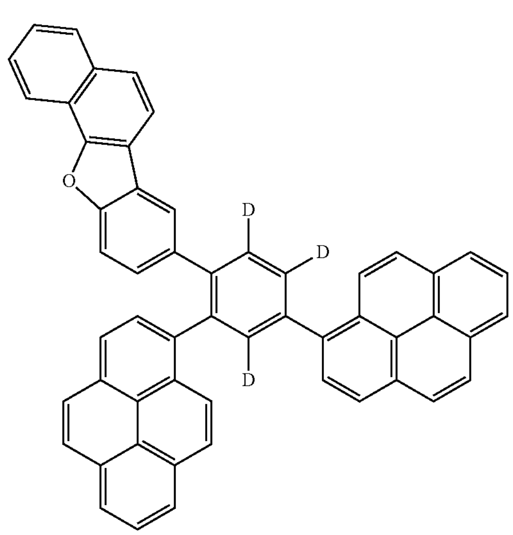
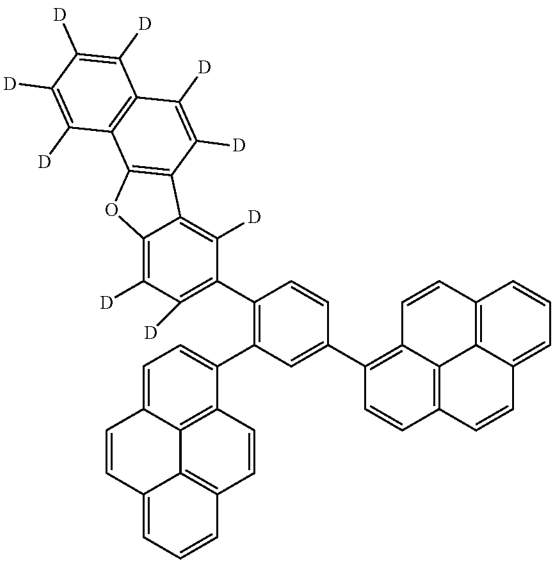

-continued
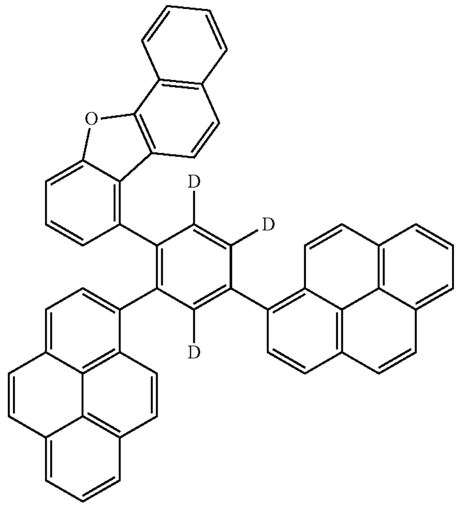
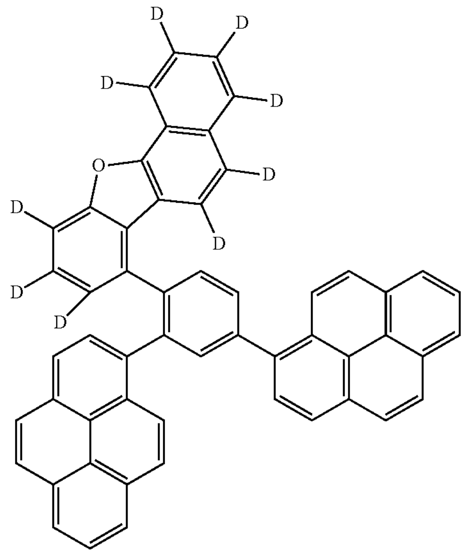
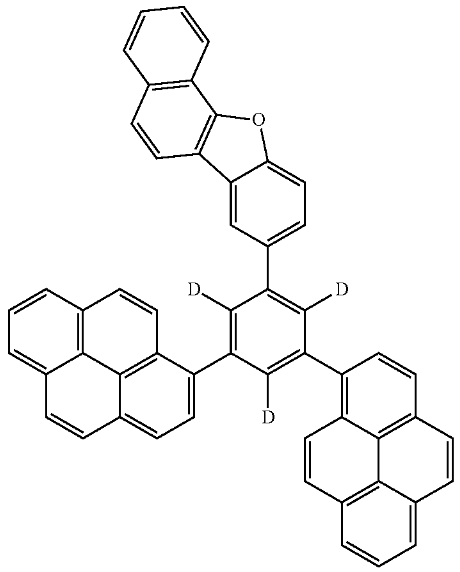
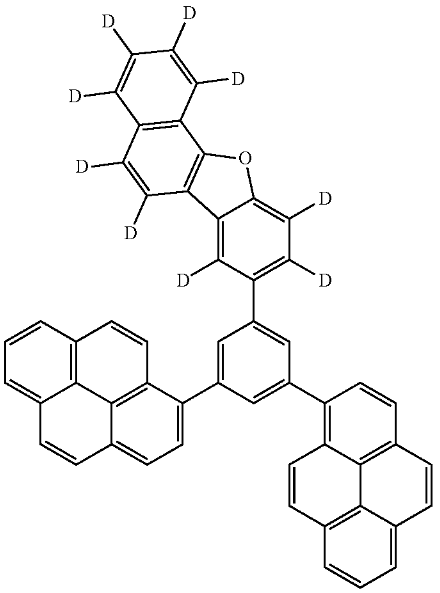

-continued
[Formula 91]
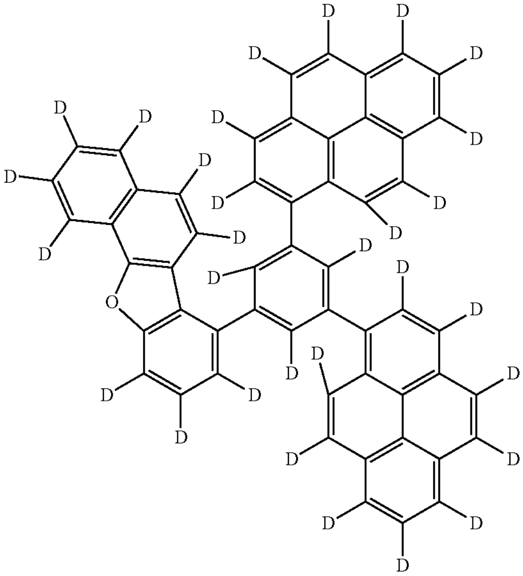
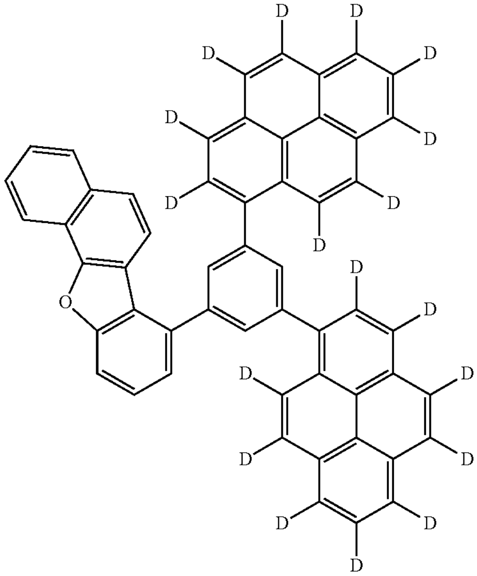
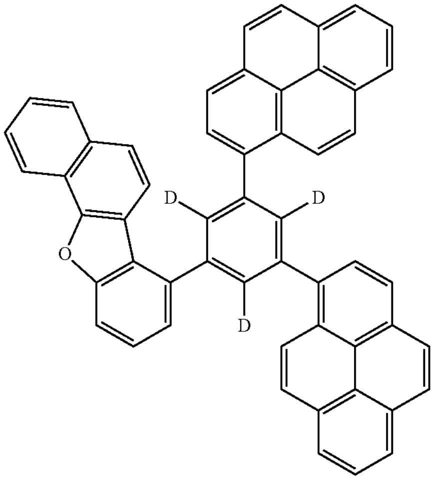
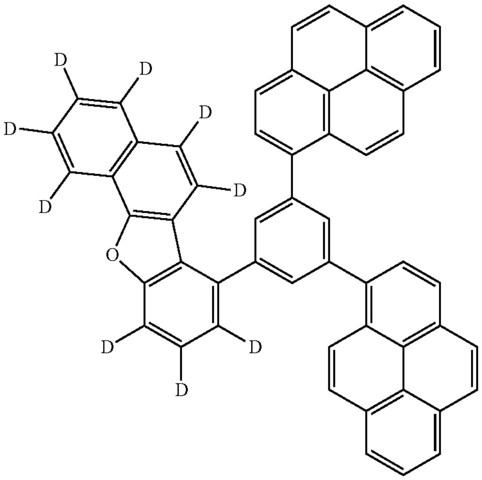

-continued
[Formula 92]
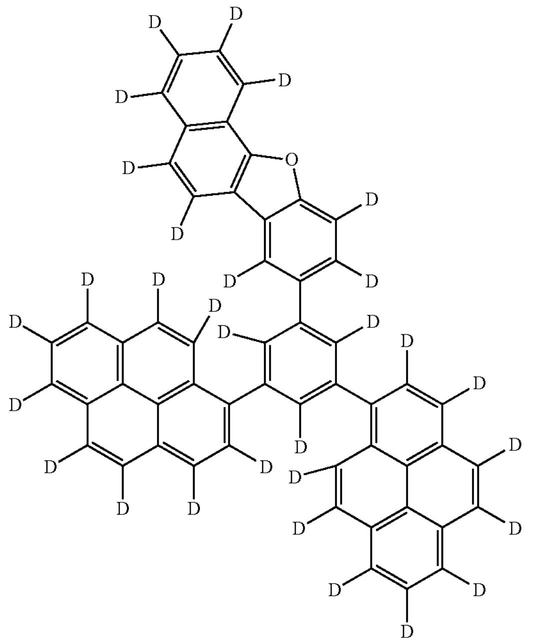
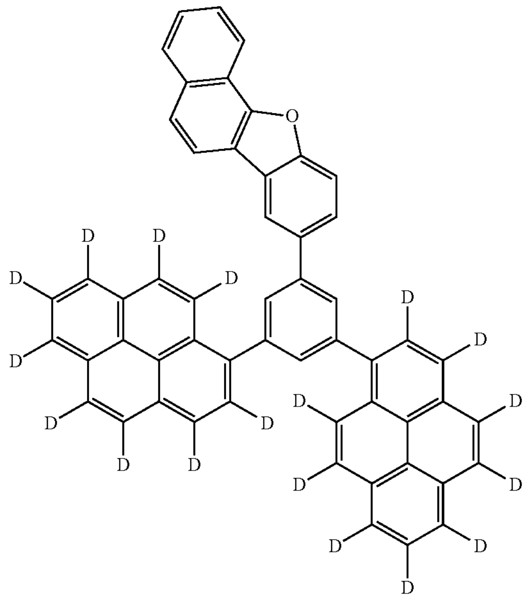
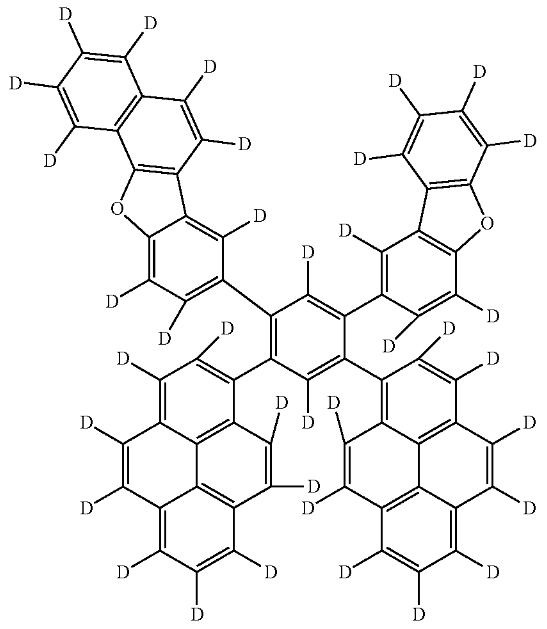
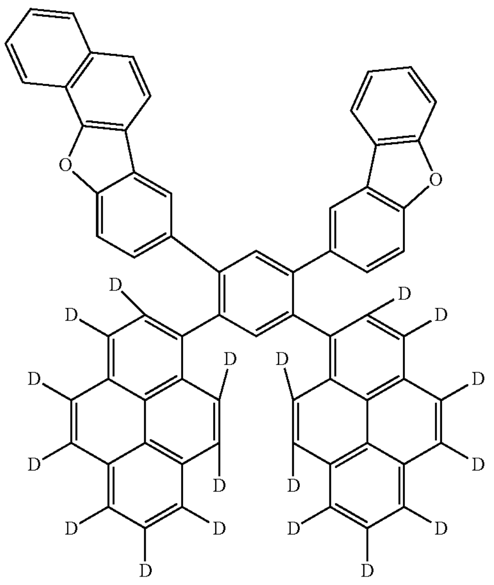

-continued
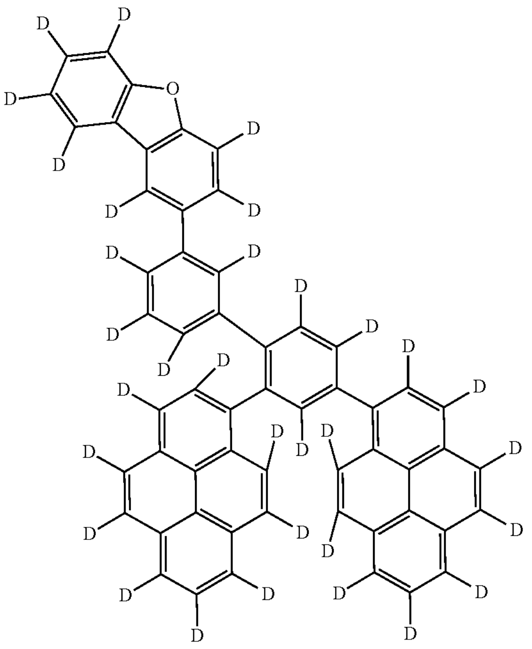
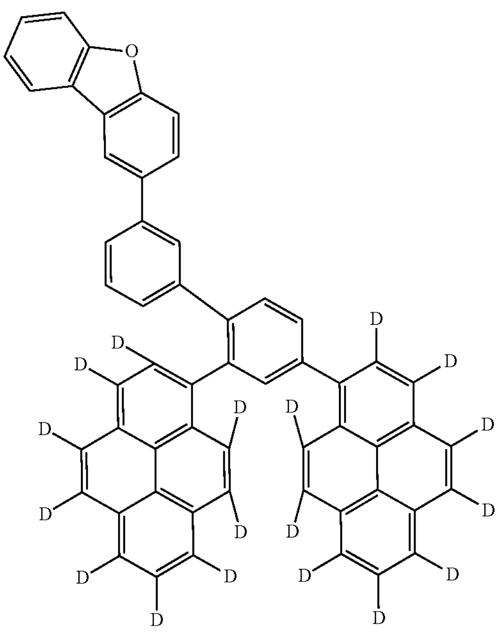
[Formula 93]
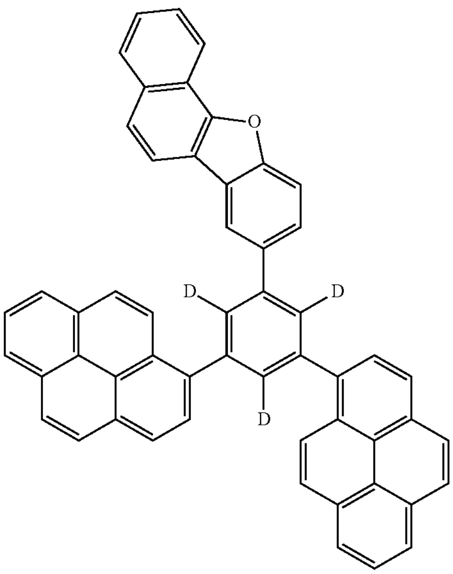
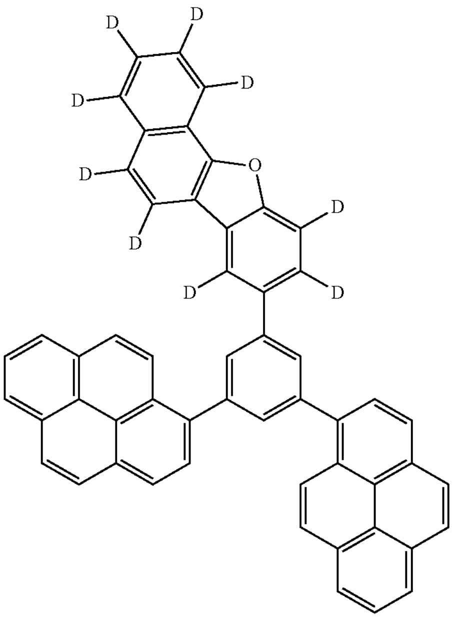

-continued
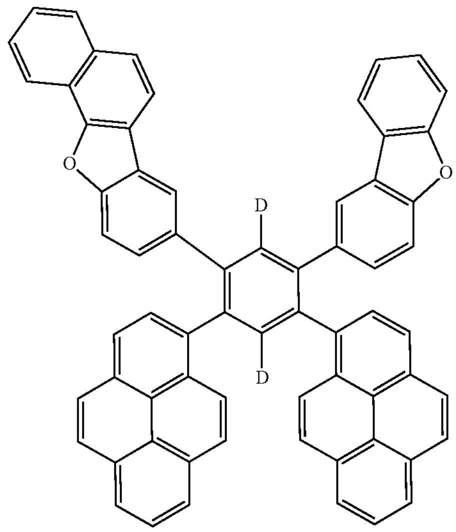
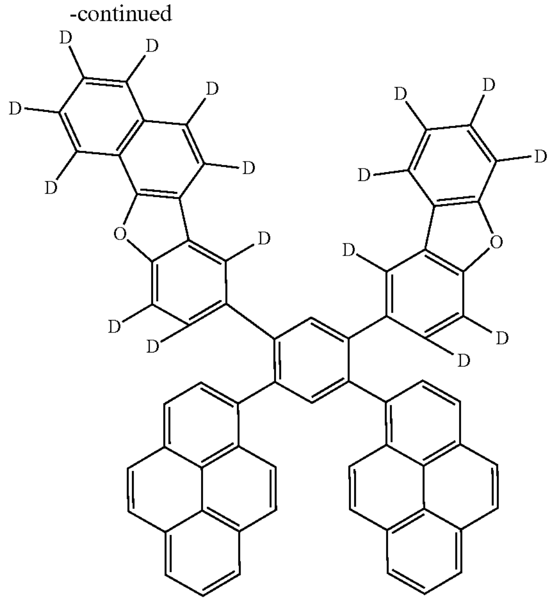
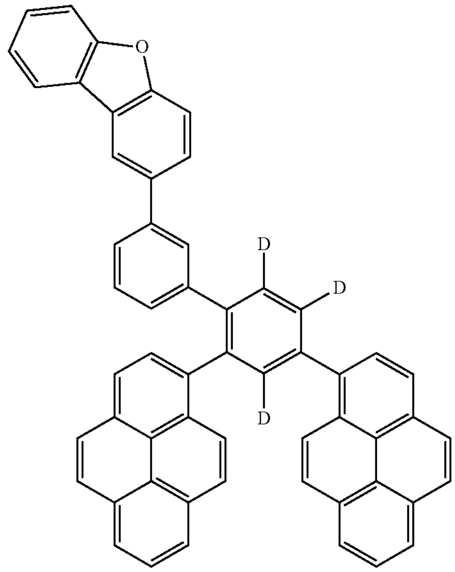
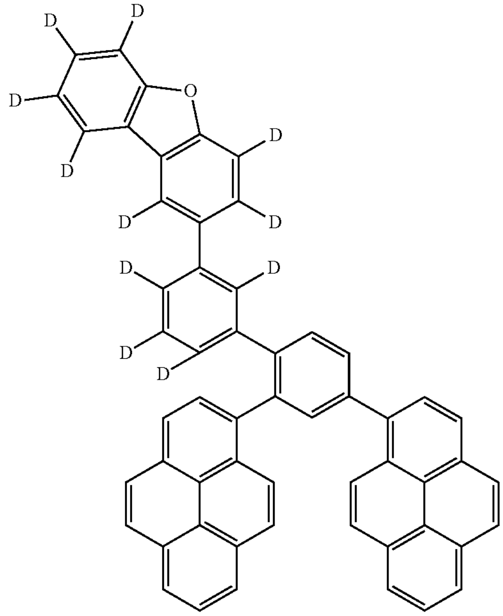
[Formula 94]
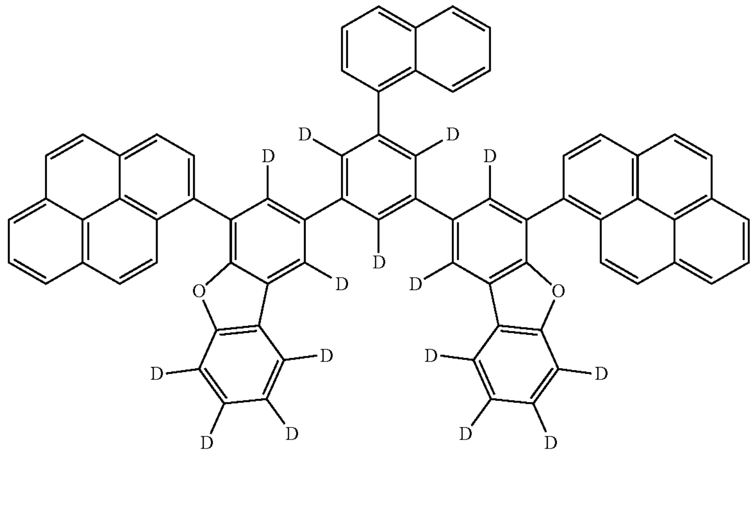

-continued
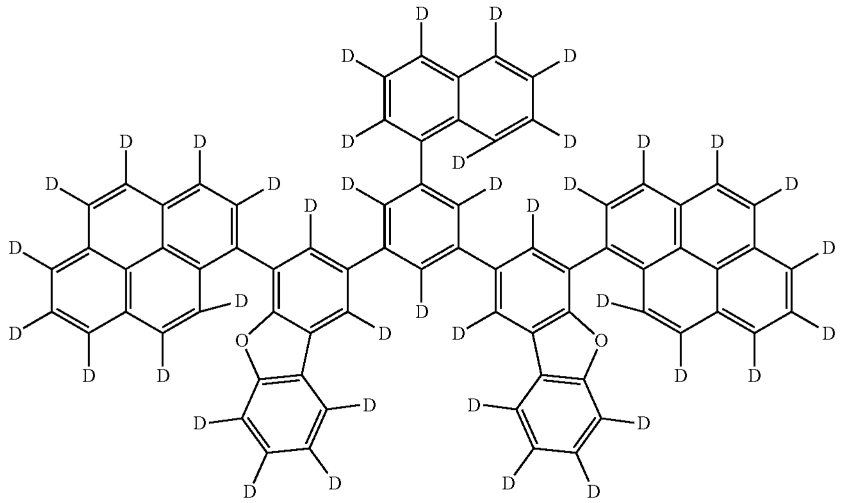
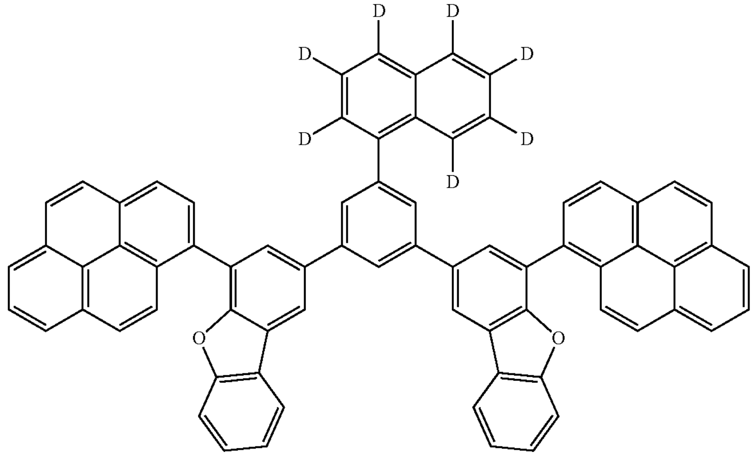
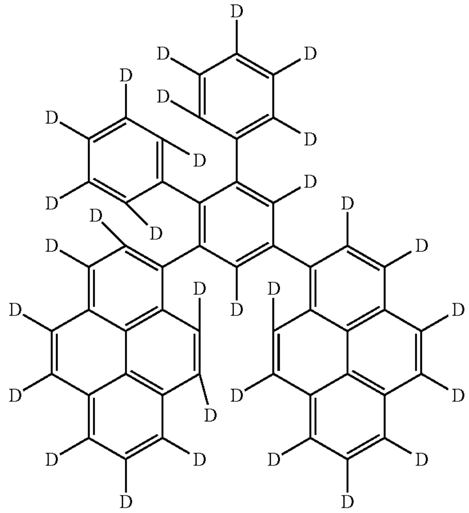
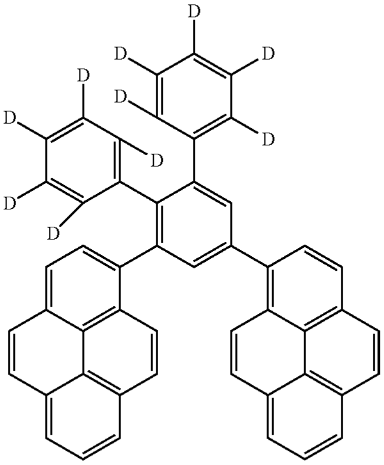

-continued
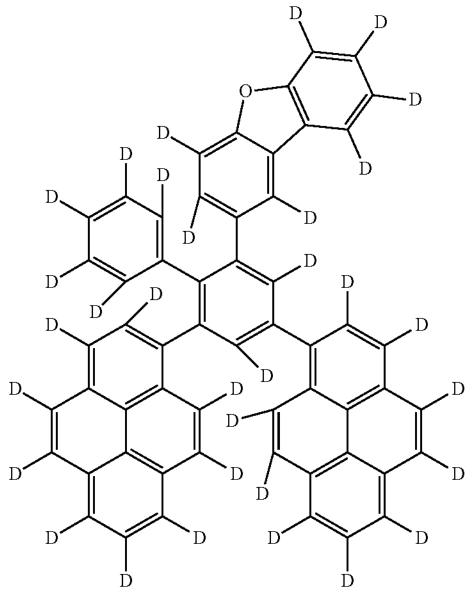
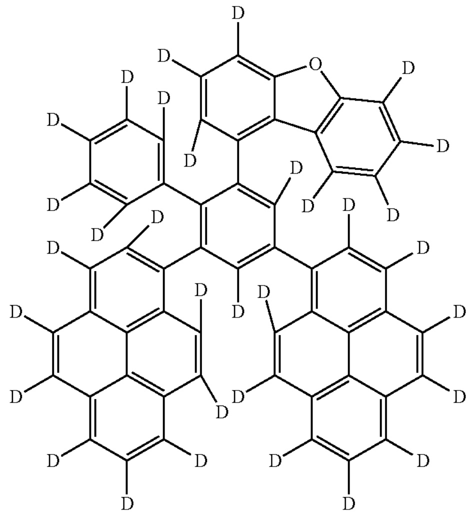
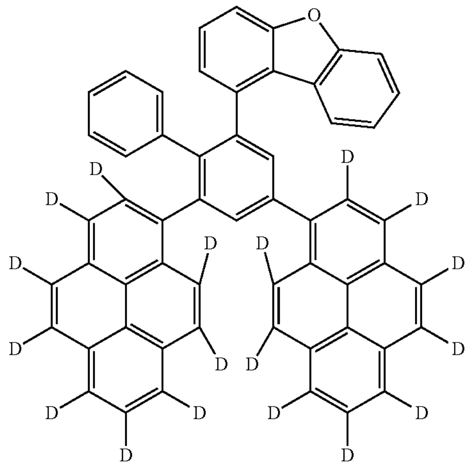
[Formula 95]
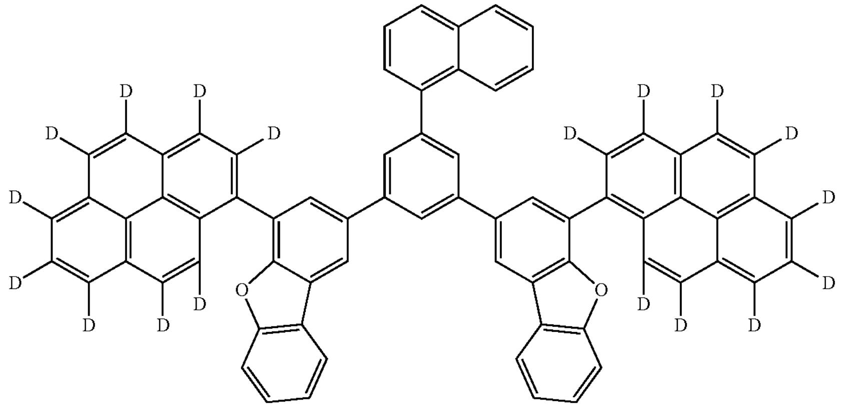

-continued
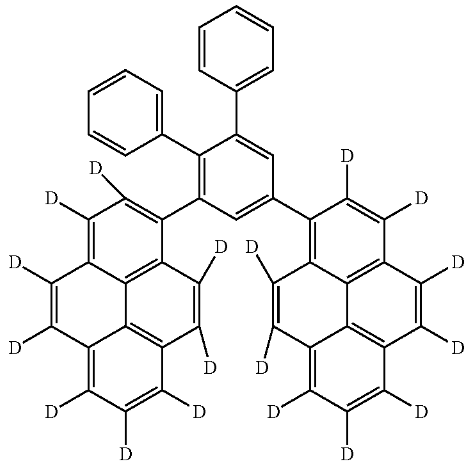
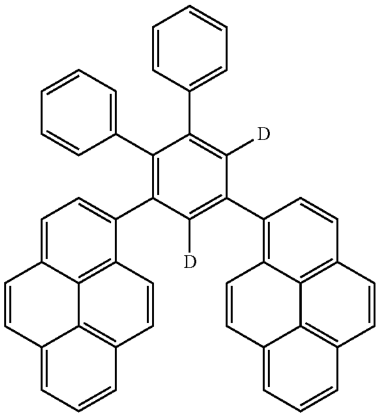
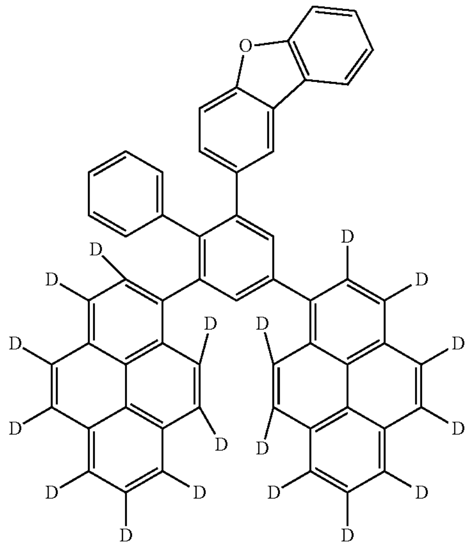
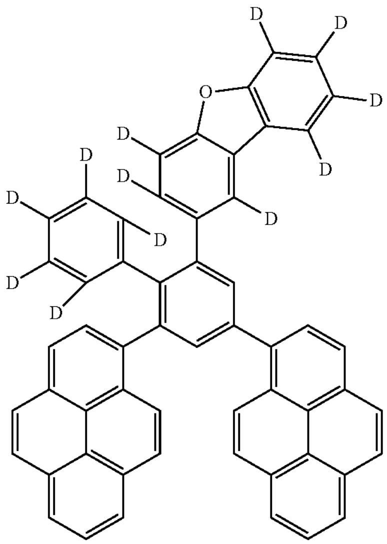
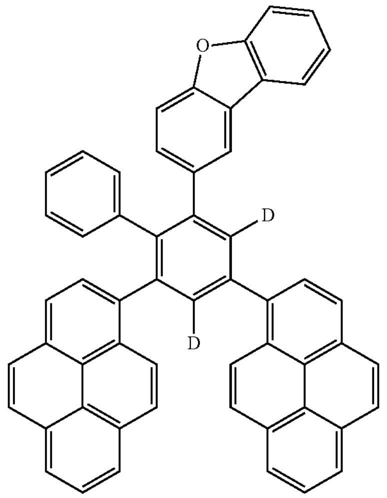
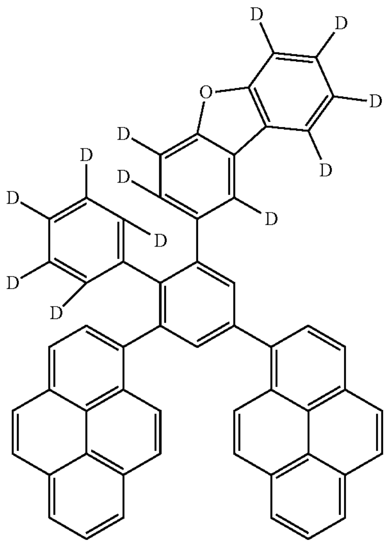

-continued
[Formula 96]
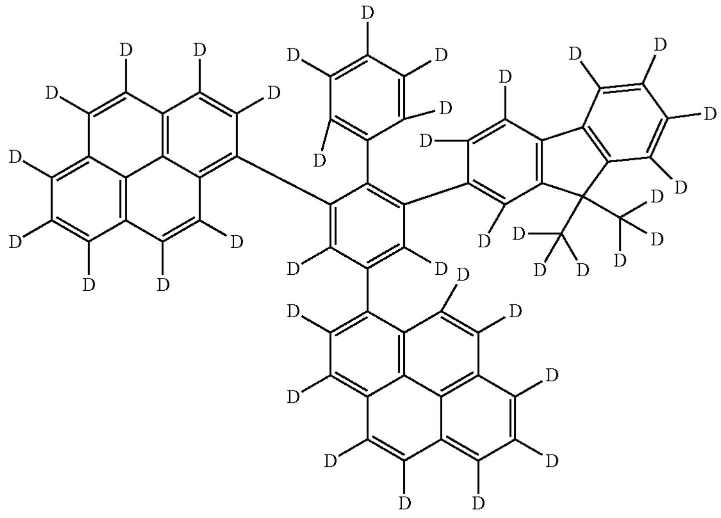
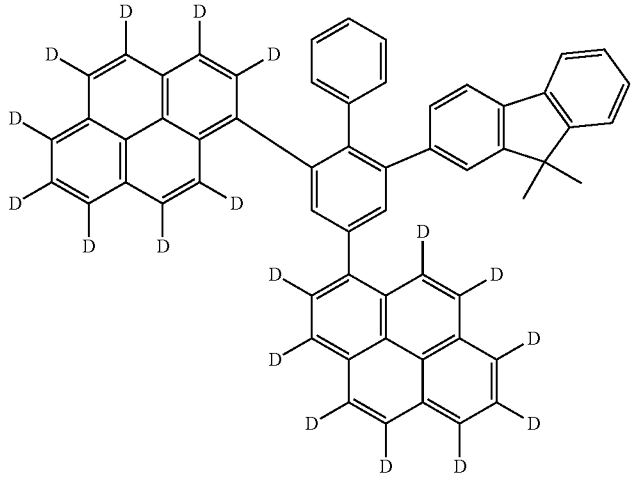
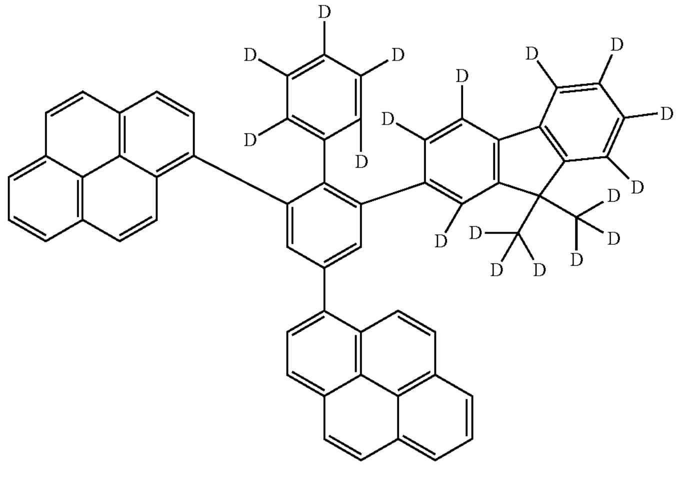
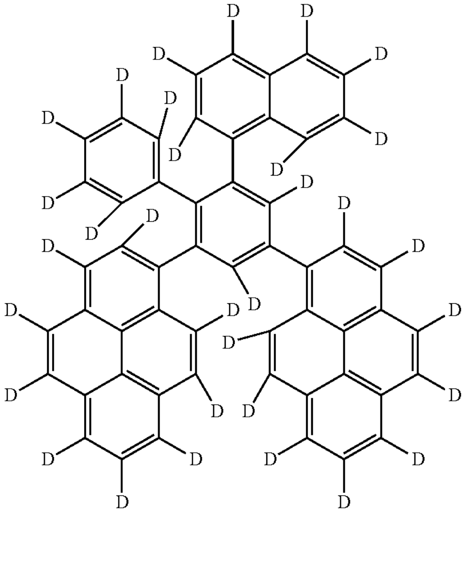

-continued
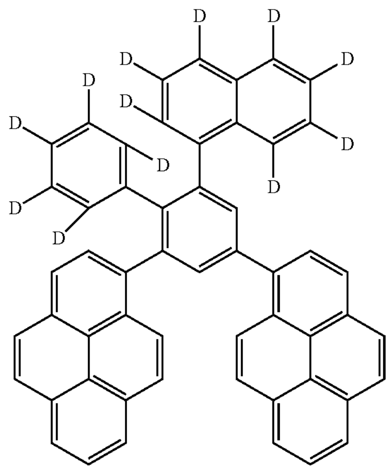
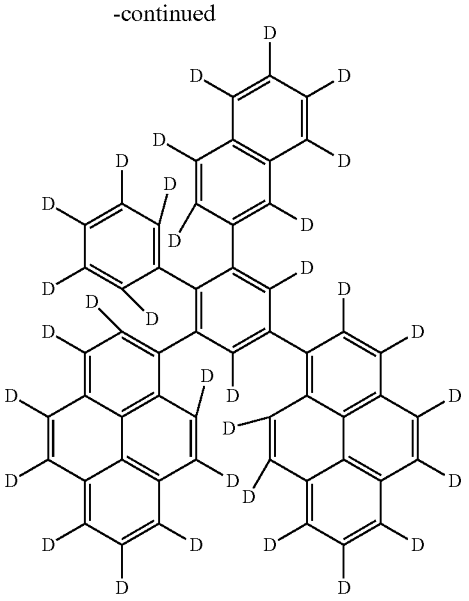
[Formula 97]
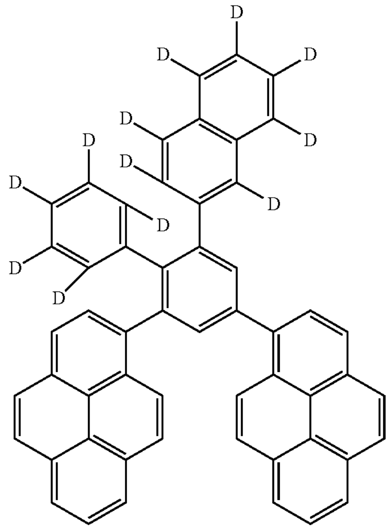
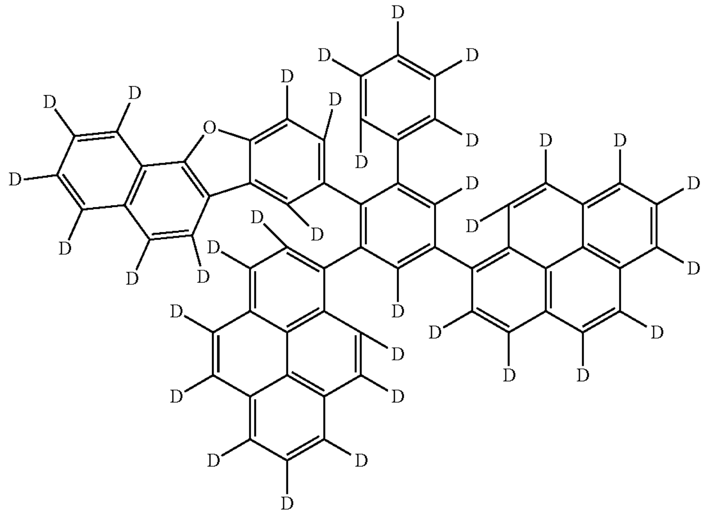
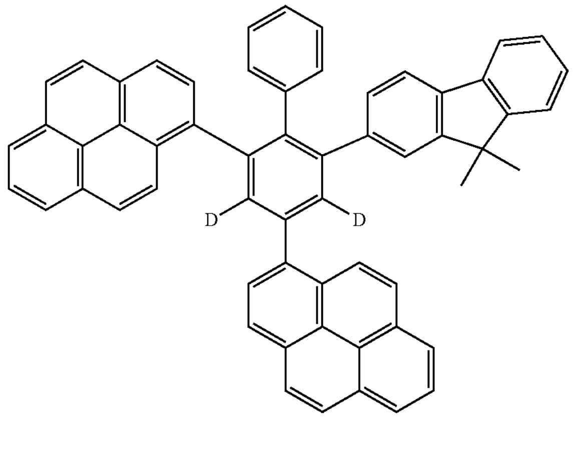

-continued
[Formula 98]
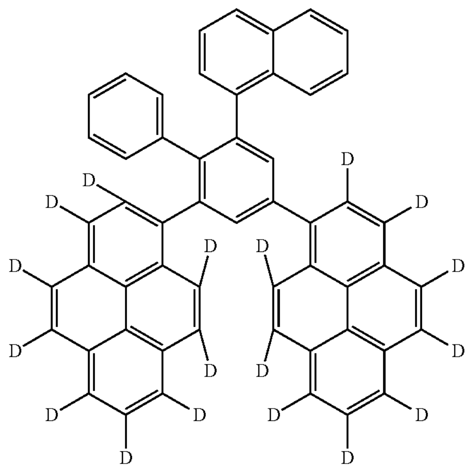
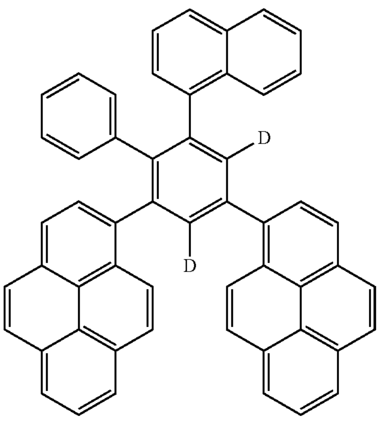
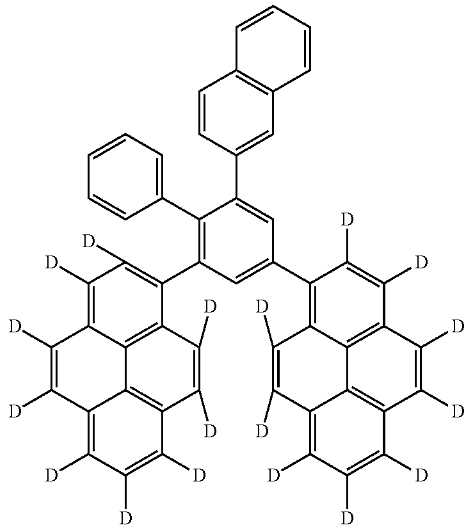
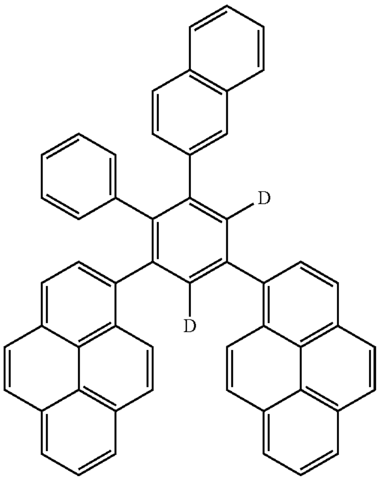
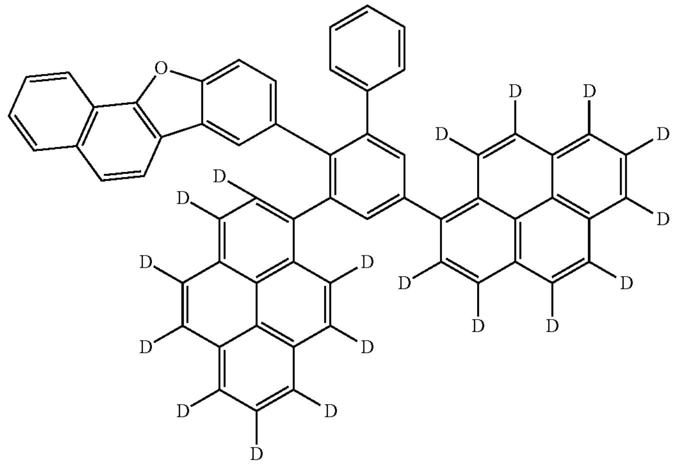

-continued
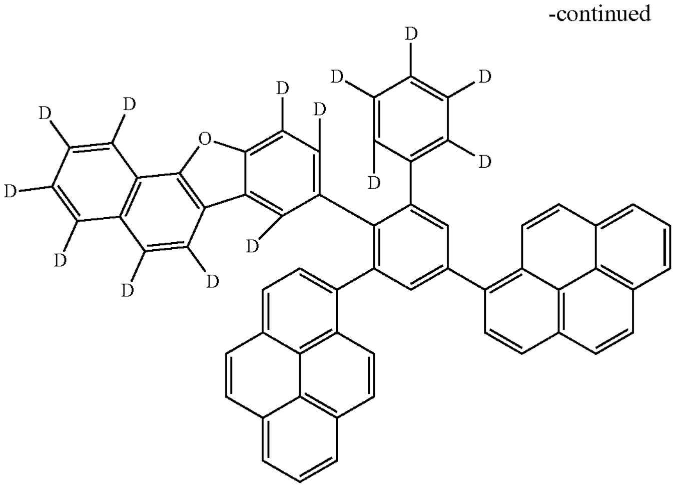
[Formula 99]
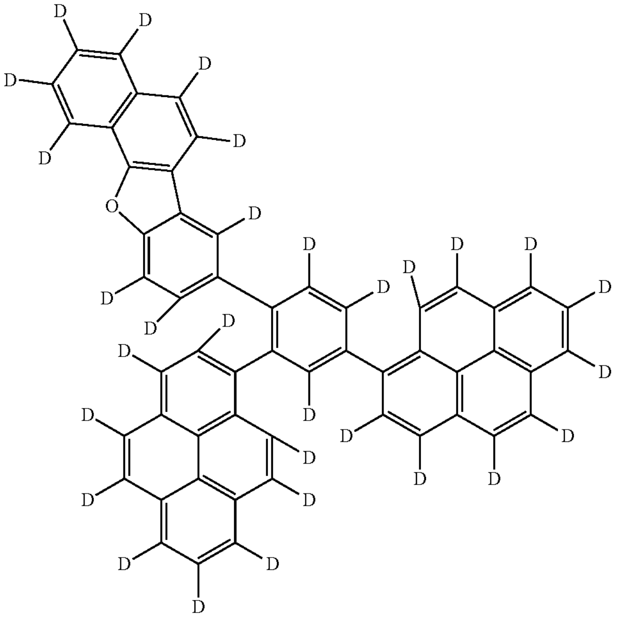
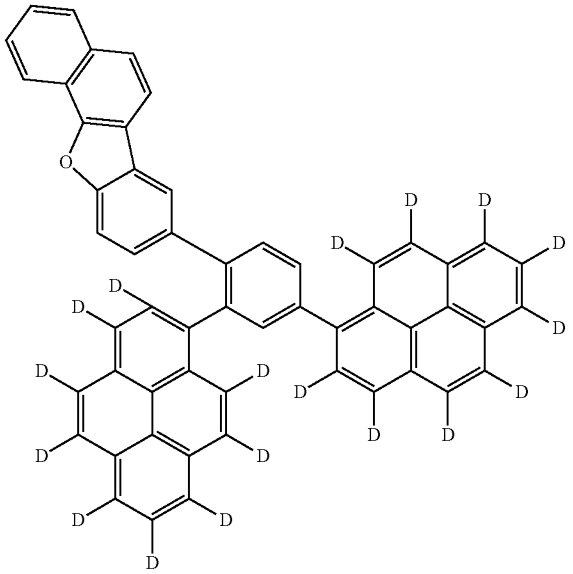
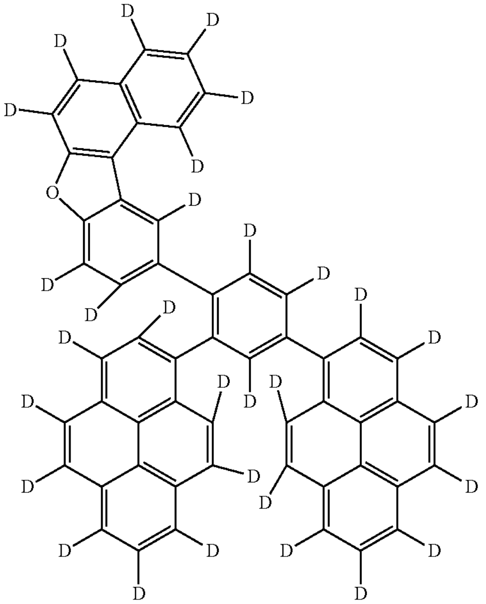
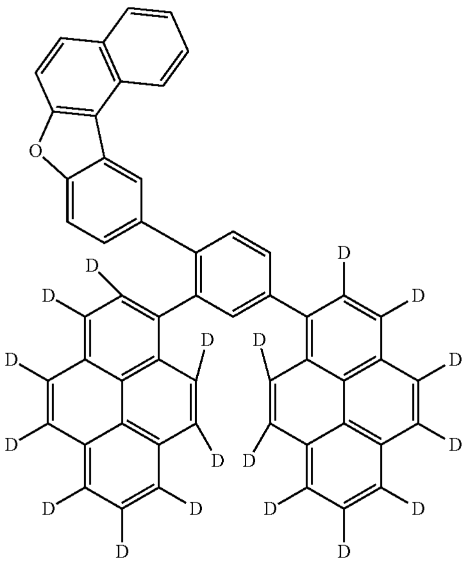

-continued
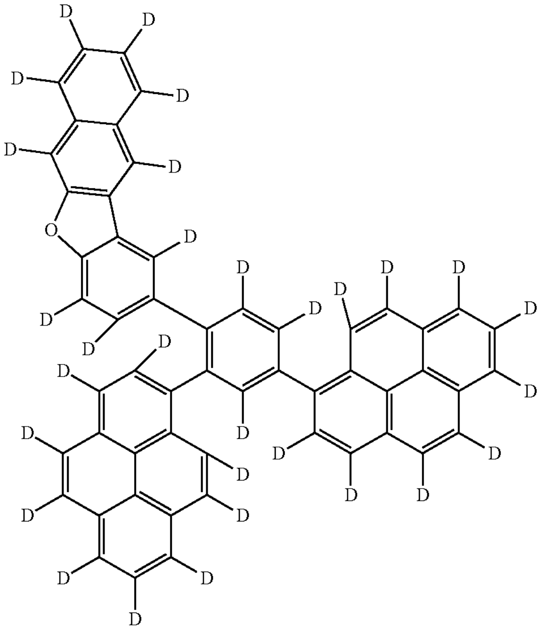
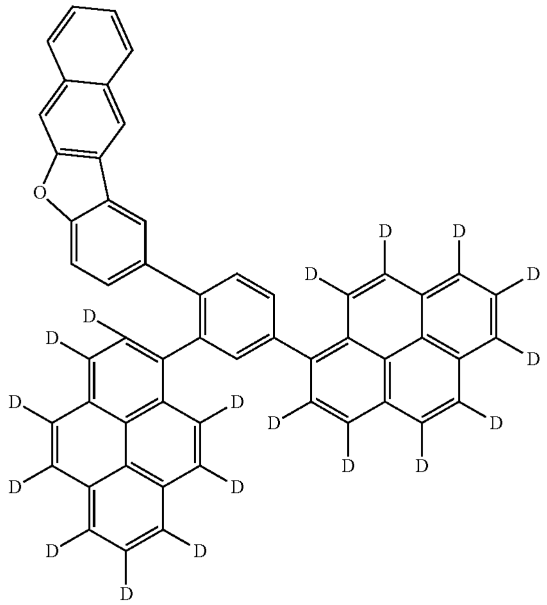
[Formula 100]
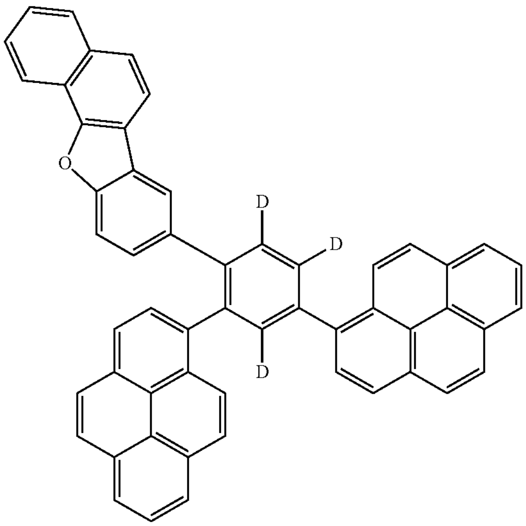
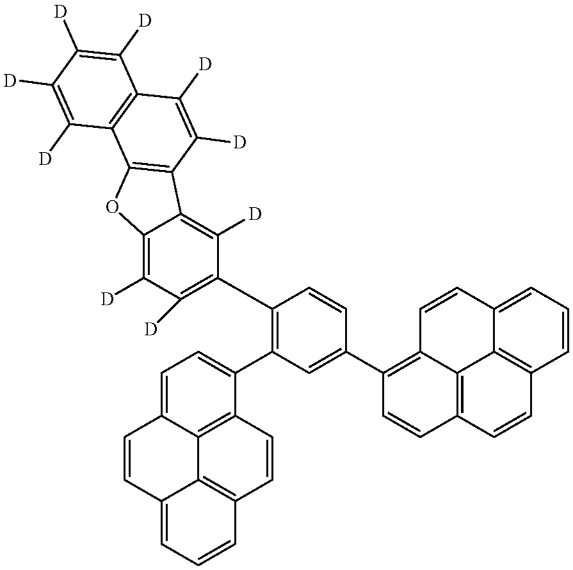

-continued
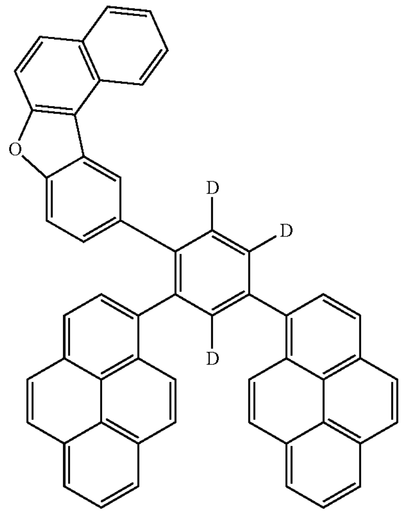
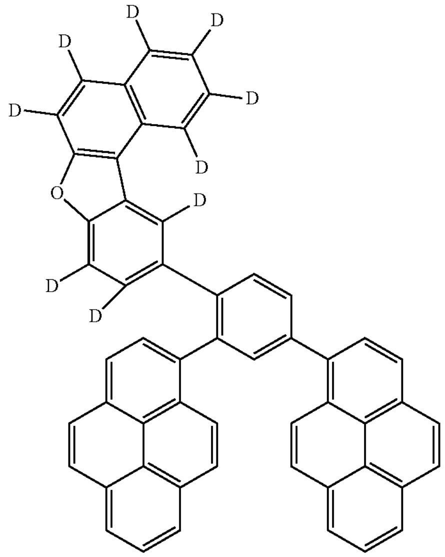
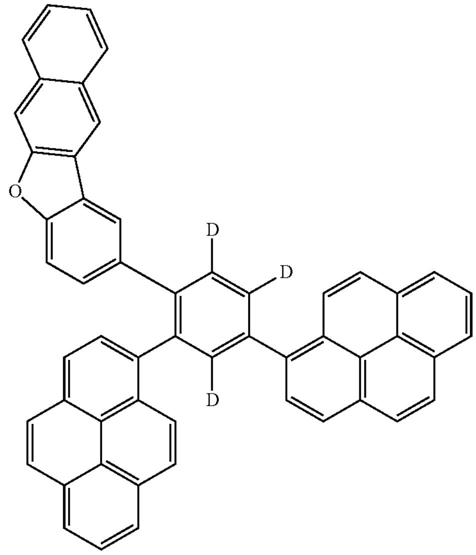
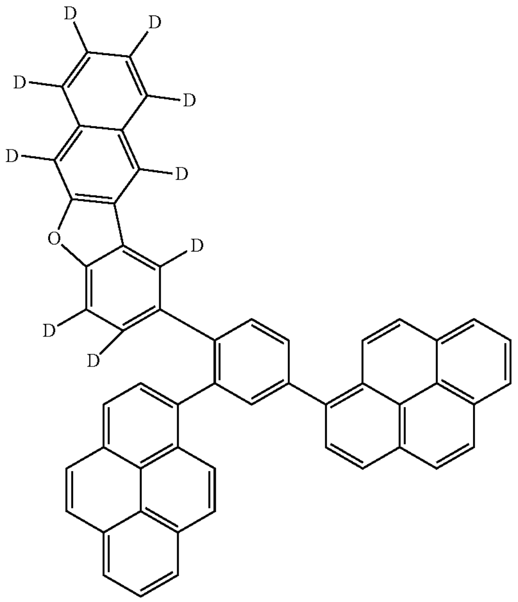
[Formula 101]
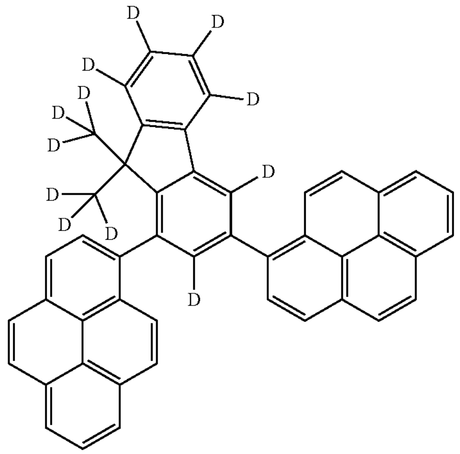
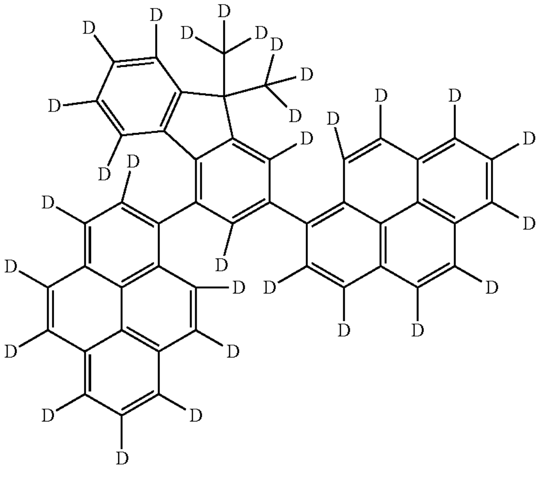

-continued
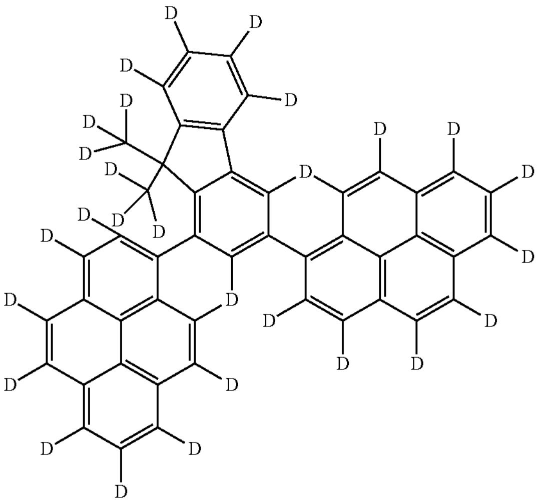
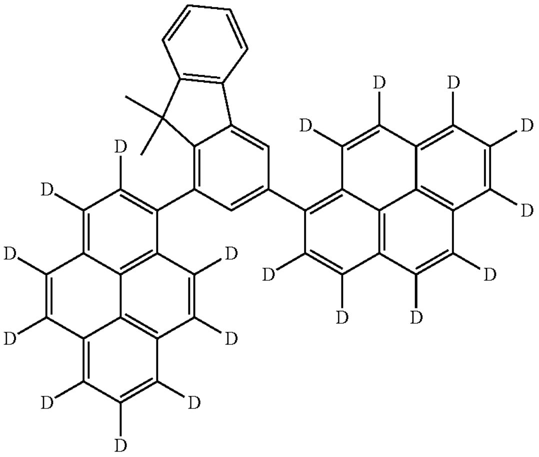
[Formula 102]
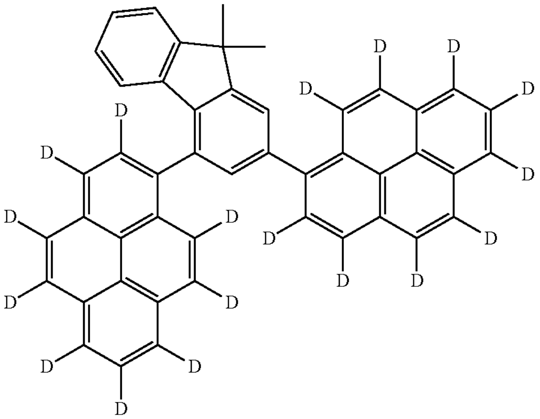
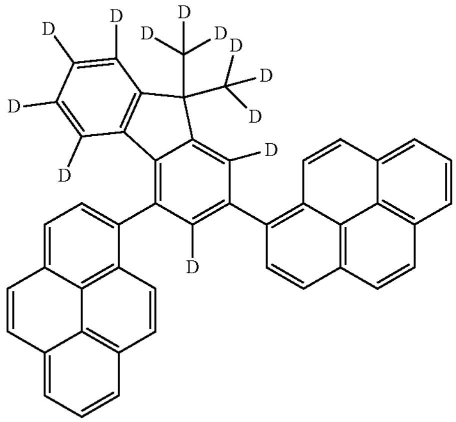
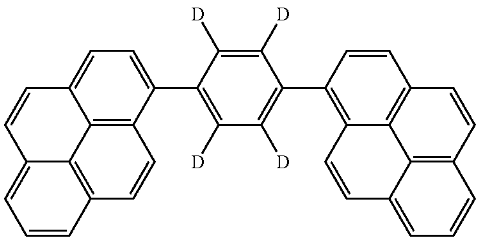
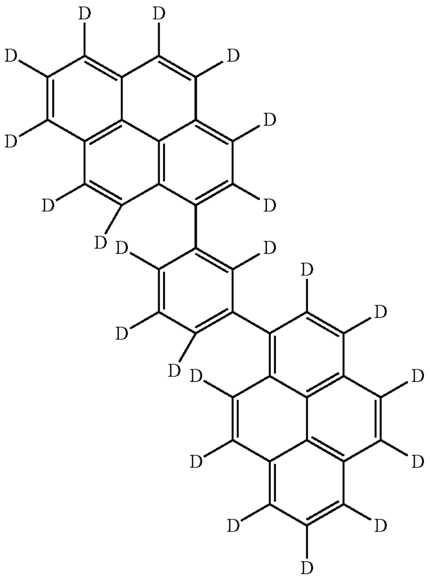

-continued
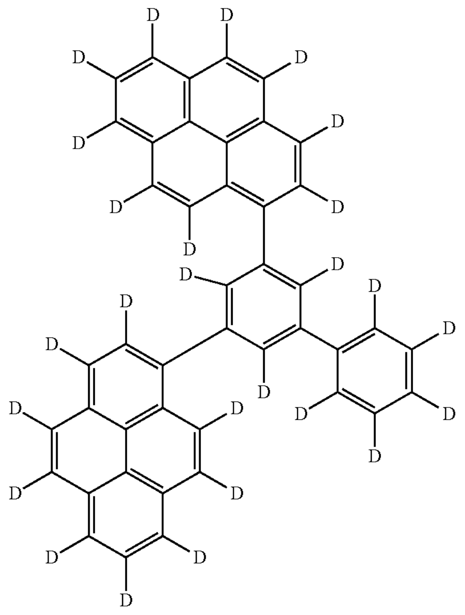
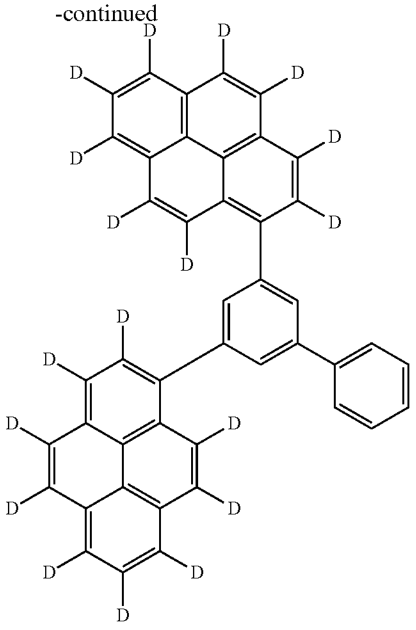
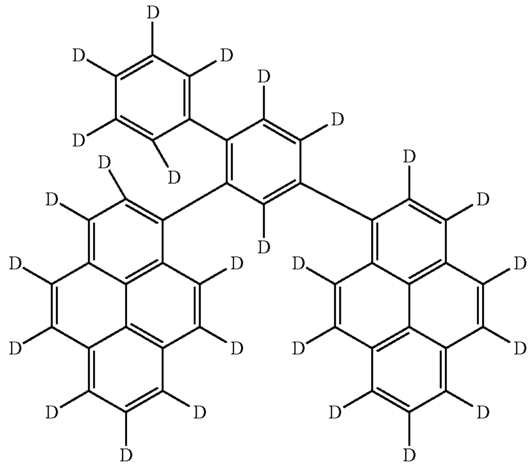
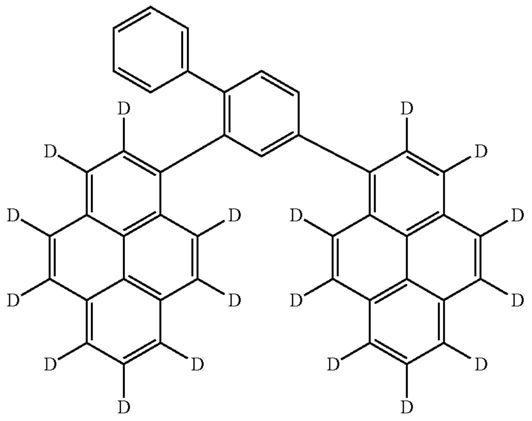
[Formula 103]
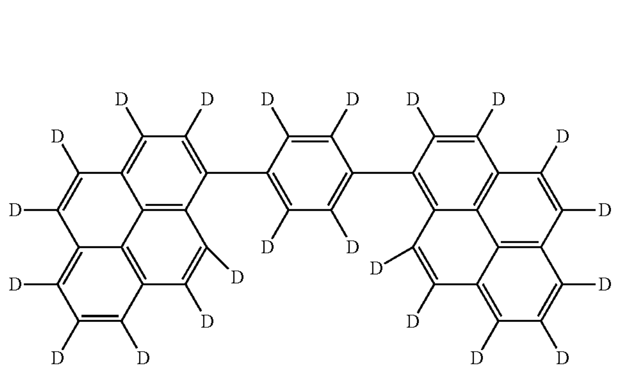
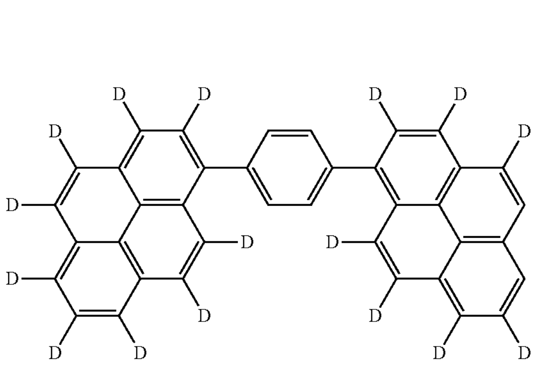

-continued
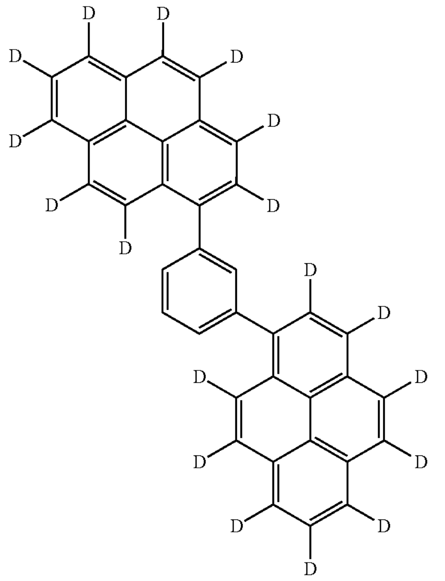
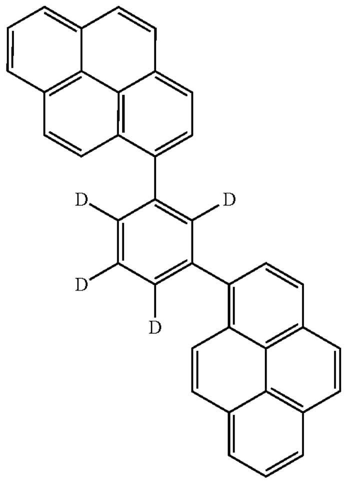
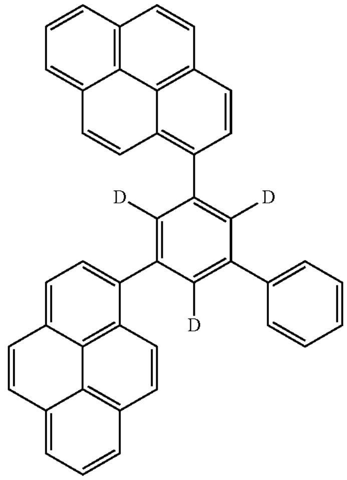
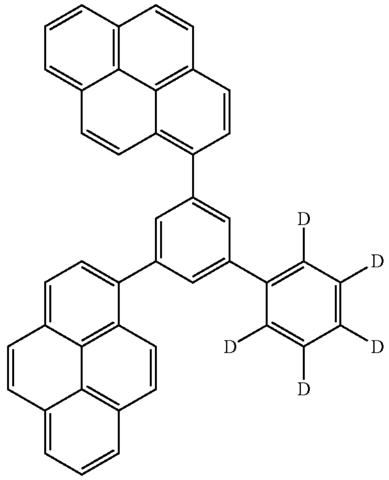
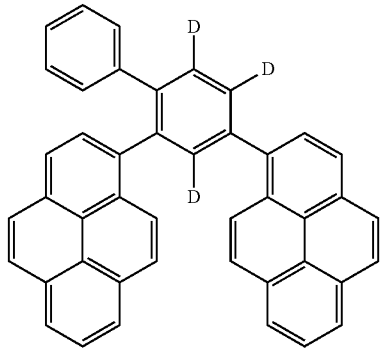
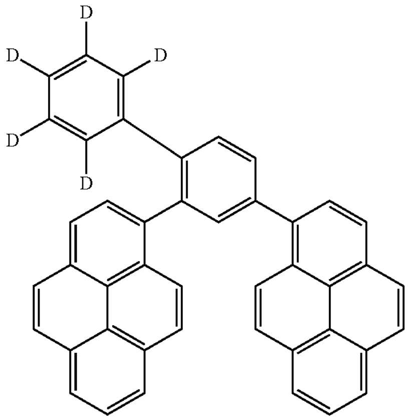

-continued
[Formula 104]
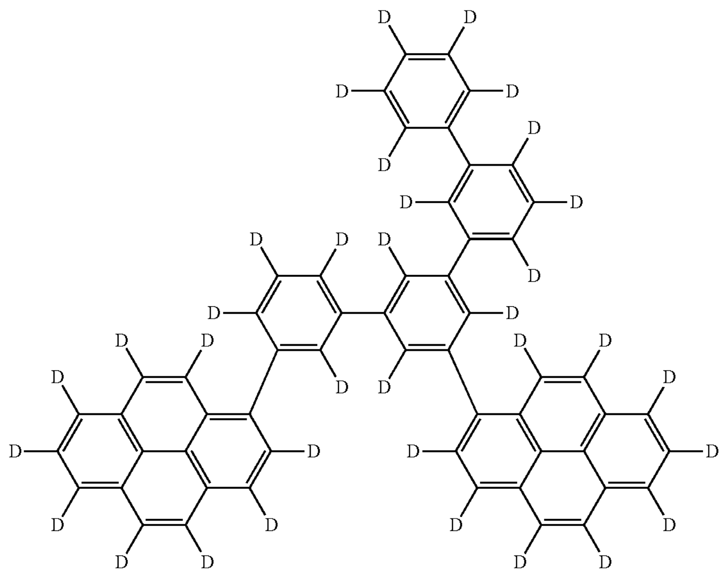
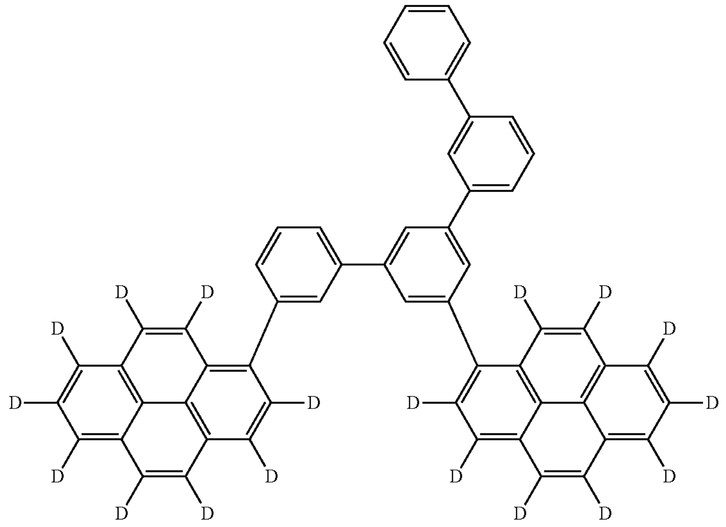
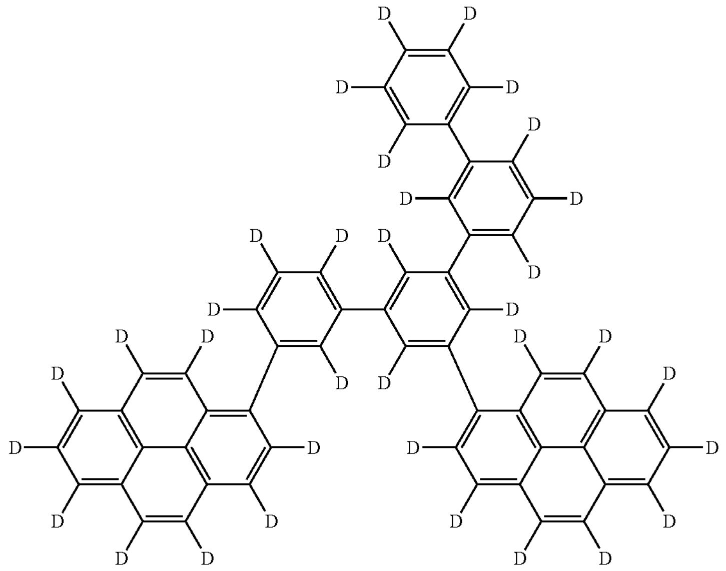

-continued
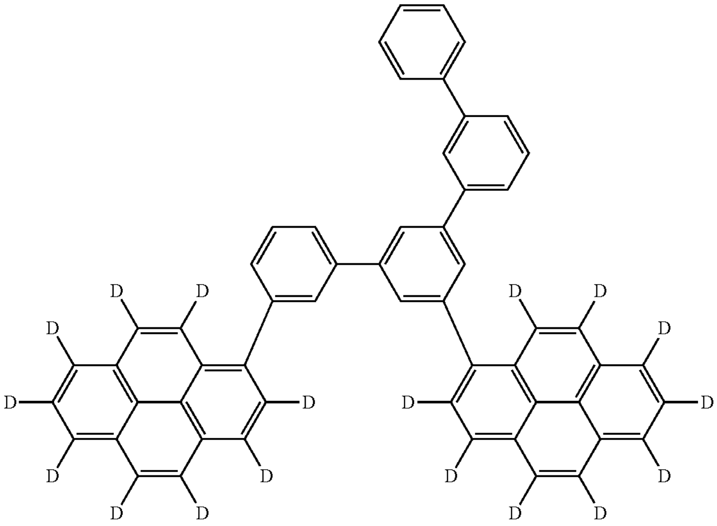
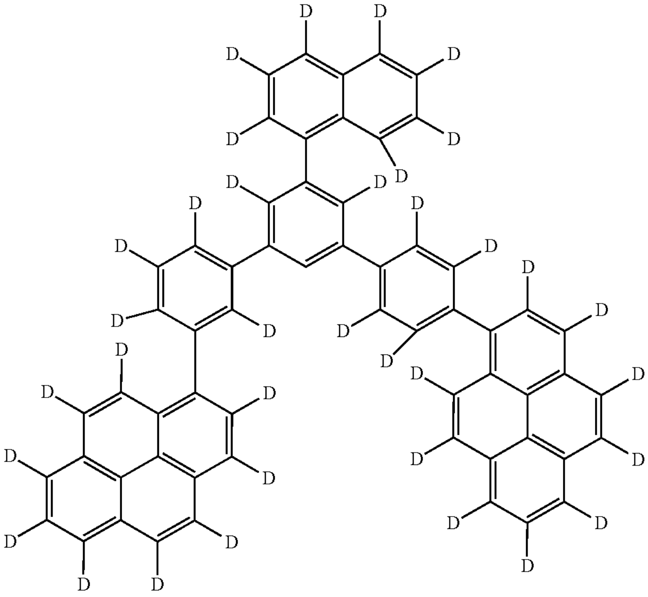
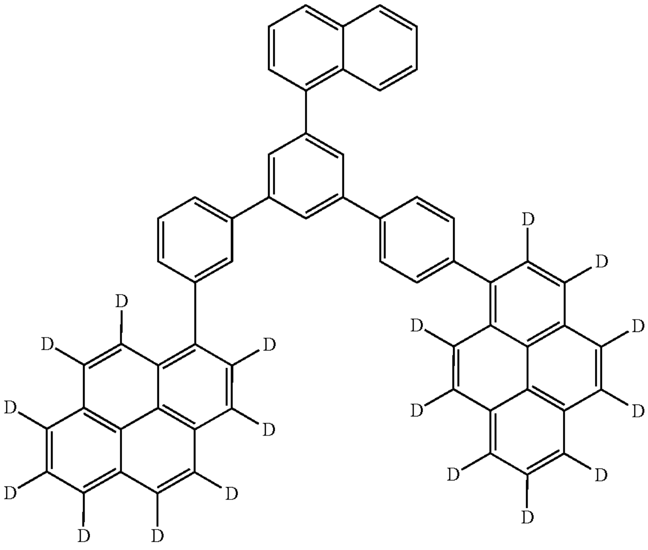

-continued
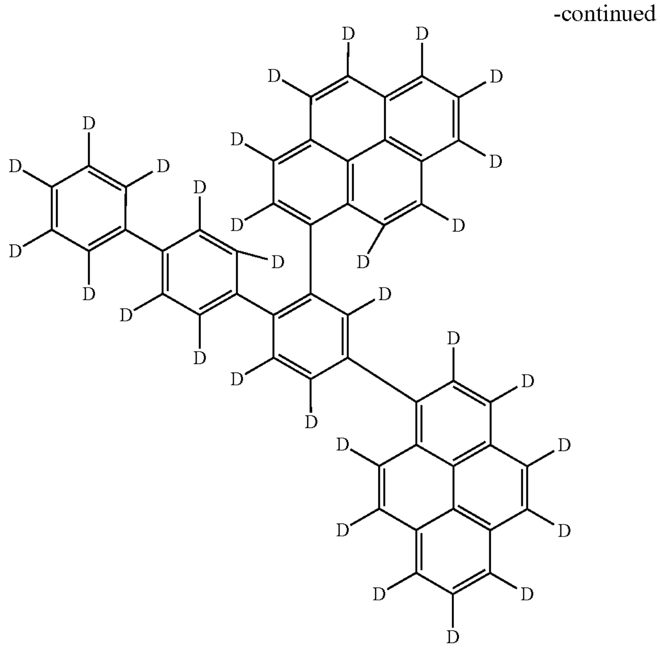
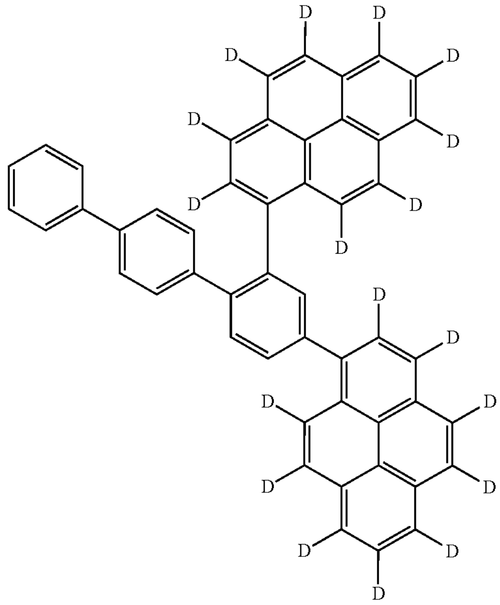

-continued
[Formula 105]
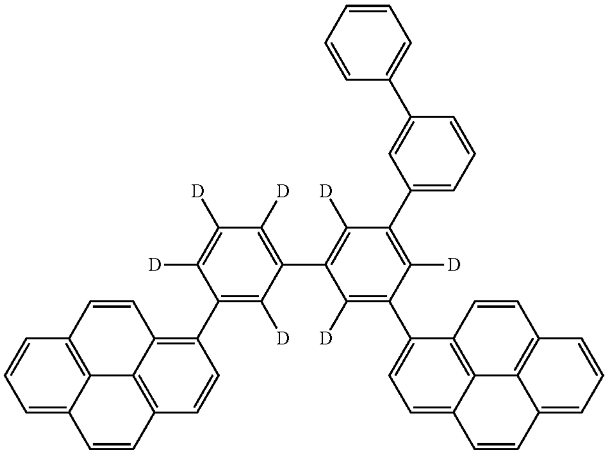
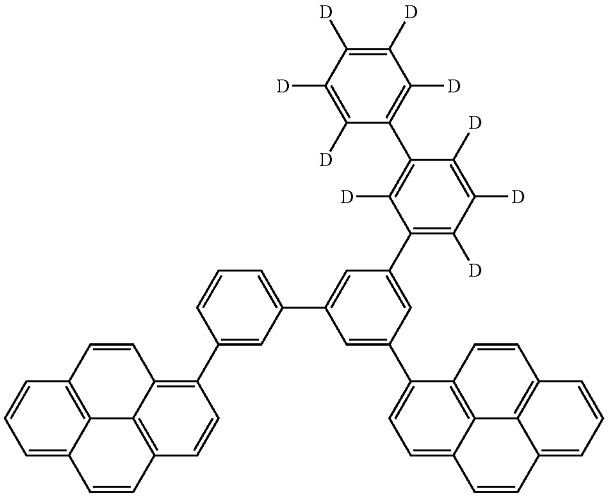
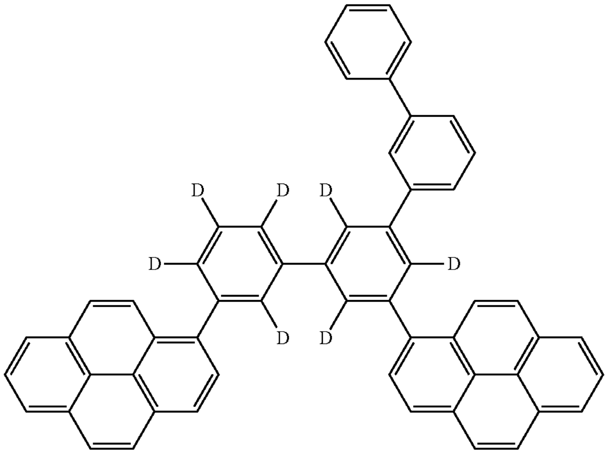

-continued
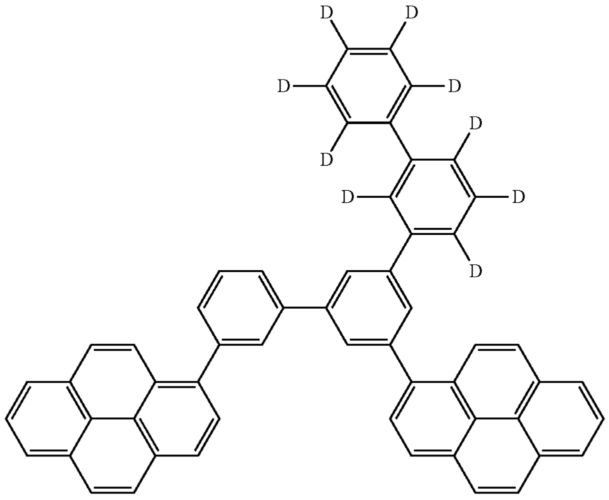
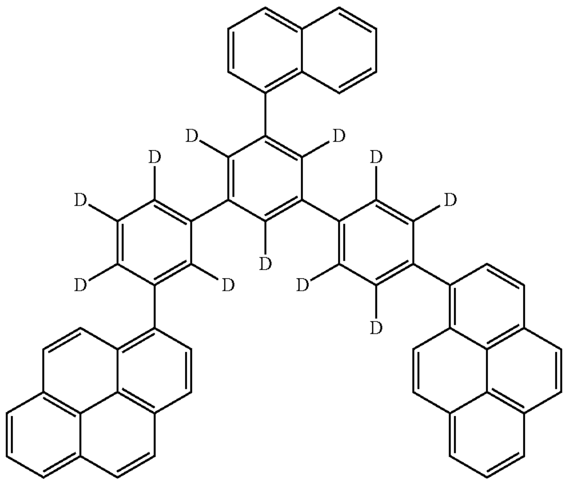
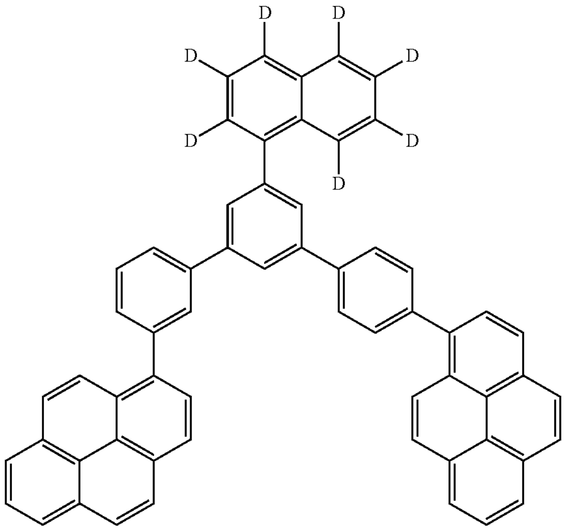
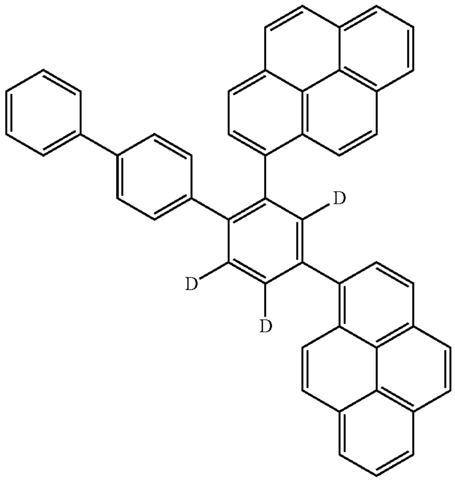
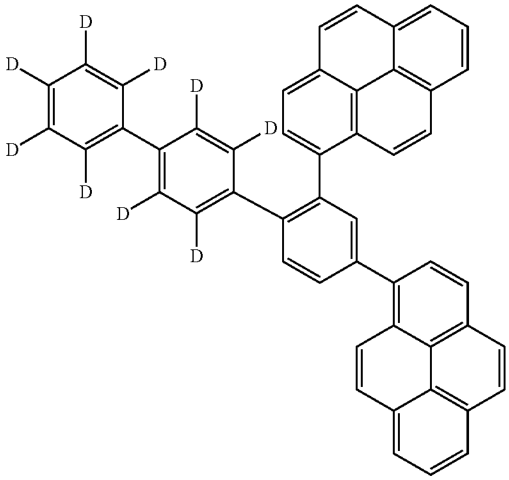

-continued
[Formula 106]
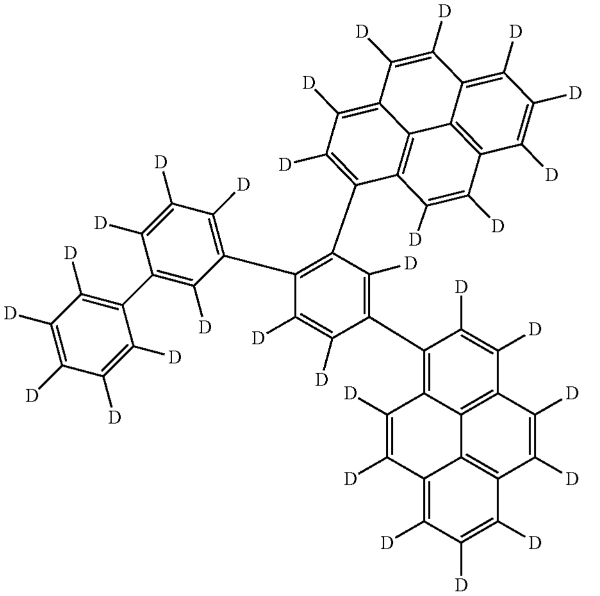
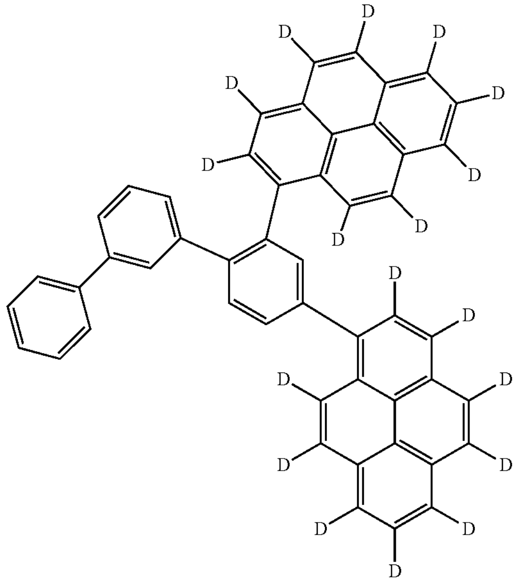
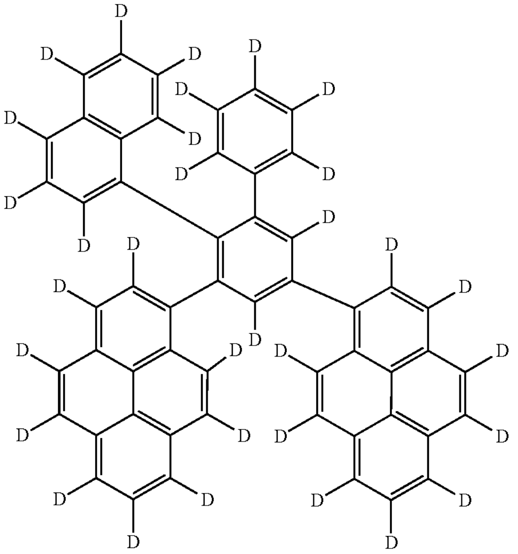
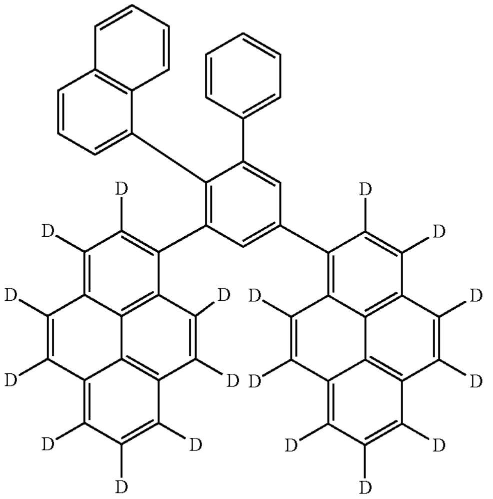
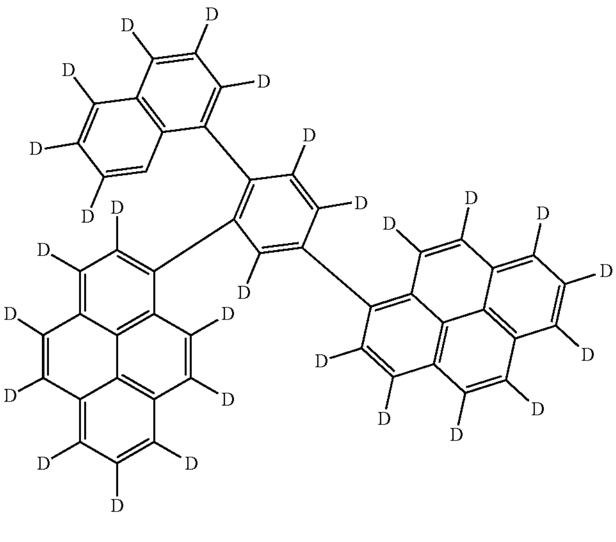
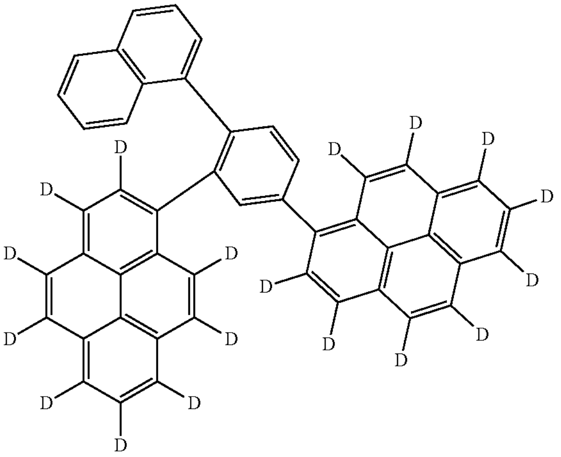

-continued
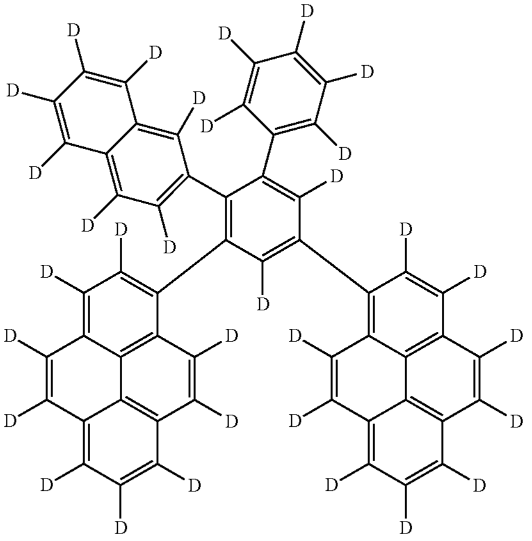
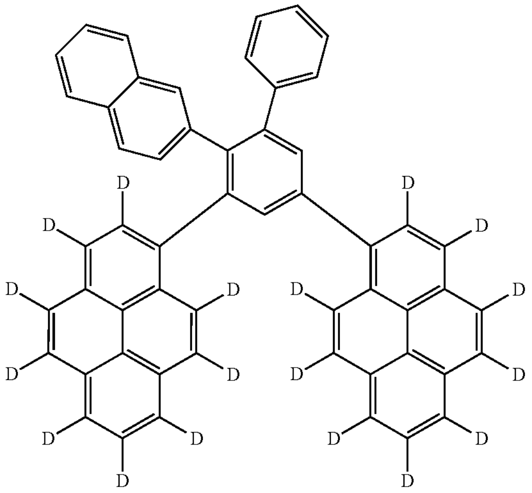
[Formula 107]
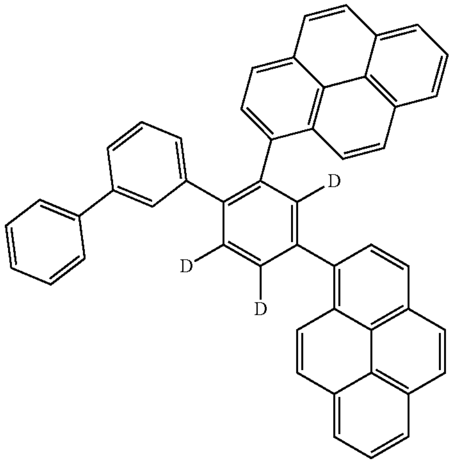
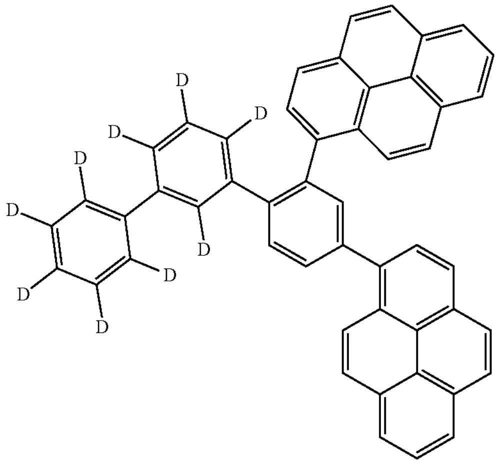
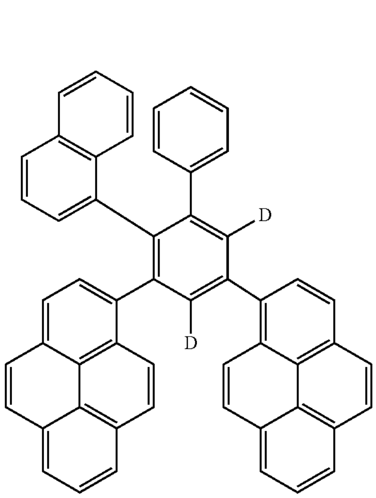
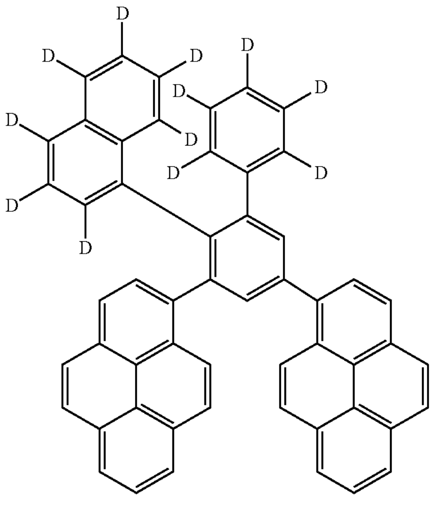

-continued
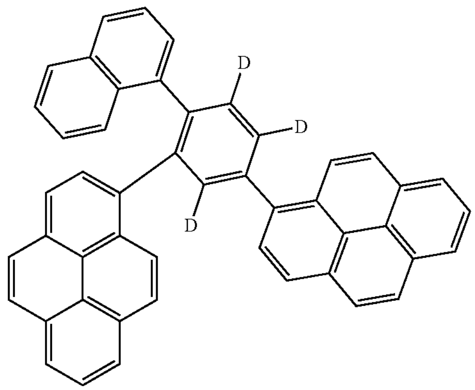
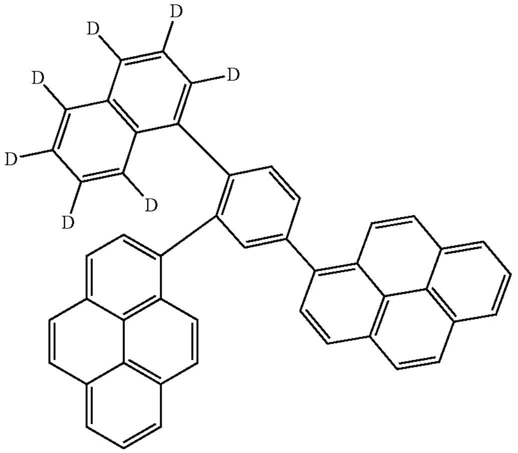
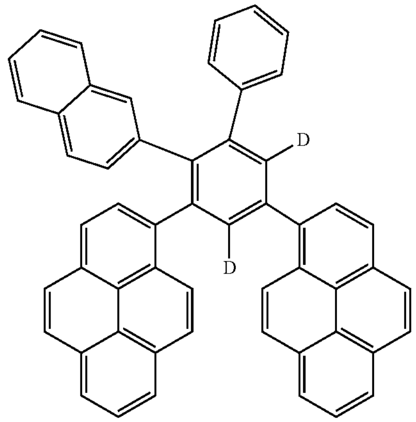
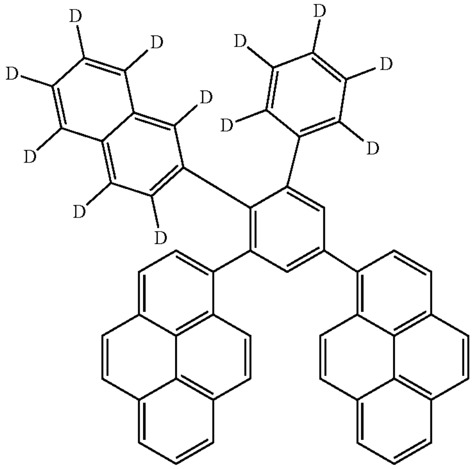
[Formula 108]
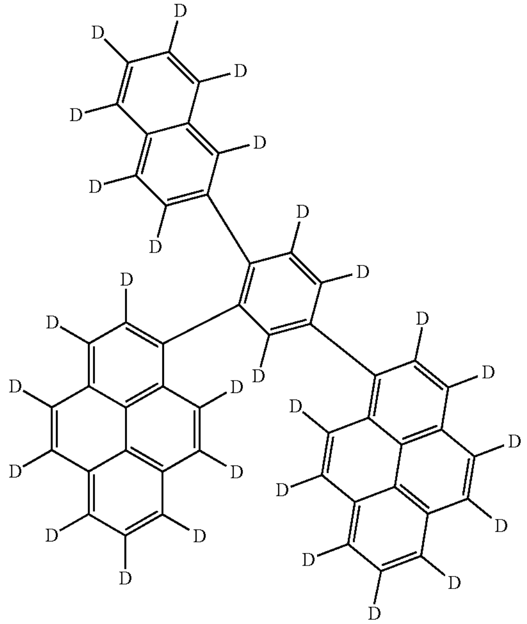
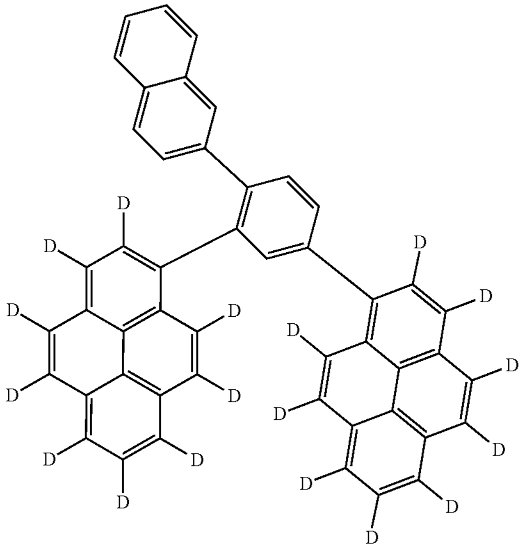

-continued
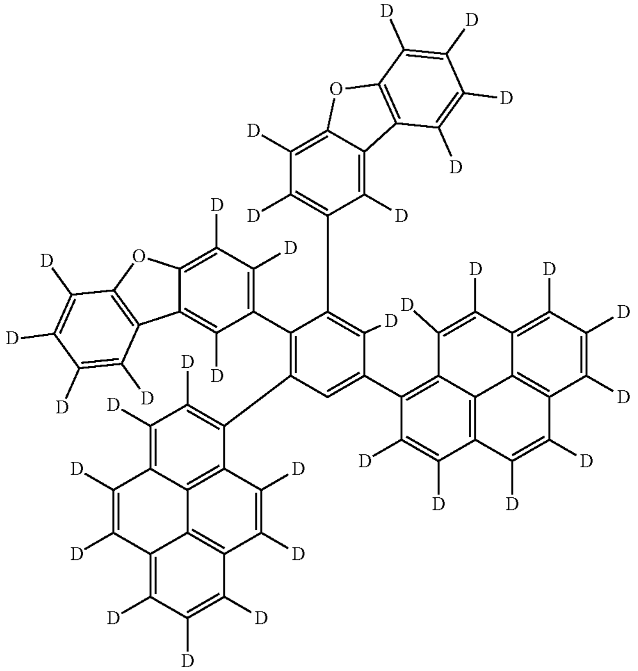
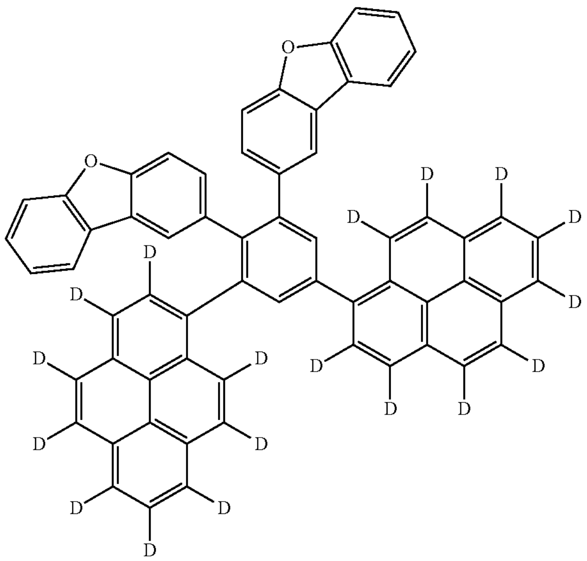
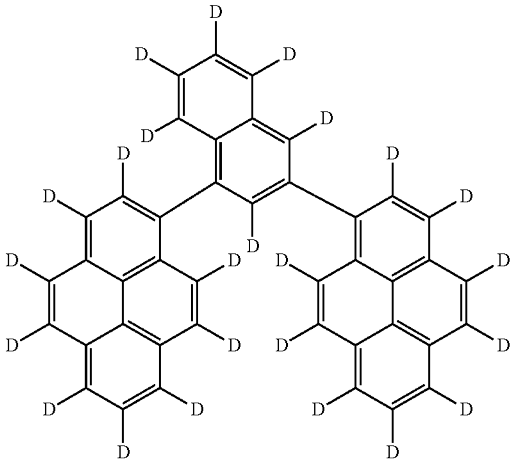
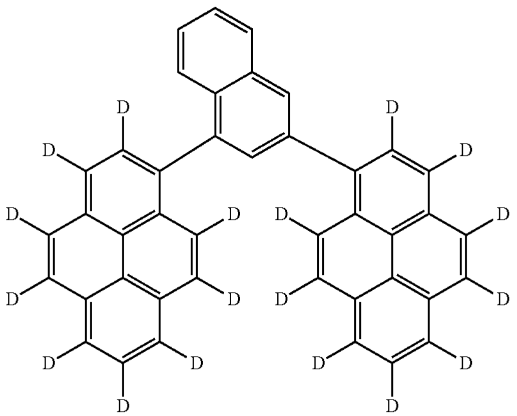
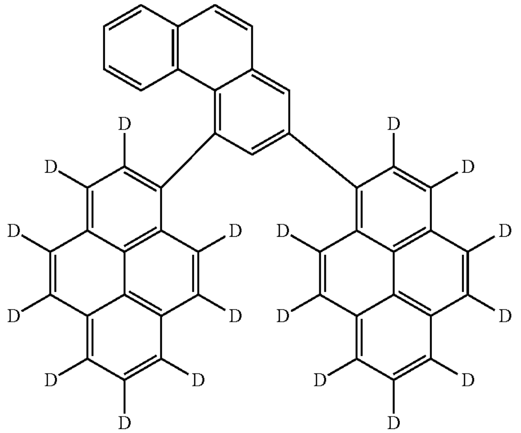

-continued
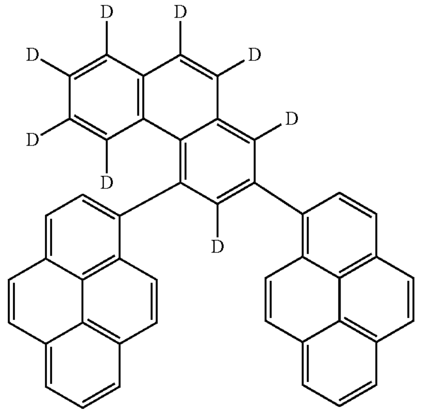
[Formula 109]
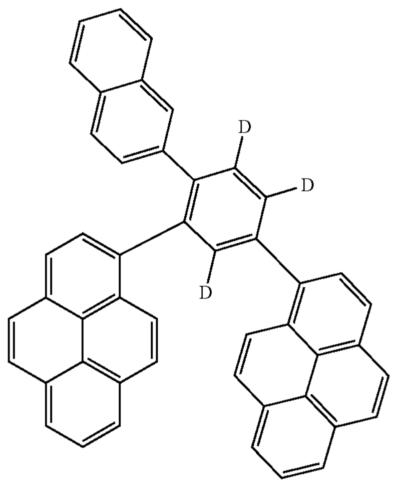
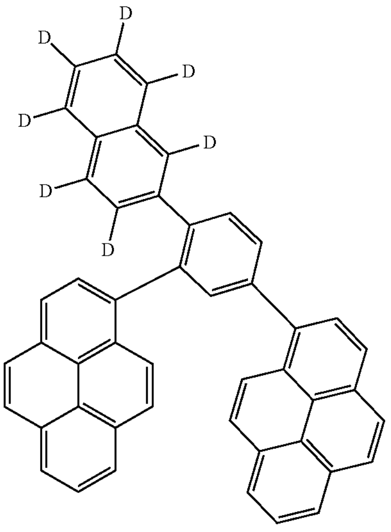
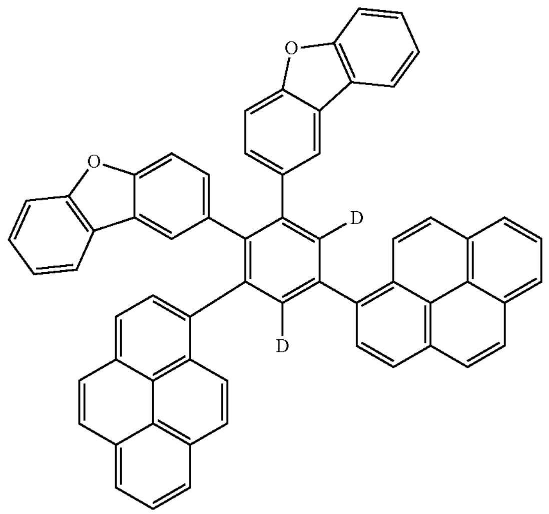
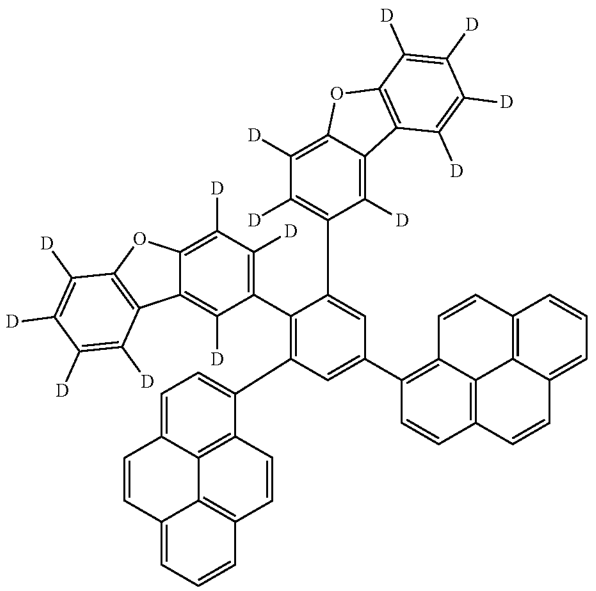

-continued
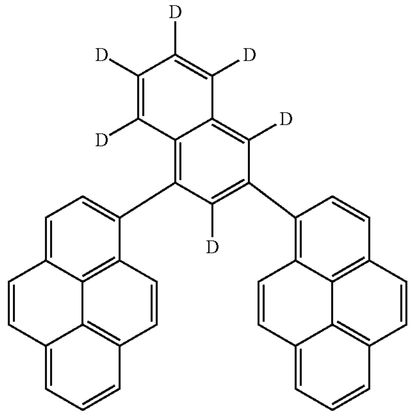
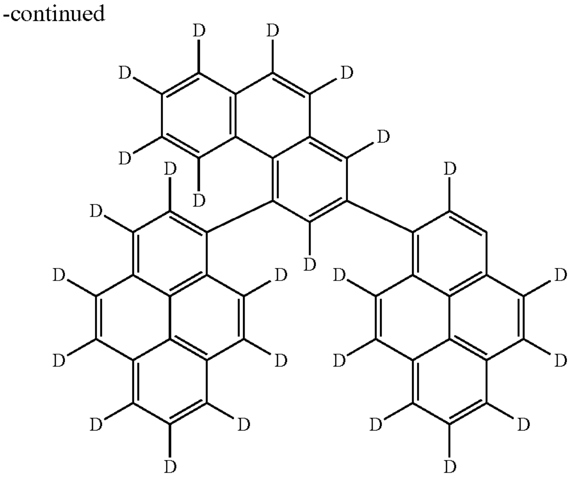
[Formula 110]
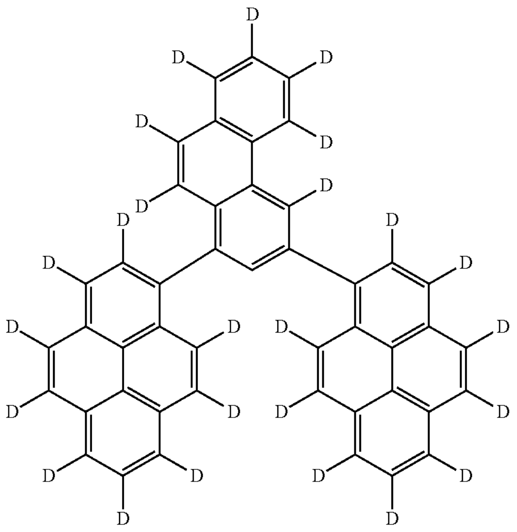
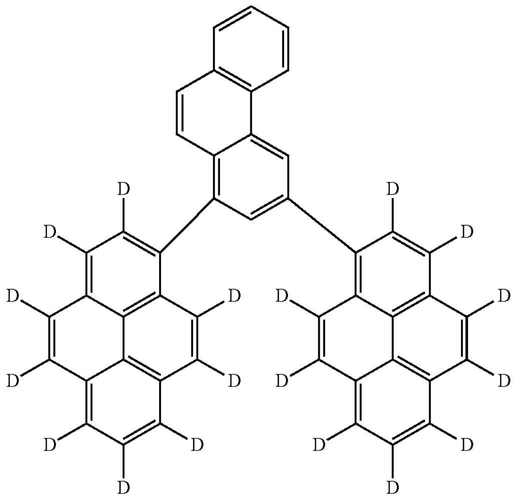
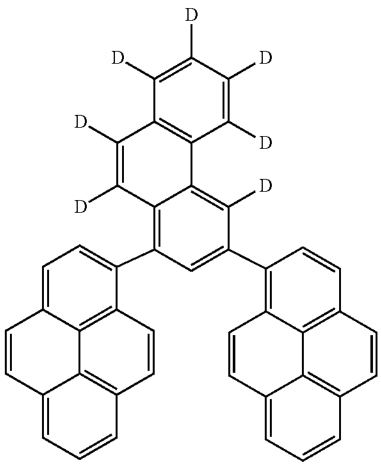
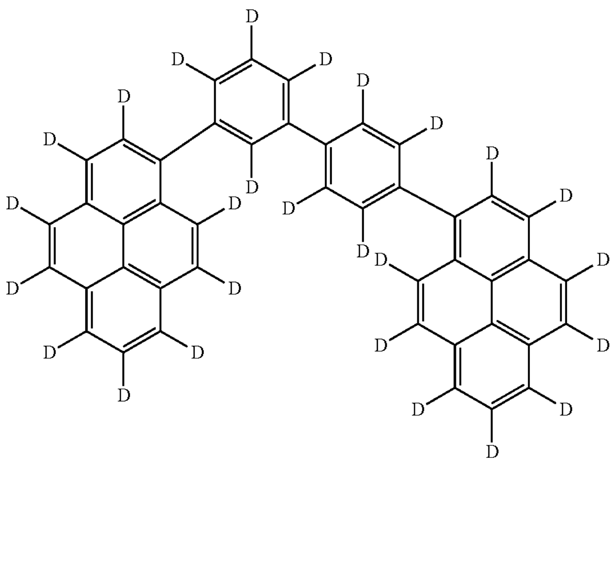

-continued
[Formula 111]
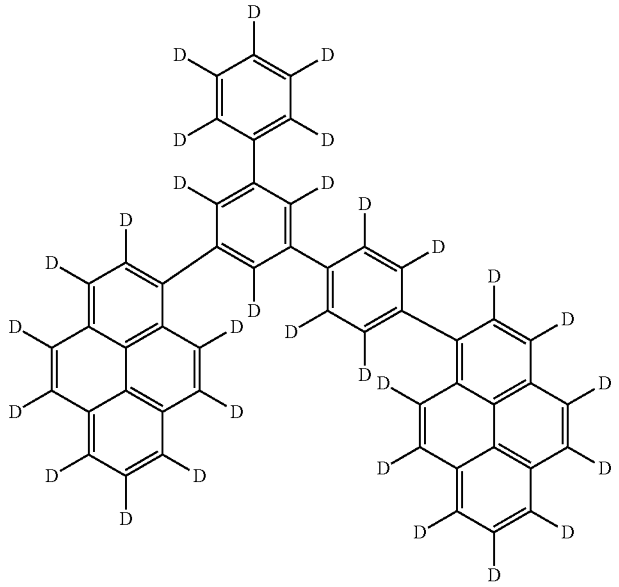
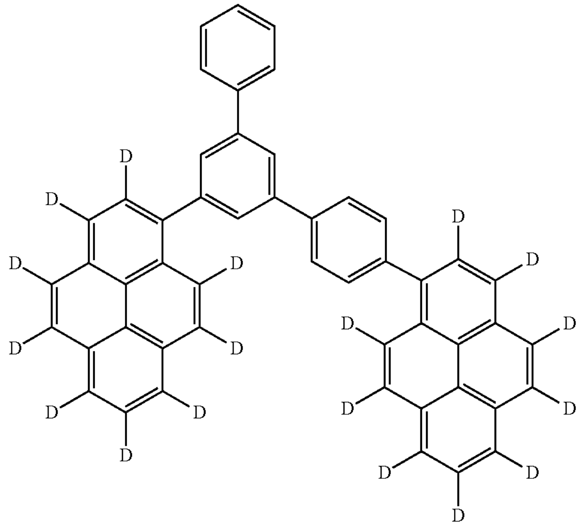
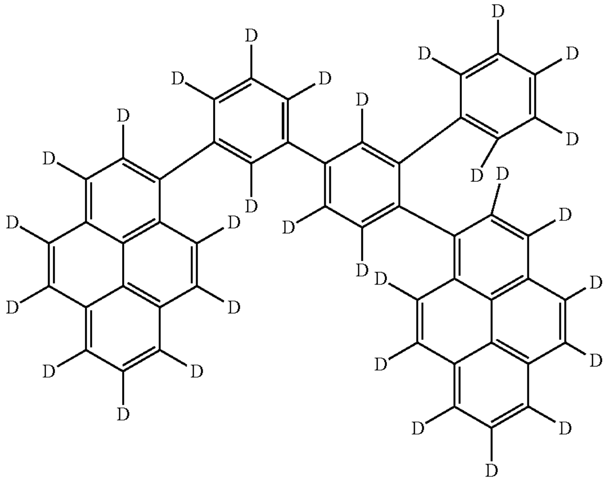
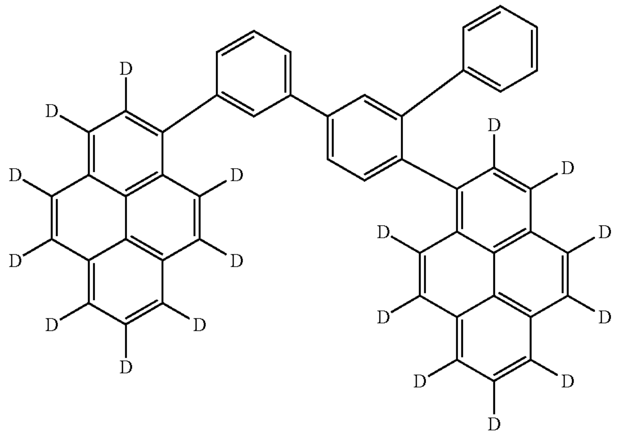

-continued
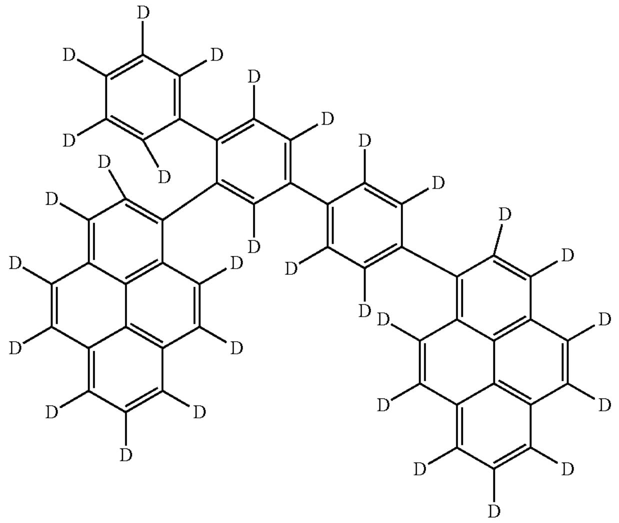
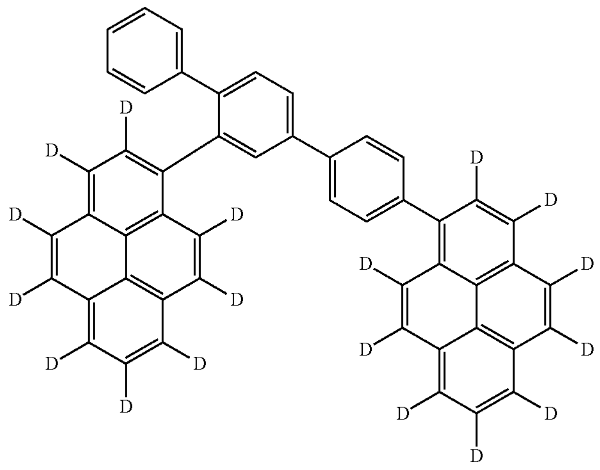
[Formula 112]
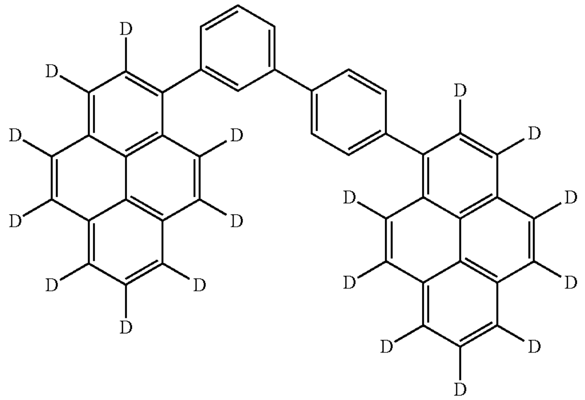
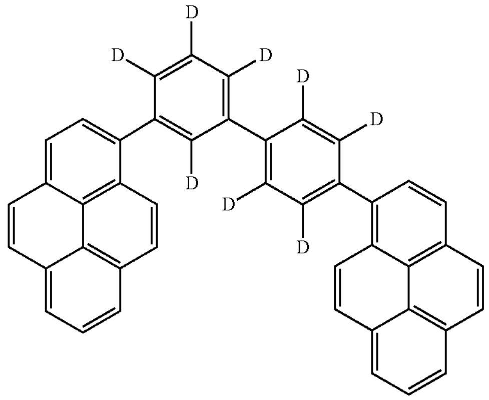

-continued
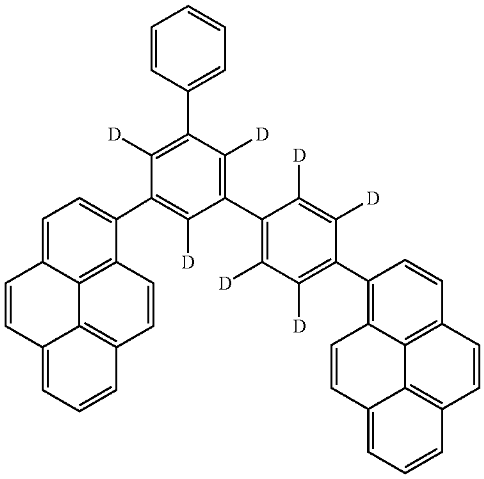
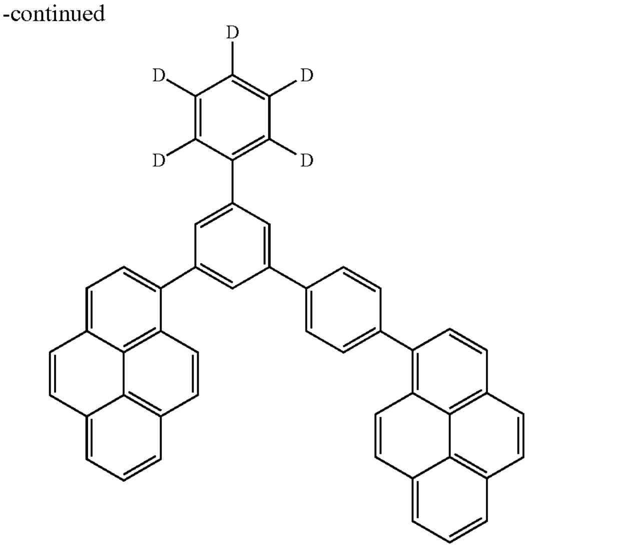
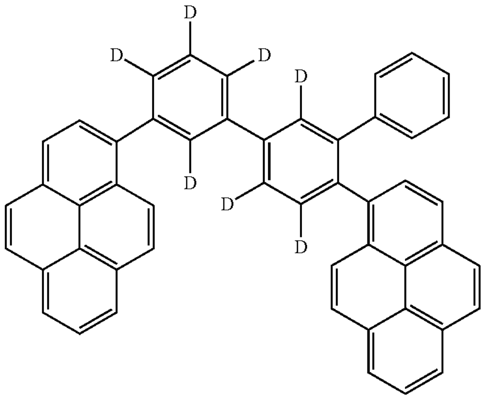
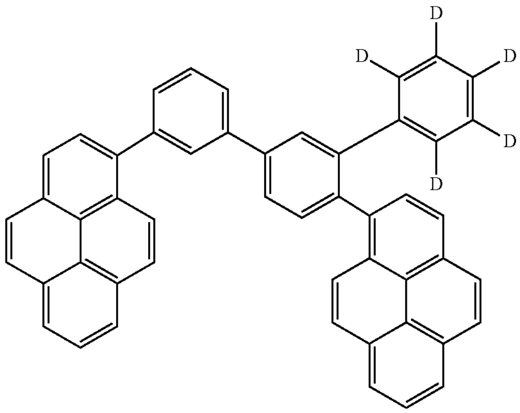
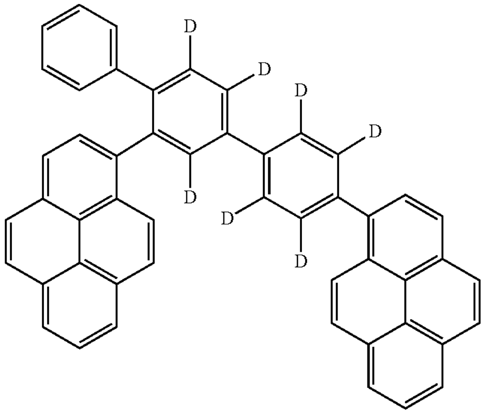
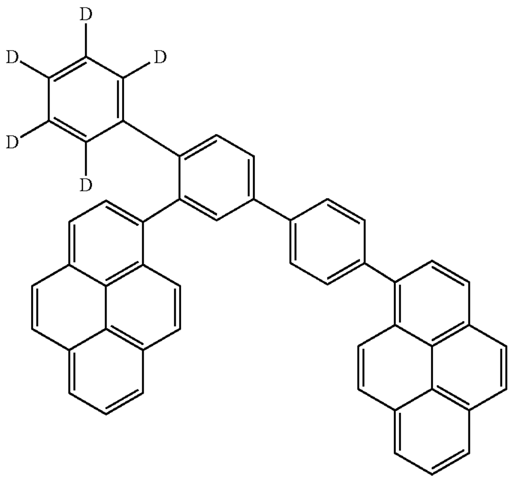

-continued
[Formula 113]
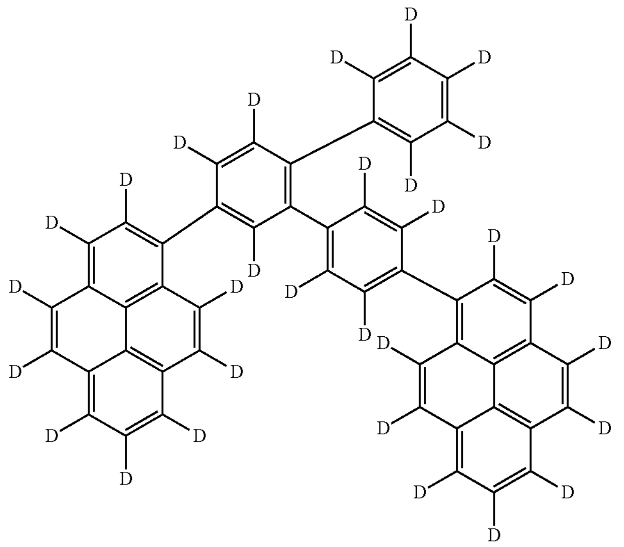
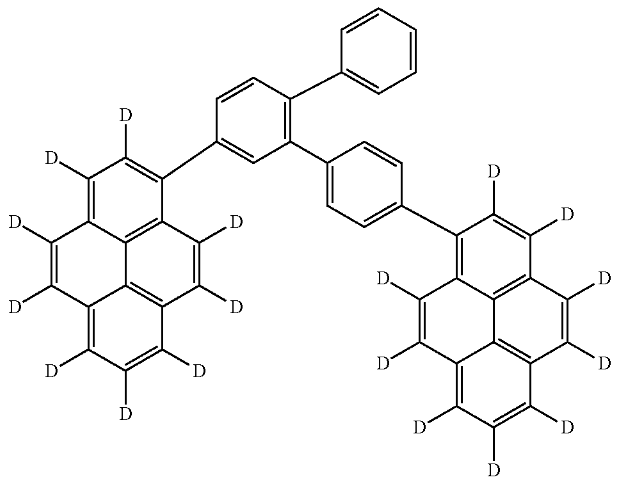
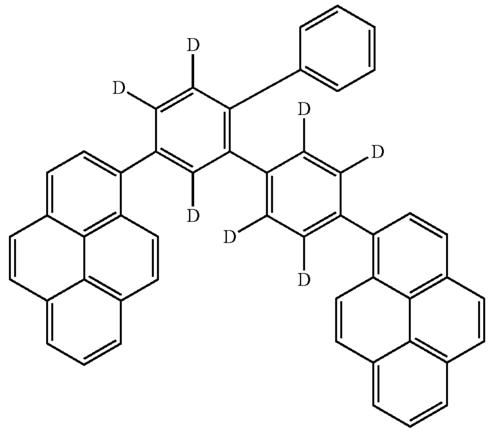
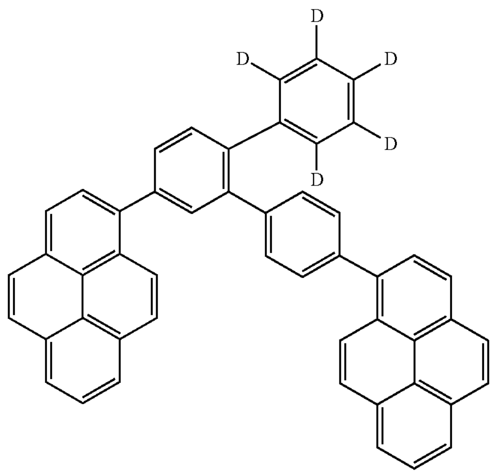

-continued
[Formula 114]
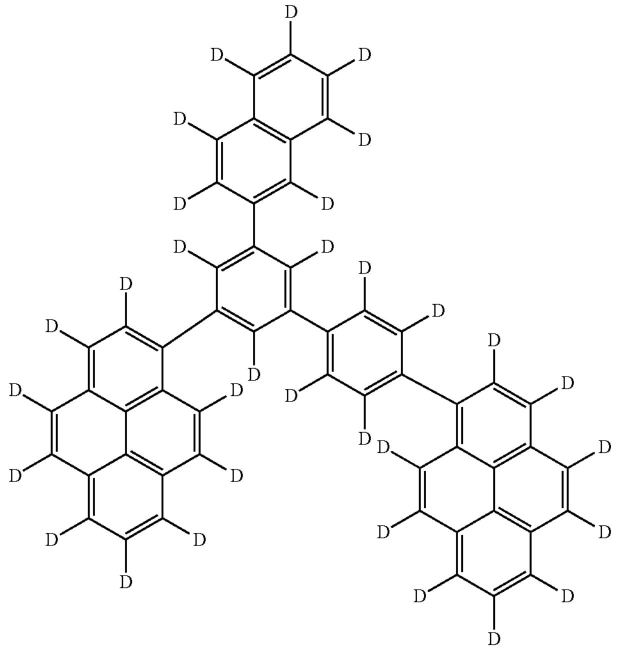
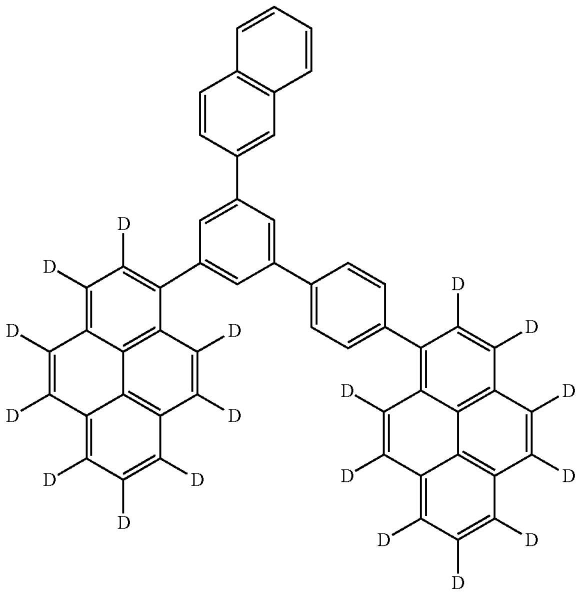
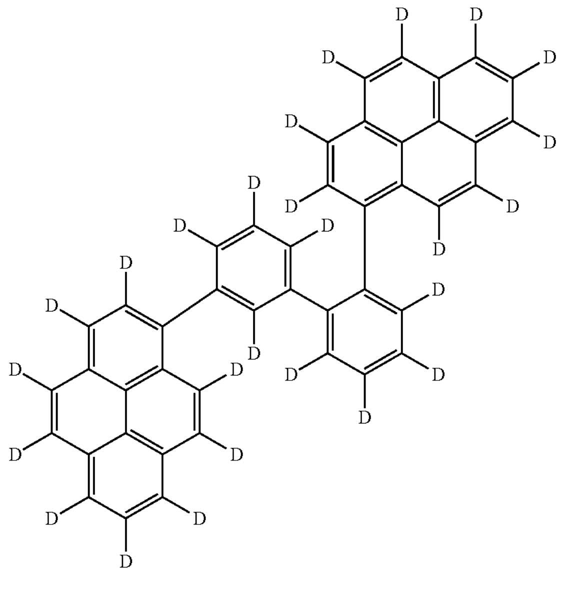
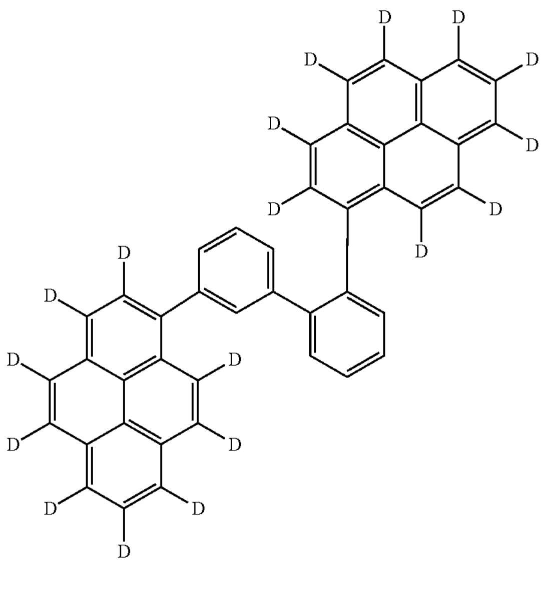

-continued
[Formula 115]
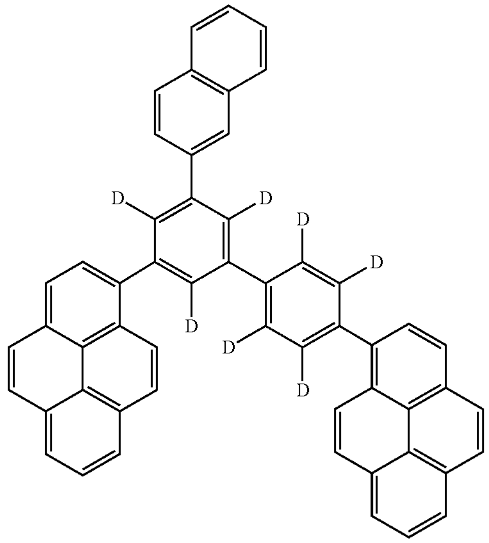
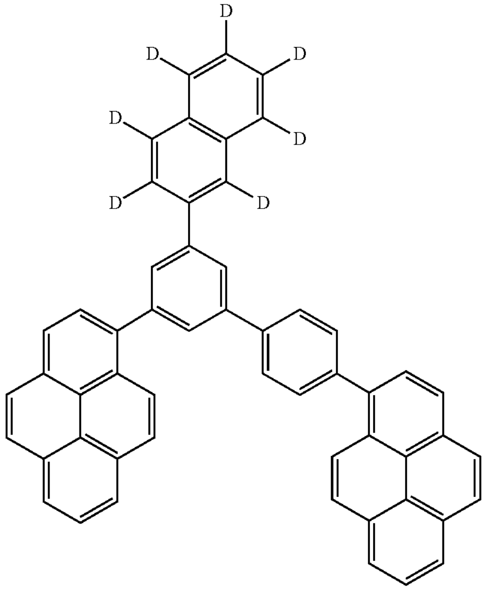
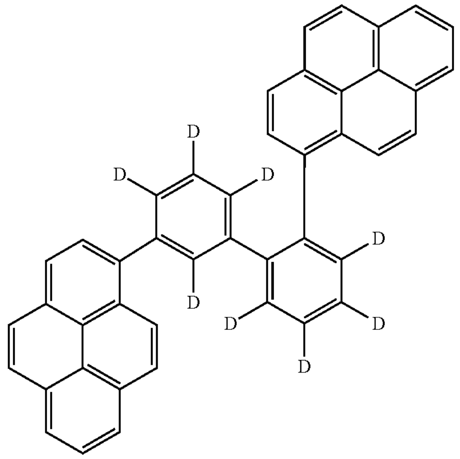
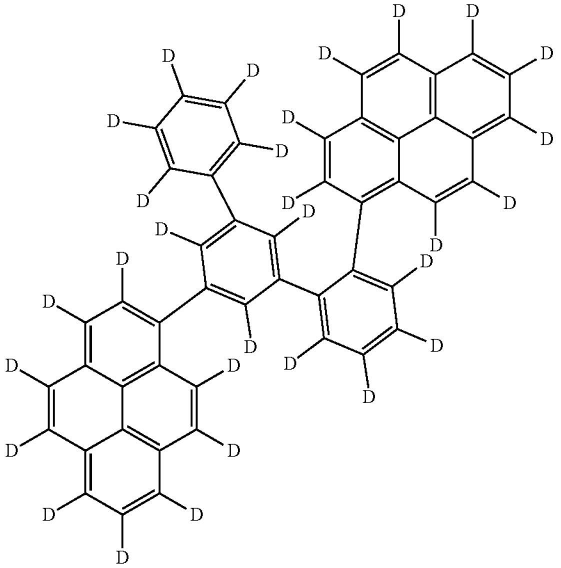

-continued
[Formula 116]
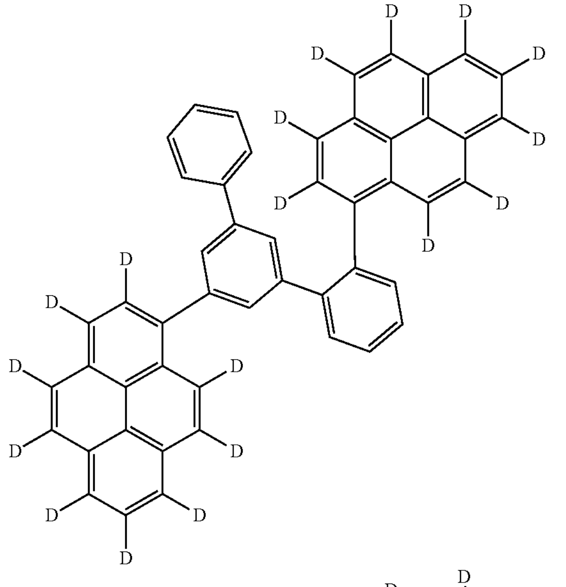
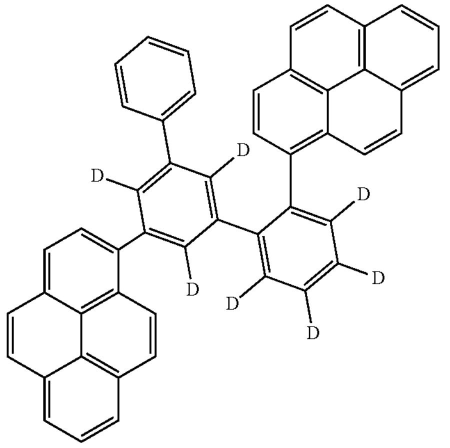
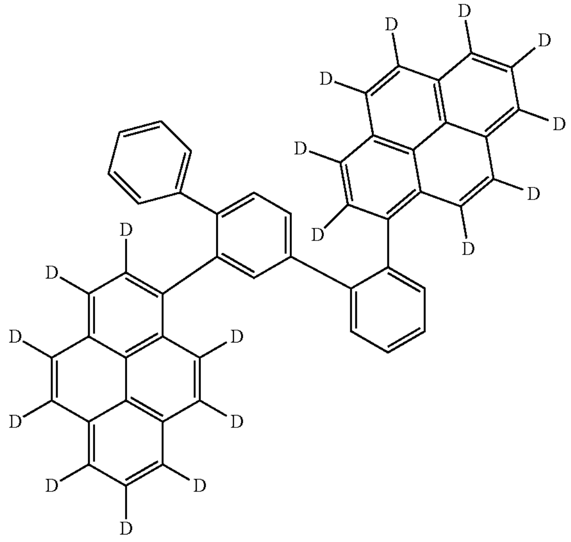
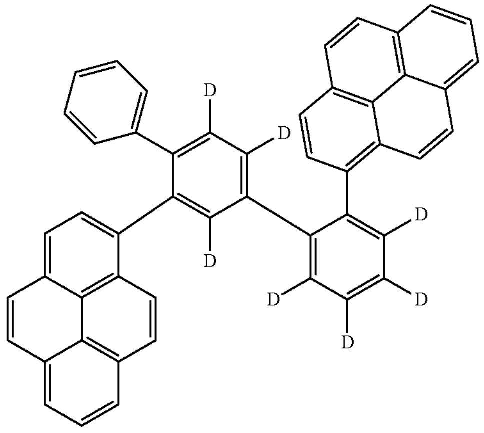
[Formula 117]
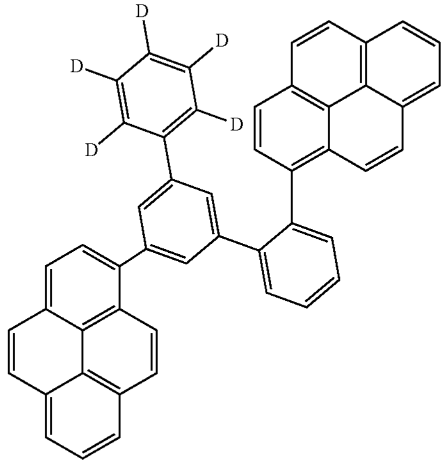
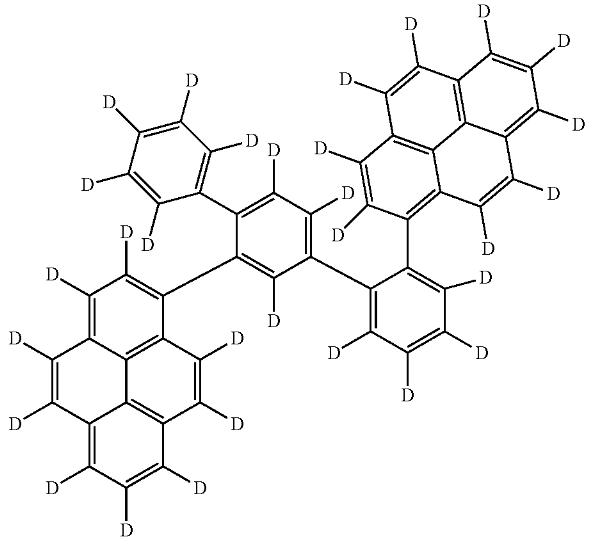

-continued
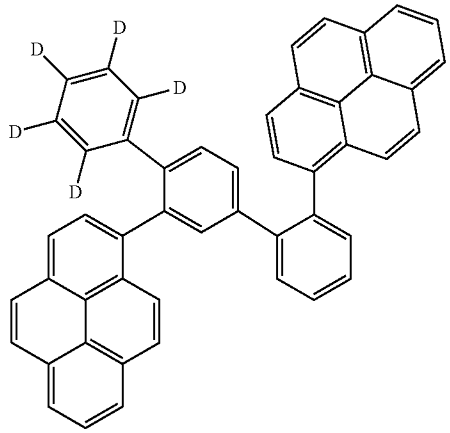
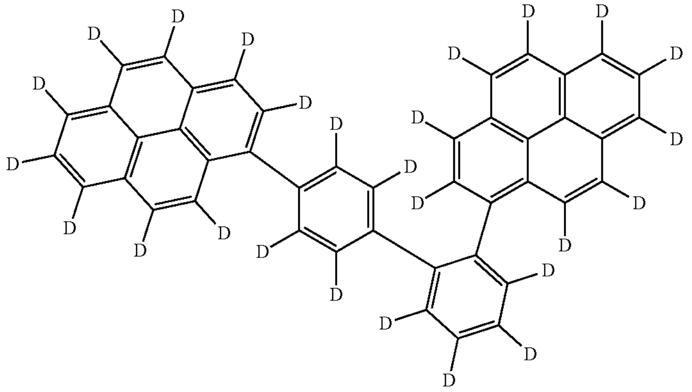
[Formula 118]
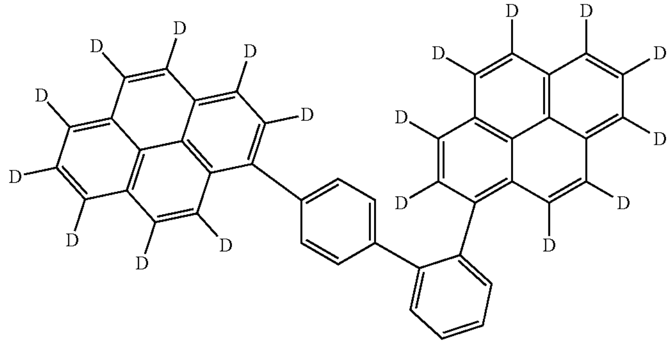
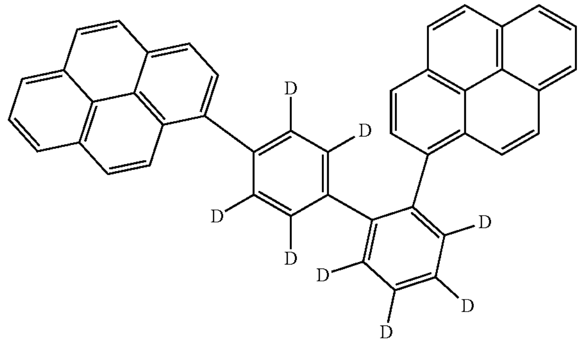
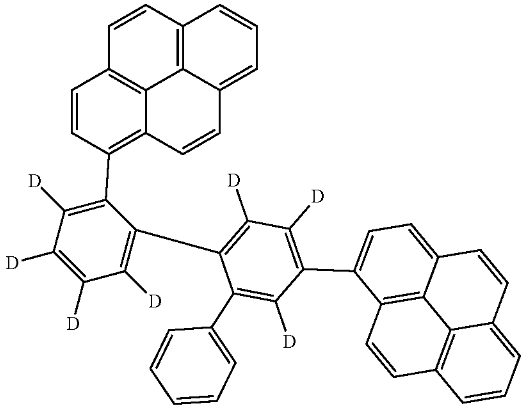
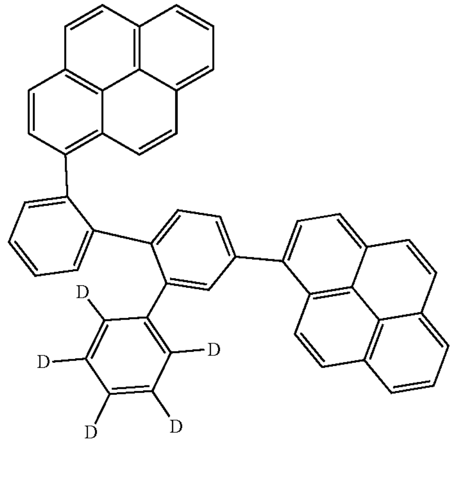
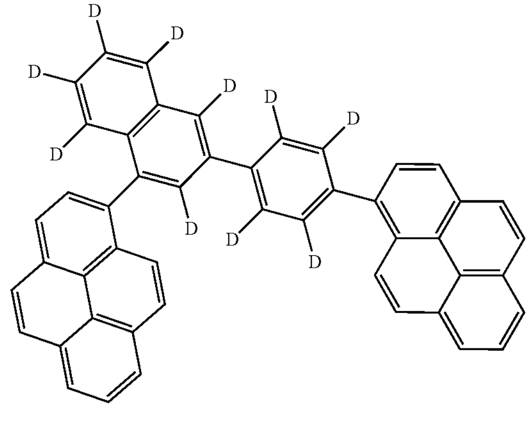

-continued
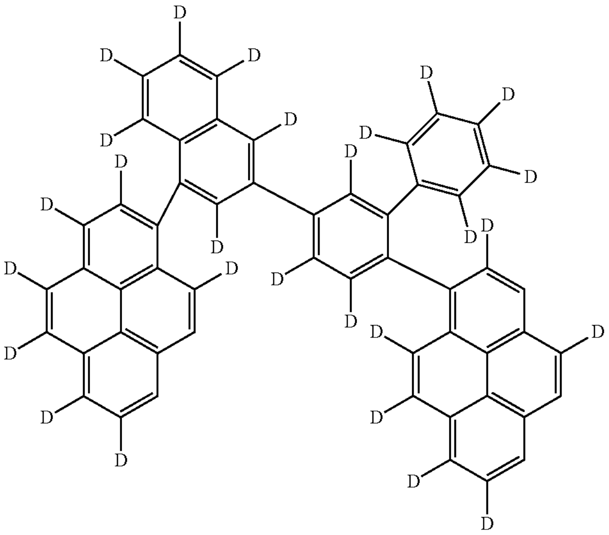
[Formula 119]
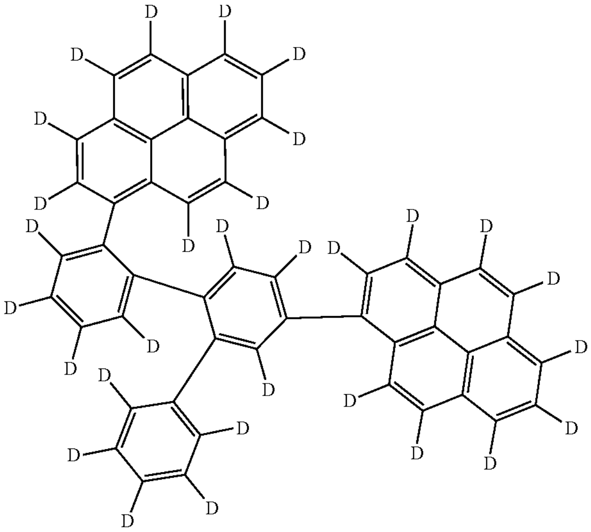
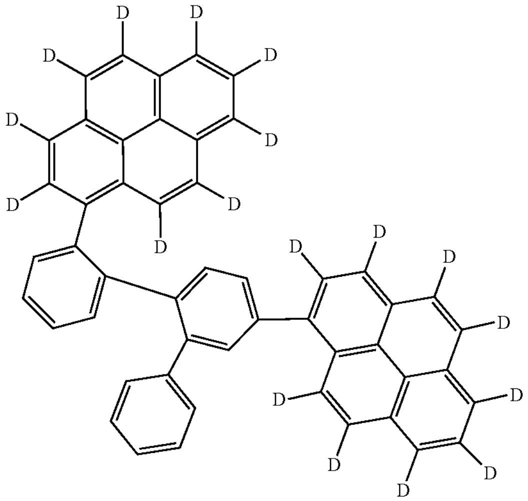
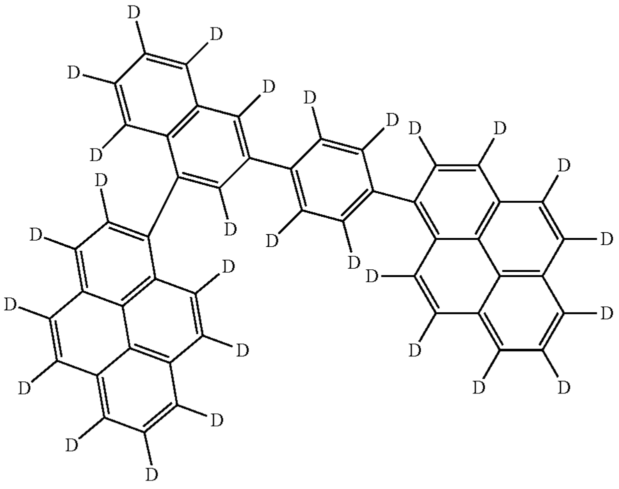

-continued
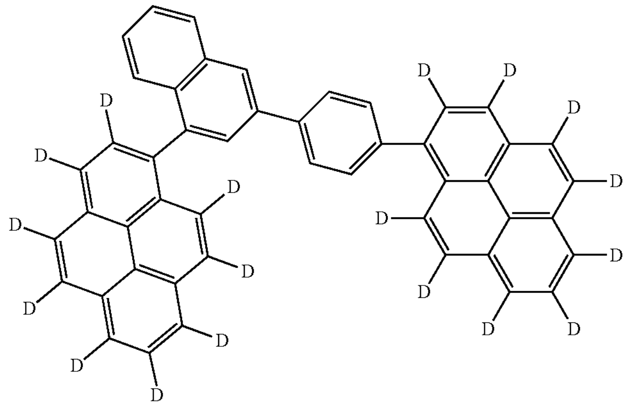
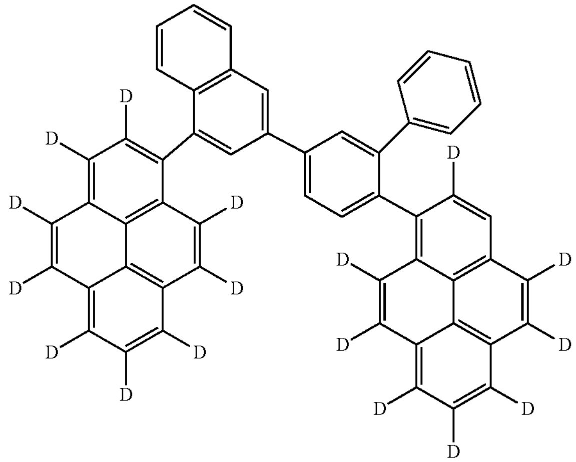
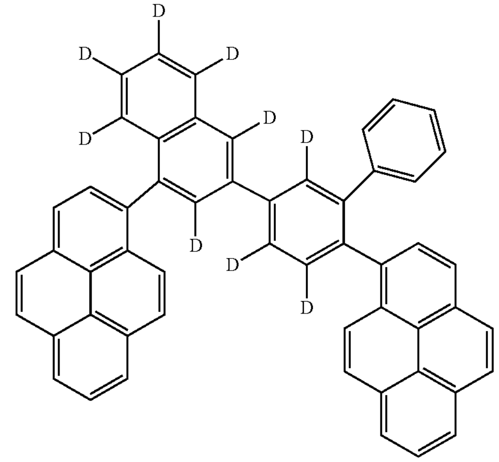
[Formula 120]
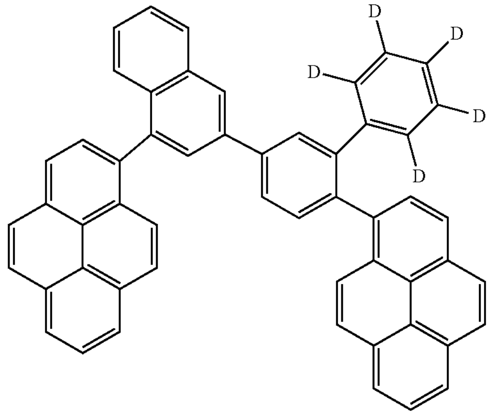
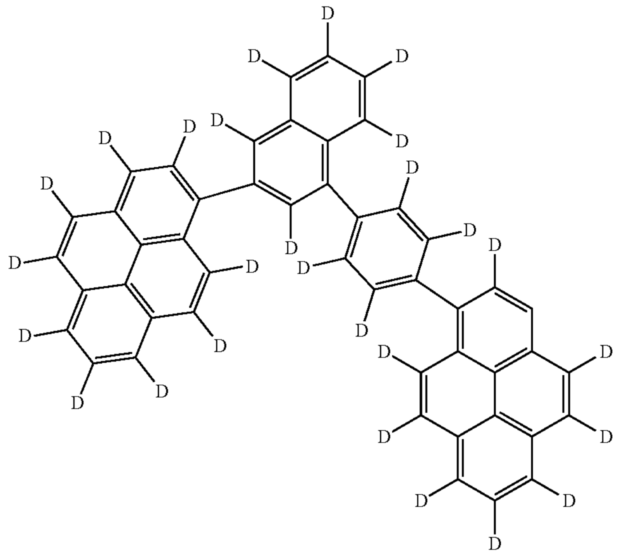

-continued
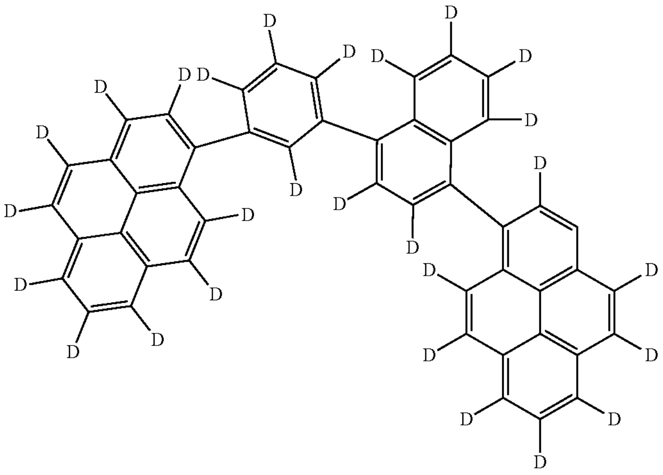
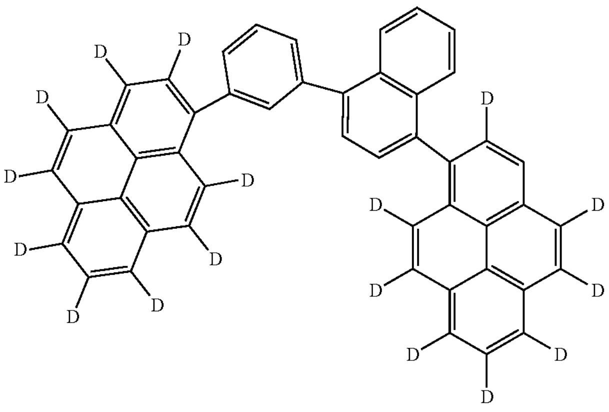
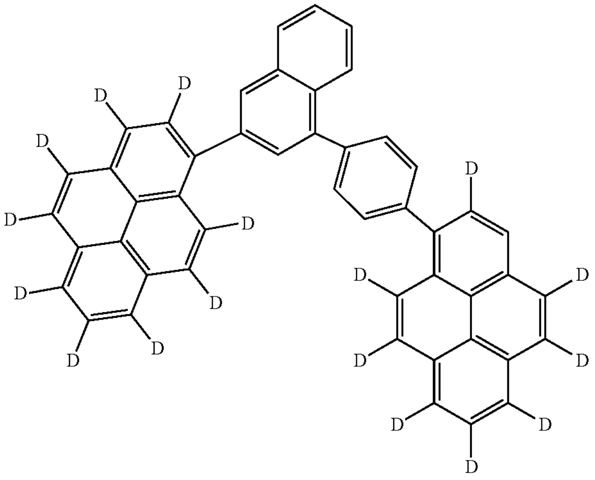
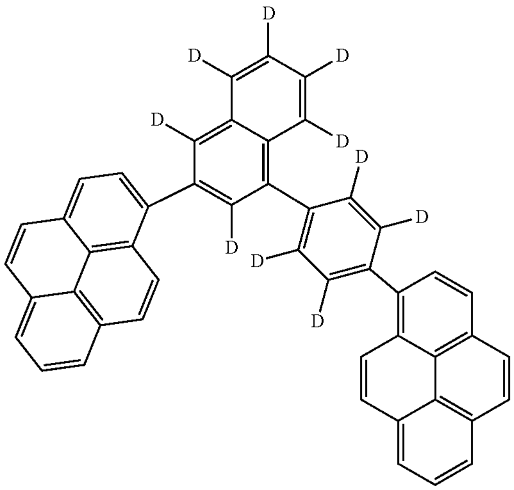

-continued
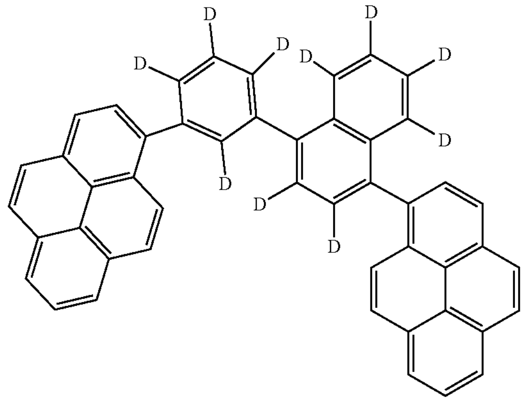
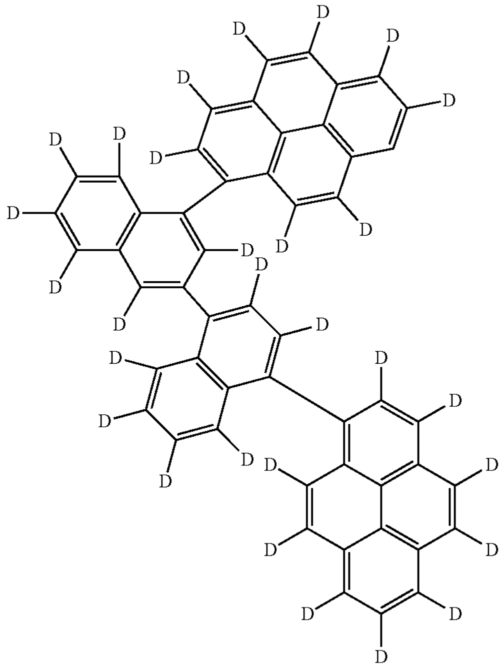
[Formula 121]
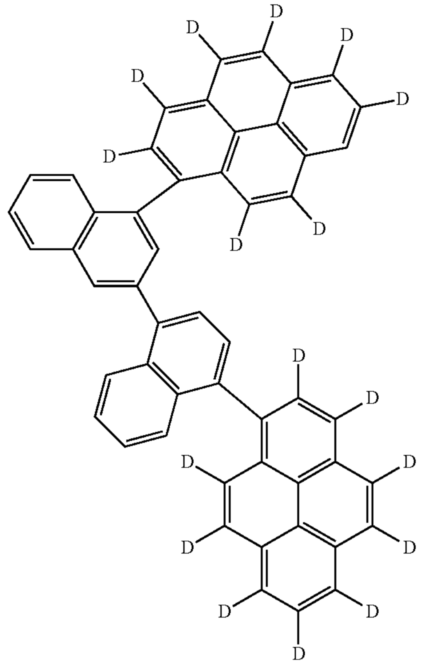
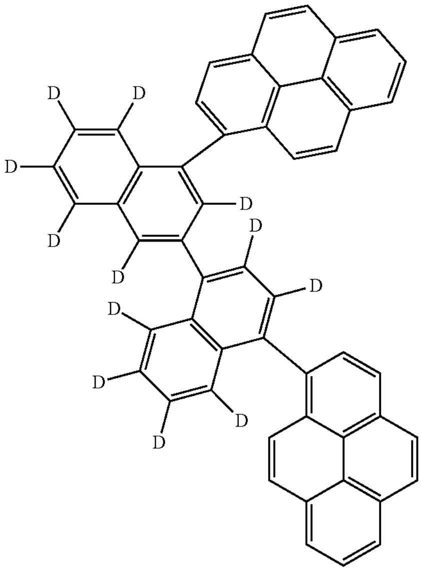

-continued
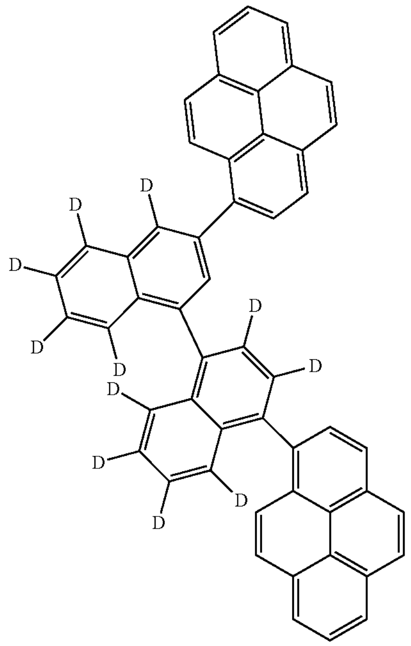
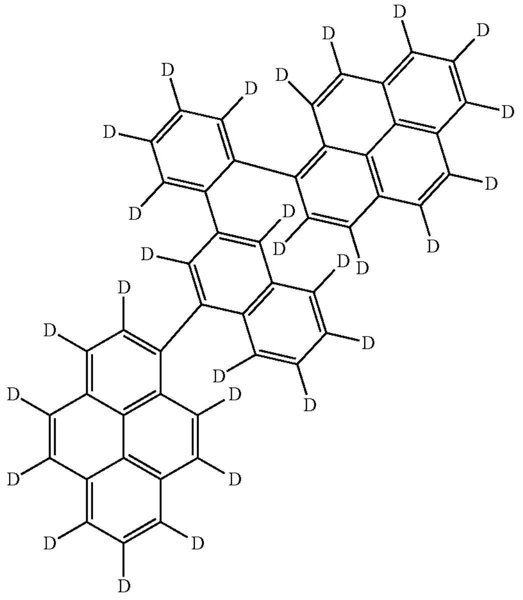
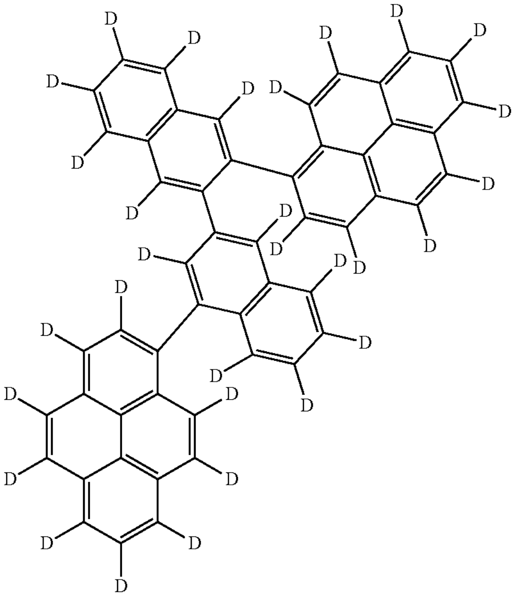
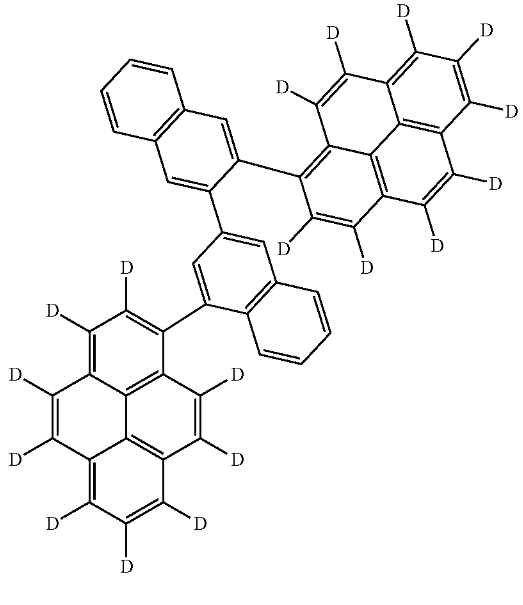

-continued
[Formula 122]
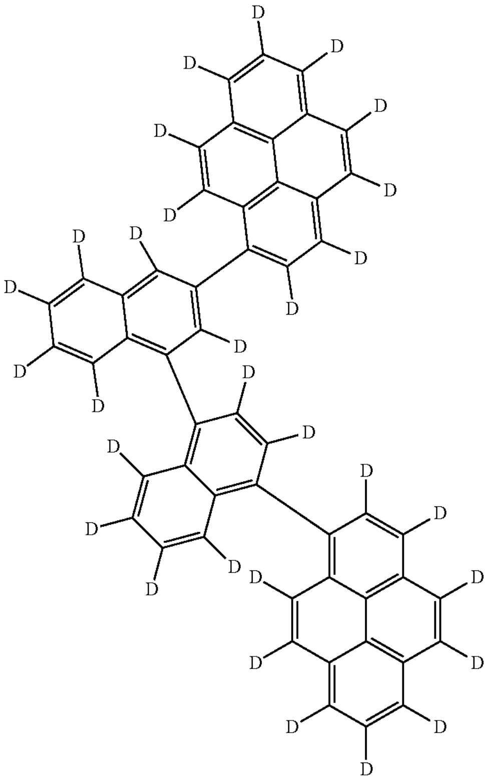
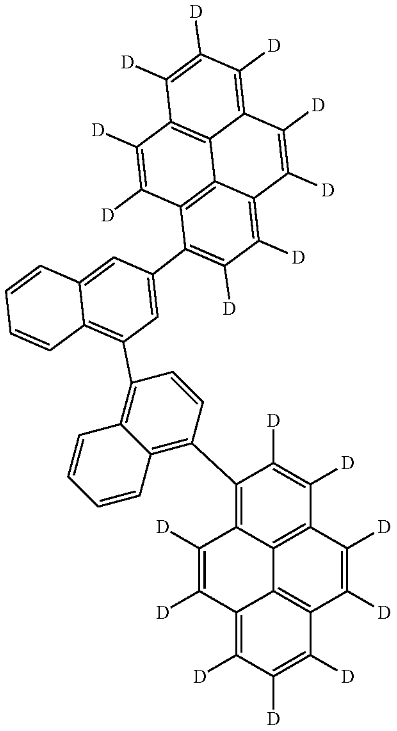
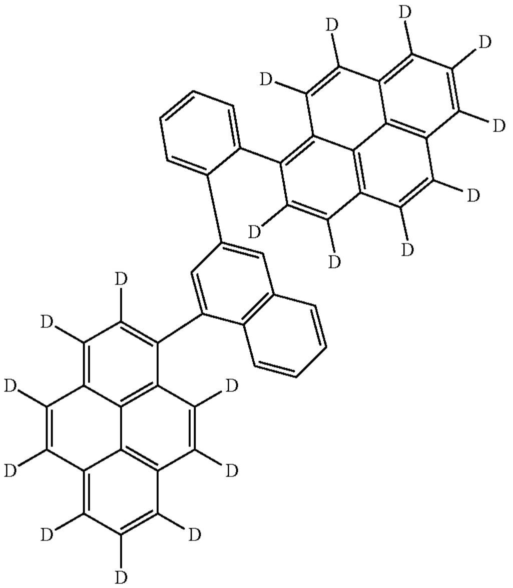
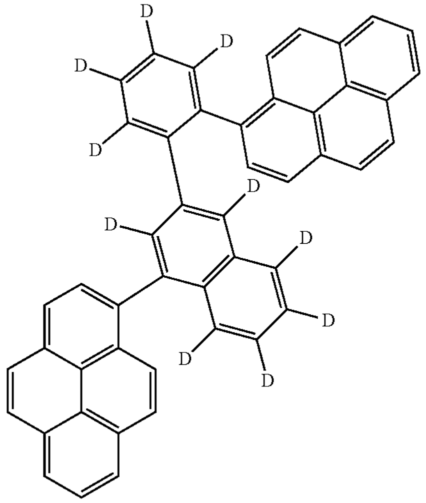

-continued
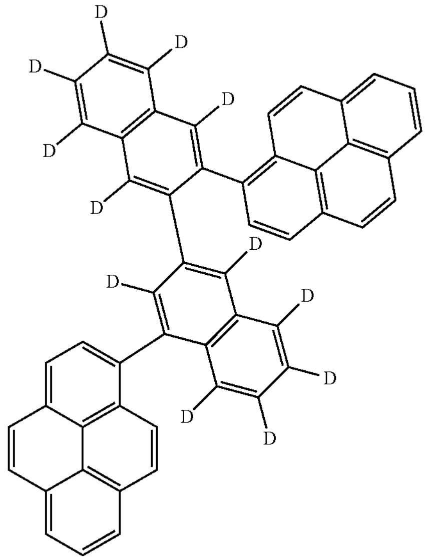
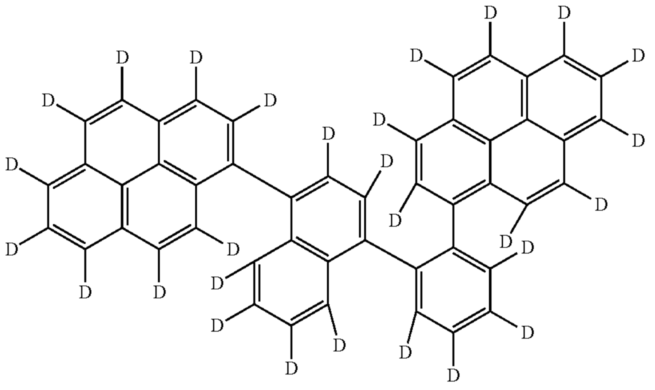
[Formula 123]
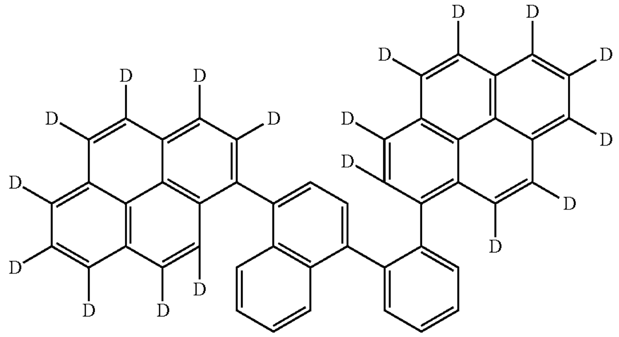
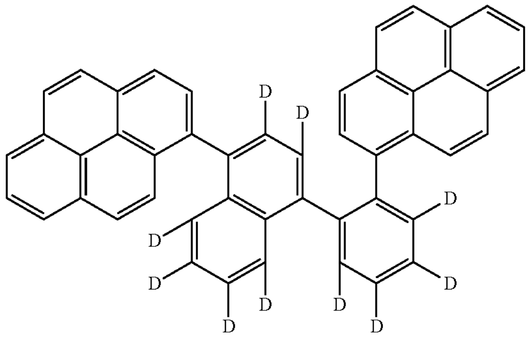
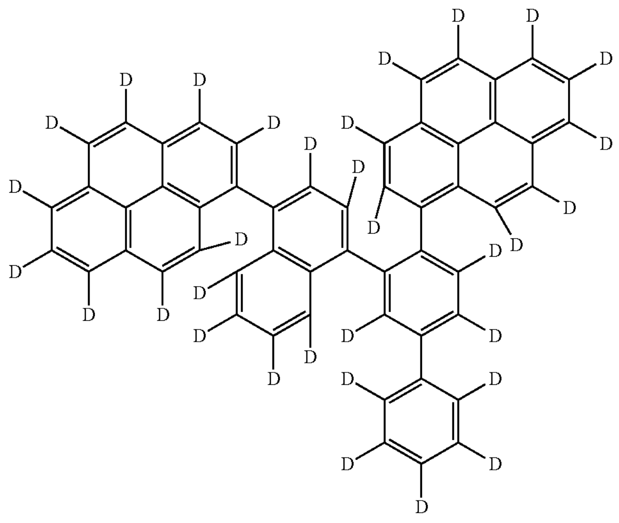

-continued
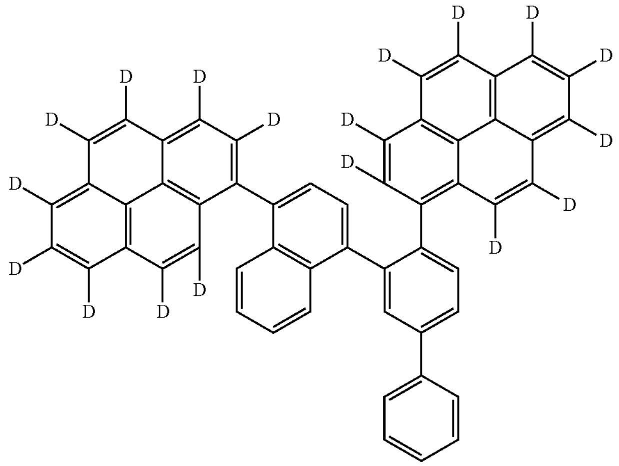
[Formula 124]
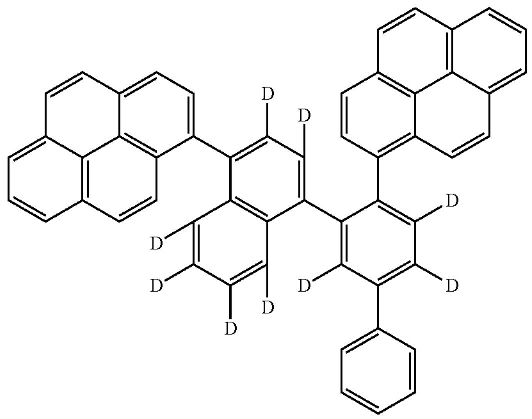
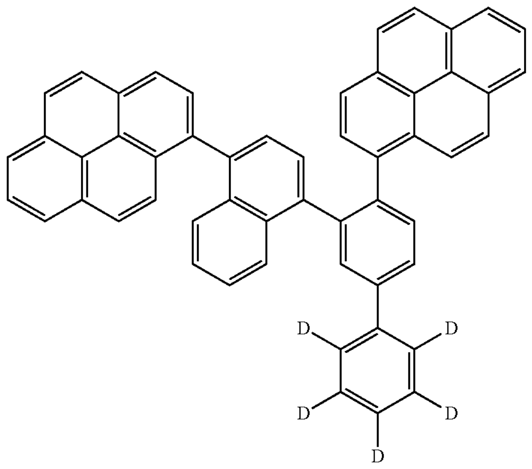
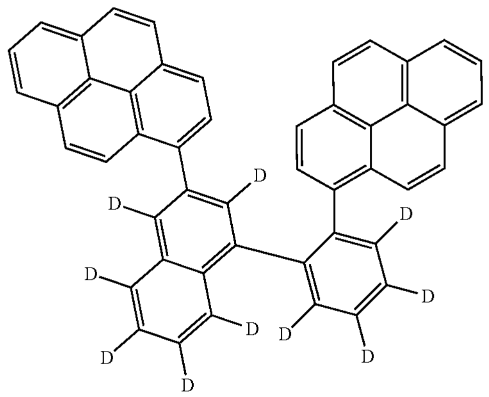
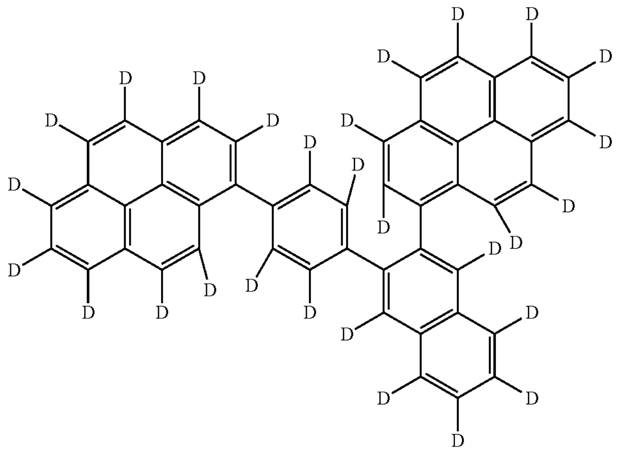

-continued
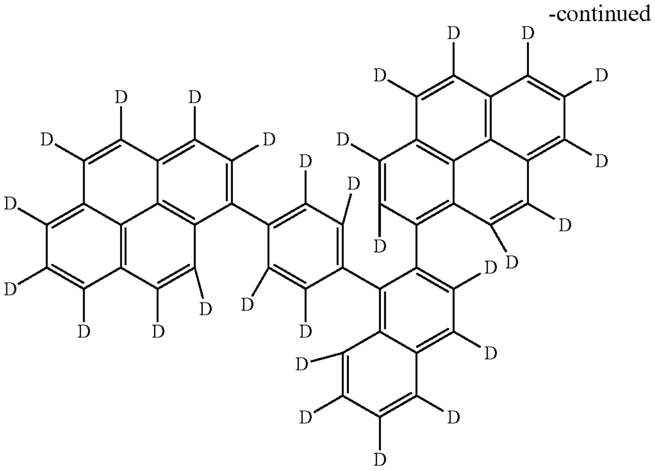
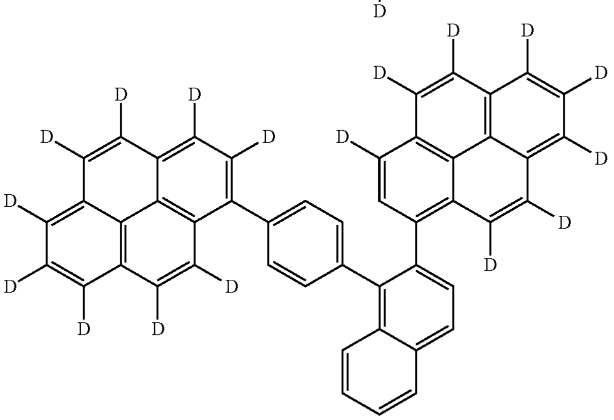
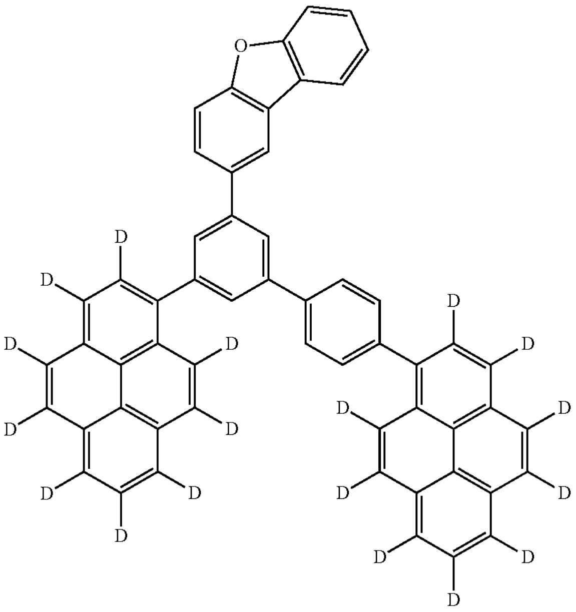
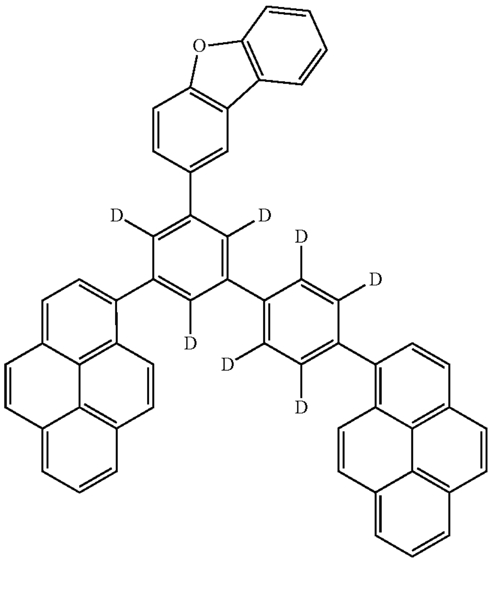

-continued
[Formula 125]
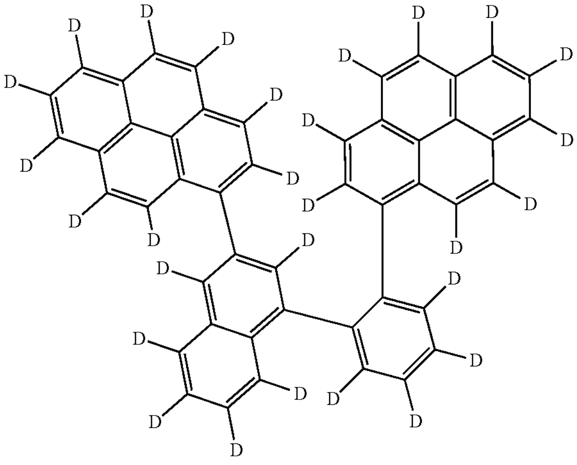
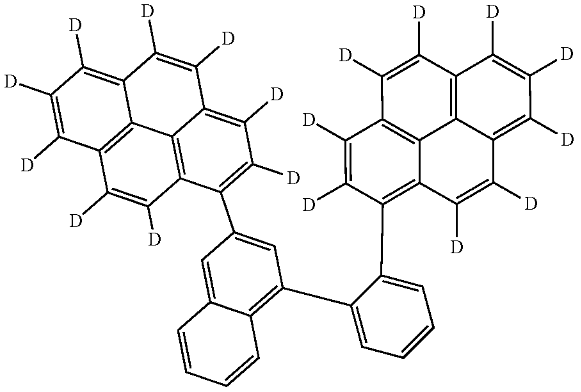
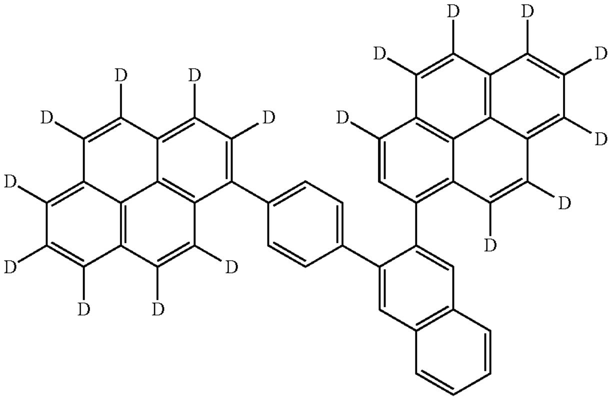
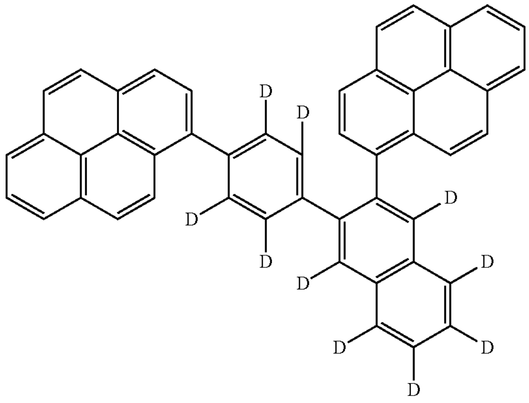
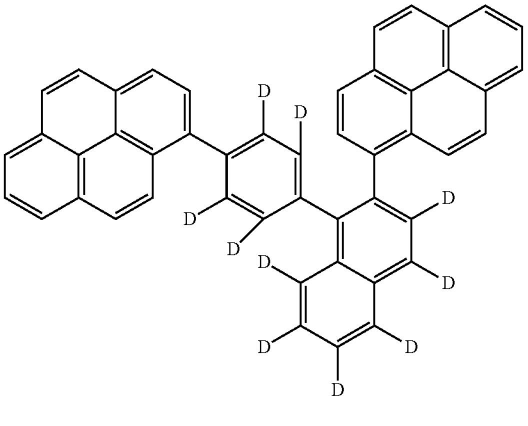
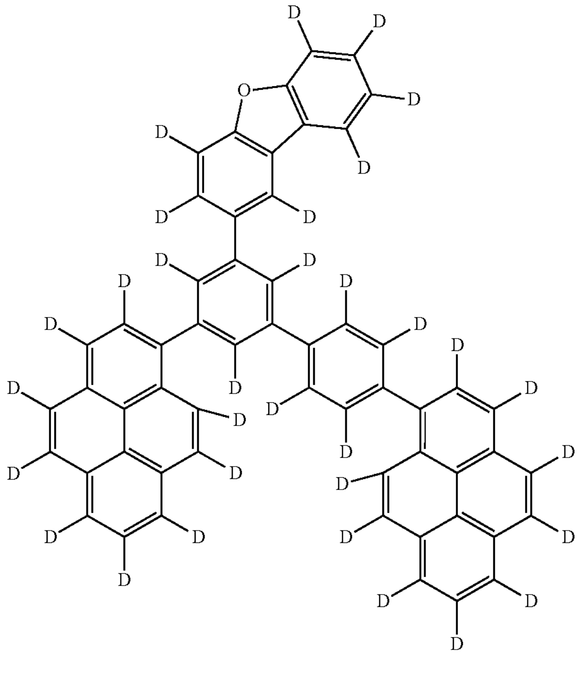

-continued
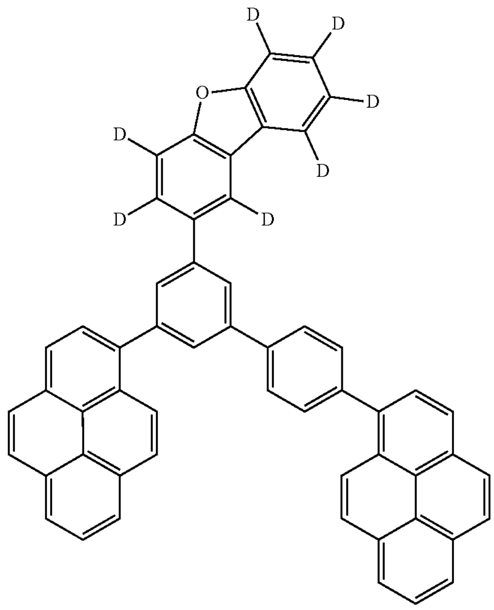
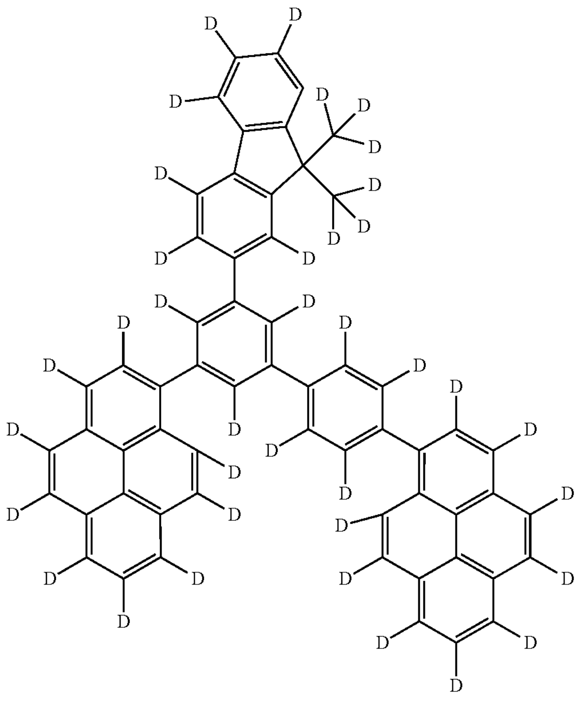
[Formula 126]
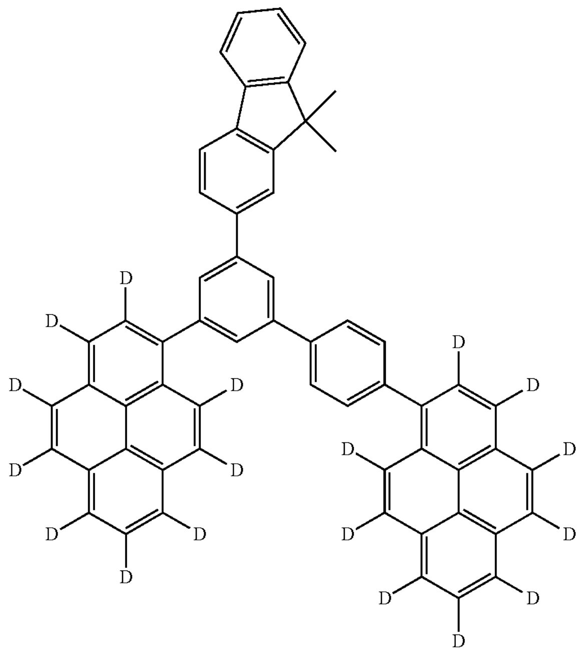
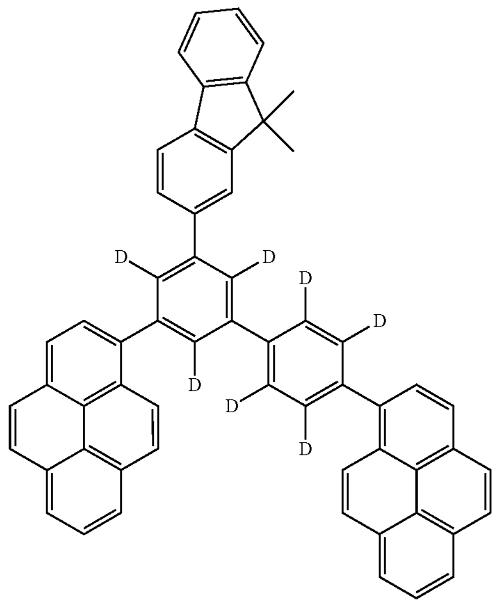

-continued
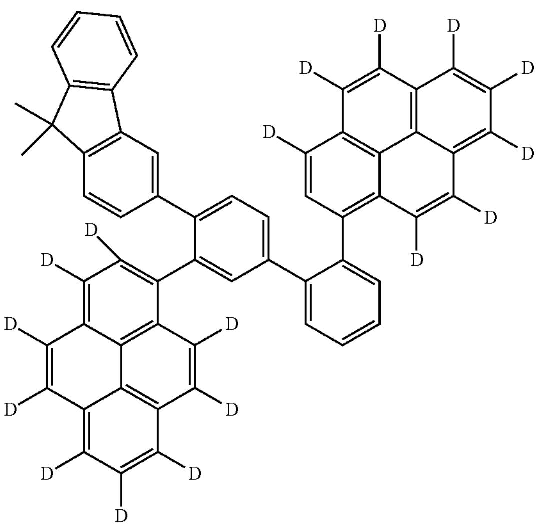
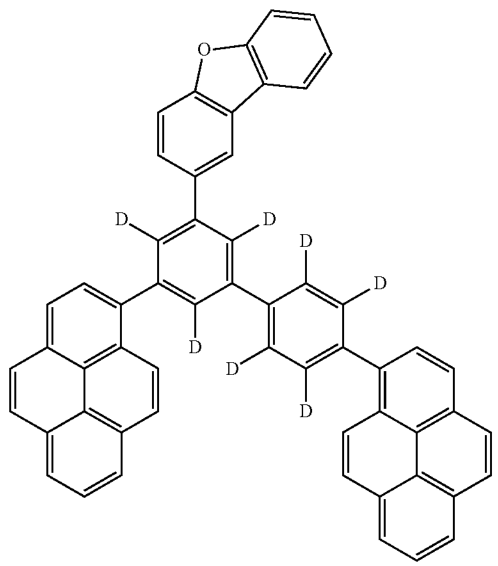
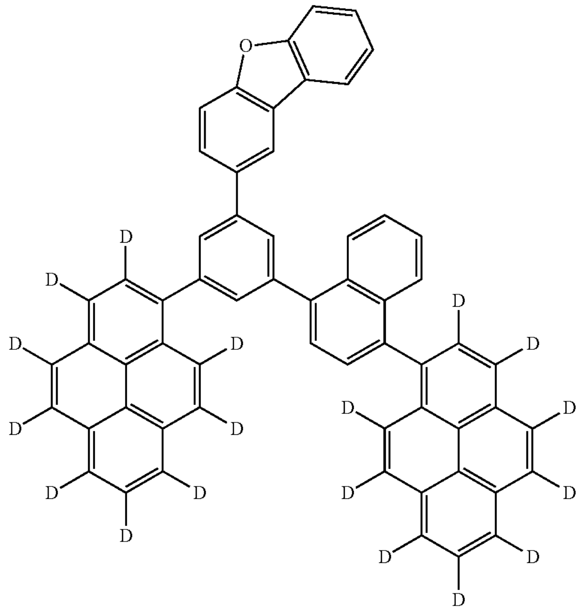
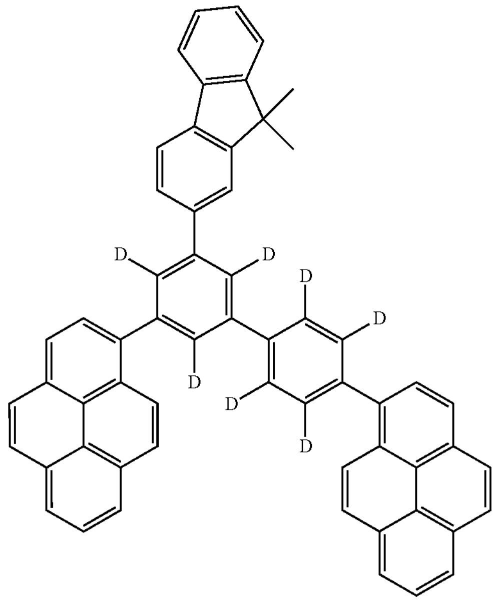

-continued
[Formula 127]
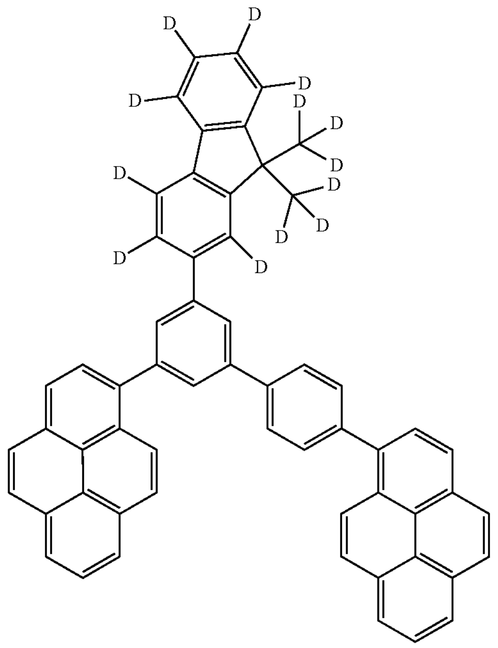
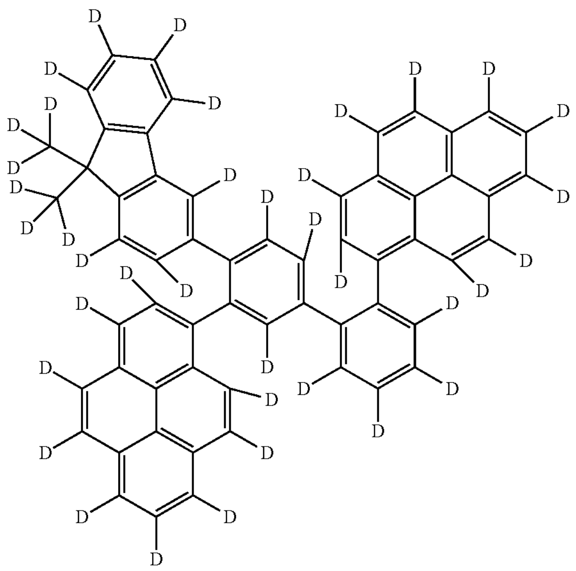
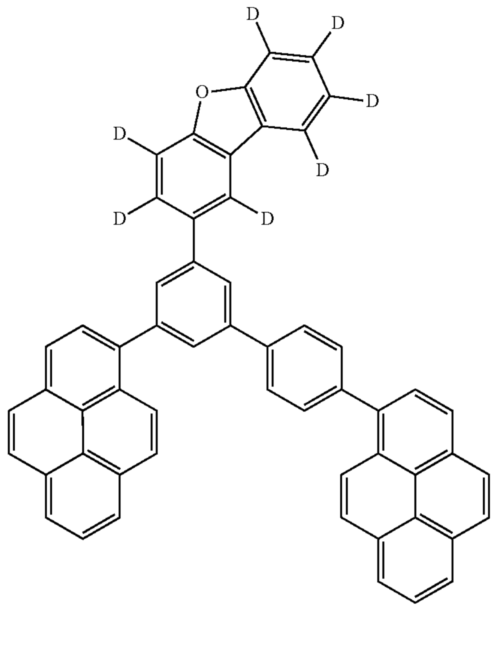
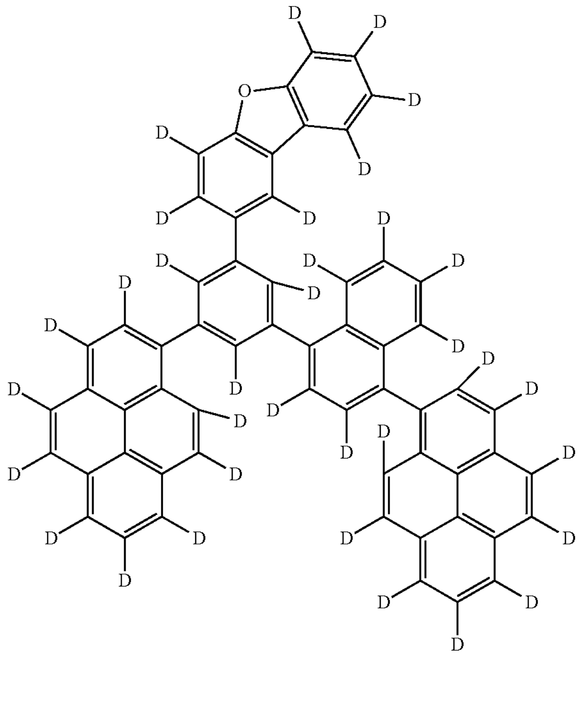

-continued
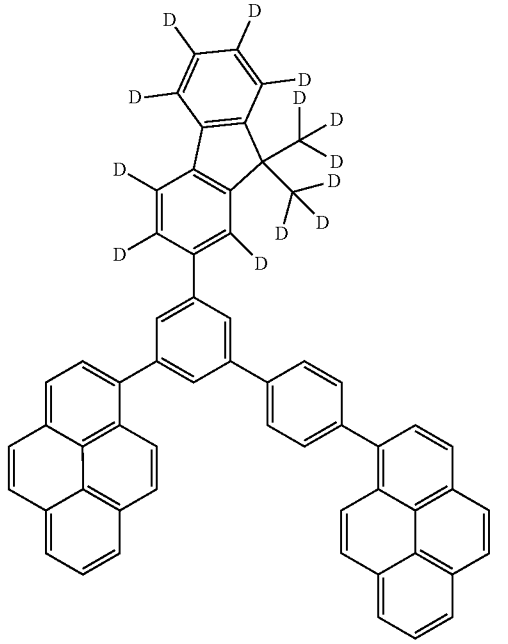
[Formula 128]
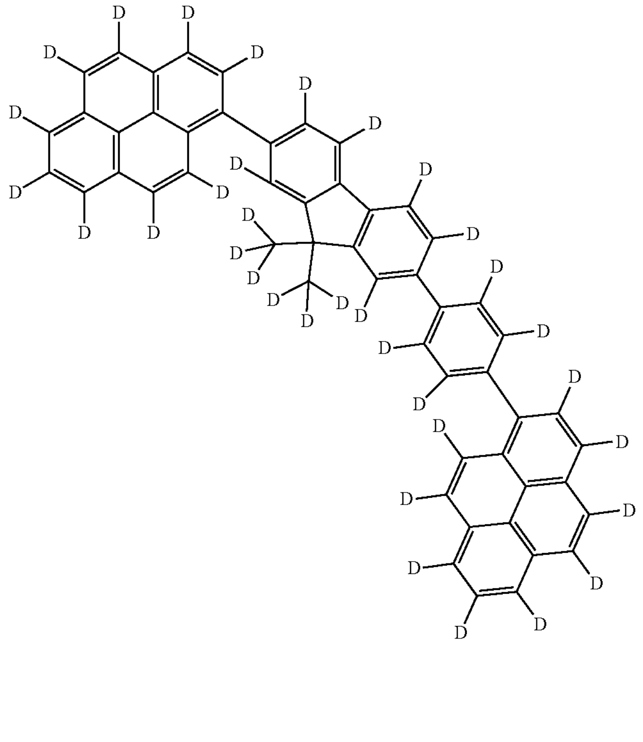

-continued
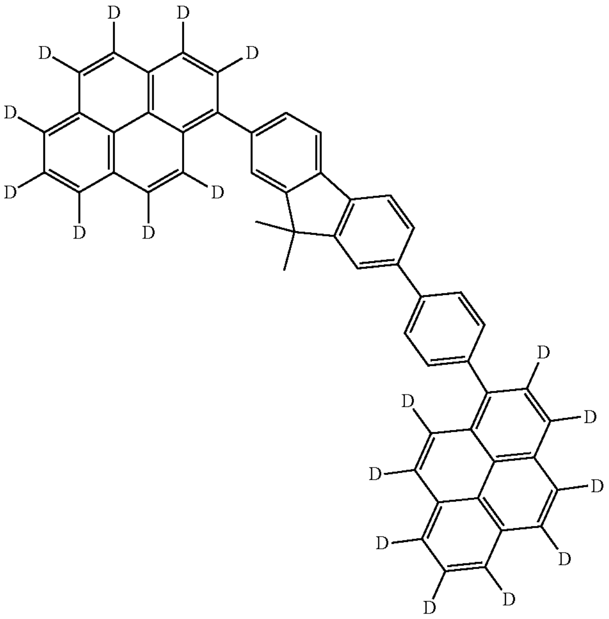
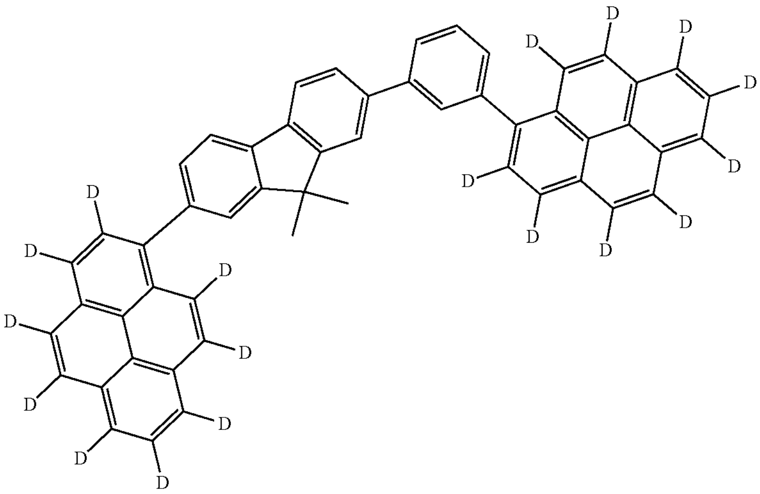
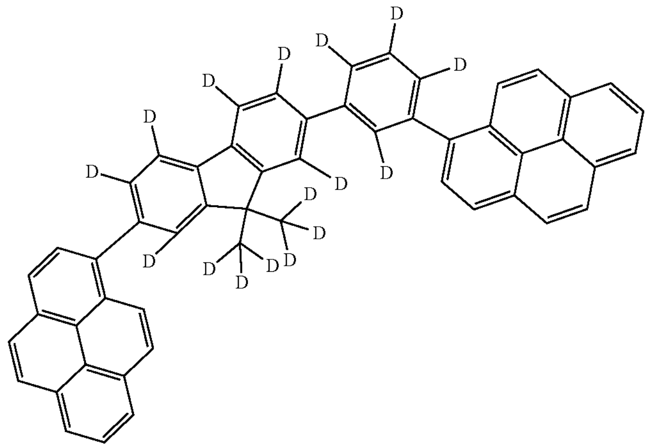

-continued
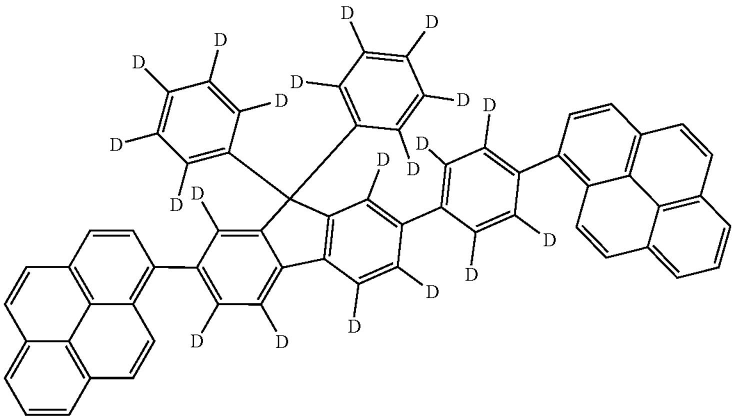
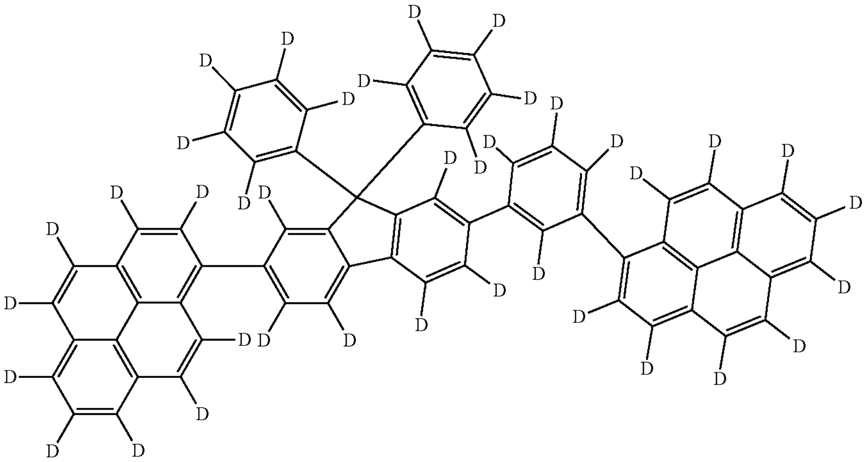
[Formula 129]
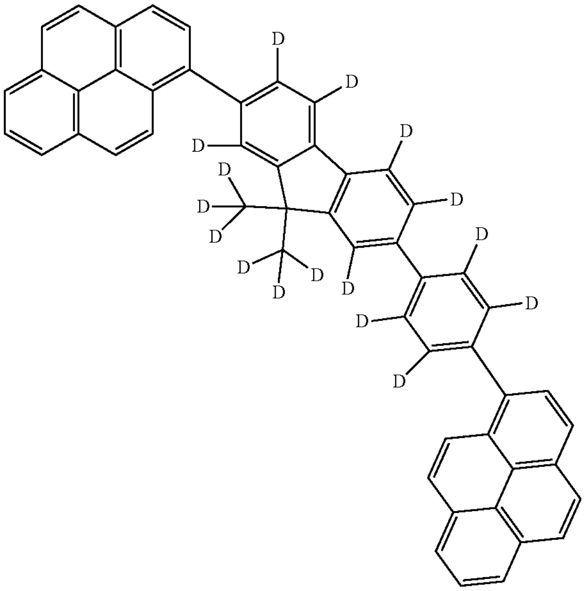

-continued
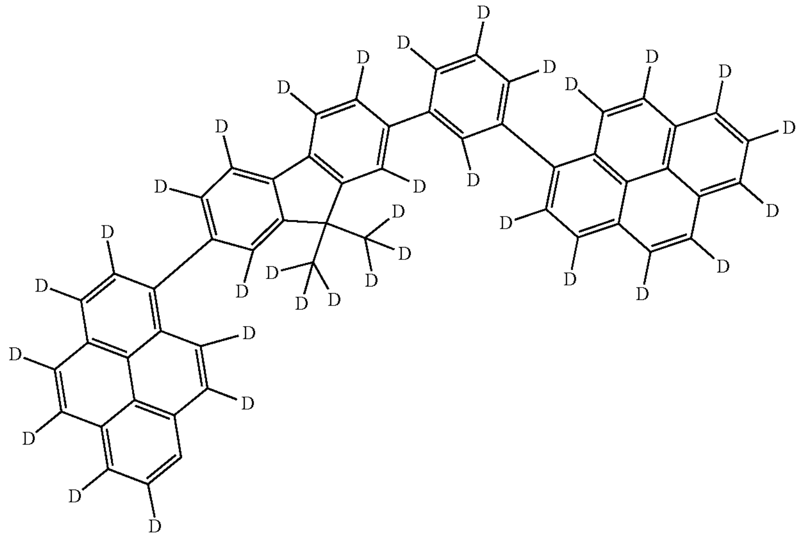
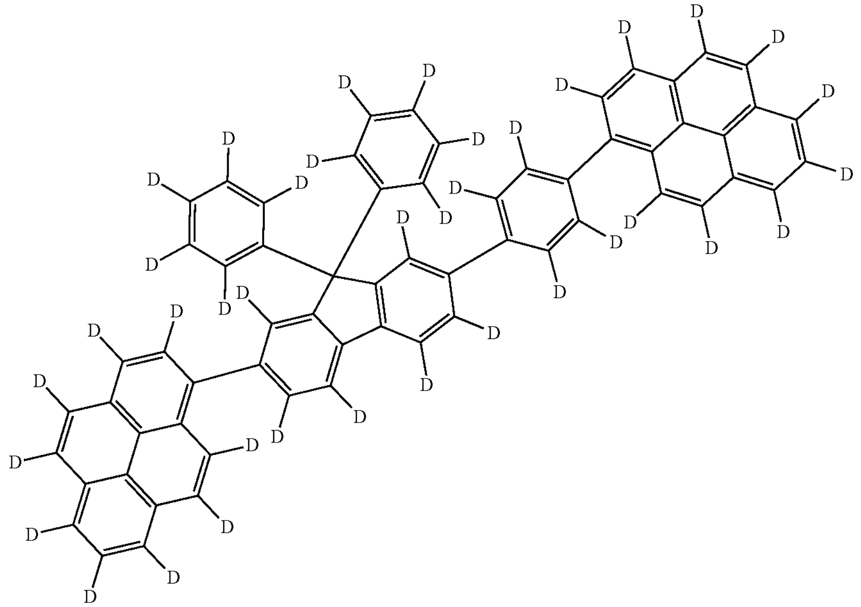
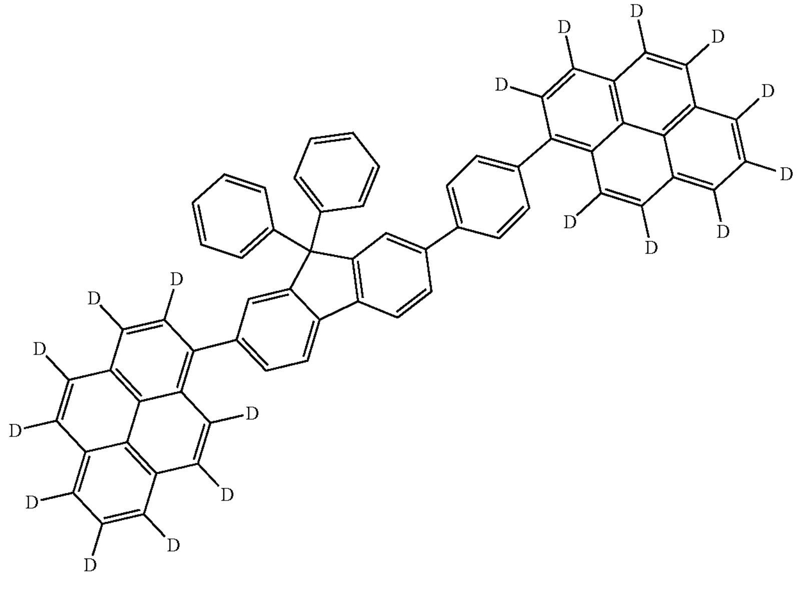

-continued
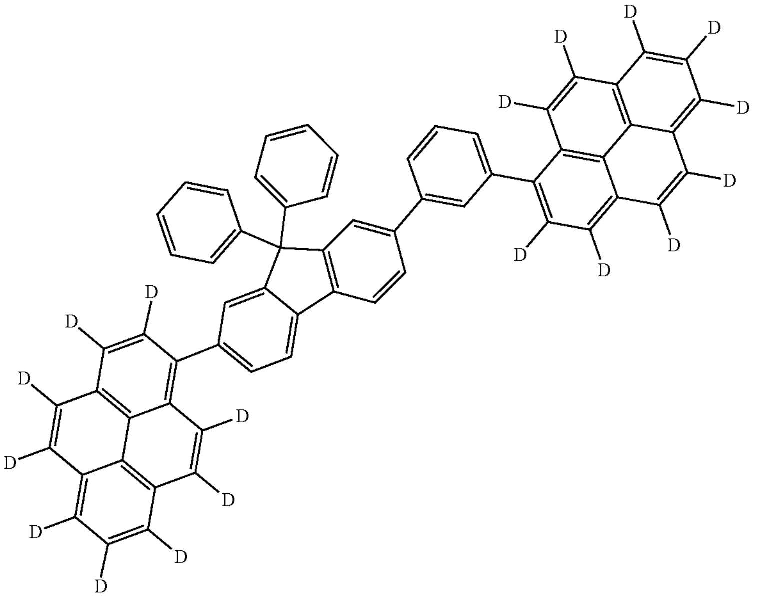
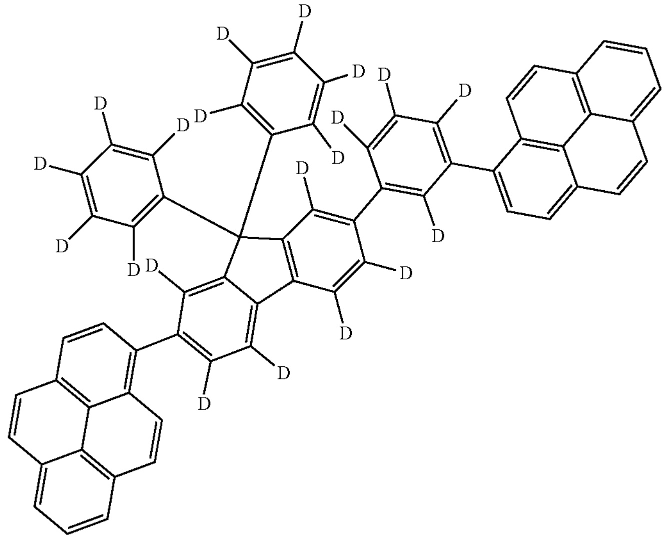
[Formula 130]
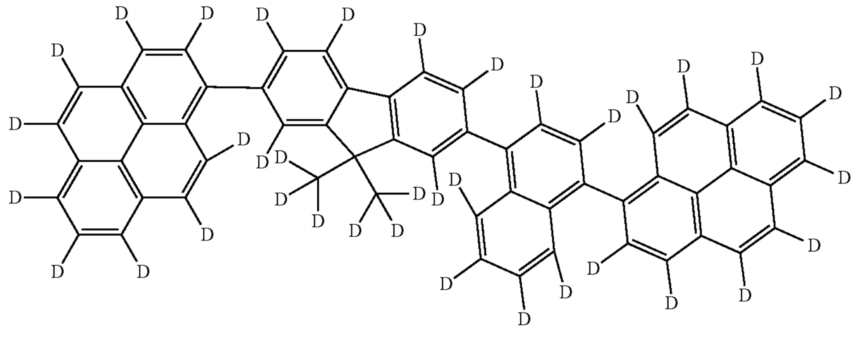

-continued
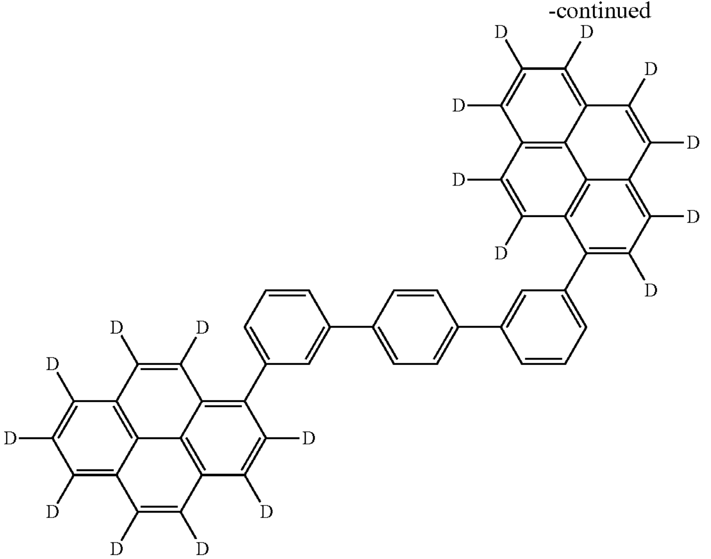
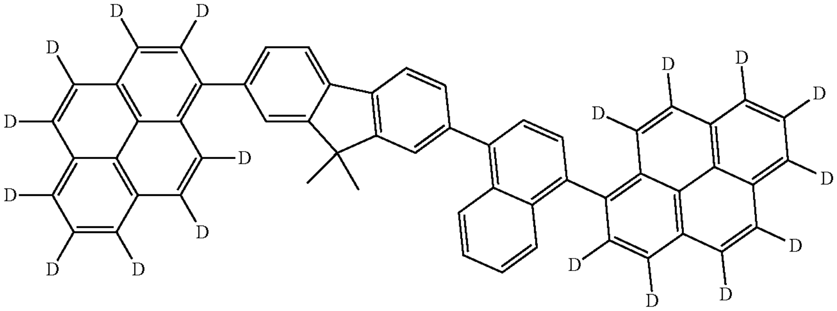
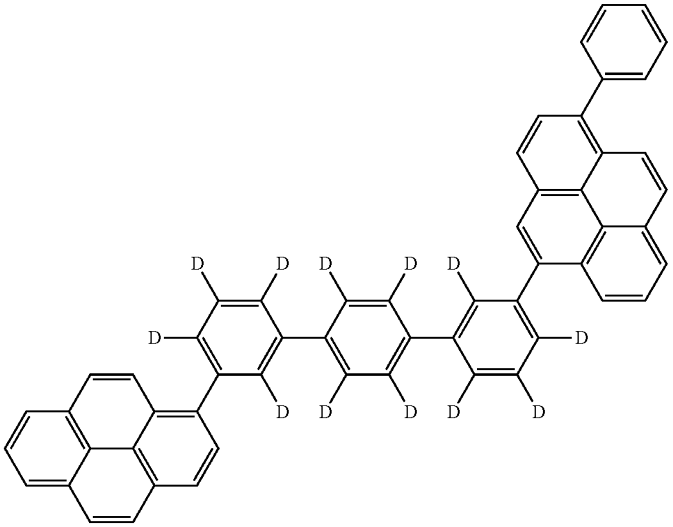

-continued
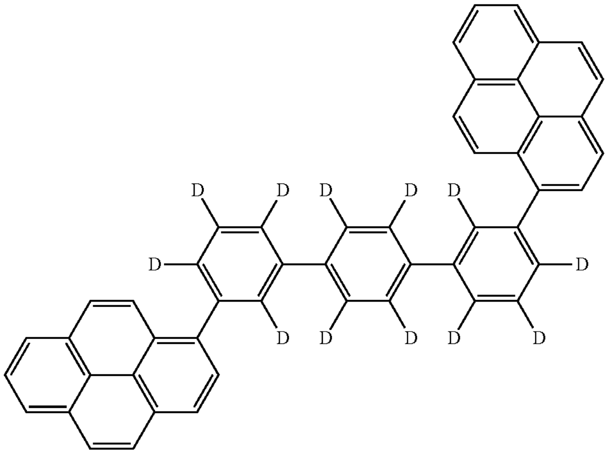
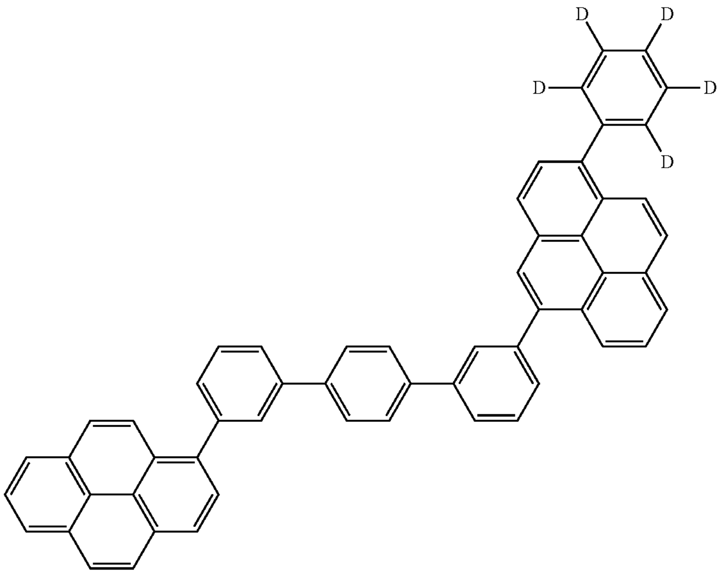
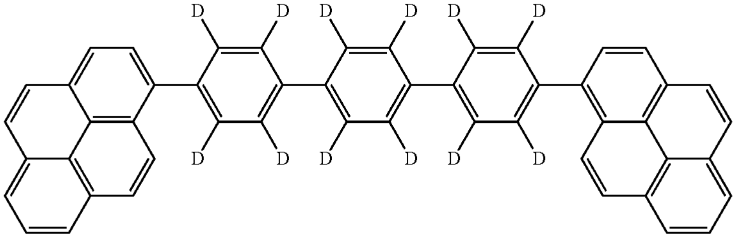

-continued
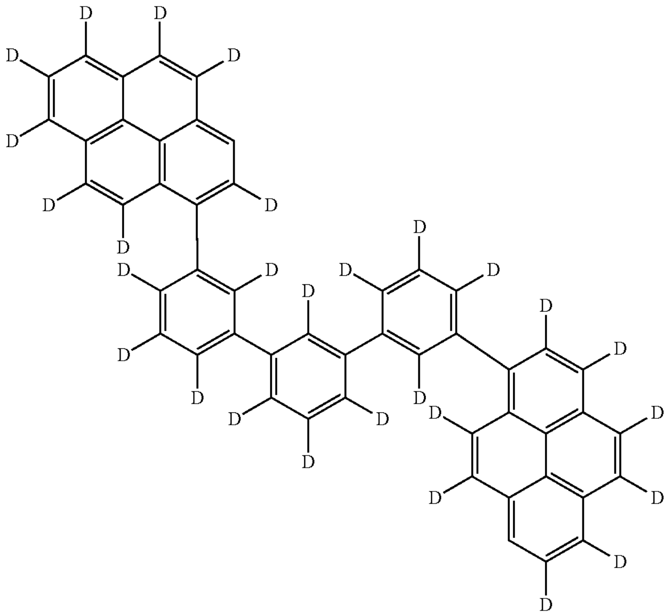
[Formula 131]
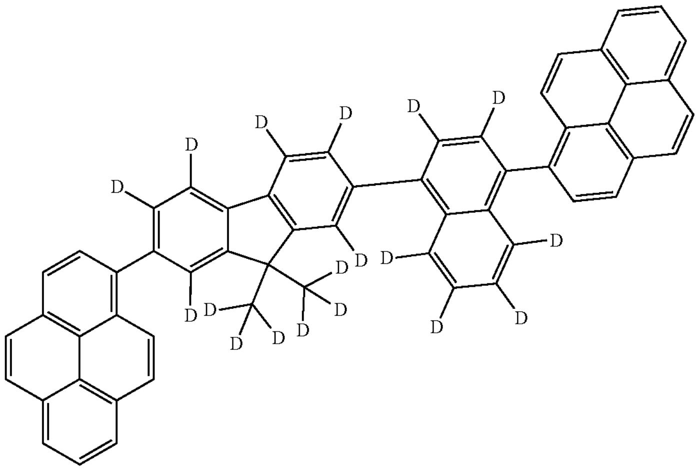
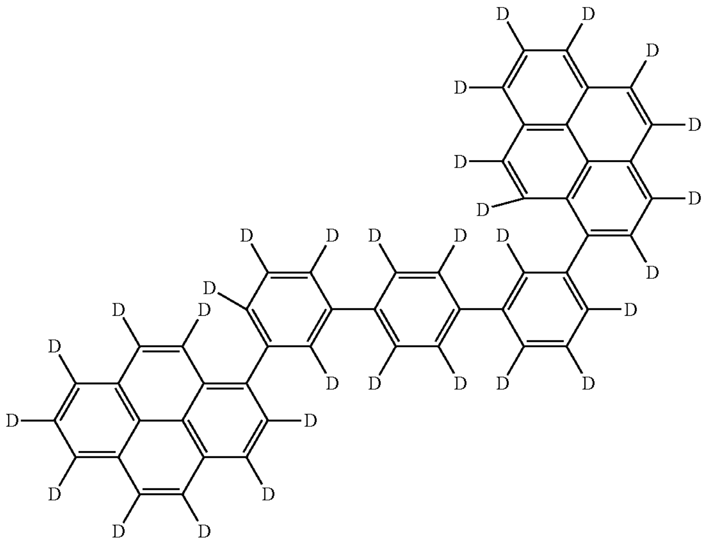

-continued
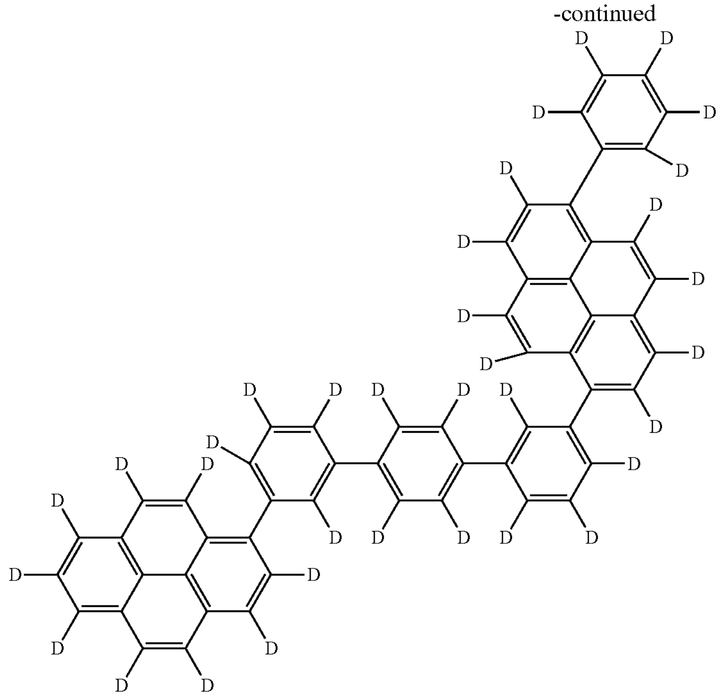
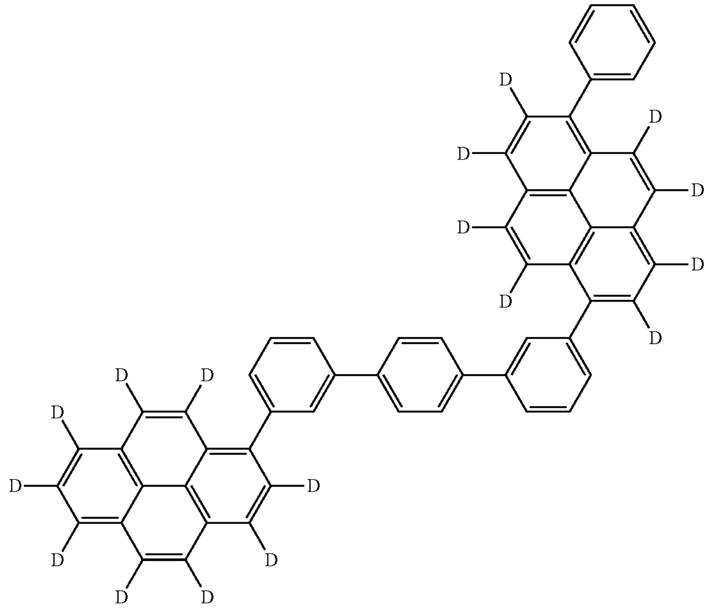
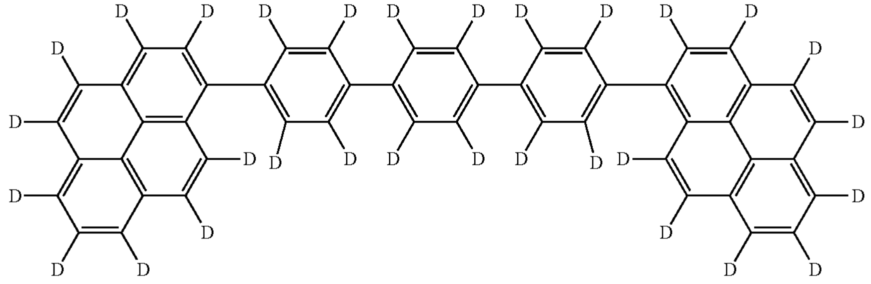

-continued
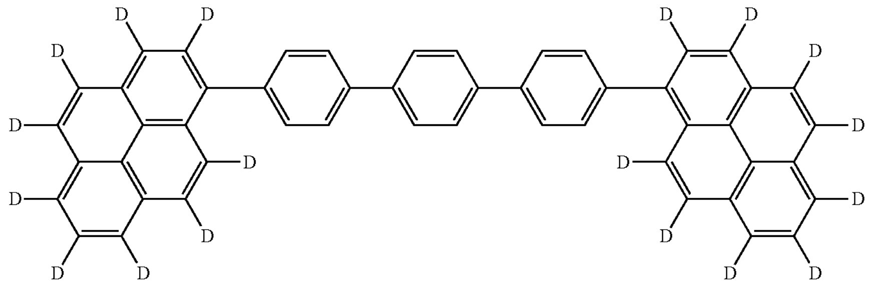
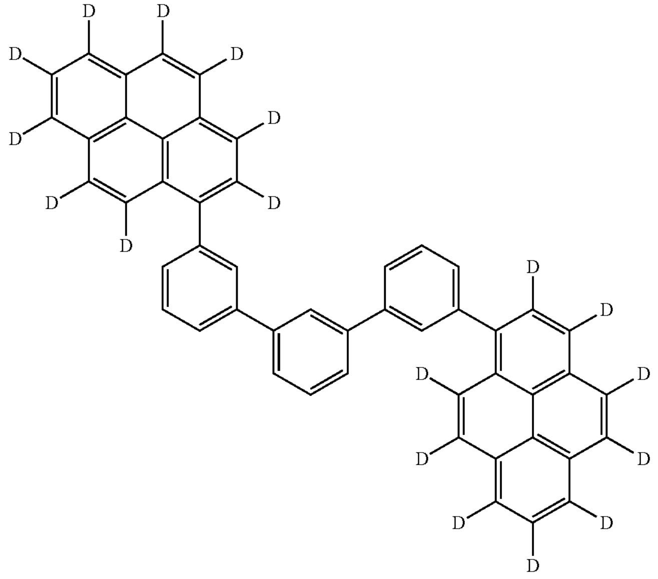
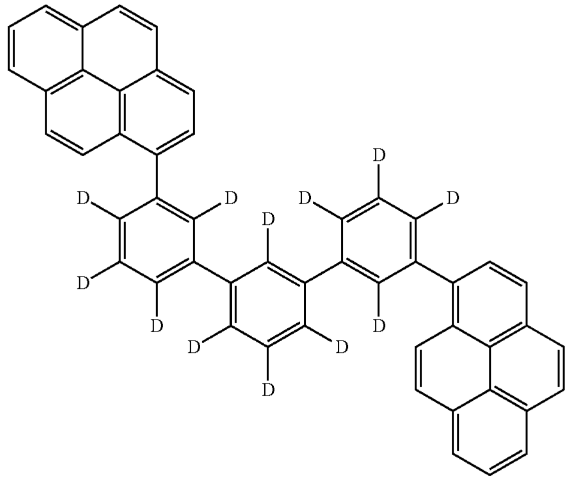

-continued
[Formula 132]
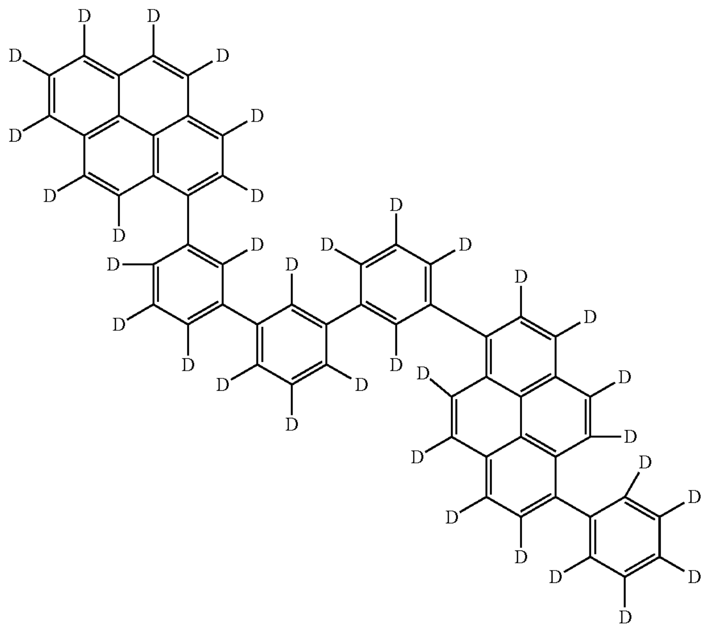
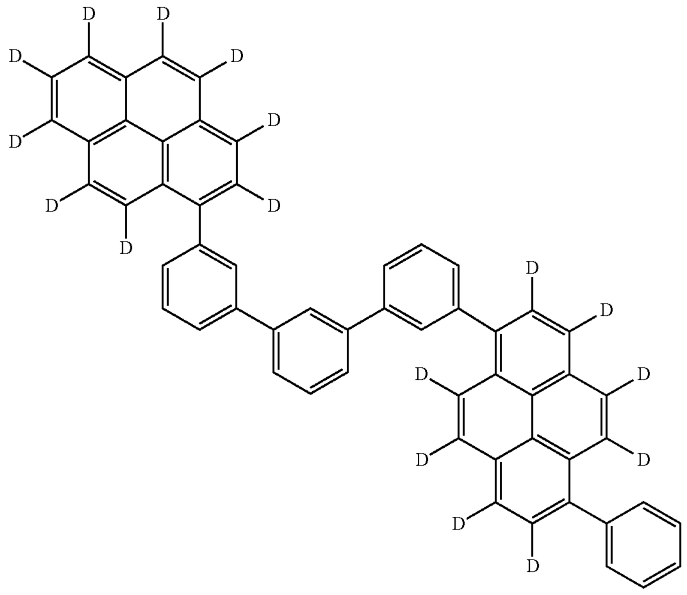

-continued
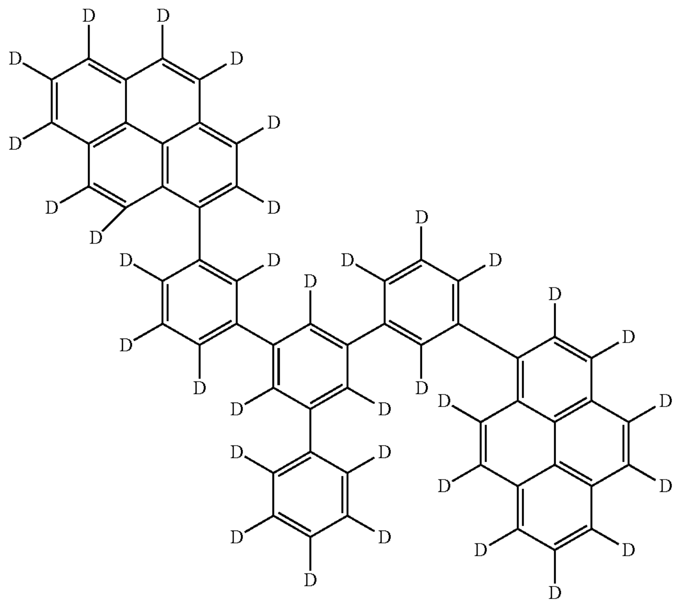
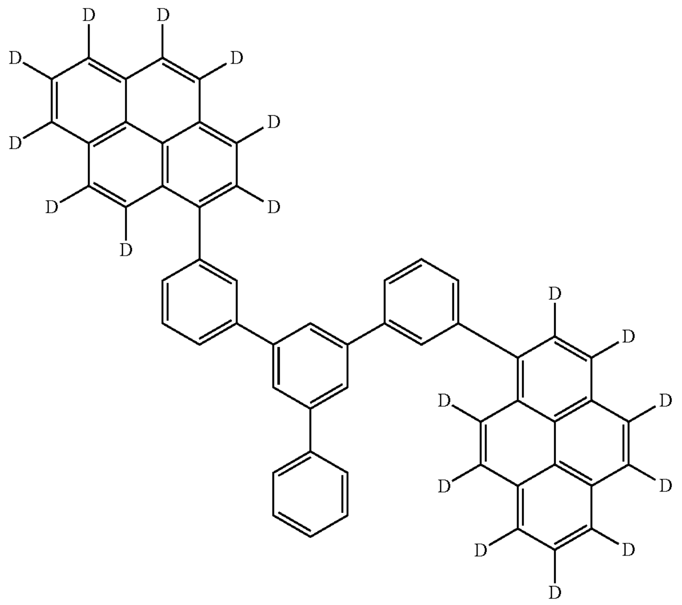

-continued
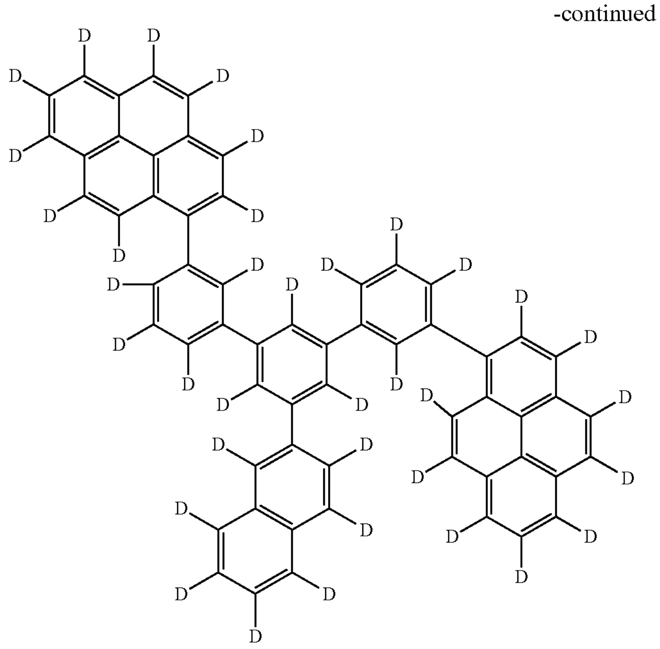
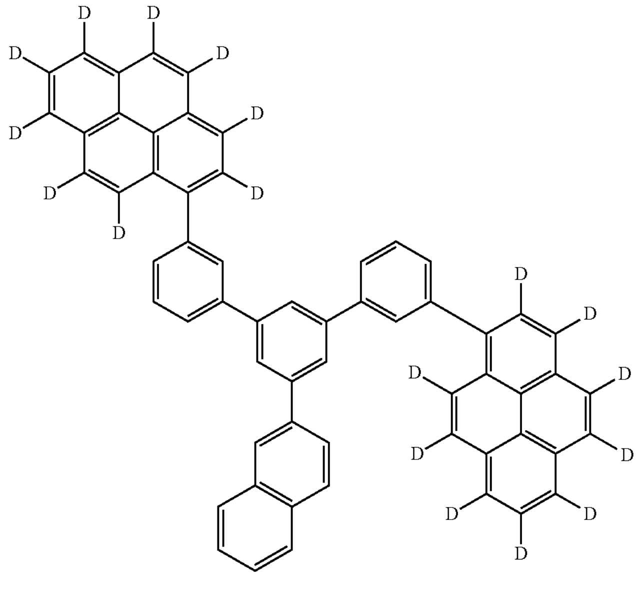

-continued
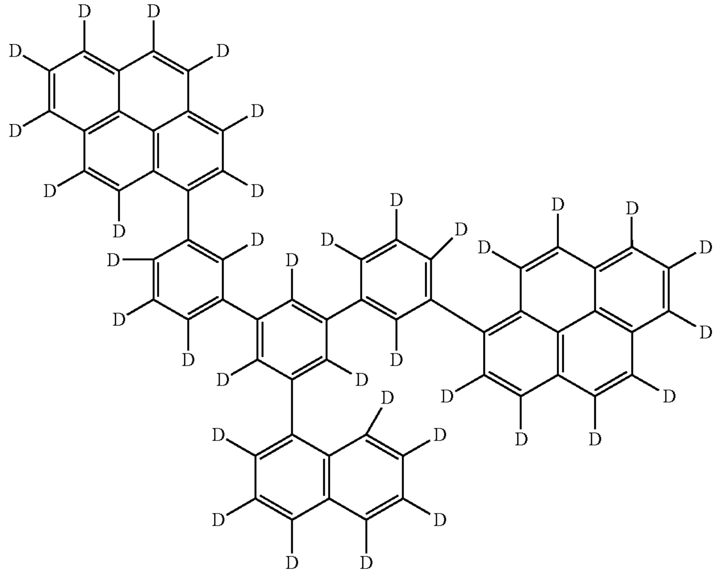
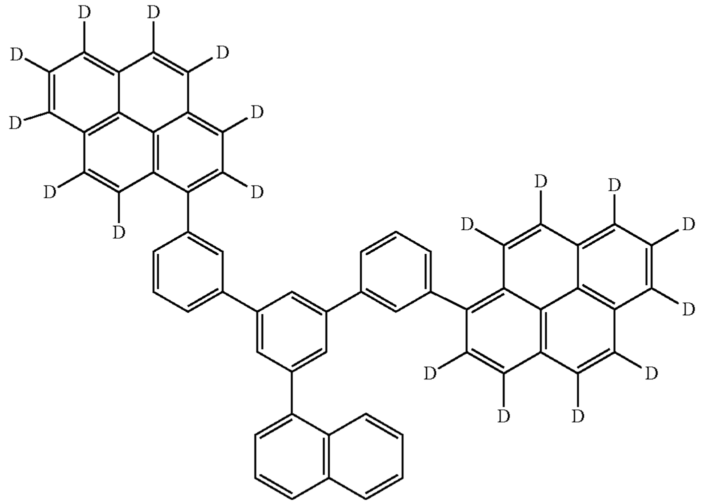
[Formula 133]
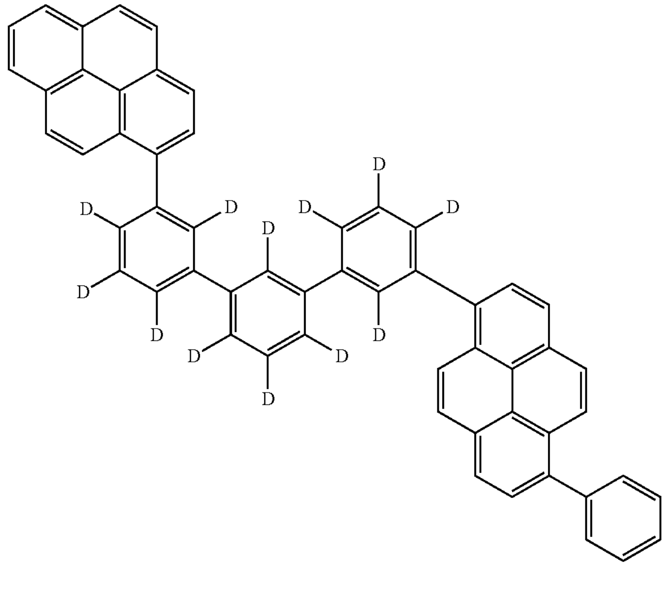

-continued
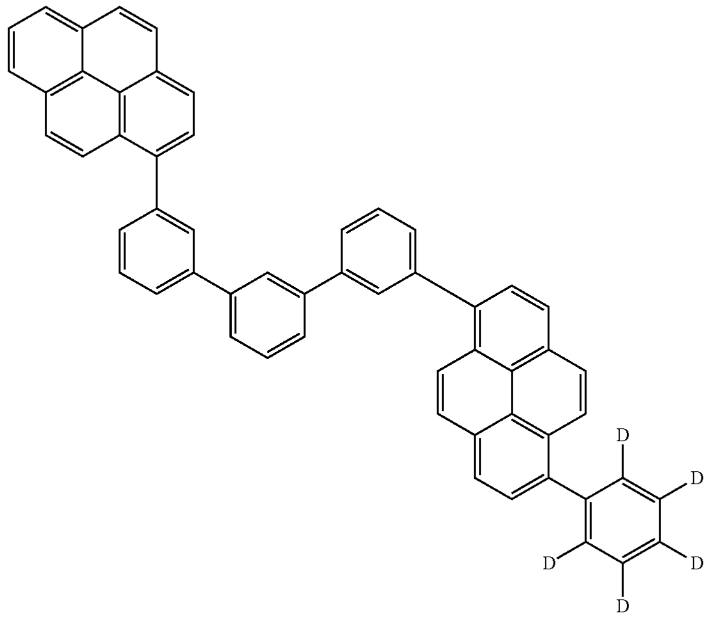
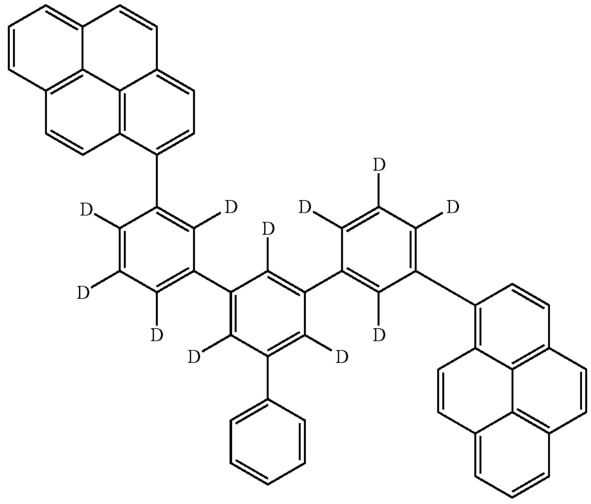
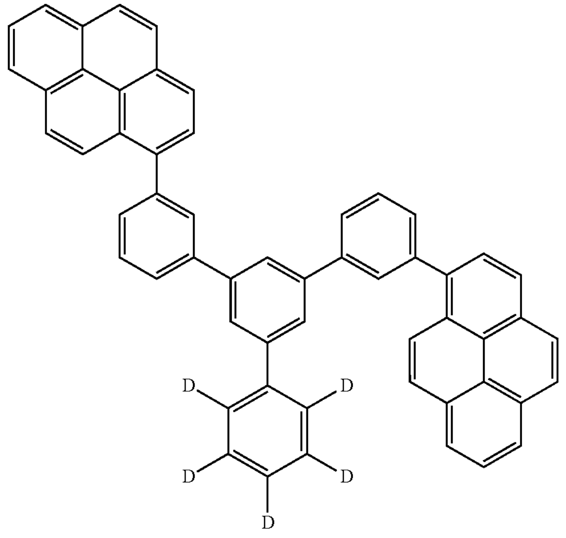
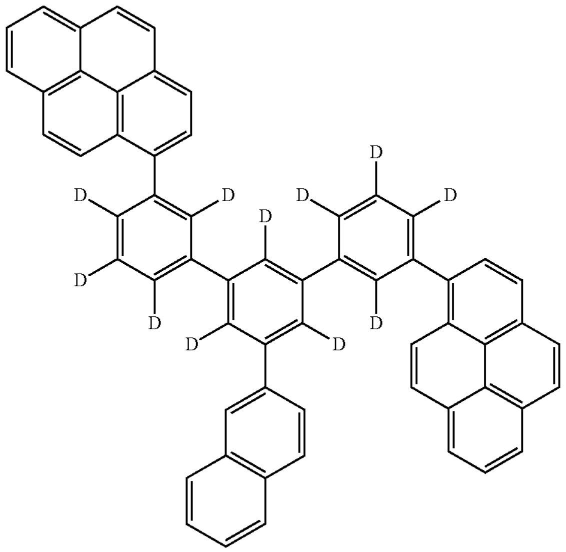

-continued
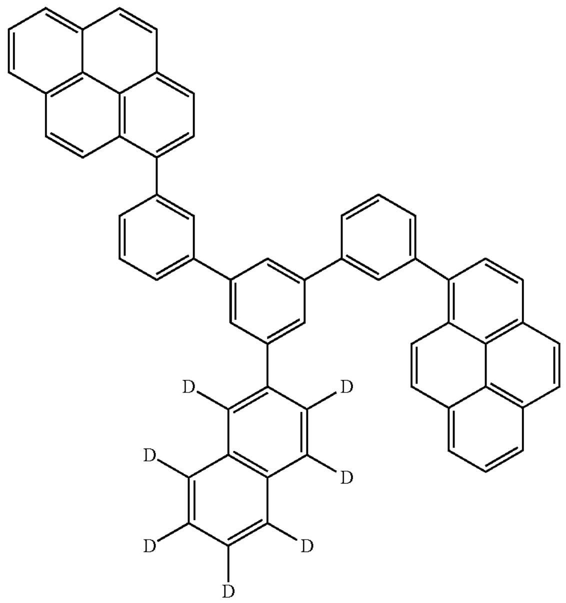
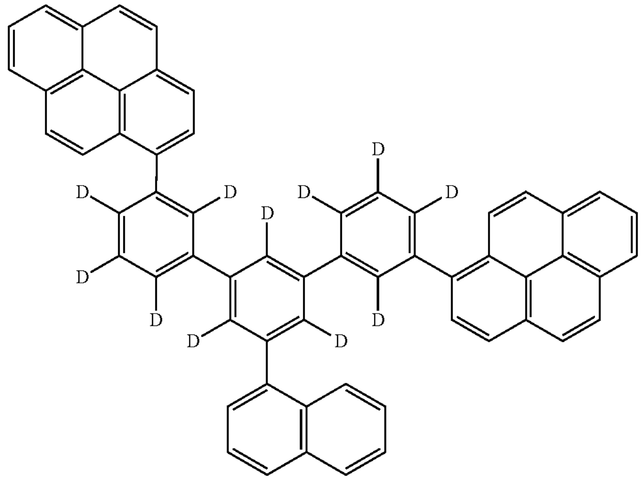
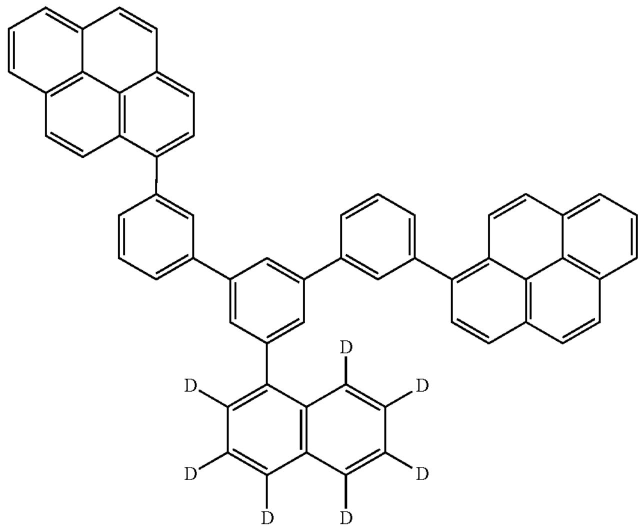

-continued
[Formula 134]
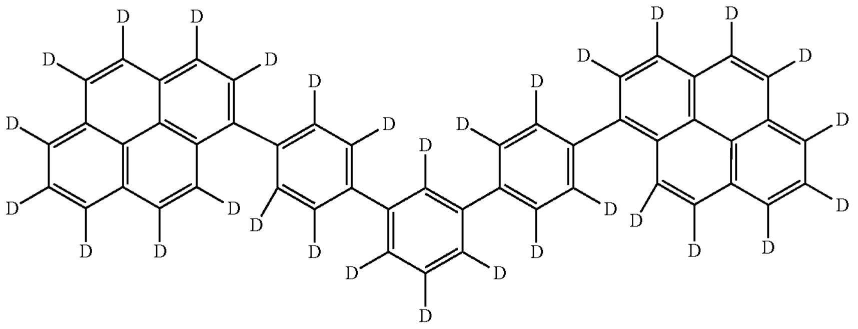
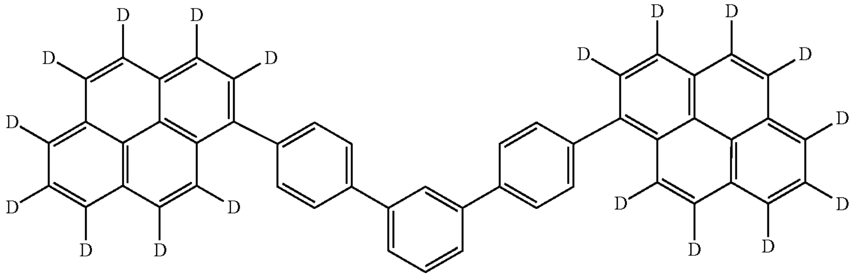
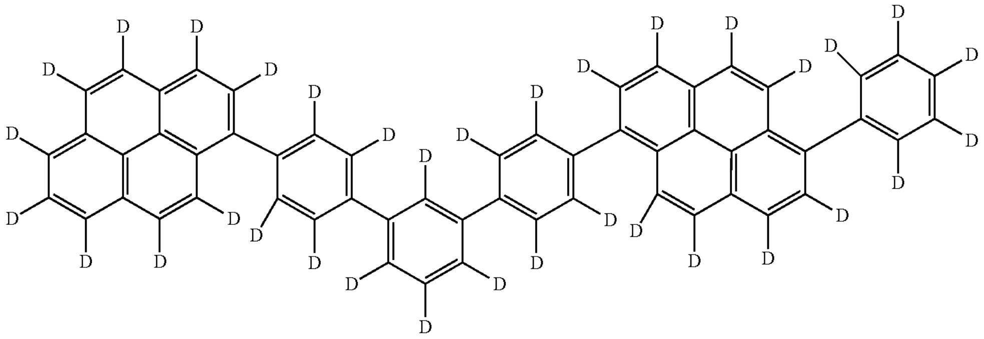
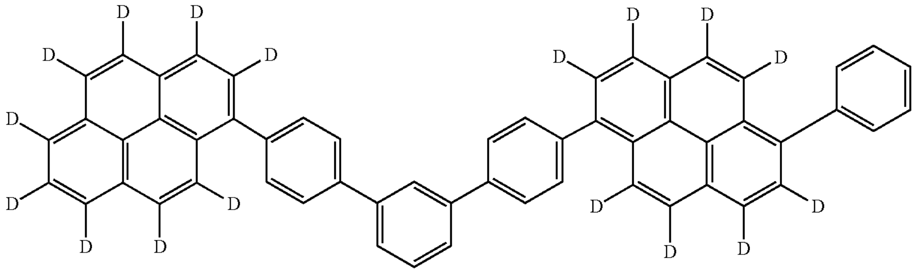
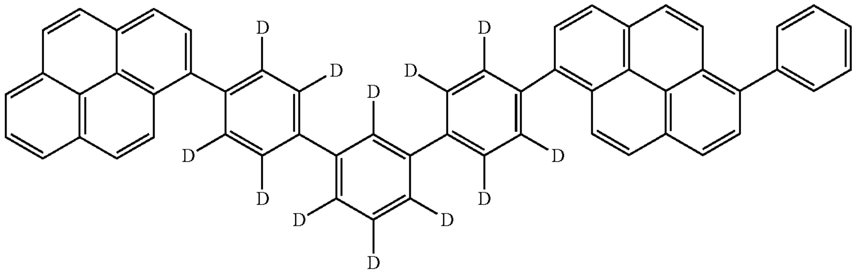

-continued
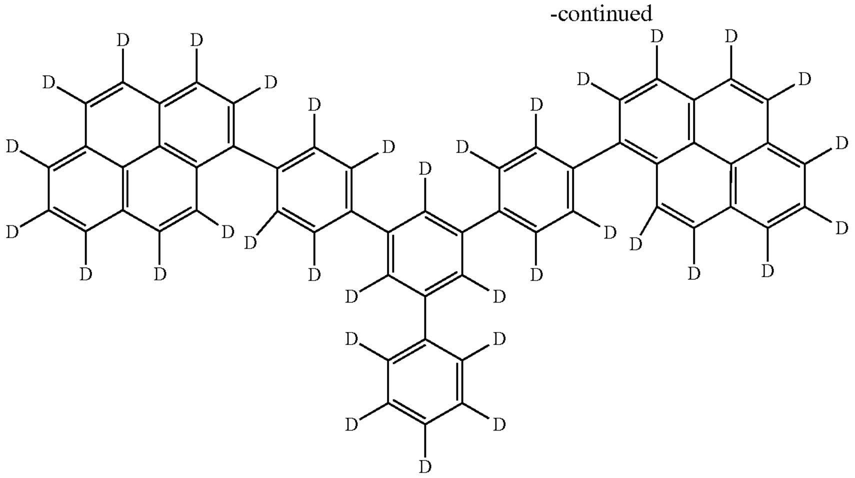
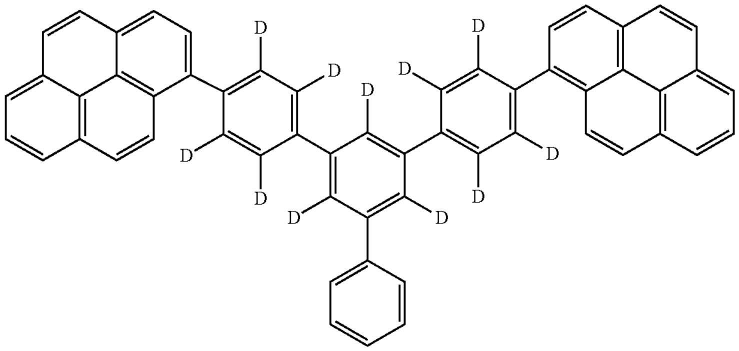
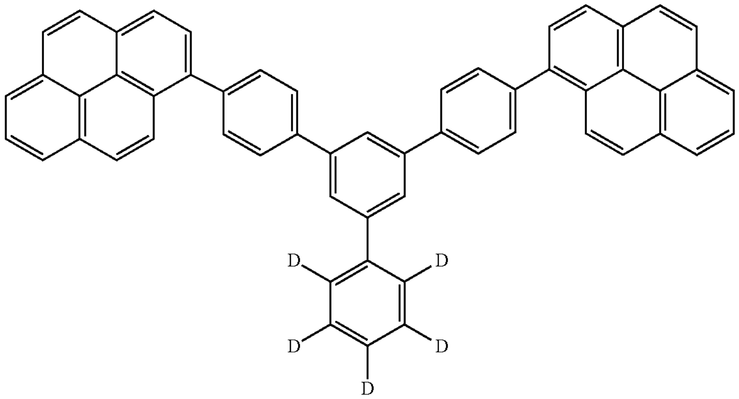
[Formula 135]
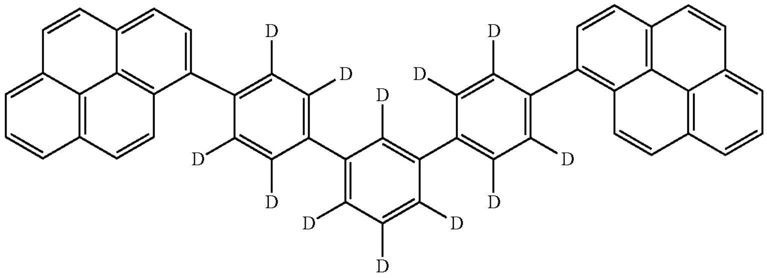

-continued
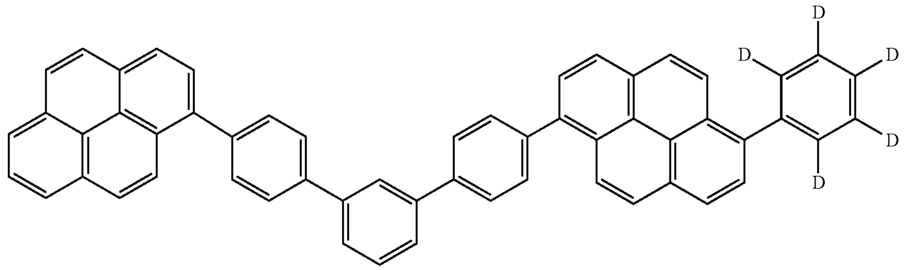
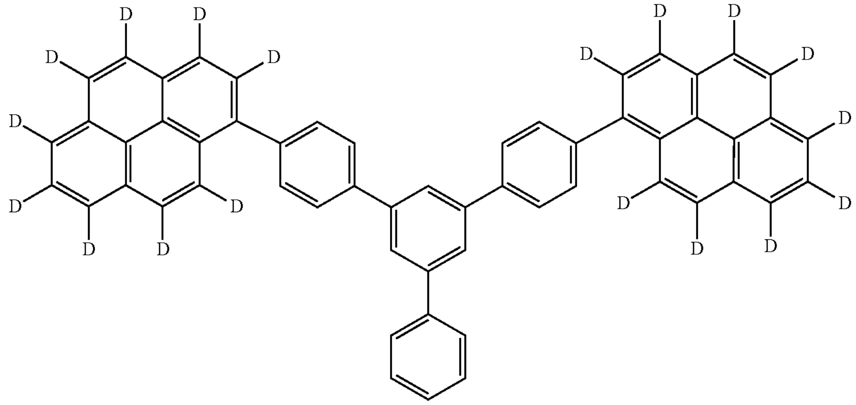
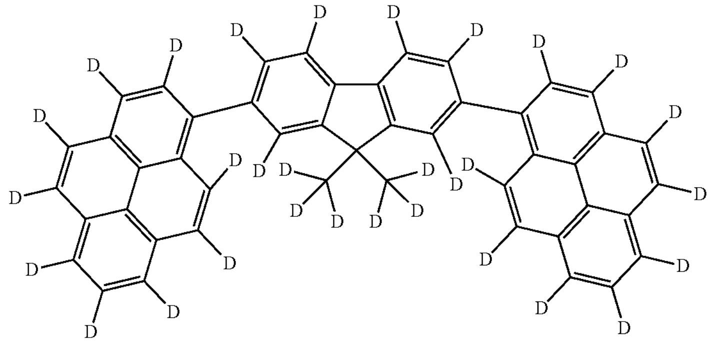
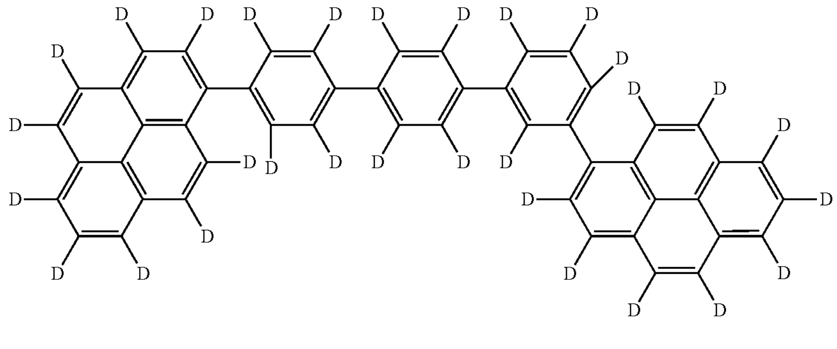
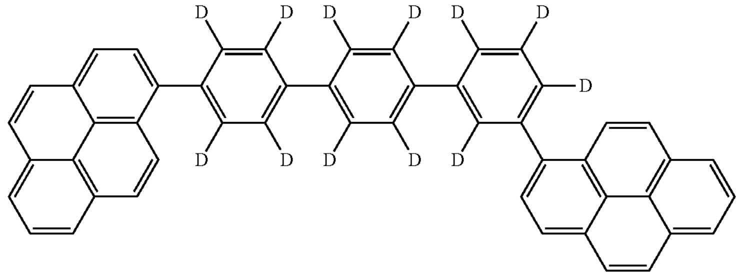

-continued
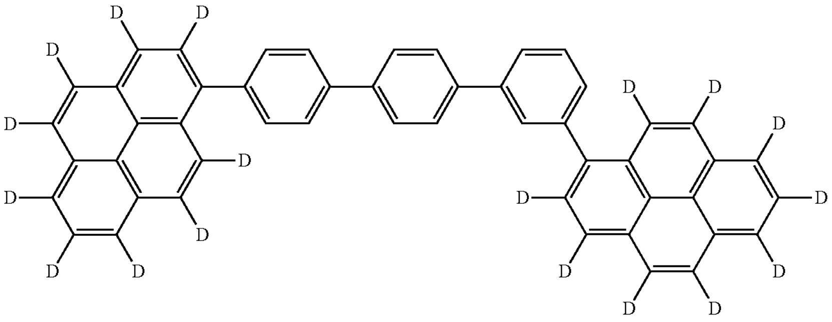
[Formula 136]
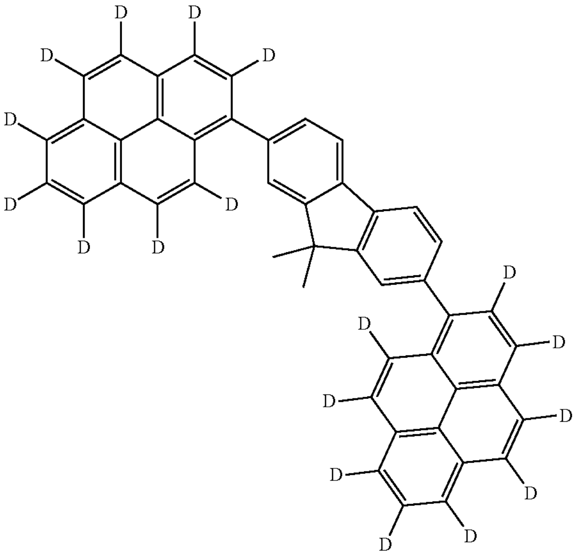
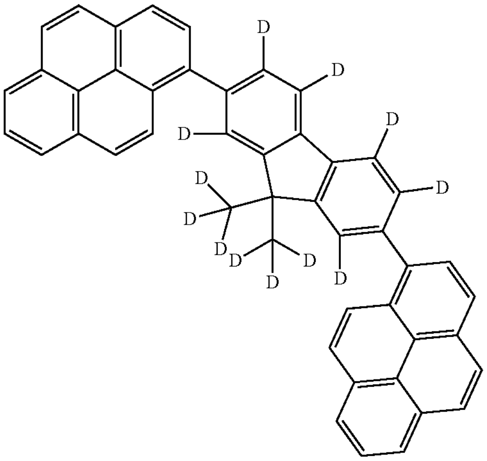
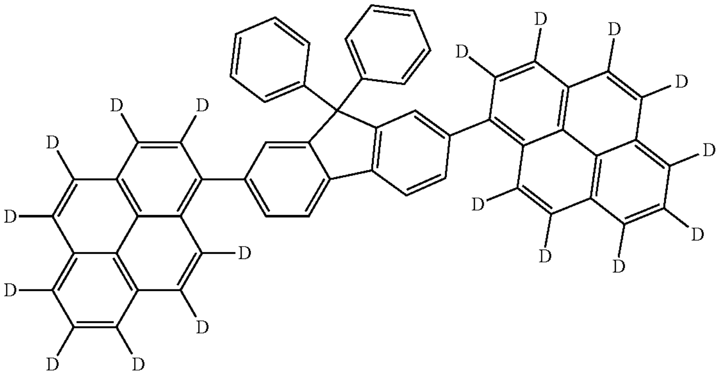
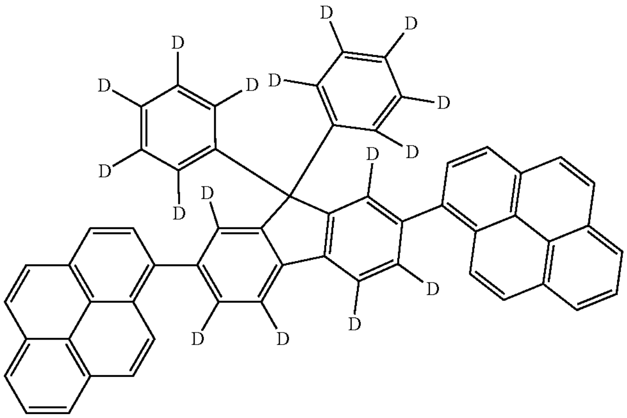

-continued
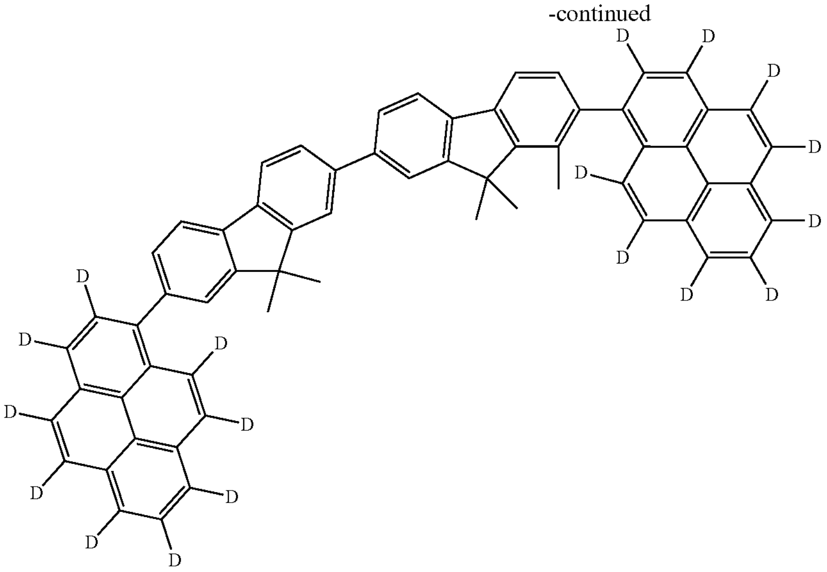
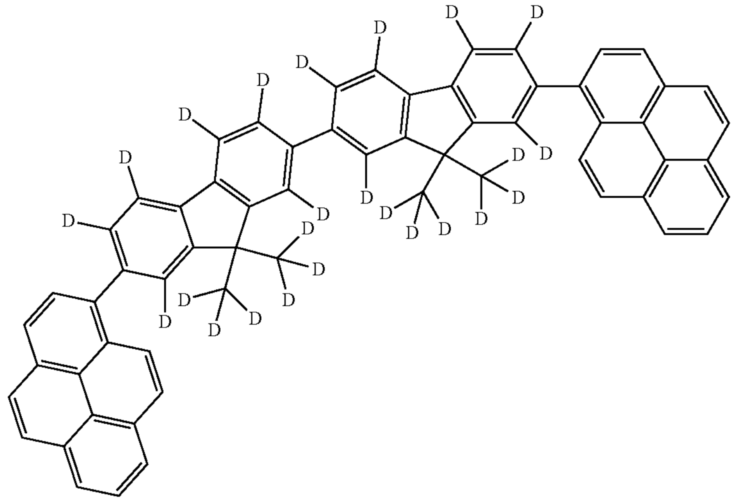
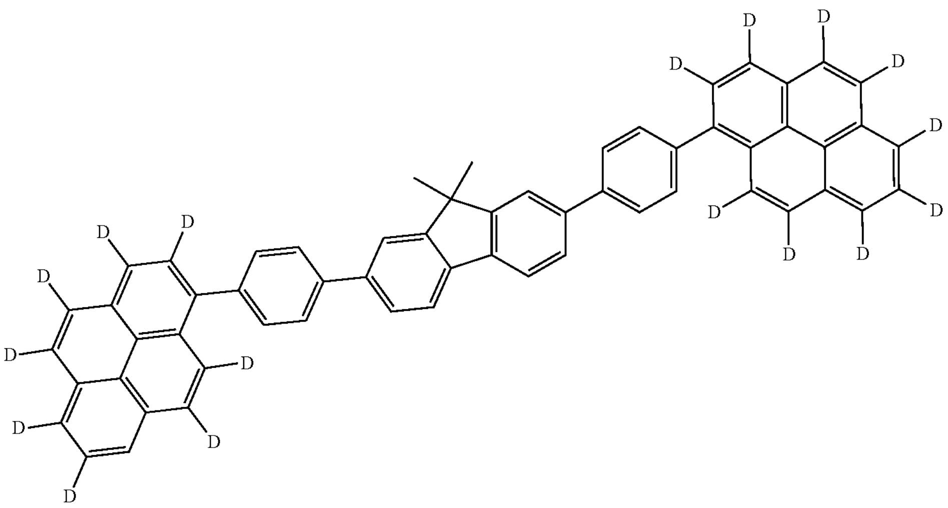

-continued
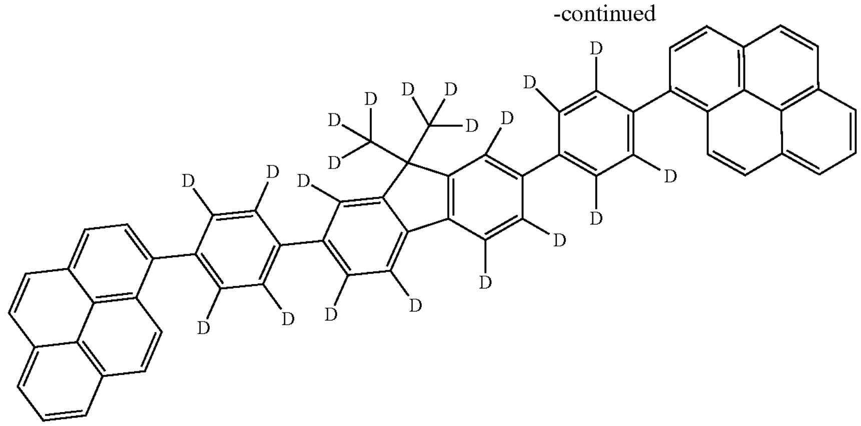
[Formula 137]
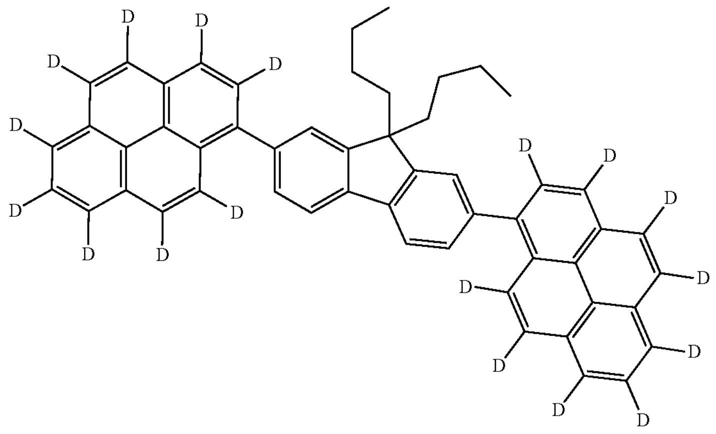
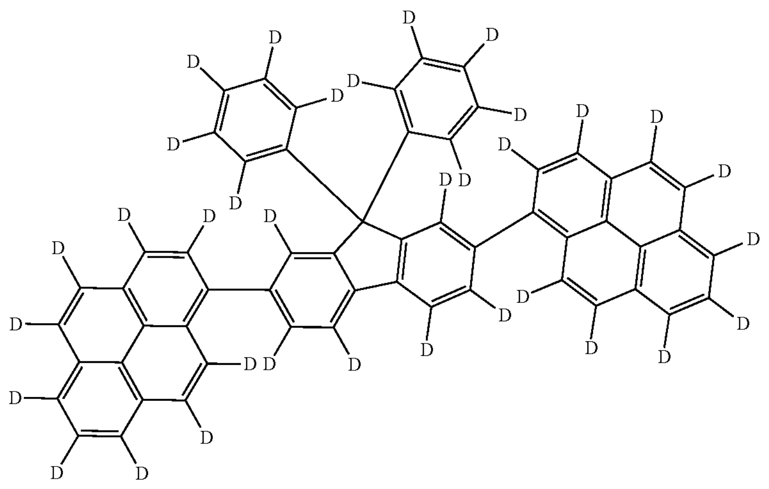

-continued
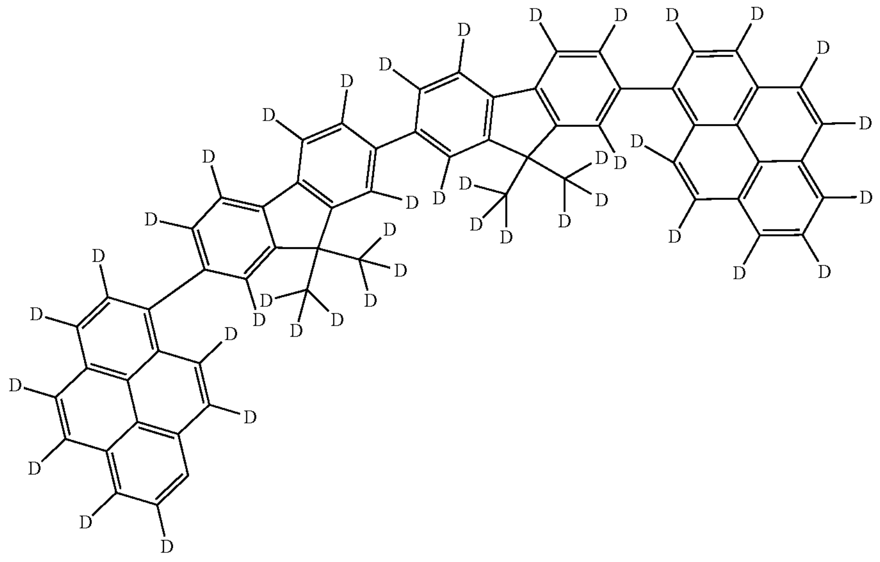
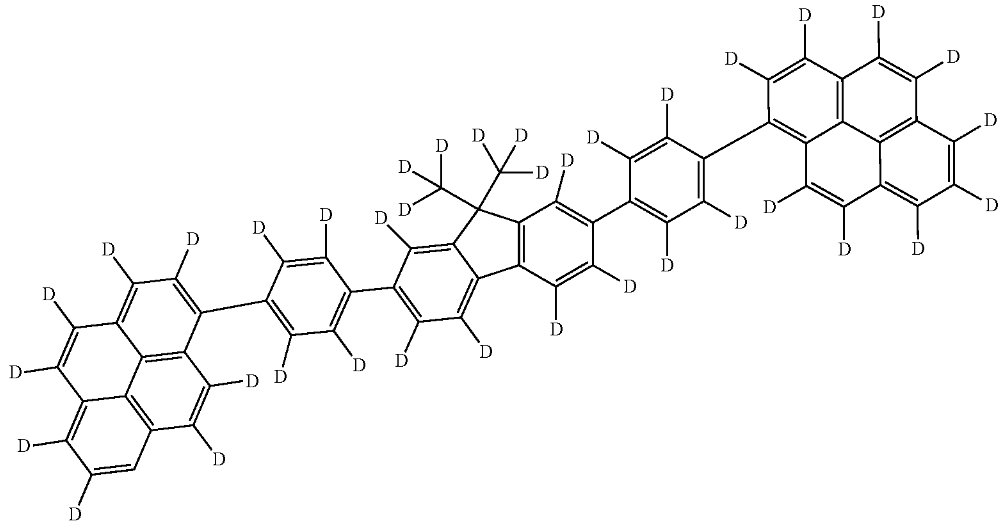
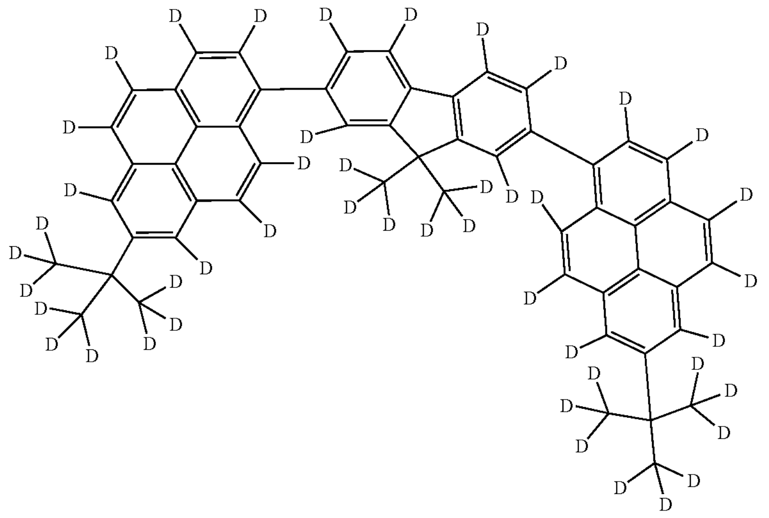

-continued
[Formula 138]
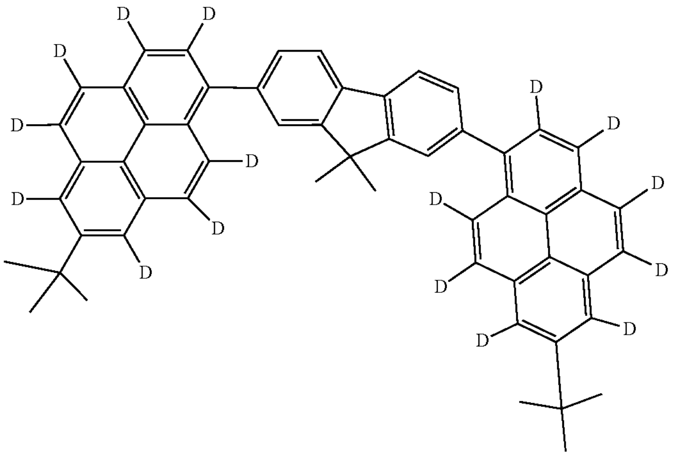
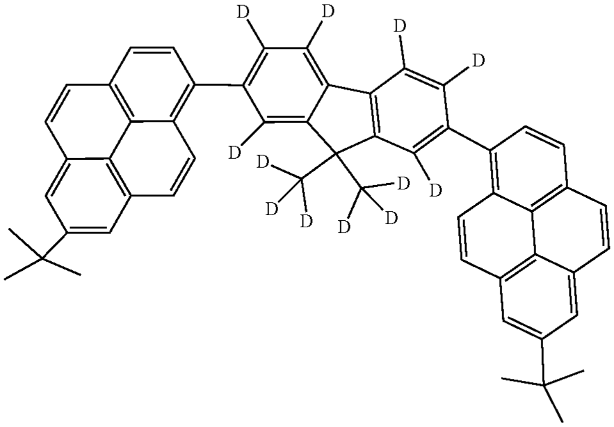
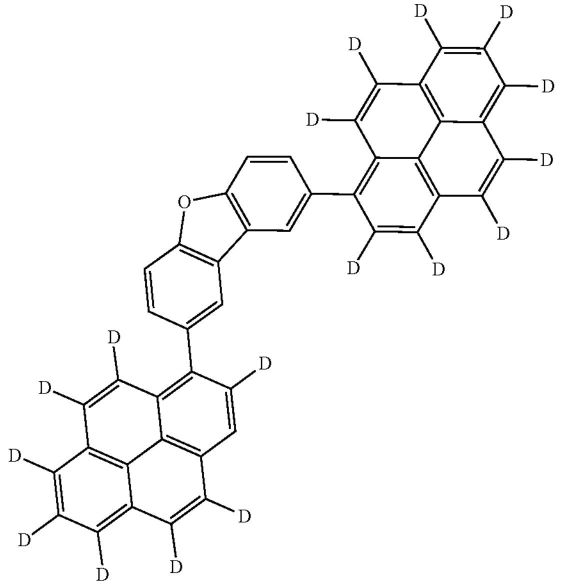
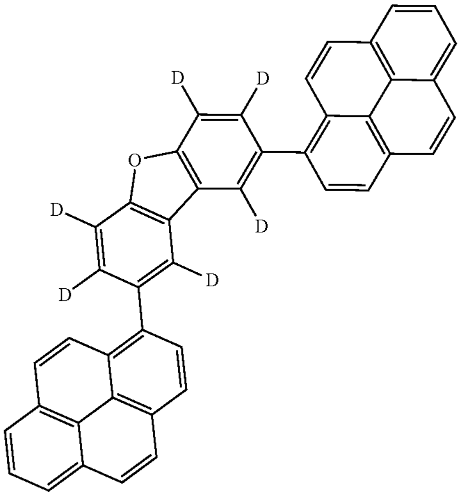
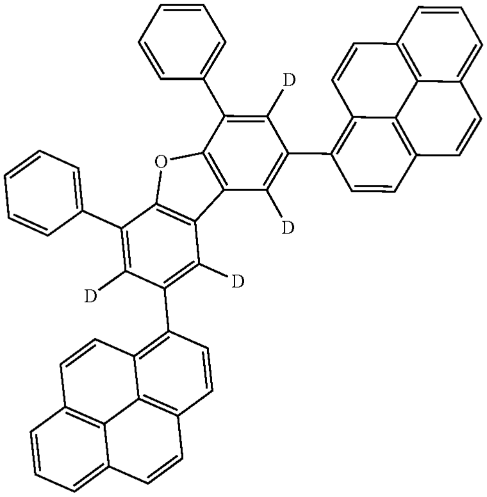

-continued
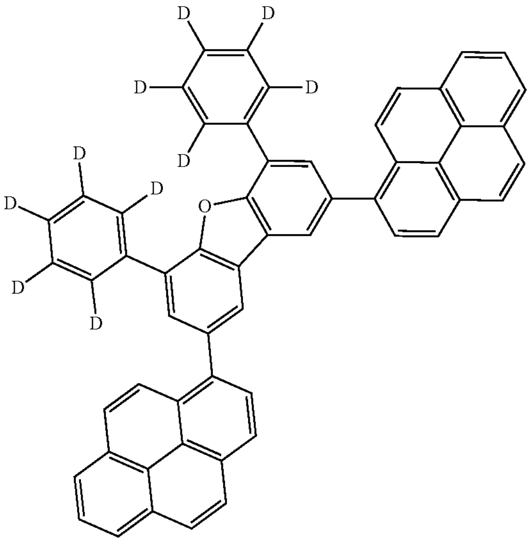
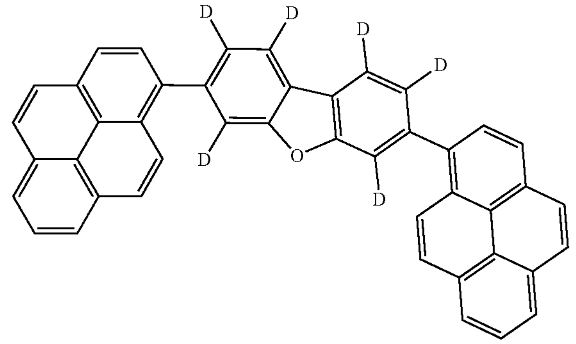
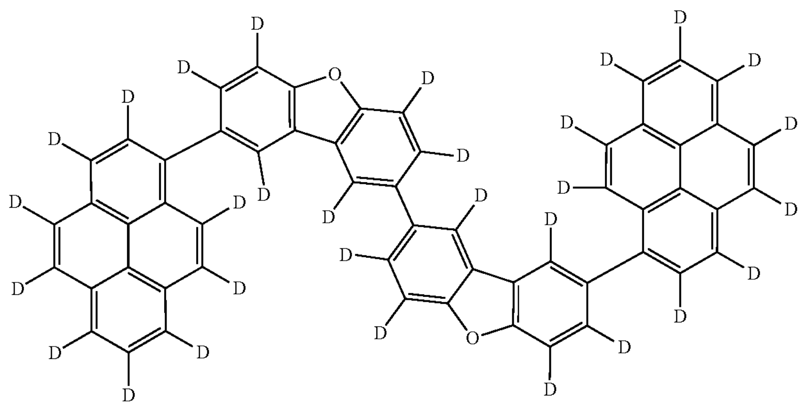
[Formula 139]
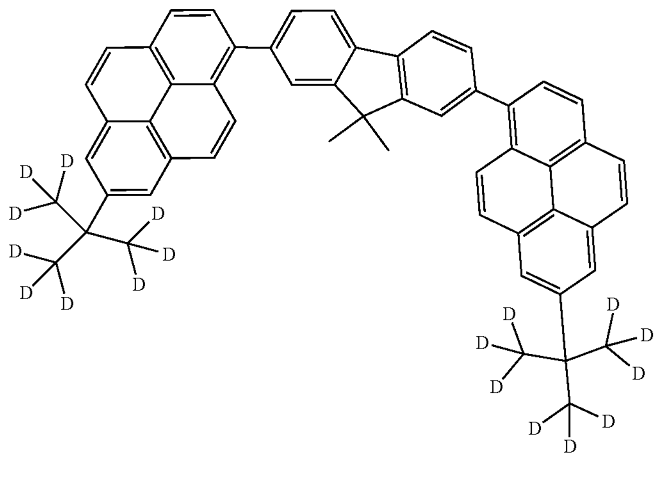

-continued
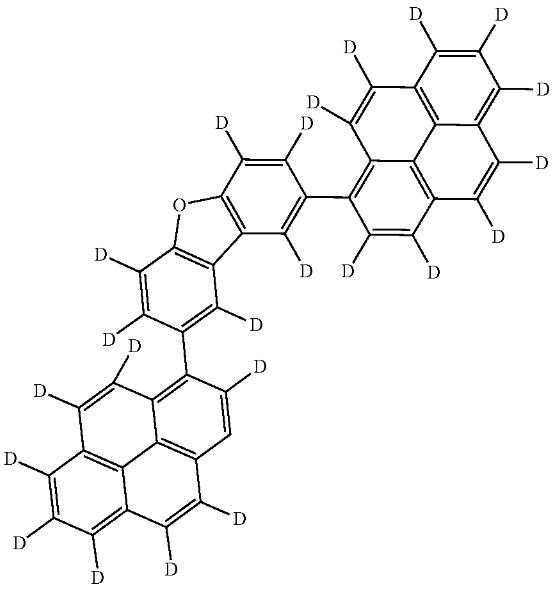
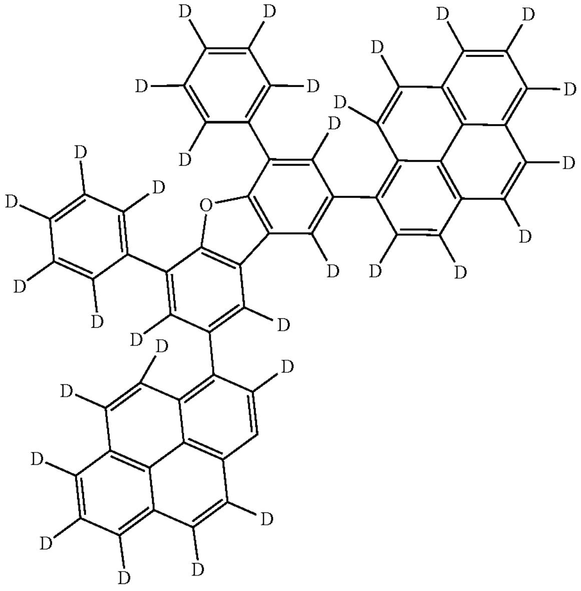
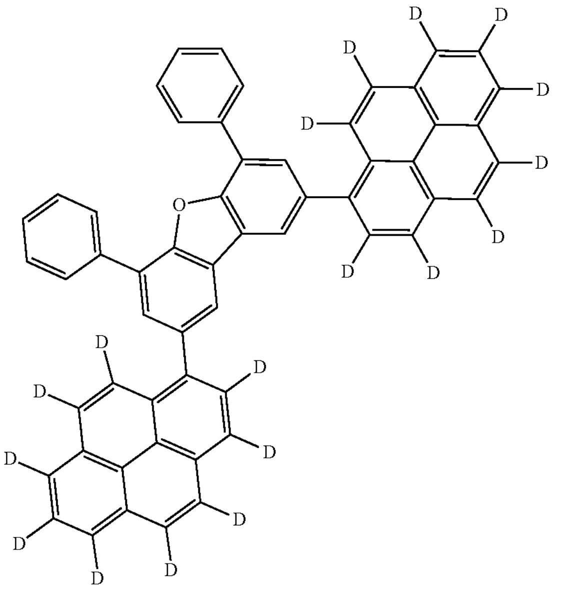
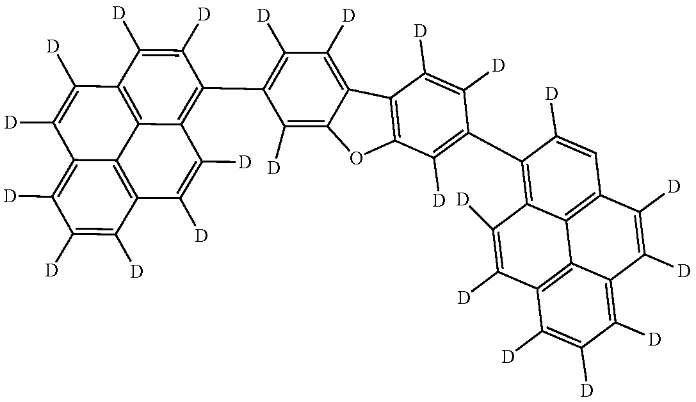

-continued
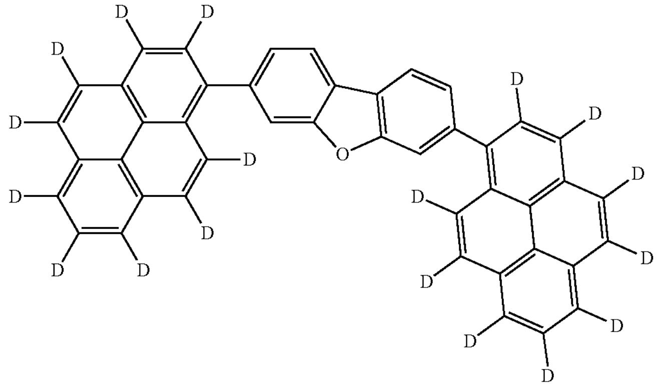
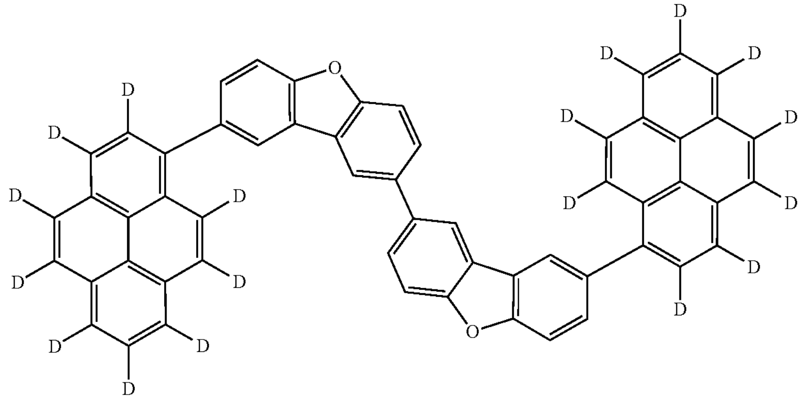
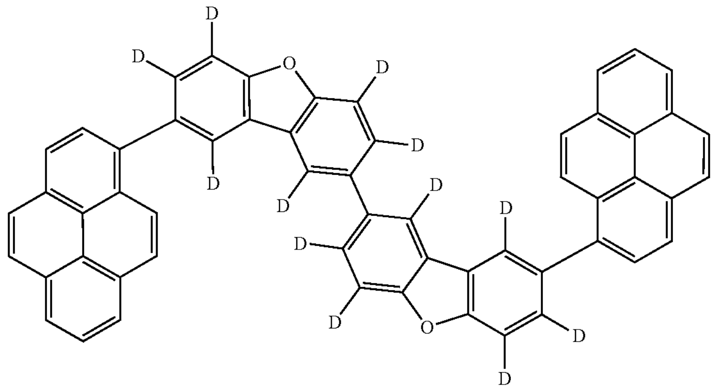
[Formula 140]
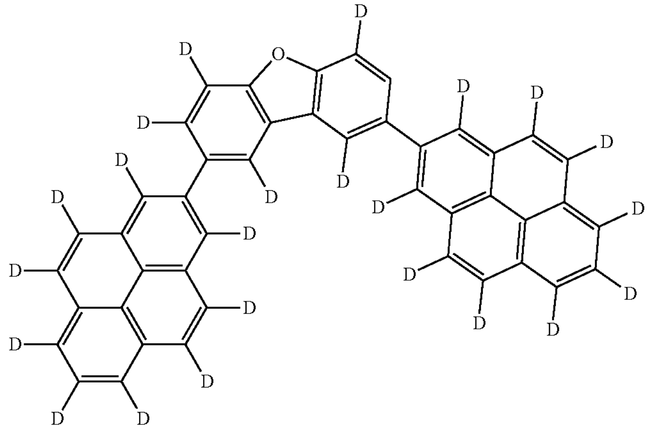

-continued
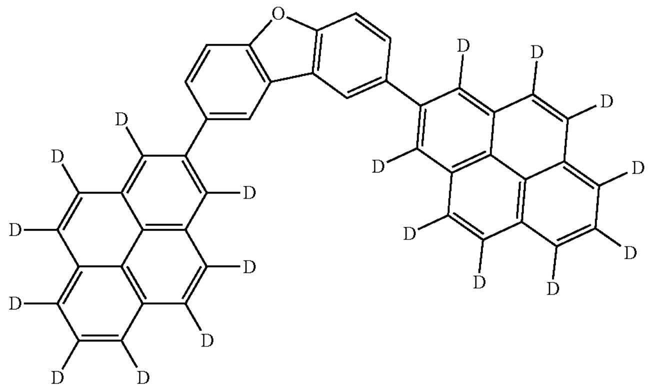
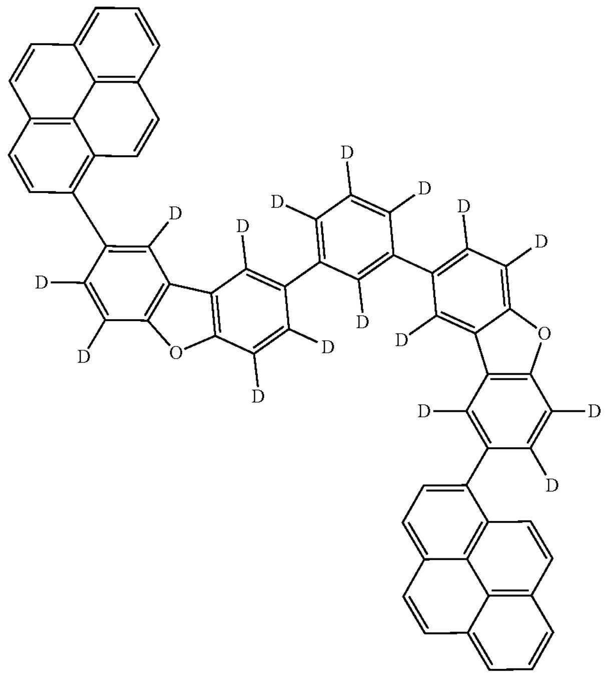
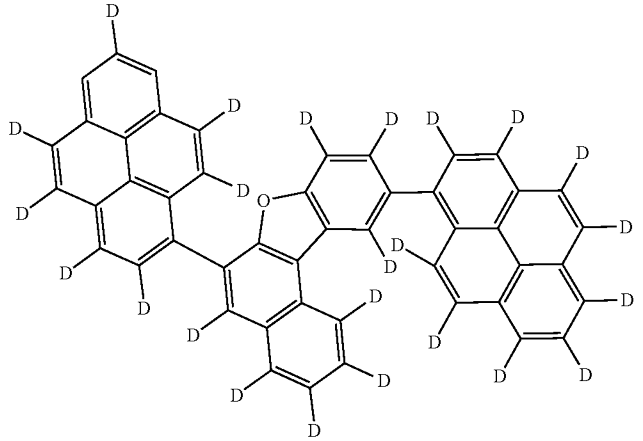
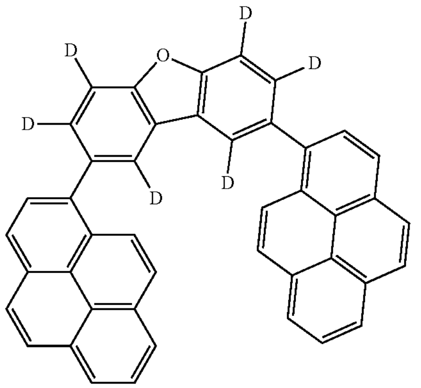

-continued

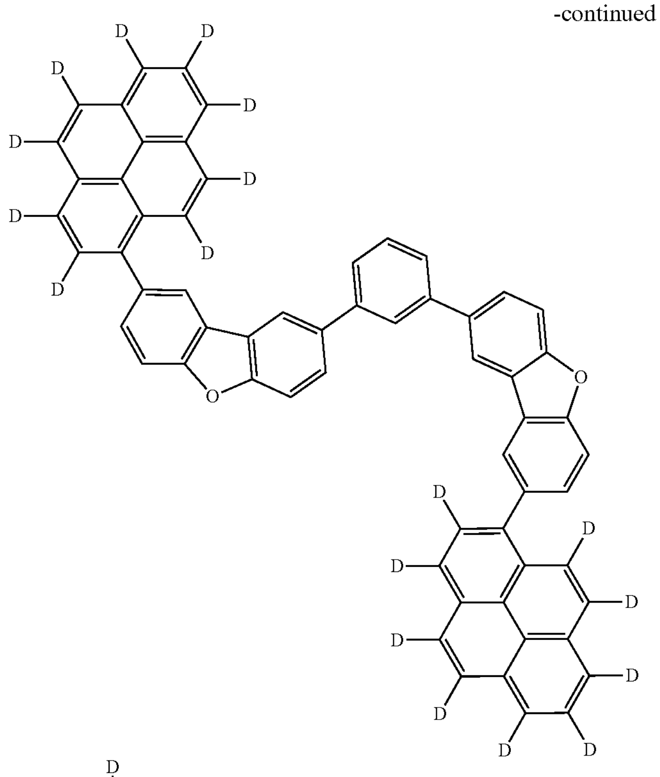

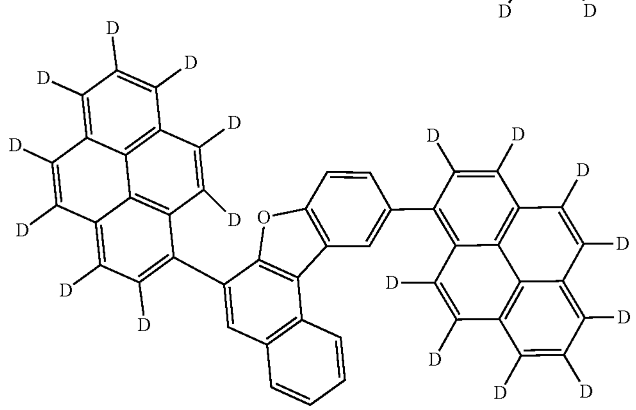

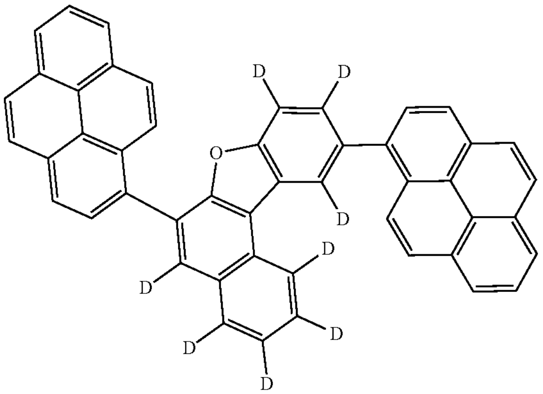

Second Exemplary Embodiment

Organic-EL-Device Material

An organic-EL-device material according to a second exemplary embodiment contains the compound according to the first exemplary embodiment (the compound represented by the formula (1)).

According to the second exemplary embodiment, an organic-EL-device material capable of increasing the lifetime can be provided.

The organic-EL-device material according to the second exemplary embodiment optionally further contains an additional compound. When the organic-EL-device material according to the second exemplary embodiment further contains the additional compound, the additional compound may be solid or liquid.

Third Exemplary Embodiment

Organic EL Device

An arrangement of an organic EL device according to a third exemplary embodiment will be described below.

The organic EL device according to the third exemplary embodiment includes an anode, a cathode, and an emitting layer interposed between the anode and the cathode.

The emitting layer contains a compound M2 in a form of the compound according to the first exemplary embodiment (the compound represented by the formula (1)). The emitting layer preferably contains the compound represented by the formula (1) as a host material.

Herein, the "host material" refers to, for instance, a material that accounts for "50 mass % or more of the layer." Accordingly, for instance, the emitting layer contains the compound represented by the formula (1) at 50 mass % or more of the total mass of the emitting layer.

In the third exemplary embodiment, the compound M2 (the compound represented by the formula (1)) includes at least one deuterium atom. In the following description, the "compound M2 having at least one deuterium atom" will be sometimes referred to as a "deuterated compound M2." Further, a "compound produced by replacing all of the deuterium atom(s) of the compound M2 with a protium atom(s)" will be sometimes referred to as a "non-deuterated compound m2" hereinafter.

In the third exemplary embodiment, a content ratio of the non-deuterated compound m2 to a sum of the deuterated compound M2 and the non-deuterated compound m2 contained in the emitting layer is 99 mol % or less. The content ratio of the non-deuterated compound m2 is determined through mass spectrometry.

In the third exemplary embodiment, the content ratio of the deuterated compound M2 to the sum of the deuterated compound M2 and the non-deuterated compound m2 contained in the emitting layer is preferably 30 mol % or more, 50 mol % or more, 70 mol % or more, 90 mol % or more, 95 mol % or more, 99 mol % or more, or 100 mol %.

The content ratio of the non-deuterated compound m2 and the content ratio of the deuterated compound M2 to the sum of the deuterated compound M2 and the non-deuterated compound m2 contained in a first or second emitting layer in a later-described fourth exemplary embodiment are preferably in the same ranges.

Emission Wavelength of Organic EL Device

The organic EL device according to the present exemplary embodiment preferably emits light whose main peak wavelength is in a range from 430 nm to 480 nm when the device is driven.

The main peak wavelength of the light emitted from the organic EL device when being driven is measured as follows. Voltage is applied on the organic EL devices such that a current density becomes 10 $mA/cm^2$, where spectral radiance spectrum is measured by a spectroradiometer CS-2000 (manufactured by Konica Minolta, Inc.). A peak wavelength of an emission spectrum, at which the luminous intensity of the resultant spectral radiance spectrum is at the maximum, is measured and defined as the main peak wavelength (unit: nm).

The organic EL device according to the present exemplary embodiment optionally includes one or more organic layer in addition to the emitting layer. Examples of the organic layer includes, for instance, at least one layer selected from the group consisting of a hole injecting layer, a hole transporting layer, an electron injecting layer, an electron transporting layer, a hole blocking layer and an electron blocking layer. It should be noted that two or more emitting layers are optionally provided.

In the organic EL device according to the present exemplary embodiment, the organic layer may consist of the emitting layer. Alternatively, the organic layer may further include, for instance, at least one layer selected from the group consisting of the hole injecting layer, the hole transporting layer, the electron injecting layer, the electron transporting layer, the hole blocking layer, and the electron blocking layer.

The organic EL device according to the present exemplary embodiment preferably includes a hole transporting layer between the anode and the emitting layer.

The organic EL device according to the present exemplary embodiment preferably includes an electron transporting layer between the anode and the emitting layer.

FIG. 1 schematically shows an arrangement of the organic EL device of the present exemplary embodiment.

An organic EL device 1 includes a light-transmissive substrate 2, an anode 3, a cathode 4, and an organic layer 10 provided between the anode 3 and the cathode 4. The organic layer 10 includes a hole injecting layer 6, a hole transporting layer 7, an emitting layer 5, an electron transporting layer 8, and an electron injecting layer 9, which are sequentially layered on the anode 3. The emitting layer 5 contains the compound according to the first exemplary embodiment (the compound represented by the formula (1)) as the compound M2.

Compound M2

In the organic EL device 1 according to the present exemplary embodiment, the compound M2 is the compound represented by the formula (1).

Compound M1

In the organic EL device 1 according to the present exemplary embodiment, the emitting layer 5 preferably further contains a fluorescent compound M1.

In the organic EL device 1 according to the present exemplary embodiment, the fluorescent compound M1 is preferably at least one compound selected from the group consisting of a compound represented by a formula (10) below, a compound represented by a formula (11) below, a compound represented by a formula (21) below, a compound represented by a formula (31) below, a compound represented by a formula (41) below, a compound represented by a formula (51) below, a compound represented by a formula (61) below, a compound represented by a formula (71) below, and a compound represented by a formula (81) below.

Compound Represented by Formula (10)

The compound represented by the formula (10) will be described below.

[Formula 141]

(10)

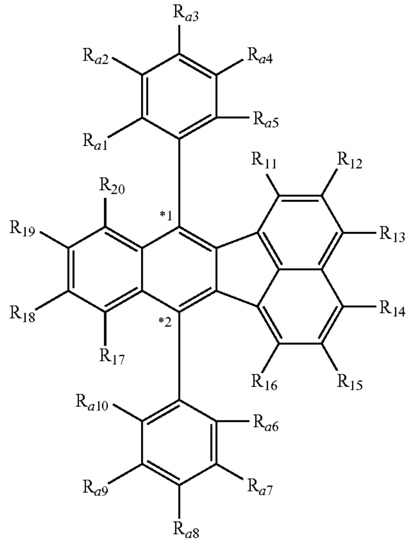

In the formula (10):

at least one combination of a combination of mutually adjacent two or more of $R_{11}$ to $R_{16}$, a combination of mutually adjacent two or more of $R_{17}$ to $R_{20}$, a combination of mutually adjacent two or more of $R_{a1}$ to $R_{a5}$, or a combination of mutually adjacent two or more of $R_{a6}$ to $R_{a10}$ are mutually bonded to form a substituted or unsubstituted monocyclic ring having 3 to 30 ring atoms, mutually bonded to form a substituted or unsubstituted fused ring having 3 to 30 ring atoms, or not mutually bonded.

$R_{11}$ to $R_{20}$, $R_{a1}$ to $R_{a5}$, and $R_{a6}$ to $R_{a10}$ forming neither the substituted or unsubstituted monocyclic ring nor the substituted or unsubstituted fused ring are each independently a hydrogen atom, a substituted or unsubstituted alkyl group having 1 to 30 carbon atoms, a substituted or unsubstituted cycloalkyl group having 3 to 30 ring carbon atoms, a substituted or unsubstituted alkoxy group having 1 to 30 carbon atoms, a substituted or unsubstituted alkylthio group having 1 to 30 carbon atoms, a substituted or unsubstituted amino group, a substituted or unsubstituted aryl group having 6 to 30 ring carbon atoms, a substituted or unsubstituted heterocyclic group having 5 to 30 ring atoms, a substituted or unsubstituted alkenyl group having 2 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted phosphanyl group, a substituted or unsubstituted phosphoryl group, a substituted or unsubstituted silyl group, a substituted or unsubstituted arylcarbonyl group having 6 to 30 ring carbon atoms, a cyano group, a nitro group, a carboxy group, or a halogen atom.

A specific example, in which "at least one combination of a combination of mutually adjacent two or more of $R_{11}$ to $R_{16}$, a combination of mutually adjacent two or more of $R_{17}$ to $R_{20}$, a combination of mutually adjacent two or more of $R_{a1}$ to $R_{a5}$, or a combination of mutually adjacent two or more of $R_{a6}$ to $Ra_{10}$" are mutually bonded to form a substituted or unsubstituted monocyclic ring or fused ring having 3 to 30 ring atoms, will be described below.

A specific example, in which a combination of mutually adjacent two or more of, for instance, $R_{17}$ to $R_{20}$ in the formula (10) are mutually bonded to form a fused ring, is a compound represented by a formula (10A) below. In the compound represented by the formula (10A) below, mutually adjacent three (i.e. $R_{18}$, $R_{19}$, and $R_{20}$) are mutually bonded to form a fused ring.

[Formula 142]

(10A)

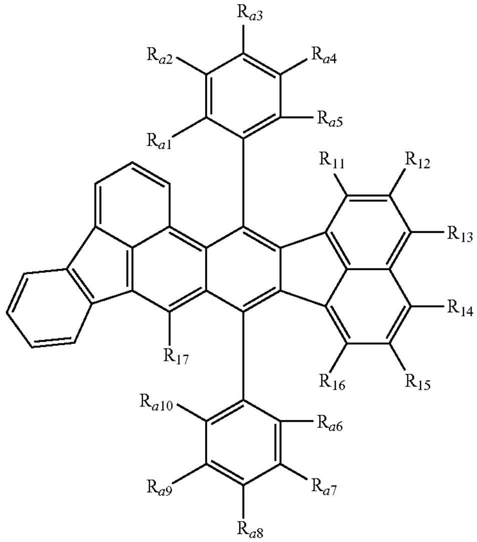

In the formula (10A): $R_{a1}$ to $R_{a10}$ and $R_{11}$ to $R_{17}$ each independently represent the same as $R_{a1}$ to $R_{a10}$ and $R_{11}$ to $R_{17}$ in the formula (10).

A specific example, in which a combination of mutually adjacent two or more of, for instance, $R_{11}$ to $R_{16}$ in the formula (10) are mutually bonded to form a monocyclic ring, is a compound represented by a formula (10B) below. In the compound represented by the formula (10B) below, two combinations (i.e. a combination of $R_{12}$ and $R_{13}$, and a combination of $R_{14}$ and $R_{15}$) are mutually bonded to form two separate monocyclic rings.

[Formula 143]

(10B)

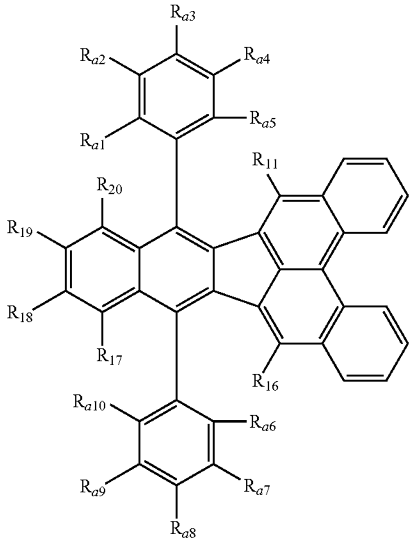

In the formula (10B): $R_{a1}$ to $R_{a10}$, $R_{11}$, and $R_{16}$ to $R_{20}$ each independently represent the same as $R_{a1}$ to $R_{a10}$, $R_{11}$, and $R_{16}$ to $R_{20}$ in the formula (10).

In an exemplary embodiment, the compound represented by the formula (10) is a compound represented by a formula (10-1) below.

[Formula 144]

(10-1)

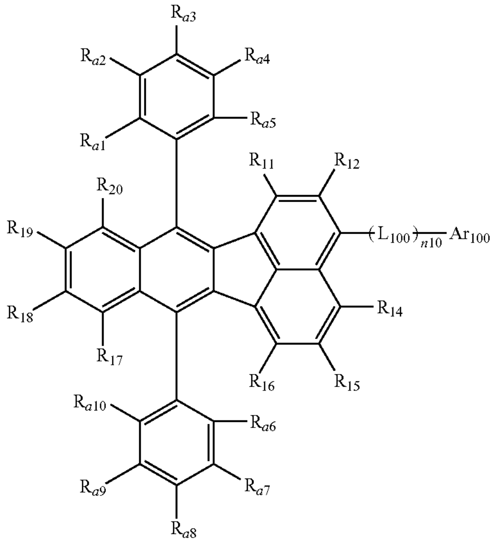

In the formula (10-1): $R_{11}$ to $R_{12}$, $R_{14}$ to $R_{20}$, and $R_{a1}$ to $R_{a10}$ each independently represent the same as $R_{11}$ to $R_{12}$, $R_{14}$ to $R_{20}$, and $R_{a1}$ to $R_{a10}$ in the formula (10);

$n_{10}$ is 0, 1, 2, or 3;

$L_{100}$ is a substituted or unsubstituted arylene group having 6 to 50 ring carbon atoms or a substituted or unsubstituted divalent heterocyclic group having 5 to 50 ring atoms;

when $n_{10}$ is 2, a plurality of $L_{100}$ are mutually the same or different;

when $n_{10}$ is 3, a plurality of $L_{100}$ are mutually the same or different; and $Ar_{100}$ is a substituted or unsubstituted aryl group having 6 to 50 ring carbon atoms, a substituted or unsubstituted heterocyclic group having 5 to 50 ring atoms, a cyano group, or a substituted silyl group.

In the formula (10-1), $n_{10}$ is preferably 0, 1, or 2.

In the formula (10-1), $L_{100}$ is preferably a single bond, or a divalent group derived by removing one hydrogen atom from a group selected from the group consisting of a substituted or unsubstituted phenyl group, a substituted or unsubstituted biphenyl group, a substituted or unsubstituted terphenyl group, a substituted or unsubstituted naphthyl group, a substituted or unsubstituted anthryl group, a substituted or unsubstituted phenanthryl group, a substituted or unsubstituted fluorenyl group, a substituted or unsubstituted 9,9'-spirobifluorenyl group, a substituted or unsubstituted 9,9-dimethylfluorenyl group, a substituted or unsubstituted 9,9-diphenylfluorenyl group, a substituted or unsubstituted dibenzofuranyl group, a substituted or unsubstituted naphthobenzofuranyl group, a substituted or unsubstituted dibenzothiophenyl group, and a substituted or unsubstituted naphthobenzothiophenyl group.

In the formula (10-1), $Ar_{100}$ is preferably a cyano group, a substituted silyl group, a substituted or unsubstituted phenyl group, a substituted or unsubstituted biphenyl group, a substituted or unsubstituted terphenyl group, a substituted or unsubstituted naphthyl group, a substituted or unsubstituted anthryl group, a substituted or unsubstituted phenanthryl group, a substituted or unsubstituted fluorenyl group, a substituted or unsubstituted 9,9'-spirobifluorenyl group, a substituted or unsubstituted 9,9-dimethylfluorenyl group, a substituted or unsubstituted 9,9-diphenylfluorenyl group, a substituted or unsubstituted dibenzofuranyl group, a substituted or unsubstituted naphthobenzofuranyl group, a substituted or unsubstituted dibenzothiophenyl group, or a substituted or unsubstituted naphthobenzothiophenyl group.

In the formula (10-1), at least one combination of a combination of mutually adjacent two or more of $R_{11}$ to $R_{12}$, $R_{14}$ to $R_{16}$, and $R_{17}$ to $R_{20}$, a combination of mutually adjacent two or more of $R_{a1}$ to $R_{a5}$, or a combination of mutually adjacent two or more of $R_{a6}$ to $R_{a10}$ are mutually bonded to form a substituted or unsubstituted monocyclic ring having 3 to 30 ring atoms, mutually a substituted or unsubstituted fused ring having 3 to 30 ring atoms, or not mutually bonded.

In an exemplary embodiment, $R_{12}$ and $R_{13}$ in the formula (10) are mutually bonded to form a substituted or unsubstituted monocyclic ring having 3 to 30 ring atoms or a substituted or unsubstituted fused ring having 3 to 30 ring atoms.

In an exemplary embodiment, the compound represented by the formula (10) is a compound represented by a formula (10-2) below.

[Formula 145]

(10-2)

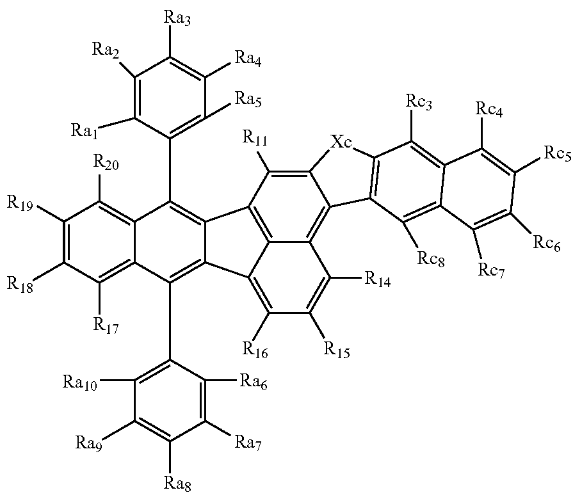

In the formula (10-2): $X_C$ is an oxygen atom, sulfur atom, or $CR_{c1}R_{c2}$, $R_{11}$, $R_{14}$ to $R_{20}$, $R_{a1}$ to $R_{a10}$, and $R_{c3}$ to $R_{c8}$ each independently represent the same as $R_{11}$ to $R_{20}$ in the formula (10);

$R_{c1}$ and $R_{c2}$ are each independently a hydrogen atom, an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, $-Si(R_{901})(R_{902})(R_3)$, $-O-(R_{904})$, $-S-(R_{905})$, $-N(R_{906})(R_{907})$, a halogen atom, a cyano group, a nitro group, an unsubstituted aryl group having 6 to 50 ring carbon atoms, or an unsubstituted monovalent heterocyclic group having 5 to 50 ring atoms; and $R_{901}$ to $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

When a plurality of $R_{901}$ are present, the plurality of $R_{901}$ are mutually the same or different; when a plurality of $R_{902}$ are present, the plurality of $R_{902}$ are mutually the same or different; when a plurality of $R_{903}$ are present, the plurality of $R_{903}$ are mutually the same or different; when a plurality of $R_{904}$ are present, the plurality of $R_{904}$ are mutually the same or different; when a plurality of $R_{905}$ are present, the plurality of $R_{905}$ are mutually the same or different; when a plurality of $R_{906}$ are present, the plurality of $R_{906}$ are mutually the same or different; and when a plurality of $R_{907}$ are present, the plurality of $R_{907}$ are mutually the same or different.

In the formula (10-2), at least one combination of a combination of mutually adjacent two or more of $R_{14}$ to $R_{16}$ and $R_{17}$ to $R_{20}$, a combination of mutually adjacent two or more of $R_{a1}$ to $R_{a5}$, a combination of mutually adjacent two or more of $R_{a6}$ to $R_{a10}$, a combination of mutually adjacent two or more of $R_{c3}$ to $R_{c8}$, or a combination of $R_{c1}$ and $R_{c2}$ are mutually bonded to form a substituted or unsubstituted monocyclic ring having 3 to 30 ring atoms a substituted or unsubstituted fused ring having 3 to 30 ring atoms, or not mutually bonded.

In an exemplary embodiment, two or more of $R_{18}$ and $R_{20}$ in the formula (10) are mutually bonded to form a substituted or unsubstituted monocyclic ring having 3 to 30 ring atoms or a substituted or unsubstituted fused ring having 3 to 30 ring atoms.

In an exemplary embodiment, the compound represented by the formula (10) is a compound represented by a formula (10-3) below.

[Formula 146]

(10-3)

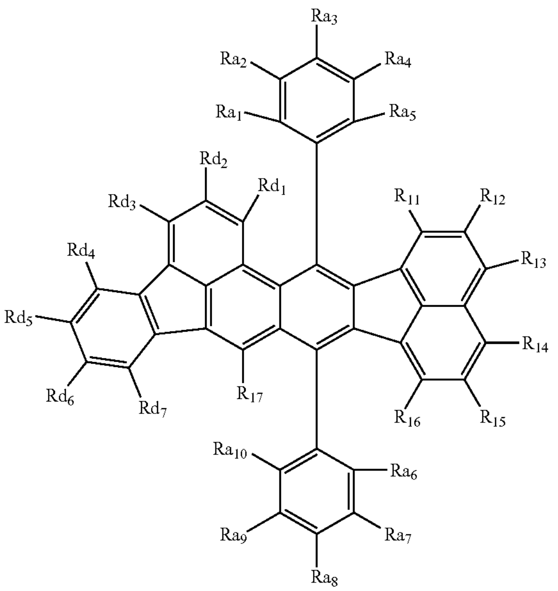

In the formula (10-3): $R_{11}$ to $R_{17}$, $R_{a1}$ to $R_{a10}$, and $R_{d1}$ to $R_{d7}$ each independently represent the same as $R_{11}$ to $R_{20}$ in the formula (10).

In the formula (10-3), at least one combination of a combination of mutually adjacent two or more of $R_{11}$ to $R_{16}$, a combination of adjacent two or more of $R_{17}$ and $R_{d1}$ to $R_{d7}$, a combination of mutually adjacent two or more of $R_{a1}$ to $R_{a5}$, or a combination of mutually adjacent two or more of $R_{a6}$ to $R_{a10}$ are mutually bonded to form a substituted or unsubstituted monocyclic ring having 3 to 30 ring atoms or a substituted or unsubstituted fused ring having 3 to 30 ring atoms, or not mutually bonded.

In an exemplary embodiment, $R_{11}$ to $R_{20}$, $R_{a1}$ to $R_{a5}$, $R_{a6}$ to $R_{a10}$, $R_{c1}$ to $R_{c8}$, and $R_{d1}$ to $R_{d7}$ not involved in ring formation in the formulae (10) and (10-1) to (10-3) are each independently a hydrogen atom, an unsubstituted aryl group having 6 to 50 ring carbon atoms, or an unsubstituted monovalent heterocyclic group having 5 to 50 ring atoms.

Specific examples of the compound represented by the formula (10) include compounds shown below.

[Formula 147]

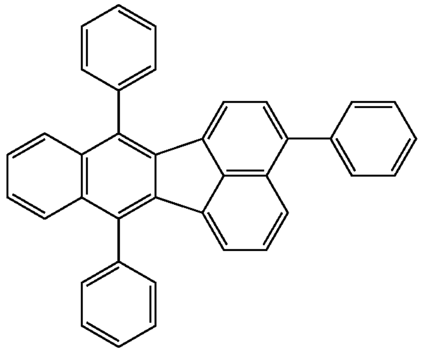

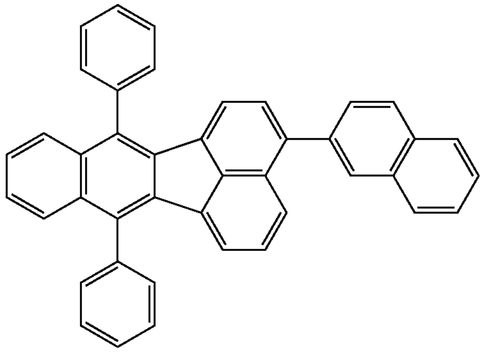

-continued
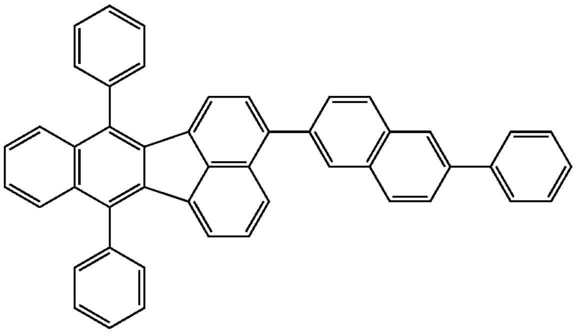
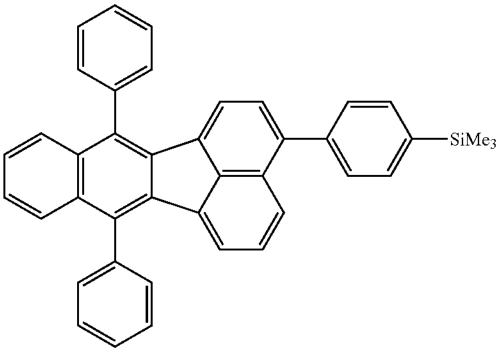
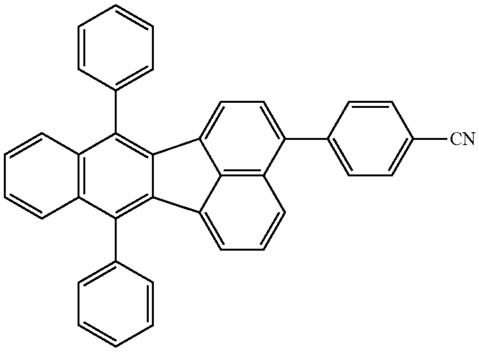
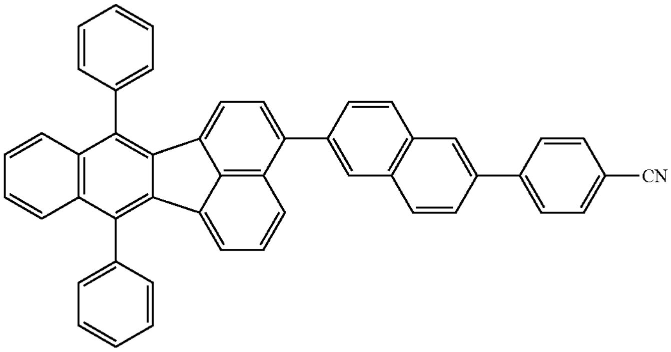
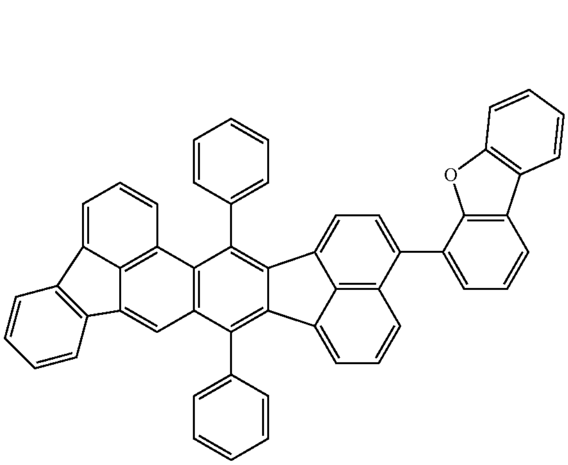

-continued
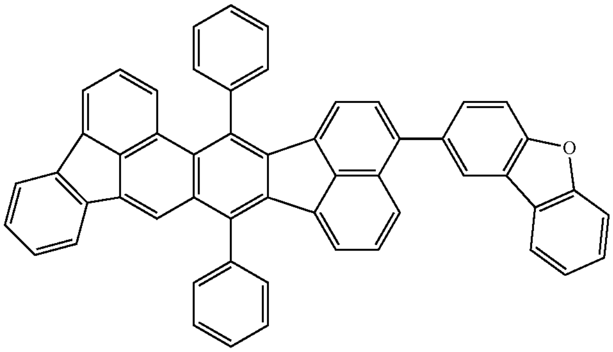
[Formula 148]
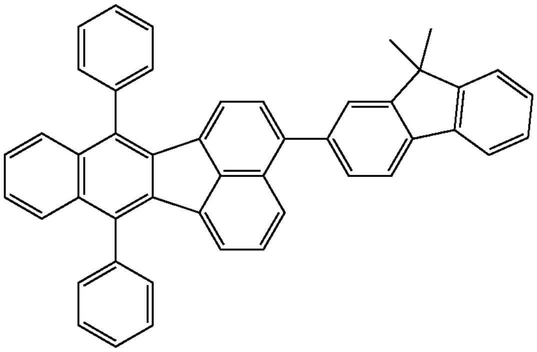
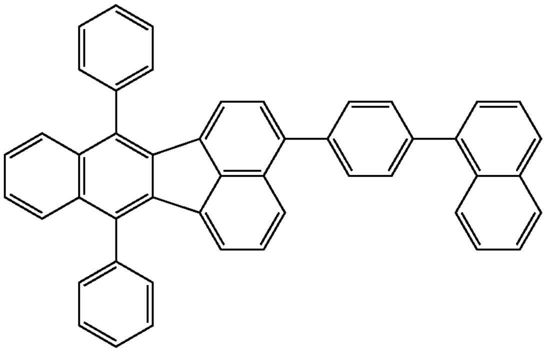
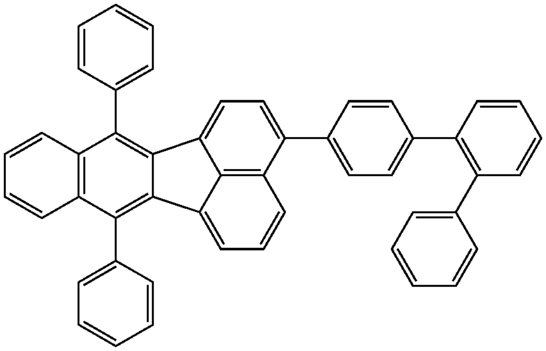
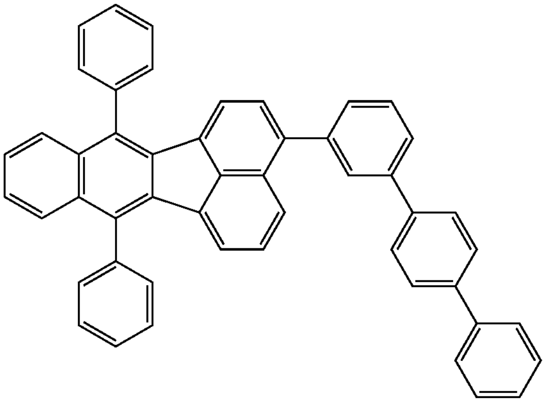
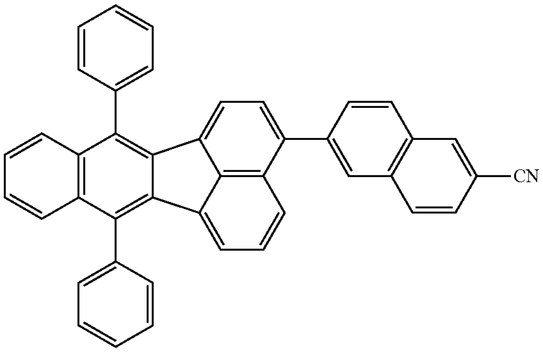

-continued
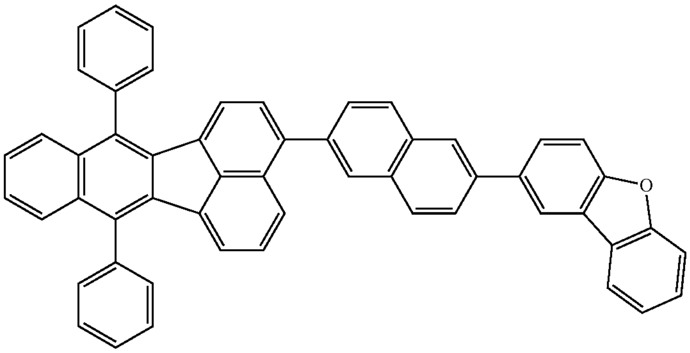
[Formula 149]
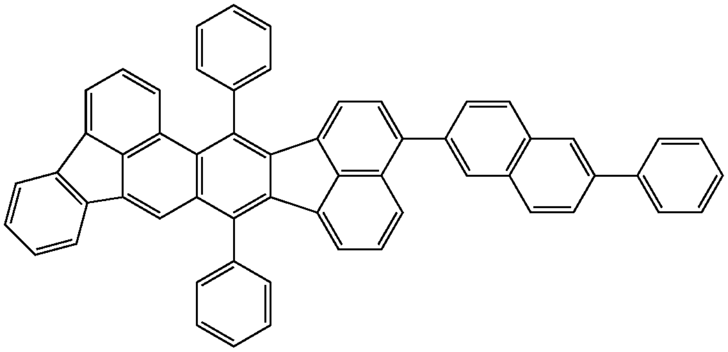
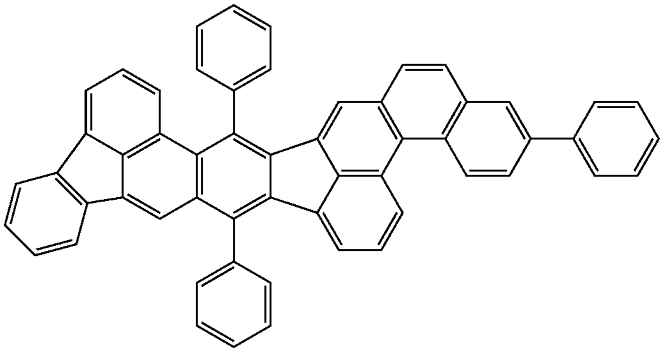
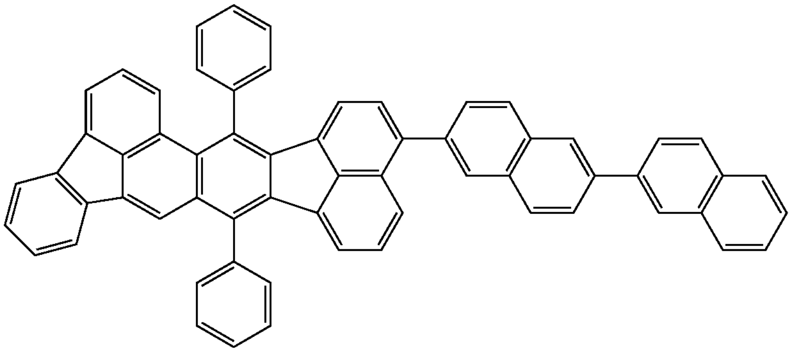

-continued
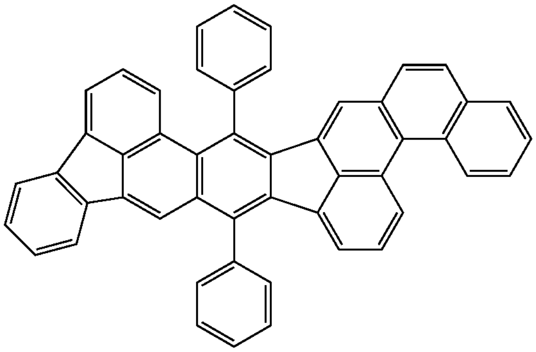
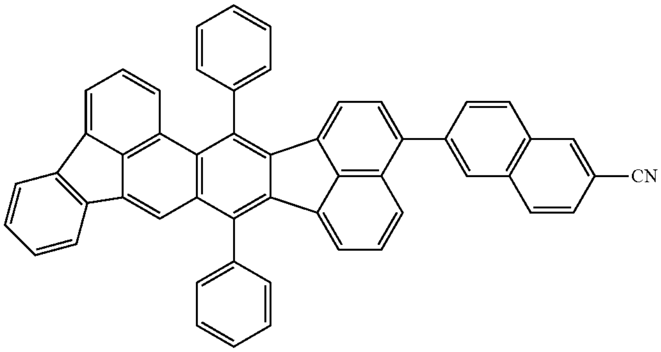
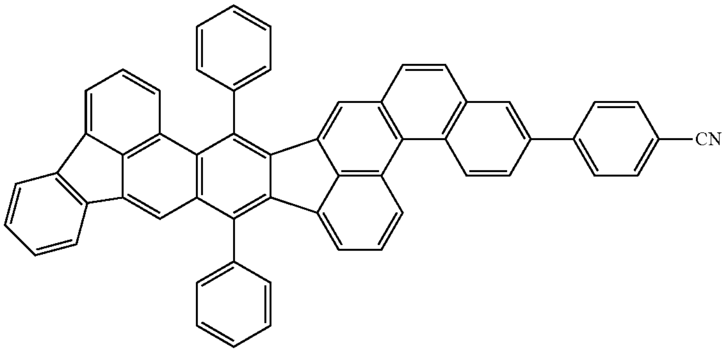
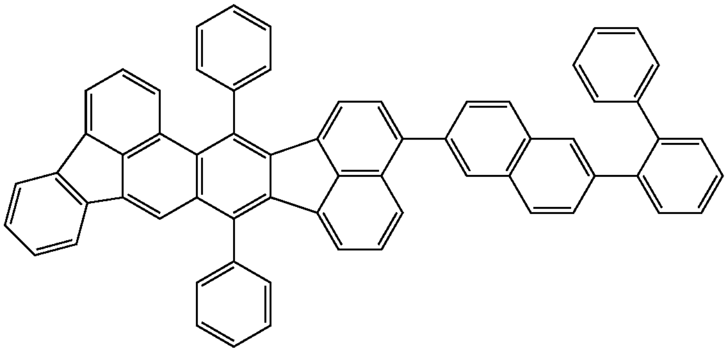

-continued
[Formula 150]
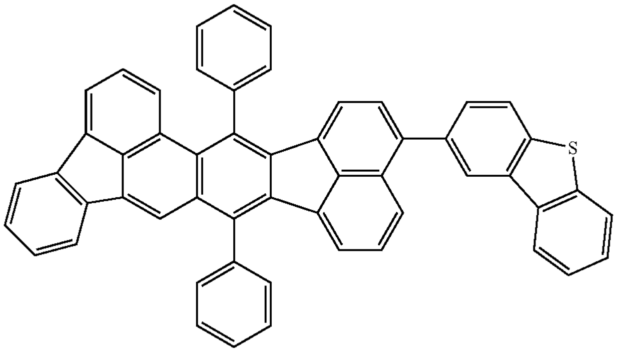
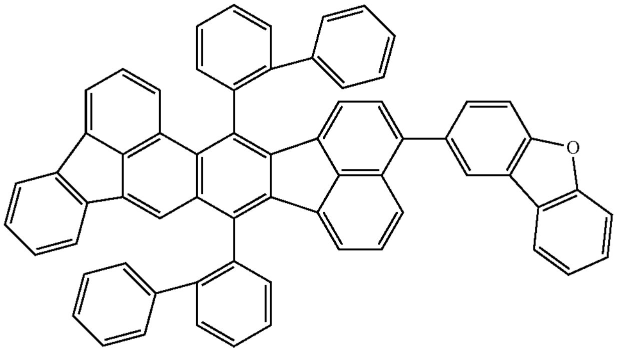
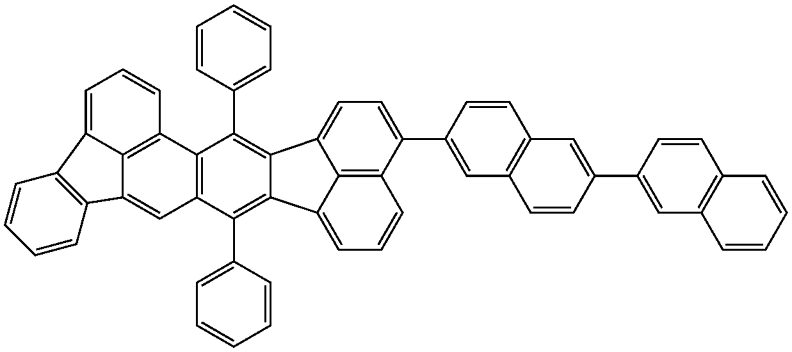
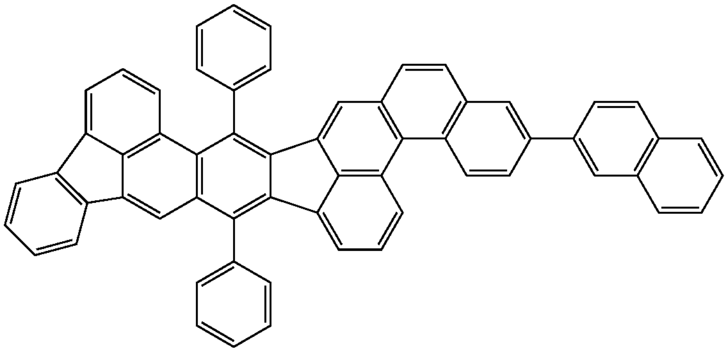

-continued
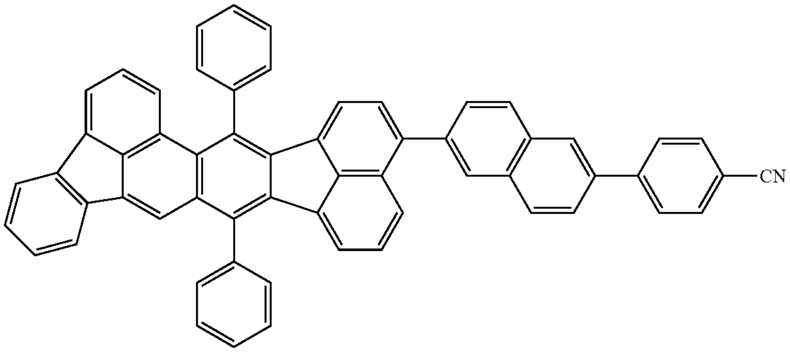
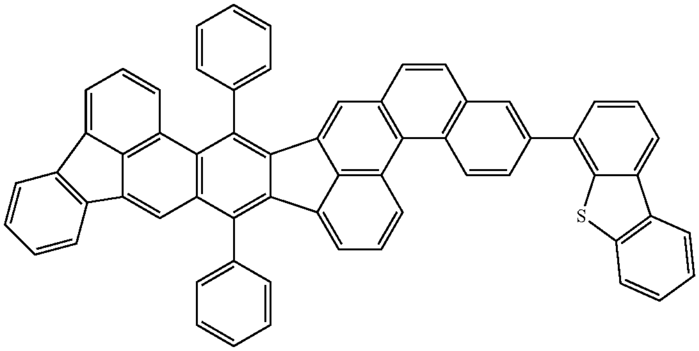
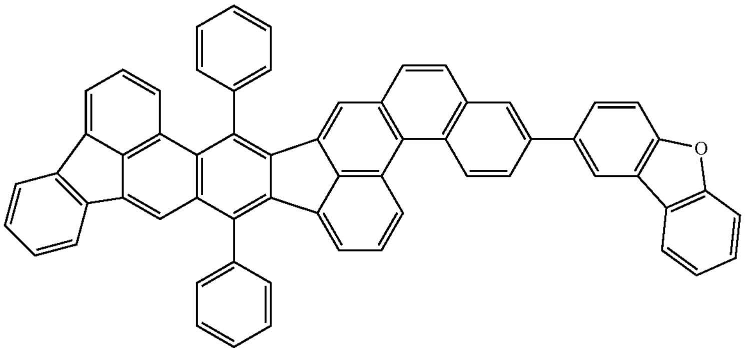
[Formula 151]
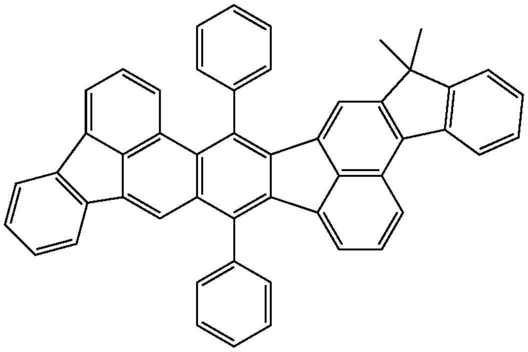
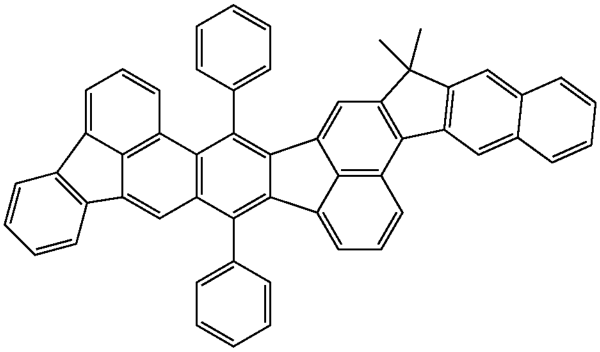

-continued
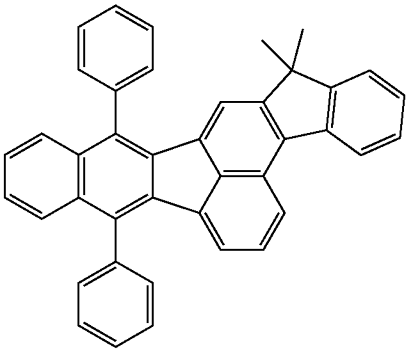
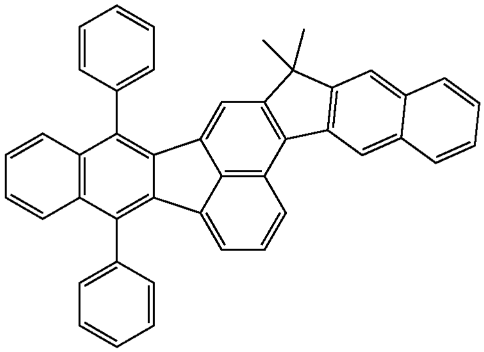
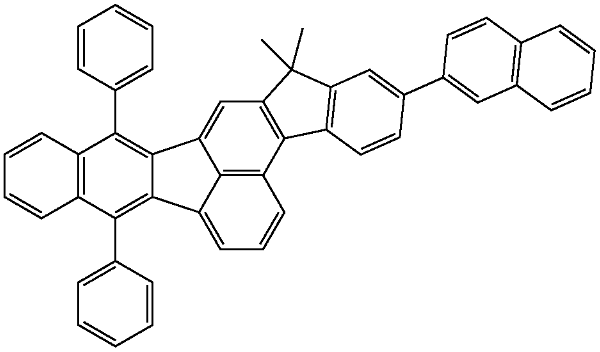
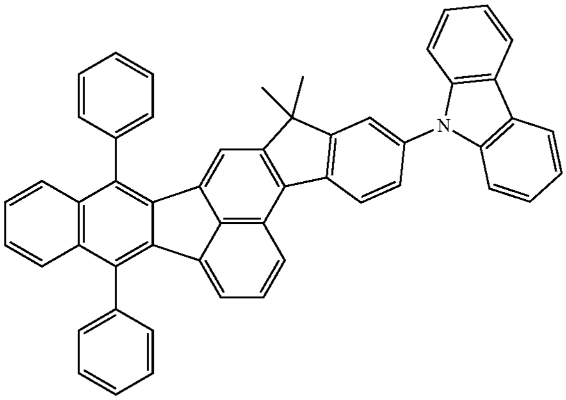
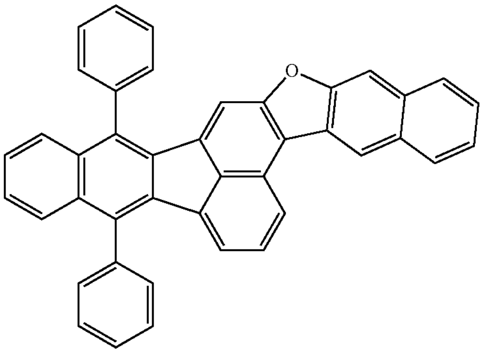
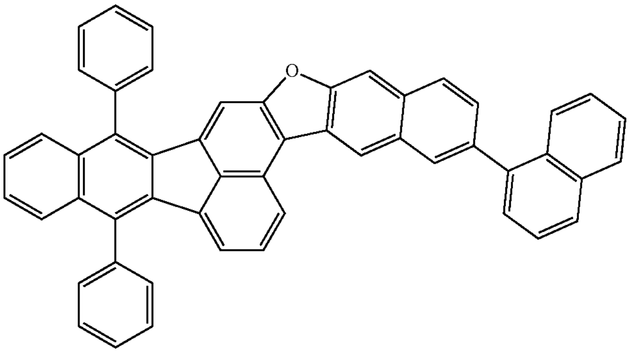
[Formula 152]
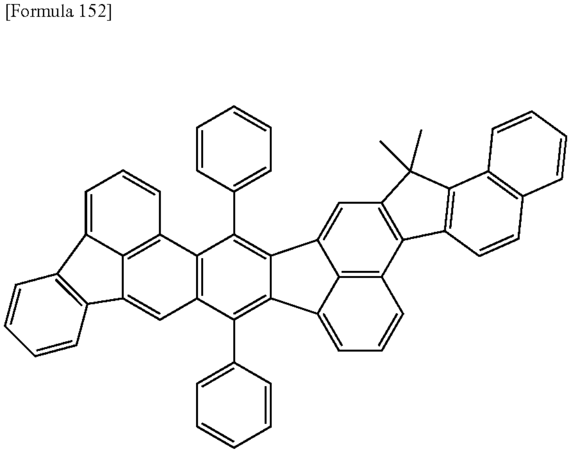
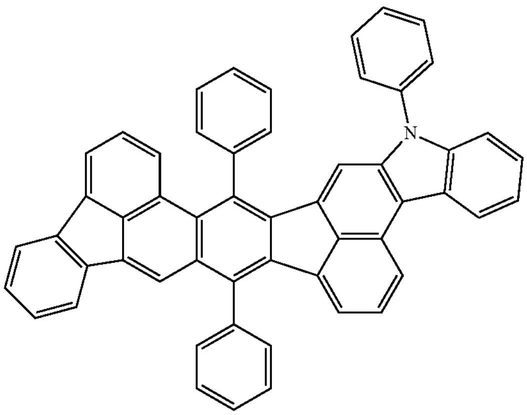

-continued
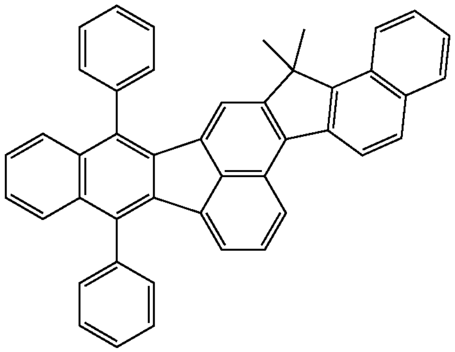
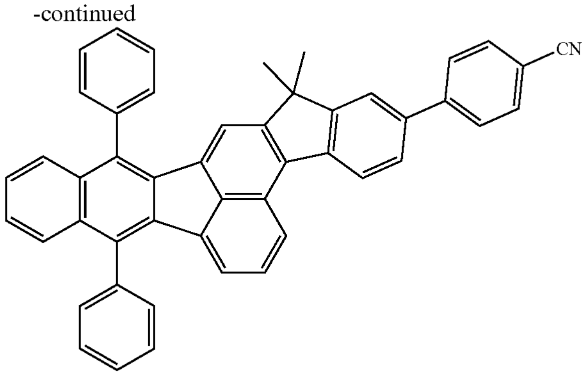
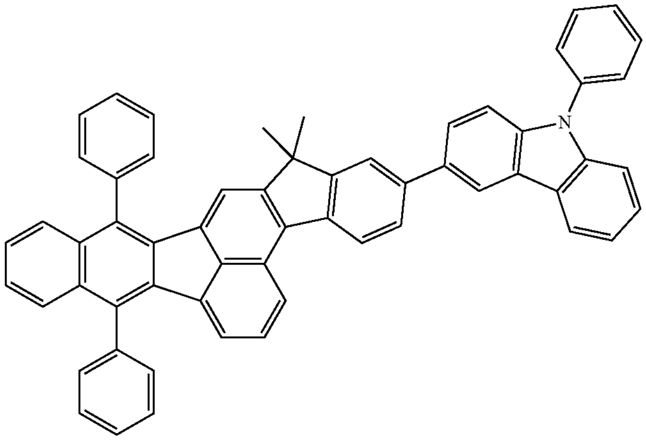
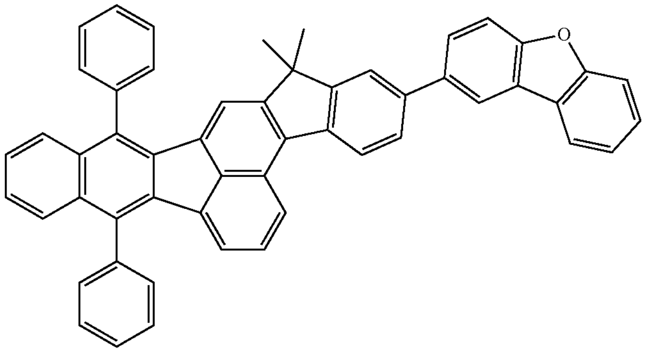
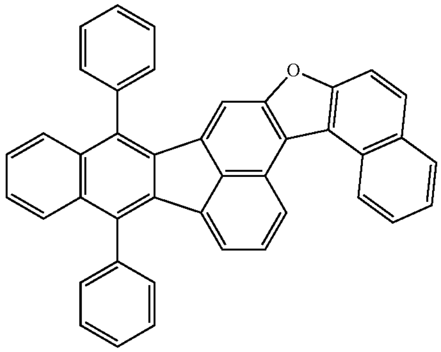
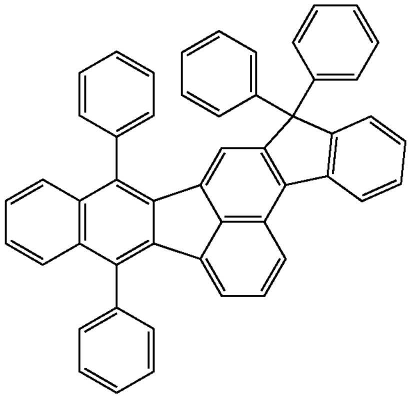

-continued

[Formula 153]

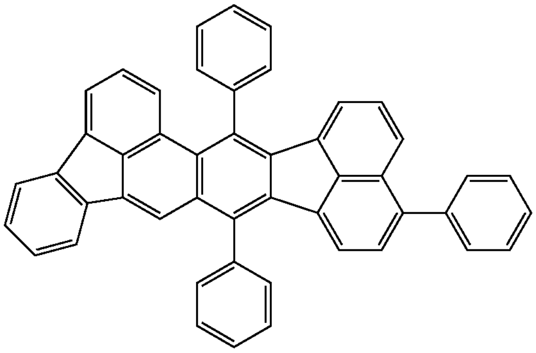

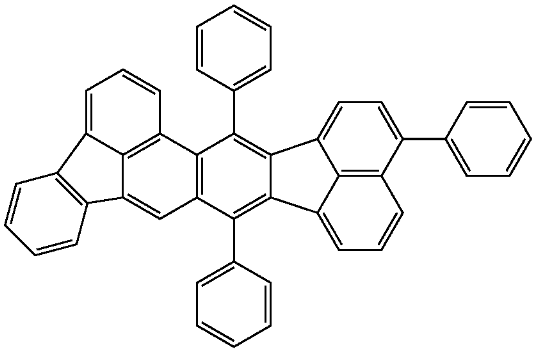

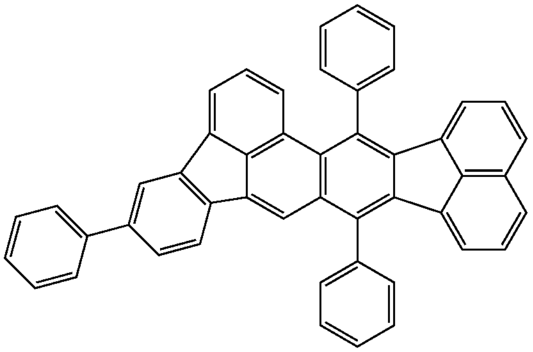

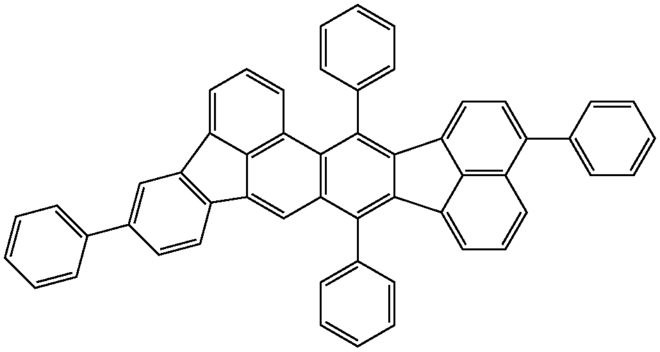

Compound Represented by Formula (11)

The compound represented by the formula (11) below will be described below.

[Formula 154]

(11)

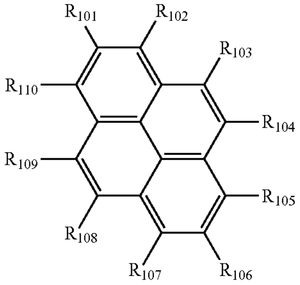

In the formula (11):

at least one combination of adjacent two or more of $R_{101}$ to $R_{110}$ are mutually bonded to form a substituted or unsubstituted monocyclic ring or a substituted or unsubstituted fused ring, or not mutually bonded;

at least one of $R_{101}$ to $R_{110}$ is a monovalent group represented by a formula (12) below;

$R_{101}$ to $R_{110}$ forming neither the substituted or unsubstituted monocyclic ring nor the substituted or unsubstituted fused ring and not being the monovalent group represented by the formula (12) below are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{905}$ are mutually the same or different; and when a plurality of $R_{907}$ are present, the plurality of $R_{907}$ are mutually the same or different.

[Formula 155]

(12)

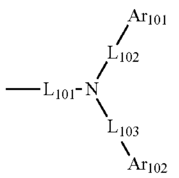

In the formula (12): $Ar_{101}$ and $Ar_{102}$ are each independently a substituted or unsubstituted aryl group having 6 to 50 ring carbon atoms, or a substituted or unsubstituted monovalent heterocyclic group having 5 to 50 ring atoms; and $L_{101}$ to $L_{103}$ are each independently a single bond, a substituted or unsubstituted arylene group having 6 to 30 ring carbon atoms, or a substituted or unsubstituted divalent heterocyclic group having 5 to 30 ring atoms.

In the formula (11), two of $R_{100}$ to $R_{110}$ are each preferably a group represented by the formula (12).

In an exemplary embodiment, the compound represented by the formula (11) is represented by a formula (13) below.

[Formula 156]

(13)

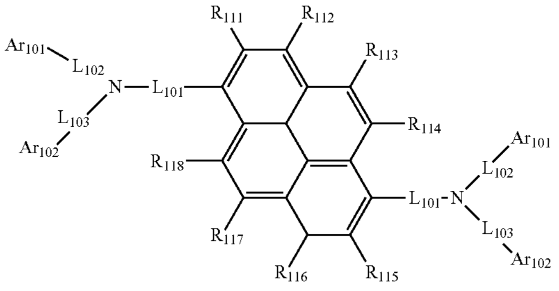

In the formula (13): $R_{111}$ to $R_{118}$ each independently represent the same as $R_{101}$ to $R_{110}$ not being the monovalent group represented by the formula (12) in the formula (11); and $Ar_{101}$, $Ar_{102}$, $L_{101}$, $L_{102}$, and $L_{103}$ represent the same as $Ar_{101}$, $Ar_{102}$, $L_{101}$, $L_{102}$, and $L_{103}$ in the formula (12).

In the formula (11), $L_{101}$ is preferably a single bond and $L_{102}$ and $L_{103}$ are each preferably a single bond.

In an exemplary embodiment, the compound represented by the formula (11) is represented by a formula (14) or (15) below.

[Formula 157]

(14)

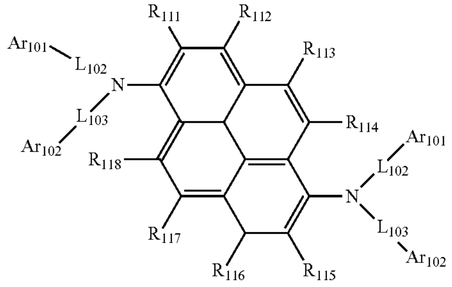

In the formula (14): $R_{111}$ to $R_{118}$ each independently represent the same as $R_{111}$ to $R_{118}$ in the formula (13); and $Ar_{101}$, $Ar_{102}$, $L_{102}$, and $L_{103}$ each independently represent the same as $Ar_{101}$, $Ar_{102}$, $L_{102}$, and $L_{103}$ in the formula (12).

[Formula 158]

(15)

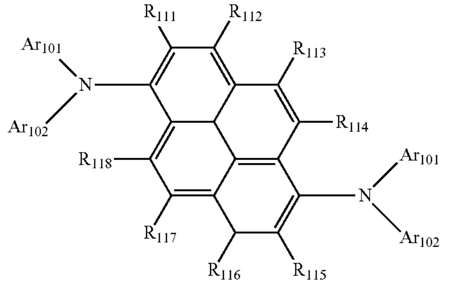

In the formula (15): $R_{111}$ to $R_{118}$ each independently represent the same as $R_{111}$ to $R_{118}$ in the formula (13) and $Ar_{101}$ and $Ar_{102}$ each independently represent the same as $Ar_{101}$ and $Ar_{102}$ in the formula (12).

In the formula (11) (the formula (12)), at least one of $Ar_{101}$ or $Ar_{102}$ is preferably a group represented by a formula (16) below.

[Formula 159]

(16)

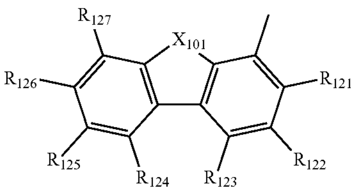

In the formula (16):

$X_{101}$ represents an oxygen atom or a sulfur atom;

at least one combination of adjacent two or more of $R_{121}$ to $R_{127}$ are mutually bonded to form a substituted or unsubstituted monocyclic ring or a substituted or unsubstituted fused ring, or not mutually bonded;

$R_{121}$ to $R_{127}$ forming neither the substituted or unsubstituted monocyclic ring nor the substituted or unsubstituted fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ each independently represent the same as $R_{901}$ to $R_{907}$ in the formula (11).

$X_{101}$ is preferably an oxygen atom.

At least one of $R_{121}$ to $R_{127}$ is preferably a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

In the formula (11) (the formula (12)), it is preferable that $Ar_{101}$ is a group represented by the formula (16) and $Ar_{102}$ is a substituted or unsubstituted aryl group having 6 to 50 ring carbon atoms.

In an exemplary embodiment, the compound represented by the formula (11) is represented by a formula (17) below.

[Formula 160]

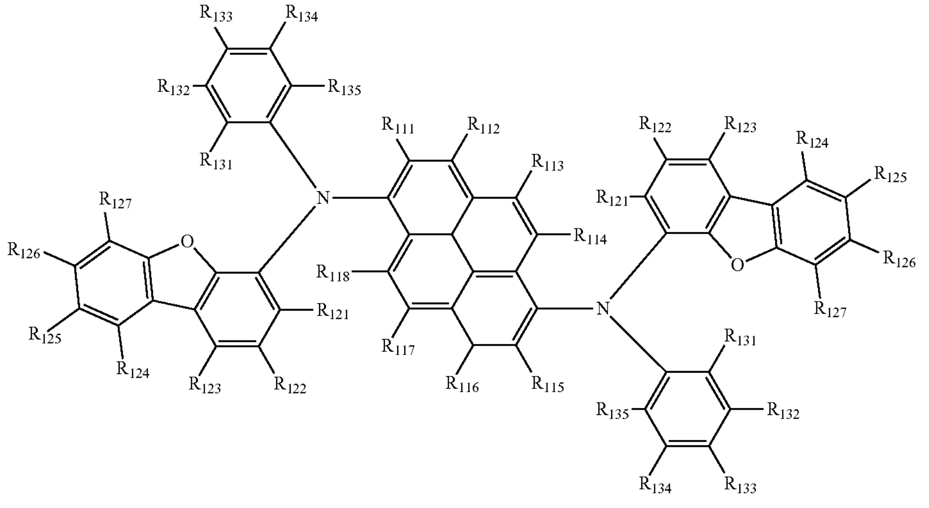

(17)

In the formula (17): $R_{111}$ to $R_{118}$ each independently represent the same as $R_{111}$ to $R_{11}$ in the formula (13) and $R_{121}$ to $R_{127}$ each independently represent the same as $R_{121}$ to $R_{127}$ in the formula (16);

$R_{131}$ to $R_{135}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ each independently represent the same as $R_{901}$ to $R_{907}$ in the formula (11).

Specific examples of the compound represented by the formula (11) include compounds shown below.

[Formula 161]

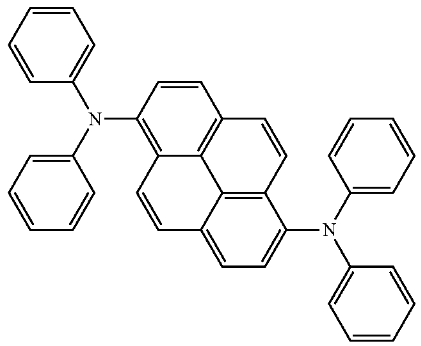

-continued
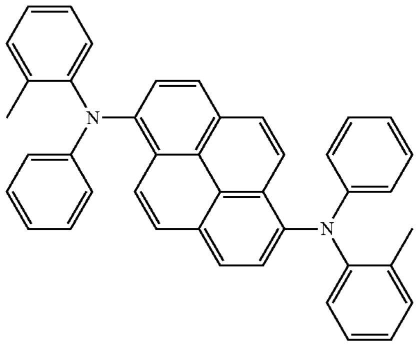
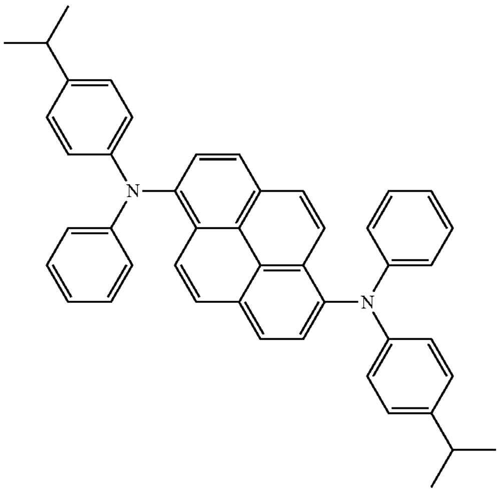
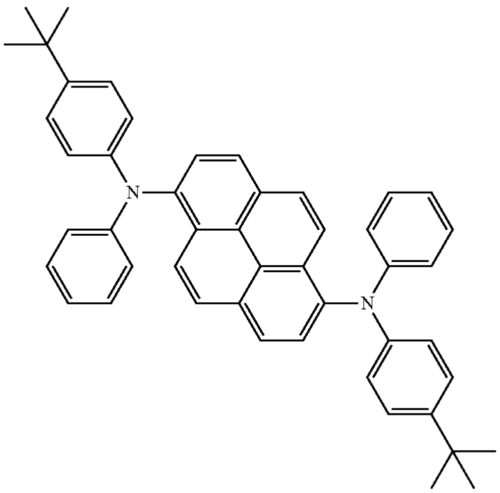
-continued
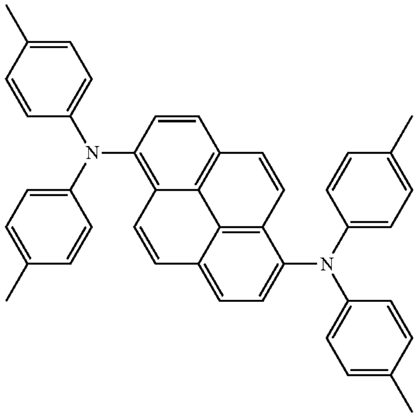
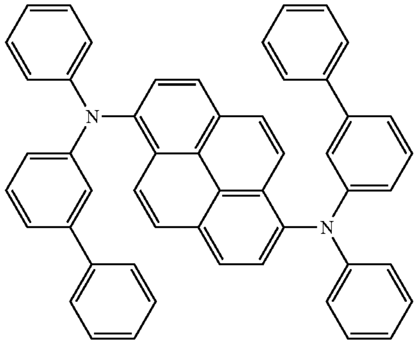
[Formula 162]
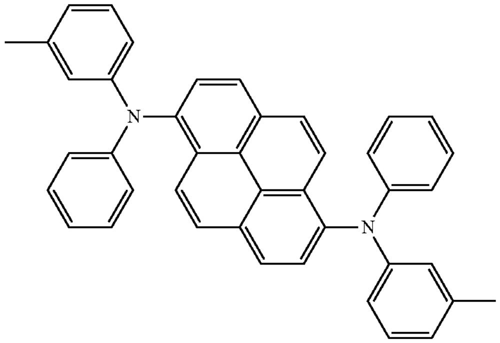
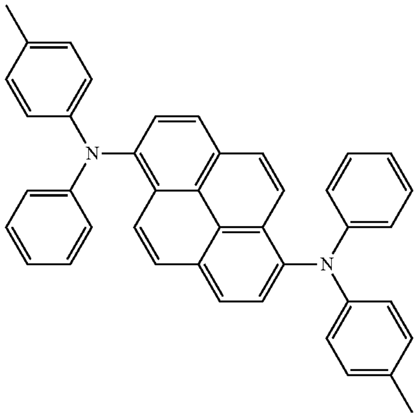

-continued
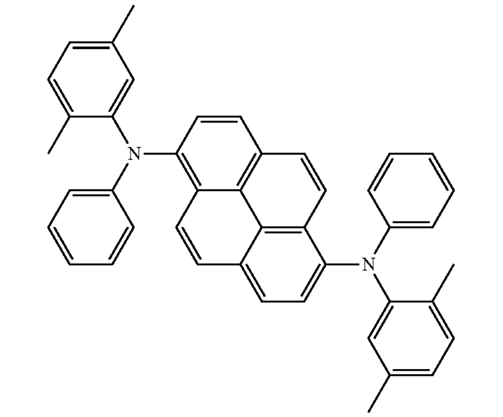
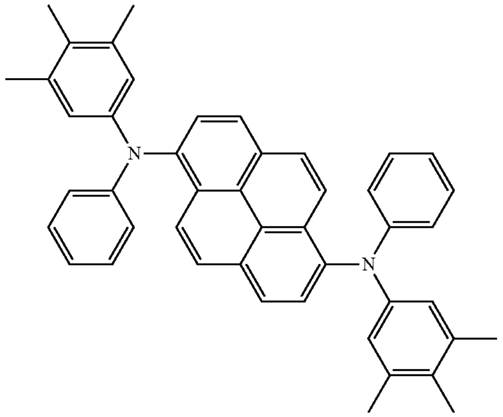
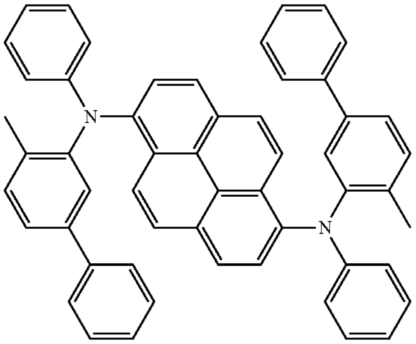
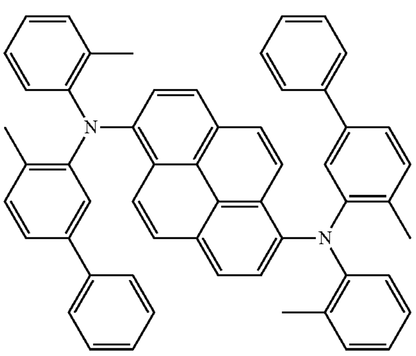
-continued
[Formula 163]
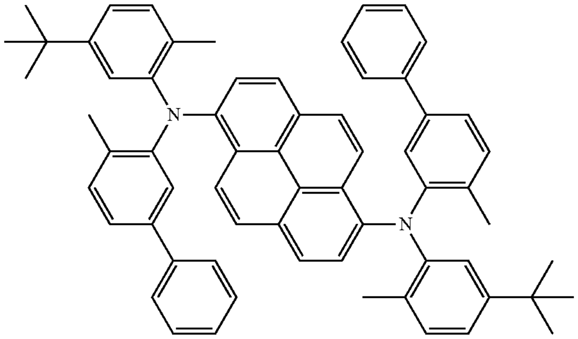
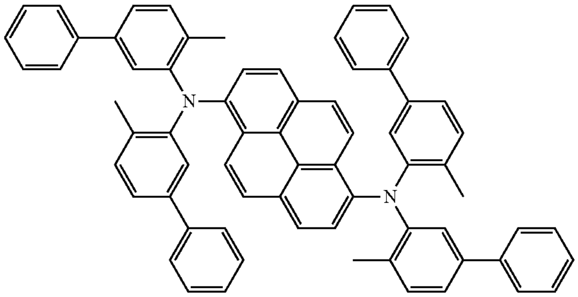
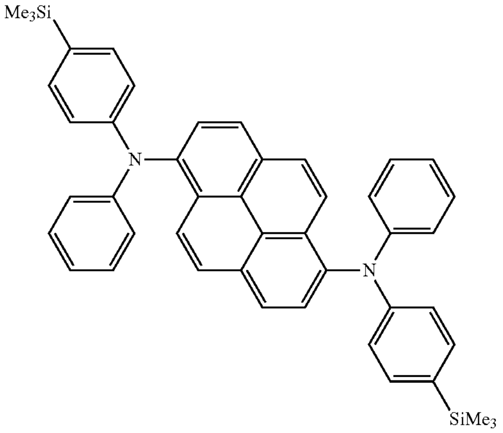
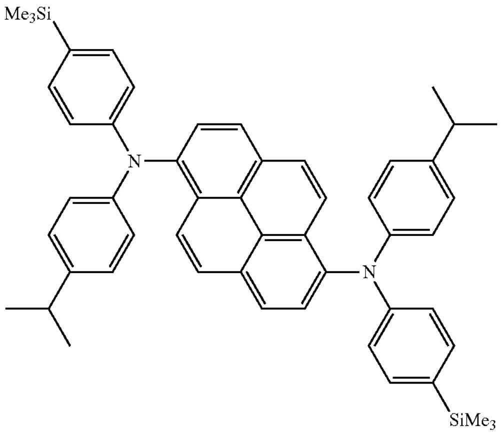

-continued
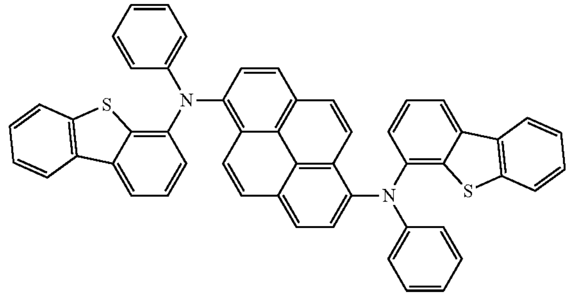
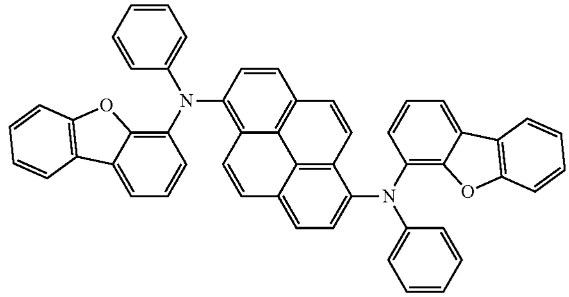
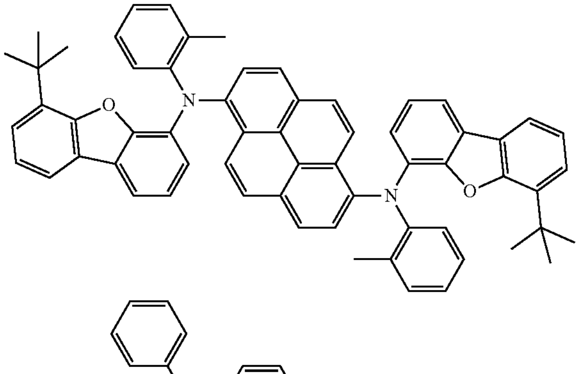
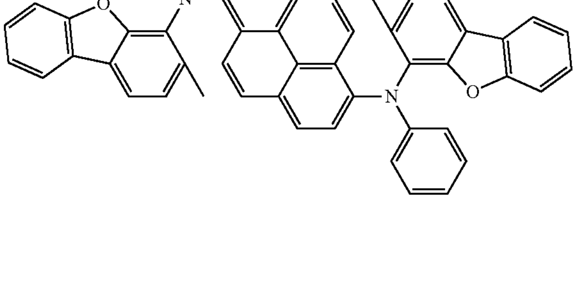
-continued
[Formula 164]
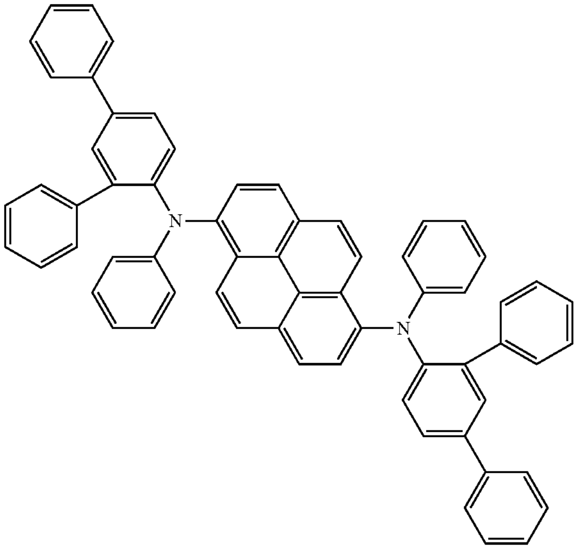
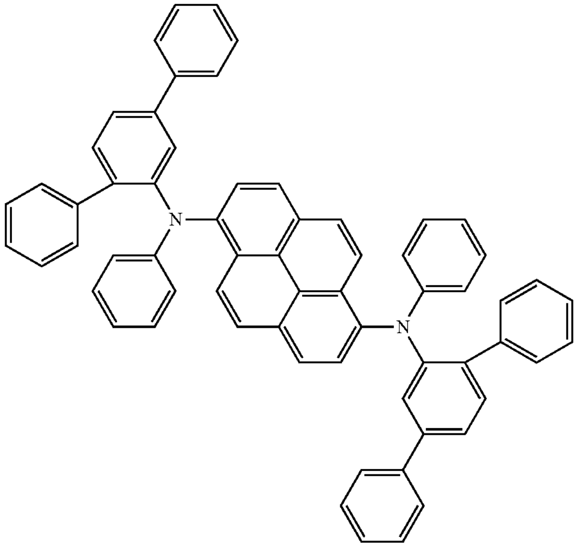
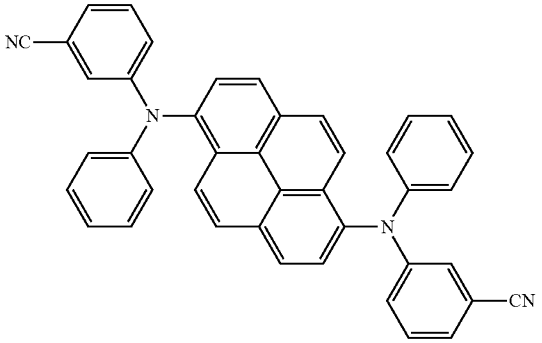

-continued
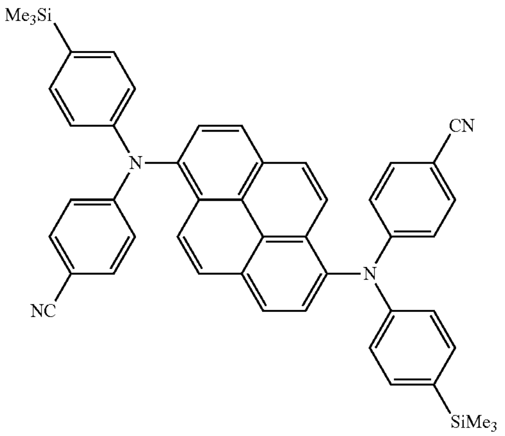
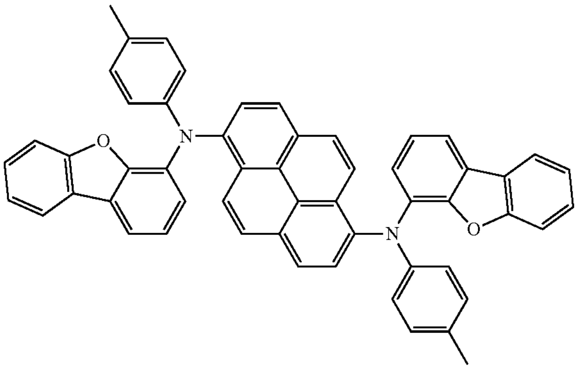
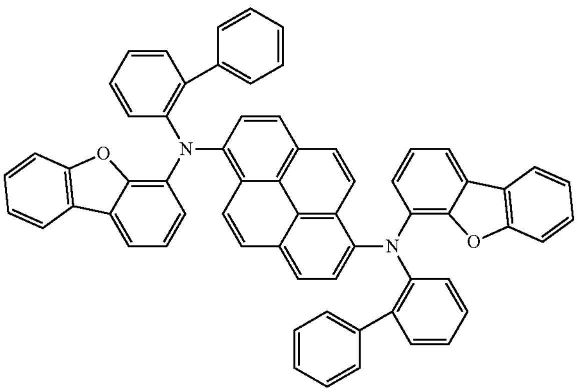
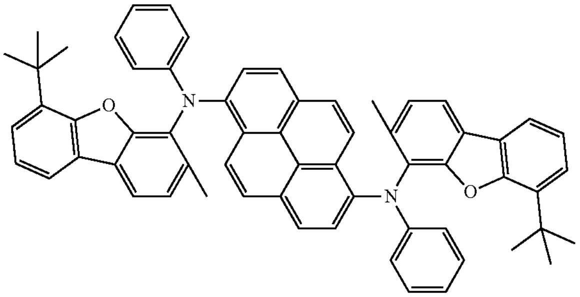
-continued
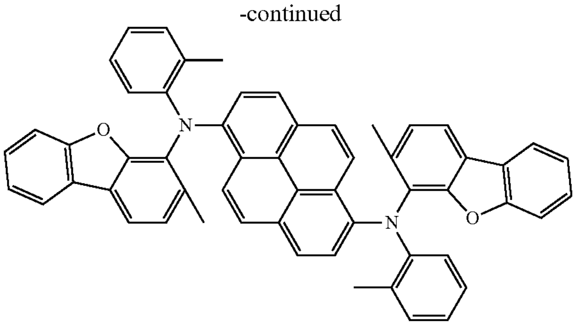
[Formula 165]
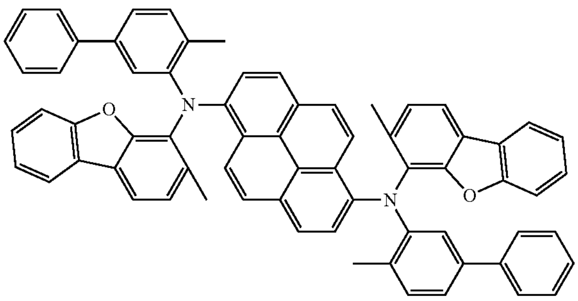
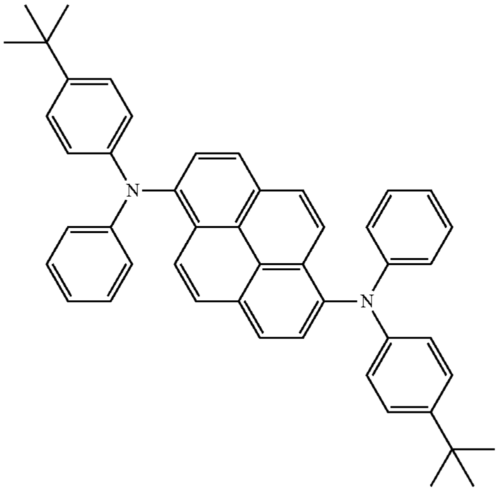
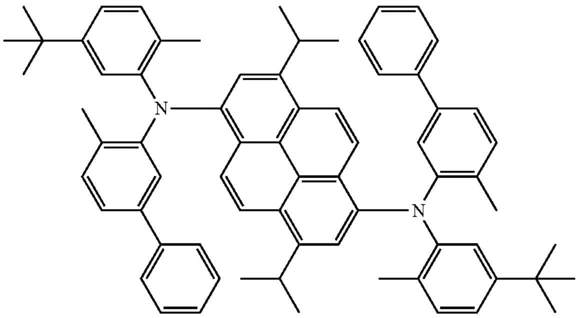
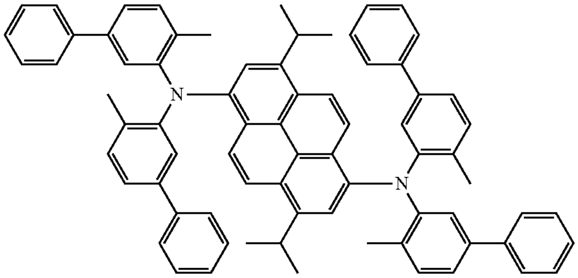

-continued

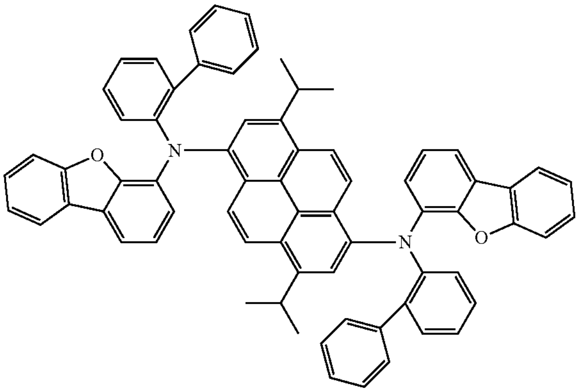

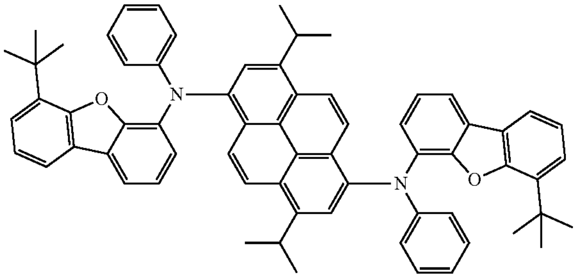

[Formula 166]

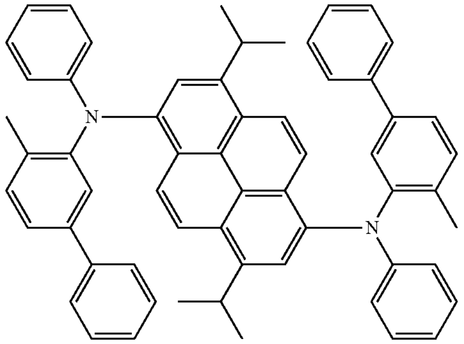

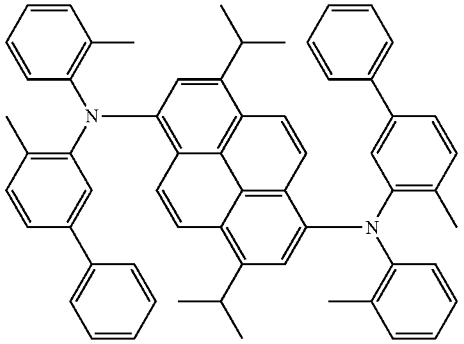

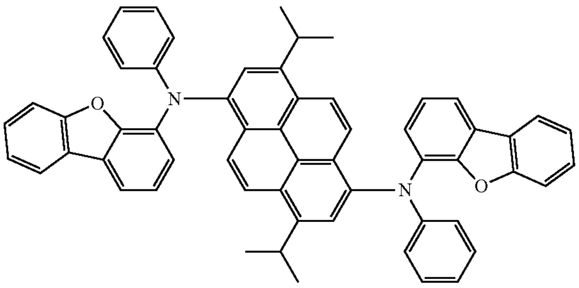

-continued

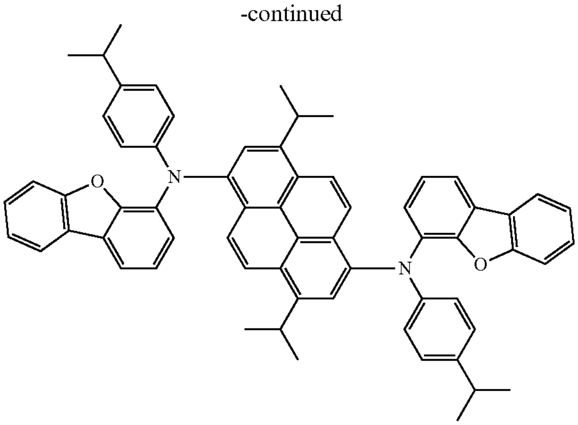

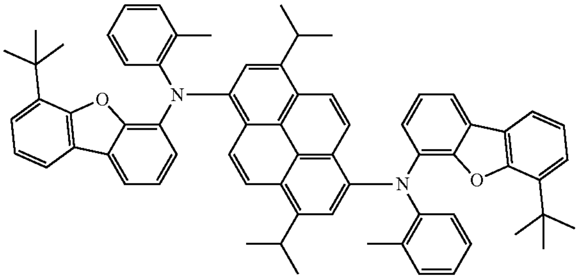

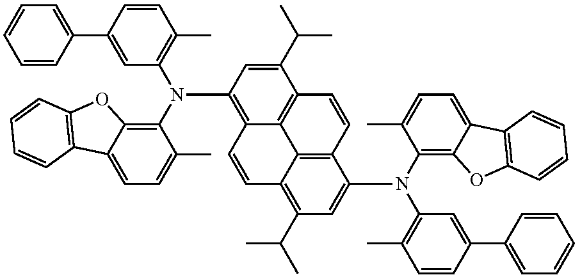

Compound Represented by Formula (21)

The compound represented by the formula (21) will be described below.

[Formula 167]

(21)

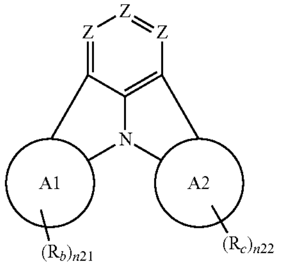

In the formula (21):

Z are each independently $CR_a$ or N;

A1 and A2 rings are each independently a substituted or unsubstituted aromatic hydrocarbon ring having 6 to 50 ring carbon atoms or a substituted or unsubstituted heterocycle having 5 to 50 ring atoms;

when a plurality of $R_a$ are present, at least one combination of adjacent two or more of the plurality of $R_a$ are mutually bonded to form a substituted or unsubstituted monocyclic ring or a substituted or unsubstituted fused ring, or not mutually bonded;

when a plurality of $R_b$ are present, at least one combination of adjacent two or more of the plurality of $R_b$ are mutually bonded to form a substituted or unsubstituted monocyclic ring or a substituted or unsubstituted fused ring, or not mutually bonded;

when a plurality of $R_c$ are present, at least one combination of adjacent two or more of the plurality of $R_c$ are mutually bonded to form a substituted or unsubstituted monocyclic ring or a substituted or unsubstituted fused ring, or not mutually bonded;

n21 and n22 are each independently an integer in a range from 0 to 4;

$R_a$ to $R_c$ forming neither the substituted or unsubstituted monocyclic ring nor the substituted or unsubstituted fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ each independently represent the same as $R_{901}$ to $R_{907}$ in the formula (11).

The "aromatic hydrocarbon ring" for the A1 and A2 rings has the same structure as a compound formed by introducing a hydrogen atom to the "aryl group" described in the specific example group G1. Ring atoms of the "aromatic hydrocarbon ring" for the A1 ring and the A2 ring include two carbon atoms on a fused bicyclic structure at the center of the formula (21). Specific examples of the "substituted or unsubstituted aromatic hydrocarbon ring having 6 to 50 ring carbon atoms" include a compound formed by introducing a hydrogen atom to the "aryl group" described in the specific example group G1.

The "heterocycle" for the A1 and A2 rings has the same structure as a compound formed by introducing a hydrogen atom to the "heterocyclic group" described in the specific example group G2. Ring atoms of the "heterocycle" for the A1 ring and the A2 ring include two carbon atoms on a fused bicyclic structure at the center of the formula (21). Specific examples of the "substituted or unsubstituted heterocycle having 5 to 50 ring atoms" include a compound formed by introducing a hydrogen atom to the "heterocyclic group" described in the specific example group G2.

$R_b$ is bonded to any of carbon atoms forming the aromatic hydrocarbon ring for the A1 ring or any of atoms forming the heterocycle for the A1 ring.

$R_c$ is bonded to any of carbon atoms forming the aromatic hydrocarbon ring for the A2 ring or any of atoms forming the heterocycle for the A2 ring.

At least one (preferably two) of $R_a$ to $R_c$ is preferably a group represented by a formula (21a) below.

$$-L_{201}-Ar_{201} \quad (21a)$$

In the formula (21a):

$L_{201}$ is a single bond, a substituted or unsubstituted arylene group having 6 to 30 ring carbon atoms, or a substituted or unsubstituted divalent heterocyclic group having 5 to 30 ring atoms; and $Ar_{201}$ is a substituted or unsubstituted aryl group having 6 to 50 ring carbon atoms, a substituted or unsubstituted monovalent heterocyclic group having 5 to 50 ring atoms, or a group represented by a formula (21b) below.

[Formula 168]

(21b)

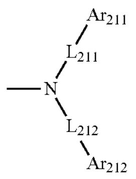

In the formula (21b):

$L_{211}$ and $L_{212}$ are each independently a single bond, a substituted or unsubstituted arylene group having 6 to 30 ring carbon atoms, or a substituted or unsubstituted divalent heterocyclic group having 5 to 30 ring atoms;

$Ar_{211}$ and $Ar_{212}$ are mutually bonded to form a substituted or unsubstituted monocyclic ring or a substituted or unsubstituted fused ring, or not mutually bonded; and $Ar_{211}$ and $Ar_{212}$ forming neither the substituted or unsubstituted monocyclic ring nor the substituted or unsubstituted fused ring are each independently a substituted or unsubstituted aryl group having 6 to 50 ring carbon atoms, or a substituted or unsubstituted monovalent heterocyclic group having 5 to 50 ring atoms.

In an exemplary embodiment, the compound represented by the formula (21) is represented by a formula (22) below.

[Formula 169]

(22)

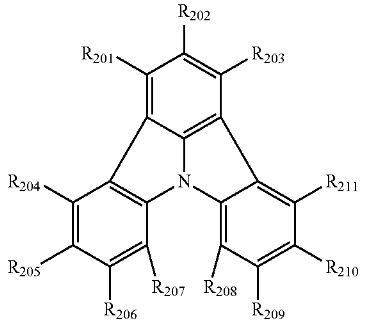

In the formula (22):

at least one combination of adjacent two or more of $R_{201}$ to $R_{211}$ are mutually bonded to form a substituted or unsubstituted monocyclic ring or a substituted or unsubstituted fused ring, or not mutually bonded;

$R_{201}$ to $R_{211}$ forming neither the substituted or unsubstituted monocyclic ring nor the substituted or unsubstituted fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)

($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ each independently represent the same as $R_{901}$ to $R_{907}$ in the formula (11).

At least one (preferably two) of $R_{201}$ to $R_{211}$ is preferably a group represented by the formula (21a). Preferably, $R_{204}$ and $R_{211}$ are each the group represented by the formula (21a).

In an exemplary embodiment, the compound represented by the formula (21) is a compound formed by bonding a structure represented by a formula (21-1) or (21-2) below to the A1 ring. In an exemplary embodiment, the compound represented by the formula (22) is a compound formed by bonding the structure represented by the formula (21-1) or (21-2) below to a ring bonded with $R_{204}$ to $R_{207}$.

[Formula 170]

(21-1)

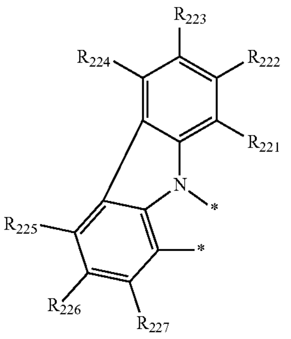

(21-2)

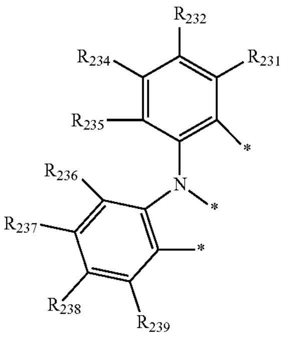

In the formula (21-1): the two * are each independently bonded to the ring carbon atom of the aromatic hydrocarbon ring or the ring atom of the heterocycle for the A1 ring in the formula (21), or bonded to any of $R_{204}$ to $R_{207}$ of the formula (22).

Three * in the formula (21-2) are each independently bonded to the ring carbon atom of the aromatic hydrocarbon ring or the ring atom of the heterocycle for the A1 ring in the formula (22), or bonded to any of $R_{204}$ to $R_{207}$ of the formula (22).

At least one combination of adjacent two or more of $R_{221}$ to $R_{227}$ and $R_{231}$ to $R_{239}$ are mutually bonded to form a substituted or unsubstituted monocyclic ring or a substituted or unsubstituted fused ring, or not mutually bonded.

$R_{221}$ to $R_{227}$ and $R_{231}$ to $R_{239}$ forming neither the substituted or unsubstituted monocyclic ring nor the substituted or unsubstituted fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms.

$R_{901}$ to $R_{907}$ each independently represent the same as $R_{901}$ to $R_{907}$ in the formula (11).

In an exemplary embodiment, the compound represented by the formula (21) is a compound represented by a formula (21-3), (21-4), or (21-5) below.

[Formula 171]

(21-3)

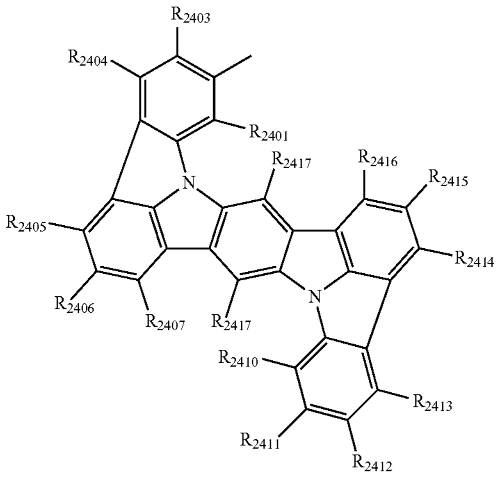

(21-4)

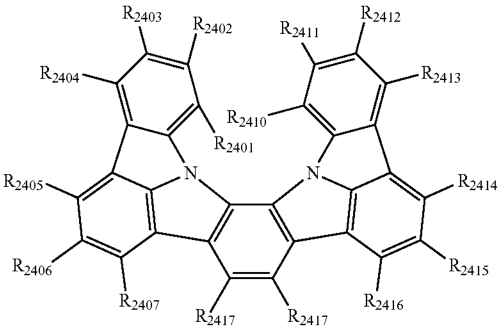

-continued (21-5)

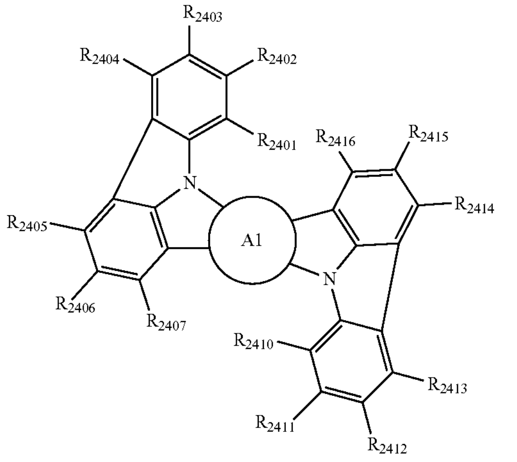

In the formulae (21-3), (21-4), and (21-5): A1 ring is the same as the A1 ring in the formula (21); and $R_{2401}$ to $R_{2407}$ each independently represent the same as $R_{221}$ to $R_{227}$ in the formulae (21-1) and (21-2) and $R_{2410}$ to $R_{2417}$ each independently represent the same as $R_{201}$ to $R_{211}$ in the formula (22).

In an exemplary embodiment, a substituted or unsubstituted aromatic hydrocarbon ring having 6 to 50 ring carbon atoms for the A1 ring of the formula (21-5) is a substituted or unsubstituted naphthalene ring or a substituted or unsubstituted fluorene ring.

In an exemplary embodiment, a substituted or unsubstituted heterocycle having 5 to 50 ring atoms for the A1 ring of the formula (21-5) is a substituted or unsubstituted dibenzofuran ring, substituted or unsubstituted carbazole ring, or substituted or unsubstituted dibenzothiophene ring.

In an exemplary embodiment, the compound represented by the formula (21) or (22) is selected from the group consisting of compounds represented by formulae (21-6-1) to (21-6-7) below.

[Formula 172]

(21-6-1)

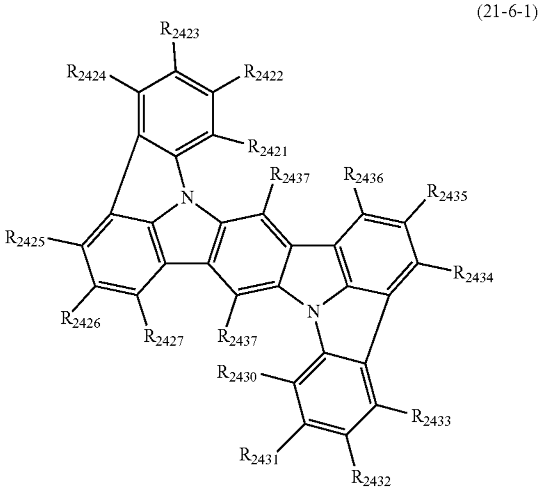

-continued (21-6-2)

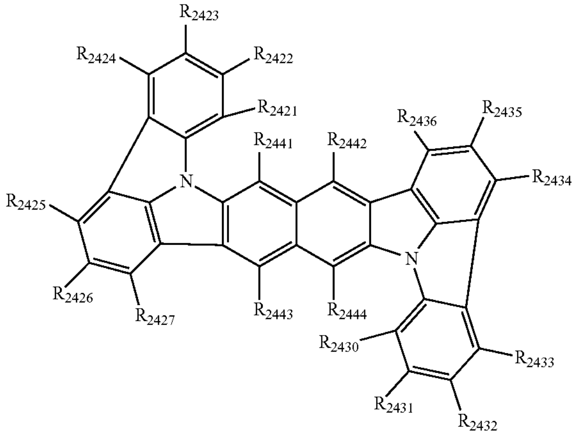

(21-6-3)

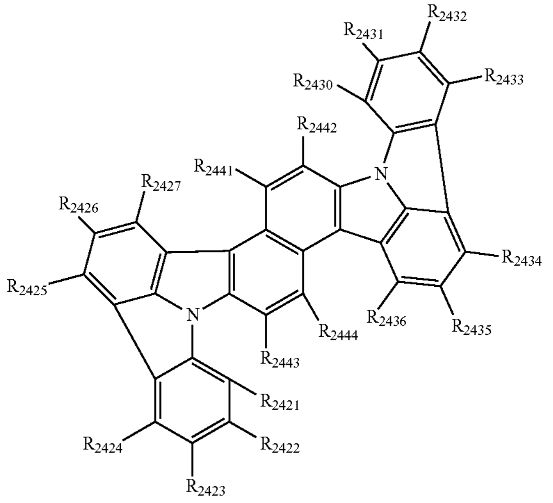

(21-6-4)

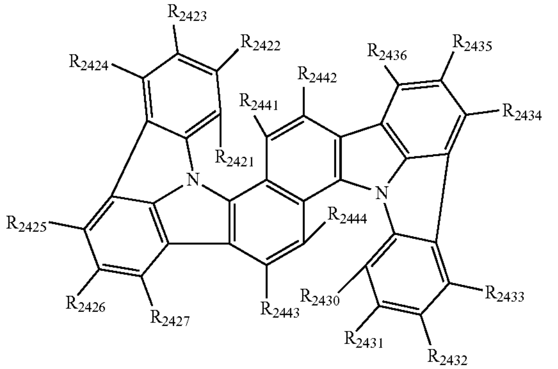

-continued (21-6-5)

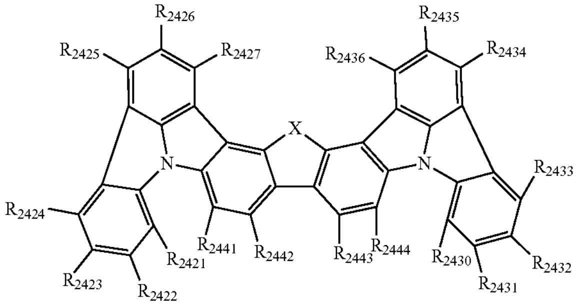

(21-6-6)

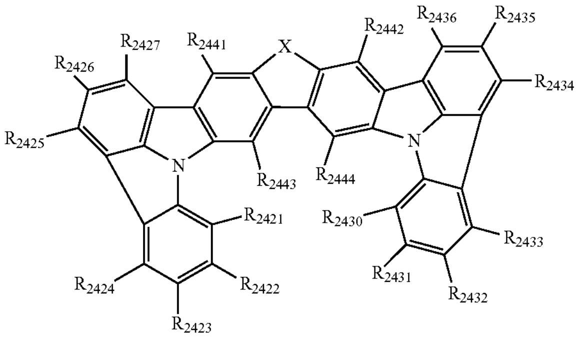

(21-6-7)

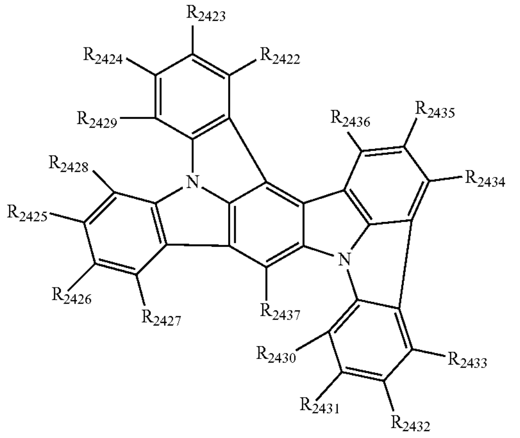

In the formulae (21-6-1) to (21-6-7): $R_{2421}$ to $R_{2427}$ each independently represent the same as $R_{221}$ to $R_{227}$ in the formulae (21-1) and (21-2), and $R_{2430}$ to $R_{2437}$ and $R_{2441}$ to $R_{2444}$ each independently represent the same as $R_{201}$ to $R_{211}$ in the formula (22);

X is O, $NR_{901}$, or $C(R_{902})(R_{903})$; and $R_{901}$ to $R_{903}$ each independently represent the same as $R_{901}$ to $R_{903}$ in the formula (11).

In an exemplary embodiment, at least one combination of adjacent two or more of $R_{201}$ to $R_{211}$ in the compound represented by the formula (22) are mutually bonded to form a substituted or unsubstituted monocyclic ring or a substituted or unsubstituted fused ring. The compound represented by the formula (22) in the exemplary embodiment is described in detail as a compound represented by a formula (25).

Compound Represented by Formula (25)

The compound represented by the formula (25) will be described.

[Formula 173]

(25)

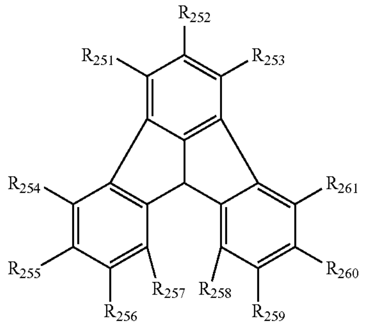

In the formula (25):

two or more combinations selected from the group consisting of a combination of $R_{251}$ and $R_{252}$, a combination of $R_{252}$ and $R_{253}$, a combination of $R_{254}$ and $R_{255}$, a combination of $R_{255}$ and $R_{256}$, a combination of $R_{255}$ and $R_{257}$, a combination of $R_{255}$ and $R_{259}$, a combination of $R_{255}$ and $R_{260}$, and a combination of $R_{260}$ and $R_{261}$ are mutually bonded to form a substituted or unsubstituted monocyclic ring or a substituted or unsubstituted fused ring;

the combination of $R_{251}$ and $R_{252}$ and the combination of $R_{252}$ and $R_{253}$ do not simultaneously form a monocyclic or fused ring, the combination of $R_{254}$ and $R_{255}$ and the combination of $R_{255}$ and $R_{256}$ do not simultaneously form a monocyclic or fused ring, the combination of $R_{255}$ and $R_{256}$ the combination of and $R_{255}$ and $R_{256}$ do not simultaneously form a monocyclic or fused ring, the combination of $R_{258}$ and $R_{259}$ and the combination of $R_{259}$ and $R_{260}$ do not simultaneously form a monocyclic or fused ring, and the combination of $R_{259}$ and $R_{260}$ and the combination of $R_{260}$ and $R_{261}$ do not simultaneously form a monocyclic or fused ring;

the two or more monocyclic rings formed by $R_{251}$ to $R_{261}$ are optionally the same or different; the two or more fused rings formed by $R_{251}$ to $R_{261}$ are optionally the same or different;

$R_{251}$ to $R_{261}$ forming neither the substituted or unsubstituted monocyclic ring nor the substituted or unsubstituted fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ each independently represent the same as $R_{901}$ to $R_{907}$ in the formula (11).

In the formula (25), $R_n$ and $R_{n+1}$ (n being an integer selected from 251, 252, 254 to 256, and 258 to 260) are mutually bonded to form a substituted or unsubstituted monocyclic ring or fused ring together with two ring carbon atoms bonded with $R_n$ and $R_{n+1}$. The monocyclic or fused ring is preferably formed of atoms selected from the group consisting of a carbon atom, an oxygen atom, a sulfur atom, and a nitrogen atom, and is preferably made of 3 to 7, more preferably 5 or 6 atoms.

The number of the above cyclic structures in the compound represented by the formula (25) is, for instance, 2, 3, or 4. The two or more of the cyclic structures may be present on the same benzene ring on the basic skeleton represented by the formula (25) or may be present on different benzene rings. For instance, when three cyclic structures are present, each of the cyclic structures may be present on corresponding one of the three benzene rings of the formula (25).

Examples of the above cyclic structures in the compound represented by the formula (25) include structures represented by formulae (251) to (260) below.

[Formula 174]

(251)

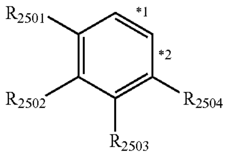

(252)

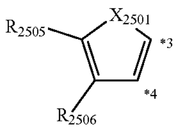

(253)

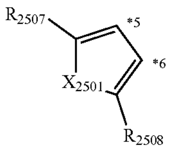

(254)

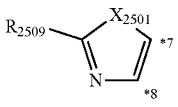

(255)

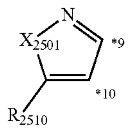

(256)

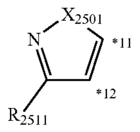

(257)

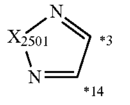

In the formulae (251) to (257): each combination of *1 and *2, *3 and *4, *5 and *6, *7 and *8, *9 and *10, *11 and *12, and *13 and *14 are each represent the two ring carbon atoms bonded with $R_n$ and $R_{n+1}$, the ring carbon atom bonded with $R_n$ being optionally either one of the two ring carbon atoms represented by *1 and *2, *3 and *4, *5 and *6, *7 and *8, *9 and *10, *11 and *12, and *13 and *14;

$X_{2501}$ is $C(R_{2512})(R_{2513})$, $NR_{2514}$, O or S;

at least one combination of adjacent two or more of $R_{2501}$ to $R_{2506}$ and $R_{2512}$ to $R_{2513}$ are mutually bonded to form a substituted or unsubstituted monocyclic ring or a substituted or unsubstituted fused ring, or not mutually bonded; and $R_{2501}$ to $R_{2514}$ forming neither the substituted or unsubstituted monocyclic ring nor the substituted or unsubstituted fused ring each independently represent the same as $R_{251}$ to $R_{261}$ in the formula (25).

[Formula 175]

(258)

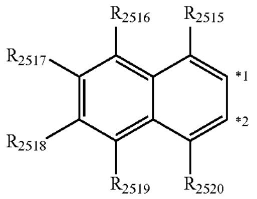

(259)

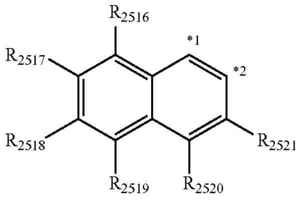

(260)

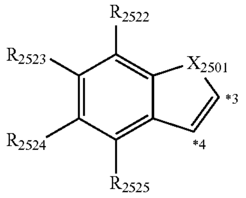

In the formulae (258) to (260): each combination of *1 and *2, and *3 and *4 represent the two ring carbon atoms bonded with $R_n$ and $R_{n+1}$, the ring carbon atom bonded with $R_n$ being optionally either one of the two ring carbon atoms represented by *1 and *2 or *3 and *4;

$X_{2501}$ is $C(R_{2512})(R_{2513})$, $NR_{2514}$, O or S;

at least one combination of adjacent two or more of $R_{2515}$ to $R_{2525}$ are mutually bonded to form a substituted or unsubstituted monocyclic ring or a substituted or unsubstituted fused ring, or not mutually bonded; and $R_{2515}$ to $R_{2521}$ and $R_{2522}$ to $R_{2525}$ forming neither the substituted or unsubstituted monocyclic ring nor the substituted or unsubstituted fused ring each independently represent the same as $R_{251}$ to $R_{261}$ in the formula (25).

In the formula (25), at least one of $R_{252}$, $R_{254}$, $R_{255}$, $R_{260}$, or $R_{261}$ (preferably at least one of $R_{252}$, $R_{255}$, or $R_{260}$, more preferably $R_{252}$) is preferably a group not forming a cyclic structure.

(i) A substituent, if present, for a cyclic structure formed by $R_n$ and $R_{n+1}$ in the formula (25), (ii) $R_{251}$ to $R_{261}$ not forming a cyclic structure in the formula (25), and (iii) $R_{2501}$ to $R_{2514}$ and $R_{2515}$ to $R_{2525}$ in the formulae (251) to (260) are preferably each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$N(R_{906})(R_{907})$, a substituted or unsubstituted aryl group having 6 to 50 ring carbon atoms, a substituted or unsubstituted monovalent heterocyclic group having 5 to 50 ring atoms, or a group selected from the group shown below.

[Formula 176]

(261)

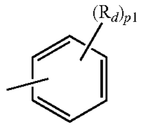

(262)

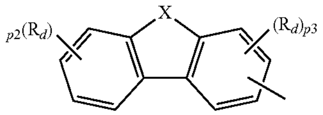

(263)

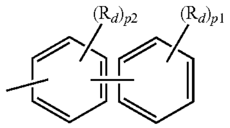

(264)

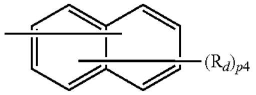

In the formulae (261) to (264): $R_d$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$, —O—$(R_{904})$, —S—$(R_{905})$, —$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

X is $C(R_{901})(R_{902})$, $NR_{903}$, O, or S;

$R_{901}$ to $R_{907}$ each independently represent the same as $R_{901}$ to $R_{907}$ in the formula (11); and p1 is an integer in a range from 0 to 5, p2 is an integer in a range from 0 to 4, p3 is an integer in a range from 0 to 3, and p4 is an integer in a range from 0 to 7.

In an exemplary embodiment, the compound represented by the formula (25) is represented by any one of formulae (25-1) to (25-6) below.

[Formula 177]

(25-1)

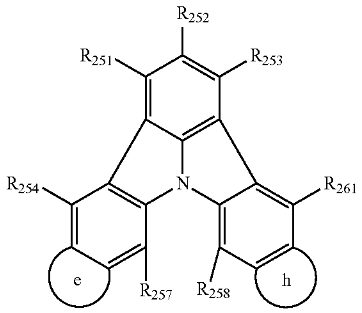

(25-2)

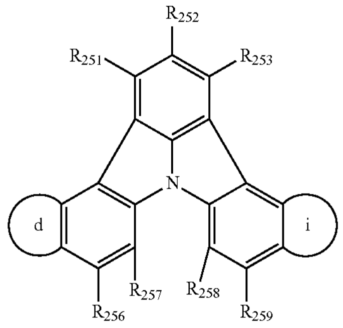

(25-3)

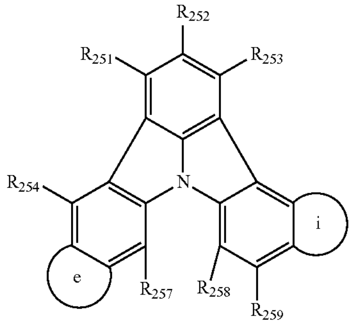

(25-4)

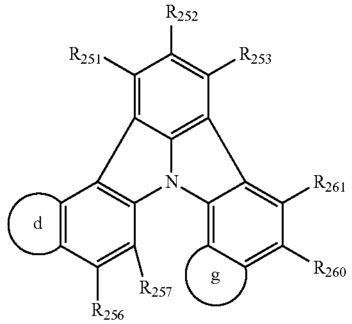

(25-5)

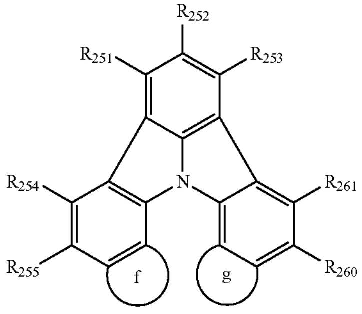

-continued (25-6)

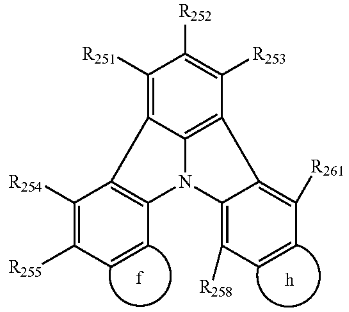

In the formulae (25-1) to (25-6), rings d to i are each independently a substituted or unsubstituted monocyclic ring or a substituted or unsubstituted fused ring; and $R_{251}$ to $R_{261}$ each independently represent the same as $R_{251}$ to $R_{261}$ in the formula (25).

In an exemplary embodiment, the compound represented by the formula (25) is represented by any one of formulae (25-7) to (25-12) below.

[Formula 178]

(25-7)

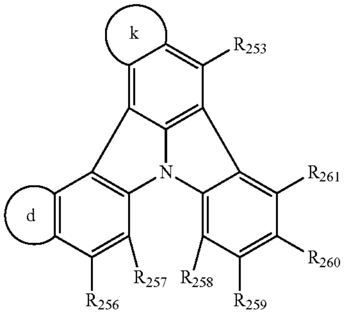

(25-8)

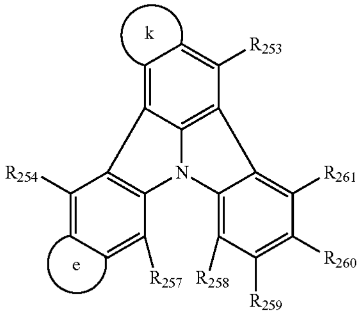

(25-9)

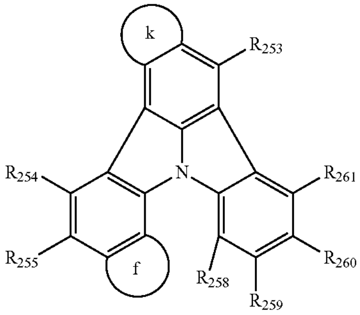

-continued (25-10)

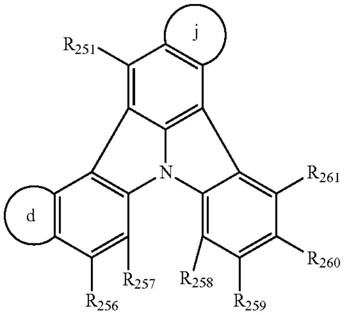

(25-11)

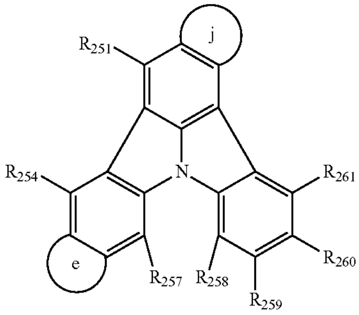

(25-12)

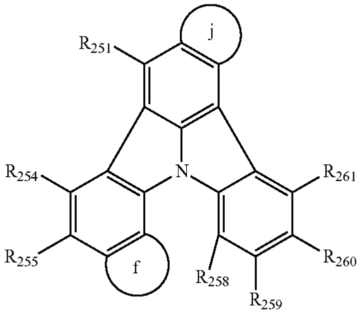

In the formulae (25-7) to (25-12), rings d to f, k, and j are each independently a substituted or unsubstituted monocyclic ring or a substituted or unsubstituted fused ring; and $R_{251}$ to $R_{261}$ each independently represent the same as $R_{251}$ to $R_{261}$ in the formula (25).

In an exemplary embodiment, the compound represented by the formula (25) is represented by any one of formulae (25-13) to (25-21) below.

[Formula 179]

(25-13)

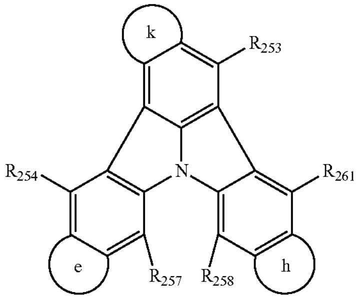

-continued (25-14)

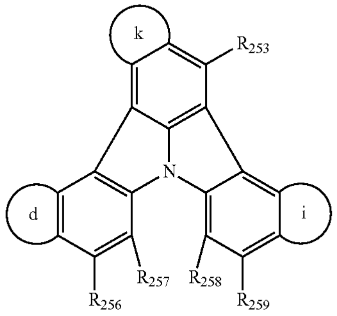

(25-15)

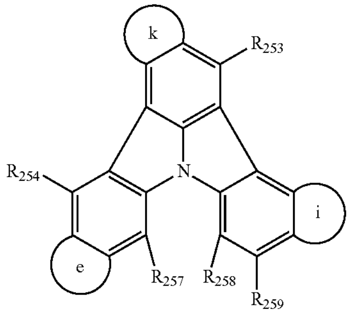

(25-16)

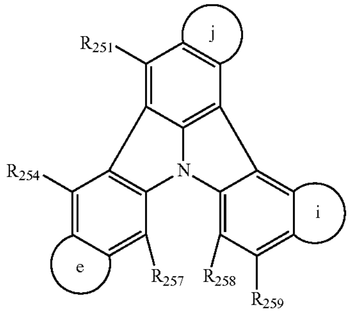

(25-17)

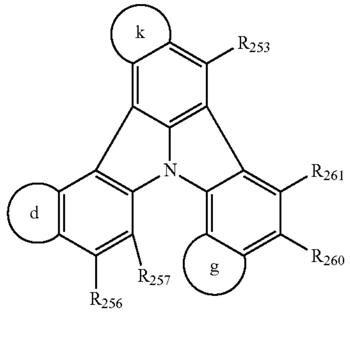

(25-18)

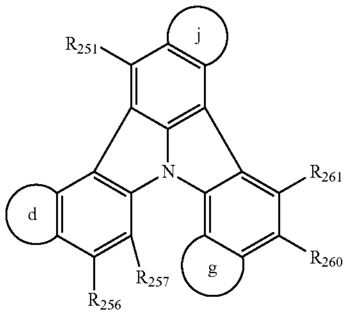

-continued (25-19)

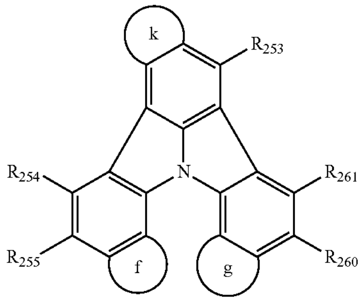

(25-20)

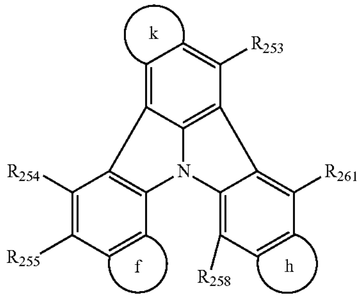

(25-21)

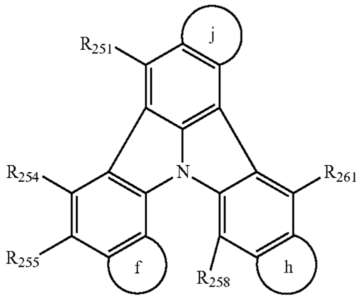

In the formulae (25-13) to (25-21), rings d to k are each independently a substituted or unsubstituted monocyclic ring or a substituted or unsubstituted fused ring, and $R_{251}$ to $R_{261}$ each independently represent the same as $R_{251}$ to $R_{261}$ in the formula (25).

When the ring g or the ring h further has a substituent, examples of the substituent include a substituted or unsubstituted alkyl group having 1 to 50 carbon atoms, a substituted or unsubstituted aryl group having 6 to 50 ring carbon atoms, or a group represented by the formula (261), (263), or (264).

In an exemplary embodiment, the compound represented by the formula (25) is represented by any one of formulae (25-22) to (25-25) below.

[Formula 180]

(25-22)

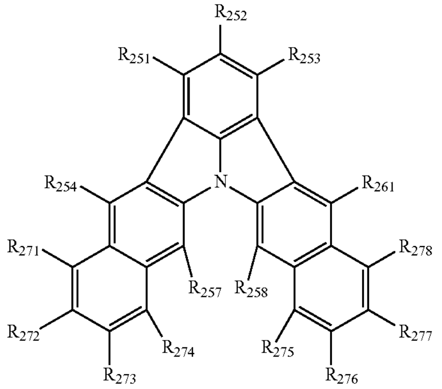

(25-23)

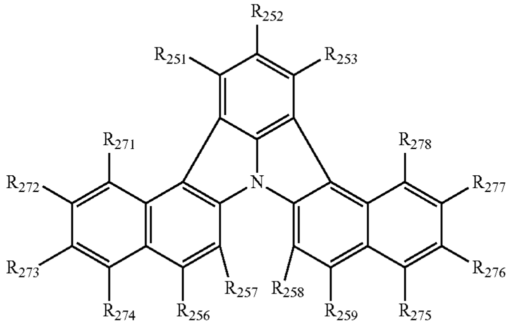

(25-24)

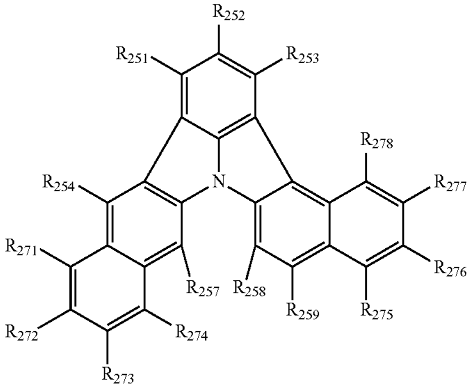

(25-25)

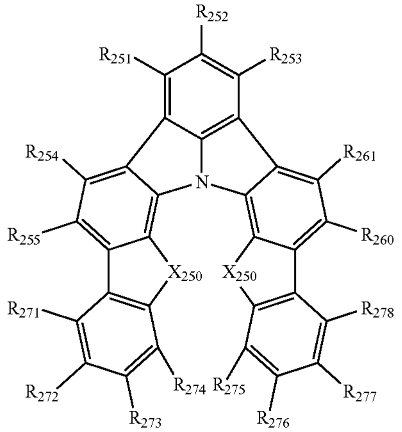

In the formulae (25-22) to (25-25), $X_{250}$ is $C(R_{901})(R_{902})$, $NR_{903}$, O, or S; $R_{251}$ to $R_{261}$ and $R_{271}$ to $R_{278}$ each independently represent the same as $R_{251}$ to $R_{261}$ in the formula (25); and $R_{901}$ to $R_{903}$ each independently represent the same as $R_{901}$ to $R_{903}$ in the formula (11).

In an exemplary embodiment, the compound represented by the formula (25) is represented by a formula (25-26) below.

[Formula 181]

(25-26)

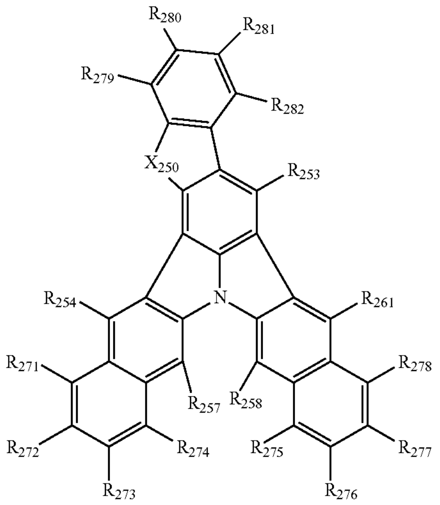

In the formula (25-26), $X_{250}$ is $C(R_{901})(R_{902})$, $NR_{903}$, O, or S; $R_{253}$, $R_{254}$, $R_{257}$, $R_{258}$, $R_{261}$, and $R_{271}$ to $R_{282}$ each independently represent the same as $R_{251}$ to $R_{261}$ in the formula (25); and $R_{901}$ to $R_{903}$ each independently represent the same as $R_{901}$ to $R_{903}$ in the formula (11).

Specific examples of the compound represented by the formula (21) include compounds shown below.

[Formula 182]

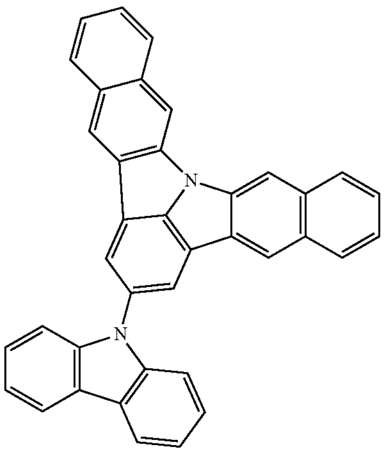

-continued
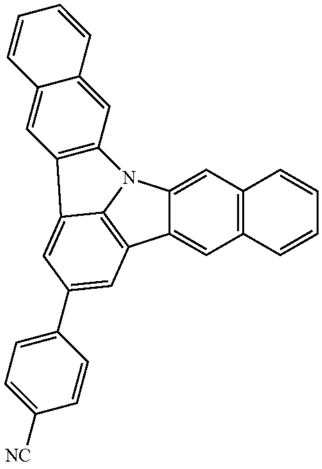
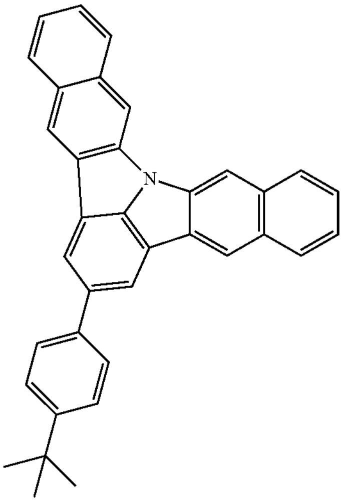
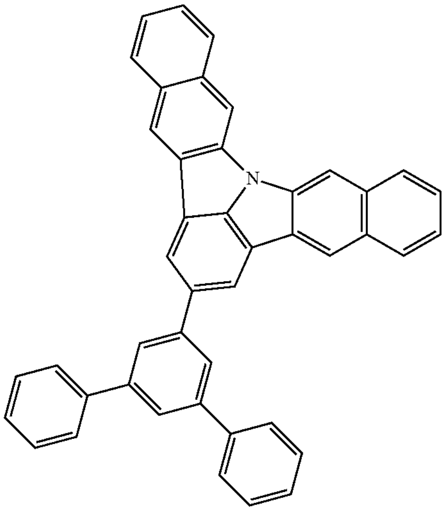
-continued
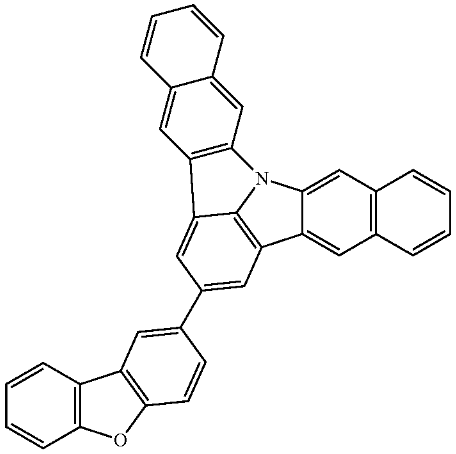
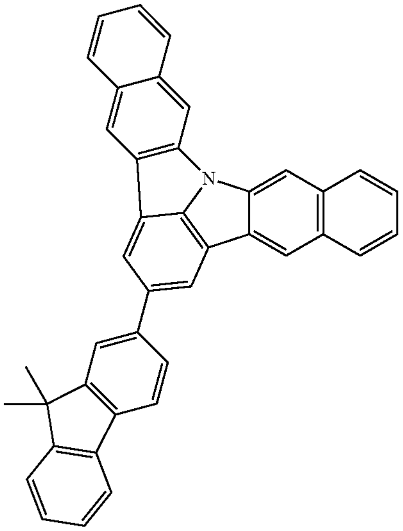
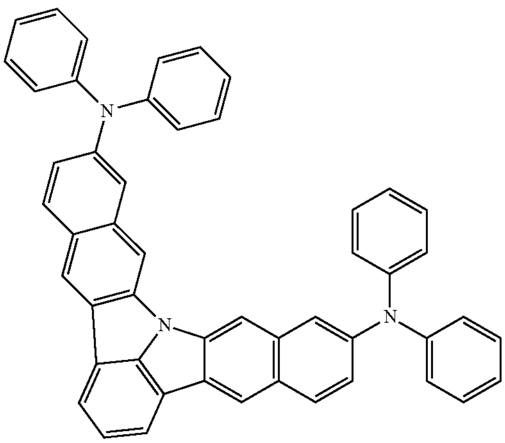

-continued
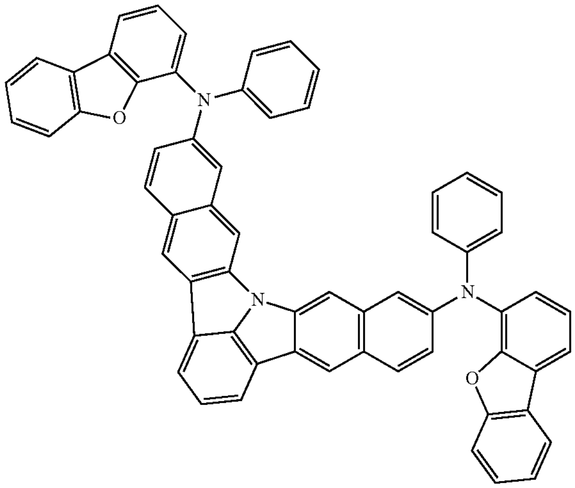
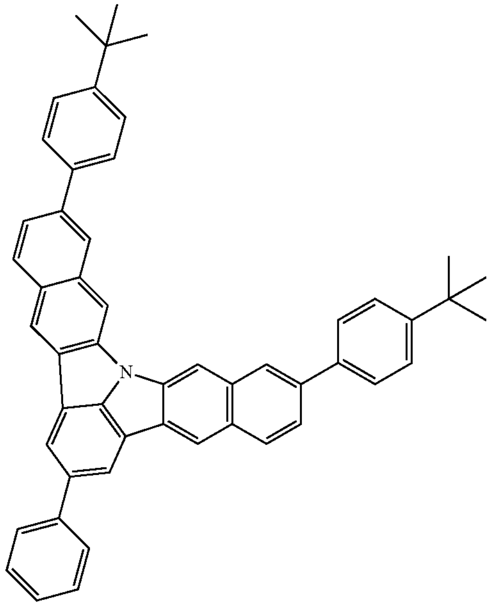
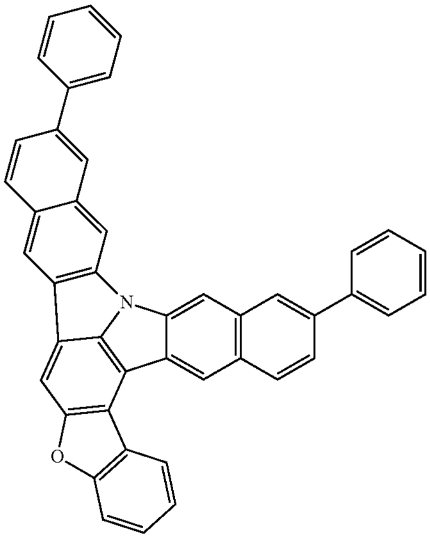
-continued
[Formula 183]
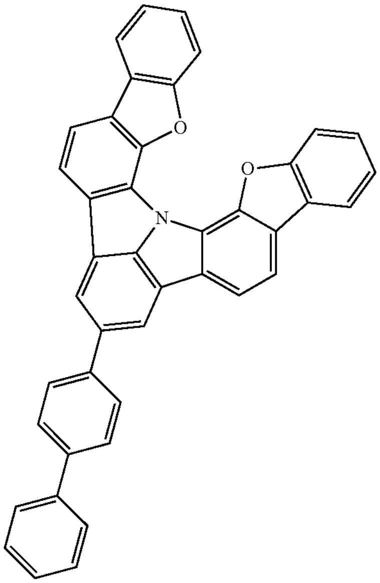
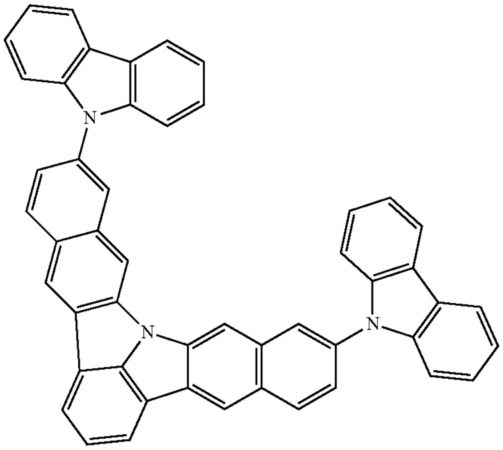
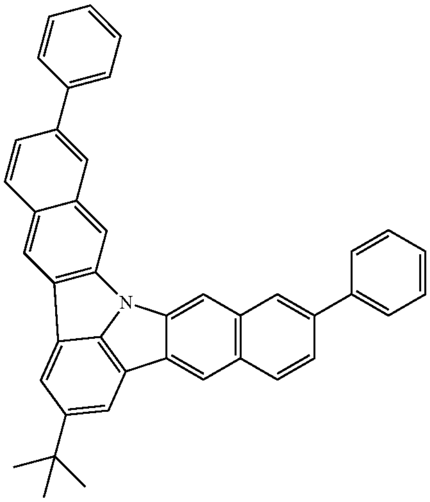

-continued
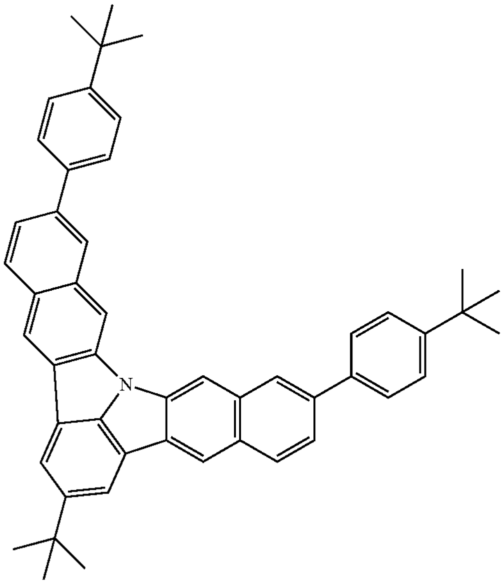
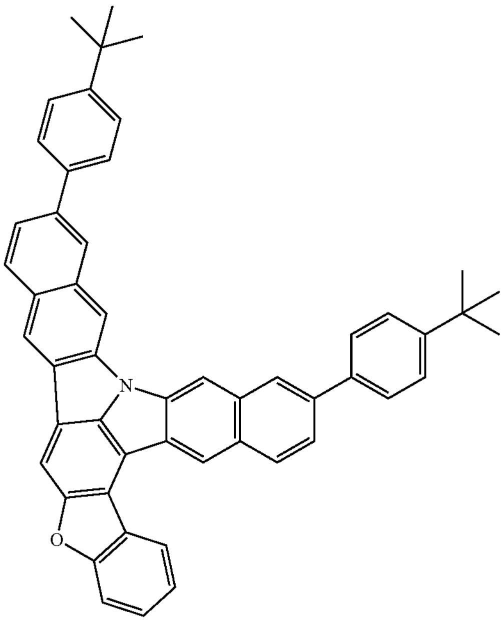
-continued
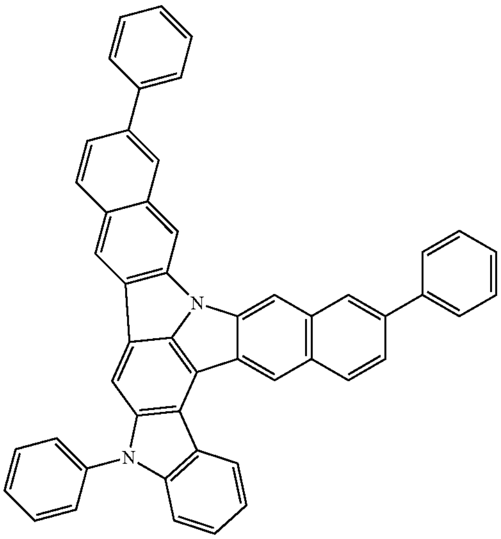
[Formula 184]
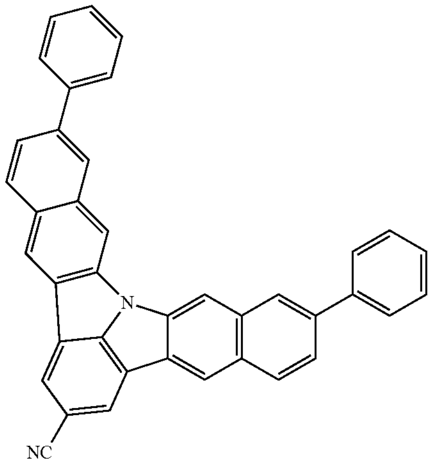
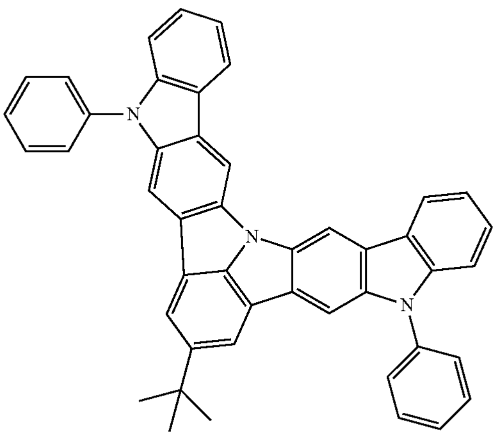

-continued
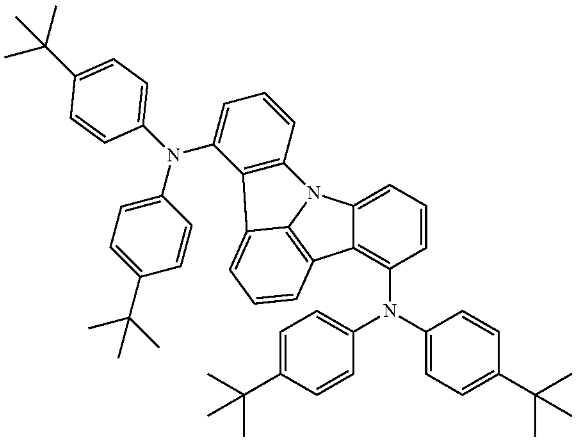
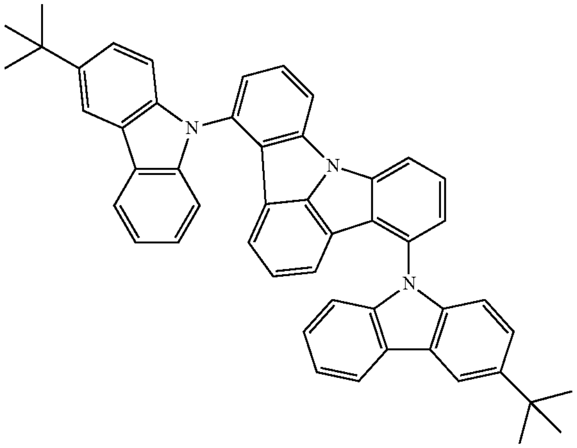
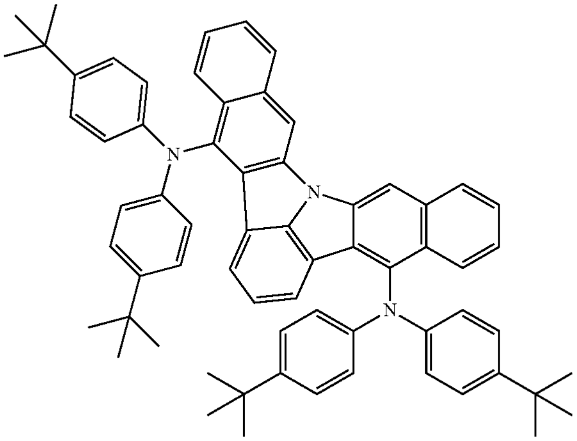
-continued
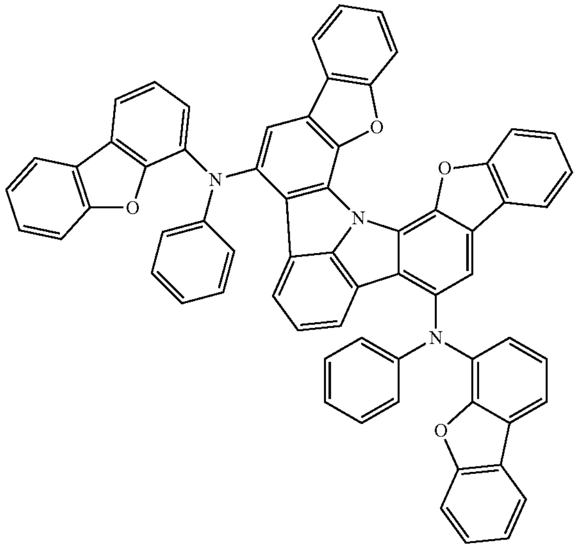
[Formula 185]
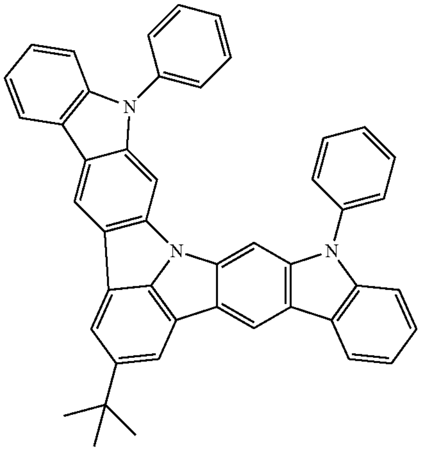
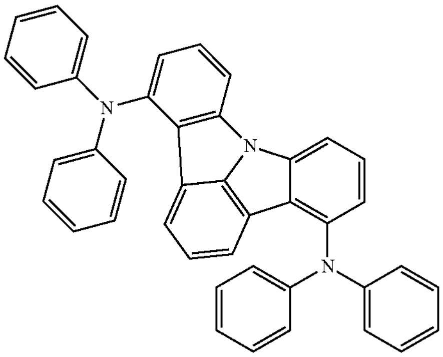

-continued

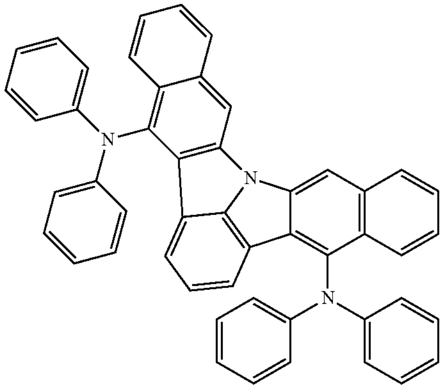

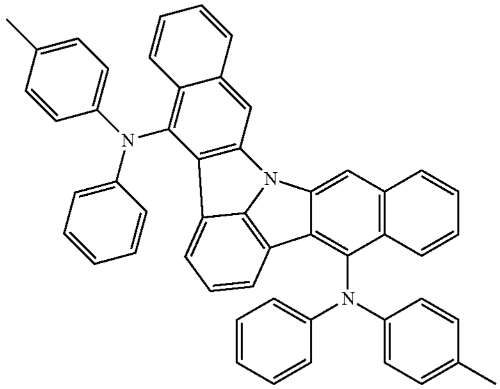

Compound Represented by Formula (31)

The compound represented by the formula (31) will be described. The compound represented by the formula (31) corresponds to the compound represented by the above-described formula (21-3).

[Formula 186]

(31)

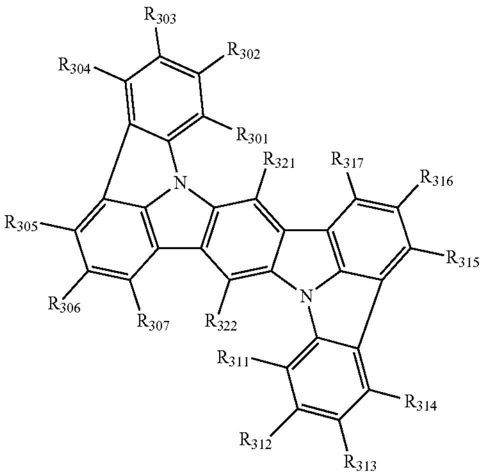

In the formula (31):

at least one combination of adjacent two or more of $R_{301}$ to $R_{307}$ and $R_{311}$ to $R_{317}$ form a substituted or unsubstituted monocyclic ring or a substituted or unsubstituted fused ring, or not mutually bonded;

$R_{301}$ to $R_{307}$ and $R_{311}$ to $R_{317}$ forming neither the substituted or unsubstituted monocyclic ring nor the substituted or unsubstituted fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{321}$ and $R_{322}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ each independently represent the same as $R_{901}$ to $R_{907}$ in the formula (11).

"A combination of adjacent two or more of $R_{301}$ to $R_{307}$ and $R_{311}$ to $R_{317}$" refers to, for instance, a combination of $R_{301}$ and $R_{302}$, a combination of $R_{302}$ and $R_{303}$, a combination of $R_{303}$ and $R_{304}$, a combination of $R_{305}$ and $R_{306}$, a combination of $R_{306}$ and $R_{307}$, and a combination of $R_{301}$, $R_{302}$, and $R_{303}$.

In an exemplary embodiment, at least one, preferably two of $R_{301}$ to $R_{307}$ and $R_{311}$ to $R_{317}$ is a group represented by —N($R_{906}$)($R_{907}$).

In an exemplary embodiment, $R_{301}$ to $R_{307}$ and $R_{311}$ to $R_{317}$ are each independently a hydrogen atom, a substituted or unsubstituted aryl group having 6 to 50 ring carbon atoms, or a substituted or unsubstituted monovalent heterocyclic group having 5 to 50 ring atoms.

In an exemplary embodiment, the compound represented by the formula (31) is a compound represented by a formula (32) below.

[Formula 187]

(32)

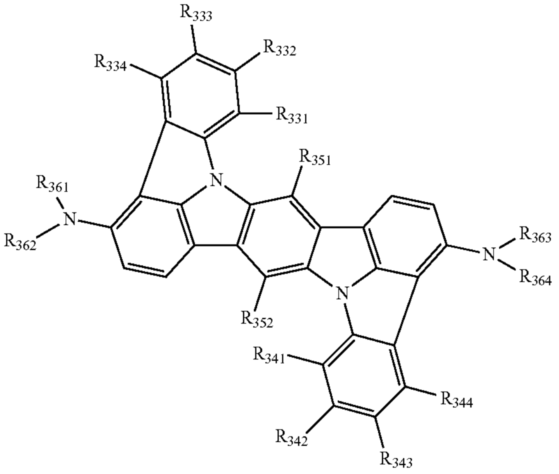

In the formula (32): at least one combination of adjacent two or more of $R_{331}$ to $R_{334}$ and $R_{341}$ to $R_{344}$ form a substituted or unsubstituted monocyclic ring or a substituted or unsubstituted fused ring, or not mutually bonded;

$R_{331}$ to $R_{334}$ and $R_{341}$ to $R_{344}$ forming neither the substituted or unsubstituted monocyclic ring nor the substituted or unsubstituted fused ring, $R_{351}$, and $R_{352}$ are each independently a hydrogen atom, a substituted or unsubstituted aryl group having 6 to 50 ring carbon atoms, or a substituted or unsubstituted monovalent heterocyclic group having 5 to 50 ring atoms; and $R_{361}$ to $R_{364}$ are each independently a substituted or unsubstituted aryl group having 6 to 50 ring carbon atoms, or a substituted or unsubstituted monovalent heterocyclic group having 5 to 50 ring atoms.

In an exemplary embodiment, the compound represented by the formula (31) is a compound represented by a formula (33) below.

[Formula 188]

(33)

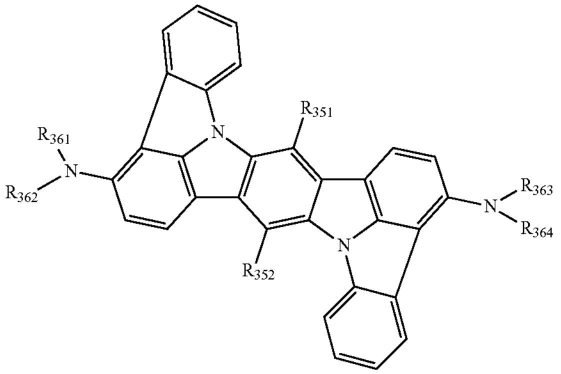

In the formula (33): $R_{351}$, $R_{352}$ and $R_{361}$ to $R_{364}$ each independently represent the same as $R_{351}$, $R_{352}$, and $R_{361}$ to $R_{364}$ in the formula (32).

In an exemplary embodiment, $R_{361}$ to $R_{364}$ in the formulae (32) and (33) are each independently a substituted or unsubstituted aryl group having 6 to 50 ring carbon atoms (preferably a phenyl group).

In an exemplary embodiment, $R_{321}$ and $R_{322}$ in the formula (31) and $R_{351}$ and $R_{352}$ in the formulae (32) and (33) are hydrogen atoms.

In an exemplary embodiment, a substituent for "substituted or unsubstituted" group in the formulae (31) to (33) is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

Specific examples of the compound represented by the formula (31) include compounds shown below.

[Formula 189]

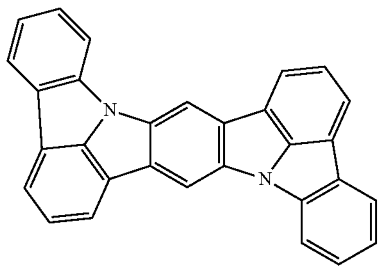

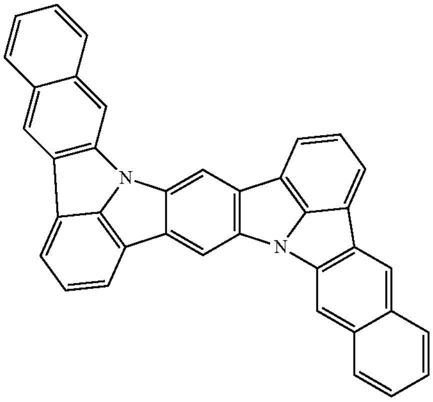

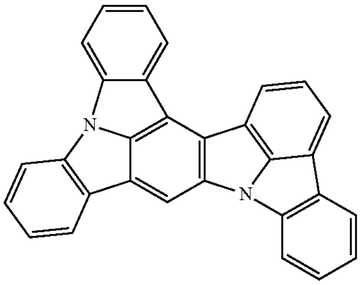

-continued
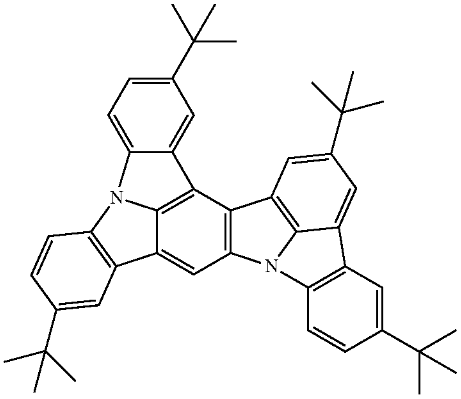
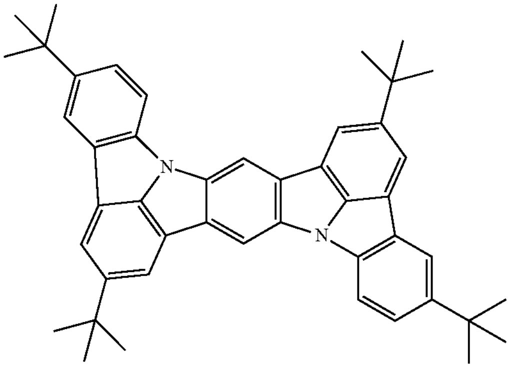
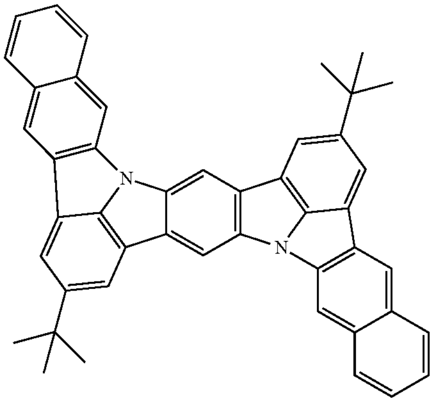
[Formula 190]
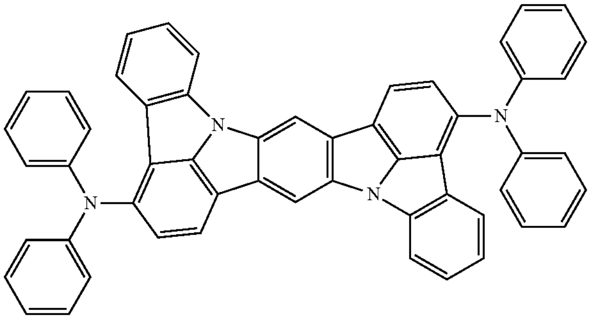
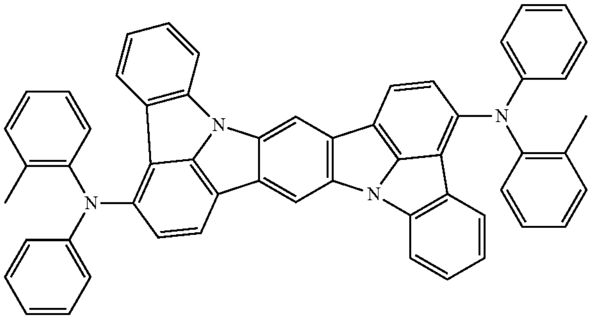
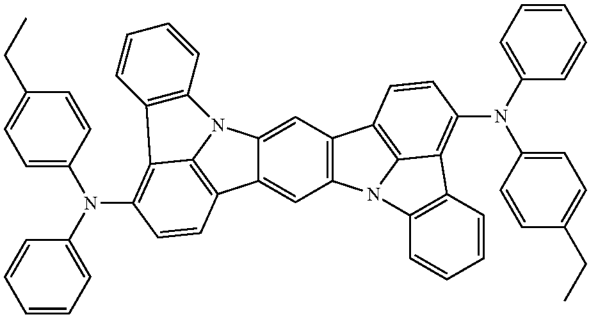

-continued
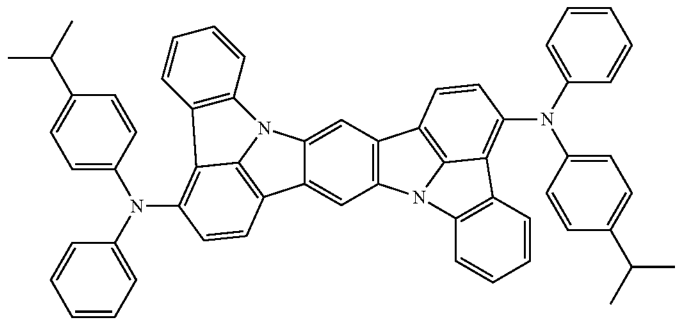
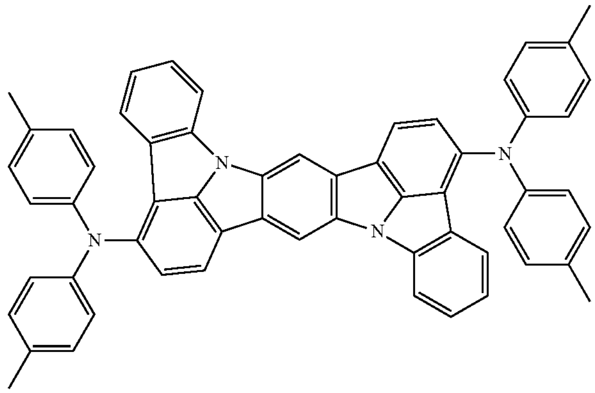
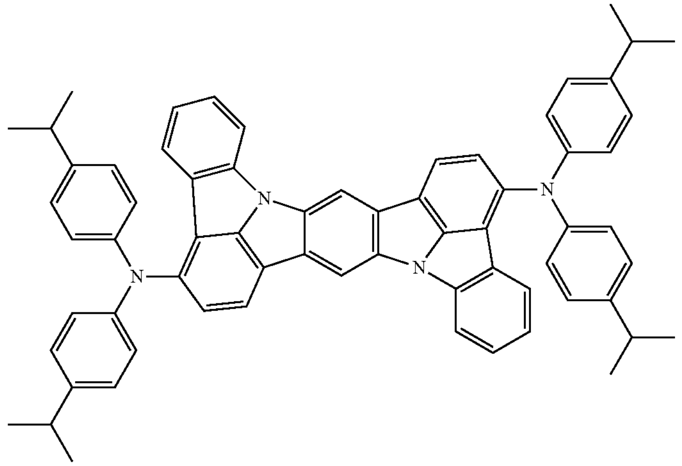
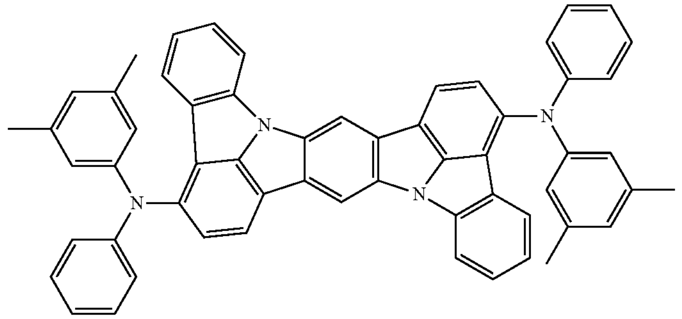

-continued
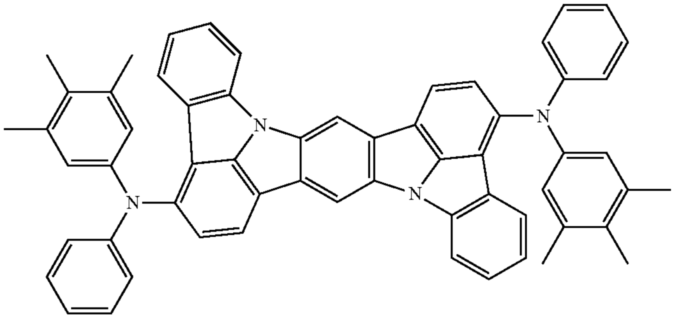
[Formula 191]
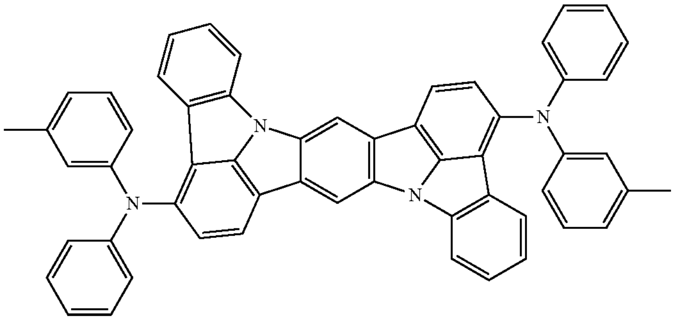
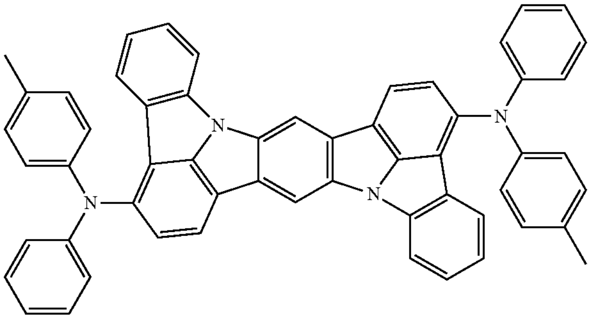
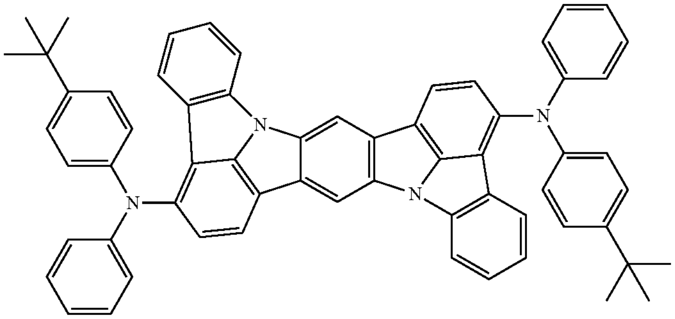
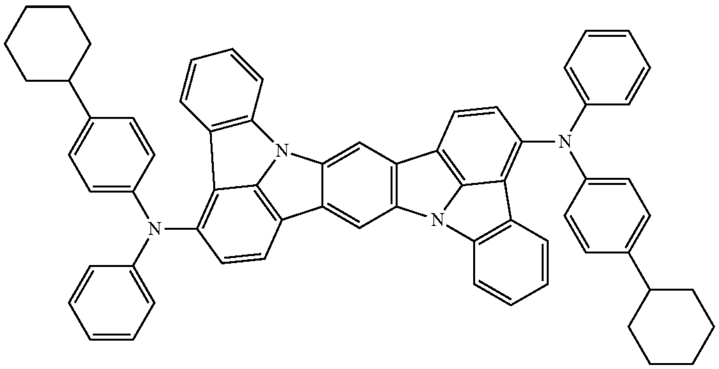

-continued
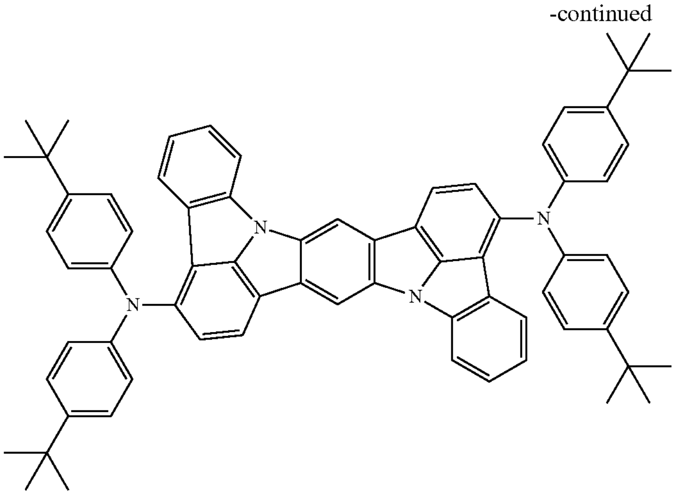
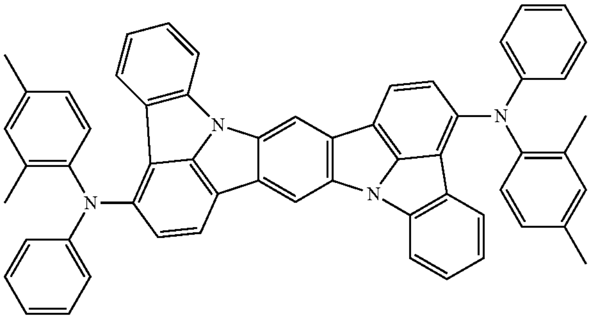
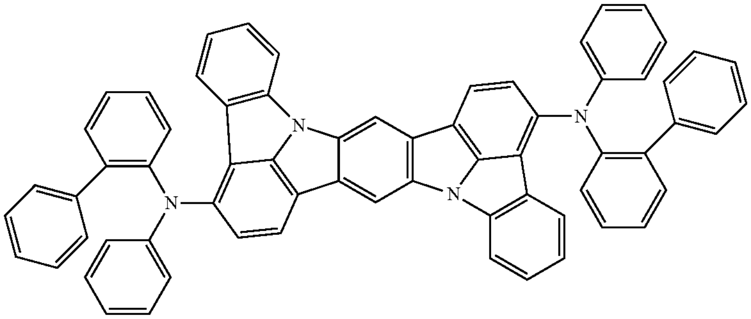
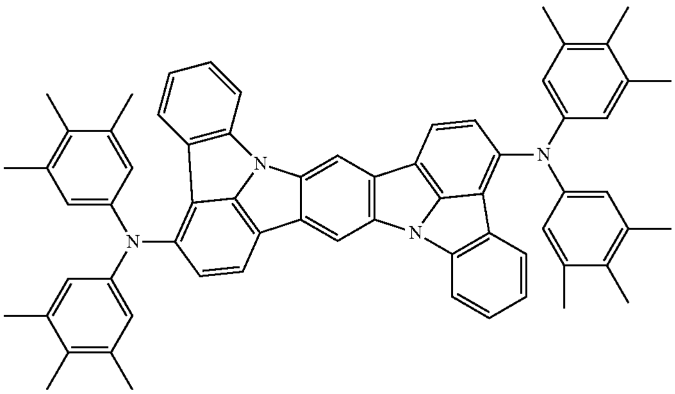

-continued
[Formula 192]
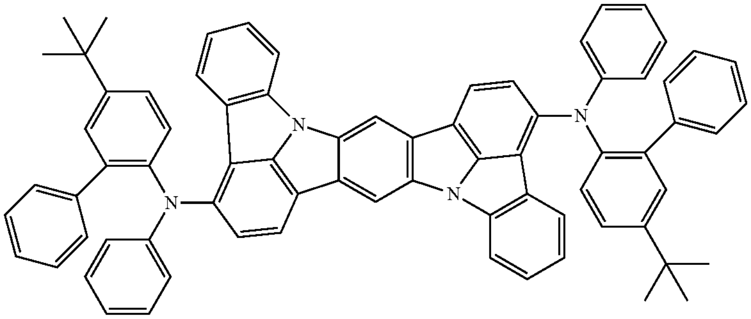
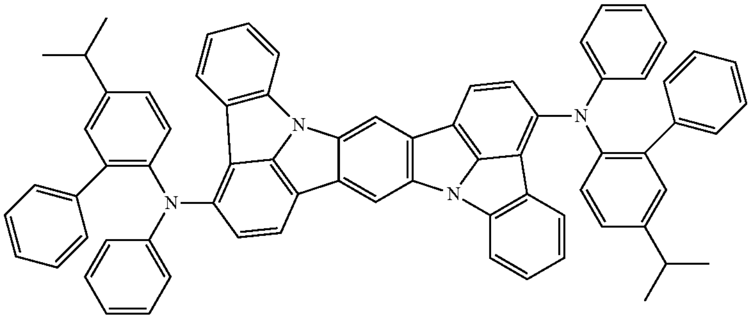
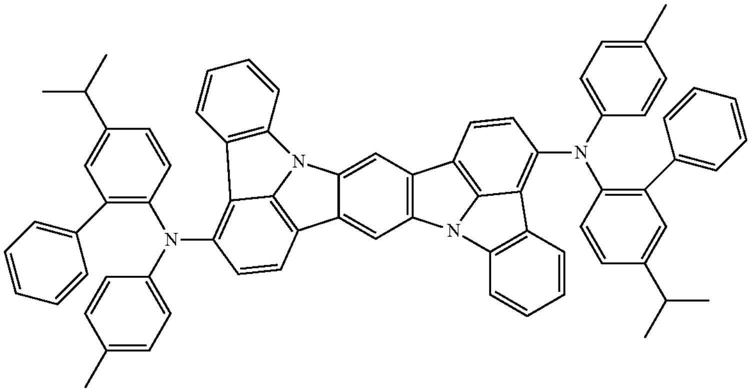
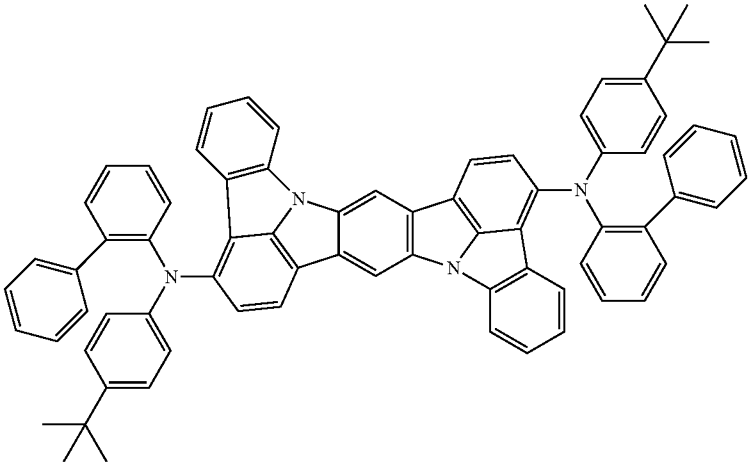

-continued
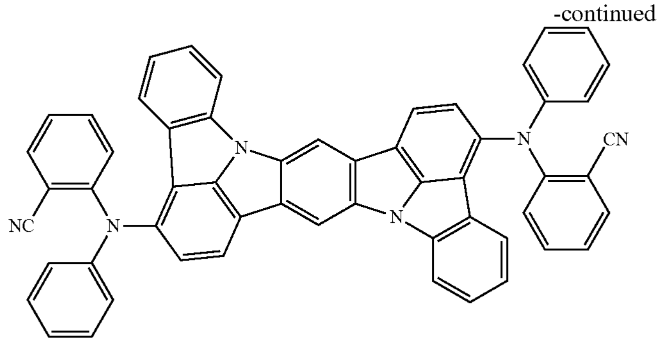
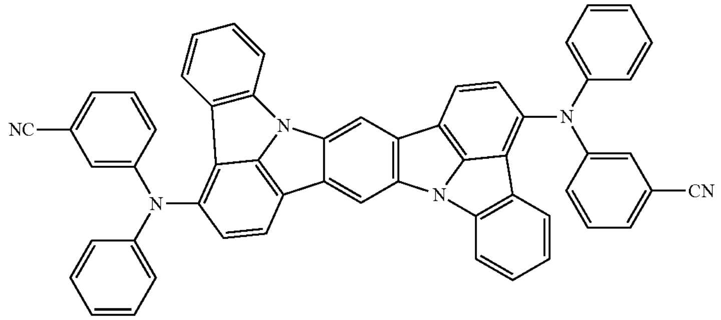
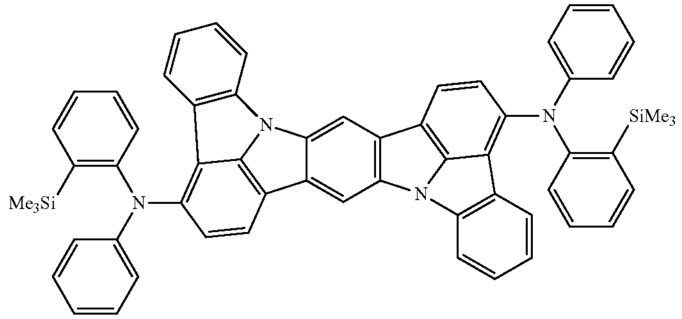
[Formula 193]
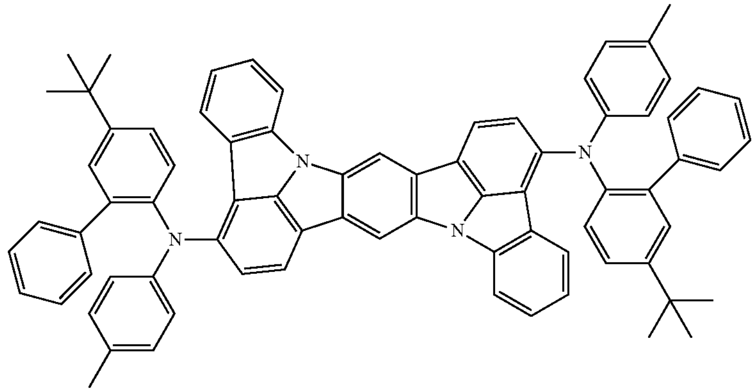
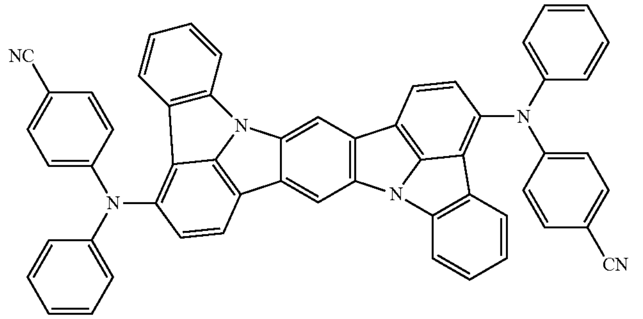 [SMILES: N#Cc1ccccc1N(c1ccccc1)c1ccc2c3cc4c(cc3n3c5ccccc5c1c23)c1ccc(N(c2ccccc2)c2ccccc2C#N)c2c3ccccc3n4c12]

-continued
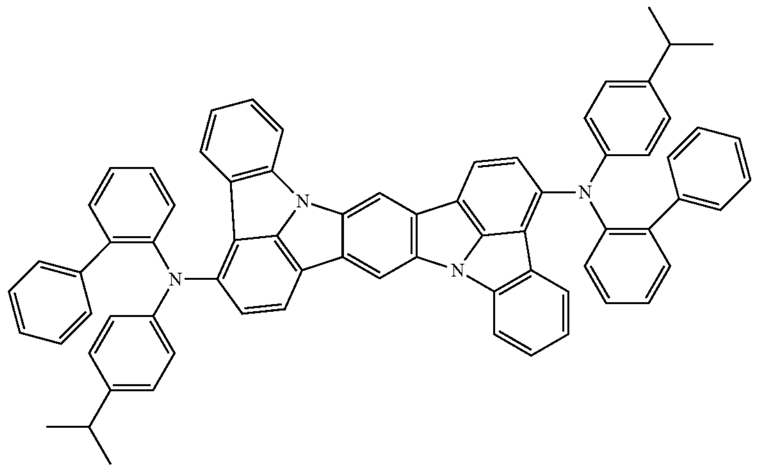
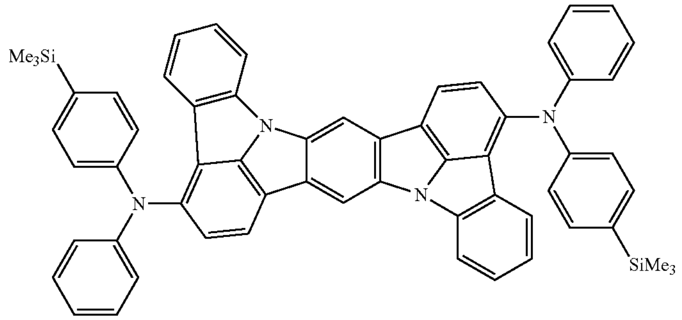
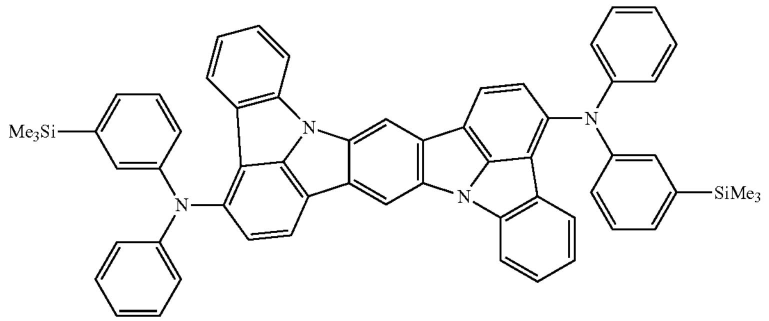
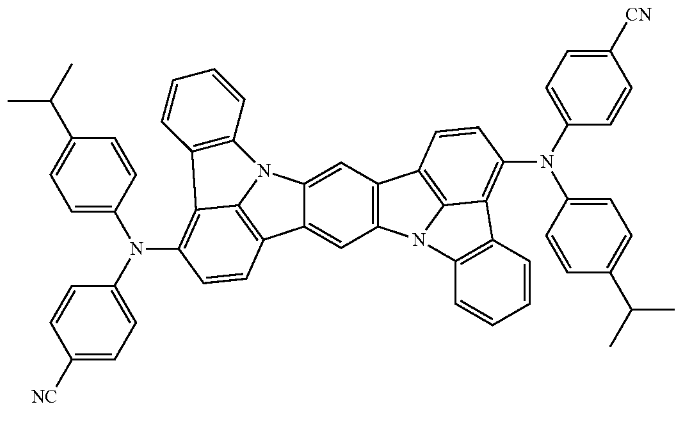

-continued
[Formula 194]
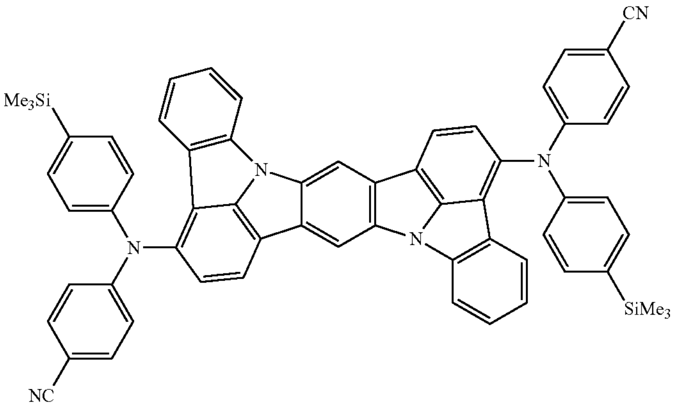
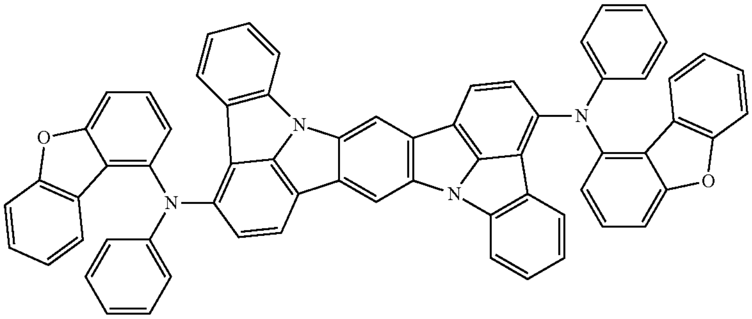
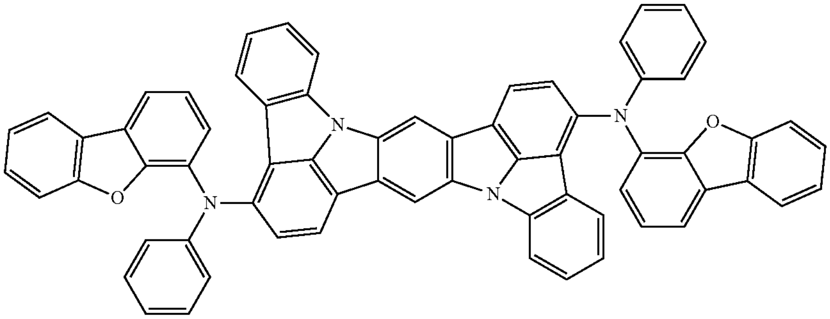
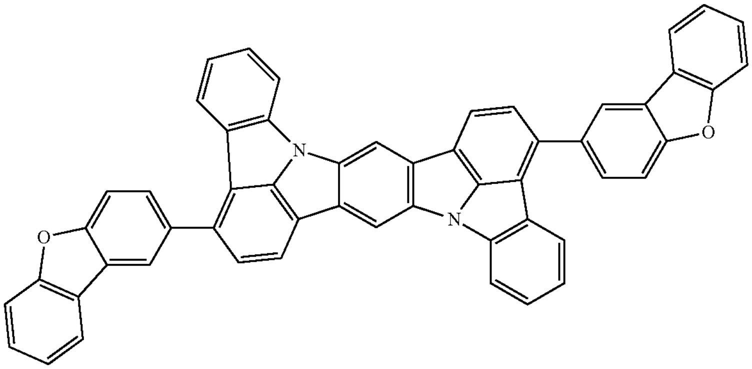
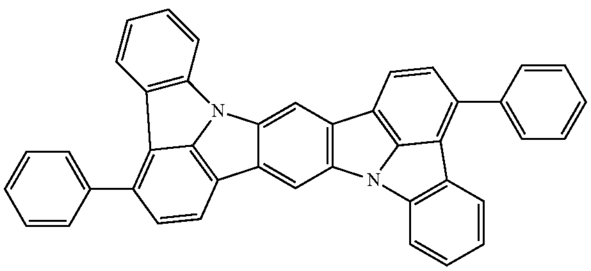

-continued
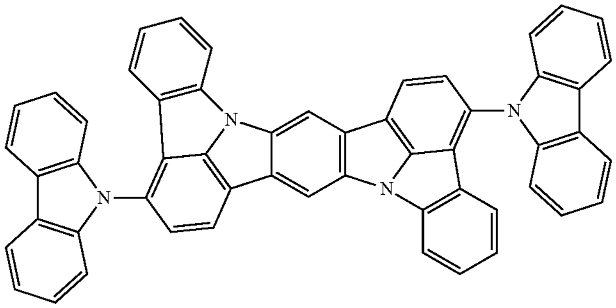
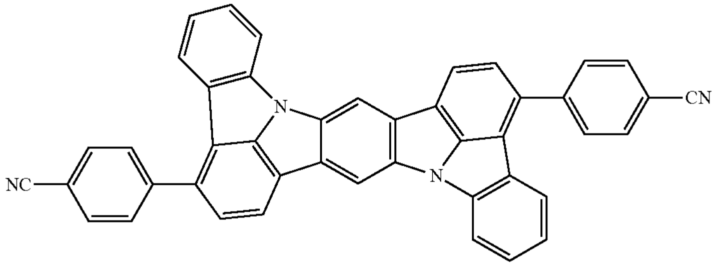
[Formula 195]
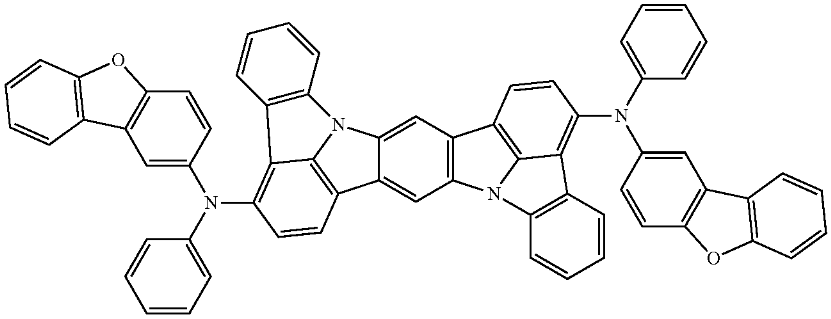
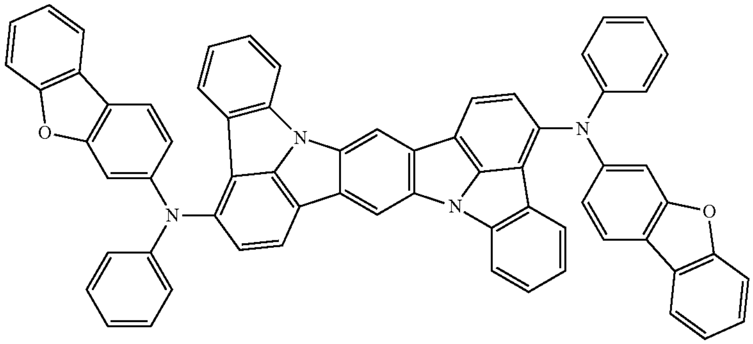
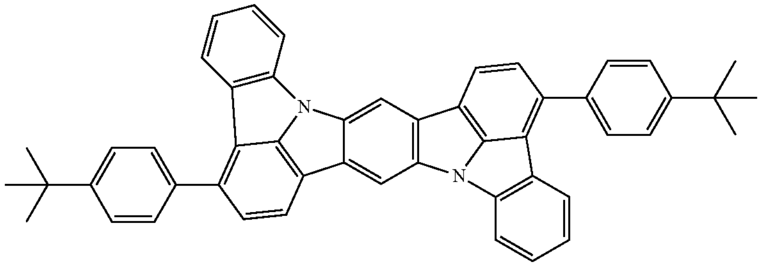

-continued
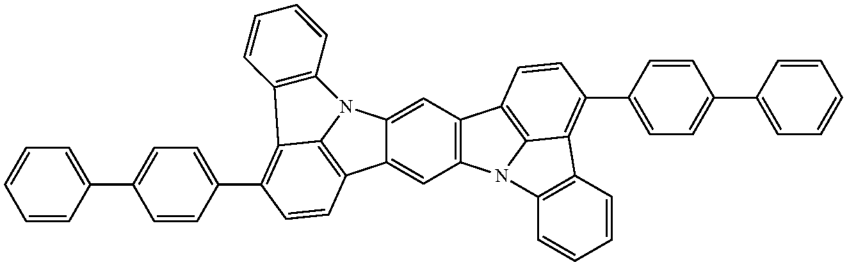
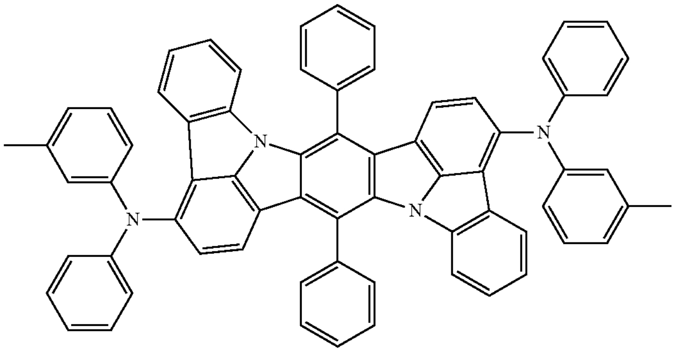
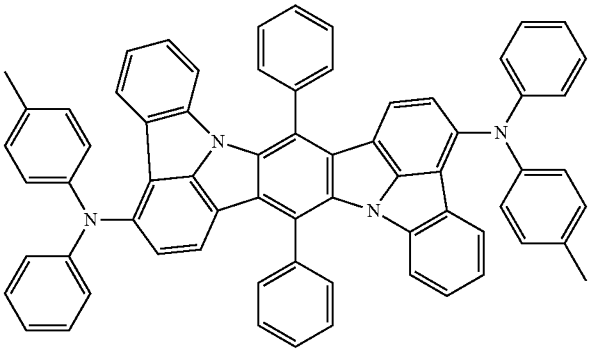
[Formula 196]
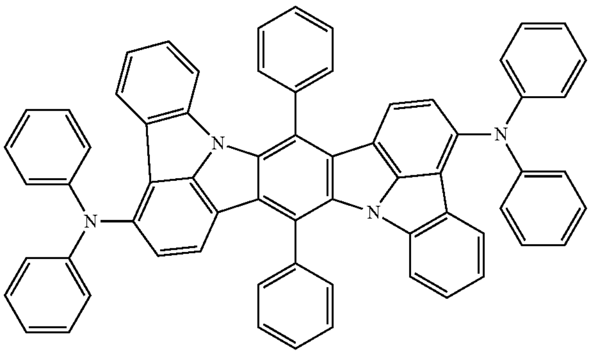
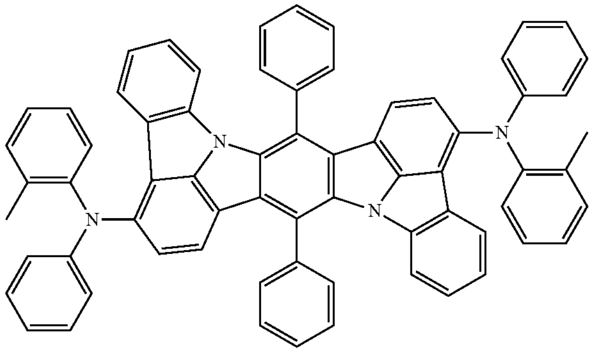
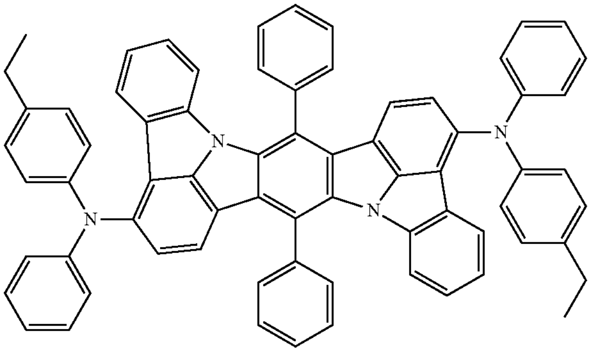

-continued
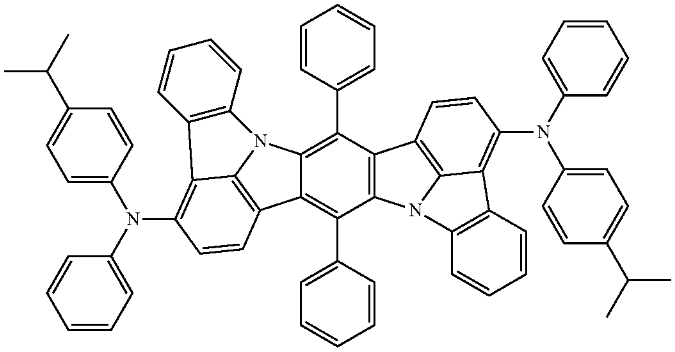
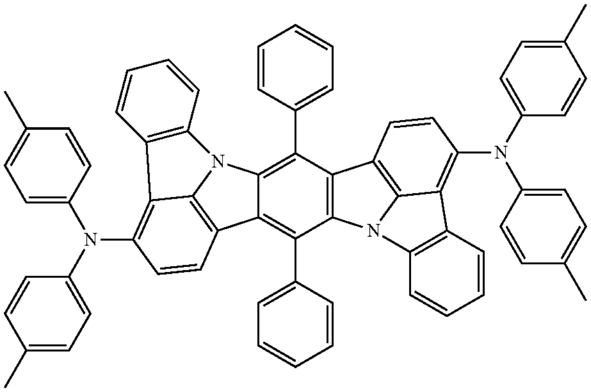
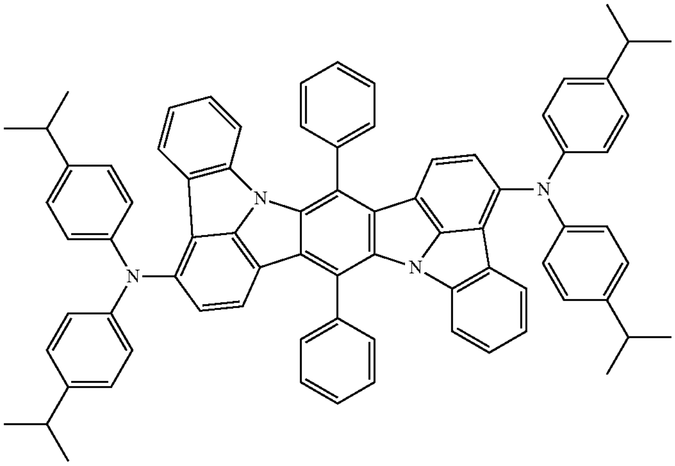
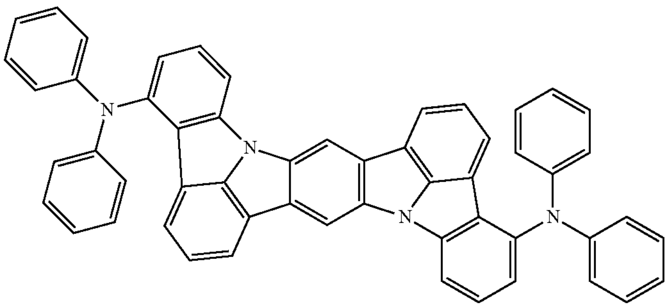

-continued
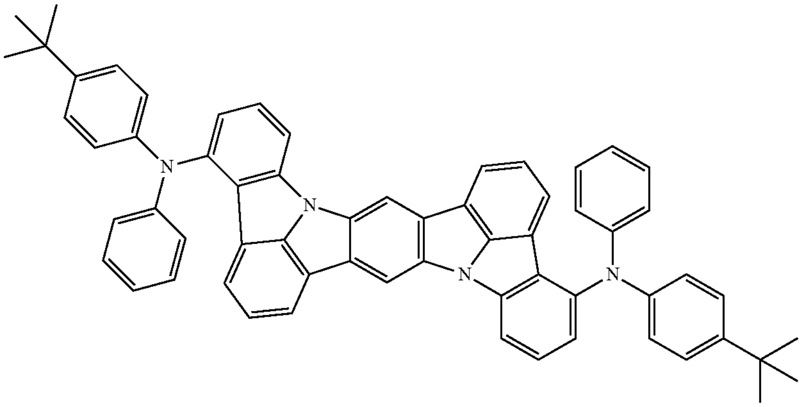
[Formula 197]
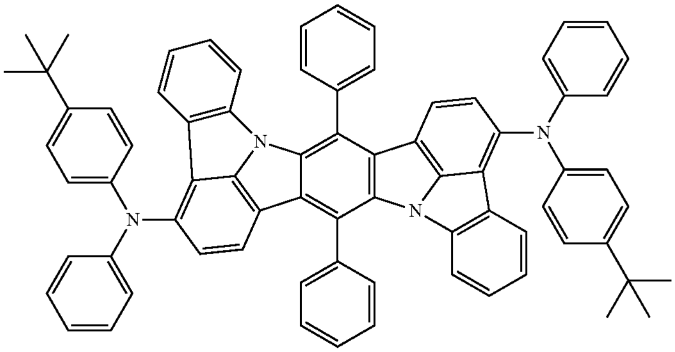
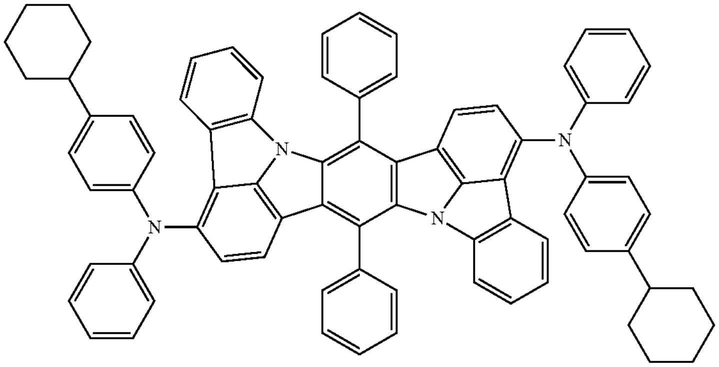
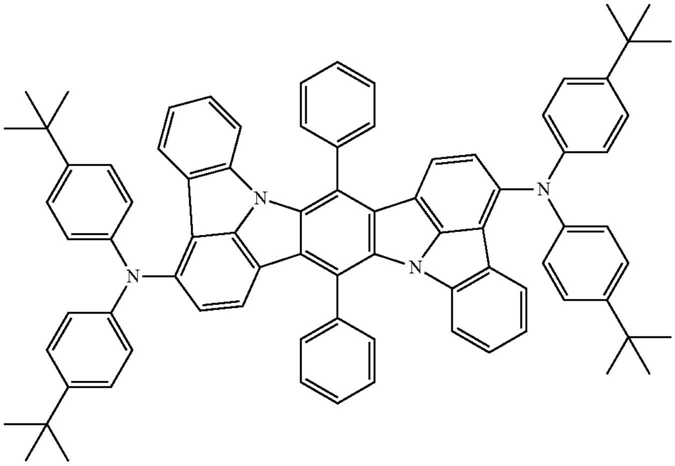

-continued
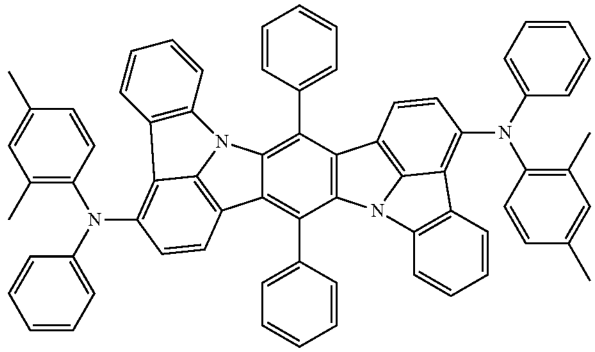
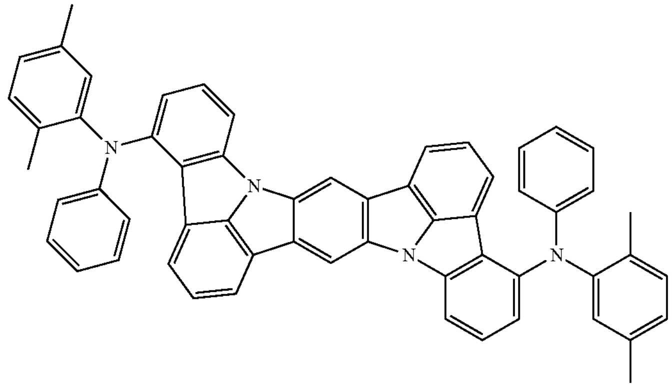
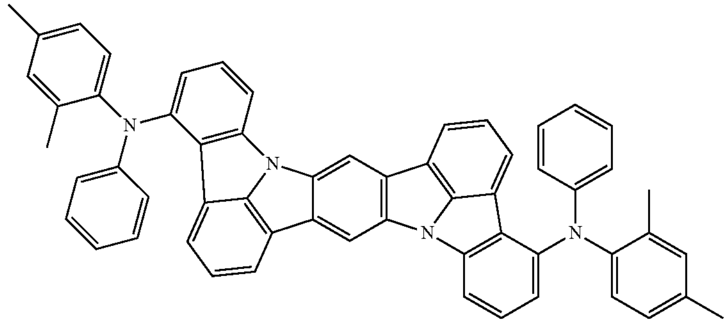
[Formula 198]
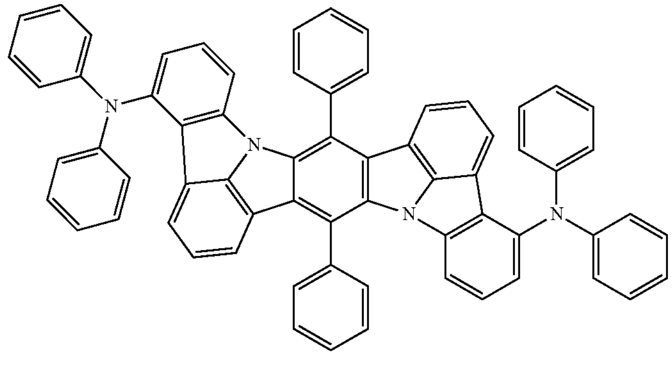
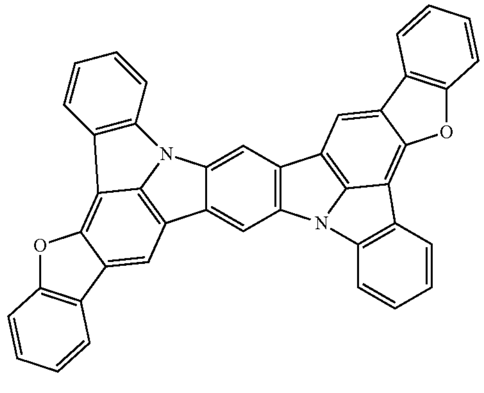

-continued
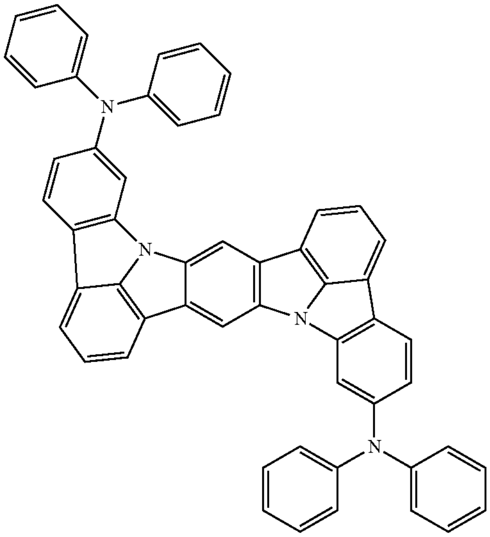
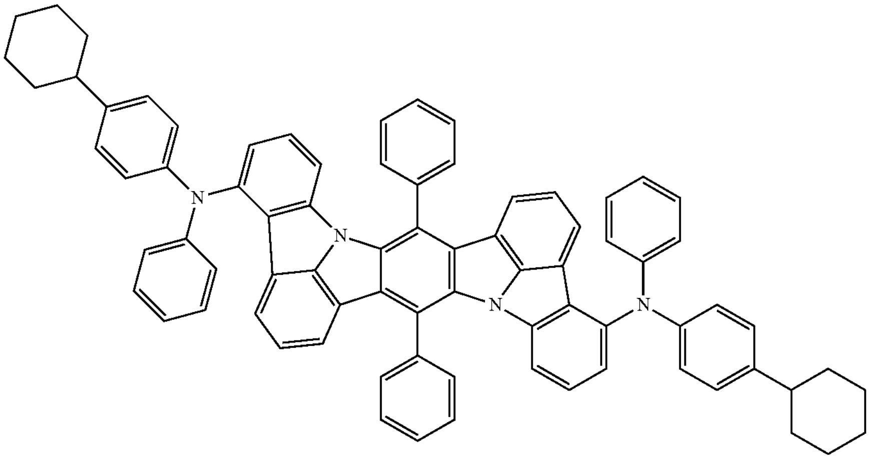
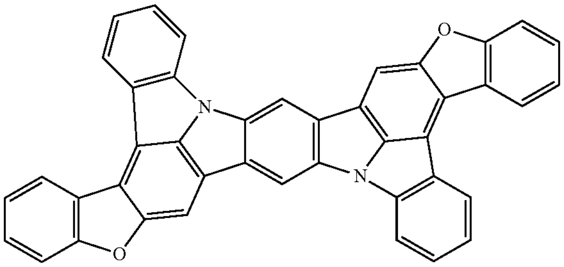
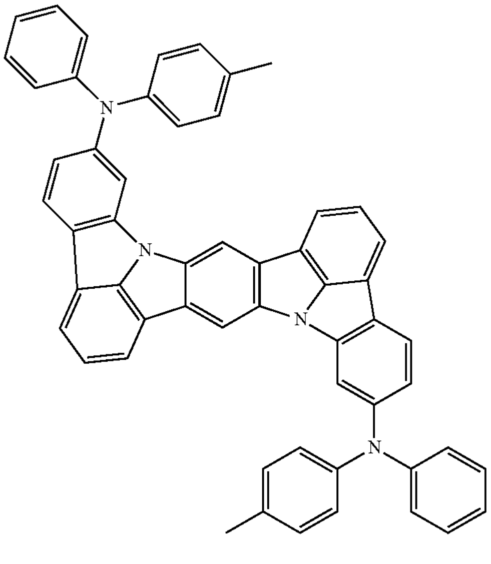

-continued
[Formula 199]
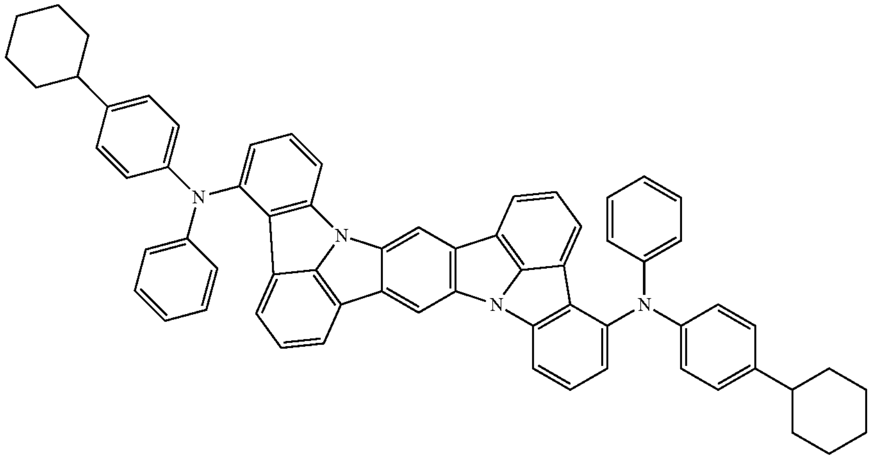
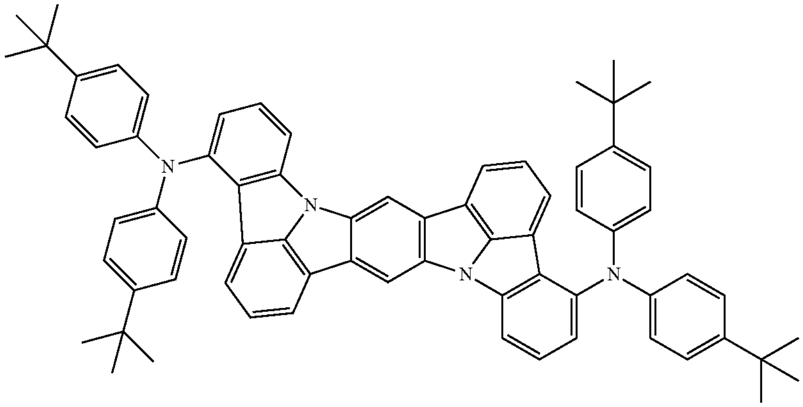
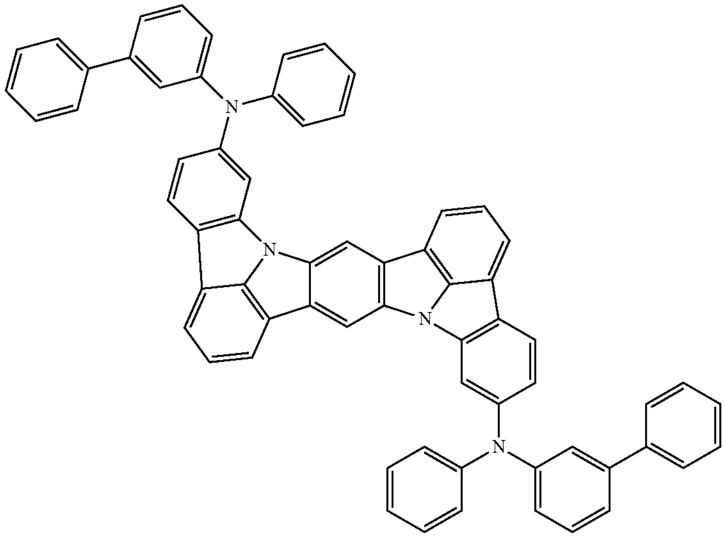

-continued
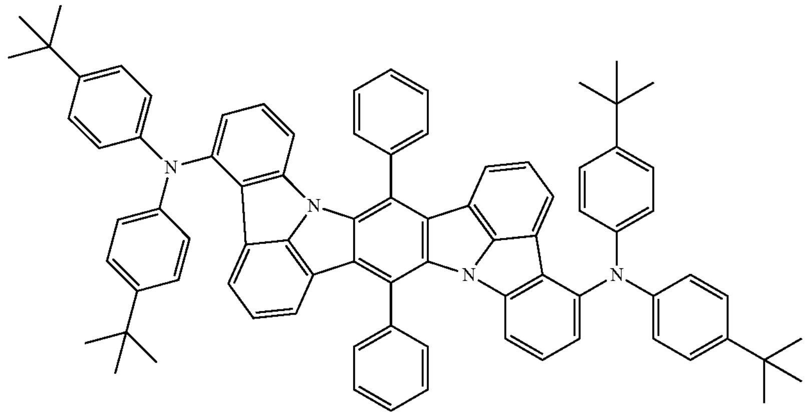
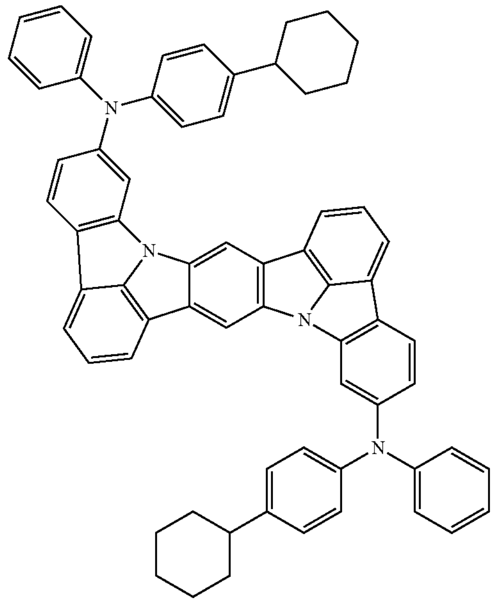
[Formula 200]
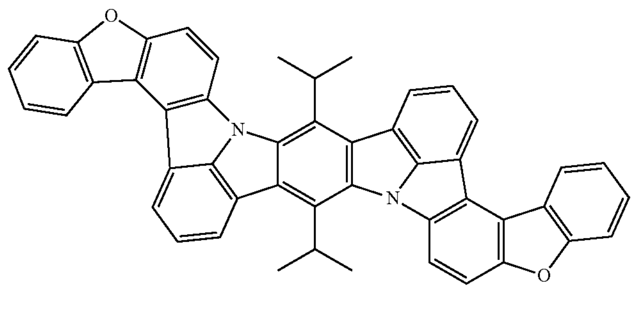

-continued
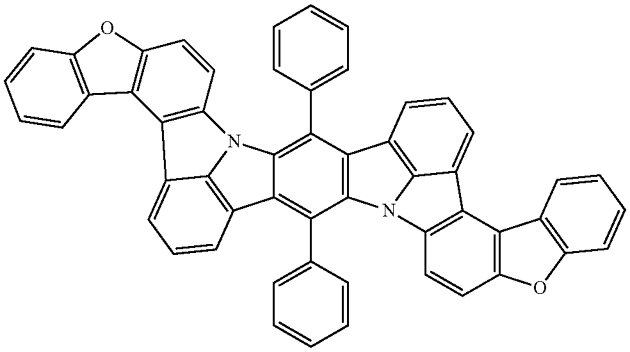
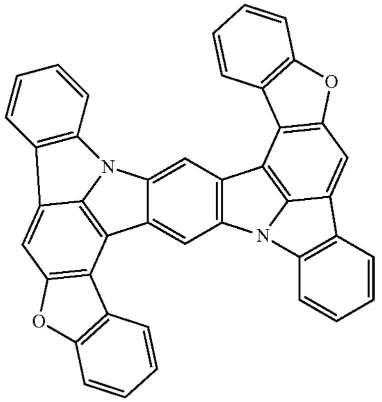
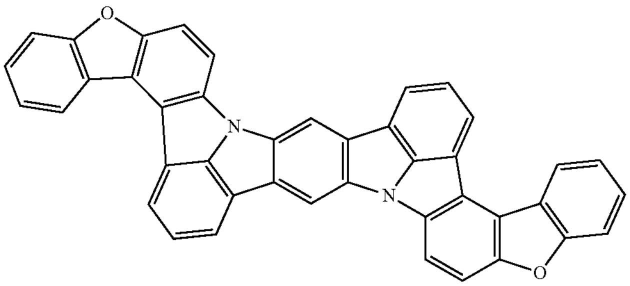
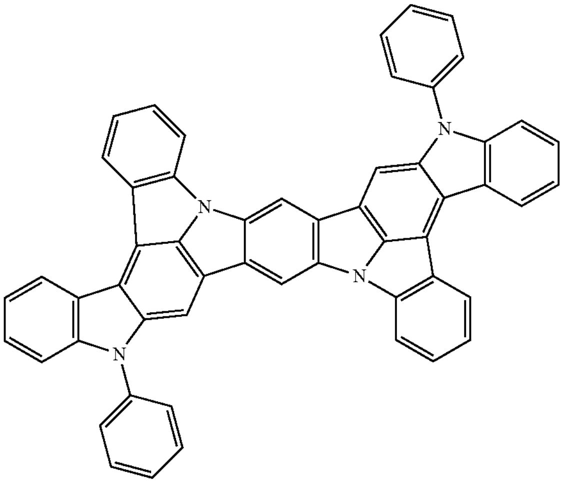
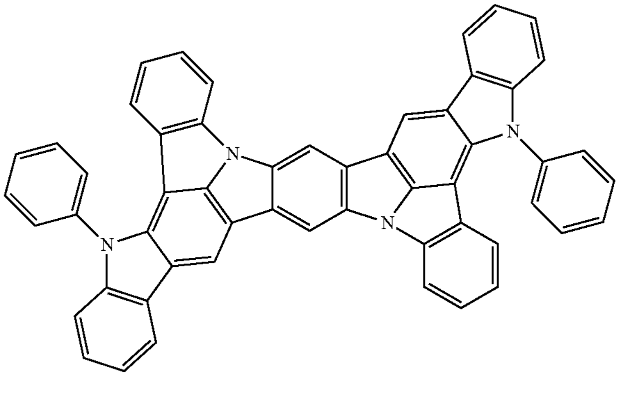

Compound Represented by Formula (41)

The compound represented by the formula (41) will be described.

[Formula 201]

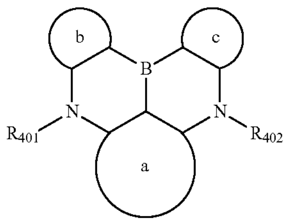

(41)

In the formula (41):

a ring, b ring and c ring are each independently a substituted or unsubstituted aromatic hydrocarbon ring having 6 to 50 ring carbon atoms or a substituted or unsubstituted heterocycle having 5 to 50 ring atoms;

$R_{401}$ and $R_{402}$ are each independently bonded with the a ring, b ring, or c ring to form a substituted or unsubstituted heterocycle, or not bonded to form no substituted or unsubstituted heterocycle; and $R_{401}$ and $R_{402}$ not forming the substituted or unsubstituted heterocycle are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

The a ring, b ring and c ring are each a ring (a substituted or unsubstituted aromatic hydrocarbon ring having 6 to 50 ring carbon atoms, or a substituted or unsubstituted heterocycle having 5 to 50 ring atoms) fused with the fused bicyclic structure formed of a boron atom and two nitrogen atoms at the center of the formula (41).

The "aromatic hydrocarbon ring" for the a, b, and c rings has the same structure as a compound formed by introducing a hydrogen atom to the "aryl group" described in the specific example group G1. Ring atoms of the "aromatic hydrocarbon ring" for the a ring include three carbon atoms on the fused bicyclic structure at the center of the formula (41). Ring atoms of the "aromatic hydrocarbon ring" for the b and c rings include two carbon atoms on the fused bicyclic structure at the center of the formula (41). Specific examples of the "substituted or unsubstituted aromatic hydrocarbon ring having 6 to 50 ring carbon atoms" include a compound formed by introducing a hydrogen atom to the "aryl group" described in the specific example group G1.

The "heterocycle" for the a, b, and c rings has the same structure as a compound formed by introducing a hydrogen atom to the "heterocyclic group" described in the specific example group G2. Ring atoms of the "heterocycle" for the a ring include three carbon atoms on the fused bicyclic structure at the center of the formula (41). Ring atoms of the "heterocycle" for the b and c rings include two carbon atoms on the fused bicyclic structure at the center of the formula (41). Specific examples of the "substituted or unsubstituted heterocycle having 5 to 50 ring atoms" include a compound formed by introducing a hydrogen atom to the "heterocyclic group" described in the specific example group G2.

$R_{401}$ and $R_{402}$ are optionally each independently bonded with the a ring, b ring, or c ring to form a substituted or unsubstituted heterocycle. The "heterocycle" in this arrangement includes the nitrogen atom on the fused bicyclic structure at the center of the formula (41). The heterocycle in the above arrangement optionally includes a hetero atom other than the nitrogen atom. $R_{401}$ and $R_{402}$ bonded with the a ring, b ring, or c ring specifically means that atoms forming $R_{401}$ and $R_{402}$ are bonded with atoms forming the a ring, b ring, or c ring. For instance, $R_{401}$ is optionally bonded to the a ring to form a bicyclic (or tri-or-more cyclic) fused nitrogen-containing heterocycle, in which the ring including $R_{401}$ and the a ring are fused. Specific examples of the nitrogen-containing heterocycle include a compound corresponding to the nitrogen-containing bi(or-more)cyclic fused heterocyclic group in the specific example group G2.

The same applies to $R_{401}$ bonded with the b ring, $R_{402}$ bonded with the a ring, and $R_{402}$ bonded with the c ring.

In an exemplary embodiment, the a ring, b ring and c ring in the formula (41) are each independently a substituted or unsubstituted aromatic hydrocarbon ring having 6 to 50 ring carbon atoms.

In an exemplary embodiment, the a ring, b ring and c ring in the formula (41) are each independently a substituted or unsubstituted benzene ring or a substituted or unsubstituted naphthalene ring.

In an exemplary embodiment, $R_{401}$ and $R_{402}$ in the formula (41) are each independently a substituted or unsubstituted aryl group having 6 to 50 ring carbon atoms, or a substituted or unsubstituted monovalent heterocyclic group having 5 to 50 ring atoms, preferably a substituted or unsubstituted aryl group having 6 to 50 ring carbon atoms.

In an exemplary embodiment, the compound represented by the formula (41) is a compound represented by a formula (42) below.

[Formula 202]

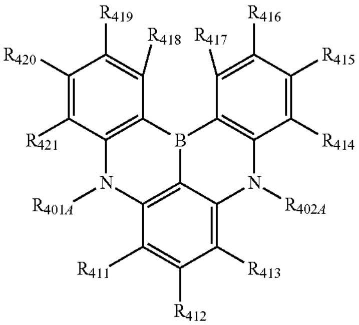

(42)

In the formula (42): $R_{401A}$ is bonded with at least one of $R_{411}$ or $R_{421}$ to form a substituted or unsubstituted heterocycle, or not bonded therewith to form no substituted or unsubstituted heterocycle; $R_{402A}$ is bonded with at least one of $R_{413}$ or $R_{414}$ to form a substituted or unsubstituted heterocycle, or not bonded therewith to form no substituted or unsubstituted heterocycle;

$R_{401A}$ and $R_{402A}$ not forming the substituted or unsubstituted heterocycle are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

at least one combination of adjacent two or more of $R_{411}$ to $R_{421}$ are mutually bonded to form a substituted or unsubstituted monocyclic ring or a substituted or unsubstituted fused ring, or not mutually bonded;

$R_{411}$ to $R_{421}$ forming neither the substituted or unsubstituted heterocycle nor the substituted or unsubstituted monocyclic ring and not forming the substituted or unsubstituted fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ each independently represent the same as $R_{901}$ to $R_{907}$ in the formula (11).

$R_{401A}$ and $R_{402A}$ in the formula (42) are groups corresponding to $R_{401}$ and $R_{402}$ in the formula (41), respectively.

For instance, $R_{401A}$ and $R_{411}$ are optionally bonded with each other to form a bicyclic (or tri-or-more cyclic) nitrogen-containing heterocycle, in which the ring including $R_{401A}$ and $R_{411}$ and a benzene ring corresponding to the a ring are fused. Specific examples of the nitrogen-containing heterocycle include a compound corresponding to the nitrogen-containing bi(or-more)cyclic fused heterocyclic group in the specific example group G2. The same applies to $R_{401A}$ bonded with $R_{412}$, $R_{402A}$ bonded with $R_{413}$, and $R_{402A}$ bonded with $R_{414}$.

At least one combination of adjacent two or more of $R_{411}$ to $R_{421}$ are optionally mutually bonded to form a substituted or unsubstituted saturated or unsaturated ring. For instance, $R_{11}$ and $R_{12}$ are optionally mutually bonded to form a structure in which a benzene ring, indole ring, pyrrole ring, benzofuran ring, benzothiophene ring or the like is fused to the six-membered ring bonded with $R_{11}$ and $R_{12}$, the resultant fused ring forming a naphthalene ring, carbazole ring, indole ring, dibenzofuran ring, or dibenzothiophene ring, respectively.

In an exemplary embodiment, $R_{411}$ to $R_{421}$ not contributing to ring formation are each independently a hydrogen atom, a substituted or unsubstituted alkyl group having 1 to 50 carbon atoms, a substituted or unsubstituted aryl group having 6 to 50 ring carbon atoms, or a substituted or unsubstituted monovalent heterocyclic group having 5 to 50 ring atoms.

In an exemplary embodiment, $R_{411}$ to $R_{421}$ not contributing to ring formation are each independently a hydrogen atom, a substituted or unsubstituted aryl group having 6 to 50 ring carbon atoms, or a substituted or unsubstituted monovalent heterocyclic group having 5 to 50 ring atoms.

In an exemplary embodiment, $R_{411}$ to $R_{421}$ not contributing to ring formation are each independently a hydrogen atom or a substituted or unsubstituted alkyl group having 1 to 50 carbon atoms.

In an exemplary embodiment, $R_{411}$ to $R_{421}$ not contributing to ring formation are each independently a hydrogen atom or a substituted or unsubstituted alkyl group having 1 to 50 carbon atoms, at least one of $R_{411}$ to $R_{421}$ being a substituted or unsubstituted alkyl group having 1 to 50 carbon atoms.

In an exemplary embodiment, the compound represented by the formula (42) is a compound represented by a formula (43) below.

[Formula 203]

(43)

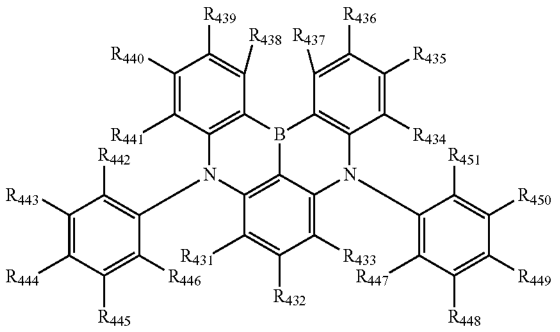

In the formula (43): $R_{431}$ is bonded with $R_{446}$ to form a substituted or unsubstituted heterocycle, or not bonded therewith to form no substituted or unsubstituted heterocycle; $R_{433}$ is bonded with $R_{447}$ to form a substituted or unsubstituted heterocycle, or not bonded therewith to form no substituted or unsubstituted heterocycle; $R_{434}$ is bonded with $R_{451}$ to form a substituted or unsubstituted heterocycle, or not bonded therewith to form no substituted or unsubstituted heterocycle; $R_{441}$ is bonded with $R_{442}$ to form a substituted or unsubstituted heterocycle, or not bonded therewith to form no substituted or unsubstituted heterocycle;

at least one combination of adjacent two or more of $R_{431}$ to $R_{451}$ are mutually bonded to form a substituted or unsubstituted monocyclic ring or a substituted or unsubstituted fused ring, or not mutually bonded;

$R_{431}$ to $R_{451}$ forming neither the substituted or unsubstituted heterocycle nor the substituted or unsubstituted monocyclic ring and not forming the substituted or unsubstituted fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ each independently represent the same as $R_{901}$ to $R_{907}$ in the formula (11).

$R_{431}$ is optionally bonded with $R_{446}$ to form a substituted or unsubstituted heterocycle. For instance, a combination of $R_{431}$ and $R_{446}$ are optionally bonded with each other to form a tri-or-more cyclic nitrogen-containing heterocycle, in which a benzene ring bonded with $R_{46}$, a ring including a nitrogen atom, and a benzene ring corresponding to the a ring are fused. Specific examples of the nitrogen-containing heterocycle include a compound corresponding to the nitrogen-containing tri(-or-more)cyclic fused heterocyclic group in the specific example group G2. The same applies when a combination of $R_{433}$ and $R_{447}$ are bonded, when a combination of $R_{434}$ and $R_{451}$ are bonded, and when a combination of $R_{441}$ and $R_{442}$ are bonded.

In an exemplary embodiment, $R_{431}$ to $R_{451}$ not contributing to ring formation are each independently a hydrogen atom, a substituted or unsubstituted alkyl group having 1 to 50 carbon atoms, a substituted or unsubstituted aryl group having 6 to 50 ring carbon atoms, or a substituted or unsubstituted monovalent heterocyclic group having 5 to 50 ring atoms.

In an exemplary embodiment, $R_{431}$ to $R_{451}$ not contributing to ring formation are each independently a hydrogen atom, a substituted or unsubstituted aryl group having 6 to 50 ring carbon atoms, or a substituted or unsubstituted monovalent heterocyclic group having 5 to 50 ring atoms.

In an exemplary embodiment, $R_{431}$ to $R_{451}$ not contributing to ring formation are each independently a hydrogen atom or a substituted or unsubstituted alkyl group having 1 to 50 carbon atoms.

In an exemplary embodiment, $R_{431}$ to $R_{451}$ not contributing to ring formation are each independently a hydrogen atom or a substituted or unsubstituted alkyl group having 1 to 50 carbon atoms, at least one of $R_{431}$ to $R_{451}$ being a substituted or unsubstituted alkyl group having 1 to 50 carbon atoms.

In an exemplary embodiment, the compound represented by the formula (43) is a compound represented by a formula (43A) below.

[Formula 204]

(43A)

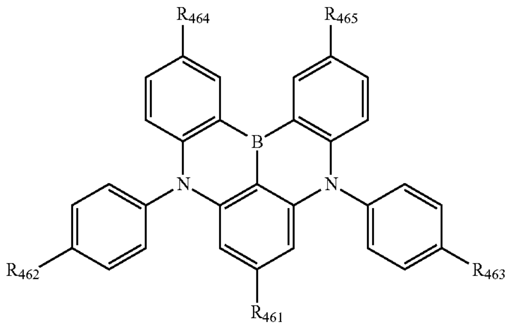

In the formula (43A): $R_{461}$ is a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms; and $R_{462}$ to $R_{465}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In an exemplary embodiment, $R_{461}$ to $R_{465}$ are each independently a substituted or unsubstituted alkyl group having 1 to 50 carbon atoms or a substituted or unsubstituted aryl group having 6 to 50 ring carbon atoms.

In an exemplary embodiment, $R_{461}$ to $R_{465}$ are each independently a substituted or unsubstituted alkyl group having 1 to 50 carbon atoms.

In an exemplary embodiment, the compound represented by the formula (43) is a compound represented by a formula (43B) below.

[Formula 205]

(43B)

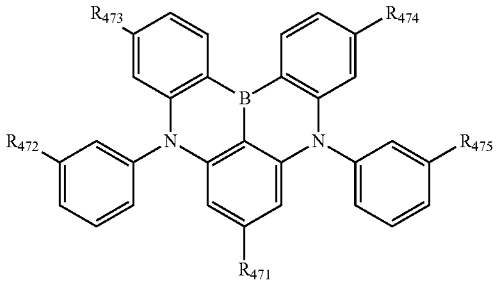

In the formula (43B): $R_{471}$ and $R_{472}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —N($R_{906}$)($R_{907}$), or a substituted or unsubstituted aryl group having 6 to 50 ring carbon atoms;

$R_{473}$ to $R_{475}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —N($R_{906}$)($R_{907}$), or a substituted or unsubstituted aryl group having 6 to 50 ring carbon atoms; and $R_{906}$ and $R_{907}$ each independently represent the same as $R_{906}$ and $R_{907}$ in the formula (11).

In an exemplary embodiment, the compound represented by the formula (43) is a compound represented by a formula (43B') below.

[Formula 206]

(43B')

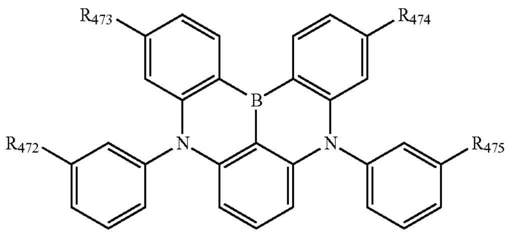

In the formula (43B'): $R_{472}$ to $R_{475}$ each independently represent the same as $R_{472}$ to $R_{475}$ in the formula (43B).

In an exemplary embodiment, at least one of $R_{471}$ to $R_{475}$ is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —N($R_{906}$)($R_{907}$), or a substituted or unsubstituted aryl group having 6 to 50 ring carbon atoms.

In an exemplary embodiment, $R_{472}$ is a hydrogen atom, a substituted or unsubstituted alkyl group having 1 to 50 carbon atoms, —N($R_{906}$)($R_{907}$), or a substituted or unsubstituted aryl group having 6 to 50 ring carbon atoms; and $R_{471}$ and $R_{473}$ to $R_{475}$ are each independently a substituted or unsubstituted alkyl group having 1 to 50 carbon atoms, —N($R_{906}$)($R_{907}$), or a substituted or unsubstituted aryl group having 6 to 50 ring carbon atoms.

In an exemplary embodiment, the compound represented by the formula (43) is a compound represented by a formula (43C) below.

[Formula 207]

(43C)

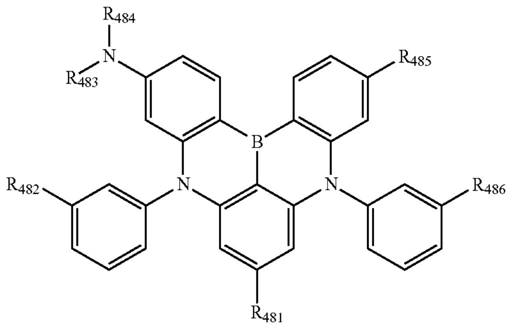

In the formula (43C):

$R_{481}$ and $R_{482}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms; and $R_{483}$ to $R_{486}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In an exemplary embodiment, the compound represented by the formula (43) is a compound represented by a formula (43C') below.

[Formula 208]

(43C')

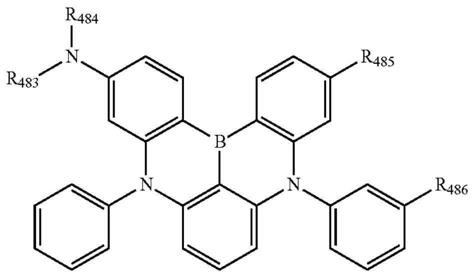

In the formula (43C'): $R_{483}$ to $R_{486}$ each independently represent the same as $R_{483}$ to $R_{486}$ in the formula (43C).

In an exemplary embodiment, $R_{481}$ to $R_{486}$ are each independently a substituted or unsubstituted alkyl group having 1 to 50 carbon atoms or a substituted or unsubstituted aryl group having 6 to 50 ring carbon atoms.

In an exemplary embodiment, $R_{481}$ to $R_{486}$ are each independently a substituted or unsubstituted aryl group having 6 to 50 ring carbon atoms.

The compound represented by the formula (41) is producible by initially bonding the a ring, b ring and c ring with linking groups (a group including N—$R_1$ and a group including N—$R_2$) to form an intermediate (first reaction), and bonding the a ring, b ring and c ring with a linking group (a group including a boron atom) to form a final product (second reaction). In the first reaction, an amination reaction (e.g. Buchwald-Hartwig reaction) is applicable. In the second reaction, Tandem Hetero-Friedel-Crafts Reactions or the like is applicable.

Specific examples of the compound represented by the formula (41) include compounds shown below.

[Formula 209]

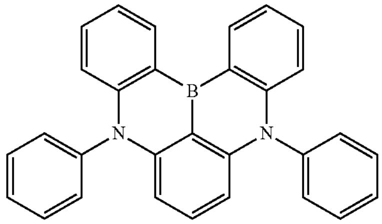

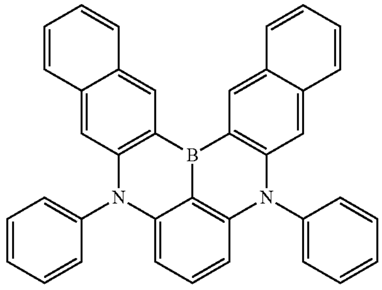

-continued
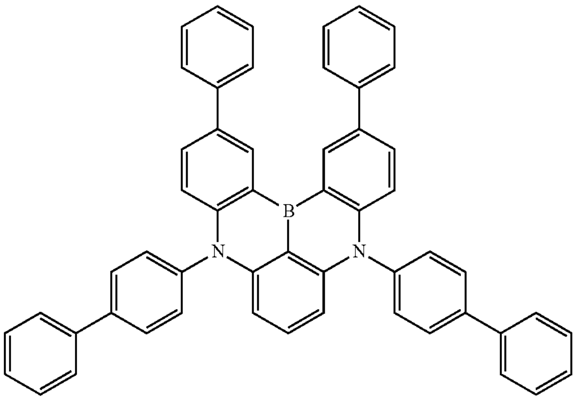
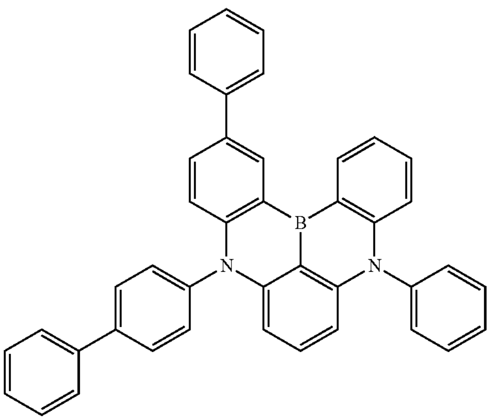
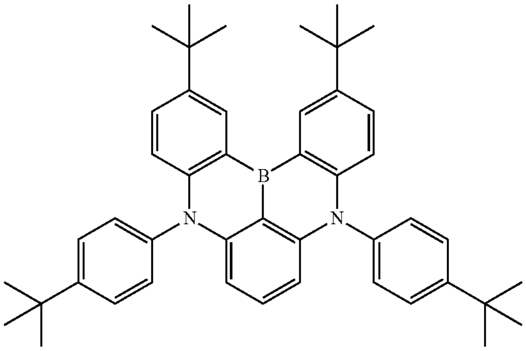
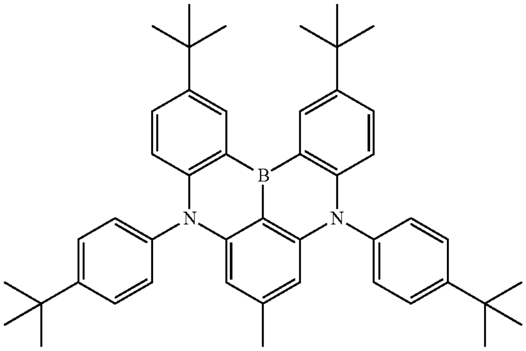
-continued
[Formula 210]
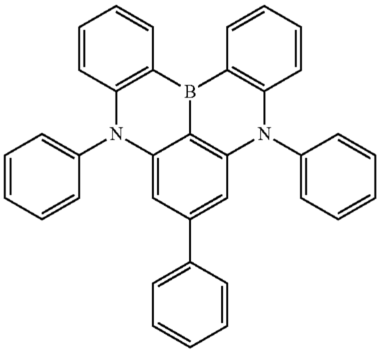
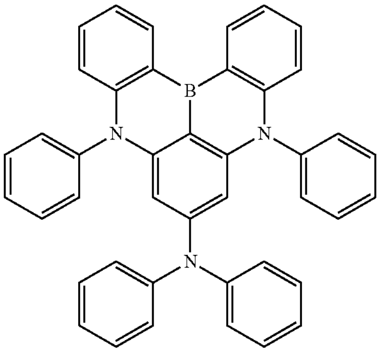
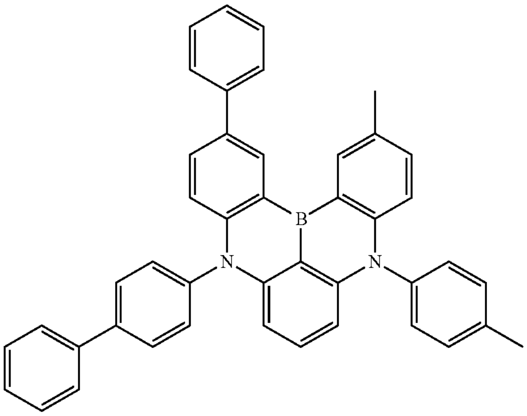
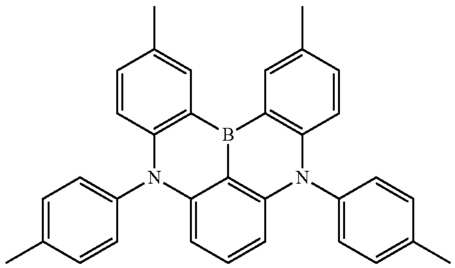

[Formula 211]
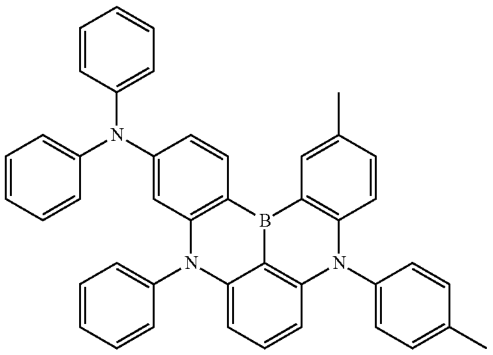
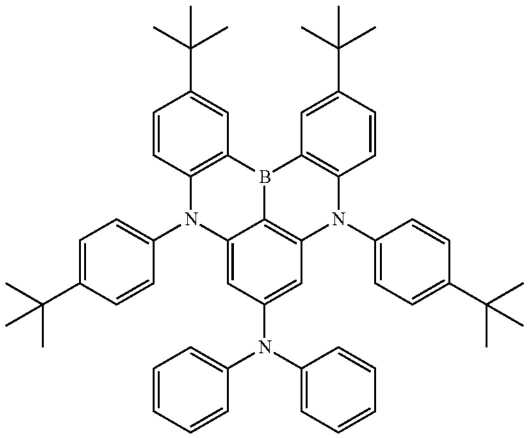
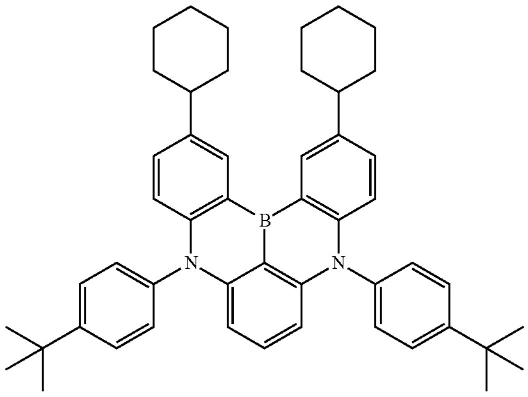
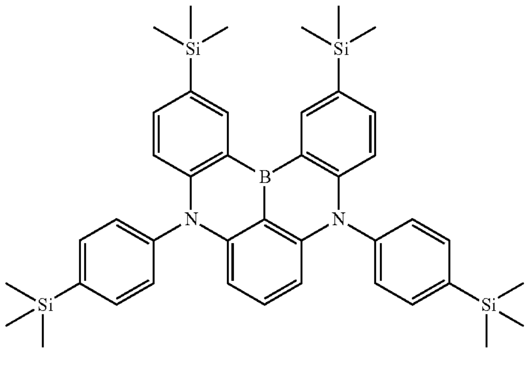
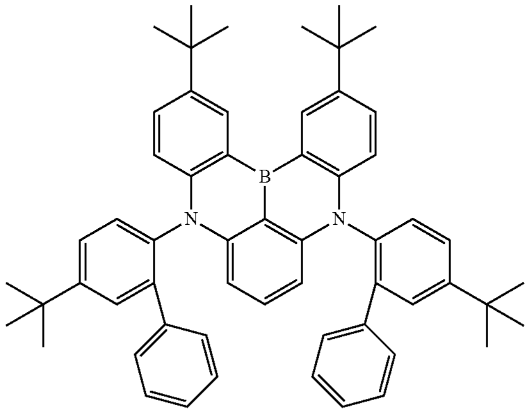
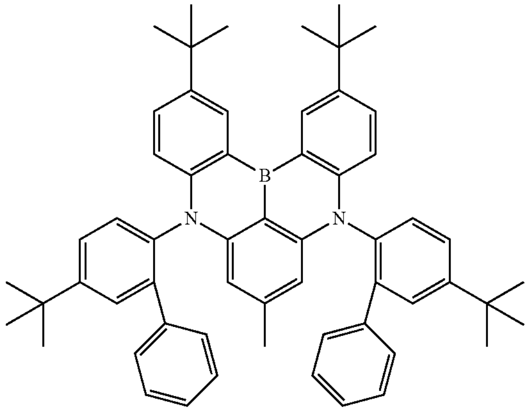
[Formula 212]
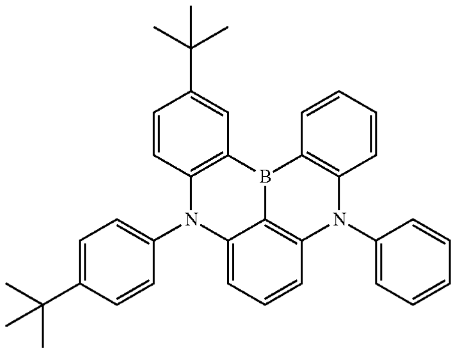
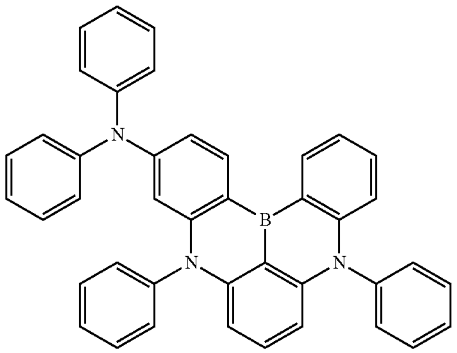

-continued
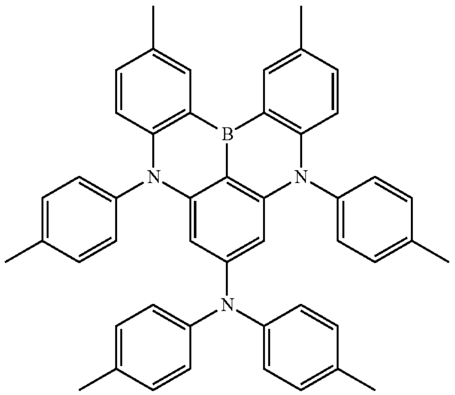
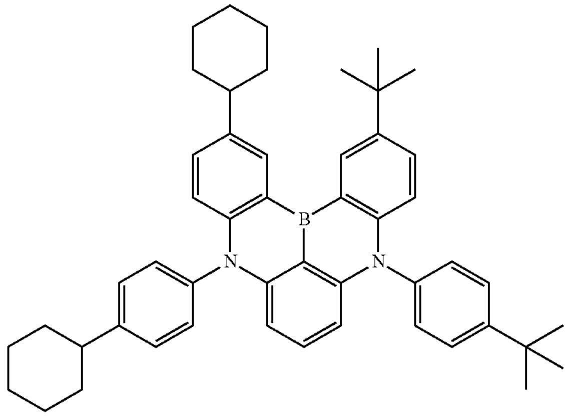
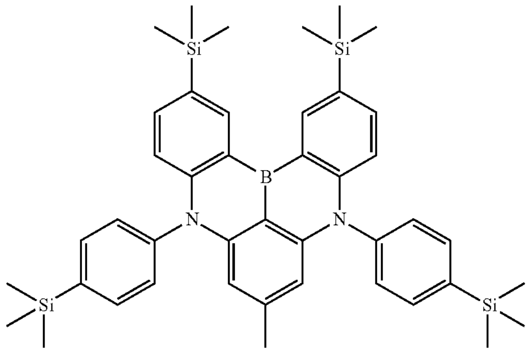
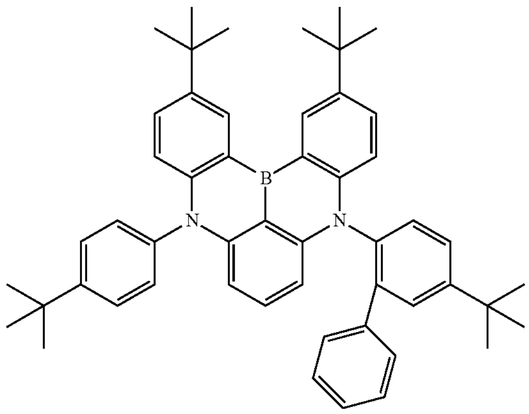
-continued
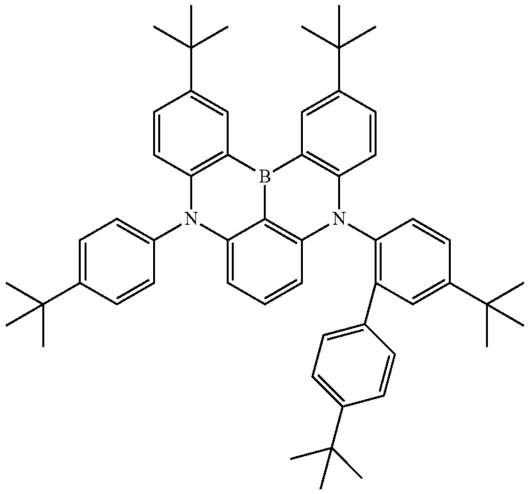
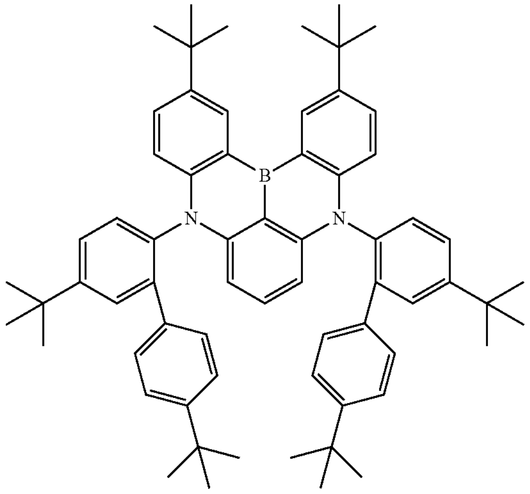
[Formula 213]
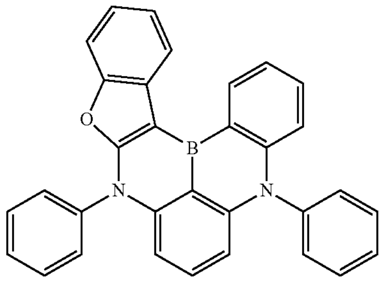
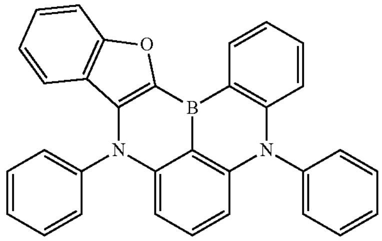

-continued

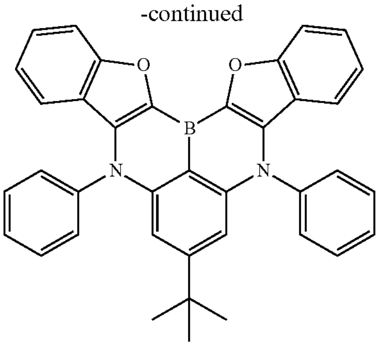

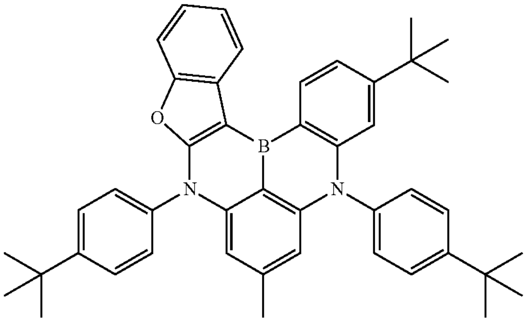

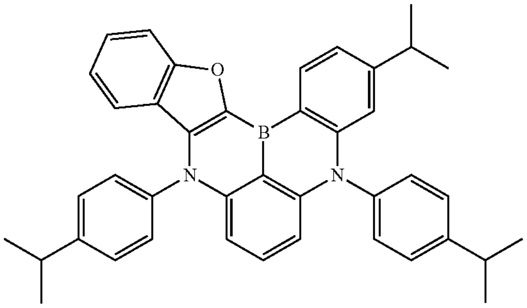

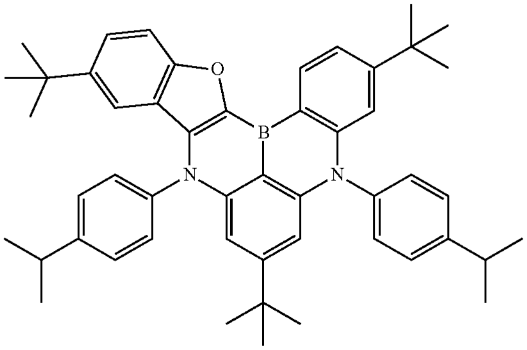

Compound Represented by Formula (51)

The compound represented by the formula (51) will be described.

[Formula 214]

(51)

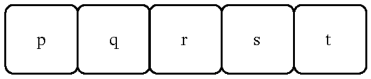

(52)

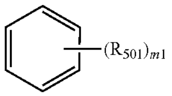

-continued (53)

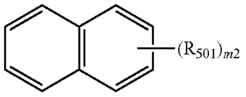

(54)

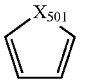

(55)

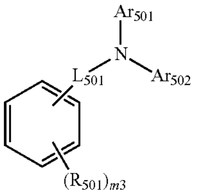

(56)

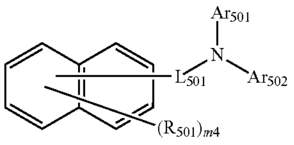

In the formula (51):

r ring is a ring represented by the formula (52) or the formula (53), the r ring being fused with adjacent ring(s) at any position(s);

q ring and s ring are each independently a ring represented by the formula (54) and fused with adjacent ring(s) at any position(s);

p ring and t ring are each independently a structure represented by the formula (55) or the formula (56) and fused with adjacent ring(s) at any position(s);

when a plurality of $R_{501}$ are present, adjacent ones of the plurality of $R_{501}$ are mutually bonded to form a substituted or unsubstituted monocyclic ring or a substituted or unsubstituted fused ring, or not mutually bonded;

$X_{501}$ is an oxygen atom, a sulfur atom, or $NR_{502}$;

$R_{501}$ and $R_{502}$ forming neither the substituted or unsubstituted monocyclic ring nor the substituted or unsubstituted fused ring are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ each independently represent the same as $R_{901}$ to $R_{907}$ in the formula (11);

$Ar_{501}$ to $Ar_{502}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms;

$L_{501}$ is a substituted or unsubstituted alkylene group having 1 to 50 carbon atoms, a substituted or unsubstituted alkenylene group having 2 to 50 carbon atoms, a substituted or unsubstituted alkynylene group having 2 to 50 carbon atoms, a substituted or unsubstituted cycloalkylene group having 3 to 50 ring carbon atoms, a substituted or unsubstituted arylene group having 6 to 50 ring carbon atoms, or a substituted or unsubstituted divalent heterocyclic group having 5 to 50 ring atoms;

m1 is an integer in a range from 0 to 2, m2 is an integer in a range from 0 to 4, m3 is each independently an integer in a range from 0 to 3, and m4 is each independently an integer in a range from 0 to 5; and when a plurality of $R_{501}$ are present, the plurality of $R_{501}$ are mutually the same or different.

In the formula (51), each of the p to t rings is fused with an adjacent ring(s) sharing two carbon atoms. The fused position and orientation are not limited but may be defined as required.

In an exemplary embodiment, in the formula (52) or (53) for the r ring, $R_{501}$ is a hydrogen atom.

In an exemplary embodiment, the compound represented by the formula (51) is represented by any one of formulae (51-1) to (51-6) below.

[Formula 215]

(51-1)

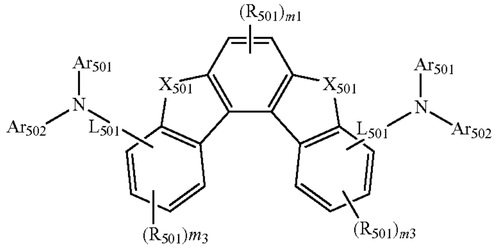

(51-2)

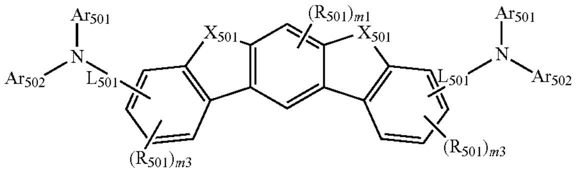

(51-3)

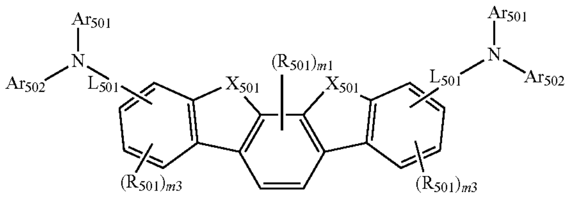

(51-4)

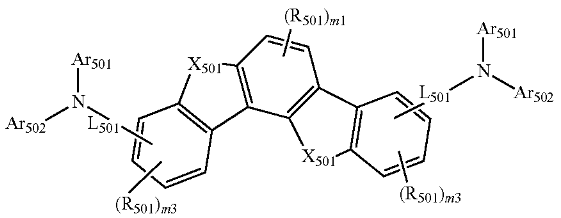

-continued (51-5)

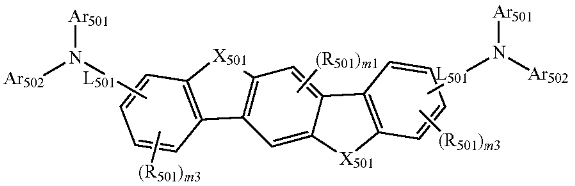

(51-6)

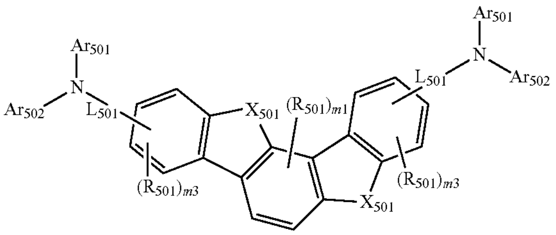

In the formulae (51-1) to (51-6): $R_{501}$, $X_{501}$, $Ar_{501}$, $Ar_{502}$, $L_{501}$, m1 and m3 each independently represent the same as $R_{501}$, $X_{501}$, $Ar_{501}$, $Ar_{502}$, $L_{501}$, m1 and m3 in the formula (51).

In an exemplary embodiment, the compound represented by the formula (51) is represented by any one of formulae (51-11) to (51-13) below.

[Formula 216]

(51-11)

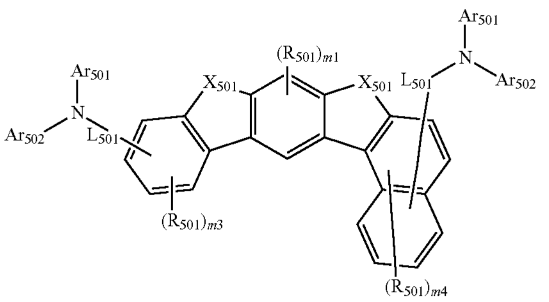

(51-12)

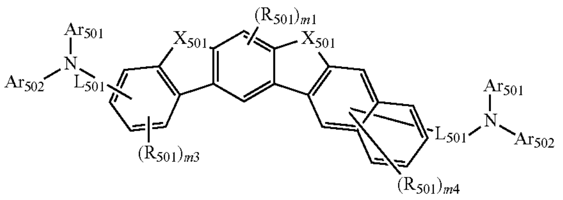

(51-13)

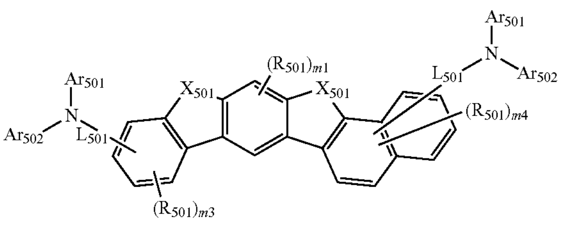

In the formulae (51-11) to (51-13): $R_{501}$, $X_{501}$, $Ar_{501}$, $Ar_{502}$, $L_{501}$, m1, m3, and m4 each independently represent the same as $R_{501}$, $X_{501}$, $Ar_{501}$, $Ar_{502}$, $L_{501}$, m1, m3, and m4 in the formula (51).
In an exemplary embodiment, the compound represented by the formula (51) is represented by any one of formulae (51-21) to (51-25) below.
[Formula 217]
(51-21)
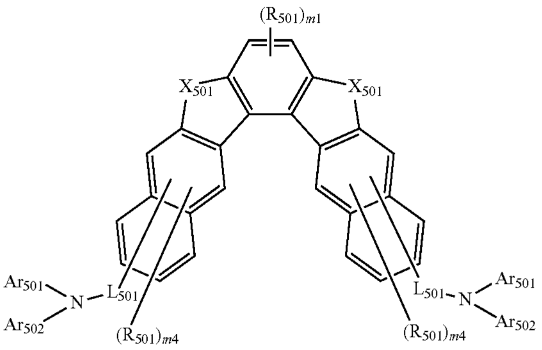
(51-22)
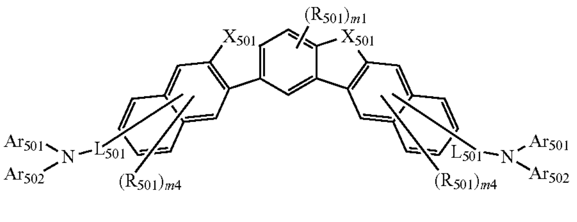
(51-23)
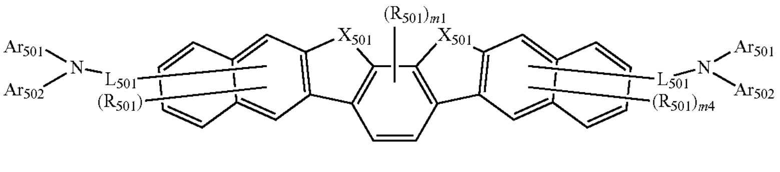
(51-24)
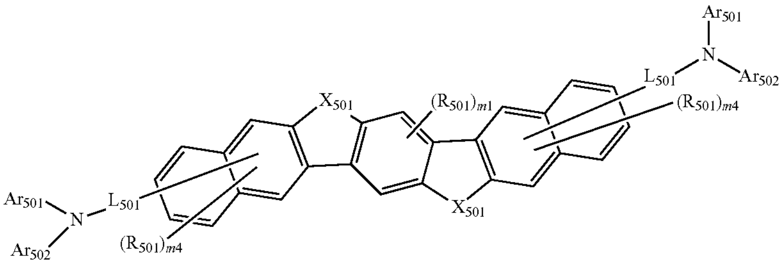
(51-25)
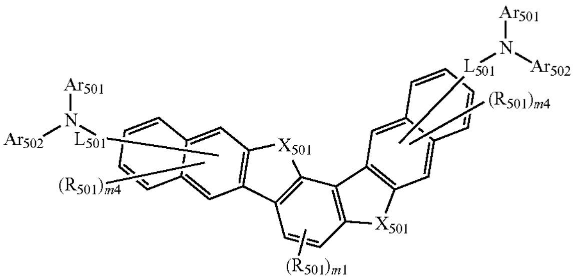

In the formulae (51-21) to (51-25): $R_{501}$, $X_{501}$, $Ar_{501}$, $Ar_{502}$, $L_{501}$, m1 and m4 each independently represent the same as $R_{501}$, $X_{501}$, $Ar_{501}$, $Ar_{502}$, $L_{501}$, m1 and m4 in the formula (51).

In an exemplary embodiment, the compound represented by the formula (51) is represented by any one of formulae (51-31) to (51-33) below.

[Formula 218]

(51-31)

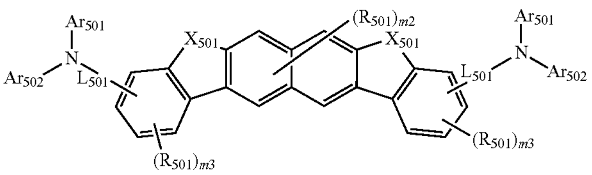

(51-32)

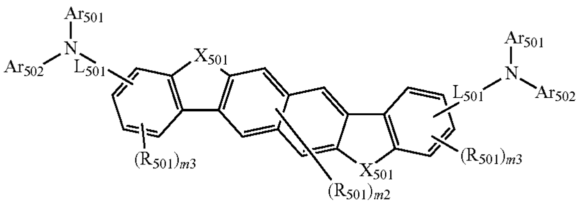

(51-33)

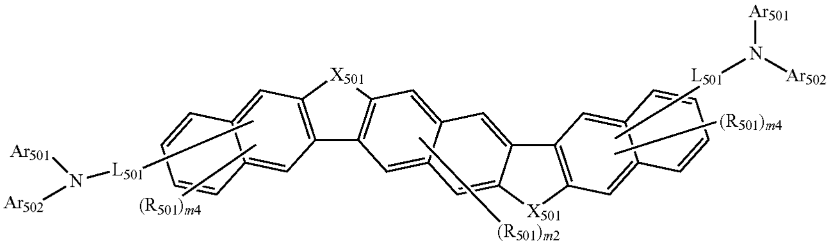

In the formulae (51-31) to (51-33): $R_{501}$, $X_{501}$, $Ar_{501}$, $Ar_{502}$, $L_{501}$, and m1 to m4 each independently represent the same as $R_{501}$, $X_{501}$, $Ar_{501}$, $Ar_{502}$, $L_{501}$, and m1 to m4 in the formula (51).

In an exemplary embodiment, $Ar_{501}$ and $Ar_{502}$ are each independently a substituted or unsubstituted aryl group having 6 to 50 ring carbon atoms.

In an exemplary embodiment, one of $Ar_{501}$ and $Ar_{502}$ is a substituted or unsubstituted aryl group having 6 to 50 ring carbon atoms and the other of $Ar_{501}$ and $Ar_{502}$ is a substituted or unsubstituted monovalent heterocyclic group having 5 to 50 ring atoms.

Specific examples of the compound represented by the formula (51) include compounds shown below.

[Formula 219]

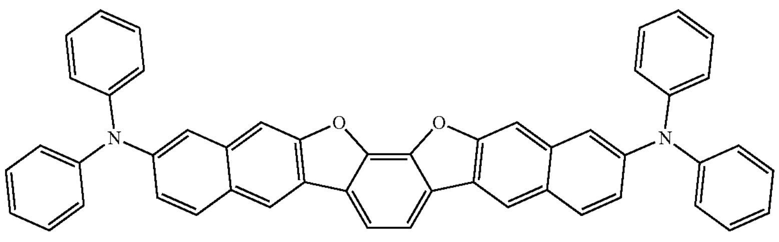

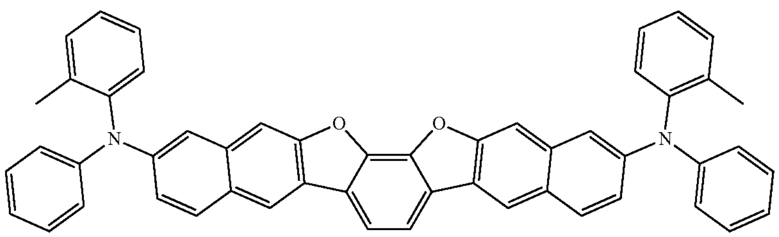

-continued
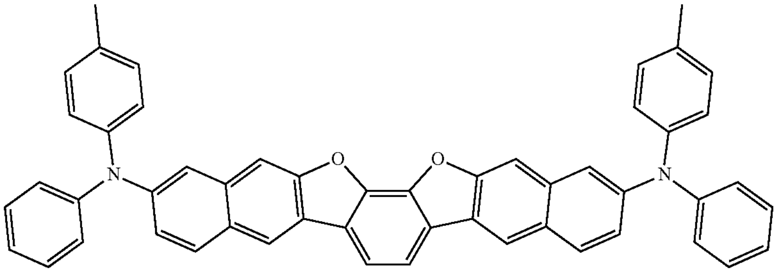
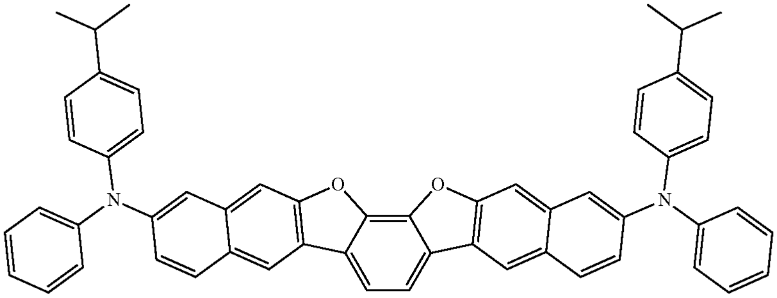
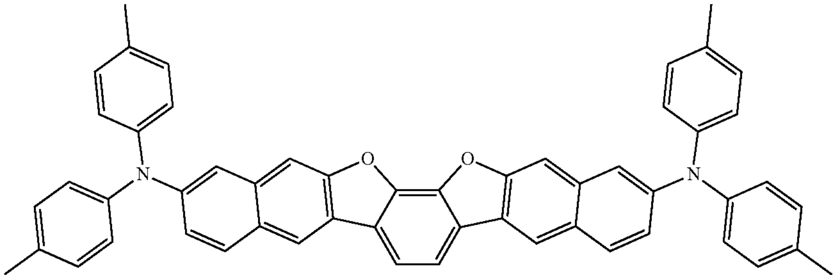
[Formula 220]
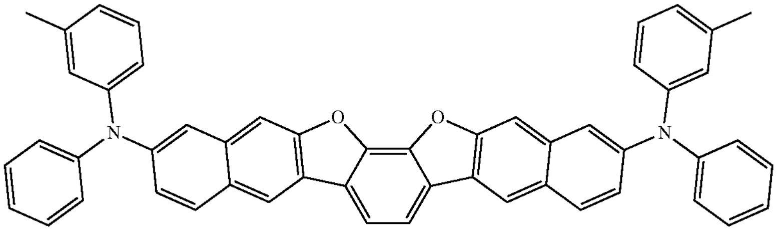
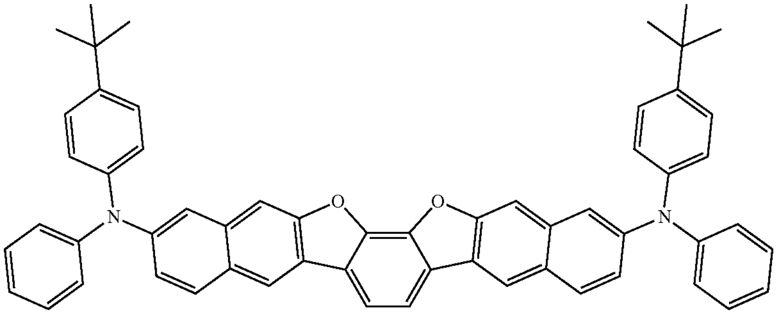
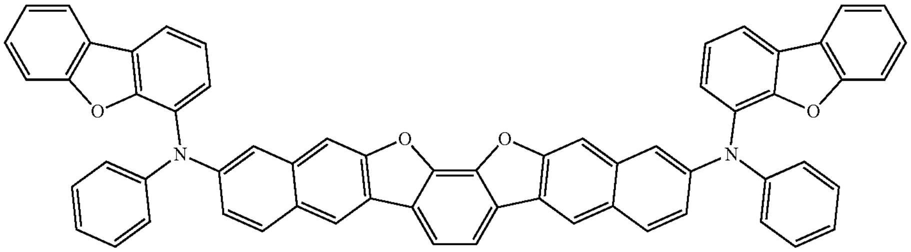

-continued
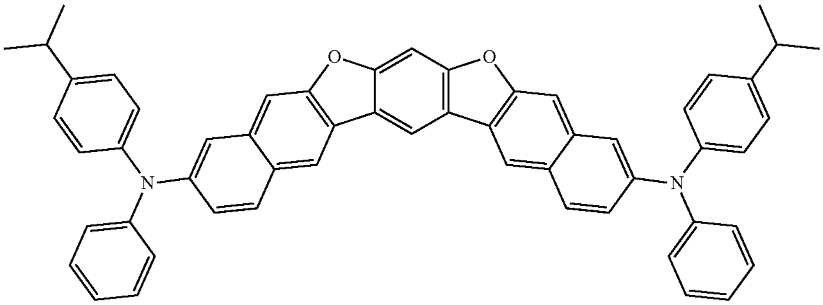
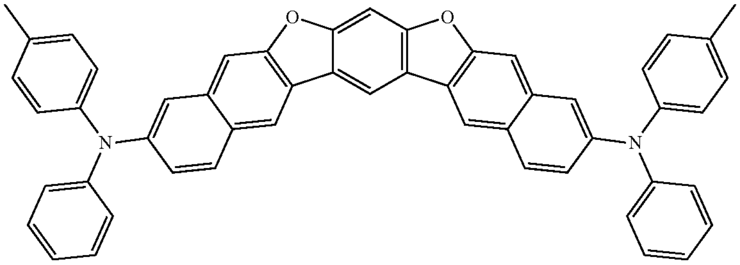
[Formula 221]
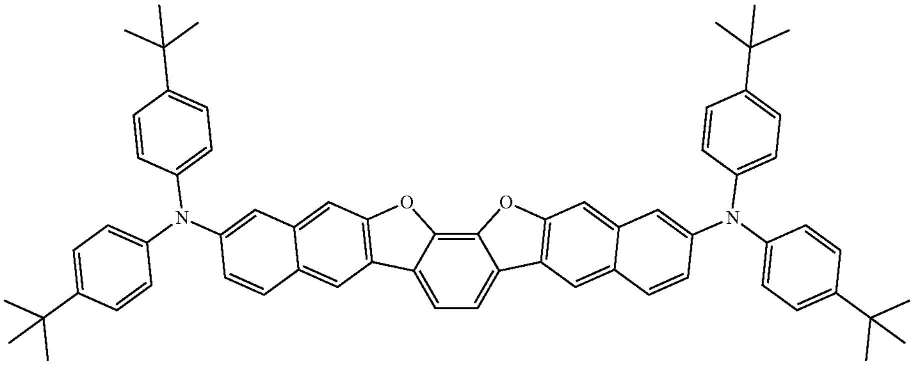
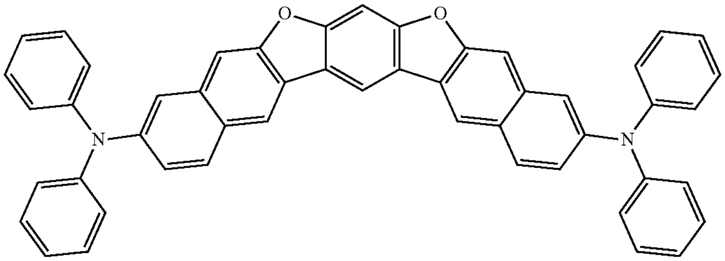
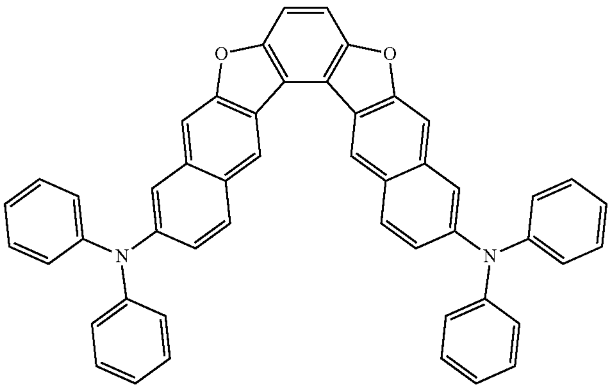

-continued
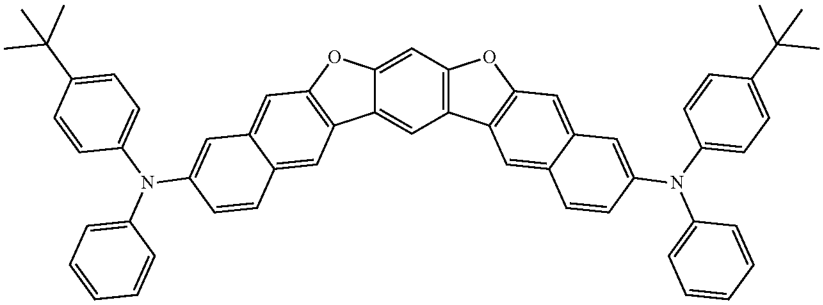
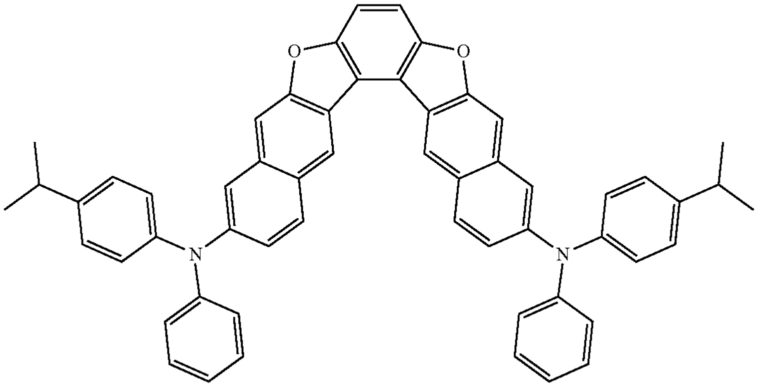
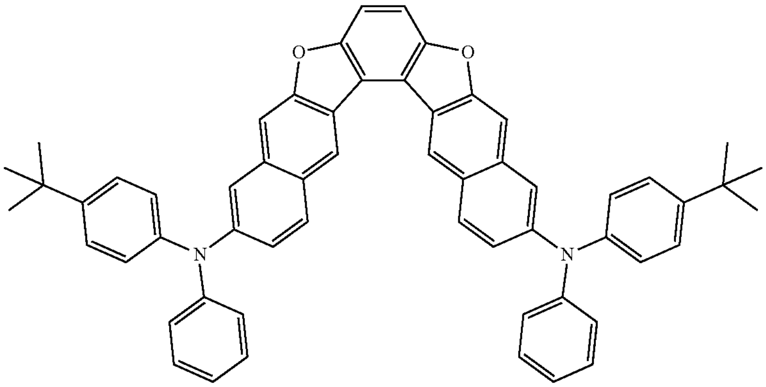
[Formula 222]
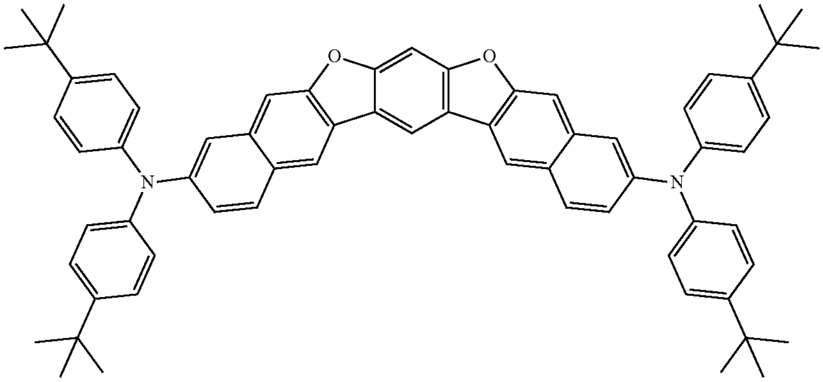

-continued
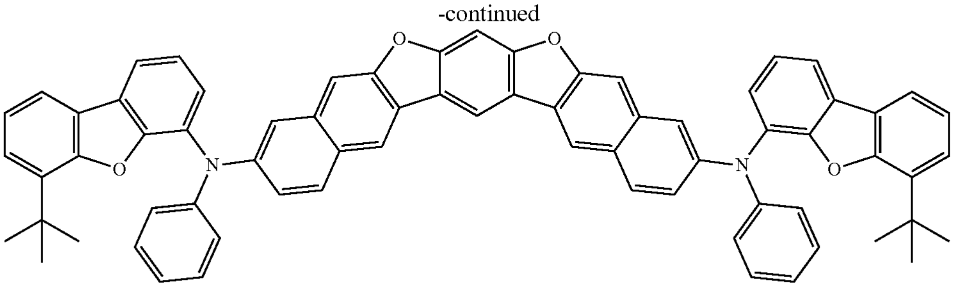
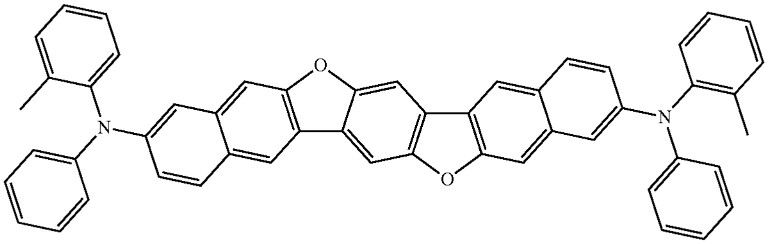
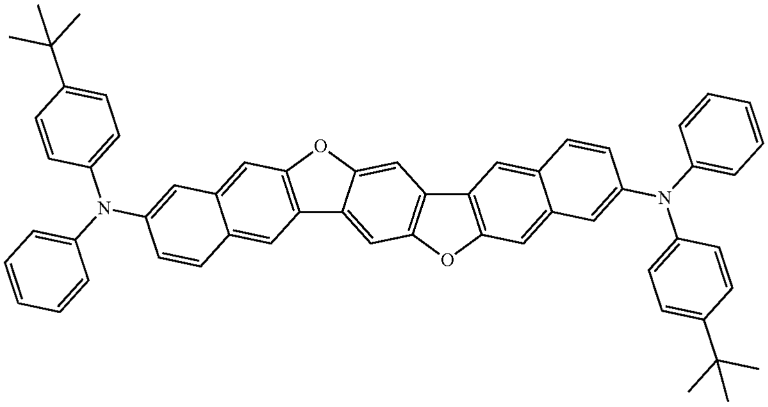
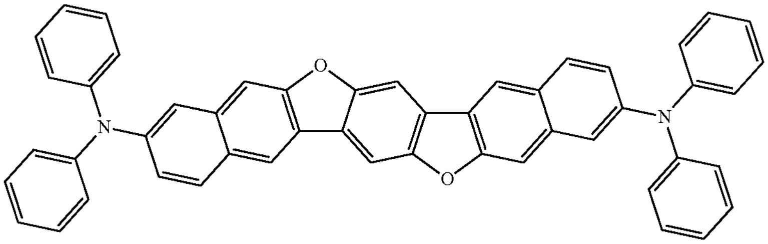
[Formula 223]
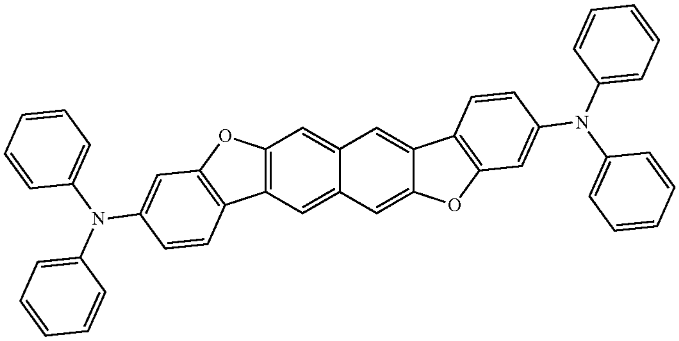

-continued

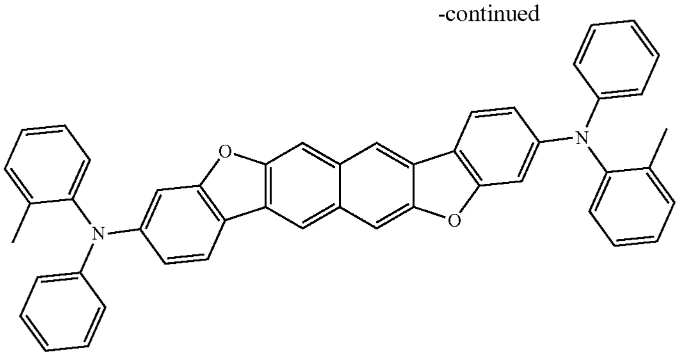

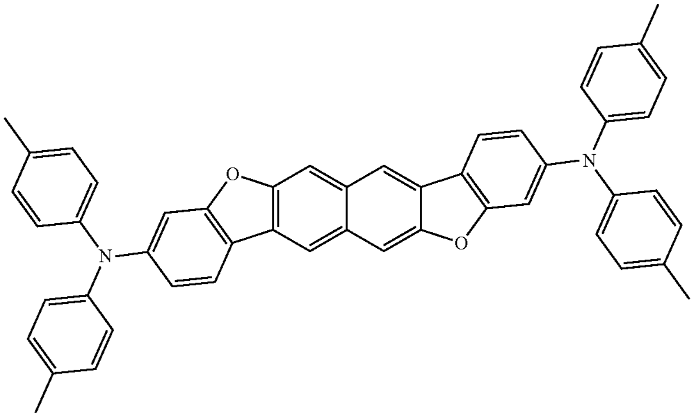

Compound Represented by Formula (61)

The compound represented by the formula (61) will be described.

[Formula 224]

(61)

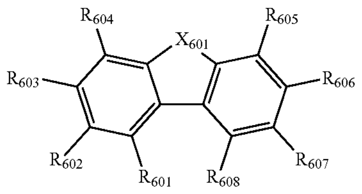

In the formula (61):

at least one combination of $R_{601}$ and $R_{602}$, $R_{602}$ and $R_{603}$, or $R_{603}$ and $R_{604}$ are mutually bonded to form a divalent group represented by a formula (62) below; and at least one combination of $R_{605}$ and $R_{606}$, $R_{606}$ and $R_{607}$, or $R_{607}$ and $R_{608}$ are mutually bonded to form a divalent group represented by a formula (63) below.

[Formula 225]

(62)

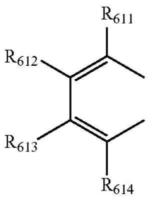

-continued (63)

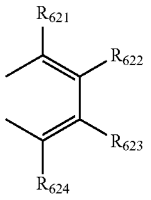

At least one of $R_{601}$ to $R_{604}$ not forming the divalent group represented by the formula (62) or $R_{611}$ to $R_{614}$ is a monovalent group represented by a formula (64) below;

at least one of $R_{605}$ to $R_{608}$ not forming the divalent group represented by the formula (63) or $R_{621}$ to $R_{624}$ is a monovalent group represented by the formula (64) below;

$X_{601}$ is an oxygen atom, a sulfur atom, or $NR_{609}$;

$R_{601}$ to $R_{608}$ not forming the divalent group represented by the formula (62) or (63) and not being the monovalent group represented by the formula (64), $R_{611}$ to $R_{614}$ and $R_{621}$ to $R_{624}$ not being the monovalent group represented by the formula (64), and $R_{609}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ each independently represent the same as $R_{901}$ to $R_{907}$ in the formula (11).

[Formula 226]

(64)

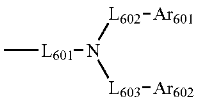

In the formula (64): $Ar_{601}$ and $Ar_{602}$ are each independently a substituted or unsubstituted aryl group having 6 to 50 ring carbon atoms, or a substituted or unsubstituted monovalent heterocyclic group having 5 to 50 ring atoms; and $L_{601}$ to $L_{603}$ are each independently a single bond, a substituted or unsubstituted arylene group having 6 to 30 ring carbon atoms, a substituted or unsubstituted divalent heterocyclic group having 5 to 30 ring atoms, or a divalent linking group formed by bonding two to four of the arylene group(s) and/or the heterocyclic group(s).

In the formula (61), the positions for the divalent group represented by the formula (62) and the divalent group represented by the formula (63) to be formed are not specifically limited but the divalent groups may be formed at any possible positions on $R_{601}$ to $R_{608}$.

In an exemplary embodiment, the compound represented by the formula (61) is represented by any one of formulae (61-1) to (61-6) below.

[Formula 227]

(61-1)

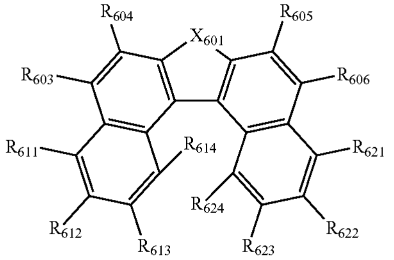

(61-2)

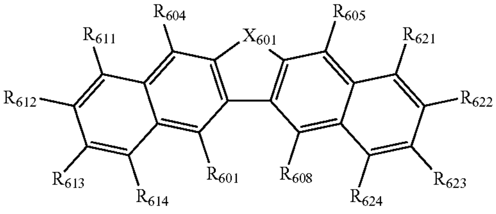

(61-3)

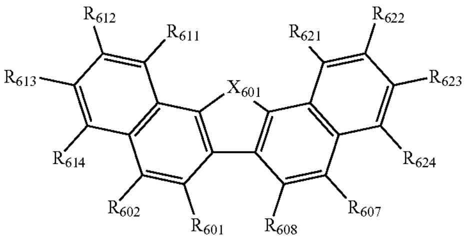

-continued (61-4)

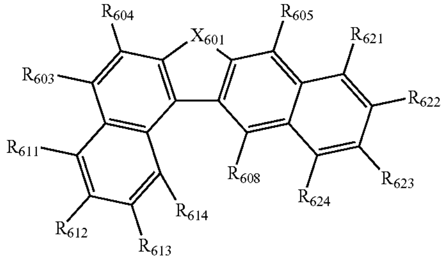

(61-5)

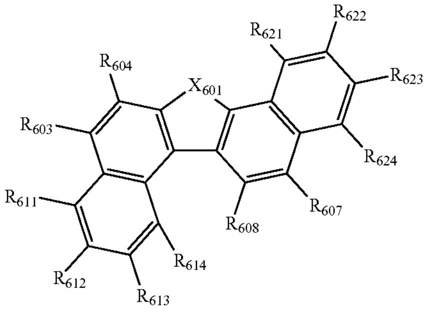

(61-6)

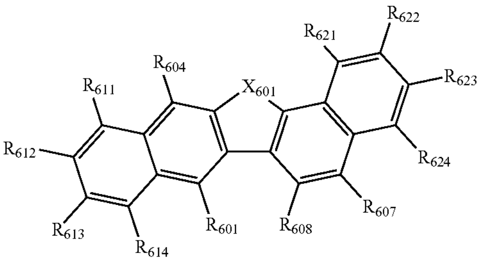

In the formulae (61-1) to (61-6): $X_{601}$ represents the same as $X_{601}$ in the formula (61);

at least two of $R_{601}$ to $R_{624}$ are each a monovalent group represented by the formula (64);

$R_{601}$ to $R_{624}$ not being the monovalent group represented by the formula (64) are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ each independently represent the same as $R_{901}$ to $R_{907}$ in the formula (11).

In an exemplary embodiment, the compound represented by the formula (61) is represented by any one of formulae (61-7) to (61-18) below.

[Formula 228]
(61-7)
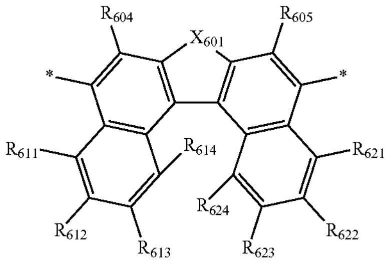
(61-8)
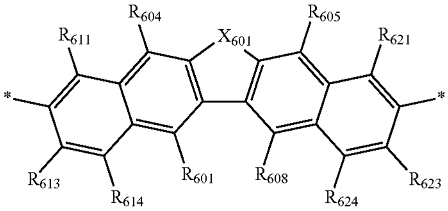
(61-9)
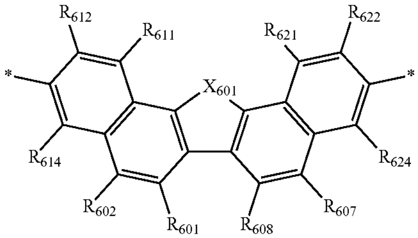
(61-10)
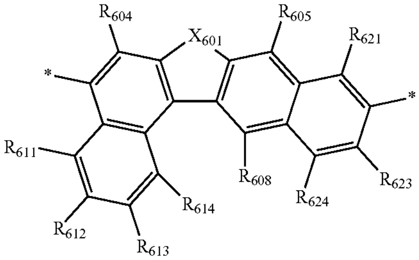
(61-11)
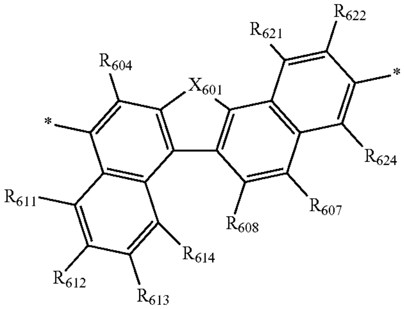
(61-12)
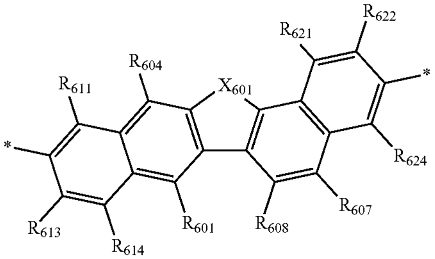
-continued
(61-13)
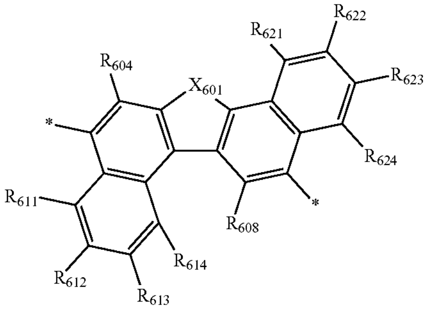
(61-14)
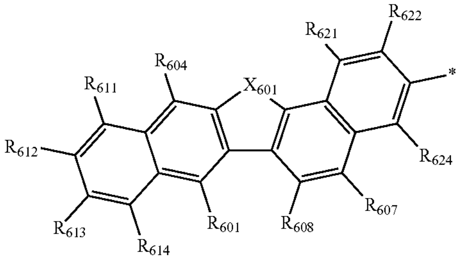
(61-15)
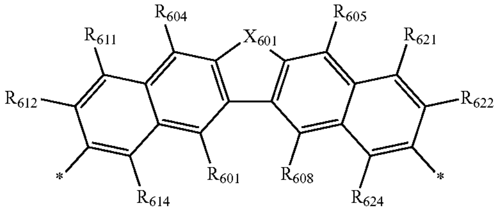
(61-16)
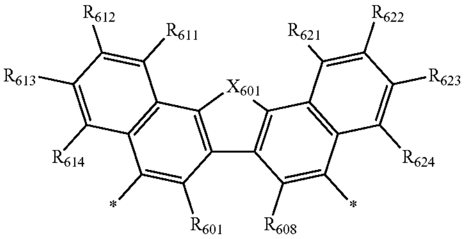
(61-17)
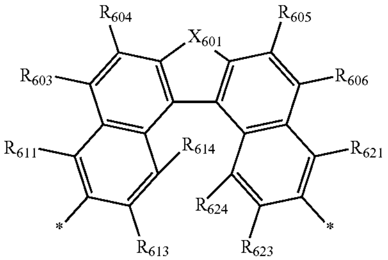

-continued (61-18)

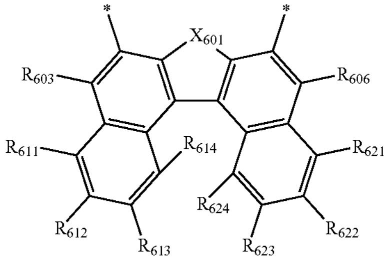

In the formulae (61-7) to (61-18): $X_{601}$ represents the same as $X_{601}$ in the formula (61); * is a single bond to be bonded with the monovalent group represented by the formula (64); and $R_{601}$ to $R_{624}$ each independently represent the same as $R_{601}$ to $R_{624}$ that are not monovalent groups represented by the formula (64).

$R_{601}$ to $R_{608}$ not forming the divalent group represented by the formula (62) or (63) and not being the monovalent group represented by the formula (64), and $R_{611}$ to $R_{614}$ and $R_{621}$ to $R_{624}$ not being the monovalent group represented by the formula (64) are preferably each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted monovalent heterocyclic group having 5 to 50 ring atoms.

The monovalent group represented by the formula (64) is preferably represented by a formula (65) or (66) below.

[Formula 229]

(65)

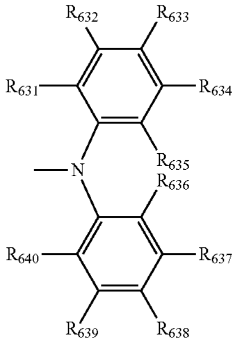

In the formula (65): $R_{631}$ to $R_{640}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$, —O—$(R_{904})$, —S—$(R_{905})$, —$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ each independently represent the same as $R_{901}$ to $R_{907}$ in the formula (11).

[Formula 230]

(66)

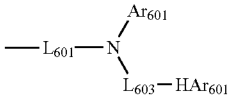

In the formula (66): $Ar_{601}$, $L_{601}$, and $L_{603}$ each independently represent the same as $Ar_{601}$, $L_{601}$, and $L_{603}$ in the formula (64); and $HAr_{601}$ is a structure represented by a formula (67) below.

[Formula 231]

(67)

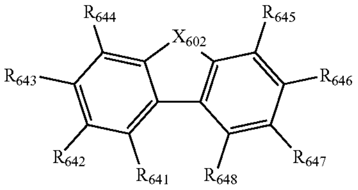

In the formula (67): $X_{602}$ is an oxygen atom or a sulfur atom;

one of $R_{641}$ to $R_{648}$ is a single bond bonded with $L_{603}$;

$R_{641}$ to $R_{648}$ not being the single bond are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —$Si(R_{901})(R_{902})(R_{903})$, —O—$(R_{904})$, —S—$(R_{905})$, —$N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ each independently represent the same as $R_{901}$ to $R_{907}$ in the formula (11).

Specific examples of the compound represented by the formula (61) include compounds shown below as well as the compounds disclosed in WO 2014/104144.

[Formula 232]
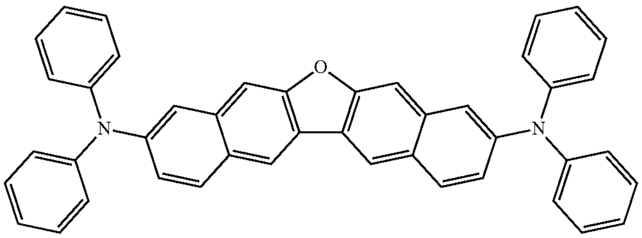
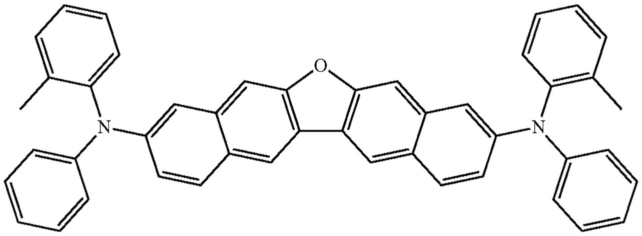
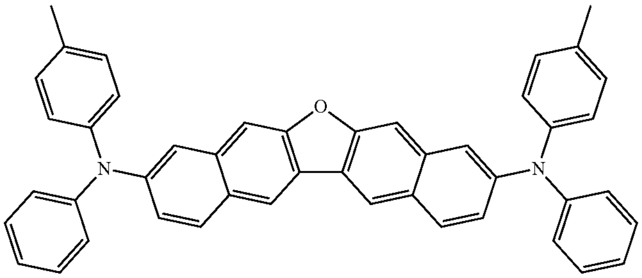
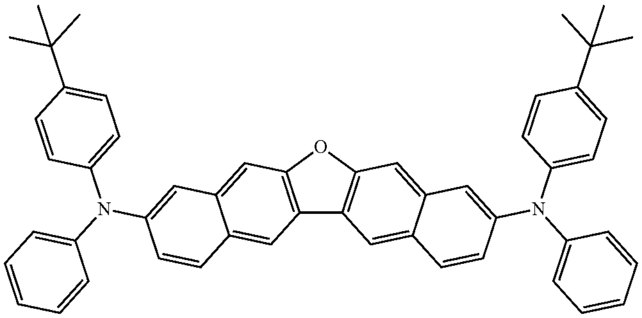
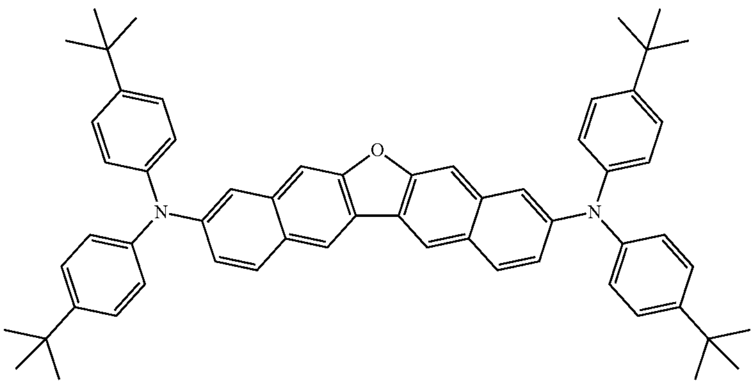

-continued
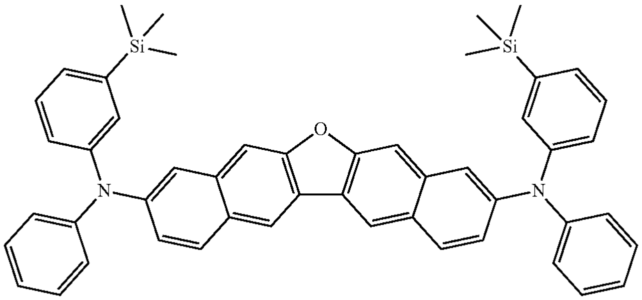
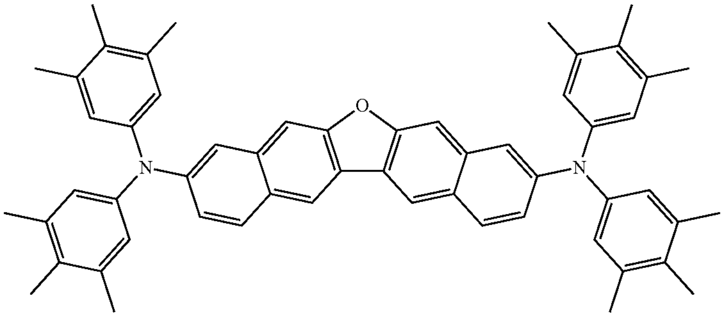
[Formula 233]
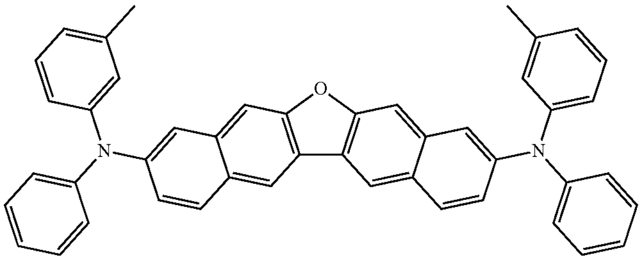
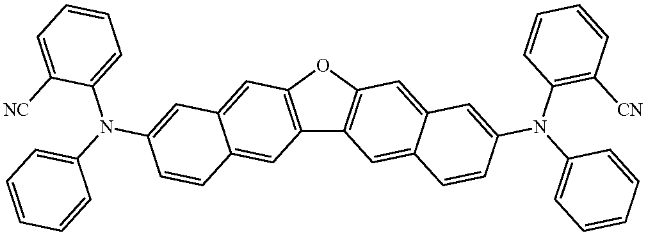
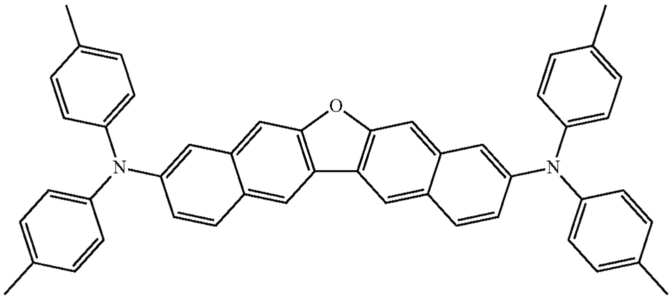
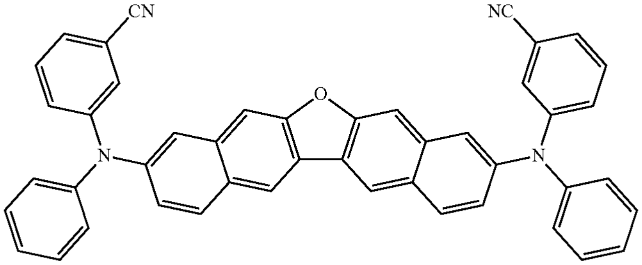

-continued
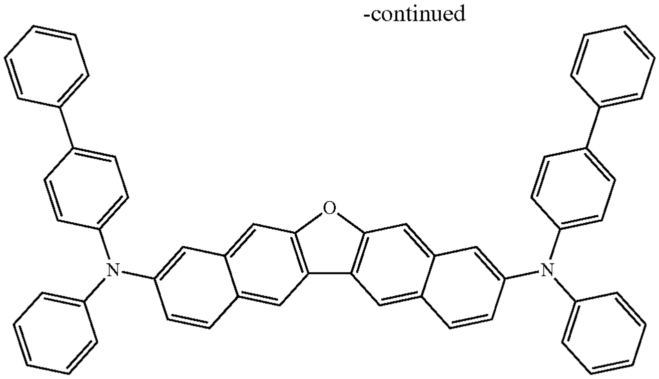
[Formula 234]
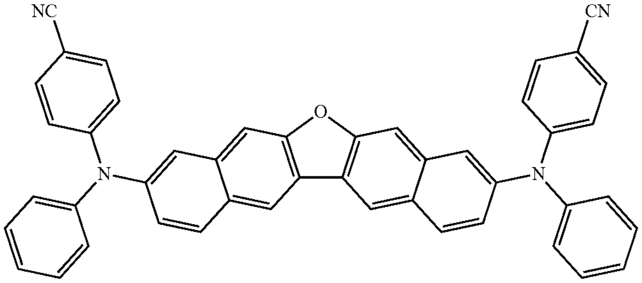
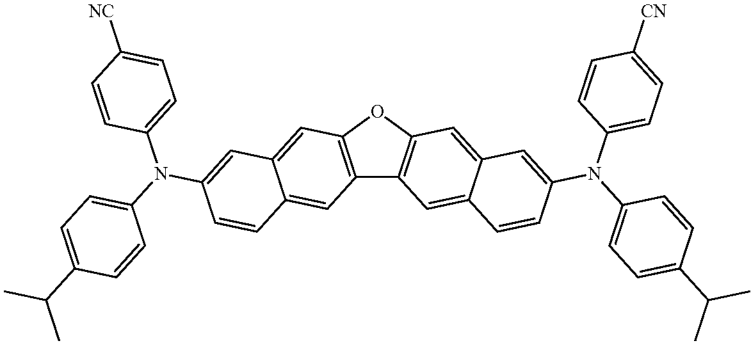
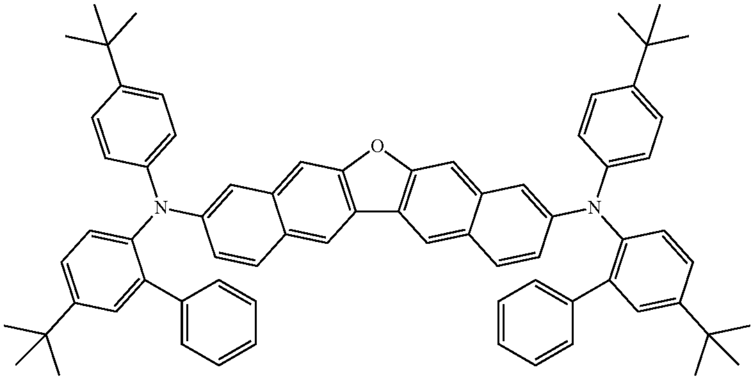

-continued
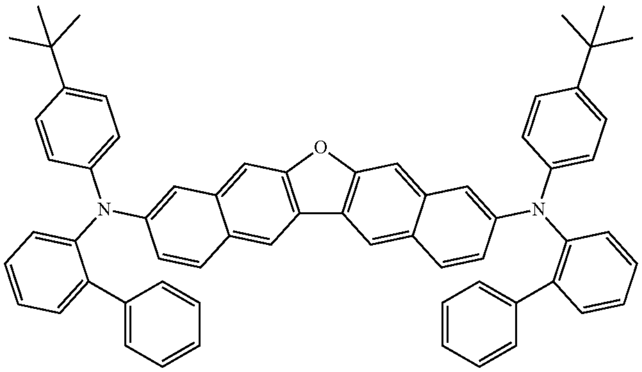
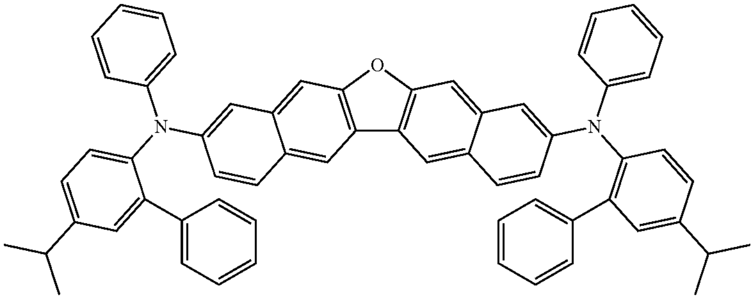
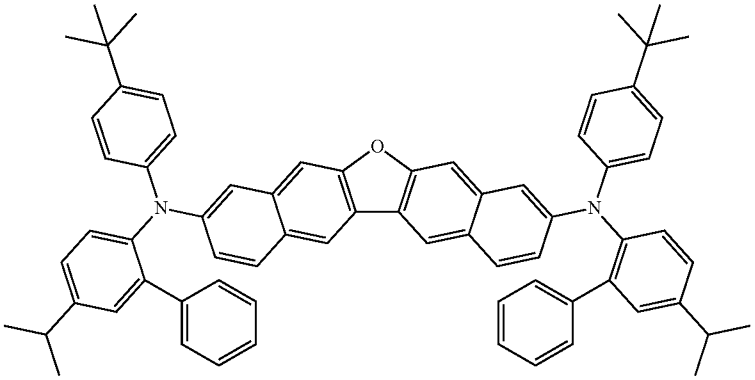
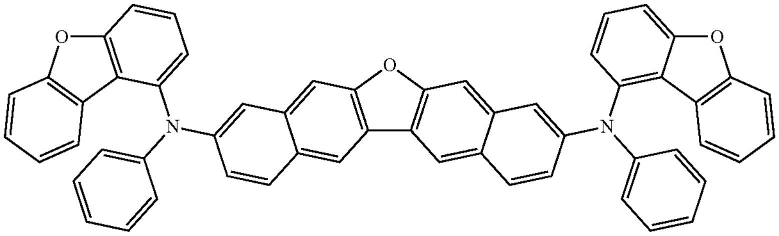
[Formula 235]
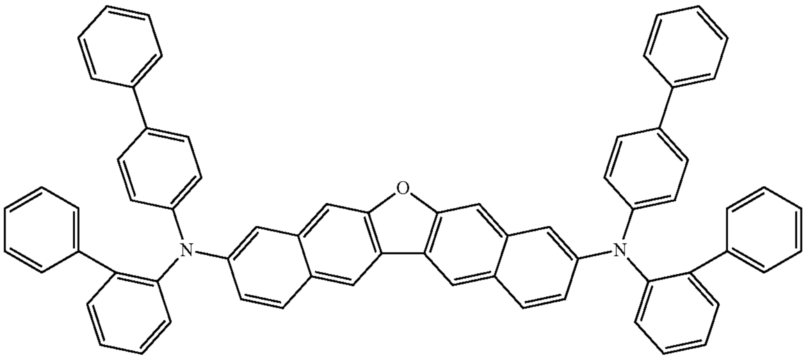

-continued
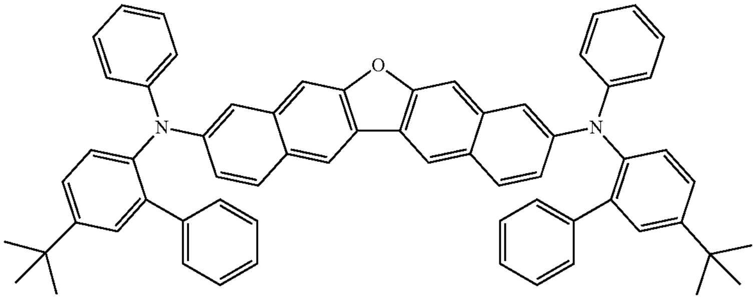
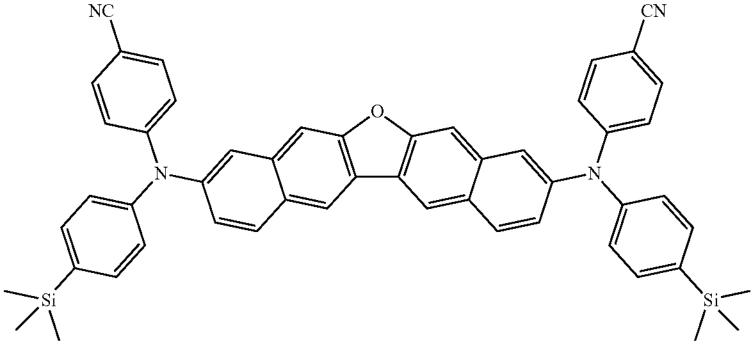
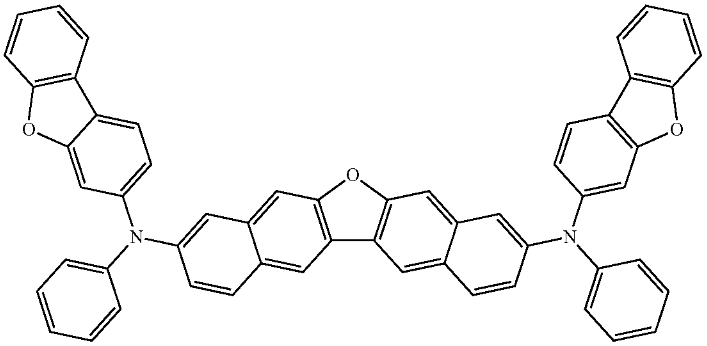
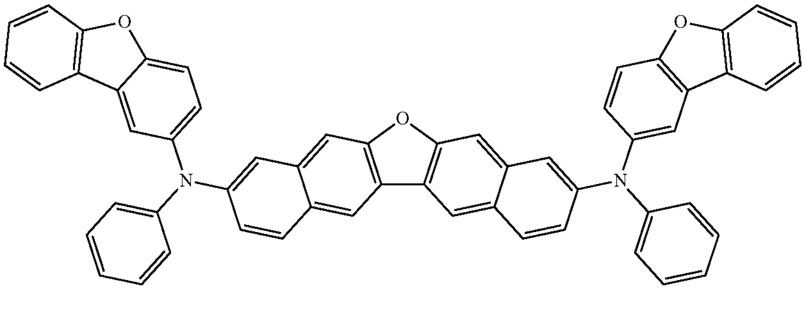

Compound Represented by Formula (71)

The compound represented by the formula (71) will be described.

[Formula 236]

(71)

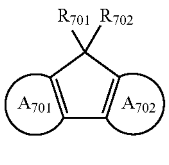

In the formula (71):

$A_{701}$ ring and $A_{702}$ ring are each independently a substituted or unsubstituted aromatic hydrocarbon ring having 6 to 50 ring carbon atoms, or a substituted or unsubstituted heterocyclic group having 5 to 50 ring atoms; and at least one ring selected from the group consisting of $A_{701}$ ring and $A_{702}$ ring is bonded to * of a structure represented by the formula (72).

[Formula 237]

(72)

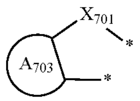

In the formula (72):

$A_{703}$ ring is a substituted or unsubstituted aromatic hydrocarbon ring having 6 to 50 ring carbon atoms, or a substituted or unsubstituted heterocycle having 5 to 50 ring atoms;

$X_{701}$ is $NR_{703}$, $C(R_{704})(R_{705})$, $Si(R_{706})(R_{707})$, $Ge(R_{708})(R_{709})$, O, S, or Se;

$R_{701}$ and $R_{702}$ are mutually bonded to form a substituted or unsubstituted monocyclic ring or a substituted or unsubstituted fused ring, or not mutually bonded;

$R_{701}$ and $R_{702}$ forming neither the substituted or unsubstituted monocyclic ring nor the substituted or unsubstituted fused ring, and $R_{703}$ to $R_{709}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ each independently represent the same as $R_{901}$ to $R_{907}$ in the formula (11).

At least one ring selected from the group consisting of $A_{701}$ ring and $A_{702}$ ring is bonded to * of the structure represented by the formula (72). In other words, the ring carbon atoms of the aromatic hydrocarbon ring or the ring atoms of the heterocycle of the $A_{701}$ ring in an exemplary embodiment are bonded to * in the structure represented by the formula (72). Further, the ring carbon atoms of the aromatic hydrocarbon ring or the ring atoms of the heterocycle of the $A_{702}$ ring in an exemplary embodiment are bonded to * in the structure represented by the formula (72).

In an exemplary embodiment, a group represented by a formula (73) below is bonded to one or both of the $A_{701}$ ring and the $A_{702}$ ring.

[Formula 238]

(73)

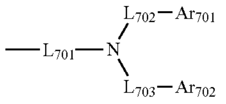

In the formula (73): $Ar_{701}$ and $Ar_{702}$ are each independently a substituted or unsubstituted aryl group having 6 to 50 ring carbon atoms, or a substituted or unsubstituted monovalent heterocyclic group having 5 to 50 ring atoms; and $L_{701}$ to $L_{703}$ are each independently a single bond, a substituted or unsubstituted arylene group having 6 to 30 ring carbon atoms, a substituted or unsubstituted divalent heterocyclic group having 5 to 30 ring atoms, or a divalent linking group formed by bonding two to four of the arylene group(s) and/or the heterocyclic group(s).

In an exemplary embodiment, in addition to the $A_{701}$ ring, the ring carbon atoms of the aromatic hydrocarbon ring or the ring atoms of the heterocycle of the $A_{702}$ ring are bonded to * in the structure represented by the formula (72). In this case, the structures represented by the formula (72) are optionally mutually the same or different.

In an exemplary embodiment, $R_{701}$ and $R_{702}$ are each independently a substituted or unsubstituted aryl group having 6 to 50 ring carbon atoms.

In an exemplary embodiment, $R_{701}$ and $R_{702}$ are mutually bonded to form a fluorene structure.

In an exemplary embodiment, the ring $A_{701}$ and the ring $A_{702}$ are each a substituted or unsubstituted aromatic hydrocarbon ring having 6 to 50 ring carbon atoms, example of which is a substituted or unsubstituted benzene ring.

In an exemplary embodiment, the ring $A_{703}$ is a substituted or unsubstituted aromatic hydrocarbon ring having 6 to 50 ring carbon atoms, example of which is a substituted or unsubstituted benzene ring.

In an exemplary embodiment, $X_{701}$ is O or S.

Specific examples of the compound represented by the formula (71) include compounds shown below.

[Formula 239]
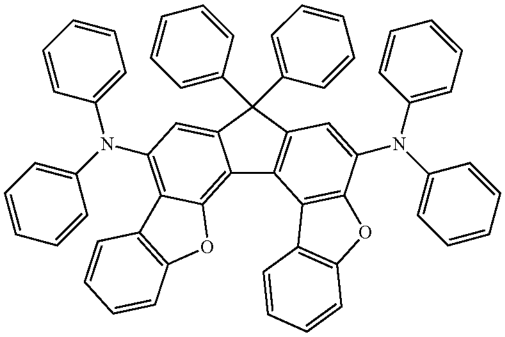
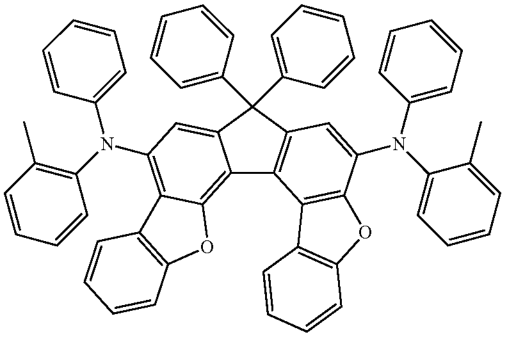
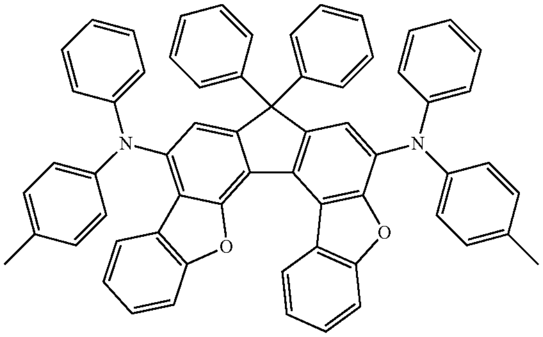
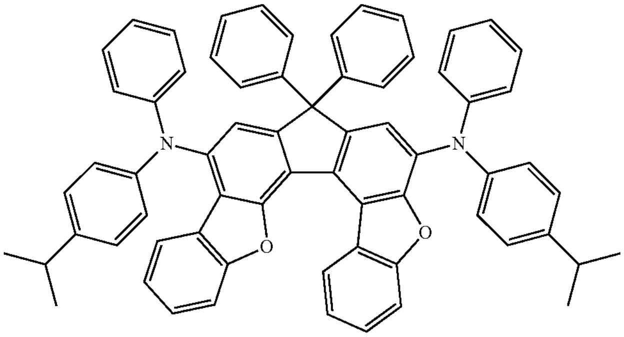
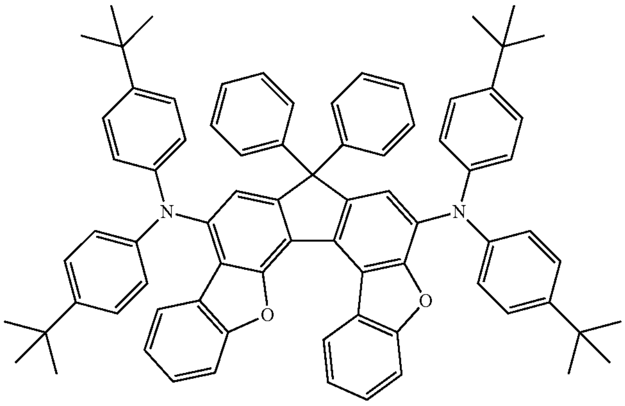
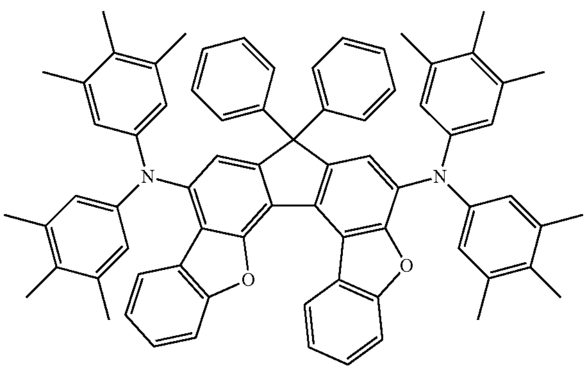
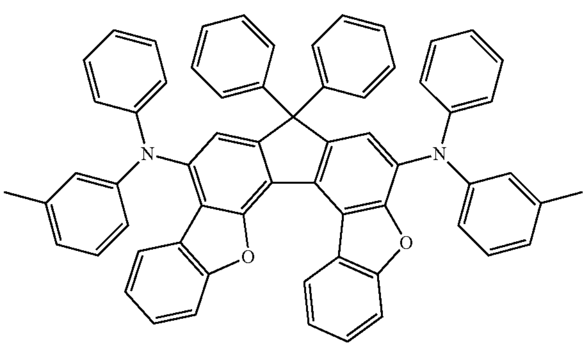

-continued
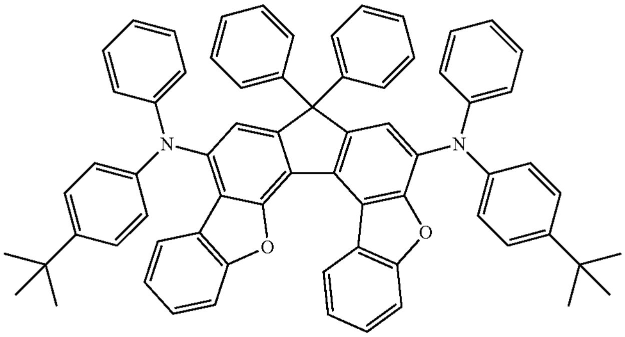
[Formula 240]
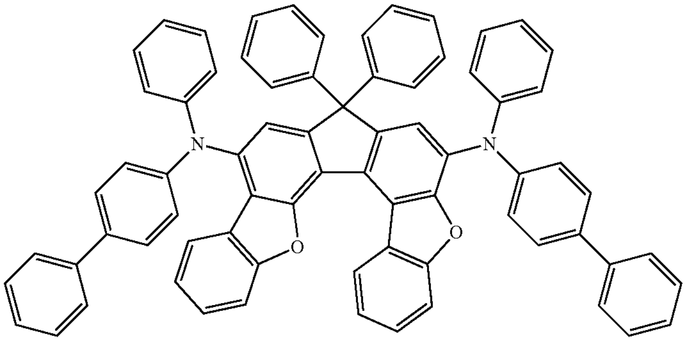
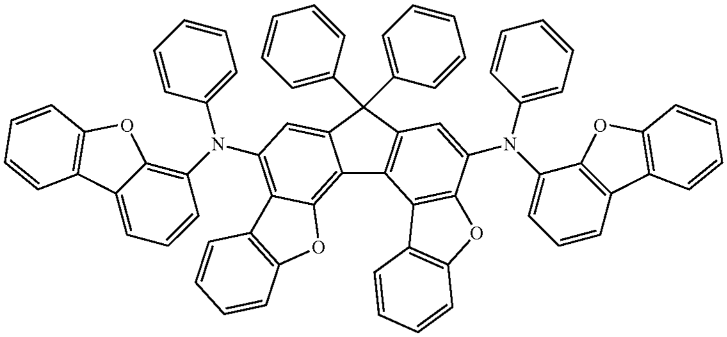
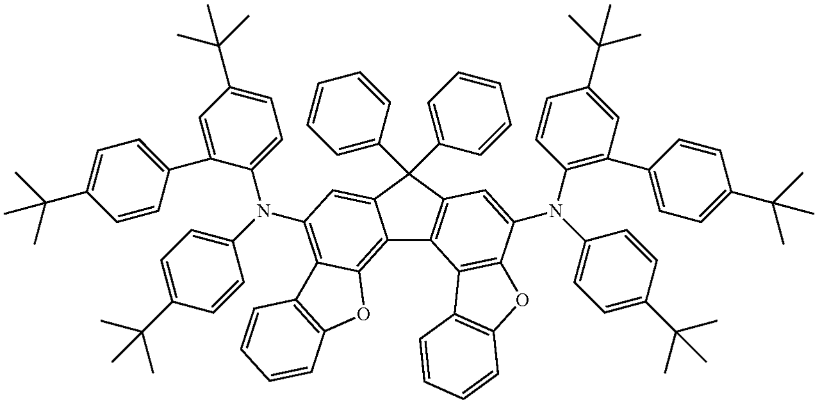

-continued
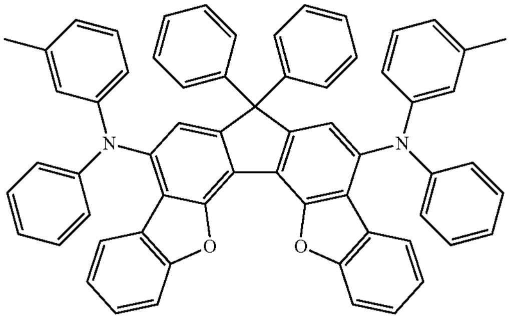
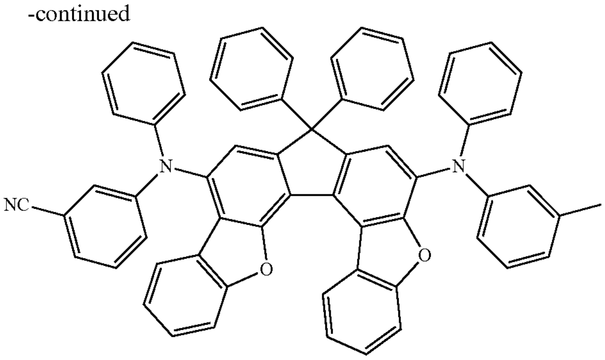
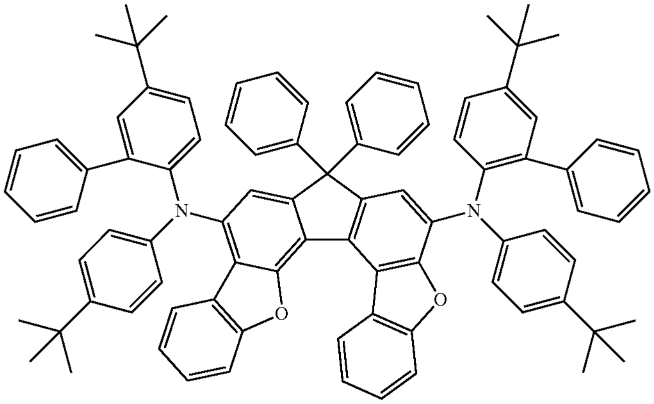
[Formula 241]
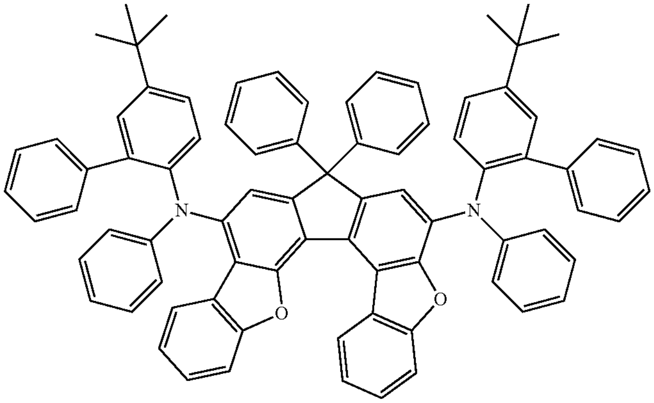
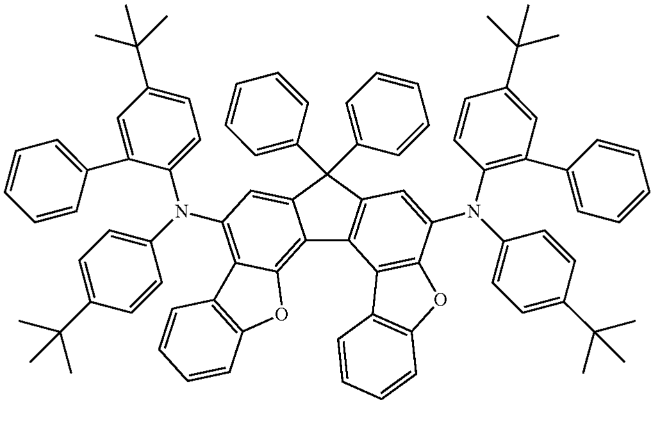

-continued
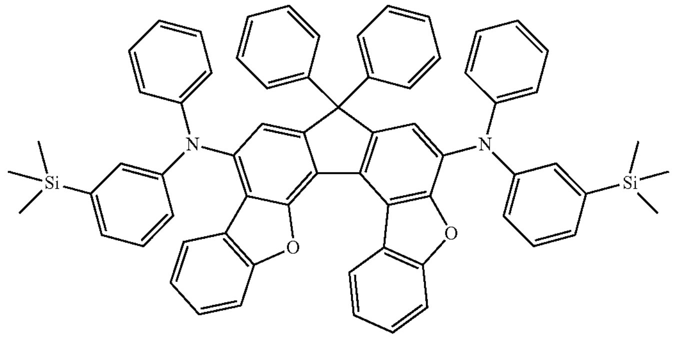
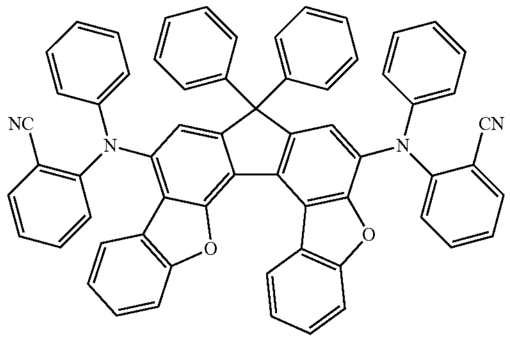
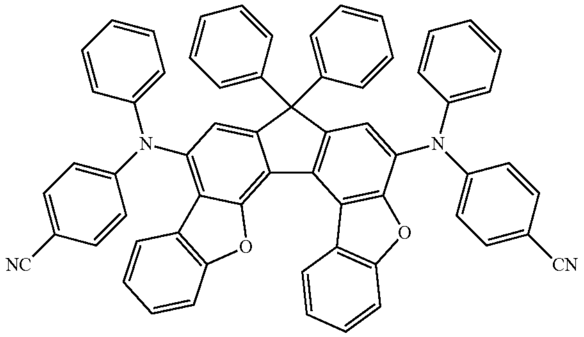
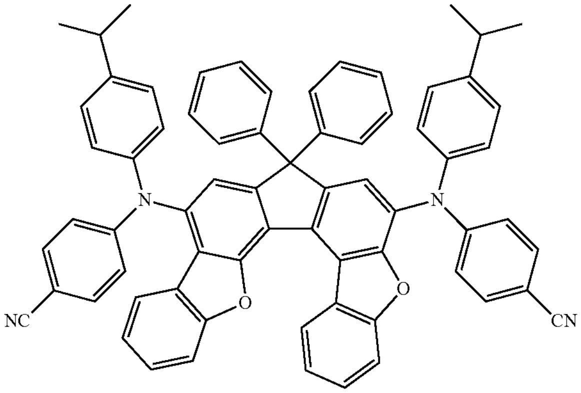
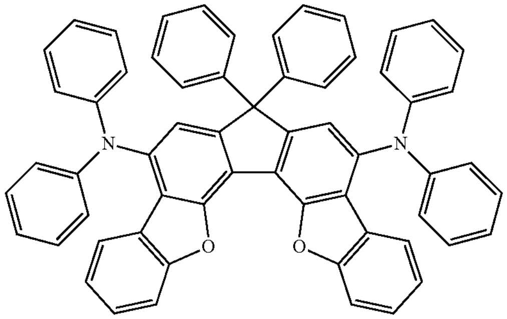
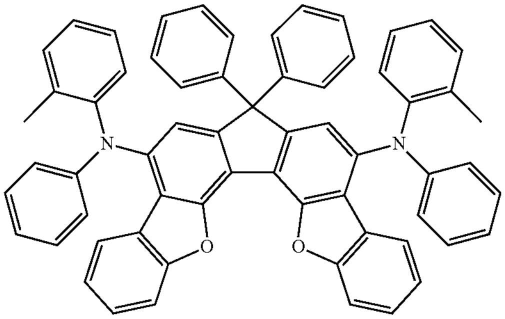
[Formula 242]
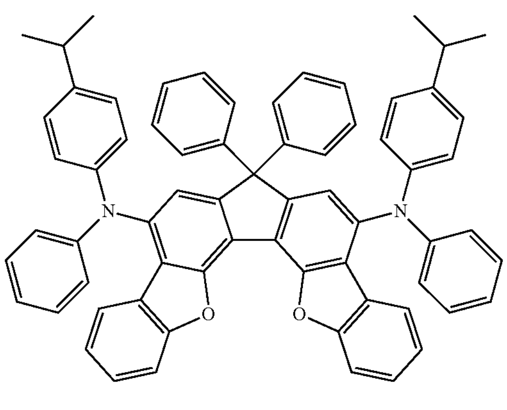
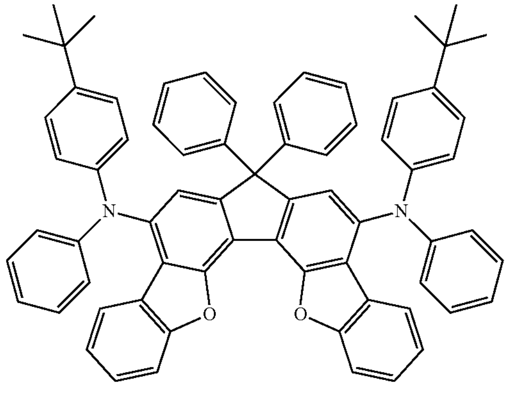

-continued
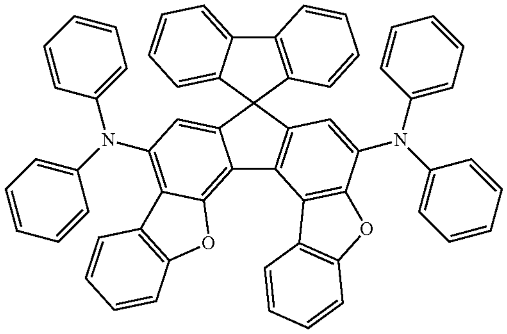
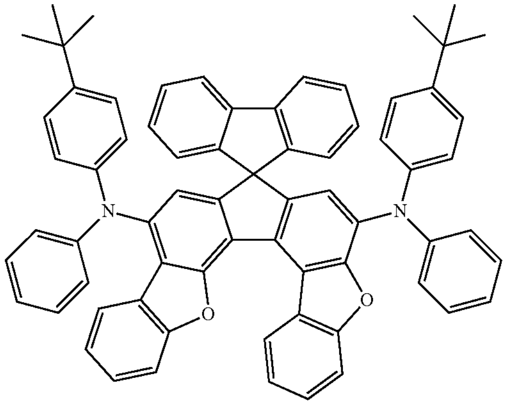
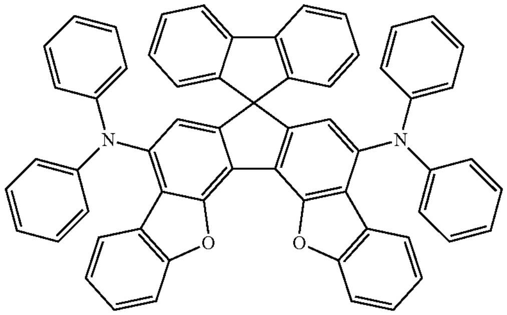
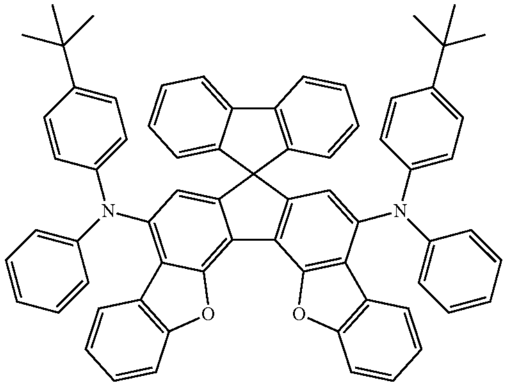
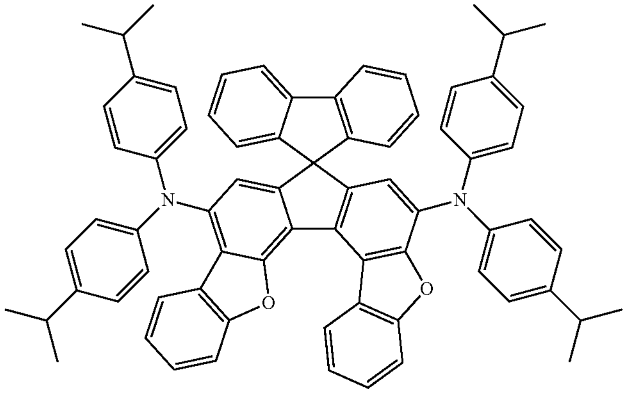
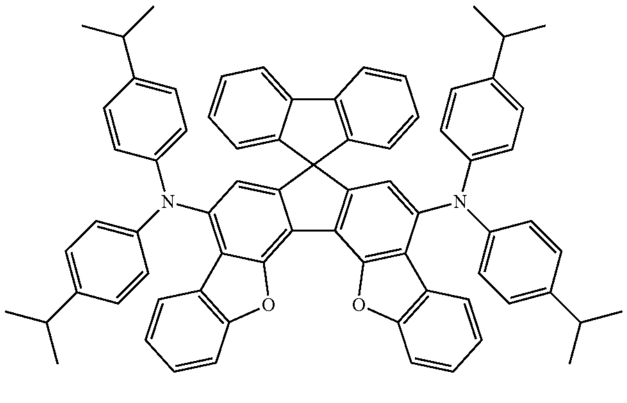 [SMILES: CC(C)c1ccc(N(c2ccc(C(C)C)cc2)c2cc3c(c4oc5ccccc5c24)-c2c(cc(N(c4ccc(C(C)C)cc4)c4ccc(C(C)C)cc4)c4c2oc2ccccc24)C32c3ccccc3-c3ccccc32)cc1]

Compound Represented by Formula (81)

The compound represented by the formula (81) will be described.

[Formula 243]

(81)

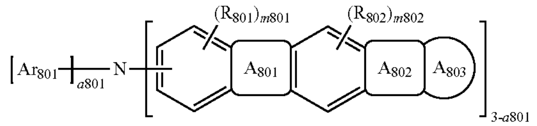

(82)

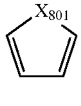

(83)

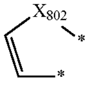

In the formula (81):

$A_{801}$ ring is a ring represented by a formula (82) and fused with adjacent ring(s) at any position(s);

$A_{802}$ ring is a ring represented by a formula (83) and fused with adjacent ring(s) at any position(s); two * are bonded with $A_{803}$ ring at any position(s);

$X_{801}$ and $X_{802}$ are each independently $C(R_{803})(R_{804})$, $Si(R_{805})(R_{806})$, an oxygen atom or a sulfur atom;

the $A_{803}$ ring is a substituted or unsubstituted aromatic hydrocarbon ring having 6 to 50 ring carbon atoms or a substituted or unsubstituted heterocycle having 5 to 50 ring atoms;

$Ar_{801}$ is a substituted or unsubstituted aryl group having 6 to 50 ring carbon atoms or a substituted or unsubstituted monovalent heterocyclic group having 5 to 50 ring atoms;

$R_{801}$ to $R_{806}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms;

$R_{901}$ to $R_{907}$ each independently represent the same as $R_{901}$ to $R_{907}$ in the formula (11);

m801 and m802 are each independently an integer in a range from 0 to 2; when m801 and/or m802 is 2, a plurality of $R_{801}$ and/or $R_{802}$ are optionally mutually the same or different;

a801 is an integer in a range from 0 to 2; when a801 is 0 or 1, structures enclosed by brackets indicated by “3-a801” are optionally mutually the same or different; and when a801 is 2, $Ar_{801}$ are optionally mutually the same or different.

In an exemplary embodiment, $Ar_{801}$ is a substituted or unsubstituted aryl group having 6 to 50 ring carbon atoms.

In an exemplary embodiment, $A_{803}$ ring is a substituted or unsubstituted aromatic hydrocarbon ring having 6 to 50 ring carbon atoms, example of which is a substituted or unsubstituted benzene ring, a substituted or unsubstituted naphthalene ring, or a substituted or unsubstituted anthracene ring.

In an exemplary embodiment, $R_{803}$ and $R_{804}$ are each independently a substituted or unsubstituted alkyl group having 1 to 50 carbon atoms.

In an exemplary embodiment, a801 is 1.

Specific examples of the compound represented by the formula (81) include compounds shown below.

[Formula 244]

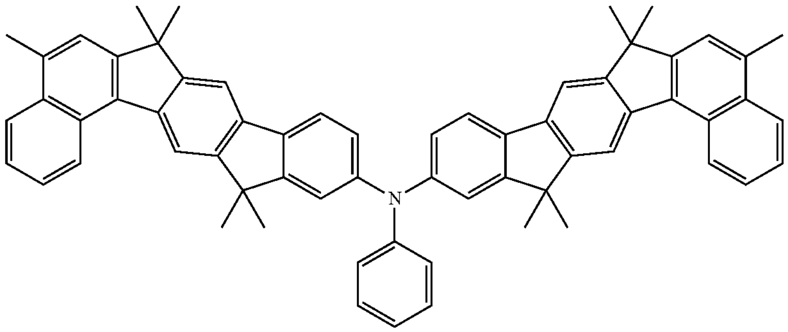

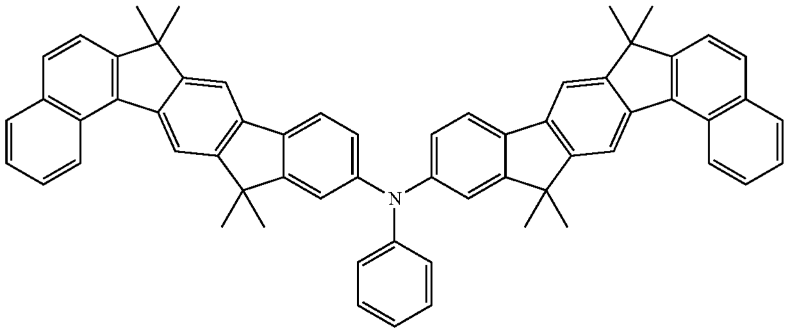

-continued

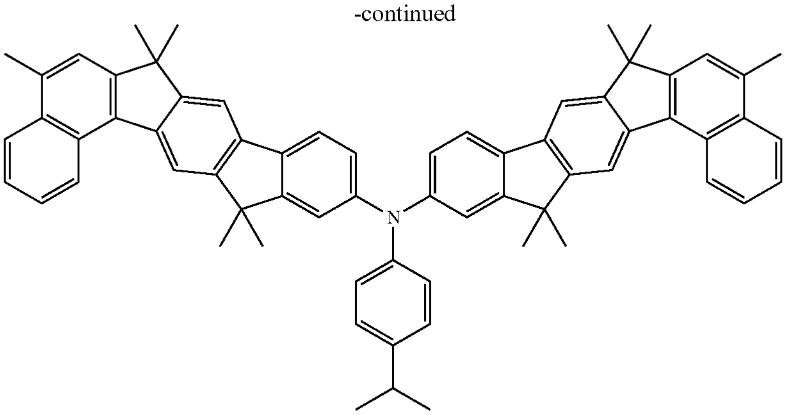

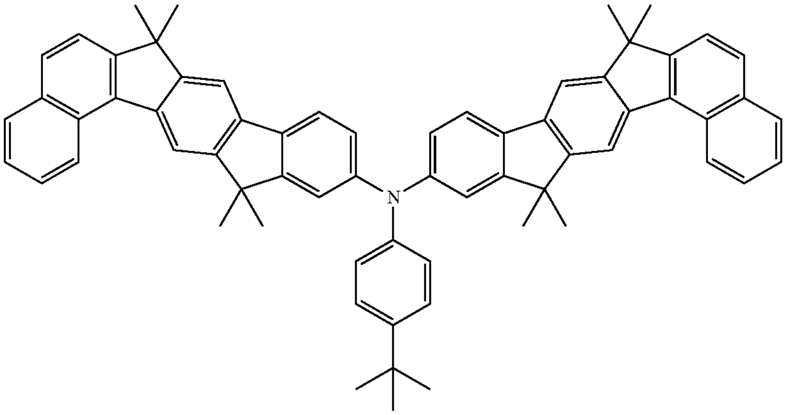

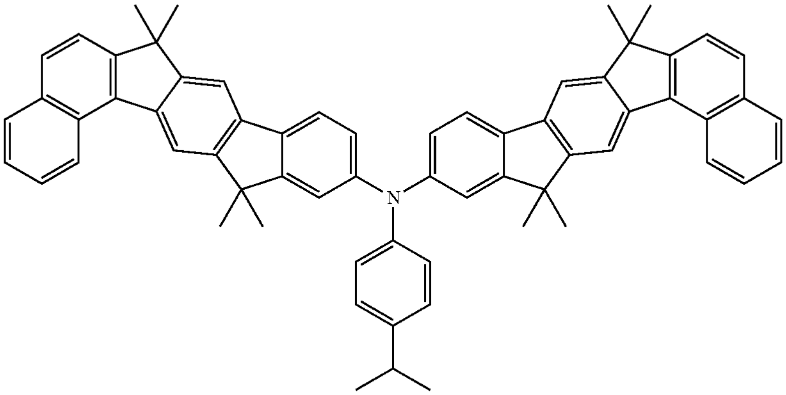

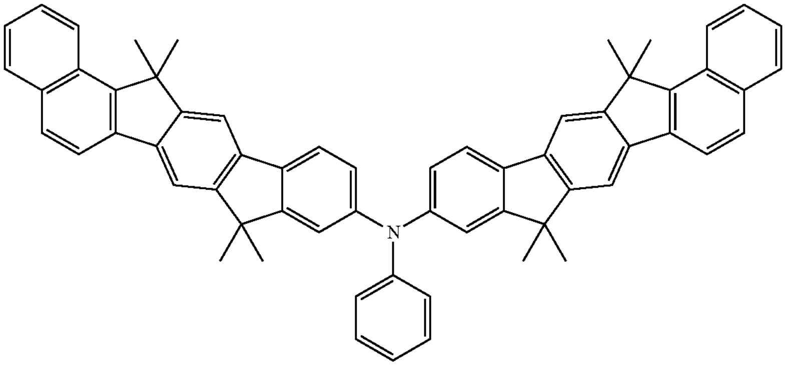

In an exemplary embodiment, the emitting layer contains the compound represented by the formula (1) and at least one compound selected from the group consisting of the compound represented by the formula (10), the compound represented by the formula (11), the compound represented by the formula (21), the compound represented by the formula (31), the compound represented by the formula (41), the compound represented by the formula (51), the compound represented by the formula (61), and the compound represented by the formula (81).

In an exemplary embodiment, the compound represented by the formula (21) is a compound represented by a formula (21-3), (21-4), or (21-5) below.

[Formula 245]

(21-3)

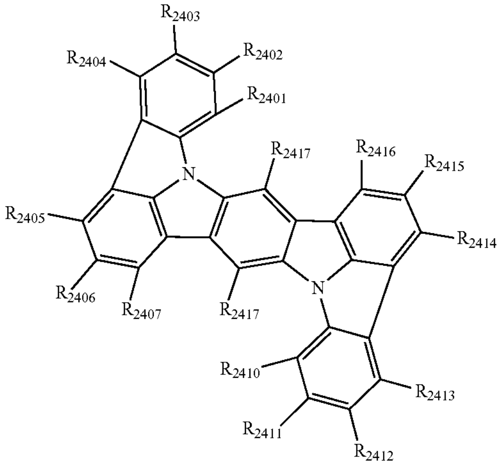

(21-4)

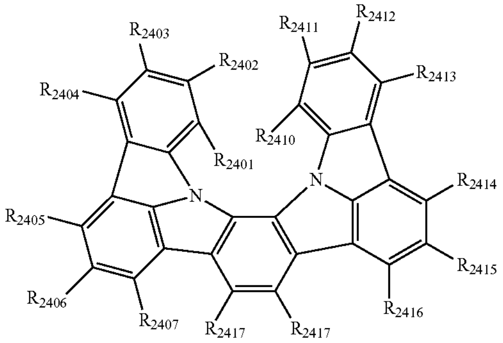

(21-5)

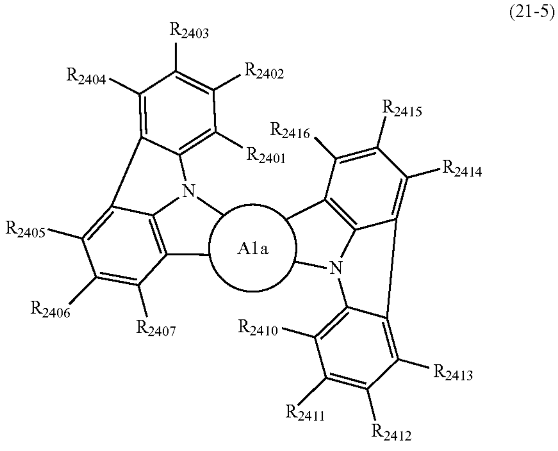

In the formulae (21-3), (21-4), and (21-5):

A1a ring is a substituted or unsubstituted fused aromatic hydrocarbon ring having 10 to 50 ring carbon atoms or a substituted or unsubstituted fused heterocycle having 8 to 50 ring atoms;

at least one combination of adjacent two or more of $R_{2401}$ to $R_{2407}$ and $R_{2410}$ to $R_{2416}$ are mutually bonded to form a substituted or unsubstituted monocyclic ring or a substituted or unsubstituted fused ring, or not mutually bonded;

$R_{2417}$, and $R_{2401}$ to $R_{2407}$ and $R_{2410}$ to $R_{2416}$ forming neither the substituted or unsubstituted monocyclic ring nor the substituted or unsubstituted fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms; and $R_{901}$ to $R_{907}$ each independently represent the same as $R_{901}$ to $R_{907}$ in the formula (11).

In an exemplary embodiment, in the formulae (21-1) to (21-3), the substituted or unsubstituted fused aromatic hydrocarbon ring having 10 to 50 ring carbon atoms is a substituted or unsubstituted naphthalene ring, substituted or unsubstituted anthracene ring, or substituted or unsubstituted fluorene ring, and the substituted or unsubstituted fused heterocycle having 8 to 50 ring atoms is a substituted or unsubstituted dibenzofuran ring, substituted or unsubstituted carbazole ring, or substituted or unsubstituted dibenzothiophene ring.

In an exemplary embodiment, in the formulae (21-1) to (21-3), the substituted or unsubstituted fused aromatic hydrocarbon ring having 10 to 50 ring carbon atoms is a substituted or unsubstituted naphthalene ring or substituted or unsubstituted fluorene ring, and the substituted or unsubstituted fused heterocycle having 8 to 50 ring atoms is a substituted or unsubstituted dibenzofuran ring, substituted or unsubstituted carbazole ring, or substituted or unsubstituted dibenzothiophene ring.

In an exemplary embodiment, the compound represented by the formula (21) is selected from the group consisting of a compound represented by a formula (21-6-1) below, a compound represented by a formula (21-6-2) below, a compound represented by a formula (21-6-3) below, a compound represented by a formula (21-6-4) below, a compound represented by a formula (21-6-5) below, a compound represented by a formula (21-6-6) below, and a compound represented by a formula (21-6-7) below.

[Formula 246]
(21-6-1)
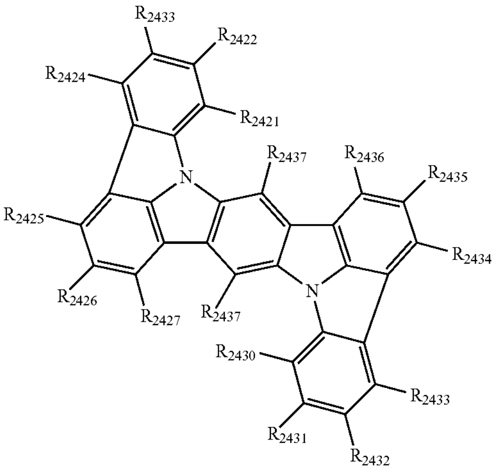
(21-6-2)
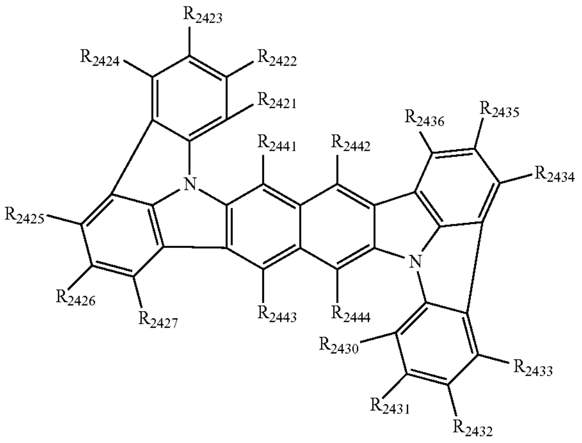
(21-6-3)
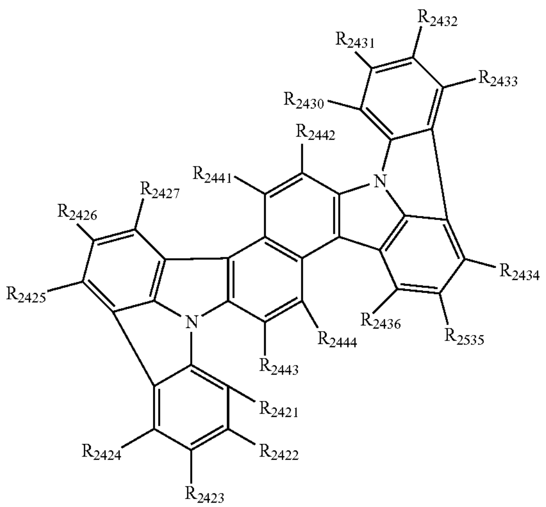
-continued
(21-6-4)
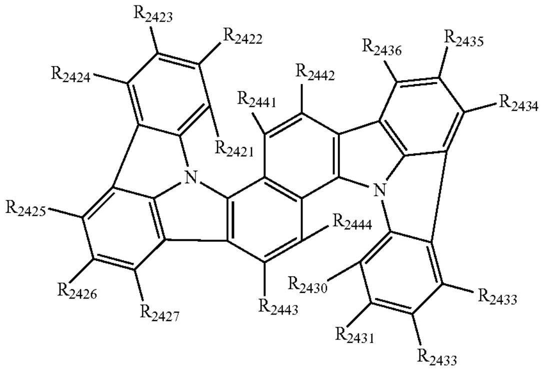
(21-6-5)
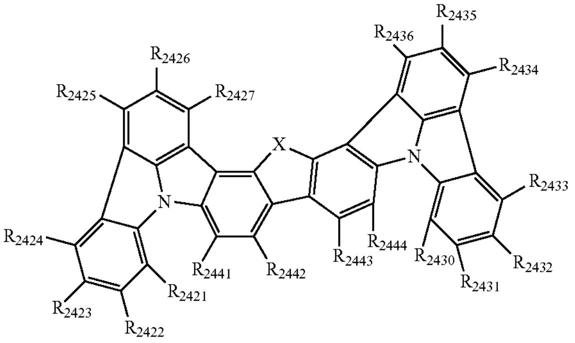
(21-6-6)
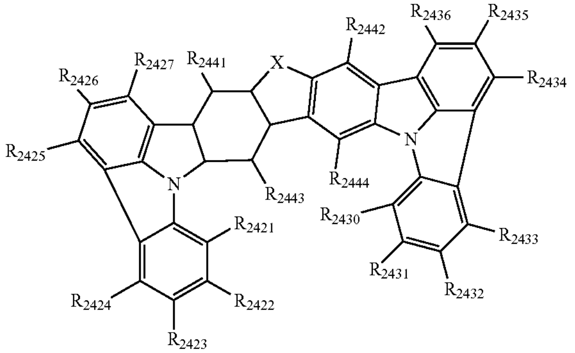
(21-6-7)
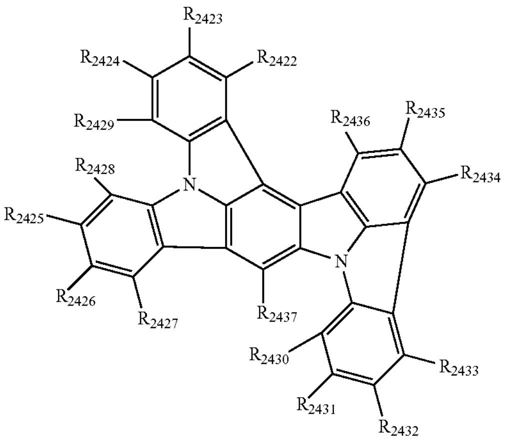

In the formulae (21-6-1) to (21-6-7):

at least one combination of adjacent two or more of $R_{2421}$ to $R_{2427}$, $R_{2430}$ to $R_{2436}$, and $R_{2441}$ to $R_{2444}$ are mutually bonded to form a substituted or unsubstituted monocyclic ring or a substituted or unsubstituted fused ring, or not mutually bonded;

$R_{2437}$, and $R_{2421}$ to $R_{2427}$, $R_{2430}$ to $R_{2436}$, and $R_{2441}$ to $R_{2444}$ forming neither the substituted or unsubstituted monocyclic ring nor the substituted or unsubstituted fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, a substituted or unsubstituted aryl group having 6 to 50 ring carbon atoms, or a substituted or unsubstituted monovalent heterocyclic group having 5 to 50 ring atoms;

X is O, $NR_{901}$, or C($R_{902}$)($R_{903}$); and $R_{901}$ to $R_{903}$ each independently represent the same as $R_{901}$ to $R_{903}$ in the formula (11).

In an exemplary embodiment, $R_{2401}$ to $R_{2407}$ and $R_{2410}$ to $R_{2417}$ are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{2401}$ to $R_{2407}$ and $R_{2410}$ to $R_{2417}$ are each independently selected from the group consisting of a hydrogen atom, a substituted or unsubstituted aryl group having 6 to 18 ring carbon atoms, and a substituted or unsubstituted heterocyclic group having 5 to 18 ring atoms.

In an exemplary embodiment, the compound represented by the formula (21-3) is a compound represented by a formula (21-3-1) below.

[Formula 247]

(21-3-1)

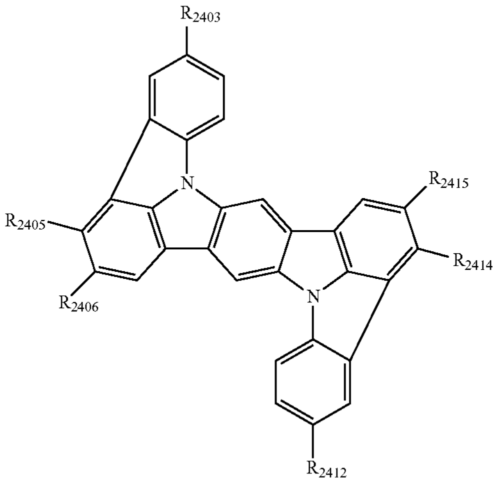

In the formula (21-3-1): $R_{2403}$, $R_{2405}$, $R_{2406}$, $R_{2412}$, $R_{2414}$, and $R_{2415}$ each independently represent the same as $R_{2403}$, $R_{2405}$, $R_{2406}$, $R_{2412}$, $R_{2414}$, and $R_{2415}$ in the formula (21-3).

In an exemplary embodiment, the compound represented by the formula (21-3) is a compound represented by a formula (21-3-2) below.

[Formula 248]

(21-3-2)

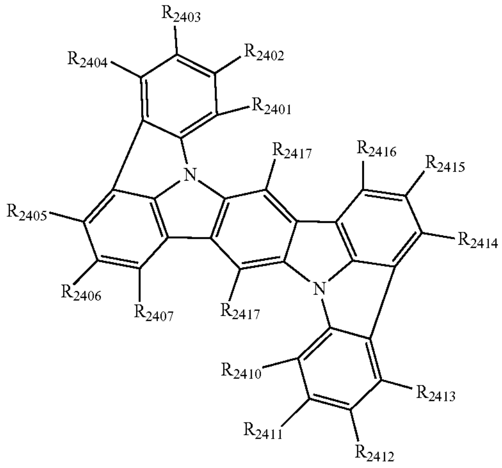

In the formula (21-3-2): $R_{2401}$ to $R_{2407}$ and $R_{2410}$ to $R_{2417}$ each independently represent the same as $R_{2401}$ to $R_{2407}$ and $R_{2410}$ to $R_{2417}$ in the formula (21-3);

at least one of $R_{2401}$ to $R_{2407}$ or $R_{2410}$ to $R_{2416}$ is —N($R_{906}$)($R_{907}$); and $R_{906}$ and $R_{907}$ each independently represent the same as $R_{906}$ and $R_{907}$ in the formula (11).

In an exemplary embodiment, two of $R_{2401}$ to $R_{2407}$ and $R_{2410}$ to $R_{2416}$ in the formula (21-3-2) are each —N($R_{906}$)($R_{907}$), and $R_{906}$ and $R_{907}$ each independently represent the same as $R_{906}$ and $R_{907}$ in the formula (11).

In an exemplary embodiment, the compound represented by the formula (21-3-2) is a compound represented by a formula (21-3-3) below.

[Formula 249]

(21-3-3)

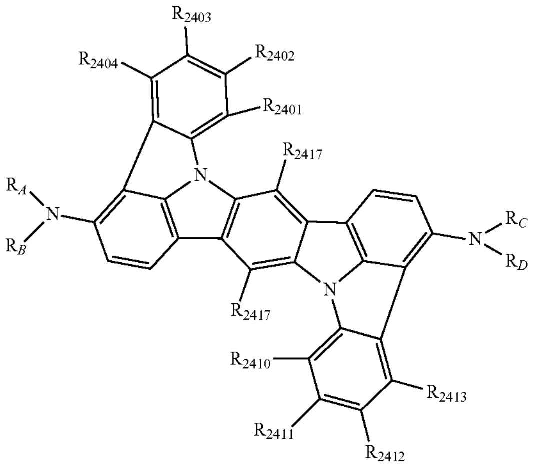

In the formula (21-3-3): $R_{2401}$ to $R_{2404}$, $R_{2410}$ to $R_{2413}$, and $R_{2417}$ each independently represent the same as $R_{2401}$ to $R_{2404}$, $R_{2410}$ to $R_{2413}$, and $R_{2417}$ in the formula (21-3); and $R_A$, $R_B$, $R_C$, and $R_D$ are each independently a substituted or unsubstituted aryl group having 6 to 18 ring carbon atoms, or a substituted or unsubstituted monovalent heterocyclic group having 5 to 18 ring atoms.

In an exemplary embodiment, the compound represented by the formula (21-3-3) is a compound represented by a formula (21-3-4) below.

[Formula 250]

(21-3-4)

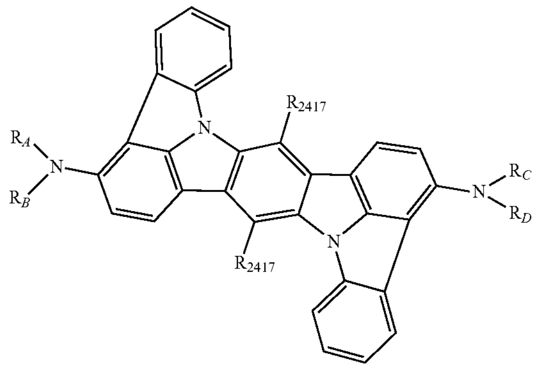

In the formula (21-3-4): $R_{2417}$, $R_A$, $R_B$, $R_C$, and $R_D$ each independently represent the same as $R_{2417}$, $R_A$, $R_B$, $R_C$, and $R_D$ in the formula (21-3-3).

In an exemplary embodiment, $R_A$, $R_B$, $R_C$, and $R_D$ are each independently a substituted or unsubstituted aryl group having 6 to 18 ring carbon atoms.

In an exemplary embodiment, $R_A$, $R_B$, $R_C$, and $R_D$ are each independently a substituted or unsubstituted phenyl group.

In an exemplary embodiment, the two $R_{2417}$ are each a hydrogen atom.

In an exemplary embodiment, the emitting layer contains the compound represented by the formula (1) and at least one compound selected from the group consisting of the compound represented by the formula (10), the compound represented by the formula (21), the compound represented by the formula (31), the compound represented by the formula (51), the compound represented by the formula (61), the compound represented by the formula (71), and a compound represented by a formula (43a) below.

[Formula 251]

(43a)

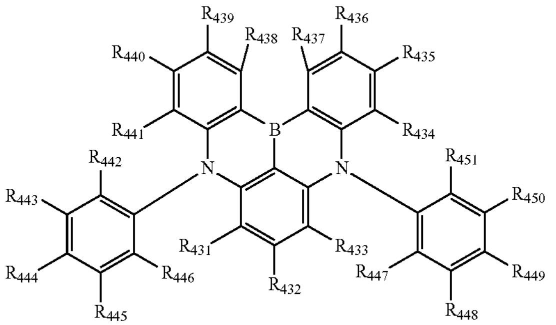

In the formula (43a):

$R_{431}$ is bonded with $R_{446}$ to form a substituted or unsubstituted heterocycle, or not bonded therewith to form no substituted or unsubstituted heterocycle; $R_{433}$ is bonded with $R_{447}$ to form a substituted or unsubstituted heterocycle, or not bonded therewith to form no substituted or unsubstituted heterocycle; $R_{434}$ is bonded with $R_{451}$ to form a substituted or unsubstituted heterocycle, or not bonded therewith to form no substituted or unsubstituted heterocycle; $R_{441}$ is bonded with $R_{442}$ to form a substituted or unsubstituted heterocycle, or not bonded therewith to form no substituted or unsubstituted heterocycle;

at least one combination of adjacent two or more of $R_{431}$ to $R_{451}$ are mutually bonded to form a substituted or unsubstituted monocyclic ring or a substituted or unsubstituted fused ring, or not mutually bonded;

$R_{431}$ to $R_{451}$ forming none of the substituted or unsubstituted heterocycle, the substituted or unsubstituted monocyclic ring, and the substituted or unsubstituted fused ring are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $-Si(R_{901})(R_{902})(R_{903})$, $-O-(R_{904})$, $-S-(R_{905})$, $-N(R_{906})(R_{907})$, a substituted or unsubstituted aryl group having 6 to 50 ring carbon atoms, or a substituted or unsubstituted monovalent heterocyclic group having 5 to 50 ring atoms;

$R_{901}$ to $R_{907}$ each independently represent the same as $R_{901}$ to $R_{907}$ in the formula (11); and at least one of $R_{431}$ to $R_{451}$ forming none of the substituted or unsubstituted heterocycle, the substituted or unsubstituted monocyclic ring, and the substituted or unsubstituted fused ring is a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, $-Si(R_{901})(R_{902})(R_{903})$, $-O-(R_{904})$, $-S-(R_{905})$, $-N(R_{906})(R_{907})$, a halogen atom, a cyano group, a nitro group, a substituted or unsubstituted aryl group having 6 to 50 ring carbon atoms, or a substituted or unsubstituted monovalent heterocyclic group having 5 to 50 ring atoms.

In an exemplary embodiment, a substituent for "substituted or unsubstituted" group in each of the formulae is an unsubstituted alkyl group having 1 to 50 carbon atoms, an unsubstituted aryl group having 6 to 50 ring carbon atoms, or an unsubstituted heterocyclic group having 5 to 50 ring atoms.

In an exemplary embodiment, a substituent for "substituted or unsubstituted" group in each of the formulae is an unsubstituted alkyl group having 1 to 18 carbon atoms, an unsubstituted aryl group having 6 to 18 ring carbon atoms, or an unsubstituted heterocyclic group having 5 to 18 ring atoms.

In the organic EL device according to the present exemplary embodiment, it is preferable that the emitting layer further contains the fluorescent compound M1 and the compound M1 is a compound that emits light having a main peak wavelength in a range from 430 nm to 480 nm.

A measurement method of a main peak wavelength of the compound is as follows. A toluene solution of a measurement target compound at a concentration ranging from $10^{-6}$ mol/L to $10^{-5}$ mol/L is prepared and put in a quartz cell. An emission spectrum (ordinate axis: emission intensity, abscissa axis: wavelength) of the thus-obtained sample is measured at a normal temperature (300K). The emission spectrum is measurable using a spectrophotometer (machine name: F-7000) manufactured by Hitachi High-Tech Science Corporation. It should be noted that the machine for measuring the emission spectrum is not limited to the machine used herein.

A peak wavelength of the emission spectrum exhibiting the maximum luminous intensity is defined as an emission main peak wavelength. It should be noted that the main peak wavelength is sometimes referred to as a fluorescence main peak wavelength (FL-peak) herein.

In the organic EL device according to the present exemplary embodiment, when the emitting layer contains the compound M2 (the compound represented by the formula (1)) and the fluorescent compound M1, the compound M2 is preferably a host material (occasionally also referred to as a matrix material) and the compound M1 is preferably a dopant material (occasionally also referred to as a guest material, emitter or luminescent material).

In the organic EL device of the present exemplary embodiment, when the emitting layer contains the compound M2 (the compound represented by the formula (1)) and the fluorescent compound M1, a singlet energy $S_1(M2)$ of the compound M2 and a singlet energy $S_1(M1)$ of the compound M1 preferably satisfy a relationship of a numerical formula (Numerical Formula 1) below.

The singlet energy $S_1$ means an energy difference between the lowest singlet state and the ground state.

$$S_1(M2)>S_1(M1) \quad \text{(Numerical Formula 1)}$$

Singlet Energy $S_1$

A method of measuring a singlet energy $S_1$ with use of a solution (occasionally referred to as a solution method) is exemplified by a method below.

A toluene solution of a measurement target compound at a concentration ranging from $10^{-5}$ mol/L to $10^{-4}$ mol/L is prepared and put in a quartz cell. An absorption spectrum (ordinate axis: absorption intensity, abscissa axis: wavelength) of the thus-obtained sample is measured at a normal temperature (300K). A tangent is drawn to the fall of the absorption spectrum close to the long-wavelength region, and a wavelength value λedge (nm) at an intersection of the tangent and the abscissa axis is assigned to a conversion equation (F2) below to calculate the singlet energy.

$$S_1\ [\text{eV}]=1239.85/\lambda\text{edge} \quad \text{Conversion Equation (F2):}$$

Any device for measuring absorption spectrum is usable. For instance, a spectrophotometer (product name: U3310) manufactured by Hitachi, Ltd. is usable.

The tangent to the fall of the absorption spectrum close to the long-wavelength region is drawn as follows. While moving on a curve of the absorption spectrum from the local maximum value closest to the long-wavelength region, among the local maximum values of the absorption spectrum, in a long-wavelength direction, a tangent at each point on the curve is checked. An inclination of the tangent is decreased and increased in a repeated manner as the curve falls (i.e., a value of the ordinate axis is decreased). A tangent drawn at a point where the inclination of the curve is the local minimum closest to the long-wavelength region (except when absorbance is 0.1 or less) is defined as the tangent to the fall of the absorption spectrum close to the long-wavelength region.

The local maximum absorbance of 0.2 or less is not counted as the above-mentioned local maximum absorbance closest to the long-wavelength region.

It is preferable that the emitting layer does not contain a phosphorescent material (dopant material).

Further, it is preferable that the emitting layer does not contain a heavy metal complex and a phosphorescent rare-earth metal complex. Examples of the heavy metal complex herein include iridium complex, osmium complex, and platinum complex.

It is also preferable that the emitting layer does not contain a metal complex.

Film Thickness of Emitting Layer

A film thickness of the emitting layer of the organic EL device according to the exemplary embodiment is preferably in a range from 5 nm to 50 nm, more preferably in a range from 7 nm to 50 nm, further preferably in a range from 10 nm to 50 nm. When the film thickness of the emitting layer is 5 nm or more, the emitting layer is easily formable and chromaticity is easily adjustable. When the film thickness of the emitting layer is 50 nm or less, a rise in the drive voltage is easily reducible.

Content Ratios of Compounds in Emitting Layer

When the emitting layer contains the compound M2 (the compound represented by the formula (1)) and the fluorescent compound M1, the content ratios of the compound M2 and the compound M1 in the emitting layer preferably falls, for instance, within a range below.

The content ratio of the compound M2 is preferably in a range from 80 mass % to 99 mass %, more preferably in a range from 90 mass % to 99 mass %, further preferably in a range from 95 mass % to 99 mass %.

The content ratio of the compound M1 is preferably in a range from 1 mass % to 10 mass %, more preferably in a range from 1 mass % to 7 mass %, further preferably in a range from 1 mass % to 5 mass %.

It should be noted that an upper limit of the total of the content ratios of the compounds M2 and M1 in the emitting layer is 100 mass %.

It should be noted that the emitting layer of the present exemplary embodiment contains a material(s) other than the compounds M2 and M1.

The emitting layer may include a single type of the compound M2 or may include two or more types of the compound M2. The emitting layer may include a single type of the compound M1 or may include two or more types of the compound M1.

An arrangement of the organic EL device 1 will be further described. It should be noted that the reference numerals will be sometimes omitted below.

Substrate

The substrate is used as a support for the organic EL device. For instance, glass, quartz, plastics and the like are usable for the substrate. A flexible substrate is also usable. The flexible substrate is a bendable substrate, which is exemplified by a plastic substrate. Examples of the material for the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal, an alloy, an electrically conductive compound, a mixture thereof, or the like having a large work function (specifically, 4.0 eV or more) is preferably used as the anode formed on the substrate. Specific examples of the material include ITO (Indium Tin Oxide), indium oxide-tin oxide containing silicon or silicon oxide, indium oxide-zinc oxide, indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of a metal material (e.g., titanium nitride) are usable.

The material is typically formed into a film by a sputtering method. For instance, the indium oxide-zinc oxide can be formed into a film by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode may be formed by a vacuum deposition method, a coating method, an inkjet method, a spin coating method or the like.

Among the organic layers formed on the anode, since the hole injecting layer adjacent to the anode is formed of a composite material into which holes are easily injectable irrespective of the work function of the anode, a material usable as an electrode material (e.g., metal, an alloy, an electroconductive compound, a mixture thereof, and the elements belonging to the group 1 or 2 of the periodic table) is also usable for the anode.

A material having a small work function such as elements belonging to Groups 1 and 2 in the periodic table of the elements, specifically, an alkali metal such as lithium ($L_1$) and cesium (Cs), an alkaline earth metal such as magnesium (Mg), calcium (Ca) and strontium (Sr), alloys (e.g., MgAg and AlLi) including the alkali metal or the alkaline earth metal, a rare earth metal such as europium (Eu) and ytterbium (Yb), alloys including the rare earth metal are also usable for the anode. It should be noted that the vacuum deposition method and the sputtering method are usable for forming the anode using the alkali metal, alkaline earth metal and the alloy thereof. Further, when a silver paste is used for the anode, the coating method and the inkjet method are usable.

Cathode

It is preferable to use metal, an alloy, an electroconductive compound, a mixture thereof, or the like having a small work function (specifically, 3.8 eV or less) for the cathode. Examples of the material for the cathode include elements belonging to Groups 1 and 2 in the periodic table of the elements, specifically, the alkali metal such as lithium (Li) and cesium (Cs), the alkaline earth metal such as magnesium (Mg), calcium (Ca) and strontium (Sr), alloys (e.g., MgAg and AlLi) including the alkali metal or the alkaline earth metal, the rare earth metal such as europium (Eu) and ytterbium (Yb), and alloys including the rare earth metal.

It should be noted that the vacuum deposition method and the sputtering method are usable for forming the cathode using the alkali metal, alkaline earth metal and the alloy thereof. Further, when a silver paste is used for the cathode, the coating method and the inkjet method are usable.

By providing the electron injecting layer, various conductive materials such as Al, Ag, ITO, graphene, and indium oxide-tin oxide containing silicon or silicon oxide may be used for forming the cathode regardless of the work function. The conductive materials can be formed into a film using the sputtering method, inkjet method, spin coating method and the like.

Hole Injecting Layer

The hole injecting layer is a layer containing a substance exhibiting a high hole injectability. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule organic compound, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

In addition, a high polymer compound (e.g., oligomer, dendrimer and polymer) is usable as the substance exhibiting a high hole injectability. Examples of the high polymer compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide](abbreviation: PTPDMA), and poly[N,N'-bis(4-butylphenyl)-N,N'-bis(phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly(styrene sulfonic acid) (PAni/PSS) are also usable.

Hole Transporting Layer

The hole transporting layer is a layer containing a highly hole-transporting substance. An aromatic amine compound, carbazole derivative, anthracene derivative and the like are usable for the hole transporting layer. Specific examples of a material for the hole transporting layer include an aromatic amine compound such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ $cm^2/(V \cdot s)$ or more.

For the hole transporting layer, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, in addition to the above substances, any substance exhibiting a higher hole transportability than an electron transportability may be used. It should be noted that the layer containing the substance exhibiting a high hole transportability may be not only a single layer but also a laminate of two or more layers formed of the above substance(s).

Electron Transporting Layer

The electron transporting layer is a layer containing a highly electron-transporting substance. For the electron transporting layer, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low-molecule organic compound, a metal complex such as Alq, tris(4-methyl-8-quinolinato)aluminum (abbreviation: $Almq_3$), bis(10-hydroxybenzo[h]quinolinato)beryllium (abbreviation: $BeBq_2$), BAlq, Znq, ZnPBO and ZnBTZ is usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) is usable. In the exemplary embodiment, a benzimidazole compound is preferably usable. The above-described substances mostly have an electron mobility of $10^{-6}$ $cm^2/Vs$ or more. It should be noted that any substance other than the above substance may be used for the electron transporting layer as long as the substance exhibits a higher electron transportability than the hole transportability. The electron transporting layer may be provided in the form of a single layer or a laminate of two or more layers of the above substance(s).

Specific examples of the compound usable for the electron transporting layer include the following compounds. It should however be noted that the invention is not limited to the specific examples of the compound.

[Formula 252]

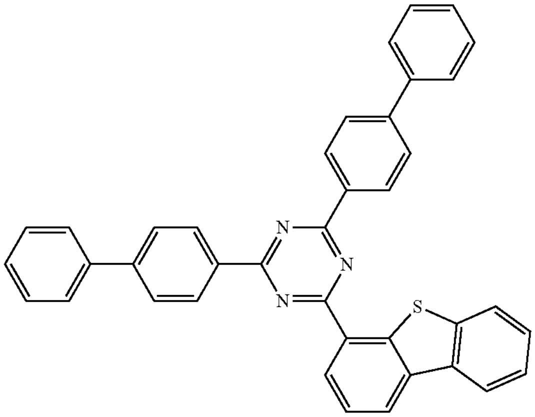

-continued

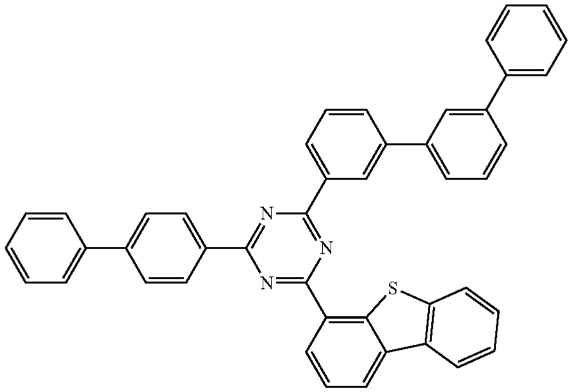

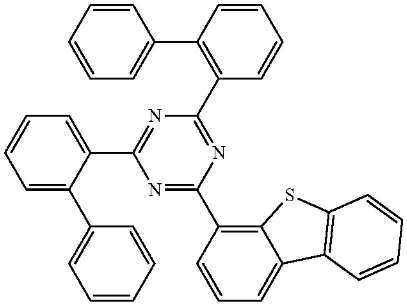

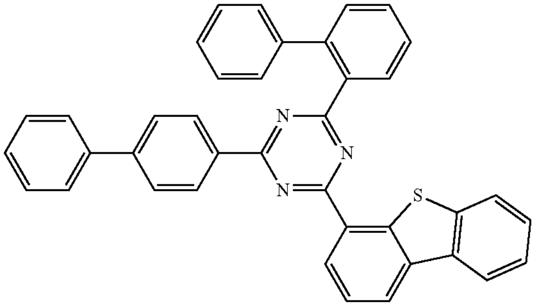

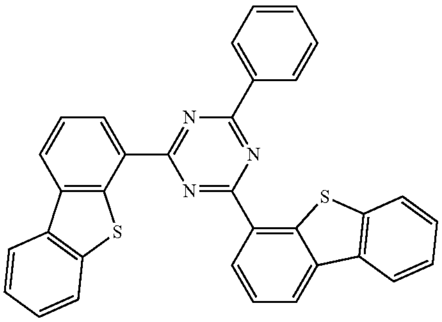

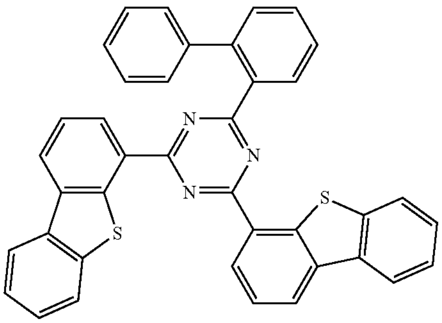

-continued
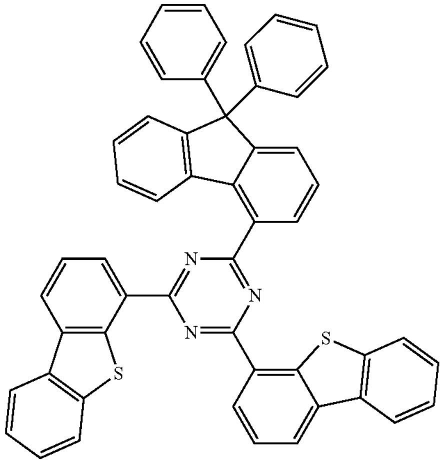
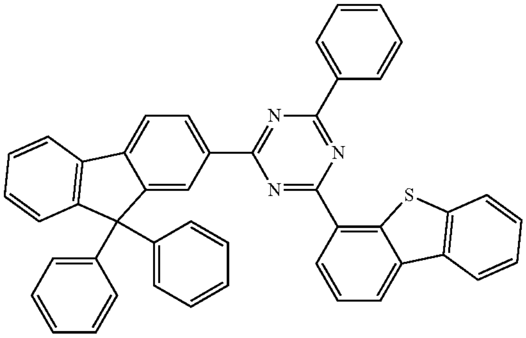
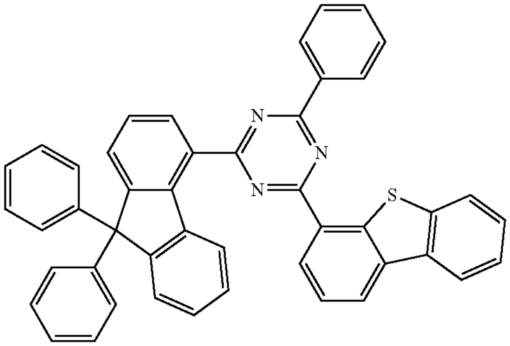
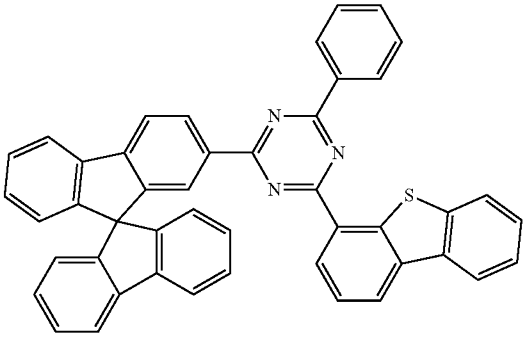
-continued
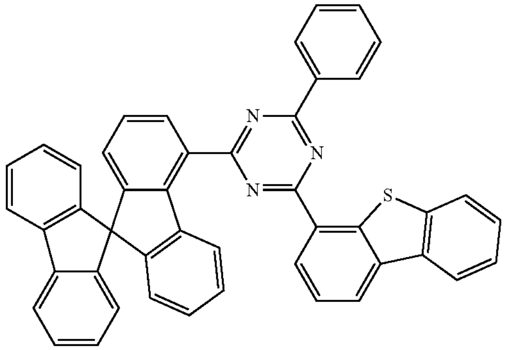
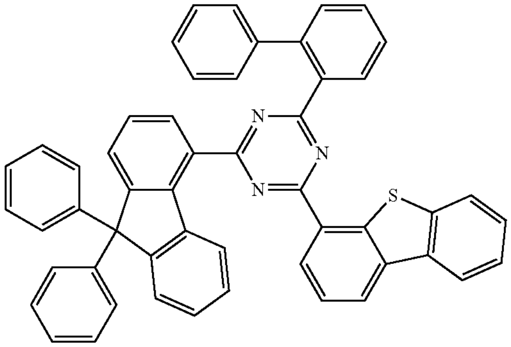
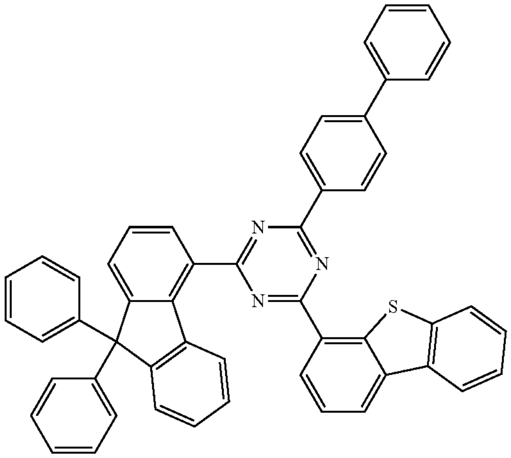
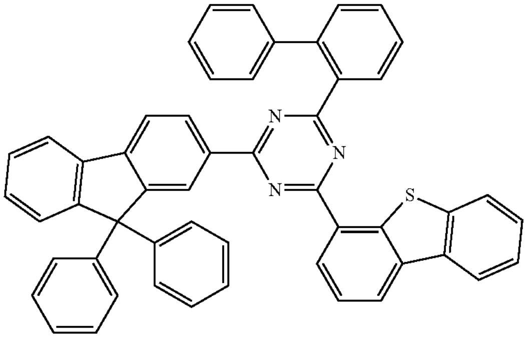

-continued

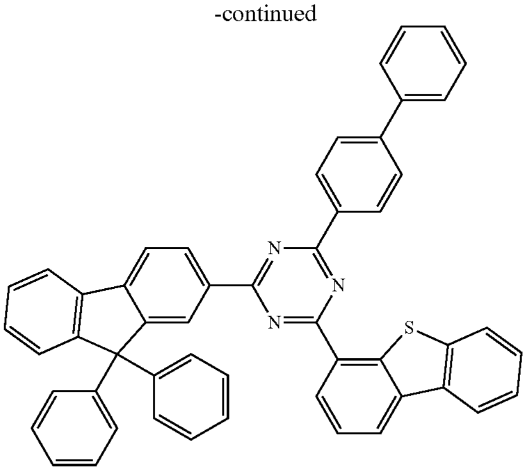

Further, a high polymer compound is usable for the electron transporting layer. For instance, poly[(9,9-dihexylfluorene-2,7-diyl)-co-(pyridine-3,5-diyl)](abbreviation: PF-Py), poly[(9,9-dioctylfluorene-2,7-diyl)-co-(2,2'-bipyridine-6,6'-diyl)](abbreviation: PF-BPy) and the like are usable.

Electron Injecting Layer

The electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride ($CaF_2$), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected from the cathode.

Alternatively, the electron injecting layer may be provided by a composite material in a form of a mixture of the organic compound and the electron donor. Such a composite material exhibits excellent electron injectability and electron transportability since electrons are generated in the organic compound by the electron donor. In this case, the organic compound is preferably a material excellent in transporting the generated electrons. Specifically, the above examples (e.g., the metal complex and the hetero aromatic compound) of the substance forming the electron transporting layer are usable. As the electron donor, any substance exhibiting electron donating property to the organic compound is usable. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

Layer Formation Method

A method for forming each layer of the organic EL device in the exemplary embodiment is subject to no limitation except for the above particular description. However, known methods of dry film-forming such as vacuum deposition, sputtering, plasma or ion plating and wet film-forming such as spin coating, dipping, flow coating or inkjet are applicable.

Film Thickness

A film thickness of each of the organic layers of the organic EL device in the exemplary embodiment is not limited unless otherwise specified in the above. In general, the thickness preferably ranges from several nanometers to 1 μm because excessively small film thickness is likely to cause defects (e.g. pin holes) and excessively large thickness leads to the necessity of applying high voltage and consequent reduction in efficiency.

According to the third exemplary embodiment, an organic electroluminescence device capable of increasing the lifetime can be provided.

Fourth Exemplary Embodiment

An arrangement of an organic EL device of a fourth exemplary embodiment will be described. In the description of the fourth exemplary embodiment, the same components as those in the third exemplary embodiment are denoted by the same reference signs and names to simplify or omit an explanation of the components. In the fourth exemplary embodiment, any materials and compounds that are not specified may be the same as those described in the first to third exemplary embodiments.

The organic EL device according to the fourth exemplary embodiment is different from the organic EL device according to the third exemplary embodiment in that the emitting layer is of a double-layer structure. The rest of the arrangement of the organic EL device according to the fourth exemplary embodiment is the same as in the third exemplary embodiment.

An example of the organic EL device having the double-layer emitting layer is as follows.

An organic electroluminescence device includes: an anode; an anode, a cathode; a first emitting layer provided between the anode and the cathode; and a second emitting layer provided between the first emitting layer and the cathode, in which the first emitting layer and the second emitting layer are in direct contact with each other.

At least one of the first emitting layer or the second emitting layer contains a host material in a form of the compound M2 (the compound represented by the formula (1)).

It is preferable that at least one of the first emitting layer or the second emitting layer contains the compound M2 and the fluorescent compound M1.

The emitting layer not containing the compound M2 is optionally a fluorescent emitting layer or a phosphorescent emitting layer with use of emission caused by electron transfer from the triplet excited state directly to the ground state.

For instance, when one of the first and second emitting layers contains the compound M2 as the host material and the fluorescent compound M1, the host material and the emitting material contained in the other emitting layer is not specifically limited.

Examples of the host material include, in addition to the compound M2 (the compound represented by the formula (1)): 1) a metal complex such as an aluminum complex, beryllium complex, or zinc complex; 2) a heterocyclic compound such as an oxadiazole derivative, benzimidazole derivative, or phenanthroline derivative; 3) a fused aromatic compound such as a carbazole derivative, anthracene derivative, phenanthrene derivative, pyrene derivative, or chrysene derivative; and 3) an aromatic amine compound such as a triarylamine derivative or a fused polycyclic aromatic amine derivative.

Examples of the emitting material include, in addition to the fluorescent compound M1, a pyrene derivative, styrylamine derivative, chrysene derivative, fluoranthene derivative, fluorene derivative, diamine derivative, triarylamine derivative, aromatic amine derivative, and tetracene derivative.

FIG. 2 schematically shows an arrangement of the organic EL device of the fourth exemplary embodiment.

An organic EL device 1A includes the light-transmissive substrate 2, the anode 3, the cathode 4, and an organic layer 10A provided between the anode 3 and the cathode 4. The organic layer 10A includes the hole injecting layer 6, the hole transporting layer 7, a first emitting layer 51, a second emitting layer 52, the electron transporting layer 8, and the electron injecting layer 9, which are sequentially layered on the anode 3. The first emitting layer 51 and the second emitting layer 52 are in direct contact with each other.

According to the fourth exemplary embodiment, an organic electroluminescence device capable of increasing the lifetime can be provided.

In the organic EL device according to the fourth exemplary embodiment, the first emitting layer and the second emitting layer are in direct contact with each other. By thus layering the first emitting layer and the second emitting layer, the generated singlet excitons and the triplet excitons can be efficiently used and, consequently, the luminous efficiency of the organic EL device can be improved.

Fifth Exemplary Embodiment

Electronic Device

An electronic device according to a fifth exemplary embodiment is installed with any one of the organic EL devices according to the above exemplary embodiments. Examples of the electronic device include a display device and a light-emitting unit. Examples of the display device include a display component (e.g., an organic EL panel module), TV, mobile phone, tablet and personal computer. Examples of the light-emitting unit include an illuminator and a vehicle light.

Modification of Embodiment(s)

The scope of the invention is not limited by the above-described exemplary embodiments but includes any modification and improvement as long as such modification and improvement are compatible with the invention.

For instance, the number of the emitting layers is not limited to one or two, and more than two emitting layers may be provided and layered with each other. When the organic EL device includes more than two emitting layers, it is only required that at least one of the emitting layers contains the compound M2 (the compound represented by the formula (1)). For instance, the rest of the emitting layers may be a fluorescent emitting layer or a phosphorescent emitting layer with use of emission caused by electron transfer from the triplet excited state directly to the ground state.

When the organic EL device includes a plurality of emitting layers, these emitting layers may be mutually adjacently provided, or may form a so-called tandem organic EL device, in which a plurality of emitting units are layered via an intermediate layer.

For instance, a blocking layer may be provided adjacent to at least one of a side of the emitting layer close to the anode or a side of the emitting layer close to the cathode. The blocking layer is preferably provided in contact with the emitting layer to block at least any of holes, electrons, excitons or combinations thereof.

For instance, when the blocking layer is provided in contact with the side of the emitting layer close to the cathode, the blocking layer permits transport of electrons and blocks holes from reaching a layer provided closer to the cathode (e.g., the electron transporting layer) beyond the blocking layer. When the organic EL device includes the electron transporting layer, the blocking layer is preferably interposed between the emitting layer and the electron transporting layer.

When the blocking layer is provided in contact with the side of the emitting layer close to the anode, the blocking layer permits transport of holes and blocks electrons from reaching a layer provided closer to the anode (e.g., the hole transporting layer) beyond the blocking layer. When the organic EL device includes the hole transporting layer, the blocking layer is preferably interposed between the emitting layer and the hole transporting layer.

Alternatively, the blocking layer may be provided adjacent to the emitting layer so that excitation energy does not leak out from the emitting layer toward neighboring layer(s). The blocking layer blocks excitons generated in the emitting layer from being transferred to a layer(s) (e.g., the electron transporting layer and the hole transporting layer) closer to the electrode(s) beyond the blocking layer.

The emitting layer is preferably bonded with the blocking layer.

Specific structure, shape and the like of the components in the invention may be designed in any manner as long as an object of the invention can be achieved.

EXAMPLES

Compounds

Structures of compounds represented by the formula (1) in Examples 1 and 2 are shown below.

[Formula 253]

BH-1

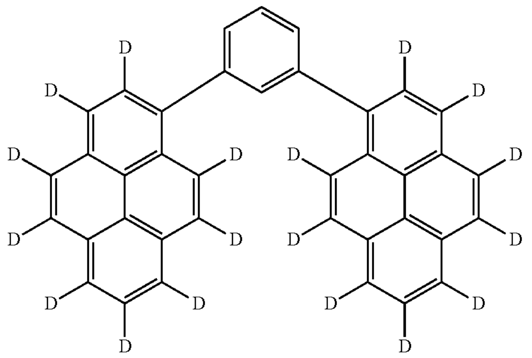

-continued
BH-2
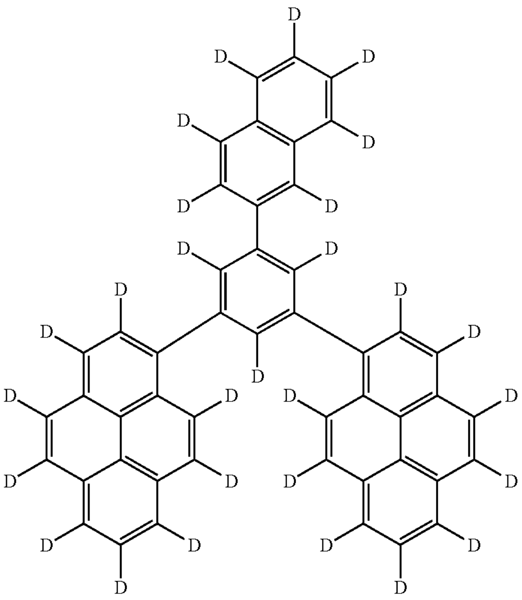
Structures of other compounds used for producing organic EL devices in Examples 1 and 2 and Comparatives 1 to 4 are shown below.
[Formula 254]
HI-1
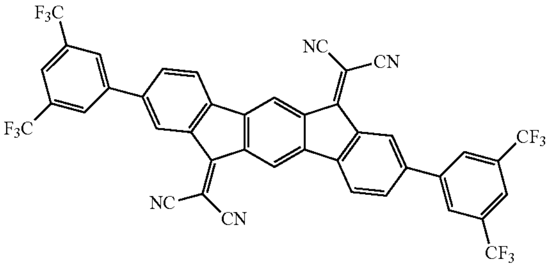
HT-1
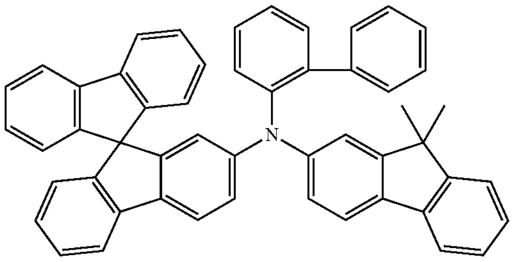
[Formula 255]
EBL-1
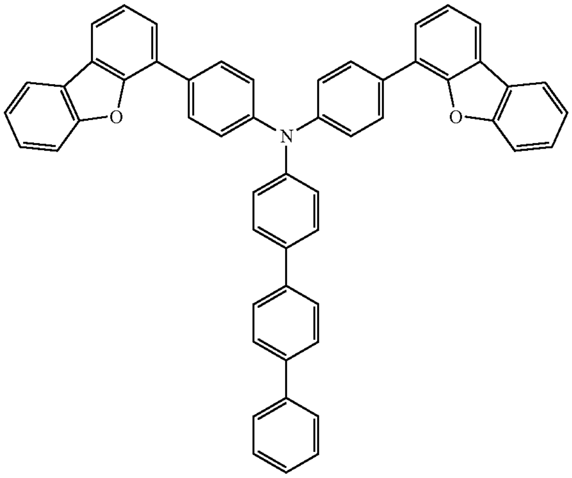
BD-1
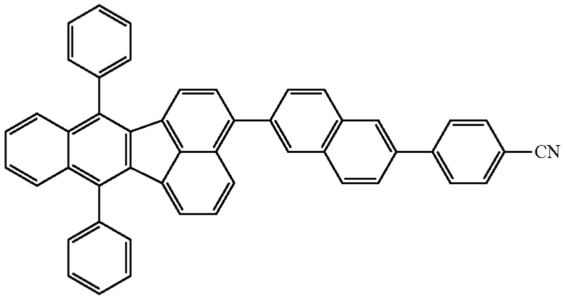

-continued
[Formula 256]
HBL-1
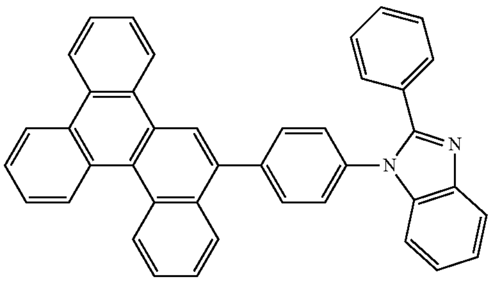
BH-3
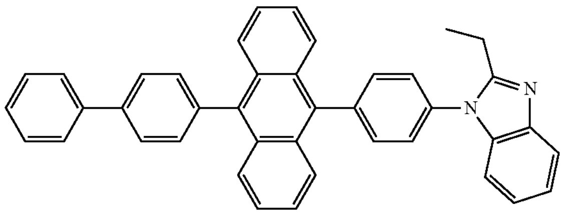
Com. BH-A
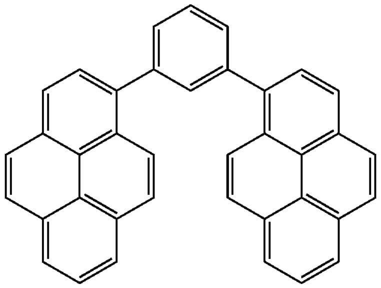
Com. BH-B
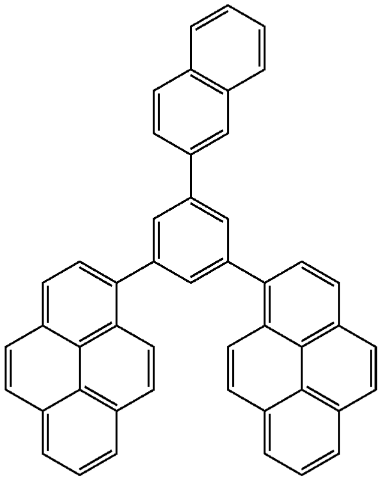
[Formula 257]
Com. BH-C
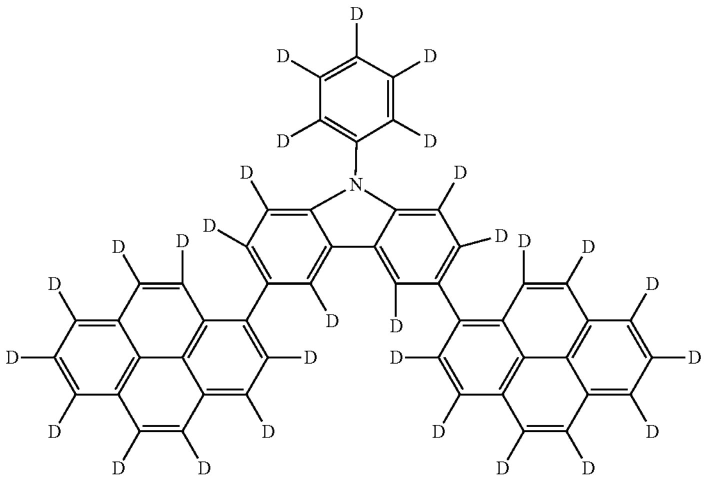

-continued

[Formula 258]

Com. BH-D

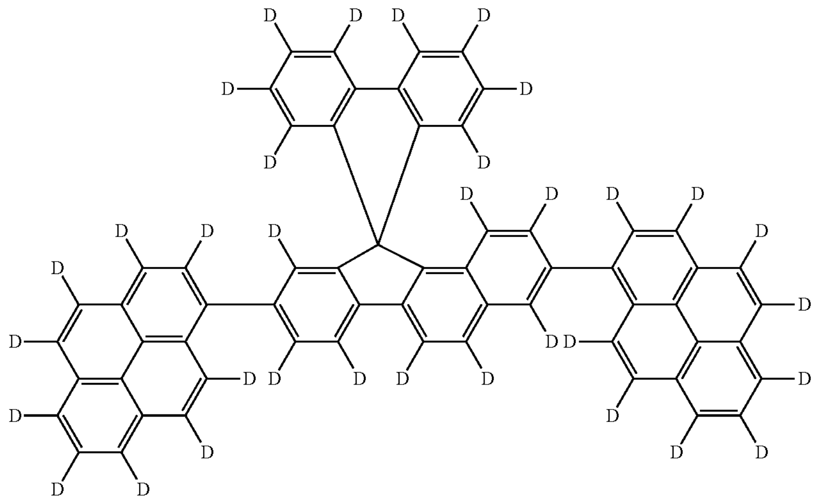

Production 1 of Organic EL Device

Organic EL devices were produced and evaluated as follows.

Example 1

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. A film thickness of the ITO transparent electrode was 130 nm.

The cleaned glass substrate having the transparent electrode line was attached to a substrate holder of a vacuum deposition apparatus. Initially, a compound HI-1 was vapor-deposited on a surface provided with the transparent electrode line to cover the transparent electrode, thereby forming a 5-nm-thick hole injecting layer (HI).

After forming the hole injecting layer, a compound HT-1 was vapor-deposited to form an 80-nm-thick first hole transporting layer (HT).

After forming the first hole transporting layer, a compound EBL-1 was vapor-deposited to form a 10-nm-thick second hole transporting layer (also referred to as an electron blocking layer (EBL)).

A compound BH-1 (host material (BH)) and a compound BD-1 (dopant material (BD)) were co-deposited on the second hole transporting layer so that the ratio of the compound BD-1 was 4 mass %, thereby forming a 25-nm-thick emitting layer.

A compound HBL-1 was vapor-deposited on the emitting layer to form a 10-nm-thick first electron transporting layer (also referred to as a hole blocking layer (HBL)).

A compound ET-1 was vapor-deposited on the first electron transporting layer to form a 15-nm-thick second electron transporting layer (ET).

LiF was vapor-deposited on the second electron transporting layer to form a 1-nm-thick electron injecting layer.

Metal Al was vapor-deposited on the electron injecting layer to form a 50-nm-thick cathode.

A device arrangement of the organic EL device in Example 1 is roughly shown as follows.

ITO(130)/HI-1(5)/HT-1(80)/EBL-1(10)/BH-1:BD-1(25, 96%:4%)/HBL-1(10)/ET-1(15)/LiF(1)/Al(50)

Numerals in parentheses represent a film thickness (unit: nm).

The numerals (96%:4%) represented by percentage in the same parentheses indicate a ratio (mass %) between the host material (compound BH-1) and the compound BD-1 in the emitting layer.

Example 2 and Comparatives 1 and 2

The organic EL devices in Example 2 and Comparatives 1 and 2 were produced in the same manner as in Example 1 except that the respective compounds shown in Table 1 were used in place of the compound BH-1 in the emitting layer of Example 1.

Evaluation 1 of Organic EL Devices

The organic EL devices produced in Examples 1 and 2 and Comparatives 1 and 2 were evaluated as follows. Evaluation results are shown in Tables 1 and 2.

Lifetime LT95

Voltage was applied using a spectroradiometer CS-200 (manufactured by Konica Minolta, Inc.) on the resultant organic EL devices so that a current density was 50 mA/cm$^2$, where a time (unit: h) elapsed before a luminance intensity was reduced to 95% of the initial luminance intensity was measured.

Hereinafter, the time elapsed before the luminance intensity is reduced to 95% of the initial luminance intensity is referred to as "Lifetime LT95(h)."

The "Lifetime LT95(h)" of Example 1 with the "Lifetime LT95(h)" of Comparative 1 being defined as 100 was calculated as a "Lifetime LT95 (relative value: %)" using a numerical formula (Numerical Formula 1) below.

Lifetime LT95(relative value:%) of Example 1=(Lifetime LT95(h) of Example 1/Lifetime LT95(h) of Comparative 1)×100 (Numerical Formula 1)

Further, the "Lifetime LT95(h)" of Example 2 with the "Lifetime LT95(h)" of Comparative 2 being defined as 100 was calculated as a "Lifetime LT95 (relative value: %)" using a numerical formula (Numerical Formula 2) below.

$$\text{Lifetime LT95(relative value:\%) of Example 2} = (\text{Lifetime LT95(h) of Example 2/Lifetime LT95(h) of Comparative 2}) \times 100 \quad \text{(Numerical Formula 2)}$$

Main Peak Wavelength λp When Device is Driven

Voltage was applied on the organic EL devices so that a current density of the organic EL device was 10 mA/cm$^2$, where spectral radiance spectrum was measured by a spectroradiometer CS-2000 (manufactured by Konica Minolta, Inc.). The main peak wavelength λp (unit: nm) was calculated based on the obtained spectral radiance spectrum.

TABLE 1

| | Emitting Layer | | | | |
|---|---|---|---|---|---|
| | Host Material (BH) | Dopant Material (BD) | Film Thickness [nm] | LT95 [Relative Value: %] | $\lambda_p$ [nm] |
| Ex. 1 | BH-1 | BD-1 | 25 | 129 | 455 |
| Comp. 1 | Com.BH-A | BD-1 | 25 | 100 | 455 |

As shown in Table 1, the organic EL device of Example 1, which contained the "compound BH-1 including a deuterium atom" in the emitting layer, exhibited a longer lifetime than that of the organic EL device of Comparative 1, which contained the "compound Com.BH-A including no deuterium atom" in place of the compound BH-1.

TABLE 2

| | Emitting Layer | | | | |
|---|---|---|---|---|---|
| | Host Material (BH) | Dopant Material (BD) | Film Thickness [nm] | LT95 [Relative Value: %] | $\lambda_p$ [nm] |
| Ex. 2 | BH-2 | BD-1 | 25 | 132 | 455 |
| Comp. 2 | Com.BH-B | BD-1 | 25 | 100 | 455 |

As shown in Table 2, the organic EL device of Example 2, which contained the "compound BH-2 including a deuterium atom" in the emitting layer, exhibited a longer lifetime than that of the organic EL device of Comparative 2, which contained the "compound Com.BH-B including no deuterium atom" in place of the compound BH-2.

Production 2 of Organic EL Device

Example 1A

As shown in Table 3, the organic EL device of Example 1A was produced in the same manner as in Example 1 except that the vapor-deposition rate of the compound BH-1 in Example 1 was changed to 20 Å/s (angstrom/sec.) in forming the emitting layer. It should be noted that the vapor-deposition rate of the compound BH-1 in Example 1 was 1 Å/s.

Comparatives 3 and 4

The organic EL devices in Comparatives 3 and 4 were produced in the same manner as in Example 1A except that the respective compounds shown in Table 3 were used in place of the compound BH-1 in the emitting layer of Example 1A.

Evaluation 2 of Organic EL Devices

The organic EL devices produced in Example 1A and Comparatives 3 and 4 were evaluated as follows. Evaluation results are shown in Table 3.

Lifetime LT95

The Lifetime LT95(h) was measured in the same manner as in Example 1.

The "Lifetime LT95(h)" of Example 1A with the "Lifetime LT95(h)" of Comparative 4 being defined as 100 was calculated as a "Lifetime LT95 (relative value: %)" using a numerical formula (Numerical Formula 3) below. The "Lifetime LT95 (relative value: %)" of Comparative 3 was also calculated by replacing Example 1A with Comparative 3 in the numerical formula (Numerical Formula 3) below.

$$\text{Lifetime LT95(relative value:\%) of Example 1}A = (\text{Lifetime LT95(h) of Example 1}A\text{/Lifetime LT95(h) of Comparative 4}) \times 100 \quad \text{(Numerical Formula 3)}$$

Main Peak Wavelength λp When Device is Driven

The maximum peak wavelength λp (unit: nm) was measured in the same manner as in Example 1.

TABLE 3

| | Emitting Layer | | | | | |
|---|---|---|---|---|---|---|
| | Host Material (BH) | Dopant Material (BD) | Vapor Deposition Rate [Å/s] | Film Thickness [nm] | LT95 [Relative Value: %] | $\lambda_p$ [nm] |
| Ex. 1A | BH-1 | BD-1 | 20 | 25 | 145 | 455 |
| Comp. 3 | Com. BH-C | BD-1 | 20 | 25 | 115 | 457 |
| Comp. 4 | Com. BH-D | BD-1 | 20 | 25 | 100 | 457 |

In the case of increasing the vapor-deposition rate for forming the emitting layer with the use of a host material including a linking group in a form of a carbazolylene group between the two pyrene rings as in Comparative 3 or in the case of increasing the vapor-deposition rate for forming the emitting layer with the use of a host material including a linking group having a large number of ring carbon atoms (e.g. benzospirofluorene) between the two pyrene rings as in Comparative 4, the effect for increasing the lifetime by deuteration was not be achieved.

In contrast, in the case of increasing the vapor-deposition rate for forming the emitting layer with the use of a host material having a linking group with a small number of ring carbon atoms between the two pyrene rings as in Example 1A, the lifetime was significantly improved.

Production of Toluene Solution

The compound BD-1 was dissolved in toluene at a concentration of 4.9×10$^{-6}$ mol/L to prepare a toluene solution of the compound BD-1.

Measurement of Fluorescence Main Peak Wavelength (FL-Peak)

A fluorescence spectrum measurement device (spectrophotofluorometer F-7000 manufactured by Hitachi High-Tech Science Corporation) was used to measure a fluorescence main peak wavelength when the toluene solution of the compound BD-1 was excited at 390 nm.

The fluorescence main peak wavelength of the compound BD-1 was 442 nm.

The invention claimed is:

1. A compound represented by a formula (1) below and comprising at least one deuterium atom, and having a ratio of the number of deuterium atoms to a total number of hydrogen atoms being 30% or more, (1)

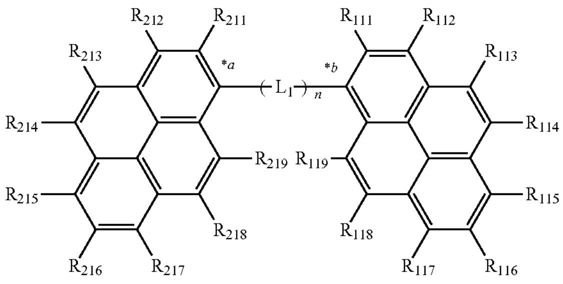

where, in the formula (1): n is 1;

$L_1$ is a group represented by any one of formulae (L-1) to (L-3) below; and $R_{111}$ to $R_{119}$ and $R_{211}$ to $R_{219}$ are each a hydrogen atom, (L-1)

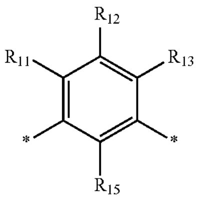

(L-2)

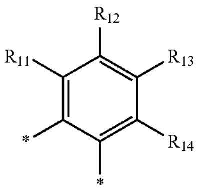

(L-3)

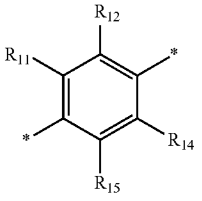

where, in the formulae (L-1) to (L-3):

one of two * represents a bonding position with *a in the formula (1) and the other * represents a bonding position with *b in the formula (1); and $R_{11}$ to $R_{15}$ are each independently a hydrogen atom, an unsubstituted phenyl group, or an unsubstituted naphthyl group.

2. The compound according to claim 1, wherein $L_1$ comprises at least one deuterium atom.

3. The compound according to claim 1, wherein at least one of $R_{11}$ to $R_{15}$ is a deuterium atom.

4. The compound according to claim 1, wherein at least one of $R_{11}$ to $R_{15}$ is a substituent, and at least one of $R_{11}$ to $R_{15}$ as the substituent each independently comprises one or more deuterium atom(s).

5. The compound according to claim 1, wherein -($L_1$)n- is a group represented by a formula ($L_n$-18) below, ($L_n$-18)

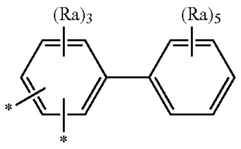

where, in the formula ($L_n$-18):

Ra is a hydrogen atom; and one of two * represents a bonding position with *a in the formula (1) and the other * represents a bonding position with *b in the formula (1).

6. The compound according to claim 5, wherein at least one of the plurality of Ra is a deuterium atom.

7. The compound according to claim 1, wherein a total number of carbon atoms comprised in -($L_1$) n- is 21 or less.

8. The compound according to claim 1, wherein at least one of $R_{111}$ to $R_{119}$ or $R_{211}$ to $R_{219}$ is a deuterium atom.

9. The compound according to claim 1, wherein $R_{111}$ to $R_{119}$ are each a deuterium atom, or $R_{211}$ to $R_{219}$ are each a deuterium atom.

10. The compound according to claim 1, wherein $R_{111}$ to $R_{119}$ and $R_{211}$ to $R_{219}$ are each a deuterium atom.

11. An organic electroluminescence device comprising:

an anode;

a cathode; and an emitting layer interposed between the anode and the cathode, wherein the emitting layer comprises a compound M2 in a form of the compound according to claim 1.

12. The organic electroluminescence device according to claim 11, wherein the emitting layer further comprises a fluorescent compound M1.

13. The organic electroluminescence device according to claim 11, wherein a singlet energy $S_1$(M2) of the compound M2 and a singlet energy $S_1$(M1) of the compound M1 satisfy a relationship of a numerical formula (Numerical Formula 1) below, $$S_1(M2)>S_1(M1) \quad \text{(Numerical Formula 1).}$$

14. The organic electroluminescence device according to claim 11, wherein the emitting layer comprises no metal complex.

15. The organic electroluminescence device according to claim 11, further comprising a hole transporting layer between the anode and the emitting layer.

16. The organic electroluminescence device according to claim 11, further comprising an electron transporting layer between the cathode and the emitting layer.

17. An electronic device comprising the organic electroluminescence device according to claim 11.

18. The compound according to claim 1, wherein $L_1$ is a group represented by the formula (L-1).

19. The compound according to claim 1, wherein the ratio of the number of deuterium atoms to the total number of hydrogen atoms of the compound represented by the formula (1) is 40% or more.

20. The compound according to claim 1, wherein the ratio of the number of deuterium atoms to the total number of hydrogen atoms of the compound represented by the formula (1) is 50% or more.

21. The compound according to claim 1, wherein the ratio of the number of deuterium atoms to the total number of hydrogen atoms of the compound represented by the formula (1) is 60% or more.

22. The compound according to claim 1, wherein the ratio of the number of deuterium atoms to the total number of hydrogen atoms of the compound represented by the formula (1) is 70% or more.

23. The compound according to claim 1, wherein the ratio of the number of deuterium atoms to the total number of hydrogen atoms of the compound represented by the formula (1) is 80% or more.

* * * * *